United States Patent
Boyce et al.

(10) Patent No.: US 9,469,615 B2
(45) Date of Patent: Oct. 18, 2016

(54) QUINOXALINES AND AZA-QUINOXALINES AS CRTH$_2$ RECEPTOR MODULATORS

(75) Inventors: Christopher W. Boyce, Flemington, NJ (US); Sylvia Joanna Degrado, Scotch Plains, NJ (US); Xiao Chen, Edison, NJ (US); Jun Qin, Edison, NJ (US); Robert D. Mazzola, Jr., Stewartsville, NJ (US); Younong Yu, East Brunswick, NJ (US); Kevin D. McCormick, Basking Ridge, NJ (US); Anandan Palani, Bridgewater, NJ (US); Dong Xiao, Warren, NJ (US); Robert George Aslanian, Rockaway, NJ (US); Jie Wu, Scotch Plains, NJ (US); Ashwin Umesh Rao, Morganville, NJ (US); Phieng Siliphaivanh, Newton, MA (US); Joey L. Methot, Westwood, MA (US); Hongjun Zhang, Newton, MA (US); Elizabeth Helen Kelley, Lynnfield, MA (US); William Colby Brown, Cleveland Heights, OH (US); Qin Jiang, Latham, NY (US); Jolicia Polivina Gauuan, Schenectady, NY (US); Andrew J. Leyhane, Latham, NY (US); Purakkattle Johny Biju, Piscataway, NJ (US); Pawan K. Dhondi, Elizabeth, NJ (US); Li Dong, Lawrenceville, NJ (US); Salem Fevrier, Cranford, NJ (US); Xianhai Huang, Warren, NJ (US); Henry M. Vaccaro, South Plainfield, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 525 days.

(21) Appl. No.: 13/996,361

(22) PCT Filed: Dec. 19, 2011

(86) PCT No.: PCT/US2011/065716
§ 371 (c)(1),
(2), (4) Date: Jun. 20, 2013

(87) PCT Pub. No.: WO2012/087861
PCT Pub. Date: Jun. 28, 2012

(65) Prior Publication Data
US 2013/0303517 A1 Nov. 14, 2013

Related U.S. Application Data

(60) Provisional application No. 61/426,886, filed on Dec. 23, 2010.

(51) Int. Cl.
*C07D 241/38* (2006.01)
*C07D 241/42* (2006.01)
(Continued)

(52) U.S. Cl.
CPC ........... *C07D 241/42* (2013.01); *A61K 31/498* (2013.01); *A61K 31/4985* (2013.01);
(Continued)

(58) Field of Classification Search
CPC   C07D 401/12; C07D 405/12; C07D 487/04; C07D 471/04; C07D 241/38; C07D 241/42; A61K 38/00
USPC ......... 514/183, 210.18, 252.1, 250; 544/350, 544/353; 540/523, 350
See application file for complete search history.

(56) References Cited

U.S. PATENT DOCUMENTS

| 5,434,155 A | 7/1995 | Fukazawa et al. |
| 7,666,878 B2 | 2/2010 | Bala et al. |

(Continued)

FOREIGN PATENT DOCUMENTS

| WO | 02/26713 A1 | 4/2002 |
| WO | 2004/009583 A2 | 1/2004 |
| WO | 2006/103120 A2 | 10/2006 |
| WO | 2007/071055 A1 | 6/2007 |
| WO | 2007/103905 A2 | 9/2007 |
| WO | 2007/138112 A2 | 12/2007 |
| WO | 2011/028947 A2 | 3/2011 |

OTHER PUBLICATIONS

Extended European Search Report for European Patent Appl. No. 11851281.3 issued Nov. 14, 2014.
(Continued)

*Primary Examiner* — Alicia L Otton
*Assistant Examiner* — Sagar Patel
(74) *Attorney, Agent, or Firm* — Eric A. Meade; Anna L. Cocuzzo

(57) ABSTRACT

The invention provides certain quinoxalines and aza-quinoxalines of the Formula (I), and their pharmaceutically acceptable salts, wherein $J^1$, $J^2$, $R^1$, $R^2$, $R^3$, $R^{22}$, $R^a$, $R^b$, $R^c$, $R^d$, X, Y, b, n, and q are as defined herein. The invention also provides pharmaceutical compositions comprising such compounds, and methods of using the compounds for treating diseases or conditions associated with uncontrolled or inappropriate stimulation of CRTH$_2$ function.

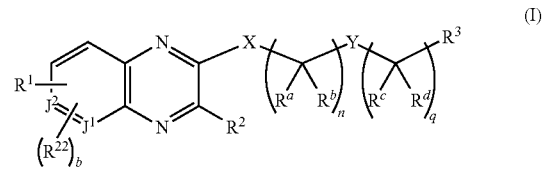

(I)

27 Claims, No Drawings

(51) Int. Cl.

| | | |
|---|---|---|
| A61K 31/498 | (2006.01) | |
| A61K 31/506 | (2006.01) | |
| A61K 31/4985 | (2006.01) | |
| A61K 31/55 | (2006.01) | |
| A61K 45/06 | (2006.01) | |
| C07D 401/12 | (2006.01) | |
| C07D 401/14 | (2006.01) | |
| C07D 405/12 | (2006.01) | |
| C07D 409/12 | (2006.01) | |
| C07D 413/12 | (2006.01) | |
| C07D 413/14 | (2006.01) | |
| C07D 417/12 | (2006.01) | |
| C07D 451/02 | (2006.01) | |
| C07D 471/08 | (2006.01) | |
| C07D 487/04 | (2006.01) | |
| C07D 487/08 | (2006.01) | |
| C07D 403/06 | (2006.01) | |
| C07D 471/04 | (2006.01) | |
| C07D 471/10 | (2006.01) | |
| C07D 491/107 | (2006.01) | |
| C07D 498/04 | (2006.01) | |
| C07D 403/12 | (2006.01) | |
| C07D 401/06 | (2006.01) | |
| C07D 403/14 | (2006.01) | |
| C07D 409/14 | (2006.01) | |
| C07D 413/06 | (2006.01) | |
| C07D 241/44 | (2006.01) | |
| C07D 417/14 | (2006.01) | |
| C07D 491/048 | (2006.01) | |
| C07D 498/10 | (2006.01) | |

(52) U.S. Cl.
CPC ............ *A61K31/506* (2013.01); *A61K 31/55* (2013.01); *A61K 45/06* (2013.01); *C07D 241/44* (2013.01); *C07D 401/06* (2013.01); *C07D 401/12* (2013.01); *C07D 401/14* (2013.01); *C07D 403/06* (2013.01); *C07D 403/12* (2013.01); *C07D 403/14* (2013.01); *C07D 405/12* (2013.01); *C07D 409/12* (2013.01); *C07D 409/14* (2013.01); *C07D 413/06* (2013.01); *C07D 413/12* (2013.01); *C07D 413/14* (2013.01); *C07D 417/12* (2013.01); *C07D 417/14* (2013.01); *C07D 451/02* (2013.01); *C07D 471/04* (2013.01); *C07D 471/08* (2013.01); *C07D 471/10* (2013.01); *C07D 487/04* (2013.01); *C07D 487/08* (2013.01); *C07D 491/048* (2013.01); *C07D 491/107* (2013.01); *C07D 498/04* (2013.01); *C07D 498/10* (2013.01); *C07D 241/38* (2013.01)

(56) References Cited

U.S. PATENT DOCUMENTS

| | | |
|---|---|---|
| 7,696,222 B2 | 4/2010 | Wang |
| 8,394,819 B2 | 3/2013 | Berthelette et al. |
| 8,546,422 B2 | 10/2013 | Leblanc et al. |
| 8,592,383 B2 | 11/2013 | Huang et al. |
| 8,637,541 B2 | 1/2014 | Wang |
| 8,637,671 B2 | 1/2014 | Colucci et al. |
| 2003/0055071 A1 | 3/2003 | Anthony et al. |
| 2005/0038076 A1 | 2/2005 | Garst et al. |
| 2010/0144786 A1 | 6/2010 | Cramp et al. |
| 2013/0210805 A1 | 8/2013 | Aslanian et al. |
| 2013/0296300 A1 | 11/2013 | Boyce et al. |

OTHER PUBLICATIONS

Ulven, T., et al., "Novel CRTH2 Antagonists: a review of patents from 2006 to 2009," Expert Opinion on Therapeutic Patents, Nov. 2010, vol. 20, Issue 11, pp. 1505-1530.

Hata, et al., "Structural determinants of arylacetic acid nonsteroidal anti-inflammatory drugs necessary for binding and activation of the prostaglandin D-2 receptor CRTH2," Molecular Pharmacology, Mar. 2005, vol. 67, Issue 3, pp. 640-647.

International Search Report & Written Opinion for PCT/US2011/65716 dated Apr. 19, 2012.

QUINOXALINES AND AZA-QUINOXALINES AS CRTH₂ RECEPTOR MODULATORS

CROSS-REFERENCE TO RELATED APPLICATIONS

This Application is a U.S. National Stage Application under 35 U.S.C. §371 of PCT Application No. PCT/US2011/065716 filed Dec. 19, 2011 which claims priority under 35 U.S.C. §119(e) of U.S. Provisional Application No. 61/426,886 filed Dec. 23, 2010.

FIELD OF THE INVENTION

The present invention relates to certain quinoxalines and aza-quinoxalines of the Formula (I) (also referred to herein as the "compounds of the Formula (I)"), compositions comprising such compounds, and methods of using such compounds for treating an inflammatory disease, or other disorder mediated by the chemoattractant receptor-homologous molecule expressed on T-helper-type-2 cells (CRTH$_2$).

BACKGROUND OF THE INVENTION

Prostaglandin D$_2$ (PGD$_2$) belongs to a class of chemical mediators which cells synthesize in response to stimuli, such as local tissue damage or hormonal stimuli, or by cellular activation pathways. Cells synthesize PGD$_2$ from arachidonic acid by cyclooxygenase and other specific synthases in the pathway.

Upon stimulation, mast cells release PGD$_2$ in major amounts and this release plays a major role in the etiology of respiratory disease, such as asthma and congestion. PGD$_2$ achieves this effect by binding with either of two G-protein coupled receptors, which are the D-prostanoid (DP) receptor and the CRTH$_2$ receptor. TH-2 cells, eosinophils, and basophils express the CRTH$_2$ receptor, which mediates the chemoattractant effect of PGD$_2$.

Scientific studies support a clear role for PGD$_2$ in an allergic inflammatory response. PGD$_2$ is found at high levels in the bronchoalveolar lavage of asthmatics. Inhalation of PGD$_2$ enhances eosinophilic and lymphocytic airway inflammation in allergic animal models. Evidence obtained by studying CRTH$_2$ knockout mice demonstrates that PGD$_2$ achieves this enhancement by binding to the CRTH$_2$ receptor. Hence, CRTH$_2$ receptor antagonists would be expected to reduce the allergic inflammatory response caused by PGD$_2$, and these compounds would be useful in the treatment or prevention of allergic/immune disorders.

Current drugs of choice for the treatment of chronic inflammatory airway disease, such as asthma or COPD, are synthetic glucocorticoids; examples of these compounds currently indicated for treating these disorders include fluticasone and mometasone. The difficulty with treating patients with this class of compounds is that the compounds possess a number of systemic side-effects; these include adrenal suppression, altered bone metabolism and growth suppression in children. These side effects limit the dose that can be administered on a daily basis to the patient. While a non-steroidal class of therapeutics that inhibit bronchoconstriction exists (CysLT$_1$ antagonists), this class of compounds has limited efficacy in achieving the endpoints of reducing inflammatory and improving in lung function when compared to the glucocorticoids. Therefore, a therapeutic that combines the efficacy of inhaled glucocorticoids without the side effects would be advantageous.

SUMMARY OF THE INVENTION

In one aspect, the present invention provides a compound of the Formula (I):

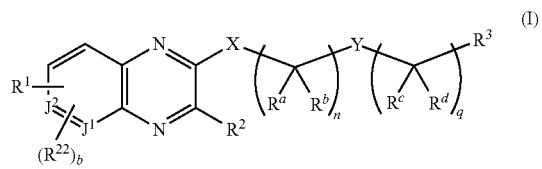

or a pharmaceutically acceptable salt thereof, wherein J$^1$ and J$^2$ are independently C(H), C(R$^1$), C(R$^{22}$), or N wherein the following provisos apply:
  (i) no more than one of J$^1$ and J$^2$ is N,
  (ii) no more than one of J$^1$ and J$^2$ is C(R$^{22}$); and
  (iii) only one R$^1$ is substituted on the illustrated ring containing J$^1$ and J$^2$;
R$^1$ is selected from the group consisting of:
  (i) —C(O)—N(R$^{6a}$)(R$^{6b}$),
  (ii) —S(O)$_2$—N(R$^{6a}$)(R$^{6b}$),
  (iii) —C(O)—C(R$^{7a}$)(R$^{7b}$)(R$^{7c}$),
  (iv) —N(H)—C(O)—C(R$^{7a}$)(R$^{7b}$)(R$^{7c}$),
  (v) —C(O)—O—C(R$^{7a}$)(R$^{7b}$)(R$^{7c}$), and
  (vi) —N(H)—S(O)$_2$—C(R$^{7a}$)(R$^{7b}$)(R$^{7c}$);
R$^{6a}$ and R$^{6b}$ are independently:
  a. H,
  b. C$_1$-C$_6$ alkyl,
  c. C$_3$-C$_6$ alkenyl,
  d. C$_3$-C$_6$ alkynyl,
  e. —O—(C$_1$-C$_3$ alkyl),
  f. -Q-R$^{AH}$, wherein R$^{AH}$ is phenyl or 5- to 6-membered heteroaryl containing 1 to 2 heteroatoms independently selected from the group consisting of N, O, and S,
    and wherein R$^{AH}$ is unsubstituted or substituted with 1 to 5 R$^8$ moieties independently selected from the group consisting of halo, C$_1$-C$_3$ alkyl, C$_1$-C$_3$ alkoxy, C$_1$-C$_3$ fluoroalkyl, —O—(C$_1$-C$_3$ fluoroalkyl), hydroxyl, phenyl, and —CN;
  Q is selected from the group consisting of a
    (a) a bond;
    (b) C$_1$-C$_6$ alkylene, wherein said C$_1$-C$_6$ alkylene is unsubstituted or substituted by 1 to 2 fluoro, C$_1$-C$_3$ alkyl, C$_1$-C$_3$ hydroxyalkyl, or C$_1$-C$_3$ fluoroalkyl; and
    (c)

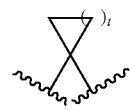

wherein t is 1, 2, 3, or 4;
  g. -Q-R$^{HC}$, wherein R$^{HC}$ is
    (i) 5- to 7-membered heterocyclyl containing 1 heteroatom selected from the group consisting of N, O, S, S(O), and S(O)$_2$, wherein said heterocyclyl of R$^{HC}$ is optionally fused to a benzene, pyridyl ring; or
    (ii) C$_3$-C$_7$ cycloalkyl, wherein said cycloalkyl of R$^{HC}$ is optionally fused to a benzene or pyridyl ring;

and wherein $R^{HC}$ is unsubstituted or substituted with 1 to 5 $R^{12}$ moieties independently selected from the group consisting of halo, $C_1$-$C_3$ alkyl, $C_1$-$C_3$ alkoxy, $C_1$-$C_3$ fluoroalkyl, —O—($C_1$-$C_3$ fluoroalkyl), hydroxyl, —CN, and —S(O)$_2$—($C_1$-$C_3$ alkyl), or wherein when two $R^{12}$ moieties are geminally substituted on the same carbon atom, the two geminally substituted $R^{12}$ moieties, together with the carbon atom on which they are attached form —C(O)—;

h. or $R^{6a}$ and $R^{6b}$ together with the N atom to which they are attached form $R^{6H}$, wherein $R^{6H}$ is independently selected from the group consisting of:
  (i) a 4- to 9-membered heterocyclyl, optionally containing one additional nitrogen atom, wherein said heterocyclyl of $R^{6H}$ is optionally fused to phenyl, $C_3$-$C_6$ cycloalkyl, or a 5-membered heteroaryl containing 1 to 3 N atoms;
  (ii) a 4- to 7-membered heterocyclenyl, optionally containing one additional nitrogen atom, wherein said heterocyclenyl of $R^{6H}$ is optionally fused to phenyl; and
  (iii) a 6- to 8-membered aza- or a diazabicycloheterocycloalkyl ring;
  wherein $R^{6H}$ is unsubstituted or substituted by 1 to 5 $R^9$ moieties wherein each $R^9$ moiety is independently $C_1$-$C_6$ alkyl, $C_1$-$C_6$ alkoxy, $C_1$-$C_3$ fluoroalkyl, fluoro, hydroxyl, —CN, —($C_1$-$C_3$ alkylene)-($C_1$-$C_3$ alkoxy), or
  $R^9$ is —Z—$R^{CY}$ wherein
    Z is
      (i) a bond,
      (ii) —C(O)—,
      (iii) —C(=N—OH)—,
      (iv) —S(O)$_2$—,
      (v) $C_1$-$C_3$ alkylene, wherein said $C_1$-$C_3$ alkylene of Z is optionally substituted by 1 to 2 fluoro or $C_1$-$C_3$ alkyl;
      (vi) —O—;
      (vii) —O—($C_1$-$C_3$ alkylene)-; or
      (viii) —C(O)—O—CH$_2$
    —$R^{CY}$ is selected from the group consisting of
      (i) phenyl
      (ii) 5- to 10-membered mono or bicyclic heteroaryl containing 1 to 3 heteroatoms independently selected from the group consisting of N, O, and S; or
      (iii) 5- to 6-membered heterocyclyl containing 1 to 2 N atoms or 1 O atom, wherein said heterocyclyl of $R^{CY}$ is optionally fused to phenyl;
    wherein $R^{CY}$ is unsubstituted or substituted by 1 to 4 $R^{10}$ moieties;
    each $R^{10}$ moiety is independently $C_1$-$C_3$ alkyl, halo, hydroxyl, $C_1$-$C_3$ alkoxy, $C_1$-$C_3$ fluoroalkyl, —($C_1$-$C_3$ alkylene)-($C_1$-$C_3$ alkoxy), —S(O)$_2$—($C_1$-$C_3$ alkyl), —C(O)—($C_1$-$C_3$ alkyl), —CN, pyridyl, or cyclopropyl or, wherein when two $R^{10}$ moieties are geminally substituted on a common carbon atom, together with the carbon atom on which they are substituted, form —C(O)—;
  or, optionally, where two $R^9$ moieties are geminally substituted on a common ring carbon of $R^{6H}$, the two $R^9$ moieties, together with the ring carbon on which they are substituted, form $R^{YC}$, wherein $R^{YC}$ is
    (i) a 4- to 7-membered cycloalkyl, wherein said cycloalkyl of $R^{YC}$ is optionally fused to phenyl or pyridyl; or
    (ii) a 4- to 7-membered heterocyclyl containing 1 to 2 N atoms or 1 O atom, wherein said heterocyclyl of $R^{YC}$ is optionally fused to phenyl;
    wherein $R^{YC}$ is unsubstituted or substituted by 1 to 4 $R^{11}$ moieties;
    each $R^{11}$ moiety is independently $C_1$-$C_3$ alkyl, halo, hydroxyl, $C_1$-$C_3$ alkoxy, —($C_1$-$C_3$ alkylene)-($C_1$-$C_3$ alkoxy), —S(O)$_2$—($C_1$-$C_3$ alkyl), —C(O)—($C_1$-$C_3$ alkyl), phenyl, or pyridyl, or, wherein when two $R^{11}$ moieties are geminally substituted on a common carbon atom, together with the carbon atom on which they are substituted, form —C(O)—;

$R^{7a}$ and $R^{7b}$ are independently
  a) H,
  b) $C_1$-$C_6$ alkyl,
  c) $R^{7a}$ and $R^{7b}$ together with the carbon atom on which they are substituted, form $R^{PC}$, wherein $R^{PC}$ is
    (i) $C_3$-$C_7$ cycloalkyl, or
    (ii) phenyl, wherein said phenyl of $R^{PC}$ is unsubstituted or substituted by 1 to 5 moieties independently selected from the group consisting of halo, trifluoromethyl, and trifluoromethoxy;

$R^{7c}$ is
  a) H, or
  b) absent, when $R^{7a}$ and $R^{7b}$ together with the carbon atom on which they are substituted form phenyl;

$R^{22}$ is halo, $C_1$-$C_3$ alkyl, or $C_1$-$C_3$ fluoroalkyl;
b is 0 or 1;
X is a bond, —O—, —S—, —S(O)—, —S(O)$_2$—, or N(H);
Y is selected from the group consisting of
  (i) a bond,

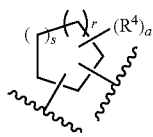

(ii)

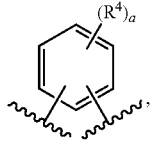

(iii)

(iv) —O—, (v) —S—, (vi) —S(O)—, and (vii) —S(O)$_2$—;
wherein
  a is 0, 1, 2, or 3;
  r is 0, 1, or 2;
  s is 0, 1, or 2;
  each occurrence of $R^4$ is independently halo, $C_1$-$C_6$ alkyl, or $C_1$-$C_6$ fluoroalkyl;
$R^a$, $R^b$, $R^e$, and $R^d$ are independently H, fluoro, hydroxyl, $C_1$-$C_6$ alkyl, $C_1$-$C_6$ fluoroalkyl, or $C_1$-$C_6$ alkoxy;
$R^2$ is selected from the group consisting of:
  (i) phenyl;
  (ii) 5- to 6-membered heteroaryl containing from 1 to 3 heteroatoms selected from the group consisting of N, O, and S;

(iii) 5- to 6-membered heterocyclenyl, containing from 1 to 2 heteroatoms selected from the group consisting of N, O, and S; and
(iv) 5- to 6-membered heterocyclyl containing from 1 to 2 heteroatoms selected from the group consisting of N, O, and S;
wherein $R^2$ is unsubstituted or substituted by 1 to 5 $R^5$ groups independently selected from the group consisting of halo, $C_1$-$C_3$ fluoroalkyl, $C_1$-$C_3$ alkyl, $C_1$-$C_3$ alkoxy, —CN, —OCF$_3$, —C(O)—($C_1$-$C_3$ alkyl), and —S(O)$_2$—($C_1$-$C_3$ alkyl);
$R^3$ is —C(O)OH,

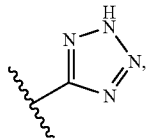 [SMILES: *c1nn[nH]n1]

or —N(H)—SO$_2$—$R^e$,
wherein $R^e$ is $C_1$-$C_6$ alkyl, $C_1$-$C_6$ fluoroalkyl, $C_1$-$C_6$ alkoxy, and phenyl;
n is 1, 2, 3, 4, or 5; and
q is 0, 1, or 2.

In another aspect, the present invention provides a compound of the Formula (I) or a pharmaceutically acceptable salt thereof, wherein
$R^1$ is selected from the group consisting of:
(i) —C(O)—N($R^{6a}$)($R^{6b}$),
(ii) —S(O)$_2$—N($R^{6a}$)($R^{6b}$),
(iii) —C(O)—C($R^{7a}$)($R^{7b}$)($R^{7c}$),
(iv) —N(H)—C(O)—C($R^{7a}$)($R^{7b}$)($R^{7c}$),
(v) —C(O)—O—C($R^{7a}$)($R^{7b}$)($R^{7c}$), and
(vi) —N(H)—S(O)$_2$—C($R^{7a}$)($R^{7b}$)($R^{7c}$);
$R^{6a}$ and $R^{6b}$ are independently:
a. H,
b. $C_1$-$C_6$ alkyl,
c. $C_3$-$C_6$ alkenyl,
d. $C_3$-$C_6$ alkynyl,
e. —O—($C_1$-$C_3$ alkyl),
f. -Q-$R^{AH}$, wherein $R^{AH}$ is phenyl or 5- to 6-membered heteroaryl containing 1 to 2 heteroatoms independently selected from the group consisting of N, O, and S,
and wherein $R^{AH}$ is unsubstituted or substituted with 1 to 5 $R^8$ moieties independently selected from the group consisting of halo, $C_1$-$C_3$ alkyl, $C_1$-$C_3$ alkoxy, $C_1$-$C_3$ fluoroalkyl, —O—($C_1$-$C_3$ fluoroalkyl), hydroxyl, phenyl, and —CN;
Q is selected from the group consisting of a
(a) a bond;
(b) $C_1$-$C_6$ alkylene, wherein said $C_1$-$C_6$ alkylene is unsubstituted or substituted by 1 to 2 fluoro, $C_1$-$C_3$ alkyl, $C_1$-$C_3$ hydroxyalkyl, or $C_1$-$C_3$ fluoroalkyl; and
(c)

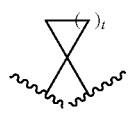

wherein t is 1, 2, 3, or 4;

g. -Q-$R^{HC}$, wherein $R^{HC}$ is
(i) 5- to 6-membered heterocyclyl containing 1 heteroatom selected from the group consisting of N and O, wherein said heterocyclyl of $R^{HC}$ is optionally fused to a benzene ring; or
(ii) $C_5$-$C_7$ cycloalkyl, wherein said cycloalkyl of $R^{HC}$ is optionally fused to a benzene ring;
and wherein $R^{HC}$ is unsubstituted or substituted with 1 to 5 $R^{12}$ moieties independently selected from the group consisting of halo, $C_1$-$C_3$ alkyl, $C_1$-$C_3$ alkoxy, $C_1$-$C_3$ fluoroalkyl, —O—($C_1$-$C_3$ fluoroalkyl), hydroxyl, and —CN, or wherein when two $R^{12}$ moieties are geminally substituted on the same carbon atom, the two geminally substituted $R^{12}$ moieties, together with the carbon atom on which they are attached form —C(O)—;
h. or $R^{6a}$ and $R^{6b}$ together with the N atom to which they are attached form $R^{6H}$, wherein $R^{6H}$ is independently selected from the group consisting of:
(i) a 4- to 7-membered heterocyclyl, optionally containing one additional nitrogen atom, wherein said heterocyclyl of $R^{6H}$ is optionally fused to phenyl; and
(ii) a 4- to 7-membered heterocyclenyl, optionally containing one additional nitrogen atom, wherein said heterocyclenyl of $R^{6H}$ is optionally fused to phenyl;
wherein $R^{6H}$ is unsubstituted or substituted by 1 to 5 $R^9$ moieties wherein each $R^9$ moiety is independently $C_1$-$C_6$ alkyl, $C_1$-$C_6$ alkoxy, fluoro, hydroxyl, —CN, —($C_1$-$C_3$ alkylene)-($C_1$-$C_3$ alkoxy), or
$R^9$ is —Z—$R^{CY}$ wherein
Z is
(i) a bond,
(ii) —C(O)—,
(iii) —C(=N—OH)—,
(iv) —S(O)$_2$—, or
(v) $C_1$-$C_3$ alkylene, wherein said $C_1$-$C_3$ alkylene of Z is optionally substituted by 1 to 2 fluoro or $C_1$-$C_3$ alkyl;
$R^{CY}$ is selected from the group consisting of:
(i) phenyl
(ii) 5- to 10-membered mono or bicyclic heteroaryl containing 1 to 3 heteroatoms independently selected from the group consisting of N, O, and S; or
(iii) 5- to 6-membered heterocyclyl containing 1 to 2 N atoms or 1 O atom, wherein said heterocyclyl of $R^{CY}$ is optionally fused to phenyl;
wherein $R^{CY}$ is unsubstituted or substituted by 1 to 4 $R^{10}$ moieties;
each $R^{10}$ moiety is independently $C_1$-$C_3$ alkyl, halo, hydroxyl, $C_1$-$C_3$ alkoxy, —($C_1$-$C_3$ alkylene)-($C_1$-$C_3$ alkoxy), —S(O)$_2$—($C_1$-$C_3$ alkyl), —C(O)—($C_1$-$C_3$ alkyl), —CN, or pyridyl, or, wherein when two $R^{10}$ moieties are geminally substituted on a common carbon atom, together with the carbon atom on which they are substituted, form —C(O)—;
or, optionally, where two $R^9$ moieties are geminally substituted on a common ring carbon of $R^{6H}$, the two $R^9$ moieties, together with the ring carbon on which they are substituted, form $R^{YC}$, wherein $R^{YC}$ is (i) a 4- to 7-membered cycloalkyl, wherein said cycloalkyl of $R^{YC}$ is optionally fused to phenyl; or (ii) a 4- to 7-membered heterocyclyl containing 1 to 2 N atoms or 1 O atom, wherein said heterocyclyl of $R^{YC}$ is optionally fused to phenyl;

wherein $R^{YC}$ is unsubstituted or substituted by 1 to 4 $R^{11}$ moieties;

each $R^{11}$ moiety is independently $C_1$-$C_3$ alkyl, halo, hydroxyl, $C_1$-$C_3$ alkoxy, —($C_1$-$C_3$ alkylene)-($C_1$-$C_3$ alkoxy), —S(O)$_2$—($C_1$-$C_3$ alkyl), —C(O)—($C_1$-$C_3$ alkyl), phenyl, or pyridyl, or, wherein when two $R^{11}$ moieties are geminally substituted on a common carbon atom, together with the carbon atom on which they are substituted, form —C(O)—;

$R^{7a}$ and $R^{7b}$ are independently
  a) H,
  b) $C_1$-$C_6$ alkyl,
  c) $R^{7a}$ and $R^{7b}$ together with the carbon atom on which they are substituted, form $R^{PC}$, wherein $R^{PC}$ is
    (i) $C_3$-$C_7$ cycloalkyl, or
    (ii) phenyl, wherein said phenyl of $R^{PC}$ is unsubstituted or substituted by 1 to 5 moieties independently selected from the group consisting of halo, trifluoromethyl, and trifluoromethoxy;

$R^{7c}$ is
  a) H, or
  b) absent, when $R^{7a}$ and $R^{7b}$ together with the carbon atom on which they are substituted form phenyl; and $J^1$, $J^2$, Y, $R^a$, $R^b$, $R^c$, $R^d$, $R^2$, $R^3$, $R^{22}$, b, n, and q are as specified in claim 1.

DETAILED DESCRIPTION OF THE INVENTION

Definitions

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name, and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "fluoroalkyl," "—O-alkyl," etc.

As used herein, and throughout this disclosure, the following terms, unless otherwise indicated, shall be understood to have the following meanings:

A "patient" is a human or non-human mammal. In one embodiment, a patient is a human. In another embodiment, a patient is a chimpanzee.

The term "therapeutically effective amount" as used herein, refers to an amount of the compound of Formula (I) and/or an additional therapeutic agent, or a composition thereof that is effective in producing the desired therapeutic, ameliorative, inhibitory or preventative effect when administered to a patient suffering from pain or an inflammatory disease or disorder. In the combination therapies of the present invention, a therapeutically effective amount can refer to each individual agent or to the combination as a whole, wherein the amounts of all agents administered are together effective, but wherein the component agent of the combination may not be present individually in an effective amount.

The term "preventing," as used herein with respect to pain or an inflammatory disease or disorder, refers to reducing the likelihood of pain or an inflammatory disease or disorder.

The term "alkyl," as used herein, refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms ($C_1$-$C_6$ alkyl) or from 1 to 3 carbon atoms ($C_1$-$C_3$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. In one embodiment, an alkyl group is linear. In another embodiment, an alkyl group is branched. Unless otherwise indicated, an alkyl group is unsubstituted.

The term "alkylene," as used herein, refers to an alkyl group, as defined above, wherein one of the alkyl group's hydrogen atoms has been replaced with a bond. Non-limiting examples of alkylene groups include —CH$_2$—, —CH$_2$CH$_2$—, —CH$_2$CH$_2$CH$_2$—, —CH$_2$CH$_2$CH$_2$CH$_2$—, —CH(CH$_3$)CH$_2$CH$_2$—, —CH(CH$_3$)— and —CH$_2$CH(CH$_3$)CH$_2$—. In one embodiment, an alkylene group has from 1 to about 6 carbon atoms. In another embodiment, an alkylene group has from 1 to 3 carbon atoms. In another embodiment, an alkylene group is branched. In another embodiment, an alkylene group is linear. In one embodiment, an alkylene group is —CH$_2$—. The term "$C_1$-$C_3$ alkylene" refers to an alkylene group having from 1 to 3 carbon atoms. Unless otherwise indicated, an alkylene group is unsubstituted.

The term "alkenyl," as used herein, refers to an aliphatic hydrocarbon group containing at least one carbon-carbon double bond and having one of its hydrogen atoms replaced with a bond. An alkenyl group may be straight or branched and contain from about 2 to about 15 carbon atoms. In one embodiment, an alkenyl group contains from about 3 to 6 carbon atoms. Non-limiting examples of alkenyl groups include ethenyl, propenyl, n-butenyl, 3-methylbut-2-enyl, n-pentenyl, octenyl and decenyl. The term "$C_2$-$C_6$ alkenyl" refers to an alkenyl group having from 2 to 6 carbon atoms. Unless otherwise indicated, an alkenyl group is unsubstituted.

The term "alkenylene," as used herein, refers to an alkenyl group, as defined above, wherein one of the alkenyl group's hydrogen atoms has been replaced with a bond. Non-limiting examples of alkenylene groups include —CH$_2$CH=CH—, —CH$_2$CH=CHCH$_2$—, and —CH(CH$_3$)CH=CH—. In one embodiment, an alkenylene group has from 3 to 6 carbon atoms. In another embodiment, an alkenylene group is branched. In another embodiment, an alkenylene group is linear. The term "$C_3$-$C_6$ alkenylene" refers to an alkenylene group having from 3 to 6 carbon atoms. Unless otherwise indicated, an alkenylene group is unsubstituted.

The term "alkynyl," as used herein, refers to an aliphatic hydrocarbon group containing at least one carbon-carbon triple bond and having one of its hydrogen atoms replaced with a bond. An alkynyl group may be straight or branched and contain from about 2 to about 15 carbon atoms. In one embodiment, an alkynyl group contains from about 3 to about 6 carbon atoms. Non-limiting examples of alkynyl groups include ethynyl, propynyl, 2-butynyl and 3-methylbutynyl. Unless otherwise indicated, an alkynyl group is unsubstituted.

The term "alkynylene," as used herein, refers to an alkynyl group, as defined above, wherein one of the alkynyl group's hydrogen atoms has been replaced with a bond. Non-limiting examples of alkynylene groups include —CH$_2$C≡C—, —CH$_2$C≡CCH$_2$—, and —CH(CH$_3$)C≡C—. In one embodiment, an alkynylene group has from 3 to 6 carbon atoms. In another embodiment, an alkynylene group is branched. In another embodiment, an alkynylene group is linear. The term "C$_3$-C$_6$ alkynylene" refers to an alkynylene group having from 3 to 6 carbon atoms. Unless otherwise indicated, an alkenylene group is unsubstituted.

The term "alkoxy" as used herein, refers to an —O-alkyl group, wherein an alkyl group is as defined above. Non-limiting examples of alkoxy groups include methoxy, ethoxy, n-propoxy, isopropoxy, n-butoxy and t-butoxy. An alkoxy group is bonded via its oxygen atom.

The term "aryl," as used herein, refers to an aromatic monocyclic or multicyclic ring system comprising from about 6 to about 14 carbon atoms. In one embodiment, an aryl group contains from about 6 to 10 carbon atoms (C$_6$-C$_{10}$ aryl). In another embodiment an aryl group is phenyl. An aryl group can be optionally substituted with one or more "ring system substituents" which may be the same or different, and are as defined herein below. In one embodiment, an aryl group can be optionally fused to a cycloalkyl or cycloalkanoyl group. Non-limiting examples of aryl groups include phenyl and naphthyl. Unless otherwise indicated, an aryl group is unsubstituted.

The terms "aza- or diazabicycloheterocycloalkyl" refer to saturated or mono-unsaturated cyclic systems having a first ring which is a 5, 6, or 7-membered ring having one or two nitrogen ring atoms with the remainder of the ring atoms being carbon atoms and a second ring formed from an alkylene bridge having 1 or 2 carbon atoms which is joined to two non-adjacent ring carbon atoms of the first ring. In one embodiment, an aza- or diabicycloheterocycloalkyl is a group selected from 2,5-diazabicyclo[2.2.1]heptane and 2,5-diazabicyclo[2.2.2]octane, 3,8-diazabicyclo[3.2.1]octane, and 8-azabyciyclo[3.2.1]oct-2-ene.

The term "carbamyl," as used herein, refers to the moiety —C(O)NH$_2$ wherein the point of attachment is through the carbonyl carbon atom.

The term "cycloalkyl," as used herein, refers to a non-aromatic mono- or multicyclic ring system comprising from about 3 to about 10 ring carbon atoms. In one embodiment, a cycloalkyl contains from about 5 to 10 ring carbon atoms. In another embodiment, a cycloalkyl contains from about 3 to about 7 ring atoms. In another embodiment, a cycloalkyl contains from about 5 to about 6 ring atoms. Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl and adamantyl. The term "C$_3$-C$_7$ cycloalkyl" refers to a cycloalkyl group having from 3 to 7 ring carbon atoms. Unless otherwise indicated, a cycloalkyl group is unsubstituted.

The term "halo," as used herein, means —F, —Cl, —Br or —I. In one embodiment, a halo group is —F or —Cl. In another embodiment, a halo group is F.

The term "fluoroalkyl," as used herein, refers to an alkyl group as defined above, wherein one or more of the alkyl group's hydrogen atoms has been replaced with a fluorine. In one embodiment, a fluoroalkyl group has from 1 to 6 carbon atoms. In another embodiment, a fluoroalkyl group is substituted with from 1 to 3 F atoms. Non-limiting examples of fluoroalkyl groups include —CH$_2$F, —CHF$_2$, and —CF$_3$. The term "C$_1$-C$_3$ fluoroalkyl" refers to a fluoroalkyl group having from 1 to 3 carbon atoms.

The term "hydroxyalkyl," as used herein, refers to an alkyl group as defined above, wherein one of the alkyl group's hydrogen atoms has been replaced with a hydroxyl moiety. In one embodiment, a hydroxyalkyl group has from 1 to 3 carbon atoms. Non-limiting examples of hydroxyalkyl groups include —CH$_2$OH, —CH$_2$CH$_2$OH, and —CH$_2$CH(CH$_3$)CH$_2$OH, and —CH(CH$_3$)CH$_2$OH. The term "C$_1$-C$_3$ hydroxyalkyl" refers to a hydroxyalkyl group having from 1 to 3 carbon atoms.

The term "heteroaryl," as used herein, refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is bicyclic. A heteroaryl group is joined via a ring carbon atom, and any nitrogen atom of a heteroaryl can be optionally oxidized to the corresponding N-oxide. The term "heteroaryl" also encompasses a heteroaryl group, as defined above, which is fused to a benzene ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, benzimidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. In one embodiment, a heteroaryl group is a 5-membered heteroaryl. In another embodiment, a heteroaryl group is a 6-membered heteroaryl. In another embodiment, a heteroaryl group comprises a 5- to 6-membered heteroaryl group fused to a benzene ring. Unless otherwise indicated, a heteroaryl group is unsubstituted.

The term "heterocyclyl," as used herein, refers to a non-aromatic saturated monocyclic or multicyclic ring system comprising 3 to about 11 ring atoms, wherein from 1 to 4 of the ring atoms are independently O, S, or N, and the remainder of the ring atoms are carbon atoms. A heterocyclyl group can be joined via a ring carbon or ring nitrogen atom. In one embodiment, a heterocyclyl group is monocyclic and has from about 3 to about 7 ring atoms. In another embodiment, a heterocyclyl group is monocyclic has from about 4 to about 7 ring atoms. In another embodiment, a heterocyclyl group is bicyclic and has from about 7 to about 11 ring atoms. In still another embodiment, a heterocyclyl group is monocyclic and has 5 or 6 ring atoms. In one embodiment, a heterocyclyl group is monocyclic. In another embodiment, a heterocyclyl group is bicyclic. The term "heterocyclyl" also encompasses a heterocyclyl group, as defined above, which is fused to an aryl (e.g., benzene) or heteroaryl ring. The nitrogen or sulfur atom of the heterocyclyl can be optionally oxidized to the corresponding N-oxide, S-oxide or S,S-dioxide. Non-limiting examples of monocyclic heterocyclyl rings include oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, delta-lactam, delta-lactone, and the like.

In one embodiment, a heterocyclyl group is a 5- to 6-membered monocyclic heterocyclyl. In another embodiment, a heterocyclyl group is a 5-membered monocyclic heterocyclyl. In another embodiment, a heterocyclyl group is a 6-membered monocyclic heterocyclyl. The term "5- to 6-membered heterocyclyl" refers to a monocyclic heterocyclyl group having from 5 to 6 ring atoms. Unless otherwise indicated, a heterocyclyl group is unsubstituted.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. In specific embodiments of the ring system, from 1 to 4 of the ring atoms are independently O, S, or N, and the remainder of the ring atoms are carbon atoms. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. Unless otherwise indicated, a heterocyclenyl group is unsubstituted. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like.

The term "substituted" means that one or more hydrogens on the atoms of the designated are replaced with a selection from the indicated group, provided that the atoms' normal valencies under the existing circumstances are not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

When any substituent or variable occurs more than one time in any constituent or the compound of Formula (I), its definition on each occurrence is independent of its definition at every other occurrence, unless otherwise indicated.

The term "in purified form," as used herein, refers to the physical state of a compound after the compound is isolated from a synthetic process (e.g., from a reaction mixture), a natural source, or a combination thereof. The term "in purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, form part of the present invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention.

All stereoisomers (for example, geometric isomers, optical isomers and the like) of the present compounds (including those of the salts and solvates of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations.

The compounds of Formula (I) can form salts which are also within the scope of this invention. Reference to a compound of Formula (I) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula (I) contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Such acidic and basic salts used within the scope of the invention are pharmaceutically acceptable (i.e., non-toxic, physiologically acceptable) salts. Salts of the compounds of Formula (I) may be formed, for example, by reacting a compound of Formula (I) with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

The present invention further includes the compounds of Formula (I) in all their isolated forms. For example, the above-identified compounds are intended to encompass all forms of the compounds such as, any solvates, hydrates, stereoisomers, and tautomers thereof.

As used herein, the term "composition" is intended to encompass a product comprising the specified ingredients in the specified amounts, as well as any product which results, directly or indirectly, from combination of the specified ingredients in the specified amounts.

In the compounds of generic Formula (I), the atoms may exhibit their natural isotopic, abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula (I). For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula (I) can be prepared without undue experimentation by conventional techniques well known to those skilled in the art or by processes analogous to those described in the Schemes and Examples herein using appropriate isotopically-enriched reagents and/or intermediates.

Compounds of the Invention

The present invention provides compound of Formula (I) or pharmaceutically acceptable salts thereof, wherein $J^1$, $J^2$, $R^2$, $R^2$, $R^3$, $R^{22}$, $R^a$, $R^b$, $R^c$, $R^d$, X, Y, b, n, and q are as defined above for the compound of Formula (I). The compounds of Formulas (IA), (IB), and (IC) as are described in detail below, are embodiments of the compound of Formula (I). The structural formula illustrated below indicates the peripheral numbering of the ring system.

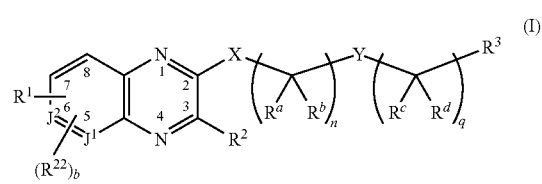

In specific embodiments of the compound of Formula (I), wherein $R^1$ is —C(O)—N($R^{6a}$)($R^{6b}$) or —S(O)$_2$—N($R^6$)($R^{6b}$); and $R^{6a}$ and $R^{6b}$ together with the N atom to which they are attached form $R^{6H}$, it is be understood that two $R^9$ moieties can be geminally substituted on a common ring carbon of $R^{6H}$ form $R^{YC}$, such that $R^1$ forms the group:

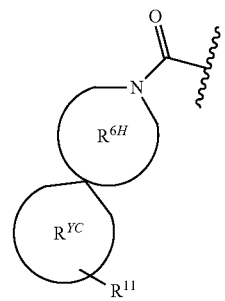

wherein $R^{6H}$ and $R^{YC}$ are as described above, and $R^{11}$ is either absent or present.

In certain embodiments of the compound of the Formula (I), wherein Y is

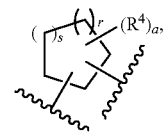

it is to be understood that the bonds joining the illustrated cycloalkyl ring to the chain can either be attached on different ring carbon atoms, e.g., on vicinal ring carbon atoms, or on the same ring carbon atom. For example, in some embodiments, the group

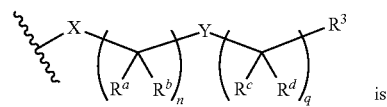

is

-continued

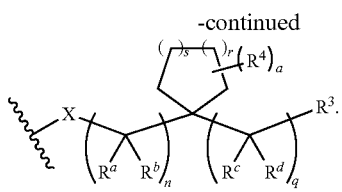

In embodiment no. 1 of the compound of Formula (I), $R^1$ is substituted on the 6 or 7 position of the illustrated bicyclic ring of Formula 1.

In embodiment no. 2, $R^1$ is substituted on the 7 or 8 position of the illustrated bicyclic ring of Formula (I), and $J^2$ is C(H), C($R^1$), or C($R^{22}$). In other words, $R^1$ is substituted on a ring carbon atom that is beta to the ring fusion of the illustrated bicyclic ring as shown below.

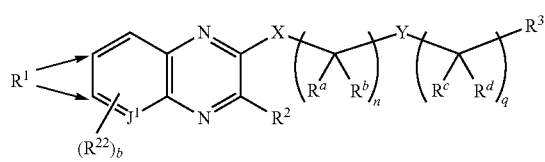

In embodiment no. 3, the compound has the formula (IA)

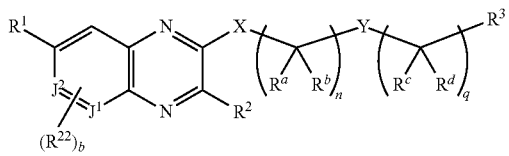

(IA)

wherein $J^1$ and $J^2$ are independently C(H) or C($R^{22}$), or N wherein the following provisos apply:
(i) no more than one of $J^1$ and $J^2$ is N, and
(ii) no more than one of $J^1$ and $J^2$ is C($R^{22}$).

In embodiment no. 4, $R^1$ is selected from the group consisting of:
(i) —C(O)—N($R^{6a}$)($R^{6B}$), and
(ii) —S(O)$_2$—N($R^{6a}$)($R^{6b}$).

In embodiment no. 5, $R^1$ is as described above in embodiment no. 4, and
(i) $R^{6a}$ is H and
$R^{6b}$ is -Q-$R^{AH}$ or -Q-$R^{HC}$; or
(ii) $R^{6a}$ and $R^{6b}$ together with the N atom to which they are attached form $R^{6H}$.

In embodiment no. 6, $R^1$ is —C(O)—N($R^{6a}$)($R^{6b}$)

In embodiment no. 7, $R^1$ is —C(O)—N($R^{6a}$)($R^{6b}$), wherein $R^{6a}$ is H, and $R^{6b}$ is -Q-$R^{AH}$ or -Q-$R^{HC}$. In specific instances of embodiment no. 7, $R^{6b}$ is -Q-$R^{HC}$, wherein Q is absent and $R^{HC}$ is

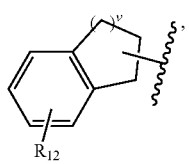

wherein v is 1 or 2, and $R^{12}$ is present or absent.

In embodiment no. 8, $R^1$ is —C(O)—N($R^{6a}$)($R^{6b}$), wherein $R^{6a}$ and $R^{6b}$ together with the N atom to which they are attached form $R^{6H}$. In specific instances of embodiment no. 8, $R^{6H}$ is

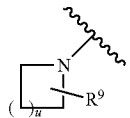

wherein u is 1, 2, or 3, and $R^9$ is present or absent.

In embodiment no. 9 of the compound of Formula (I), $R^1$ is —C(O)C($R^{7a}$)($R^{7b}$)($R^{7c}$). In specific instances of embodiment no. 9, $R^1$ is —C(O)C(H)($R^{7a}$)($R^{7b}$), wherein $R^{7a}$ and $R^{7b}$ together with the carbon atom to which they are attached form $R^{PC}$, wherein $R^{PC}$ is $C_3$-$C_7$ cycloalkyl. For example, in one instance of embodiment no. 9, $R^1$ is

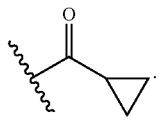 [SMILES: *C(=O)C1CC1]

In embodiment no. 10 of the compound of Formula (I), $R^1$ is —C(O)—O—C($R^{7a}$)($R^{7b}$)($R^{7c}$). For example, in one instance of embodiment no. 10, $R^1$ is —C(O)—O—CH$_3$.

In embodiment no. 11, Y is selected from the group consisting of
(i) a bond, (ii)

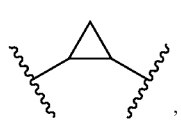

(iii)

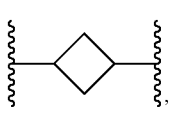

(iv)

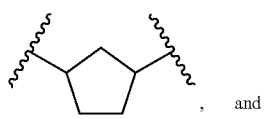

, and (v)

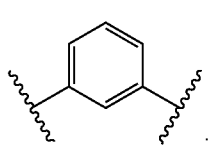

In embodiment no. 12, the group

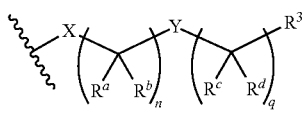

is selected from the group consisting of:

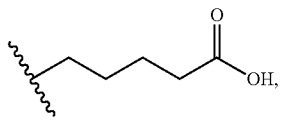

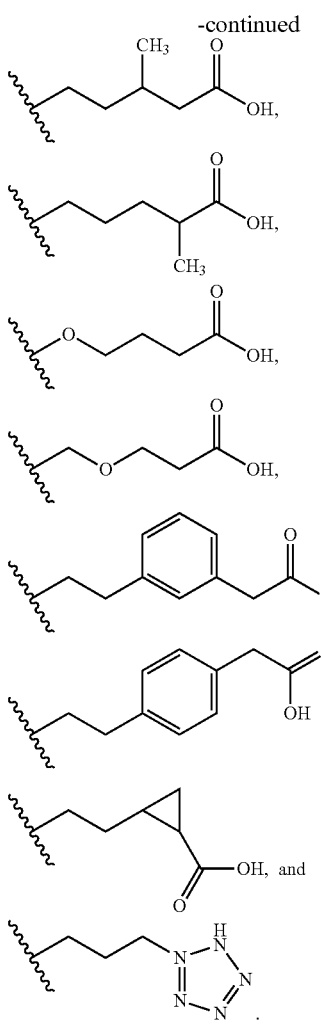

In embodiment no. 13, the compound has the Formula (IA) as described above in embodiment no. 3; and the group

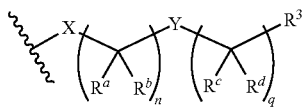

is as described above in embodiment no. 12.

In embodiment no. 14, $R^2$ is phenyl, pyridyl, or thienyl; wherein $R^2$ is unsubstituted or substituted by 1 to 2 $R^5$ groups independently selected from the group consisting of fluoro, chloro, trifluoromethyl, $C_1$-$C_3$ alkoxy, —CN, and —$OCF_3$;

In embodiment no. 15, b is 0, such that $R^{22}$ is absent.

In embodiment no. 16, the compound has the Formula (IA) as described above in embodiment no. 3, $R^1$ is as described above in embodiment no. 4, the group

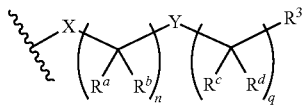

is as described above in embodiment no. 12, $R^2$ is as described in embodiment no. 14, and b is 0.

In embodiment no. 17, the compound has the Formula (IA) as described above in embodiment no. 3, $R^1$ is as described above in embodiment no. 5, the group

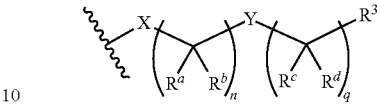

is as described above in embodiment no. 12, $R^2$ is as described in embodiment no. 14, and b is 0.

In embodiment no. 18, the compound of the Formula (I) has the Formula (IB)

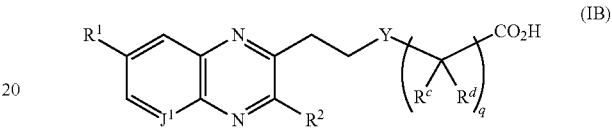

(IB)

wherein
$J^1$ is C(H) or N;
$R^1$ is —C(O)—N($R^{6a}$)($R^{6b}$);
  I) $R^{6a}$ is H and $R^{6b}$ is:
    a) -Q-$R^{AH}$, wherein $R^{AH}$ is phenyl or pyridyl,
      and wherein $R^{AH}$ is unsubstituted or substituted with 1 to 2 $R^8$ moieties independently selected from the group consisting of halo, $C_1$-$C_3$ alkyl, $C_1$-$C_3$ alkoxy, trifluoromethyl, trifluoromethoxy, and —CN;
    Q is selected from the group consisting of:
      (i) a bond;
      (ii)

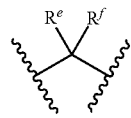

wherein $R^e$ and $R^f$ are independently H, $C_1$-$C_3$ alkyl, or trifluoromethyl;
      (iii) $C_2$-$C_4$ alkylene, wherein said $C_2$-$C_6$ alkylene is unsubstituted;
    b) -Q-$R^{HC}$, wherein $R^{HC}$ is
      (i) 5- to 6-membered heterocyclyl containing 1 heteroatom selected from the group consisting of N and O; or
      (ii) $C_5$-$C_7$ cycloalkyl, wherein said $C_5$-$C_7$ cycloalkyl is optionally fused to a benzene ring;
      and wherein $R^{HC}$ is unsubstituted or substituted with 1 to 2 $R^{12}$ moieties independently selected from the group consisting of $C_1$-$C_3$ alkyl, halo, and hydroxyl, or wherein when two $R^{12}$ moieties are geminally substituted on the same carbon atom, the two geminally substituted $R^{12}$ moieties, together with the carbon atom on which they are attached form —C(O)—;
  II) or $R^{6a}$ and $R^{6b}$ together with the N atom to which they are attached form $R^{6H}$, wherein
    $R^{6H}$ is independently selected from the group consisting of:
      a) a 4- to 6-membered heterocyclyl, optionally containing one additional nitrogen atom, wherein said 4- to 6-membered heterocyclyl is optionally fused to phenyl; and b) a 5- to 6-membered heterocyclenyl, optionally containing one additional nitrogen atom, wherein said 4- to 6-membered heterocyclyl is optionally fused to phenyl;
  wherein $R^{6H}$ is unsubstituted or substituted by 1 to 2 $R^9$ moieties wherein each $R^9$ moiety is independently $C_1$-$C_3$ alkyl, F, Cl, —CN, or
  $R^9$ is —Z—$R^{CY}$ wherein
    Z is a bond or —$CH_2$—;
    $R^{CY}$ is selected from the group consisting of:
      (i) phenyl;
      (ii) 5- to 6-membered heteroaryl containing 1 to 3 N atoms; or
      (iii) 5- to 6-membered heterocyclyl containing 2 N atoms, wherein said 5- to 6-membered heterocyclyl of $R^{CY}$ is fused to phenyl;
    wherein $R^{CY}$ is unsubstituted or substituted by 1 to 2 $R^{10}$ moieties;
    each $R^{10}$ moiety is independently $C_1$-$C_3$ alkyl, halo, $C_1$-$C_3$ alkoxy, —($C_1$-$C_3$ alkylene)-($C_1$-$C_3$ alkoxy), or —CN, or, wherein two $R^{10}$ moieties are geminally substituted on a common carbon atom, together with the carbon atom on which they are substituted, form —C(O)—;
  or, optionally, where two $R^9$ moieties are geminally substituted on a common ring carbon of $R^{6H}$, the two $R^9$ moieties, together with the ring carbon on which they are substituted, form $R^{YC}$, wherein $R^{YC}$ is
    (i) a 5- to 6-membered cycloalkyl, wherein said or 5- to 6-membered cycloalkyl is fused to phenyl; or
    (ii) a 4- to 6-membered heterocyclyl containing 1 to 2 N atoms or 1 O atom, wherein said or 4- to 6-membered heterocyclyl is optionally fused to phenyl;
    wherein $R^{YC}$ is unsubstituted or substituted by 1 to 3 $R^{11}$ moieties;
    each $R^{11}$ moiety is independently $C_1$-$C_3$ alkyl, —C(O)—($C_1$-$C_3$ alkyl), or phenyl, or, wherein two $R^{11}$ moieties are geminally substituted on a common carbon atom, together with the carbon atom on which they are substituted, form —C(O)—;
Y is selected from the group consisting of
  (i) a bond, (ii)

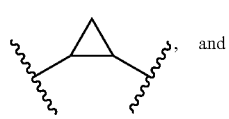
and

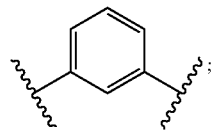

$R^c$ is H or methyl;
$R^d$ is H;
$R^2$ is phenyl, pyridyl, or thienyl;
  wherein $R^2$ is unsubstituted or substituted by 1 to 2 $R^5$ groups independently selected from the group consisting of fluoro, chloro, trifluoromethyl, $C_1$-$C_3$ alkoxy, —CN, and —$OCF_3$;
q is 0, 1, or 2.

In embodiment no. 19, $J^1$ is CH, and the structural formula and the remaining variables are as described above in embodiment no. 18.

In embodiment no. 20, $R^2$ is unsubstituted or substituted phenyl, and the structural formula and the remaining variables are as described above in embodiment no. 18.

In embodiment no. 21, the group

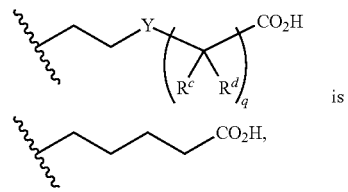
is and the structural formula and the remaining variables are as described above in embodiment no. 18.

In embodiment no. 22, the compound of the Formula (I) has the Formula (IB)
$J^1$ is C(H);
$R^1$ is —C(O)—N($R^{6a}$)($R^{6b}$);
  I) $R^{6a}$ is H and $R^{6b}$ is:
    a) -Q-$R^{AH}$, wherein $R^{AH}$ is phenyl,
      and wherein $R^{AH}$ is unsubstituted or substituted with 1 $R^8$ moiety selected from the group consisting of fluoro and chloro;
      Q is selected from the group consisting of:
        (i) a bond;
        (ii)

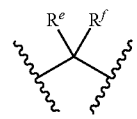

wherein $R^e$ is H, and $R^f$ is H or methyl;
    b) -Q-$R^{HC}$, wherein $R^{HC}$ is $C_5$-$C_6$ cycloalkyl, wherein said $C_5$-$C_6$ cycloalkyl is fused to a benzene ring;
      and wherein $R^{HC}$ is unsubstituted or substituted with 1 to 2 $R^{12}$ moieties independently selected from the group consisting of fluoro and chloro;
  II) or $R^{6a}$ and $R^{6b}$ together with the N atom to which they are attached form $R^{6H}$, wherein
    $R^{6H}$ is azetidinyl, pyrrolidinyl, piperidinyl, or piperazinyl:
      wherein $R^{6H}$ is substituted by —Z—$R^{CY}$;
      wherein
        Z is a bond;
        $R^{CY}$ is unsubstituted phenyl or phenyl substituted by 1 to 2 $R^{10}$ moieties selected from the group consisting of fluoro and chloro; the group

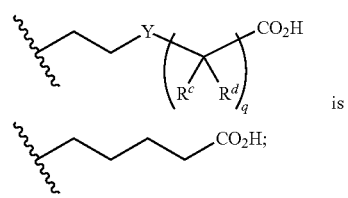

$R^2$ is unsubstituted phenyl or phenyl substituted by 1 to 2 fluoro or chloro.

In embodiment no. 23, the compound of the Formula (I) has the Formula (IC)

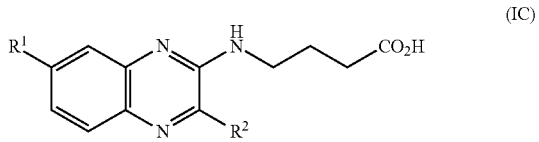

wherein
$R^{6a}$ is —C(O)—N($R^{6a}$)($R^{6b}$);
I) $R^{6a}$ is H and $R^{6b}$ is:
a) -Q-$R^{AH}$, wherein $R^{AH}$ is phenyl,
and wherein $R^{AH}$ is unsubstituted or substituted with 1 $R^8$ moiety selected from the group consisting of halo and —CN;
Q is selected from the group consisting of
(i) a bond;
(ii)

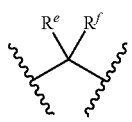

wherein $R^e$ is H, and $R^f$ is H or methyl;
b) -Q-$R^{HC}$, wherein $R^{HC}$ is $C_5$-$C_6$ cycloalkyl, wherein said $C_5$-$C_6$ cycloalkyl is fused to a benzene ring;
and wherein $R^{HC}$ is unsubstituted or substituted with 1 to 2 $R^{12}$ moieties independently selected from the group consisting of halo and —CN;
II) or $R^{6a}$ and $R^{6b}$ together with the N atom to which they are attached form $R^{6H}$, wherein
$R^{6H}$ is azetidinyl, pyrrolidinyl, piperidinyl, or piperazinyl; wherein $R^{6H}$ is substituted with —Z—$R^{CY}$ wherein
Z is a bond; and
$R^{CY}$ is unsubstituted phenyl or phenyl substituted by 1 to 2 $R^{10}$ moieties selected from the group consisting of halo and —CN;
$R^{6H}$ is optionally substituted by 1 to 2 $R^9$ moieties wherein each $R^9$ moiety is independently $C_1$-$C_3$ alkyl, halo or —CN, and
$R^2$ is unsubstituted or substituted by 1 to 2 $R^5$ groups independently selected from the group consisting of fluoro, chloro, $C_1$-$C_3$ alkyl, trifluoromethyl, $C_1$-$C_3$ alkoxy, —CN, and —OCF$_3$.
In embodiment no. 24, the compound of the Formula (I) has the Formula (IC) wherein
$R^1$ is —C(O)—N($R^{6a}$)($R^{6b}$);
I) $R^{6a}$ is H and $R^{6b}$ is:
a) -Q-$R^{AH}$, wherein $R^{AH}$ is phenyl,
and wherein $R^{AH}$ is unsubstituted or substituted with 1 $R^8$ moiety selected from the group consisting of fluoro and —CN;
b) -Q-$R^{HC}$, wherein $R^{HC}$ is $C_5$-$C_6$ cycloalkyl, wherein said $C_5$-$C_6$ cycloalkyl is fused to a benzene ring;
and wherein $R^{HC}$ is unsubstituted or substituted with 1 to 2 $R^{12}$ moieties independently selected from the group consisting of halo and —CN;
II) or $R^{6a}$ and $R^{6b}$ together with the N atom to which they are attached form $R^{6H}$, wherein
$R^{6H}$ is pyrrolidinyl, piperidinyl, or piperazinyl; wherein $R^{6H}$ is substituted with —Z—$R^{CY}$ wherein
$R^{CY}$ is unsubstituted phenyl or phenyl substituted by 1 to 2 $R^{10}$ moieties selected from the group consisting of halo and —CN;
$R^{6H}$ is optionally substituted by 1 to 2 $R^9$ moieties wherein each $R^9$ moiety is independently $C_1$-$C_3$ alkyl, halo or —CN,
$R^2$ is unsubstituted phenyl; and
Q and Z are as described above in embodiment no. 23.
In embodiment no. 25, $R^{6a}$ and $R^{6b}$ together with the N atom to which they are attached form $R^{6H}$, wherein $R^{6H}$ is piperazinyl, and the structural formula and the remaining variables are as described above in embodiment no. 24.

The invention also provides any one of the compounds specified in Tables A and B in the Examples section below, which tables include compounds 3, 3T, 3U, 3V, 3W, 3X, 3Y, 3Z, 3AA, 3AB, 3AC, 3AD, 3AE, 3AF, 3AG, 4, 4D, 4E, 4F, 4G, 5, 5G, 5N, 5o, 5P, 5Q, 5R, 5S, 6, 6F, 6G, 7, 7C, 8, 8G, 9, 10, 10C, 10D, 10E, 10F, 11, 11D, 11E, 11F, 12, 13, 14, 14C, 14D, 14E, 14F, 14G, 14H, 15A, 15B, 15C, 15D, 15E, 15F, 15G, 15H, 15i, 15J, 15K, 15L, 15M, 15N, 15o, 15P, 15Q, 15R, 15S, 15T, 15U, 15V, 15X, 15Y, 15Z, 15AA, 15AB, 15AC, 15AD, 15AE, 15AF, 15AG, 15AH, 15Ai, 15AJ, 15AK, 15AL, 15AM, 15AN, 15Ao, 15AP, 15AQ, 15AR, 15AS, 15AT, 15AU, 15AV, 15AW, 15AX, 15AY, 15AZ, 15BA, 15BB, 15BC, 15BD, 15BE, 15BF, 15BG, 15BH, 15Bi, 15BJ, 15BK, 15BL, 15BM, 15BN, 15Bo, 15BQ, 15BR, 15BS, 15BT, 15BU, 16, 16F, 16G, 16H, 16i, 16J, 16K, 16L, 16M, 16N, 16o, 16P, 16Q, 16R, 16S, 16T, 16U, 16V, 16W, 16X, 16Y, 16Z, 16AA, 16AB, 16AC, 16AD, 16AE, 16AF, 16AG, 16AH, 16Ai, 16AJ, 16AK, 16AL, 16AM, 16AN, 16Ao, 16AP, 16AQ, 16AR, 16AS, 17, 17D, 17E, 17F, 17G, 17H, 17i, 17J, 17K, 17L, 17M, 17N, 17o, 17P, 17Q, 17R, 17S, 17T, 17U, 17V, 17X, 17Y, 17Z, 18, 18D, 18E, 18F, 18G, 18H, 19, 19F, 19G, 19H, 19i, 19J, 19K, 20, 20F, 20G, 20H, 21, 22, 22D, 23, 24, 24H, 24i, 25, 26, 26E, 26F, 26G, 26H, 26i, 26J, 26K, 26L, 26M, 26N, 26o, 26P, 26Q, 26R, 26S, 26T, 26U, 26V, 26W, 26X, 26Y, 26Z, 26AA, 26AB, 28, 29, 30, 30E, 31, 31C, 32, 33, 34, 35, 36, 37, 38, 39, 40, 41, 42, 44, 44D, 44E, 44F, 44G, 44H, 44i, 44J, 44K, 44L, 44M, 44N, and 100-728, or a pharmaceutically acceptable salt thereof. The structural formulas and names of these compounds are as set forth in the Examples section below.

In another embodiment, the invention also provides any one of the compounds specified in Table A in the Examples section below, which table includes compounds 3, 3T, 3U, 3V, 3W, 3X, 3Y, 3Z, 3AA, 3AB, 3AC, 3AD, 3AE, 3AF, 3AG, 4, 4D, 4E, 4F, 4G, 5, 5G, 5N, 5o, 5P, 5Q, 5R, 5S, 6, 6F, 6G, 7, 7C, 8, 8G, 9, 10, 10C, 10D, 10E, 10F, 11, 11D, 11E, 11F, 12, 13, 14, 14C, 14D, 14E, 14F, 14G, 14H, 15A, 15B, 15C, 15D, 15E, 15F, 15G, 15H, 15i, 15J, 15K, 15L, 15M, 15N, 15o, 15P, 15Q, 15R, 15S, 15T, 15U, 15V, 15X, 15Y, 15Z, 15AA, 15AB, 15AC, 15AD, 15AE, 15AF, 15AG, 15AH, 15Ai, 15AJ, 15AK, 15AL, 15AM, 15AN, 15Ao, 15AP, 15AQ, 15AR, 15AS, 15AT, 15AU, 15AV, 15AW, 15AX, 15AY, 15AZ, 15BA, 15BB, 15BC, 15BD, 15BE, 15BF, 15BG, 15BH, 15Bi, 15BJ, 15BK, 15BL, 15BM, 15BN, 15Bo, 15BQ, 15BR, 15BS, 15BT, 15BU, 16, 16F, 16G, 16H, 16i, 16J, 16K, 16L, 16M, 16N, 16o, 16P, 16Q, 16R, 16S, 16T, 16U, 16V, 16W, 16X, 16Y, 16Z, 16AA, 16AB, 16AC, 16AD, 16AE, 16AF, 16AG, 16AH, 16Ai, 16AJ, 16AK, 16AL, 16AM, 16AN, 16Ao, 16AP, 16AQ, 16AR, 16AS, 17, 17D, 17E, 17F, 17G, 17H, 17i, 17J, 17K, 17L, 17M, 17N, 17o, 17P, 17Q, 17R, 17S, 17T, 17U, 17V, 17W, 17X, 17Y, 17Z, 18, 18D, 18E, 18F, 18G, 18H, 19, 19F, 19G, 19H, 19i, 19J, 19K, 20, 20F, 20G, 20H, 21, 22, 22D, 23, 24, 24H, 24i, 25, 26, 26E, 26F, 26G, 26H, 26i, 26J, 26K, 26L, 26M, 26N, 26o, 26P, 26Q, 26R, 26S, 26T, 26U, 26V, 26W, 26X, 26Y, 26Z, 26AA, 26AB, 28, 29, 30, 30E, 31, 31C, and 100-253, or a pharmaceutically acceptable salt thereof.

In another specific embodiment, the invention provides any one of the compounds selected from the group consisting of 14, 14D, 14G, 15A, 15B, 15C, 15D, 15E, 15K, 15N, 15P, 15Q, 15R, 15S, 15T, 15X, 15Z, 15AB, 15AC, 15AD, 15AF, 15Ai, 15AJ, 15AK, 15AL, 15AN, 15Ao, 15AP, 15AR, 15AU, 15AV, 15AW, 15AX, 15AY, 15AZ, 15BA, 15BB, 15BC, 15BD, 15BF, 15BH, 15BK, 15BM, 15BN, 15BQ, 15BR, 15BS, 15BT, 15BU, 16, 16F, 16H, 16i, 16J, 16K, 16L, 16N, 16P, 16R, 16S, 16T, 16U, 16V, 16Y, 16AB, 16AC, 16AE, 16AG, 16AH, 16AK, 16AQ, 17, 17D, 17M, 17S, 18, 19, 19G, 20, 24i, 26E, 26J, 26K, 26L, 26N, 26o, 26P, 26S, 26Y, 39, 40, 41, 44H, 44i, 100, 102-107, 109-113, 117, 119-132, 135, 136, 142, 143, 145, 147, 148, 162, 163, 164, 166, 167, 172, 174, 217, 231, 251, 254, 255, 256, 375, 412, 426, 457, 491, 507, 512, 585, and 628 or a pharmaceutically acceptable salt thereof.

In another specific embodiment, the invention provides any one of the compounds selected from the group consisting of 14, 14D, 14G, 15A, 15B, 15C, 15D, 15E, 15K, 15N, 15P, 15Q, 15R, 15S, 15T, 15X, 15Z, 15AB, 15AC, 15AD, 15AF, 15Ai, 15AJ, 15AK, 15AL, 15AN, 15Ao, 15AP, 15AR, 15AU, 15AV, 15AW, 15AX, 15AY, 15AZ, 15BA, 15BB, 15BC, 15BD, 15BF, 15BH, 15BK, 15BM, 15BN, 15BQ, 15BR, 15BS, 15BT, 15BU, 16, 16F, 16H, 16i, 16J, 16K, 16L, 16N, 16P, 16R, 16S, 16T, 16U, 16V, 16Y, 16AB, 16AC, 16AE, 16AG, 16AH, 16AK, 16AQ, 17, 17D, 17M, 17S, 18, 19, 19G, 20, 24i, 26E, 26J, 26K, 26L, 26N, 26o, 26P, 26S, 26Y, 100, 102-107, 109-113, 117, 119-132, 135, 136, 142, 143, 145, 147, 148, 162, 163, 164, 166, 167, 172, 174, 217, 231, 251, 254, and 255, or a pharmaceutically acceptable salt thereof.

The invention also provides a compound of Formula (I) or a pharmaceutically acceptable salt thereof in purified form.

Compositions and Administration

This invention is also directed to pharmaceutical compositions which comprise a compound of Formula (I), or a pharmaceutically acceptable salt of said compound and a pharmaceutically acceptable carrier.

A preferred dosage is about 0.001 to 100 mg/kg of body weight/day of the compound of Formula (I). An especially preferred dosage is about 0.01 to 10 mg/kg of body weight/day of a compound of Formula (I), or a pharmaceutically acceptable salt of said compound.

The term "pharmaceutical composition" is also intended to encompass both the bulk composition and individual dosage units comprised of more than one (e.g., two) pharmaceutically active agents such as, for example, a compound of the present invention and an additional therapeutic agent selected from the lists of the additional agents described herein below, along with any pharmaceutically inactive excipients. The bulk composition and each individual dosage unit can contain fixed amounts of the aforesaid "more than one pharmaceutically active agents". The bulk composition is material that has not yet been formed into individual dosage units. An illustrative dosage unit is an oral dosage unit such as a tablet, a pill and the like. Similarly, the herein-described method of treating a patient by administering a pharmaceutical composition of the present invention is also intended to encompass the administration of the afore-said bulk composition and individual dosage units.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, $18^{th}$ Edition, (1990), Mack Publishing Co., Easton, Pa.

Liquid form preparations include solutions, suspensions and emulsions. Examples of materials useful for forming such liquid form preparations include water or water-propylene glycol solutions for parenteral injection, or sweeteners and opacifiers for oral solutions, suspensions and emulsions. Liquid form preparations may also include solutions or suspensions for intranasal administration.

Aerosol preparations suitable for inhalation may include solutions and solids in powder form, which may be in combination with a pharmaceutically acceptable carrier, such as an inert compressed gas, e.g., nitrogen.

Also included are solid form preparations that are intended to be converted, shortly before use, to liquid form preparations for either oral or parenteral administration. Such liquid forms include solutions, suspensions and emulsions.

The compounds of the invention can also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 0.001 mg to about 100 mg per kg body weight of a mammal, preferably from about 0.01 mg to about 10 mg per kg. The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The compositions of the invention can further comprise one or more additional therapeutic agents, as discussed in further detail below. Accordingly, in one embodiment, the present invention provides compositions comprising: (i) a compound of Formula (I) or a pharmaceutically acceptable salt thereof; (ii) one or more additional therapeutic agents, that are not compounds of Formula (I); and (iii) a pharmaceutically acceptable carrier, wherein the amounts in the composition are together effective to treat one of the disease or conditions discussed above.

Uses of the Compounds

The compounds of Formula (I) bind to $CRTH_2$ and, therefore, are useful in characterizing tissues containing CRTH$_2$, and in identifying further compounds which bind to CRTH$_2$. The general value of the compounds of the invention in binding the CRTH$_2$ receptor can be determined, for example, using the radioligand binding assay described below in the Examples section.

The compounds of Formula (I) can also be useful as modulators of CRTH$_2$ receptor function. In some embodiments, compounds of Formula (I) are antagonists of the CRTH$_2$ receptor. The general value of the compounds of the invention in antagonizing CRTH$_2$ receptor function can be determined, for example, using the chemiluminescent-based cAMP assay, the β-Arrestin assay, or the eosinophil shape change assay described below in the Examples section.

While not being bound by any specific theory, Applicants believe that the compounds of Formula (I) are useful in treating the symptoms of diseases or conditions associated with uncontrolled or inappropriate stimulation of CRTH$_2$ function because of their ability to antagonize the CRTH$_2$ receptor. Accordingly, in one embodiment, the invention provides a method for treating a disease or conditions associated with uncontrolled or inappropriate stimulation of CRTH$_2$ function, comprising administering a therapeutically effective amount of a compound of Formula (I) to a patient in need of such treatment. In certain embodiments, the compound of Formula (I) used in the method is selected from one of the representative compounds listed in Table A as set forth in the Examples section.

Diseases or conditions associated with uncontrolled or inappropriate stimulation of CRTH$_2$ function include (but not limited to) asthma, congestion, allergic rhinitis, atopic dermatitis, chronic obstructive pulmonary disease ("COPD"), dermatitis, inflammatory bowel disease, rheumatoid arthritis, allergic nephritis, conjunctivitis, bronchial asthma, fold allergy, systemic mast cell disorder, anaphylactic shock, urticaria, eczema, itching, inflammation, ischemia-reperfusion injury, cerebrovascular disorders, pleuritis, ulcerative colitis, eosinophil-related diseases, such as Churg-Strauss syndrome and sinusitis, and basophile-related diseases, such as basophilic leukemia and basophilic leukocytosis, in humans and other mammals. Examples of cerebrovascular disorders include stroke.

In certain embodiments, the present invention provides a method for treating asthma, congestion, allergic rhinitis or COPD which comprises administering a therapeutically effective dose of a compound of Formula (I) or a pharmaceutically acceptable salt thereof to a patient in need of such treatment. In a specific embodiment, the disease or condition being treated is asthma. In another embodiment, the disease or condition being treated is COPD.

In addition, compounds of the Formula (I) which act as CRTH$_2$ receptor antagonists can inhibit prostanoid-induced smooth muscle contraction by antagonizing contractile prostanoids or mimicking relaxing prostanoids and hence may be used in the treatment of dysmenorrhea, premature labor and eosinophil related disorders.

In another embodiment, the present invention provides a compound of Formula (I) or a pharmaceutically acceptable salt thereof for use in the manufacture of a medicament for treating a disease or condition selected from the group consisting of asthma, congestion, allergic rhinitis, atopic dermatitis, COPD, dermatitis, inflammatory bowel disease, rheumatoid arthritis, allergic nephritis, conjunctivitis, bronchial asthma, food allergy, systemic mast cell disorder, anaphylactic shock, urticaria, eczema, itching, inflammation, ischemia-reperfusion injury, cerebrovascular disorders, pleuritis, ulcerative colitis, eosinophil-related diseases, such as Churg-Strauss syndrome and sinusitis, and basophile-related diseases, such as basophilic leukemia and basophilic leukocytosis. In certain embodiments of the use, the compound of Formula (I) is selected from one of the representative compounds listed in Table A as set forth in the Examples section.

In another embodiment, the present invention provides a compound of Formula (I) or a pharmaceutically acceptable salt thereof for use in treating a disease or condition from the group consisting of asthma, congestion, allergic rhinitis, atopic dermatitis, COPD, dermatitis, inflammatory bowel disease, rheumatoid arthritis, allergic nephritis, conjunctivitis, bronchial asthma, food allergy, systemic mast cell disorder, anaphylactic shock, urticaria, eczema, itching, inflammation, ischemia-reperfusion injury, cerebrovascular disorders, pleuritis, ulcerative colitis, eosinophil-related diseases, such as Churg-Strauss syndrome and sinusitis, and basophile-related diseases, such as basophilic leukemia and basophilic leukocytosis. In certain embodiments of the use, the compound of Formula (I) is selected from one of the representative compounds listed in Table A as set forth in the Examples section.

In specific embodiments of the methods and uses described above, the compound used in the method or use described above is selected one of the compounds 3T, 3U, 3V, 3W, 3X, 3Y, 3AA, 3AB, 3AC, 3AD, 3AE, 3AF, 4, 4D, 4E, 4F, 5N, 5P, 5R, 5S, 6F, 7C, 8, 8G, 10, 10C, 10D, 10F, 11, 11D, 11E, 11F, 12, 14, 14C, 14D, 14E, 14F, 14G, 14H, 15A, 15B, 15C, 15D, 15E, 15F, 15H, 15i, 15J, 15K, 15L, 15M, 15N, 15o, 15P, 15Q, 15R, 15S, 15T, 15X, 15Z, 15AA, 15AB, 15AC, 15AD, 15AE, 15AF, 15AG, 15AH, 15Ai, 15AJ, 15AK, 15AL, 15AM, 15AN, 15AP, 15AR, 15AU, 15AV, 15AW, 15AX, 15AY, 15AZ, 15BA, 15BB, 15BC, 15BD, 15BE, 15BF, 15BH, 15BJ, 15BK, 15BL, 15BM, 15BN, 15Bo, 15BQ, 15BR, 15BS, 15BT, 15BU, 16, 16F, 16H, 16i, 16J, 16K, 16L, 16N, 16P, 16S, 16T, 16U, 16V, 16W, 16X, 16Y, 16AB, 16AC, 16AD, 16AE, 16AG, 16AH, 16AJ, 16AK, 16AQ, 16AR, 17, 17D, 17E, 17G, 17M, 17S, 17Y, 17Z, 18, 19, 19F, 19G, 19J, 20, 20F, 20G, 20H, 22, 22D, 23, 24H, 24i, 25, 26E, 26F, 26G, 26H, 26i, 26J, 26K, 26L, 26M, 26N, 26o, 26P, 26Q, 26R, 26S, 26T, 26U, 26V, 26W, 26X, 26Y, 26AA, 26AB, 28, 29, 30, 31, 31C, 100, 102, 104-128, 130-136, 143, 145, 148, 155, 156, 160, 162-164, 166, 167, 169, 170, 172, 174-176, 180, 182-191, 198, 199, 204-212, 215, 217-222, 224-229, 231, 232, 234-243, 245-249, and 251-255 or a pharmaceutically acceptable salt thereof.

Combination Therapy

The compounds of Formula (I) or their pharmaceutically acceptable salts may be used in combination, either in a single formulation or co-administered as separate formulations with at least one additional therapeutic agent to treat or prevent the diseases and conditions described herein. These additional therapeutic agents include, but are not limited to: (1) a DP receptor antagonist, such as S-5751 and laropiprant; (2) a corticosteroid, such as triamcinolone acetonide, budesonide, beclomethasone, fluticasone and mometasone; (3) a β2-adrenergic agonist, such as salmeterol, formoterol, arformoterol, terbutaline, metaproterenol, albuterol and the like; (4) a leukotriene modifier, including a leukotriene receptor antagonist, such as montelukast, zafirlukast, pranlukast, or a lipooxygenase inhibitor including 5-lipooxygenase inhibitors and FLAP (5-lipooxygenase activating protein) inhibitors, such as zileuton; (5) an antihistamine such as brompheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (6) a decongestant, including phenylephrine, phenylpropanolamine, pseudophedrine, oxymetazoline, ephinephrine, naphazoline, xylometazoline, propylhexedrine, or levodesoxyephedrine; (7) an antiitussive, including codeine, hydrocodone, caramiphen, carbetapentane, or dextramethorphan; (8) another prostaglandin ligand, including prostaglandin F agonist such as latanoprost; misoprostol, enprostil, rioprostil, ornoprostol or rosaprostol; (9) a diuretic; (10) non-steroidal antiinflammatory agents (NSAIDs), such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenarnic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (11) cyclooxygenase-2 (COX-2) inhibitors, such as celecoxib and rofecoxib; (12) inhibitors of phosphodiesterase type IV (PDE-IV) e.g., Ariflo, roflumilast; (13) antagonists of the chemokine receptors, especially CCR-1, CCR-2, and CCR-3; (14) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (15) anti-diabetic agents such as insulin, sulfonylureas, biguanides (metformin), α-glucosidase inhibitors (acarbose) and glitazones (troglitazone, pioglitazone, englitazone, rosiglitazone and the like); (16) preparations of interferon beta (interferon beta-1a, interferon beta-1b); (17) anticholinergic agents, such as muscarinic antagonists (ipratropium bromide and tiotropium bromide), as well as selective muscarinic M3 antagonists; (18) steroids such as beclomethasone, methylprednisolone, betamethasone, prednisone, dexamethasone, and hydrocortisone; (19) triptans commonly used for the treatment of migraine such as sumitriptan and rizatriptan; (20) alendronate and other treatments for osteoporosis; (21) other compounds such as 5-aminosalicylic acid and prodrugs thereof, antimetabolites such as azathioprine and 6-mercaptopurine, cytotoxic cancer chemotherapeutic agents, bradykinin (BK2) antagonists such as FK-3657, TP receptor antagonists such as seratrodast, neurokinin antagonists (NK1/NK2), VLA-4 antagonists, such as those described in U.S. Pat. No. 5,510,332, WO97/03094, WO97/02289, WO96/40781, WO96/22966, WO96/20216, WO96/01644, WO96/06108, WO95/15973 and WO96/31206. In addition, the invention encompasses a method of treating prostaglandin D2 mediated diseases comprising: administration to a patient in need of such treatment a non-toxic therapeutically effective amount of a compound of Formula (I), optionally co-administered with one or more of such ingredients as listed immediately above.

When administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like.

In one embodiment, the compound of Formula (I) is administered during a time when the additional therapeutic agent(s) exert their prophylactic or therapeutic effect, or vice versa.

In another embodiment, the compound of Formula (I) and the additional therapeutic agent(s) are administered in doses commonly employed when such agents are used as monotherapy for treating the disorder.

In another embodiment, the compound of Formula (I) and the additional therapeutic agent(s) are administered in doses lower than the doses commonly employed when such agents are used as monotherapy for treating the disorder.

In one embodiment, the compound of Formula (I) and the additional therapeutic agent(s) are present in the same composition, which is suitable for oral administration.

The compound of Formula (I) and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

The doses and dosage regimen of the additional therapeutic agent(s) used in the combination therapies of the present invention for the treatment or prevention of a disease or disorder can be determined by the attending clinician, taking into consideration the approved doses and dosage regimen in the package insert; the age, sex and general health of the patient; and the type and severity of the viral infection or related disease or disorder.

Another aspect of this invention is a kit comprising a therapeutically effective amount of the compound of Formula (I) or a pharmaceutically acceptable salt of said compound, optionally at least one additional therapeutic agent listed above and a pharmaceutically acceptable carrier, vehicle or diluent.

Methods of Preparing the Compounds of Formula (I)

In general, the compounds in the invention may be produced by a variety of processes known to those skilled in the art and by know, processes analogous thereto. The invention disclosed herein is exemplified by the following preparations and examples which should not be construed to limit the scope of the disclosure. Alternative mechanistic pathways and analogous structures will be apparent to those skilled in the art. The practitioner is not limited to these methods.

One skilled in the art will recognize that one route will be optimized depending on the choice of appendage substituents. Additionally, one skilled in the art will recognize that in some cases the order of steps has to be controlled to avoid functional group incompatability.

The prepared compounds may be analyzed for their composition and purity as well as characterized by standard analytical techniques such as, for example, elemental analysis, NMR, mass spectroscopy and IR spectra.

One skilled in the art will recognize that reagents and solvents actually used may be selected from several reagents and solvents well known in the art to be effective equivalents. Hence, when a specific solvent or reagent is mentioned, it is meant to be an illustrative example of the conditions desirable for that particular reaction scheme or for the preparation described below.

Where NMR data are presented, $^1$H spectra were obtained on either a Varian VXR-400 (400 MHz, 1H), Varian Gemini-300 (300 MHz), Varian Mercury VX-400 (400 MHz), Bruker-Biospin AV-500 (500 MHz) or Bruker Avarice DRX-500 (500 MHz), and chemical shifts are reported as ppm with number of protons and multiplicities indicated parenthetically. Where LC/MS data are presented, analyses was performed using a 1200 series Agilent 6140 Quadrupole LCMS with a 1.8 µM Zorbax SB-C18 column (10-95% of MeCN—H$_2$O with 0.1% TFA over 2.7 min, 1 mL/min) or with an Applied Biosystems API-150 mass spectrometer and Gemini C18 column (50×4.6 mm, 10-95% CH$_3$CN—H$_2$O with 0.05% TFA over 5 min, 1 mL/min).

The following solvents and reagents may be referred to by their abbreviations in parenthesis:

Me=methyl; Et=ethyl; Pr=propyl; Bu=butyl; t-Bu=tert-butyl; Ph=phenyl, and Ac=acetyl
  µl=microliters
  Acac=acetylacetone
  AcOEt or EtOAc=ethyl acetate
  AcOH or HOAc=acetic acid
  ACN acetonitrile
  aq=aqueous
  Ar=aryl
  atm=atmosphere
  9-BBN=9-borabicyclo[3.3.1]nonane
  Bn=benzyl
  Boc or BOC=tert-butoxycarbonyl
  Bz=benzoyl
  Boc=tert-butoxycarbonyl
  BINAP=2,2'-bis(diphenylphosphino)-1,1'-bisnaphthyl
  cat=catalyst or catalytic
  Cbz=benyzloxycarbonyl
  DAST=diethylaminosulfur trifluoride
  DBU=1,8-Diaza-7-bicyclo[5.4.0]undecene
  DCM or CH$_2$Cl$_2$: dichloromethane:
  DMAP=4-Dimethylaminopyridine
  DIBAL=diisobutylaluminum hydride
  DIPEA or Hünig's Base=N,N-diisopropylethylamine
  DME=1,2-dimethoxyethane
  DMF=dimethylformamide
  DMS=dimethylsulfide
  DMSO=dimethyl sulfoxide
  Dppf=1,1'-bis(diphenylphosphino)ferrocene
  EDCI or DEC=1-(3-dimethylaminopropyl)-3-ethylcarbodiimide
  g=grams
  h=hour
  HetAr=heteroaryl
  HMDS=1,1,1,3,3,3-hexamethyldisilazane
  HATU=N,N,N',N'-tetramethyl-O-(7-azabenzotriazol-1-yl)uranium
    hexafluorophosphate
  HOBt=1-hydroxybenzotriazole
  Im=imidazole
  LAH=lithium aluminum hydride
  LDA=lithium diisopropylamide
  LCMS=liquid chromatography mass spectrometry
  LG=leaving group
  min=minute
  mg=milligrams
  mL=milliliters
  mmol=millimoles
  MeOH: methanol
  MS=mass spectrometry
  NBS=N-bromosuccimide
  NMR=nuclear magnetic resonance spectroscopy
  PG=protecting group
  Pyr=pyridine
  rac or (±)=racemic mixture or enantiomers
  RT or rt=room temperature (ambient, about 25° C.)
  sat=saturated
  SM=starting material
  TBSCl=t-butyldimethylsilyl chloride
  TBS=t-butyldimethyl silyl
  TEA=triethylamine (Et$_3$N)
  TFA=trifluoroacetic acid
  TFAA=trifluoroacetic anhydride
  THF=tetrahydrofuran
  TLC=thin layer chromatography
  TMS=trimethylsilyl
  Tos or Ts=p-toluenesulfonyl (tosyl)
  Tol=toluene
  IBMX=3-Isobutyl-1-methylxanthine
  HBSS=Hank's balanced salt solution
  HEPES=1-[4-(2-Hydroxyethyl)-1-piperazinyl]ethane-2-sulfonic acid The compounds of this invention can be prepared through the general approach outlined in the following schemes. These schemes are being provided to illustrate the present invention. To assist one in this endeavor, the ordinary practitioner would have full knowledge of literature sources such as *Chemical Abstracts*; Beilstein, *Protective Groups in Organic Synthesis* 2$^{nd}$ Edition T. W Greene, P. G. M. Wuts 1991, Wiley and Sons; *Comprehensive Organic Transformations, Advanced Organic Chemistry* etc.

Scheme 1 shows an approach in which an aminoaniline S1 is treated with a substituted oxoacetic acid (R$^2$=aryl or heteroaryl; R=H; preactivated by a chloroformate, oxalyl chloride or the like) or oxoacetic ester S4 (R$^2$=aryl or heteroaryl; R=alkyl) to provide the quinoxaline S2a (R'=OH). This intermediate is then converted to S2b (wherein R=OTf, Cl, Br or other suitable group by treatment with POCl$_3$, SOCl$_2$, P$_2$O$_5$/Bu$_4$NCl, P$_2$O$_5$/Bu$_4$NBr, Tf$_2$O, PhNTf$_2$ etc.) and coupled with S5 (which has been preactivated via a hydroboration reaction with 9-BBN or similar boron-based reagent; Y$^S$=a suitable alkyl, cycloalkyl, aryl or heterocylic linker; R$^{3S}$=ester or other appropriate group, such a as nitrile or alcohol) to provide S3a. Final conversion to S3b is then achieved by one of many appropriate synthetic methods known to practitioners in the art (such as acid- or base-hydrolysis when R$^{3S}$=ester, oxidation when R$^{3S}$=alcohol, hydrolysis when R$^{3S}$=nitrile etc.). Additionally, when R$^{3S}$ is a nitrile, conversion to a carbon linked tetrazole may be achieved by reaction with an appropriate azide.

Left side transformation, in which A is a functional group such as an ester, nitrile, halogen, optionally functionalized alcohol, sulfonic acid or other group, to A=one of the various definitions of R$^1$, such as amide, ketone, or sulfonamide) occurs by a process known to a practitioner in then art. For example, an activated alcohol or halogen may be carbonylated by a metal catalyzed or metal-facilitated process to provide an ester or acid, which may be further transformed to an amide or ketone. When converting an acid to an amide, an appropriate amine and coupling agent (as EDCI, HOBt, PyBop, HATU etc.) or activation method (oxalyl chloride, thionyl chloride etc.) may be used.

Scheme 1

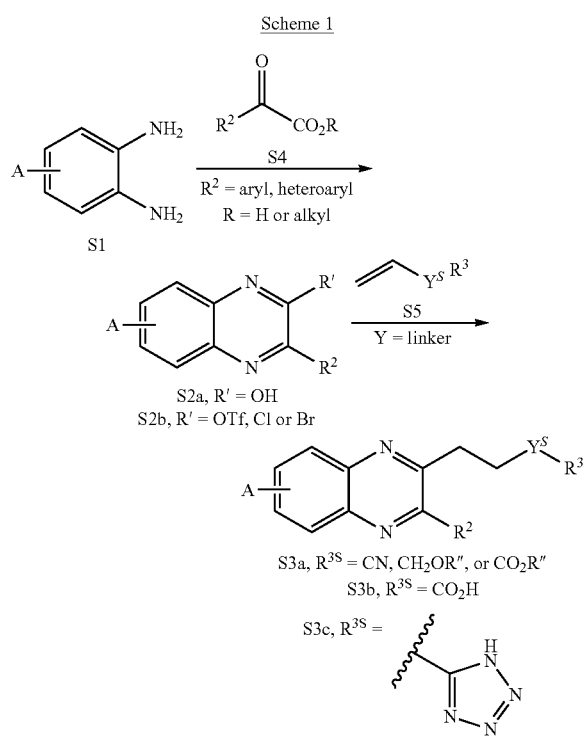

Scheme 2 shows an approach in which S1 is treated with an optionally substituted oxoacetic acid or oxoacetic ester S7 (Y=a suitable alkyl, cycloalkyl, aryl or heterocyclic linker). The resulting product S6a is then converted to S6b (wherein R'=OTf, Cl, Br or other suitable group) and coupled with an appropriately activated, and optionally substituted, partner by a metal catalyzed or metal-facilitated process (such as Stille coupling, Suzuki coupling, Negishi coupling) to provide S3a.

Scheme 2

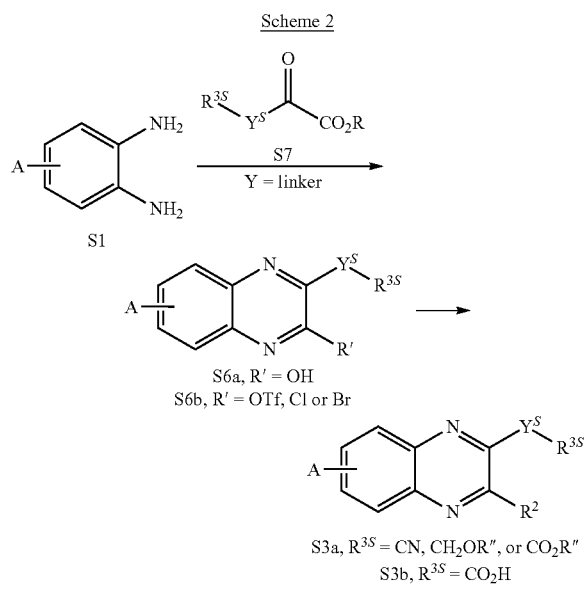

Scheme 3 shows an approach in which S2a is reacted with S9 (in which $X^S$ is a leaving group, such as halogen, activated alcohol etc.) and appropriate base (such as LiOtBu, $Cs_2CO_3$ DIPEA, LDA, NaH, or other appropriate reagent) to provide S8a.

Scheme 3

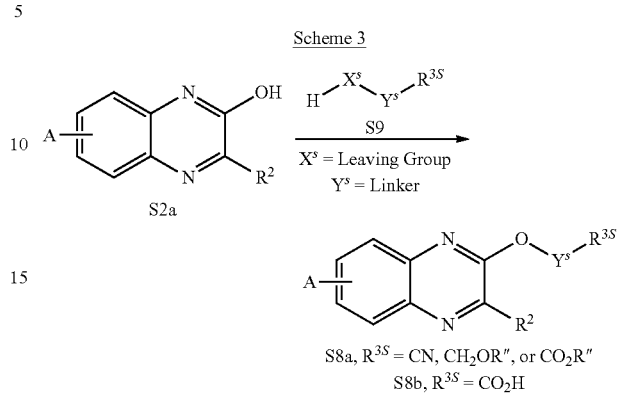

Scheme 4 shows an alternative sequence in which the quinoxaline synthesis occurs in a stepwise fashion. The nitroaniline S10 is reacted with S4 ($R^2$=aryl or heteroaryl; preactivated by a chloroformate, oxalyl chloride or the like or the like). The resulting ketamide S11 is subjected to nitro reduction (by hydrogenation, or treatment with $SnCl_2$, or other method) and concomitant cyclization to provide S2a.

Scheme 4

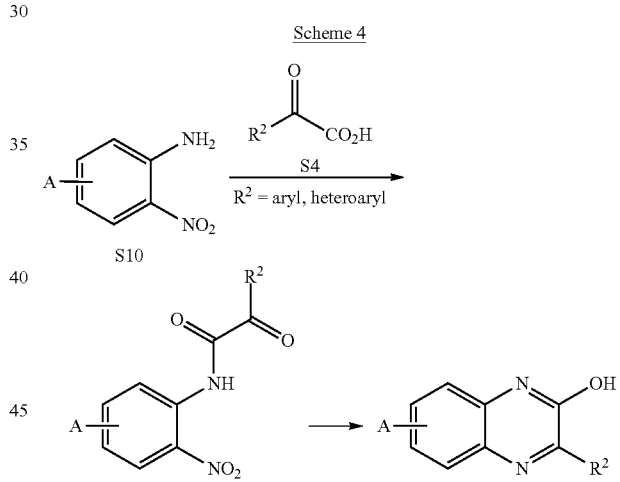

Scheme 5 shows an approach in which a substituted aminobenzaldehyde S12 is subjected to a Friedlander quinoline synthesis with ketone S14 (in which $R^2$ is aryl or heteroaryl and Y is a linker) and hydroxide base to provide S13.

Scheme 5

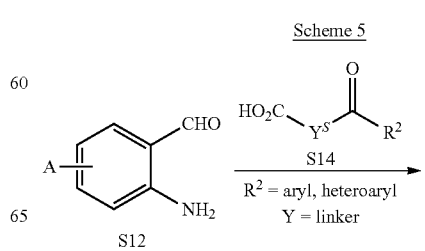

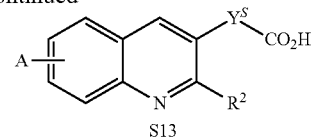

Scheme 6 shows an approach in which a substituted aminobenzaldehyde S12 is treated with the ketone S16 (in which $R^2$ is aryl or heteroaryl and $Y^S$ is an alkyl linker) and hydroxide base to provide S15.

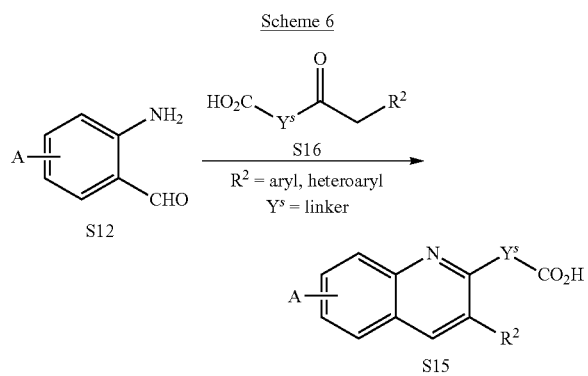

Scheme 7 shows an approach in which a substituted aminobenzaldehyde S12 is treated with the substituted acetic acid S19 (in which $R^2$ is aryl or heteroaryl; activated with acetic anhydride or the like) to provide S17a (R'=OH). This intermediate is then converted to S17b (wherein R'=OTf, Cl, Br), coupled with S5 ($Y^S$=a suitable linker; $R^{3S}$=ester) and hydrolyzed to provide the acid S18 as described for Scheme 1.

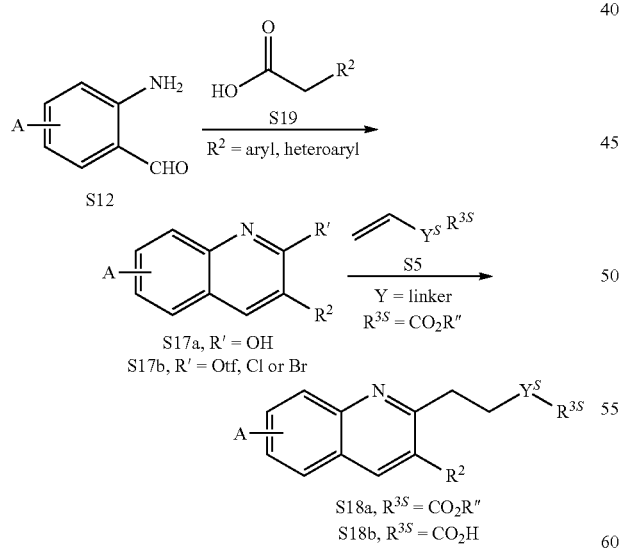

The starting materials (such as S1, S4, S5, S7, S9, S10, S12, S14, S16, and S19) and reagents used in preparing compounds described are either available from commercial suppliers such as Aldrich Chemical Co. (Wisconsin, USA) and Acros Organics Co. (New Jersey, USA) or were prepared by literature methods known to those skilled in the art.

Compounds, such as those described by formulae S3b, S3c, S8b, S13, S15, and S18b, can be prepared by the general methods outlined above. Exemplary compounds were prepared as described in the examples below or from starting materials known in the art. When unavailable from commercial suppliers, starting materials are synthesized according to methods known in the literature. These examples are being provided to further illustrate the present invention. They are for illustrative purposes only; the scope of the invention is not to be considered limited in any way thereby.

EXAMPLES

Example 1

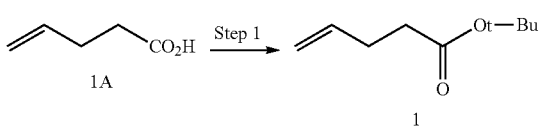

A solution of pent-4-enoic acid 1A (8.00 g, 80.0 mmol) in DCM (50 mL) was cooled to 0° C. under nitrogen. TFAA (25 mL, 180 mmol) was added and the reaction was stirred for 40 min at 0° C. tert-Butanol (86 mL, 896 mmol) was added and the reaction was warmed to RT and stirred for 16 h. After this time, the reaction was quenched with saturated aqueous $NaHCO_3$ and diluted with $Et_2O$. The aqueous layer was separated and extracted with $Et_2O$. The combined organics were dried ($Na_2SO_4$), filtered, and concentrated. The residue was purified by flash chromatography (0% to 20% $Et_2O$/pentane) to yield 1 (4.47 g, yield=18%): $^1$H NMR (500 MHz, $CDCl_3$) δ 5.92-5.76 (m, 1H), 5.12-4.96 (m, 2H), 2.49-2.43 (m, 1H), 2.42-2.36 (m, 1H), 2.36-2.27 (m, 2H), 1.44 (s, 9H).

Example 2

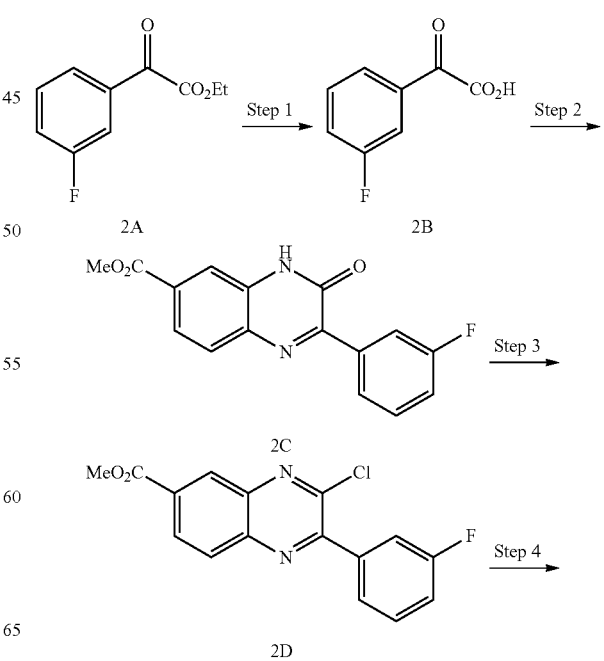

-continued

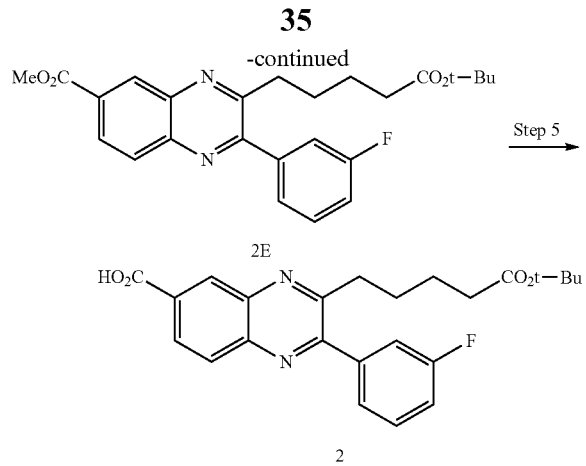

Step 1

2-(3-Fluorophenyl)-2-oxoacetic Acid

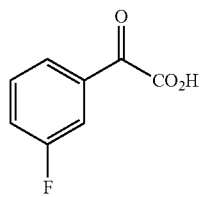

To a stirred solution of ethyl 2-(3-fluorophenyl)-2-oxoacetate (2A) (3.14 g, 16.0 mmol) in THF (120 mL) was added LiOH (1.64 g, 31.9 mmol) in water (40 mL). The reaction was stirred at RT for 1 h. After this time, the reaction was diluted with water and heptane. The aqueous layer was separated, cooled to 0° C., acidified with 1 N HCl to pH 3, and extracted with EtOAc. The combined organics were washed with water, dried ($Na_2SO_4$), filtered, and concentrated to yield 2B (2.32 g, yield=86%): $^1$H NMR (500 MHz, $CDCl_3$) δ 9.30 (br s, 1H), 8.18-8.12 (m, 1H), 8.05-7.96 (m, 1H), 7.60-7.51 (m, 1H), 7.45-7.39 (m, 1H).

Step 2

Methyl 2-(3-Fluorophenyl)-3-oxo-3,4-dihydroquinoxaline-6-carboxylate

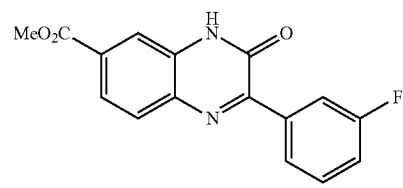

To a stirred solution of 2B (1.65 g, 9.81 mmol) and triethylamine (1.37 mL, 9.82 mmol) in THF (3 mL) was added ethyl chloroformate (0.93 mL, 9.76 mmol) at 0° C. under nitrogen. The resulting mixture was stirred at 0° C. for 20 min and a solution of methyl 3,4-diaminobenzoate (1.79 g, 10.8 mmol) in THF (27 mL) was slowly added over 50 min. The reaction was stirred at 0° C. for 1 h, then warmed to RT and stirred for 3 days. After this time, the reaction was concentrated, and the residue was triturated with $Et_2O$ and water. The solids were collected by vacuum filtration and the filter cake was washed with $Et_2O$ and dried under vacuum to yield 2C (2.56 g, yield 87%): $^1$H NMR (300 MHz, DMSO-$d_6$) δ 12.82 (s, 1H), 8.26-8.05 (m, 2H), 8.01-7.91 (m, 2H), 7.90-7.80 (m, 1H), 7.64-7.51 (m, 1H), 7.46-7.36 (m, 1H), 3.91 (s, 3H).

Step 3

Methyl 3-Chloro-2-(3-fluorophenyl)quinoxaline-6-carboxylate

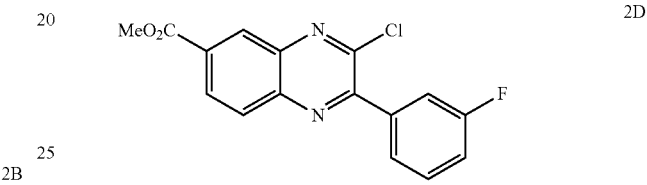

A suspension of 2C (2.56 g, 8.58 mmol) and $POCl_3$ (23 mL) was stirred at 110° C. under nitrogen for 24 h. The reaction was cooled to RT and concentrated. The residue was dissolved in DCM and ice was slowly added. The mixture was stirred at 0° C. for 1 h. The aqueous layer was separated and extracted with DCM. The combined organics were dried ($Na_2SO_4$), filtered, and concentrated to yield 2D (2.00 g, yield=74%): MS (M+H)=317.

Step 4

Methyl 3-(5-tert-Butoxy-5-oxopentyl)-2-(3-fluorophenyl)quinoxaline-6-carboxylate

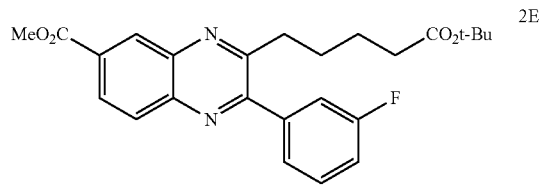 [SMILES: COC(=O)c1ccc2nc(-c3cccc(F)c3)c(CCCCC(=O)OC(C)(C)C)nc2c1]

To a solution of 1 (1.14 g, 7.30 mmol) in anhydrous THF (10 mL) was added 9-BBN (0.5 M in THF, 14.6 mL, 7.30 mmol) at 0° C. under nitrogen. The reaction was stirred at 0° C. for 30 min and warmed to RT for 3 h. 2D (1.00 g, 3.16 mmol), Pd(dppf)$Cl_2$.$CH_2Cl_2$ (310 mg, 0.380 mmol), and $K_3PO_4$ (1.88 g, 8.86 mmol) were added. The suspension was degassed (3× vacuum/nitrogen) and heated at 60° C. for 18 h. After this time, the reaction was cooled to RT and filtered. The filtrate was diluted with DCM and water. The aqueous layer was separated and extracted with DCM. The combined organics were dried ($Na_2SO_4$), filtered, and concentrated. The residue was purified by column chromatography (10% EtOAc/heptane) to yield 2E (1.43 g, yield=>99%): MS (M+H)=439.

Step 5

3-(5-tert-Butoxy-5-oxopentyl)-2-(3-fluorophenyl)quinoxaline-6-carboxylic Acid

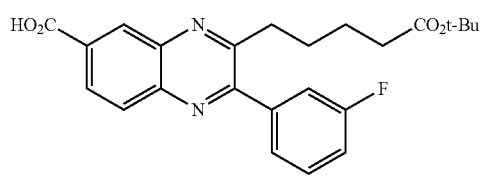

2

A solution of 2E (1.43 g, 3.16 mmol) and LiOH (265 mg, 6.32 mmol) in THF (20 mL) and water (10 mL) was stirred at RT for 1 h. After this time, the reaction was diluted with water and extracted with heptane. The aqueous layer was acidified with 1 N HCl, then extracted with DCM. The combined organics were washed with water, dried ($Na_2SO_4$), filtered, and concentrated to yield 2 (1.13 g, yield=84%): MS (M+H)=425.

In a manner similar to that described above, compound 2F was treated with LiOH to provide 2G ($^1$H NMR, 300 MHz, $CDCl_3$ δ 8.48 (d, J=8.1 Hz, 2H), 7.81 (d, J=8.3 Hz, 2H)) and then reacted with methyl 3,4-diaminobenzoate. The resulting 3-oxo-quinoxaline 2H (MS: M+H=349) was sequentially reacted with $POCl_3$ (to provide 2i, MS: M+H 367), coupled with compound 1 (to provide 2J, MS: M+H 489), and hydrolyzed with LiOH to provide 2K (MS: M+H=475)

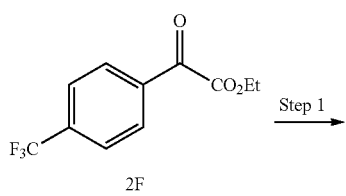

2F

Step 1

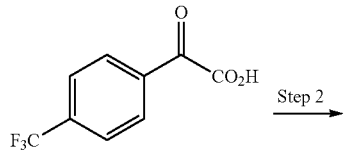

2G

Step 2

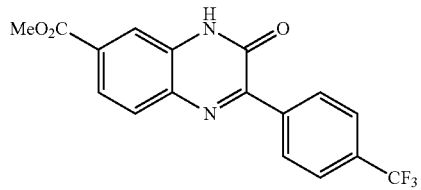

2H

Step 3

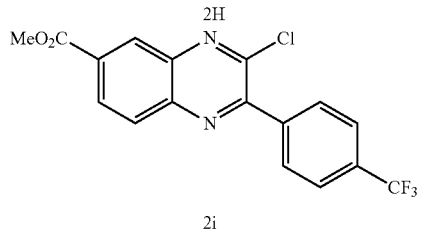

2i

Step 4

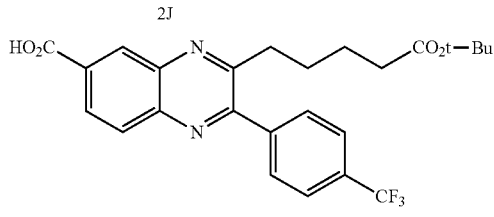

2J

Step 5

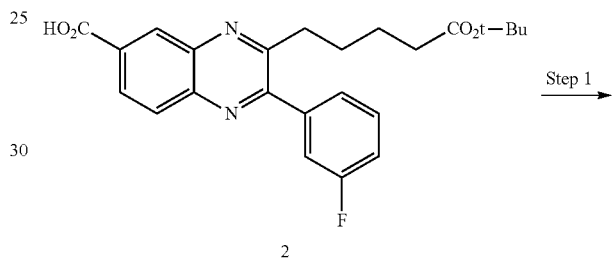

2K

Example 3

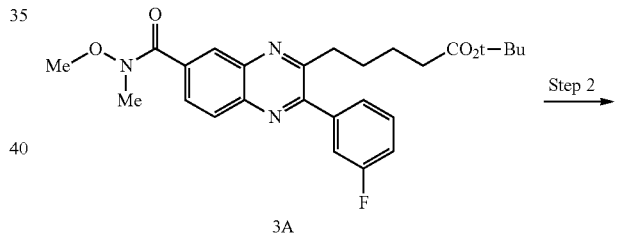

2

Step 1

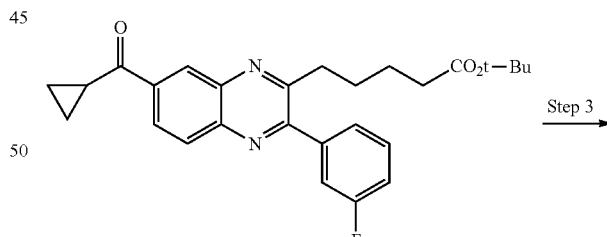

3A

Step 2

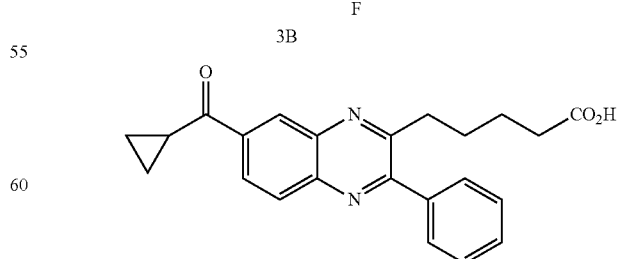

3B

Step 3

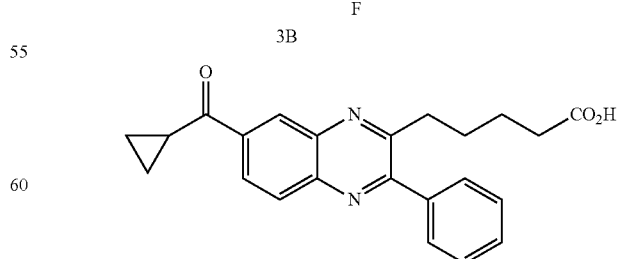

3

Step 1 tert-Butyl 5-{3-(3-Fluorophenyl)-7-[methoxy(methyl)carbamoyl]quinoxalin-2-yl}pentanoate

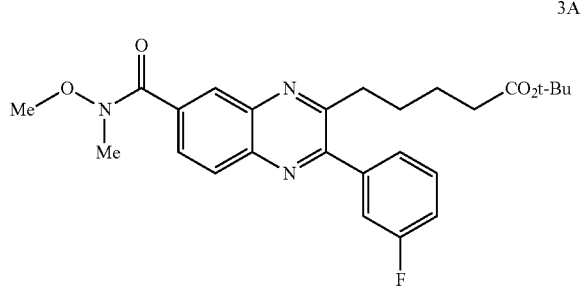 [SMILES: CON(C)C(=O)c1ccc2nc(-c3cccc(F)c3)c(CCCCC(=O)OC(C)(C)C)nc2c1]

3A

A solution of 2 (304 mg, 0.716 mmol), O,N-dimethylhydroxylamine hydrochloride (175 mg, 1.79 mmol), diisopropylethylamine (0.62 mL, 3.56 mmol), and BOP—Cl (547 mg, 2.15 mmol) in anhydrous THF (10 mL) was stirred at RT for 18 h under nitrogen. After this time, the reaction was diluted with EtOAc and washed with water. The organic layer was separated, dried (Na$_2$SO$_4$), filtered, and concentrated. The residue was purified by column chromatography (30% to 50% EtOAc/heptane) to yield 3A (308 mg, yield=92%): MS (M+H)=468.

Step 2 tert-Butyl 5-[7-(Cyclopropanecarboyl)-3-(3-fluorophenyl)quinoxalin-2-yl]pentanoate

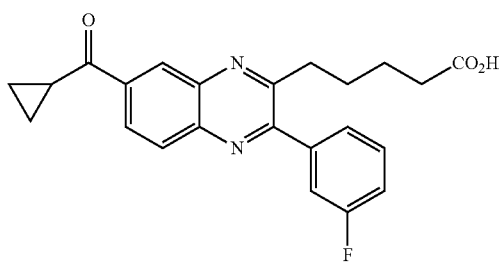

3B

To a stirred solution of 3A (150 mg, 0.321 mmol) in anhydrous THF (1 mL) was added cyclopropylmagnesium bromide (0.5 M in THF, 1.93 mL, 0.965 mmol) at −40° C. under nitrogen. After the addition, the reaction was warmed to 10° C. over 1 h. After this time, the reaction was quenched with saturated aqueous NH$_4$Cl and extracted with EtOAc. The combined organics were dried (Na$_2$SO$_4$), filtered, and concentrated. The residue was purified by column chromatography (30% EtOAc/heptane) to yield 3B (102 mg, yield=71%): MS (M+H)=449.

Step 3

5-[7-(Cyclopropanecarbonyl)-3-(3-fluorophenyl)quinoxalin-2-yl]pentanoic Acid

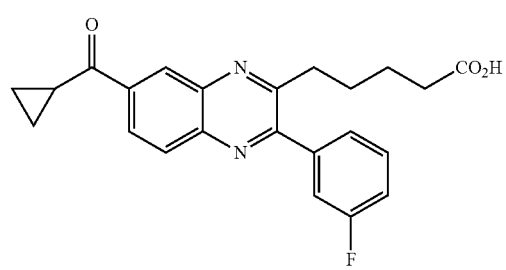

3

To a solution of 3B (102 mg, 0.227 mmol) in DCM (2 mL) was added TFA (1 mL) and the solution stirred for 1.5 h at RT. After this time, the reaction was concentrated and the residue was triturated with a mixture of water (0.1 mL), DCM (3 mL), and heptane (20 mL). The solids were collected by vacuum filtration and the filter cake was dissolved in 2:2:0.2 CH$_3$CN/H$_2$O/1 M NH$_4$OH (2.2 mL), and lyophilized to yield 3 (70 mg, yield=75%): MS (M+H)=393.

In a manner similar to that described for 3A above, compound 2 was coupled with the appropriate amine to provide the following compounds:

| Compound Number | Coupling Partner | Compound | M + H |
|---|---|---|---|
| 3C | ![NH2-C6H4-F] | ![structure] | 518 |

-continued

| Compound Number | Coupling Partner | Compound | M + H |
|---|---|---|---|
| 3D | 3-fluoroaniline | quinoxaline-6-carboxamide derivative with 3-fluoroanilide and 3-fluorophenyl substituents, butanoate Ot-Bu ester | 518 |
| 3E | 2-fluoroaniline | quinoxaline-6-carboxamide derivative with 2-fluoroanilide and 3-fluorophenyl substituents, butanoate Ot-Bu ester | 518 |

In a manner similar to that described for 3A above, compound 2K was coupled with the appropriate amine to provide the following compounds:

| Compound Number | Coupling Partner | Compound | M + H |
|---|---|---|---|
| 3F | (R)-α-methylbenzylamine | (R)-α-methylbenzyl quinoxaline-6-carboxamide with 4-CF₃-phenyl substituent, Ot-Bu ester | 578 |
| 3G | (S)-α-methylbenzylamine | (S)-α-methylbenzyl quinoxaline-6-carboxamide with 4-CF₃-phenyl substituent, Ot-Bu ester | 578 |
| 3H | 1-phenylpiperazine | 4-phenylpiperazine-1-carbonyl quinoxaline with 4-CF₃-phenyl substituent, Ot-Bu ester | 619 |
| 3i | N,O-dimethylhydroxylamine·HCl | N-methoxy-N-methyl quinoxaline-6-carboxamide with 4-CF₃-phenyl substituent, Ot-Bu ester | 518 |

-continued

| Compound Number | Coupling Partner | Compound | M + H |
|---|---|---|---|
| 3J | | | 579 |
| 3K | | | 579 |
| 3L | | | 656 |
| 3M | | | 656 |
| 3N | | | 656 |
| 3o | | | 565 |

-continued

| Compound Number | Coupling Partner | Compound | M + H |
|---|---|---|---|
| 3P | pyridin-3-ylmethanamine | [structure] | 565 |
| 3Q | pyridin-2-ylmethanamine | [structure] | 565 |
| 3R | (6-(trifluoromethyl)pyridin-3-yl)methanamine | [structure] | 633 |

In a manner similar to that described for 3B above, compound 3i was reacted with cyclopropylmagnesium bromide to provide the following compound:

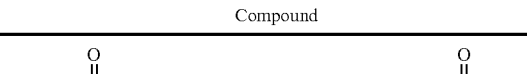

| Compound Number | Starting Material | Compound | M + H |
|---|---|---|---|
| 3S | 3i | [structure] | 499 |

In a manner similar to that described above for compound 3, the following compounds were prepared from the TFA deprotection of the indicated starting materials (SM):

| No. | SM | Compound | M + H | |
|---|---|---|---|---|
| 3T | 3C | [structure] | 3-(3-fluorophenyl)-7-[[(4-fluorophenyl)amino]carbonyl]-2-quinoxalinepentanoic acid | 462 |

-continued

| No. | SM | Compound | | M + H |
|---|---|---|---|---|
| 3U | 3D | 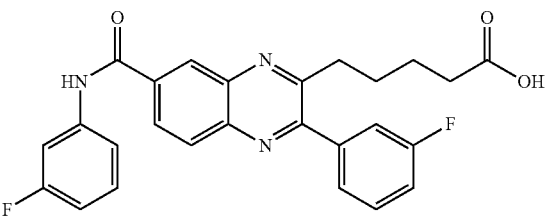 [SMILES: O=C(O)CCCCc1nc2cc(C(=O)Nc3cccc(F)c3)ccc2nc1-c1cccc(F)c1] | 3-(3-fluorophenyl)-7-[[(3-fluorophenyl)amino]carbonyl]-2-quinoxalinepentanoic acid | 462 |
| 3V | 3E | 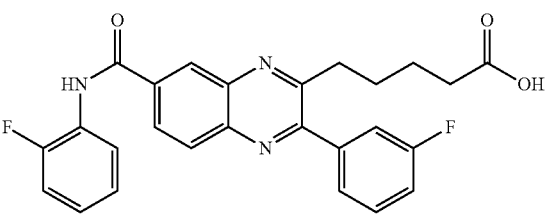 [SMILES: O=C(O)CCCCc1nc2cc(C(=O)Nc3ccccc3F)ccc2nc1-c1cccc(F)c1] | 3-(3-fluoropheny)-7-[[(2-fluorophenyl)amino]carbonyl]-2-quinoxalinepentanoic acid | 462 |
| 3W | 3F | 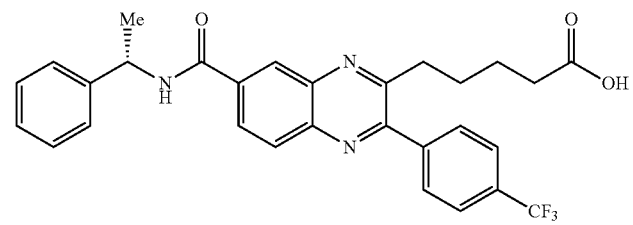 [SMILES: C[C@H](NC(=O)c1ccc2nc(-c3ccc(C(F)(F)F)cc3)c(CCCCC(=O)O)nc2c1)c1ccccc1] | 7-[[(1-(S)-phenylethyl)amino]carbonyl]-3-[4-(trifluoromethyl)phenyl]-2-quinoxalinepentanoic acid | 522 |
| 3X | 3G | 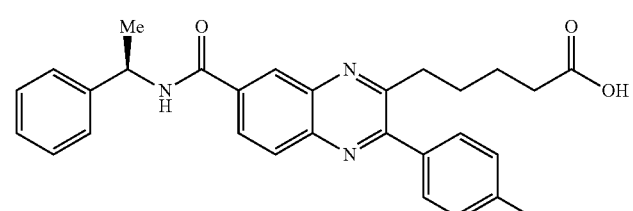 | 7-[[(1-(R)-phenylethyl)amino]carbonyl]-3-[4-(trifluoromethyl)phenyl]-2-quinoxalinepentanoic acid | 522 |
| 3Y | 3H | 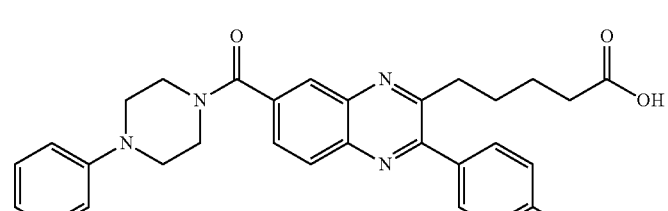 | 7-[(4-phenyl-1-piperazinyl)carbonyl]-3-[4-(trifluoromethyl)phenyl]-2-quinoxalinepentanoic acid | 563 |
| 3Z | 3S | 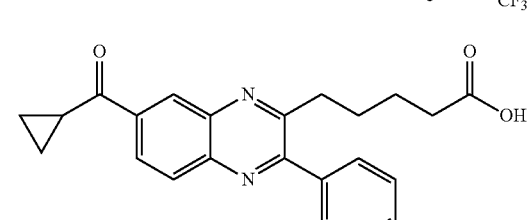 | 7-(cyclopropylcarbonyl)-3-[4-(trifluoromethyl)phenyl]-2-quinoxalinepentanoic acid | 443 |
| 3AA | 3J | 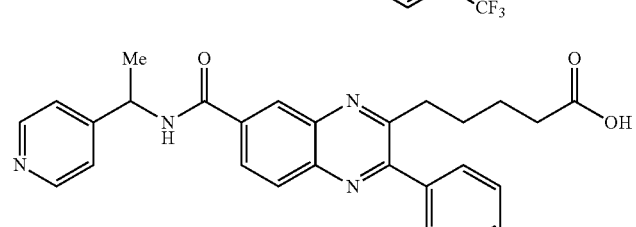 | 7-[[[1-(4-pyridinyl)ethyl]-amino]carbonyl]-3-[4-(trifluoromethyl)-phenyl]-2-quinoxaline-pentanoic acid | 523 |

| No. | SM | Compound | | M + H |
|---|---|---|---|---|
| 3AB | 3K | | 7-[[[1-(2-pyridinyl)ethyl]-amino]carbonyl]-3-[4-(trifluoromethyl)phenyl]-2-quinoxalinepentanoic acid | 523 |
| 3AC | 3o | | 7-[[[(4-pyridinylmethyl)-amino]carbonyl]-3-[4-(trifluoromethyl)phenyl]-2-quinoxalinepentanoic acid | 509 |
| 3AD | 3P | | 5-(7-pyridin-3-ylmethylcarbamoyl)-3-(4-(trifluoromethyl)phenyl)quinoxalin-2-yl)pentanoic acid | 509 |
| 3AE | 3Q | | 7-[[[(2-pyridinylmethyl)-amino]carbonyl]-3-[4-(trifluoromethyl)phenyl]-2-quinoxalinepentanoic acid | 509 |
| 3AF | 3R | | 3-[4-(trifluoromethyl)phenyl]-7-[[[[6-(trifluoromethyl)-3-pyridinyl]methyl]amino]-carbonyl]-2-quinoxaline-pentanoic acid | 577 |
| 3AG | 2J | | 7-(methoxycarbonyl)-3-[4-(trifluoromethyl)phenyl]-2-quinoxalinepentanoic acid | 433 |

Example 4

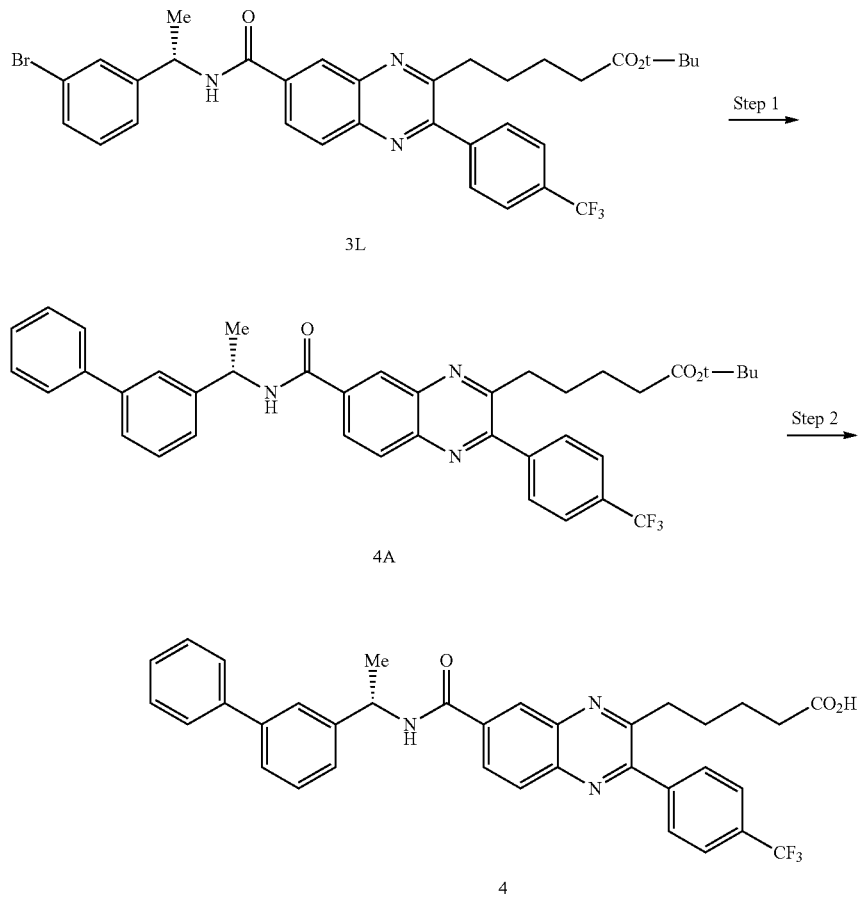

Step 1

(S)-tert-Butyl 5-{7-[1-(biphenyl-3-yl)ethylcarbamoyl]-3-[4-(trifluoromethyl)-phenyl]quinoxalin-2-yl}pentanoate

Step 2

(S)-5-{7-[1-(biphenyl-3-yl)ethylcarbamoyl]-3-[4-(trifluoromethyl)phenyl]quinoxalin-2-yl}pentanoic Acid

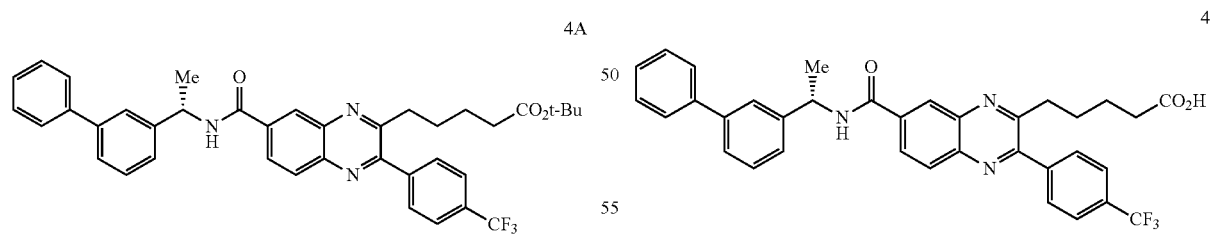

A stirred solution of 3L (59 mg, 0.090 mmol), phenylboronic acid (11 mg, 0.090 mmol), Pd(PPh$_3$)$_4$ (0.46 mg, 0.005 mmol), and sodium carbonate (25 mg, 0.225 mmol) in toluene (2 mL) and water (0.1 mL) was heated at reflux for 16 h. After this time, the reaction was cooled to RT, filtered through a short pad of CELITE, and the filter cake was washed with EtOAc. The filtrate was diluted with EtOAc, washed with water, dried (Na$_2$SO$_4$), filtered, and concentrated to yield 4A (47 mg, yield=79%): MS (M+H)=654.

To a stirred solution of 4A (47 mg, 0.071 mmol) in DCM (2 mL) was added TFA (1 mL) and the solution stirred for 1.5 h at RT. After this time, the reaction was concentrated and the residue was triturated with a mixture of water (0.1 mL), DCM (3 mL) and heptane (20 mL). The solids collected by vacuum filtration and the filter cake was dissolved in 2:2:0.2 CH$_3$CN/H$_2$O/1 M NH$_4$OH (2.2 mL) and lyophilized to yield 4 (21 mg, yield=47%): MS (M+H)=598.

In a manner similar to that described above for 4A, the following compounds were prepared:

| Compound Number | Starting Material | Compound | M + H |
|---|---|---|---|
| 4B | 3M | | 654 |
| 4C | 3N | | 654 |

In a manner similar to that described above for compound 4, the following compounds were prepared via a TFA deprotection of the indicated starting materials (SM):

| No. | SM | Compound | Name | M + H |
|---|---|---|---|---|
| 4D | 4B | | 7-[[[1-(R)-[1,1'-biphenyl]-3-ylethyl]amino]carbonyl]-3-[4-(trifluoromethyl)-phenyl]-2-quinoxaline-pentanoic acid | 598 |
| 4E | 4C | | 7-[[(1-[1,1'-biphenyl]-4-ylethyl)amino]carbonyl]-3-[4-(trifluoromethyl)-phenyl]-2-quinoxaline-pentanoic acid | 598 |

The racemic mixture 4E was separated on a semi-preparative Chiralpak IC column (15% ethanol-hexanes-0.1% diethylamine) to provide the pure enantiomers 4F (Enantiomer 1, >99% ee, LCMS: M+H=598) and 4G (Enantiomer 2, >99% ee, LCMS: M+H=598).

Example 5

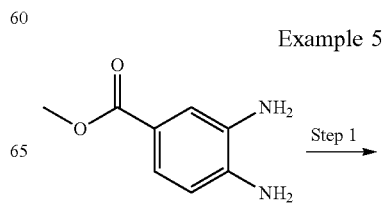

Step 1

-continued

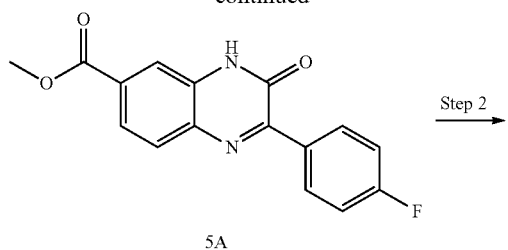

5A

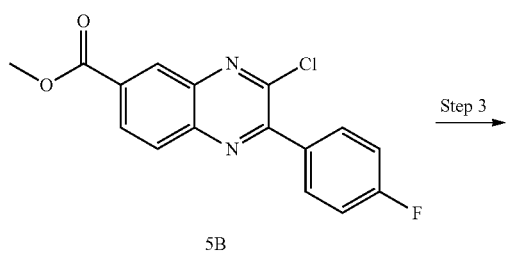

5B

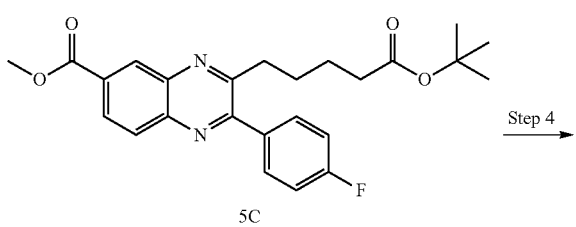

5C

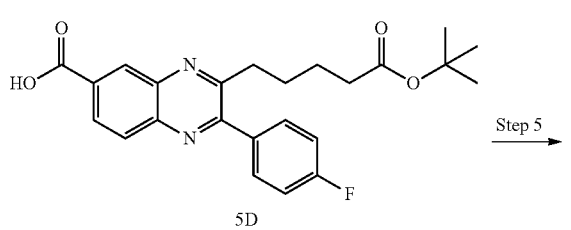

5D

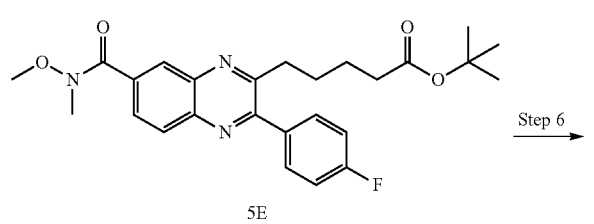

5E

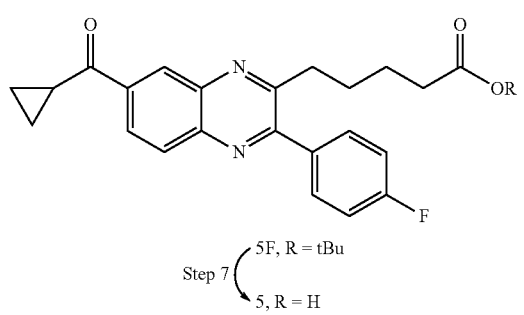

5F, R = tBu
Step 7
5, R = H

Step 1

Methyl 2-(4-fluorophenyl)-3-oxo-3,4-dihydroquinoxaline-6-carboxylate

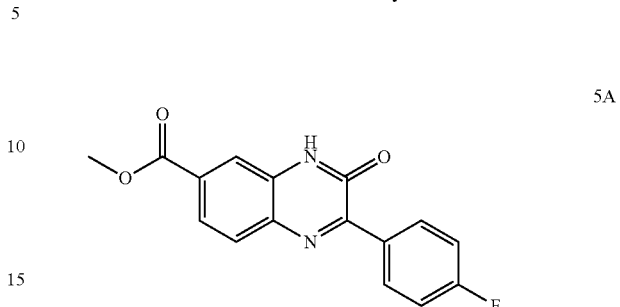

5A

To a solution of 2-(4-fluorophenyl)-2-oxoacetic acid (507 mg, 3.02 mmol, prepared from ethyl 2-(4-fluorophenyl)-2-oxoacetate as described in Example 2) and triethylamine (0.42 mL, 3.0 mmol) cooled to 0° C. was added ethyl chloroformate (0.29 mL, 3.0 mmol). The resulting mixture was stirred at 0° C. for 20 minutes and methyl 3,4-diaminobenzoate (551 mg, 3.32 mmol) was added slowly over 50 minutes as a solution in THF (10 mL). The reaction was stirred at 0° C. for 1 h and at RT for 72 h. The reaction was concentrated to remove most of the THF. The solid was diluted with Et$_2$O and water and cooled to 0° C. The solid was filtered and washed with Et$_2$O (1×20 mL) and DCM (1×20 mL) to yield methyl 2-(4-fluorophenyl)-3-oxo-3,4-dihydroquinoxaline-6-carboxylate (5A, 665 mg; Yield=73.9%). $^1$H NMR (300 MHz, DMSO-d$_6$) δ 12.77 (s, 1H), 8.50-8.38 (m, 2H), 7.98-7.89 (m, 2H), 7.84 (dd, J=8.5, 1.8 Hz, 1H), 7.41-7.29 (m, 2H), 3.91 (s, 3H).

Step 2

Methyl 3-chloro-2-(4-fluorophenyl)quinoxaline-6-carboxylate

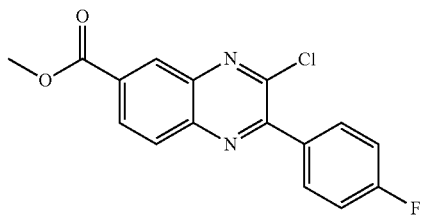

5B

A suspension of methyl 2-(4-fluorophenyl)-3-oxo-3,4-dihydroquinoxaline-6-carboxylate (5A, 2.20 g, 7.38 mmol), phosphoryl chloride (20 mL, 200 mmol), and was degassed and stirred at 110° C. for 40 h. The reaction was cooled to RT, some of the excess POCl$_3$ was concentrated, and then cooled to at 0° C. The mixture was diluted with DCM and ice was added slowly. This mixture was stirred at 0° C. for 1 h. The organic layer was removed and the aqueous phase was extracted with DCM (3×). The combined organics were dried (Na$_2$SO$_4$), filtered, and concentrated. The residue was purified by flash chromatography (0% to 50% EtOAc/hexanes) to yield methyl 3-chloro-2-(4-fluorophenyl)quinoxaline-6-carboxylate (5B, 2.1 g; Yield=90%), MS (M+H)=317.

Step 3

Methyl 3-(5-tert-butoxy-5-oxopentyl)-2-(4-fluorophenyl)quinoxaline-6-carboxylate

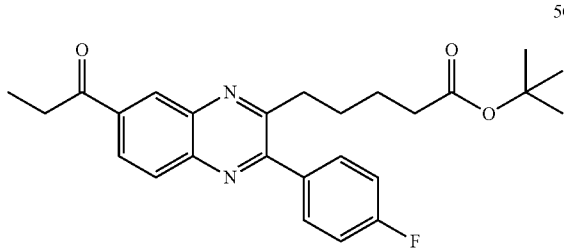

5C

To a solution of tert-butyl pent-4-enoate (1, 1.5 g, 9.8 mmol) in THF (10 mL, 100 mmol) cooled to 0° C. was added 0.5 M of 9-Borabicyclo[3.3.1]nonane in THF (19.6 mL). The reaction was stirred at 0° C. for 30 minutes and at RT for 3 h. To this solution was added methyl 3-chloro-2-(4-fluorophenyl)quinoxaline-6-carboxylate (5B, 1.33 g, 4.20 mmol), [1,1'-Bis(diphenylphosphino)ferrocene]dichloropalladium(II)-complex with dichloromethane (1:1) (0.423 g, 0.518 mmol), and potassium phosphate (2.5 g, 12 mmol). The resulting solution was degassed and stirred at 60° C. for 16 h. The filtrate was diluted with DCM and water. The organic layer was removed and the aqueous phase was extracted with DCM (2×). The combined organics were dried (Na$_2$SO$_4$), filtered, and concentrated. The residue was purified by flash chromatography (0% to 60% EtOAc/hexanes) to yield methyl 3-(5-tert-butoxy-5-oxopentyl)-2-(4-fluorophenyl)quinoxaline-6-carboxylate (5C, 1.82 g; Yield=98%), MS (M+H)=439.

Step 4

3-(5-tert-butoxy-5-oxopentyl)-2-(4-fluorophenyl)quinoxaline-6-carboxylic acid

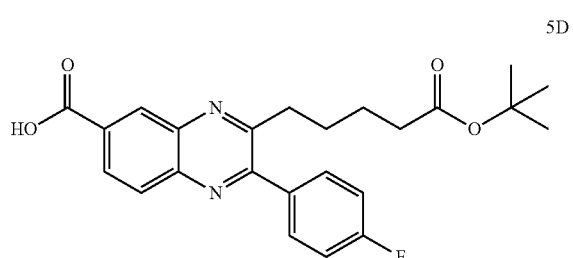

5D

To a solution of methyl 3-(5-tert-butoxy-5-oxopentyl)-2-(4-fluorophenyl)quinoxaline-6-carboxylate (5C, 1.82 g, 4.15 mmol) in THF (30 mL, 400 mmol) and water (15 mL, 830 mmol) was added lithium hydroxide monohydrate (352 mg, 8.39 mmol). The reaction was stirred at RT for 1 h and quenched with 0.1N HCl. The reaction was diluted with EtOAc and the organic layer was removed. The aqueous phase was extracted with EtOAc (3×) and the combined organics were dried (Na$_2$SO$_4$), filtered, and concentrated to yield 5D (1.67 g; Yield=94.8%, MS: M+H=425). The material was used without purification.

Step 5 tert-butyl 5-(3-(4-fluorophenyl)-7-(methoxy(methyl)carbamoyl)quinoxalin-2-yl)pentanoate

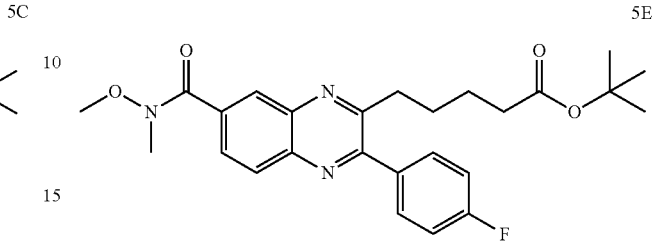

5E

To a solution of crude 3-(5-tert-butoxy-5-oxopentyl)-2-(4-fluorophenyl)quinoxaline-6-carboxylic acid (5D, 1.67 g, 3.93 mmol), N,O-dimethylhydroxylamine hydrochloride (534 mg, 5.47 mmol), and N,N-diisopropylethylamine (2.40 mL, 13.8 mmol) in DCM (40 mL, 600 mmol) was added 1-hydroxybenzotriazole (0.802 g, 5.94 mmol) and N-(3-dimethylaminopropyl)-N'-ethylcarbodiimide hydrochloride (1.53 g, 7.98 mmol). The reaction was stirred at RT for 18 h. The reaction was diluted with 0.3N HCl. The organic layer was removed and the aqueous phase was extracted with DCM (3×). The combined organics were dried (Na$_2$SO$_4$), filtered, and concentrated. The residue was purified by flash chromatography (0% to 100% EtOAc/hexanes) to yield tert-butyl 5-(3-(4-fluorophenyl)-7-(methoxy(methyl)carbamoyl)quinoxalin-2-yl)pentanoate (5E, 1.50 g; Yield=81.5%), MS (M+H)=468.

Step 6 tert-butyl 5-(7-(cyclopropanecarbonyl)-3-(4-fluorophenyl)quinoxalin-2-yl)pentanoate

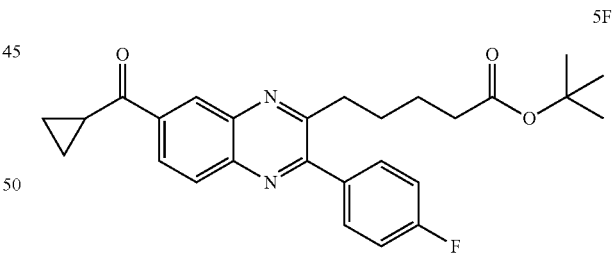

5F

To a solution of tert-butyl 5-(3-(4-fluorophenyl)-7-(methoxy(methyl)carbamoyl)quinoxalin-2-yl)pentanoate (5E, 80 mg, 0.2 mmol) in THF (2 mL, 20 mmol) cooled to −40° C. was added 0.5 M of cyclopropylmagnesium bromide in THF (0.530 mL). The reaction was stirred for 45 minutes gradually warming to 10° C. The reaction was quenched with dilute HCl and diluted with DCM. The organic layer was removed and the aqueous phase was extracted with DCM (3×). The combined organics were dried and concentrated. The residue was purified by flash chromatography (0% to 70% EtOAc/hexanes) to yield tert-butyl 5-(7-(cyclopropanecarbonyl)-3-(4-fluorophenyl)quinoxalin-2-yl)pentanoate (5F, 58 mg; Yield=80%), MS (M+H)=449.

Step 7

5-(7-(cyclopropanecarbonyl)-3-(4-fluorophenyl)quinoxalin-2-yl)pentanoic acid

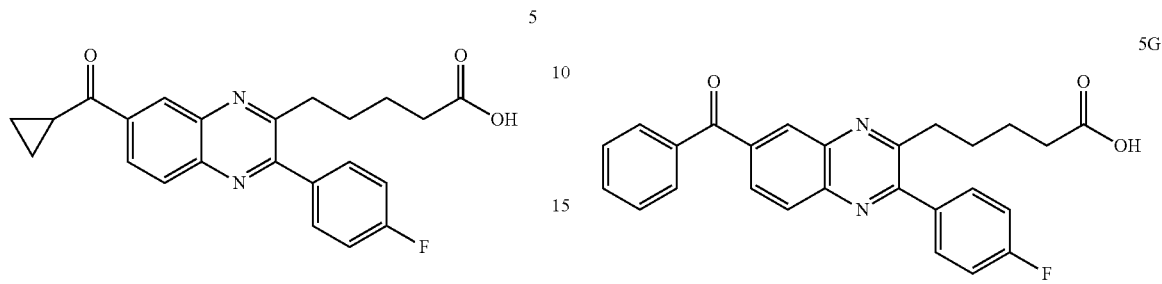

A solution of tert-butyl 5-(7-(cyclopropanecarbonyl)-3-(4-fluorophenyl)quinoxalin-2-yl)pentanoate (5F, 57 mg, 0.13 mmol) and TFA (0.4 mL, 5 mmol) in DCM (1.6 mL, 25 mmol) was stirred for 2 h. The residue was purified by reverse phase chromatography (10:90 to 100:00 $CH_3CN/H_2O$ (0.1% TFA)) to yield 5-(7-(cyclopropanecarbonyl)-3-(4-fluorophenyl)quinoxalin-2-yl)pentanoic acid (5). MS (M+H)=393.

In a manner similar to that described above, the compound 5G (MS, M+H=429) was prepared from 5E:

In a manner similar to that described for 3A above, compound 5D was coupled with the appropriate amine to provide the following compounds:

| Compound Number | Coupling Partner | Compound | M + H |
|---|---|---|---|
| 5H | 3-fluoroaniline | | 518 |
| 5i | 4-fluoroaniline | | 518 |
| 5J | 2-fluoroaniline | | 518 |
| 5K | dimethylamine·HCl | | 452 |

-continued

| Compound Number | Coupling Partner | Compound | M + H |
|---|---|---|---|
| 5L | NH₂ / Me-CH-Me (isopropylamine) | [quinoxaline with isopropyl amide at 7-position, 4-fluorophenyl at 3-position, and pentanoate t-Bu ester] | 466 |
| 5M | azetidine·HCl | [quinoxaline with azetidinyl amide at 7-position, 4-fluorophenyl at 3-position, and pentanoate t-Bu ester] | 464 |

In a manner similar to that described above, the following compounds were prepared from the TFA deprotection of the indicated starting materials (SM):

| No. | SM | Compound | Name | M + H |
|---|---|---|---|---|
| 5N | 5H | [quinoxaline with (3-fluorophenyl)amide, 4-fluorophenyl, and pentanoic acid] | 3-(4-fluorophenyl)-7-[[(3-fluorophenyl)amino]carbonyl]-2-quinoxalinepentanoic acid | 462 |
| 5o | 5i | [quinoxaline with (4-fluorophenyl)amide, 4-fluorophenyl, and pentanoic acid] | 3-(4-fluorophenyl)-7-[[(4-fluorophenyl)amino]carbonyl]-2-quinoxalinepentanoic acid | 462 |
| 5P | 5J | [quinoxaline with (2-fluorophenyl)amide, 4-fluorophenyl, and pentanoic acid] | 3-(4-fluorophenyl)-7-[[(2-fluorophenyl)amino]carbonyl]-2-quinoxalinepentanoic acid | 462 |
| 5Q | 5K | [quinoxaline with dimethylamide, 4-fluorophenyl, and pentanoic acid] | 7-[(dimethylamino)carbonyl]-3-(4-fluorophenyl)-2-quinoxalinepentanoic acid | 396 |

| No. | SM | Compound | Name | M + H |
|---|---|---|---|---|
| 5R | 5L | | 3-(4-fluorophenyl)-7-[[(1-methylethyl)amino]carbonyl]-2-quinoxalinepentanoic acid | 410 |
| 5S | 5M | | 7-(1-azetidinylcarbonyl)-3-(4-fluorophenyl)-2-quinoxalinepentanoic acid | 408 |

Example 6

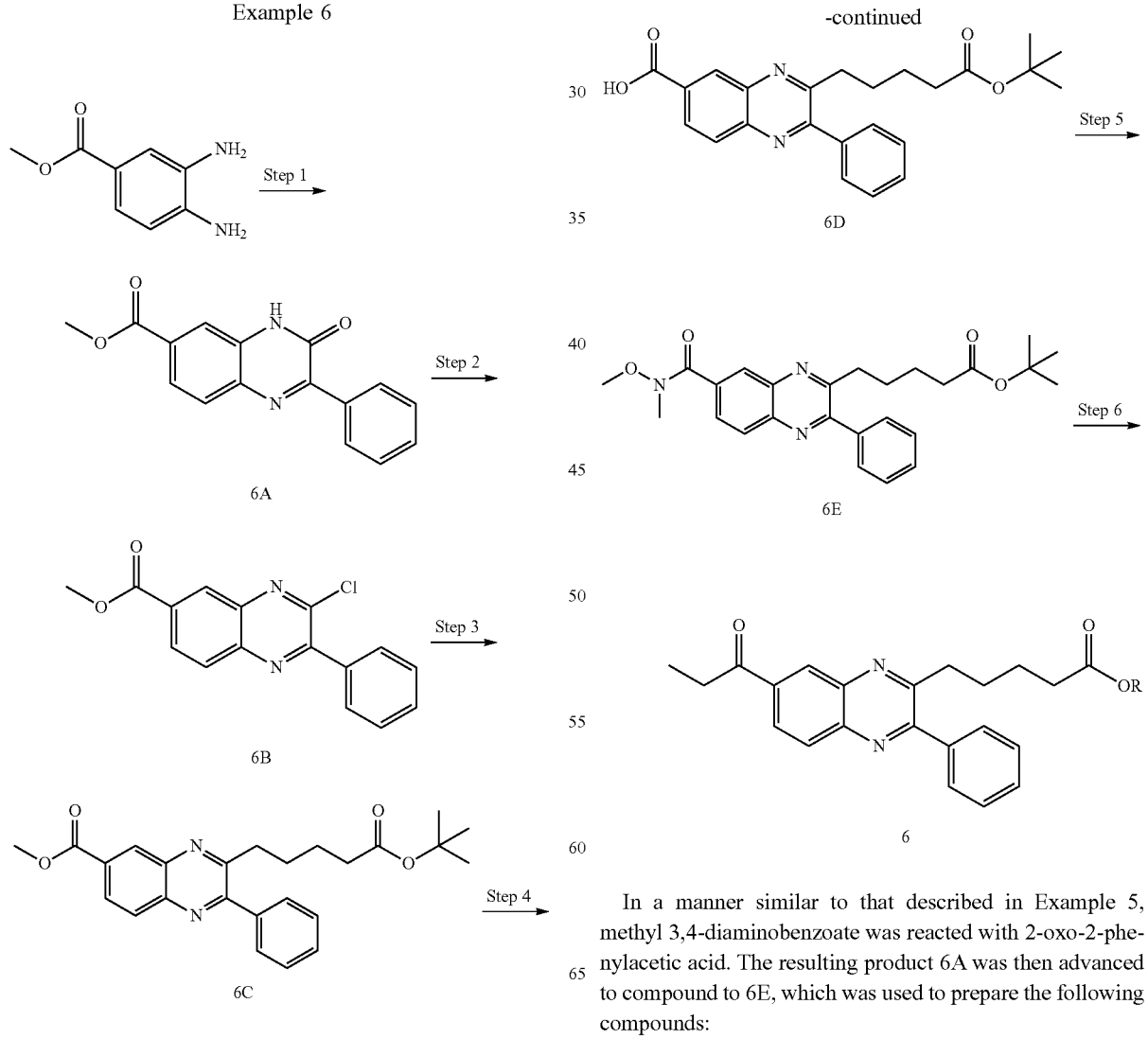

In a manner similar to that described in Example 5, methyl 3,4-diaminobenzoate was reacted with 2-oxo-2-phenylacetic acid. The resulting product 6A was then advanced to compound to 6E, which was used to prepare the following compounds:

| No. | Compound | Name | M + H |
|---|---|---|---|
| 6 | 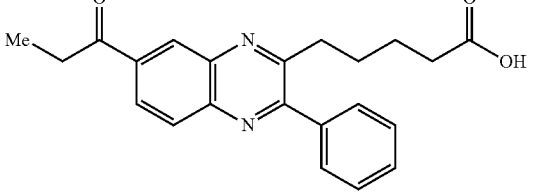 | 7-(1-oxopropyl)-3-phenyl-2-quinoxalinepentanoic acid | 363 |
| 6F | 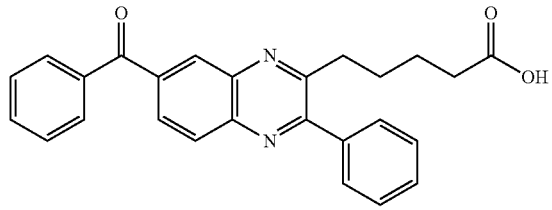 [SMILES: O=C(O)CCCCc1nc2cc(C(=O)c3ccccc3)ccc2nc1-c1ccccc1] | 7-benzoyl-3-phenyl-2-quinoxalinepentanoic acid | 411 |
| 6G | 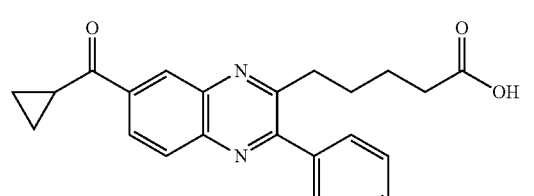 | 7-(cyclopropylcarbonyl)-3-phenyl-2-quinoxalinepentanoic acid | 375 |

In a manner similar to that previously described, 6C was deprotected with TFA to provide 7-(methoxycarbonyl)-3-phenyl-2-quinoxalinepentanoic acid 6H (MS, M+H=365).

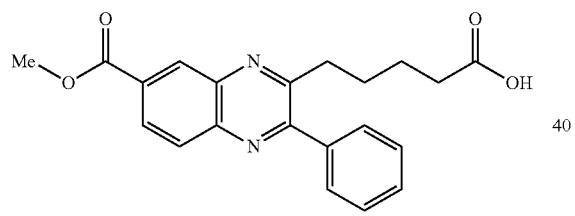

6H

Example 7

-continued

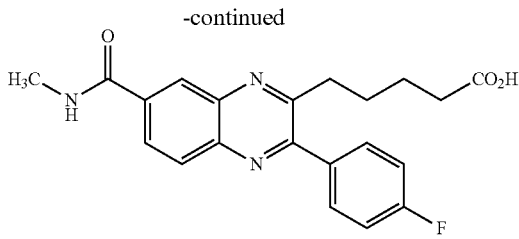

7

Step 1 tert-Butyl 5-[3-(4-Fluorophenyl)-7-(methylcarbamoyl)quinoxalin-2-yl]pentanoate

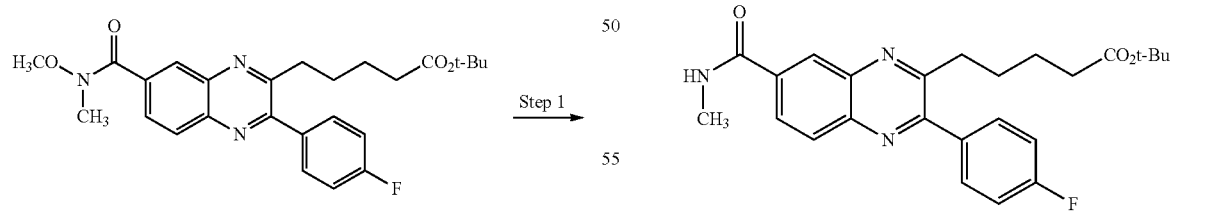

To a stirred solution of 5E (154 mg, 0.329 mmol) in anhydrous THF (5 mL) was added tert-butylmagnesium chloride (2 M in THF, 0.330 mL, 0.660 mmol) at −20° C. under nitrogen. The reaction mixture was slowly warmed to 10° C. over 40 min and then quenched with saturated aqueous NH$_4$Cl. The resulting mixture was extracted with DCM. The combined extracts were dried (Na$_2$SO$_4$), filtered, and concentrated. The residue was purified by column chromatography (50% to 70% EtOAc/heptane) to yield 7A (58 mg, yield=40%): MS (M+H)=438.

Step 2

5-[3-(4-Fluorophenyl)-7-(methylcarbamoyl)quinoxalin-2-yl]pentanoic Acid

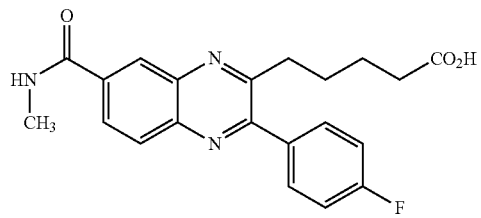

A solution of 7A (58 mg, 0.133 mmol) and TFA (1 mL) in ACM (2 mL) was stirred at RT for 2 h. After this time, the reaction mixture was concentrated and the resulting residue was purified by column chromatography (2% to 10% MeOH/DCM) and lyophilized from $CH_3CN$ (2 mL), $H_2O$ (1 mL), and 1 M $NH_4OH$ (0.2 mL) to yield 3-(4-fluorophenyl)-7-[(methylamino)carbonyl]-2-quinoxalinepentanoic acid 7 (43 mg, yield=81%): MS (M+H)=382.

In a manner similar to that described above, compound 5E was reacted with isopropylmagnesium bromide to provide 7B (MS, M+H=451) and then deprotected with TFA to provide 3-(4-fluorophenyl)-7-(2-methyl-1-oxopropyl)-2-quinoxalinepentanoic acid 7C (MS, M+H=395):

7B

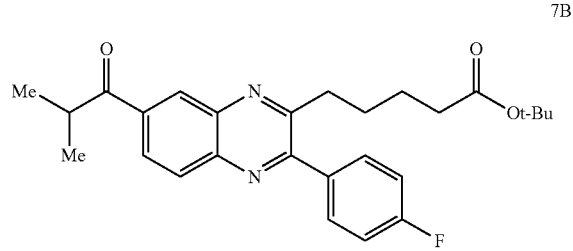

7C

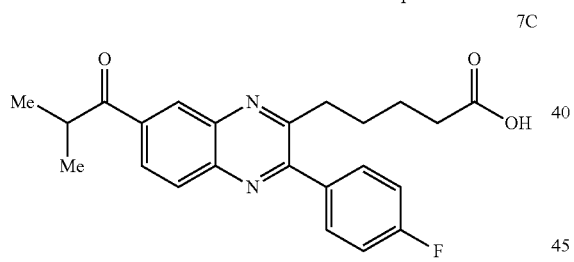

Example 8

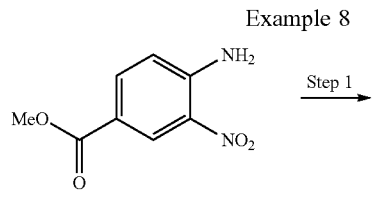

8A

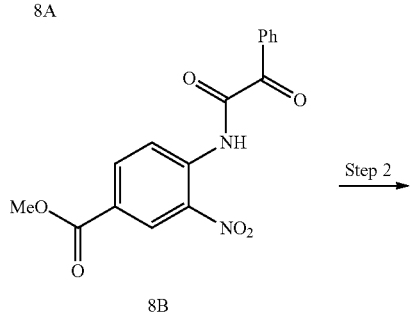

8B

-continued

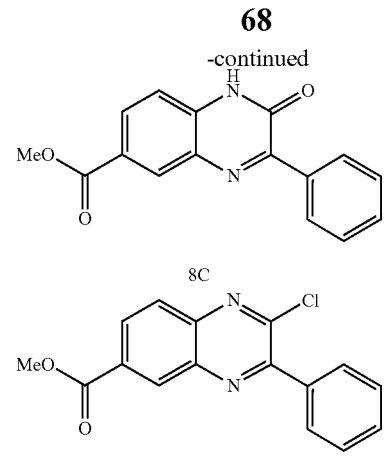

8C

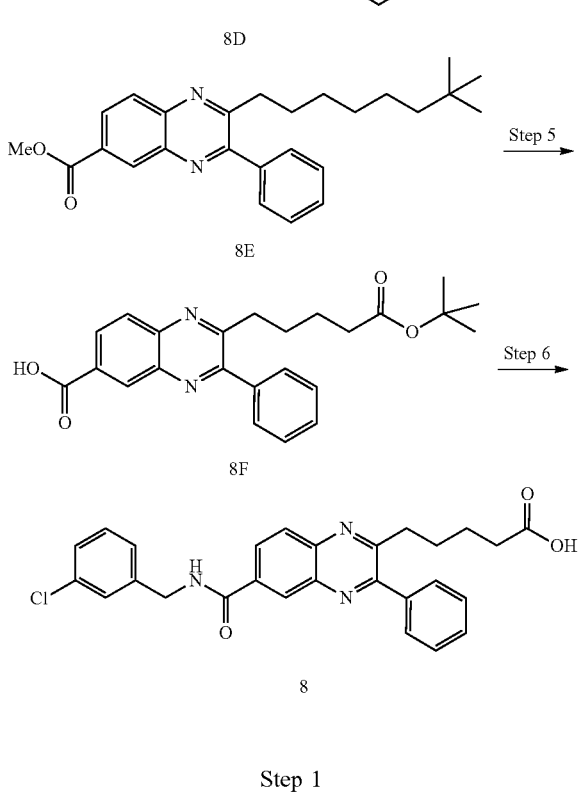

8D

8E

8F

8

Step 1

Methyl 3-Nitro-4-{[oxo(phenyl)acetyl]amino}benzoate

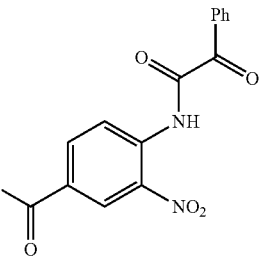

8B

Following the addition of DMF (0.030 mL, 0.382 mmol) to a chilled solution of benzoylformic acid (1.26 g, 8.41 mmol) in THF (19 mL) at 0° C., oxalyl chloride (0.74 mL, 8.4 mmol) was added dropwise (to give vigorous bubbling)

and the reaction mixture was stirred at 0° C. for 30 min, then allowed to warm to RT over 2 h. The reaction solution was then added dropwise to a chilled solution of methyl 4-amino-3-nitrobenzoate (8A, 1.5 g, 7.7 mmol) and triethylamine (2.1 mL, 15 mmol) in THF (57 mL) at 0° C. and allowed to warm to RT overnight. The reaction was partitioned between EtOAc and aqueous NaHCO$_3$ (sat'd). The organics were then washed with brine, dried over Na$_2$SO$_4$, and concentrated to give a yellow solid 8B.

Step 2

Methyl 2-Oxo-3-phenyl-1,2-dihydroquinoxaline-6-carboxylate

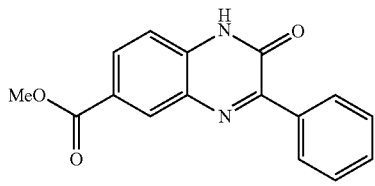

8C

A solution of the yellow solid 8B (2.45 g, 7.46 mmol) and Pt/V (0.73 g, 0.037 mmol) in THF (50 mL) and MeOH (50 mL) was stirred under an atmosphere of hydrogen (balloon) at RT for 30 min. The reaction was filtered through CELITE and concentrated to a yellow solid. Purification by chromatography on SiO$_2$ (0-20% EtOAc/DCM) gave 8C. $^1$H NMR (500 MHz, DMSO-d$_6$) δ 12.85 (s, 1H), 8.33 (s, 1H), 8.29 (d, J=8.1 Hz, 2H), 8.06 (d, J=8.6 Hz, 1H), 7.48-7.52 (m, 3H), 7.39 (d, J=8.6 Hz, 1H), 3.88 (s, 3H); MS (M+H)=281.

Step 3

Methyl 2-Chloro-3-phenylquinoxaline-6-carboxylate

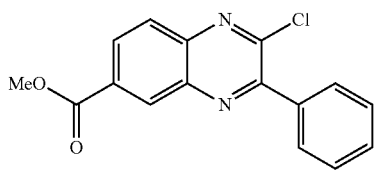

8D

A suspension of 8C (300 mg, 1.1 mmol) in POCl$_3$ (3 mL) was stirred overnight at 110° C. and concentrated to dryness. The residue was dissolved in DCM and extracted with 1 N NaOH, water, dried (Na$_2$SO$_4$), and concentrated. Purification by chromatography on SiO$_2$ (0-50% EtOAc/DCM) gave 8D. $^1$H NMR (500 MHz, CDCl$_3$) δ 8.87 (s, 1H), 8.39 (d, J=8.8 Hz, 1H), 8.11 (d, J=8.6 Hz, 1H), 7.87-7.89 (m, 2H), 7.55-7.56 (m, 3H), 4.02 (s, 3H); MS (M+H)=299.

Step 4

Methyl 2-(5-tert-Butoxy-5-oxopentyl)-3-phenylquinoxaline-6-carboxylate

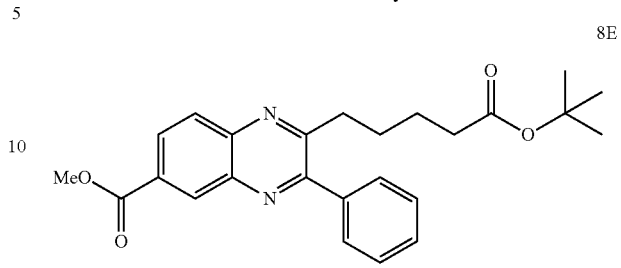

8E

A chilled solution of tert-butyl pent-4-enoate (1, 230 mg, 1.47 mmol) in THF (2 mL) at 0° C. was charged with a 0.5 M solution of 9-BBN in THF (3.0 mL, 1.47 mmol) and stirred at 0° C. for 30 min. The reaction was allowed to warm to RT over 2.5 h, then added to a flask containing 8D (110 mg, 0.368 mmol), PdCl$_2$(dppf)-CH$_2$Cl$_2$ (39 mg, 0.048 mmol), and K$_3$PO$_4$ (190 mg, 0.88 mmol). The new solution was degassed for 15 min by bubbling nitrogen gas, heated to 60° C., and stirred overnight. The reaction was diluted with DCM and water and the layers were then separated. The aqueous layer was then extracted with DCM. Organics were combined, dried (Na$_2$SO$_4$), and concentrated. Chromatography on SiO$_2$ (0-50% EtOAc/hexanes) provided 8E. MS (M+H)=421.

Step 5

2-(5-tert-Butoxy-5-oxopentyl)-3-phenylquinoxaline-6-carboxylic Acid

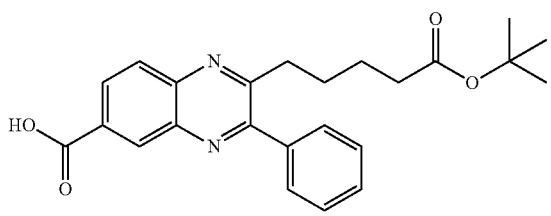

8F

A solution of the methyl ester 5E (85 mg, 0.20 mmol) in 1 mL of THF was charged with a 1 M solution of LiOH in water (1 mL) After stirring for 2 hours, the reaction mixture was diluted with EtOAc, extracted with 1 N HCl, water, dried (Na$_2$SO$_4$) and concentrated to give 8F. MS (M+H)=407.

Step 6

5-(6-{[(3-Chlorobenzyl)oxy]carbonyl}-3-phenylquinoxalin-2-yl)pentanoic Acid

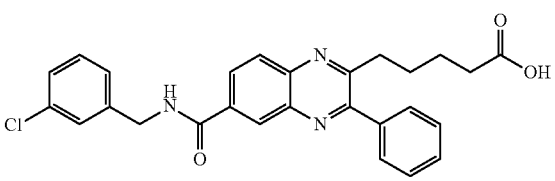

8

A solution of the acid 8F (20 mg, 0.049 mmol), 3-chlorobenzylamine (9 µL, 0.07 mmol), HOBT (11 mg, 0.074 mmol), and EDC (19 mg, 0.098 mmol) in DCM (1 mL) was stirred at RT overnight. The reaction was charged with TFA (160 μL) and stirred for 2 h and concentrated. Reverse phase chromatography (MeCN/water) provided the desired final product 8. ¹H NMR (500 MHz, DMSO-d₆) δ 9.44 (t, J=5.9 Hz, 1H), 8.62 (s, 1H), 8.25 (d, J=8.8 Hz, 1H), 8.14 (d, J=8.8 Hz, 1H), 7.69 (m, 2H), 7.55 (m, 3H), 7.30-7.40 (m, 3H), 4.53 (d, J=6.1 Hz, 2H), 3.02 (t, J=7.4 Hz, 2H), 2.14 (t, J=7.5 Hz, 2H), 1.71 (t, J=7.5 Hz, 2H), 1.46 (m, 2H); MS (M+H)=474.

In a manner similar to that described for the synthesis of 8, compound 8G (MS, M+H=472) was prepared by coupling acid 8F to (R)-1-(4-fluorophenyl)-ethanamine followed by a TFA deprotection

8G

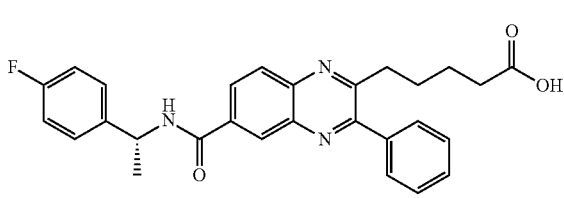

Example 9

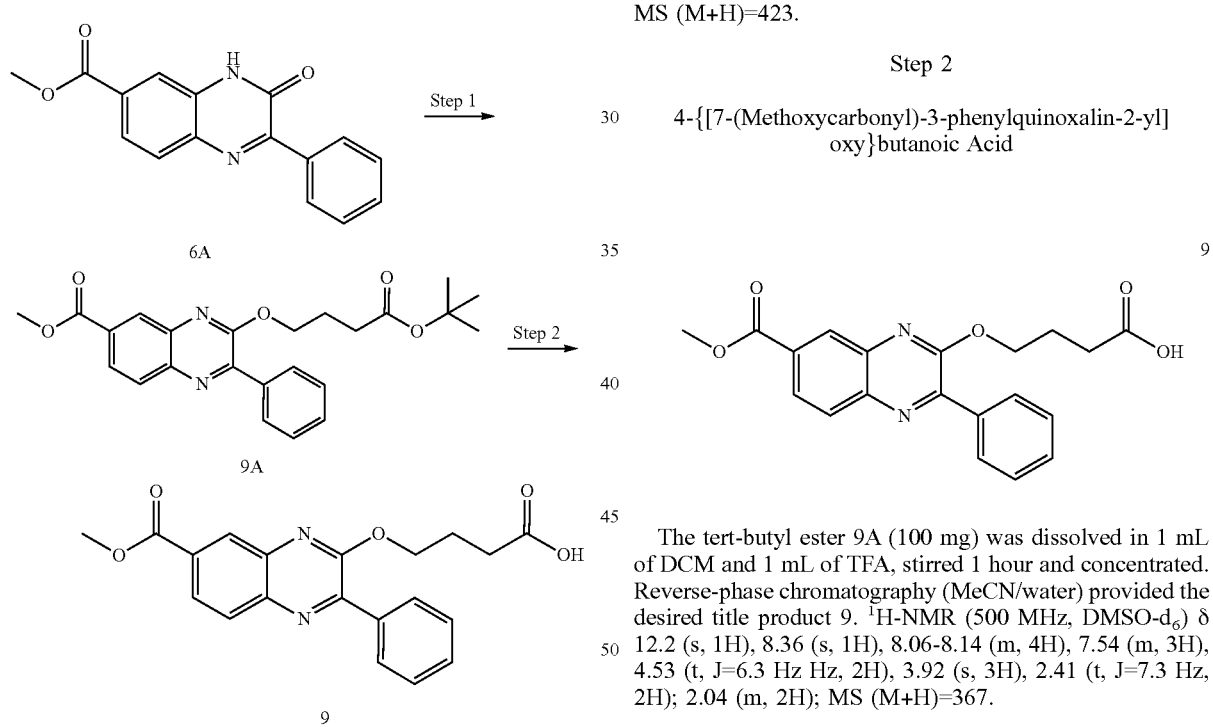

Step 1

Methyl 3-(4-tert-Butoxy-4-oxobutoxy)-2-phenylquinoxaline-6-carboxylate

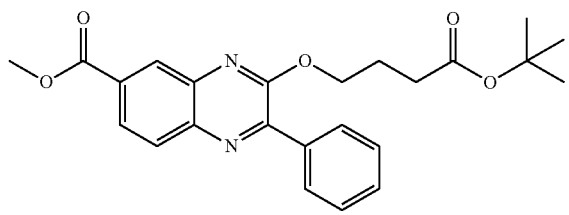

9A

A suspension of 6A (300 mg, 1.1 mmol) and Cs₂CO₃ (500 mg, 1.5 mmol) in 5 mL of DMF was treated with tert-butyl 4-bromobutanoate (300 mg, 1.3 mmol) and stirred for 3 hours at 100° C. Diluted with DCM, extracted with 2 N HCl, water, dried, conc. Chromatography on SiO₂ (0-100% EtOAc/hexanes) gave the desired O-alkylation product 9A along with a small amount of undesired N-alkylated product. MS (M+H)=423.

Step 2

4-{[7-(Methoxycarbonyl)-3-phenylquinoxalin-2-yl]oxy}butanoic Acid

The tert-butyl ester 9A (100 mg) was dissolved in 1 mL of DCM and 1 mL of TFA, stirred 1 hour and concentrated. Reverse-phase chromatography (MeCN/water) provided the desired title product 9. ¹H-NMR (500 MHz, DMSO-d₆) δ 12.2 (s, 1H), 8.36 (s, 1H), 8.06-8.14 (m, 4H), 7.54 (m, 3H), 4.53 (t, J=6.3 Hz Hz, 2H), 3.92 (s, 3H), 2.41 (t, J=7.3 Hz, 2H); 2.04 (m, 2H); MS (M+H)=367.

Example 10

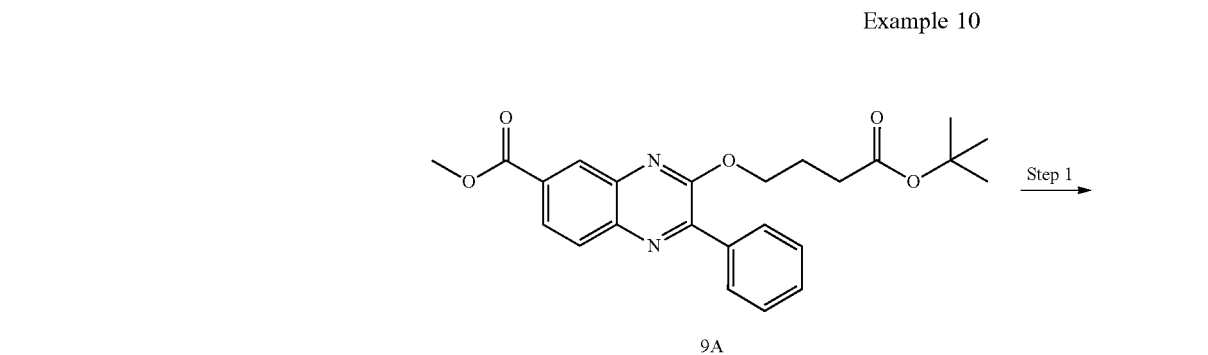

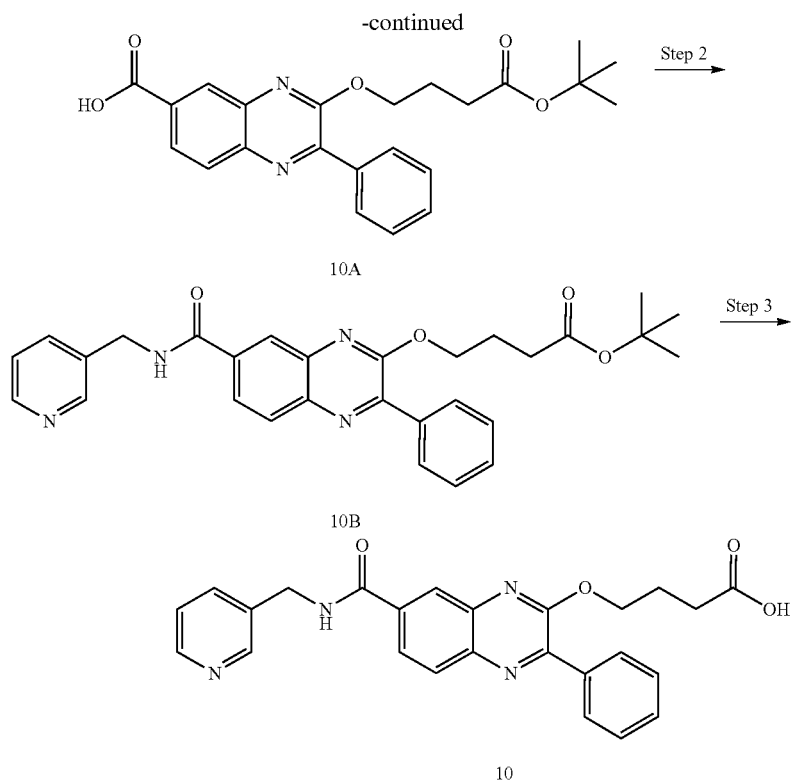

Step 1

3-(4-tert-Butoxy-4-oxobutoxy)-2-phenylquinoxaline-6-carboxylic Acid

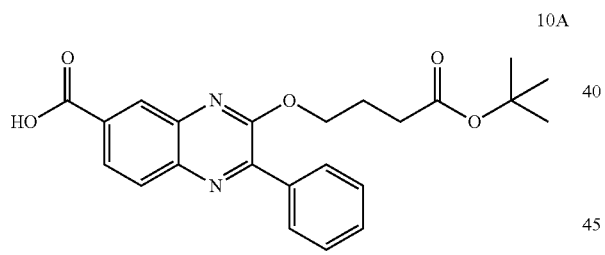

10A

A solution of the methyl ester 9A (200 mg, 0.47 mmol) in 3 mL of THF and 1 mL of water was treated with LiOH (20 mg, 0.84 mmol) and stirred overnight. The reaction mixture was diluted with DCM and extracted with 1 N HCl, water, dried (Na$_2$SO$_4$), and concentrated to provide the intermediate acid 10A.

Step 2 tert-Butyl 4-({3-Phenyl-7-[(pyridin-3-ylmethyl)car-bamoyl]quinoxalin-2-yl}oxy)butanoate

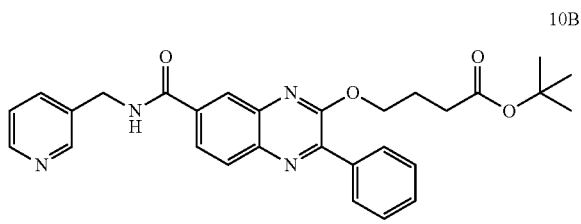 [SMILES: CC(C)(C)OC(=O)CCCOc1nc2cc(C(=O)NCc3cccnc3)ccc2nc1-c1ccccc1]

10B

A solution of the acid 10A (20 mg, 0.05 mmol), 1-(pyridin-3-yl)methanamine (15 mg, 0.14 mmol), EDC (20 mg, 0.10 mmol) and HOBt (10 mg, 0.065 mmol) in 1 mL of DCM was stirred overnight. The reaction mixture was diluted with EtOAc, washed with 2 N HCl, 2 N NaOH, and water, dried (Na$_2$SO$_4$), and concentrated to provide 10B.

Step 3

4-({3-Phenyl-7-[(pyridin-3-ylmethyl)carbamoyl]quinoxalin-2-yl}oxy)butanoic Acid

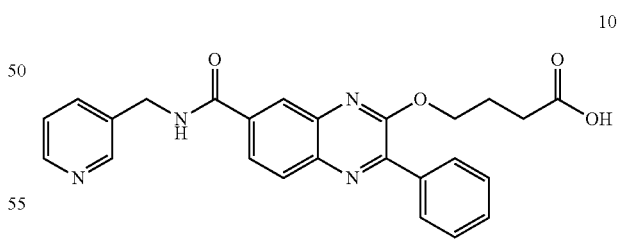

10

A solution of the intermediate tert-butyl ester 10B (24 mg) in 1 mL of DCM and 1 mL of TFA was stirred for 1 hour and concentrated. The residue was purified by reverse phase chromatography (MeCN/water) to provide the final acid 10. MS (M+H)=443.

In a manner similar to that described for the synthesis of 10, the following compounds were prepared by coupling acid 10A to the appropriate amine reagent followed by a TFA deprotection:

| No. | Reagent | Compound Structure | Name | M + H |
|---|---|---|---|---|
| 10C | (4-chlorobenzyl)amine | 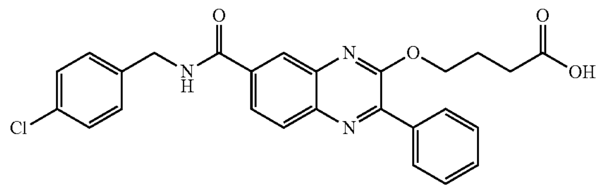 [SMILES: O=C(O)CCCOc1nc2cc(C(=O)NCc3ccc(Cl)cc3)ccc2nc1-c1ccccc1] | 4-({7-[(4-chlorobenzyl)carbamoyl]-3-phenylquinoxalin-2-yl}oxy)butanoic acid | 476 |
| 10D | (S)-1-phenylethylamine | 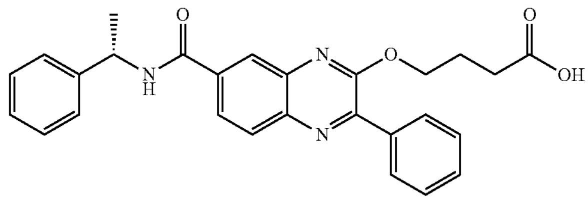 [SMILES: C[C@H](NC(=O)c1ccc2nc(-c3ccccc3)c(OCCCC(=O)O)nc2c1)c1ccccc1] | 4-[(3-phenyl-7-{[(1S)-1-phenylethyl]carbamoyl}quinoxalin-2-yl)oxy]butanoic acid | 456 |
| 10E | N-methylbenzylamine | 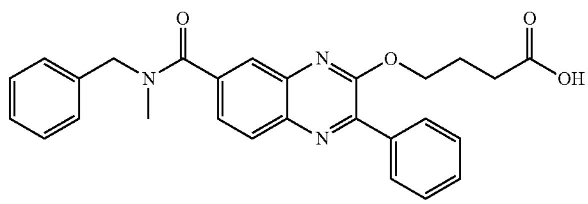 | 4-({7-[benzyl(methyl)carbamoyl]-3-phenylquinoxalin-2-yl}oxy)butanoic acid | 456 |
| 10F | 1,2,3,4-tetrahydroisoquinoline | 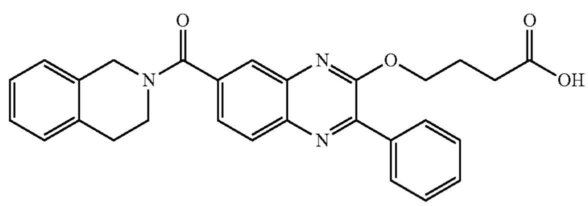 [SMILES: O=C(O)CCCOc1nc2cc(C(=O)N3CCc4ccccc4C3)ccc2nc1-c1ccccc1] | 4-{[7-(3,4-dihydroisoquinolin-2(1H)-ylcarbonyl)-3-phenylquinoxalin-2-yl]oxy}butanoic acid | 468 |

Example 11

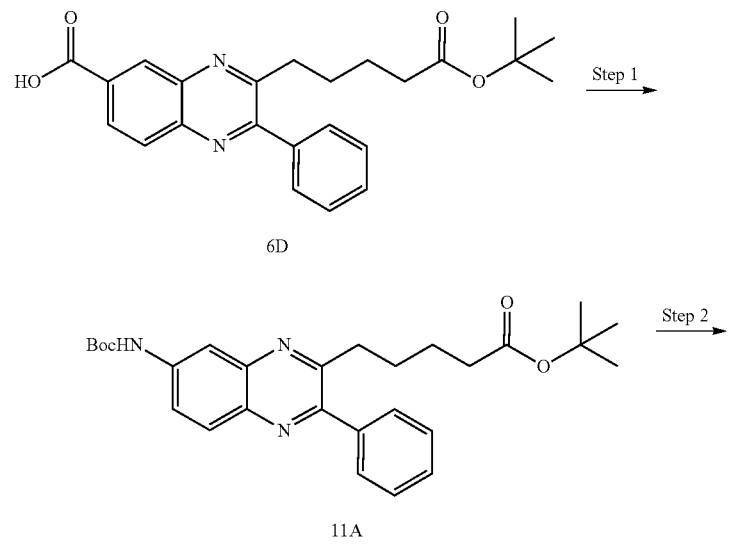

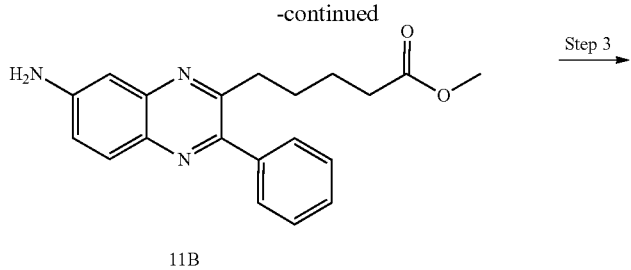

11B

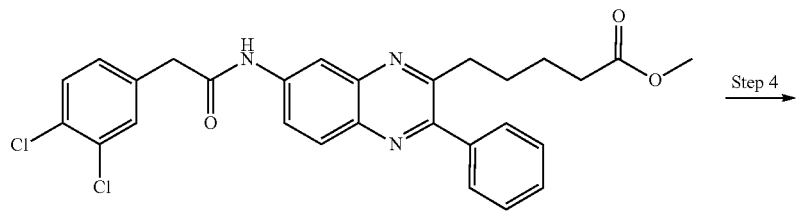

11C

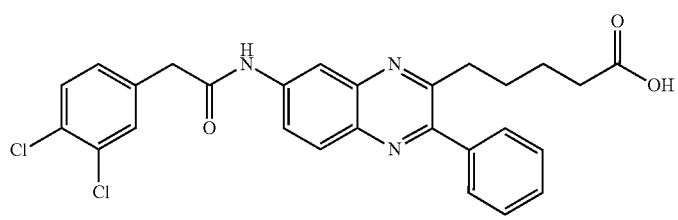

11

Step 1 tert-Butyl 5-{7-[(tert-Butoxycarbonyl)amino]-3-phenylquinoxalin-2-yl}pentanoate

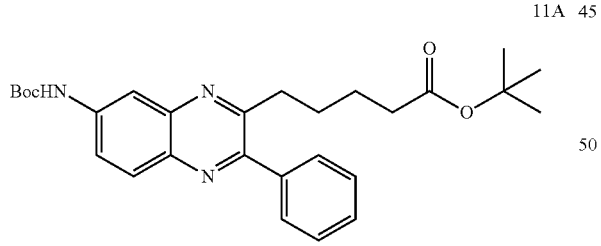

11A

To a flask containing 3-(5-tert-butoxy-5-oxopentyl)-2-phenylquinoxaline-6-carboxylic acid 6D (0.8 g, 1.97 mmol) was added tBuOH (13 mL), Et₃N (6.0 eq), and diphenylphosphoryl azide (2.0 eq). The mixture was heated at reflux for 20 h. The mixture was cooled to RT, and concentrated to remove most of tBuOH, then diluted with EtOAc and sat. NaHCO₃. The organic layer was separated and the aqueous layer was extracted with EtOAc. The combined organic layers were washed with brine, dried over MgSO₄. Concentration and flash chromatography (0-15% EtOAc/CH₂Cl₂) gave 11A. MS (M+H)=478.

Step 2

Methyl 5-(7-amino-3-phenylquinoxalin-2-yl)pentanoate

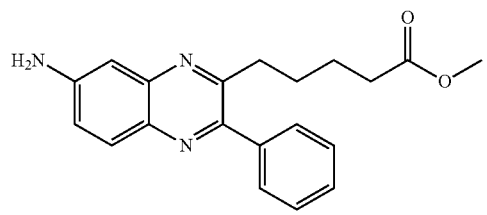

11B

To a solution tert-butyl 5-{7-[(tert-butoxycarbonyl)amino]-3-phenylquinoxalin-2-yl}pentanoate 11A (0.5 g, 1.1 mmol) in DCM (6 mL) at RT was added. TFA (2 mL), and the mixture was stirred at RT for 4 h. The mixture was concentrated under reduced pressure and the crude residue was taken up in MeOH (0.15M). Then SOCl₂ (3 eq) was added at 0° C. and the reaction mixture was stirred at the same temperature for 1.5 h. The mixture was then diluted with EtOAc, and quenched slowly with sat. NaHCO₃. The organic layer was separated, and the aqueous layer was extracted with EtOAc. The combined organics were washed with H₂O, brine, and dried over MgSO₄. Concentration afforded the title compound, which was contaminated by some minor impurities. This material 11B was used for next step without purification. MS (M+H)=336.

Step 3

Methyl 5-(7-{[(3,4-Dichlorophenyl)carbonyl]amino}-3-phenylquinoxalin-2-yl)pentanoate

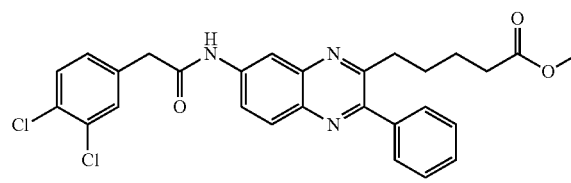

To a solution of methyl 5-(7-amino-3-phenylquinoxalin-2-yl)pentanoate 11B (50 mg, 0.15 mmol) in CH₂Cl₂ (2 mL) was added 3,4-dichlorophenylacetic acid (1.0 eq), Hunig's Base (3.0 eq), HOBt (1.2 eq), and EDC (1.4 eq). The mixture was stirred at ambient temperature overnight, and purified without workup by flash chromatography to afford 11C. MS (M+H)=522.

Step 4

5-(7-{[(3,4-Dichlorophenyl)carbonyl]amino}-3-phenylquinoxalin-2-yl)pentanoic Acid

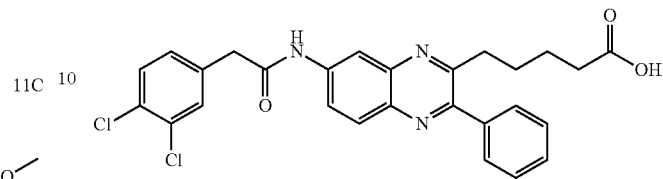

To a solution of methyl 5-(7-{[(3,4-dichlorophenyl)carbonyl]amino}-3-phenylquinoxalin-2-yl)pentanoate 11C (68 mg, 0.13 mmol) in a mixture of THF (1.5 mL) and MeOH (0.7 mL) was added 1N NaOH (3 eq). The mixture was stirred at RT for 4 h, and then acidified with 1N HCl. The mixture was purified by reverse chromatography (MeCN/water) to provide the desired acid 11. $^1$H-NMR (600 MHz, DMSO-$d_6$) δ 12.0 (brs, 1H), 10.72 (s, 1H), 8.52 (s, 1H), 8.03 (d, J=9.0 Hz, 1H), 7.86 (d, J=7.8 Hz, 1H), 7.62-7.70 (m, 4H), 7.52-7.60 (m, 3H), 7.40 (d, J=8.4 Hz, 1H), 3.85 (s, 2H), 2.99 (t, J=7.2 Hz, 2H), 2.17 (t, J=7.2 Hz, 2H), 1.69-1.74 (m, 2H), 1.45-1.51 (m, 2H). MS (M+H)=508.

In a manner similar to that described for the synthesis of 11, the following compounds were prepared by coupling aniline 11B to the appropriate acid reagent followed by ester hydrolysis:

| No. | Reagent | Compound Structure | Name | M + H |
|---|---|---|---|---|
| 11D | | 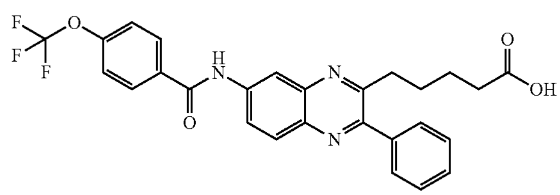 [SMILES: O=C(O)CCCCc1nc2cc(NC(=O)c3ccc(OC(F)(F)F)cc3)ccc2nc1-c1ccccc1] | 5-[3-phenyl-7-({[4-(trifluoromethoxy)phenyl]carbonylamino)quinoxalin-2-yl]pentanoic acid | 510 |
| 11E | | 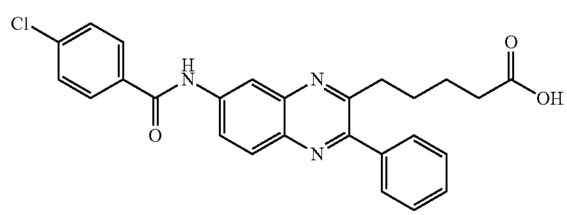 [SMILES: O=C(O)CCCCc1nc2cc(NC(=O)c3ccc(Cl)cc3)ccc2nc1-c1ccccc1] | 5-(7-{[(4-chlorophenyl)carbonyl]amino}-3-phenyl-quinoxalin-2-yl)pentanoic acid | 460 |
| 11F | | 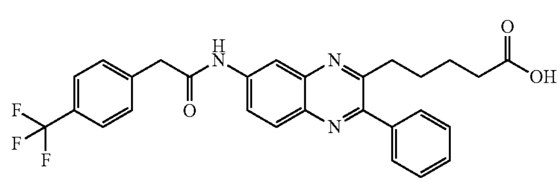 [SMILES: O=C(O)CCCCc1nc2cc(NC(=O)Cc3ccc(C(F)(F)F)cc3)ccc2nc1-c1ccccc1] | 5-[3-phenyl-7-({[4-(trifluoromethyl)phenyl]acetyl}amino)quinoxalin-2-yl]pentanoic acid | 508 |

Example 12

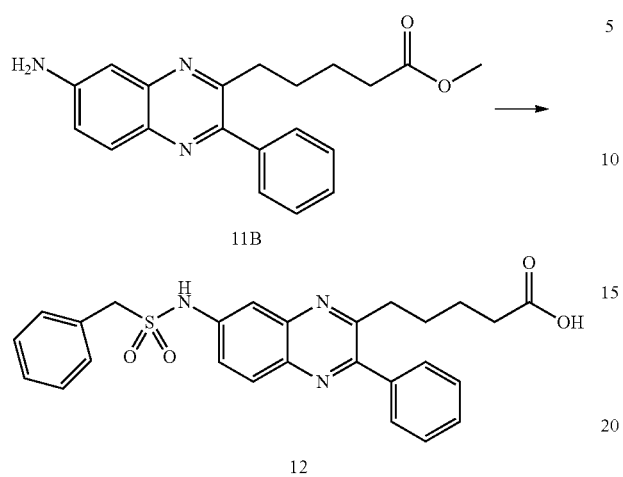

Triethylamine (0.083 mL, 0.596 mmol) and alpha-toluenesulfonyl chloride (56.8 mg, 0.298 mmol) were added to methyl 5-(7-amino-3-phenylquinoxalin-2-yl)pentanoate (11B, 50 mg, 0.149 mmol) stirred in $CH_2Cl_2$ (1 mL) and the mixture was stirred at RT for 1 h. The reaction was then concentrated. The residue was then diluted with THF and NaOH (0.5 mL, 0.500 mmol) along with MeOH (0.05) were then added. The mixture was stirred at RT for overnight. The next day the reaction was concentrated in vacuo and then 1N HCl (0.5 mL) was added before the reaction was concentrated again. The residue was then diluted with MeOH and purified (reversed phase C18 HPLC eluting with 1% TFA acetonitrile/water gradient and then column chromatography on silica gel Biotage SNAP KP-Sil 10 g, eluting with EtOAc/hexanes and flushed with 5% MeOH/ethyl acetate) to provide 5-{7-[(benzylsulfonyl)amino]-3-phenylquinoxalin-2-yl}pentanoic Acid (12). $^1$H NMR (600 MHz, $CDCl_3$) δ 8.01 (d, J=8.9 Hz, 1H), 7.83 (d, J=2.4 Hz, 1H), 7.56 (d, J=6.9 Hz, 2H), 7.44-7.50 (m, 3H), 7.42 (dd, J=9.0, 2.4 Hz, 1H), 7.20-7.36 (m, 6H), 4.44 (s, 2H), 3.02 (dd, J=17.3, 9.5 Hz, 2H), 2.22-2.35 (m, 2H), 1.72-1.83 (m, 2H), 1.56-1.67 (m, 2H). MS (M+H)=476.

Example 13

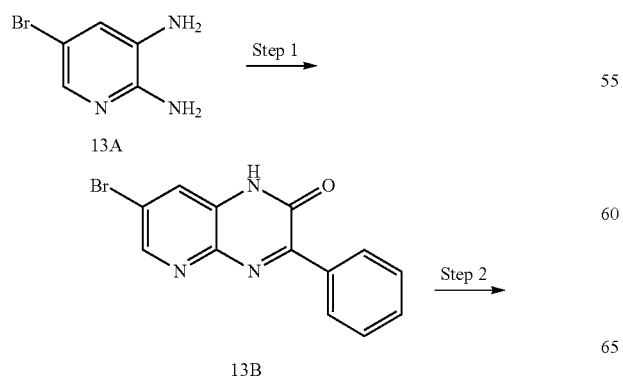

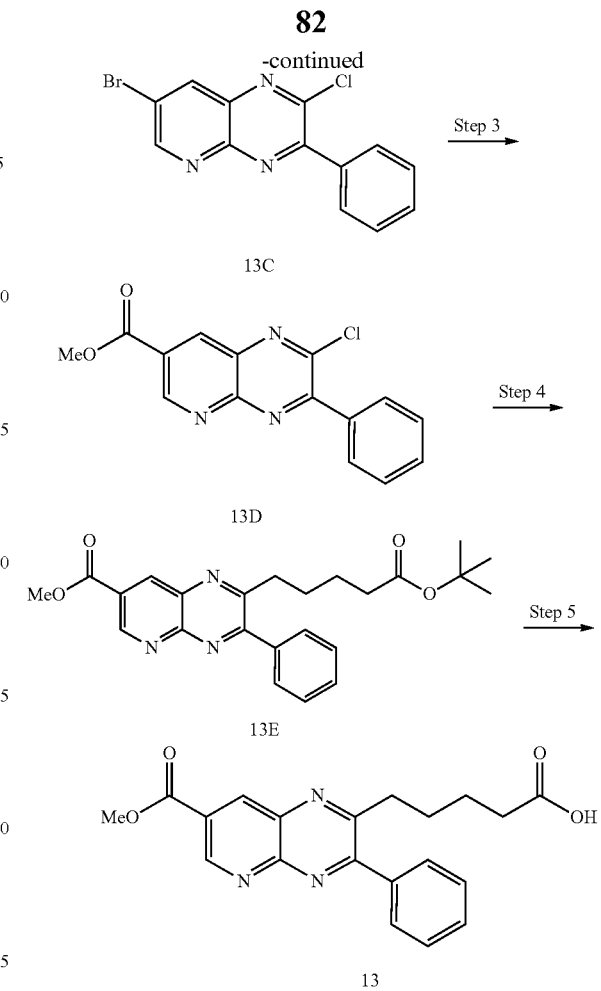

Step 1

7-Bromo-3-phenylpyrido[2,3-b]pyrazin-2(1H)-one

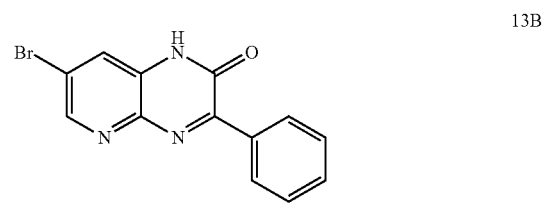 [SMILES: O=c1[nH]c2cc(Br)cnc2nc1-c1ccccc1]

To a solution of benzoylformic acid (4.0 g, 27 mmol) in $CH_2Cl_2$ was added catalytic DMF (0.05 eq), followed by the addition of oxalyl chloride (1.0 eq) slowly. The reaction mixture was stirred for 4 h, and then concentrated under reduced pressure. The residue was taken up in THF (20 mL) and the resulting solution was added slowly to a mixture of 5-bromopyridine-2,3-diamine (13A, 1.0 eq) and $Et_3N$ (1.0 eq) in THF (100 mL) at 0° C. The reaction mixture was kept stirring at 0° C. for 30 min, then RT for 2 h, then heated at reflux overnight. The reaction mixture was cooled to RT, diluted with aqueous $NaHCO_3$ and $CH_2Cl_2$. The organic layer was separated, and the aqueous layer was extracted with $CH_2Cl_2$. The combined organics were washed with H₂O, brine, dried over MgSO₄, and concentrated. To the resultant viscous dark oil was added CH₂Cl₂ (~80 mL), stirred vigorously for 15 min. The mixture was filtered and the brown solid obtained was washed with CH₂Cl₂ to give 13B, which was contaminated by some minor impurities. This material was used for next step without purification. ¹H-NMR (600 MHz, DMSO-d₆) δ 12.7 (s, 1H), 8.58 (s, 1H), 8.28-8.30 (m, 2H), 7.83 (s, 1H), 7.45-7.55 (m, 3H). MS (M+H)=302.

Step 2

7-Bromo-2-chloro-3-phenylpyrido[2,3-b]pyrazine

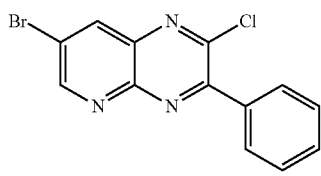

13C

To a flask containing 7-bromo-3-phenylpyrido[2,3-b]pyrazin-2(1H)-one (13B, 1.2 g, 4.0 mmol) was added phosphorus oxychloride (20 eq), and the mixture was heated at reflux for 2 h. The reaction mixture was then cooled to RT, slowly poured a beaker containing aqueous NaHCO₃ solution, and extracted with CH₂Cl₂. The combined organics were washed with H₂O, brine, dried over MgSO₄. Concentration and purification by flash chromatography 13C which was contaminated by some minor impurities. The pure title compound was obtained through recrystallization from EtOAc. MS (M+H)=320.

Step 3

Methyl 2-Chloro-3-phenylpyrido[2,3-b]pyrazine-7-carboxylate

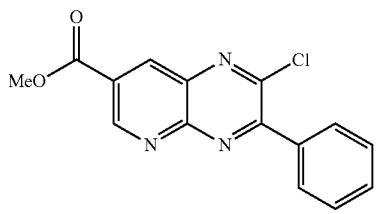

13D

To a flask containing a solution of 7-bromo-2-chloro-3-phenylpyrido[2,3-b]pyrazine (13C, 1 g, 3.1 mmol) in dioxane (20 mL) was added Et₃N (10 mL) and MeOH (10 eq). The mixture was degassed by bubbling N₂ for 10 min. Then Pd(OAc)₂ (0.1 eq) and xanphos (0.2 eq) were added, and a balloon filled with CO (g) was connected to the reaction flask via three-way adapter. The mixture was vacuumed and back-filled with CO(g) three times from CO(g) balloon. The mixture was then heated at 70° C. overnight. The reaction mixture was cooled to RT, diluted with CH₂Cl₂, and aqueous NaHCO₃. The organic layer was separated, and the aqueous layer was extracted with CH₂Cl₂. The combined organics were washed with brine, dried over MgSO₄. Concentration and flash chromatography afforded 13D. ¹H-NMR (600 MHz, CDCl₃) δ 9.70 (d, J=2.4 Hz, 1H), 9.15 (d, J=2.4 Hz, 1H), 8.01-8.03 (m, 2H), 7.54-7.60 (m, 3H), 4.07 (s, 3H). MS (M+H)=300.

Step 4

Methyl 2-(5-tert-Butoxy-5-oxopentyl)-3-phenylpyrido[2,3-b]pyrazine-7-carboxylate

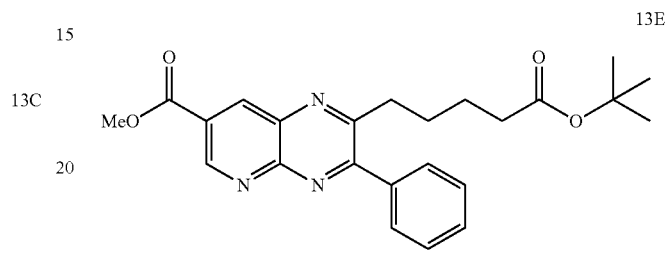

13E

To a solution of tert-butyl pent-4-enoate (0.47 g, 3.0 mmol) in 3 mL THF at 0° C. was added 0.5 M 9-BBN in THF (1.05 eq) dropwise, and the reaction mixture was stirred at 0° C. for 30 min, then RT for 3 h.

To a microwave reaction vessel containing ethyl 2-chloro-3-phenylpyrido[2,3-b]pyrazine-7-carboxylate (13D, 0.28 g, 0.95 mmol) in THF (0.3 M) was added K₃PO₄.H₂O (2.5 eq), and a solution of alkyl 9-BBN reagent from pot above (1.8 eq). The mixture was degassed by bubbling argon for 10 min. Then Pd(OAc)₂ (0.08 eq) and S-Phos (0.16 eq) was added, and the mixture was heated at 70° C. for 1.5 h. The reaction mixture was cooled to RT, diluted with aq. NaHCO₃, and extracted with EtOAc. The combined organics were washed with brine, dried over MgSO₄. Concentration and flash chromatography gave 13E. MS (M+H)=422.

Step 5

5-[7-(Methoxycarbonyl)-3-phenylpyrido[2,3-b]pyrazin-2-yl]pentanoic Acid

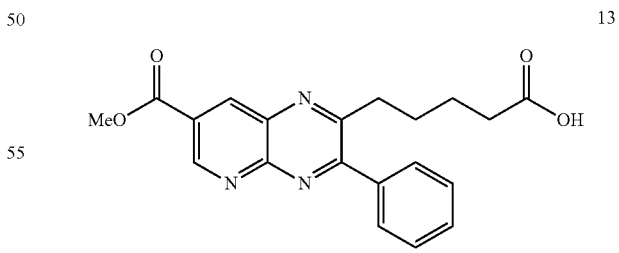

13

To a solution of methyl 2-(5-tert-butoxy-5-oxopentyl)-3-phenylpyrido[2,3-b]pyrazine-7-carboxylate (13E, 35 mg, 0.08 mmol) in CH₂Cl₂ (2.0 mL) was added TFA (0.5 mL). The reaction mixture was stirred at RT for 4 h. The mixture was concentrated, and minimal amount of THF was added. The title compound precipitated 13 and was collected through filtration. MS (M+H)=366.

Example 14

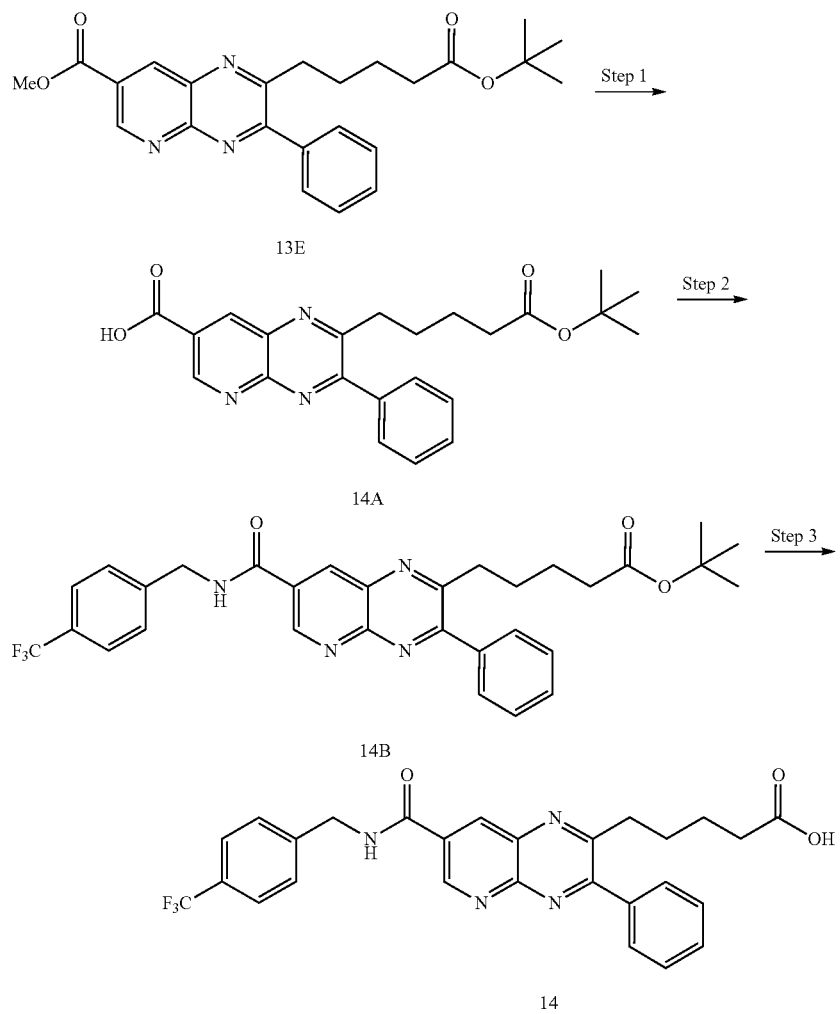

Step 1

Methyl 2-(5-tert-Butoxy-5-oxopentyl)-3-phenylpyrido[2,3-b]pyrazine-7-carboxylate

Step 2 tert-Butyl 5-(3-Phenyl-7-{[4-(trifluoromethyl)benzyl]carbamoyl}pyrido[2,3-b]pyrazin-2-yl)pentanoate

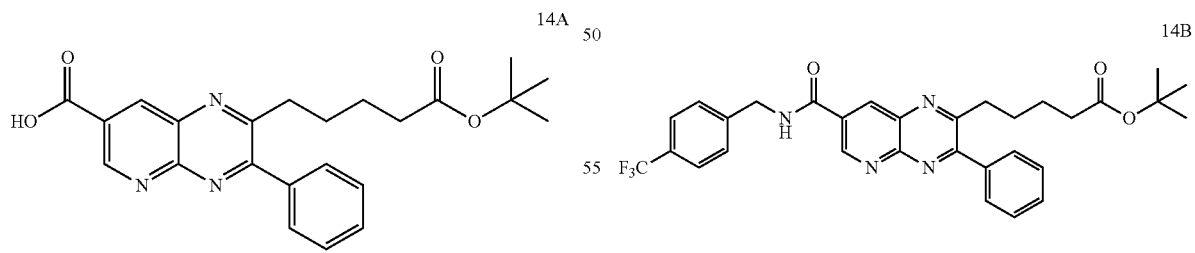

To a solution of methyl 2-(5-tert-butoxy-5-oxopentyl)-3-phenylpyrido[2,3-b]pyrazine-7-carboxylate (13E, 0.25 g, 0.60 mmol) in a mixture of THF/H$_2$O (3.0 mL/I 5 mL) was added LiOH (2.0 eq), and the mixture was stirred at RT for 3 h. The mixture was then diluted with EtOAc and H$_2$O, and acidified with 1N HCl to pH=3~4. The organic layer was separated, washed with brine, dried over MgSO$_4$. Concentration afforded the desired carboxylic acid 14A, which was used for next step without purification.

To a flask containing the carboxylic acid 14A (40 mg, 0.1 mmol) in DMF (0.05) was added amine (1.5 eq), Hunig's Base (3.0 eq), HOBT (1.7 eq), and EDC (1.3 eq). The mixture was stirred at ambient temperature overnight. The mixture was purified by flash chromatography to afford 14B. $^1$H-NMR (600 MHz, CDCl$_3$) δ 9.49 (s, 1H), 8.75 (d, J=2.0 Hz, 1H), 7.46-7.63 (m, 10H), 7.24 (d, J=2.0 Hz, 1H), 4.74 (d, J=5.4 Hz, 2H), 3.08 (t, J=7.2 Hz, 2H), 2.15 (t, J=7.2 Hz, 2H), 1.75-1.80 (m, 2H), 1.54-1.58 (m, 2H). MS (M+H)=565.

Step 3

5-(3-Phenyl-7-{[(4-(trifluoromethyl)benzyl]carbamoyl}pyrido[2,3-b]pyrazin-2-yl)pentanoic Acid

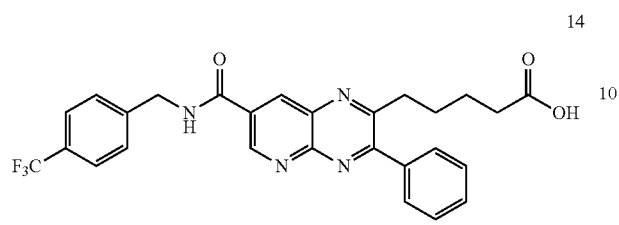

14

To a solution of [tert-butyl 5-(3-phenyl-7-{[4-(trifluoromethyl)benzyl]-carbamoyl}pyrido[2,3-b]pyrazin-2-yl)pentanoate (14B, 41 mg, 0.07 mmol) in DCM (2 mL) at RT was added TFA (0.5 mL), and the mixture was stirred at RT for 3 h. The mixture was concentrated, and the title compound 14 precipitated out after the addition of minimal amount of $Et_2O$, which was collected by filtration. MS (M+H)=509.

In a manner similar to that described for the synthesis of 14, the following compounds were prepared by coupling acid 14A to the appropriate amine reagent followed by a TFA deprotection:

| No. | Reagent | Compound Structure | Name | M + H |
|---|---|---|---|---|
| 14C | | 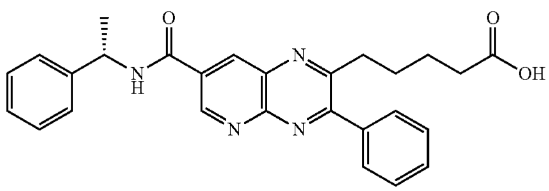 [SMILES: C[C@H](NC(=O)c1cnc2nc(-c3ccccc3)c(CCCCC(=O)O)nc2c1)c1ccccc1] | 5-(3-phenyl-7-{[(1S)-1-phenylethyl]carbamoyl}pyrido[2,3-b]pyrazin-2-yl)pentanoic acid | 455 |
| 14D | | 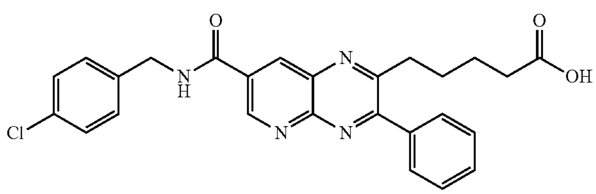 [SMILES: O=C(O)CCCCc1nc2cc(C(=O)NCc3ccc(Cl)cc3)cnc2nc1-c1ccccc1] | 5-{7-[(4-chlorobenzyl)-carbamoyl]-3-phenylpyrido[2,3-b]pyrazin-2-yl}pentanoic acid | 475 |
| 14E | | 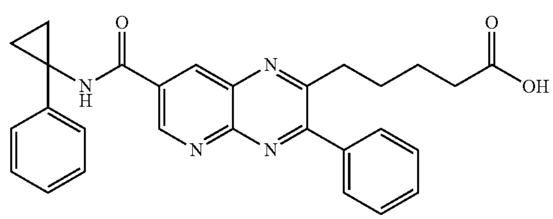 [SMILES: O=C(O)CCCCc1nc2cc(C(=O)NC3(c4ccccc4)CC3)cnc2nc1-c1ccccc1] | 5-{3-phenyl-7-[(1-phenylcyclopropyl)carbamoyl]-pyrido[2,3-b]pyrazin-2-yl}pentanoic acid | 467 |
| 14F | | 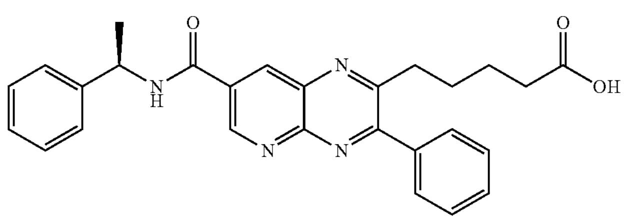 [SMILES: C[C@@H](NC(=O)c1cnc2nc(-c3ccccc3)c(CCCCC(=O)O)nc2c1)c1ccccc1] | 5-(3-phenyl-7-{[(1R)-1-phenylethyl]carbamoyl}pyrido[2,3-b]pyrazin-2-yl)pentanoic acid | 455 |
| 14G | | 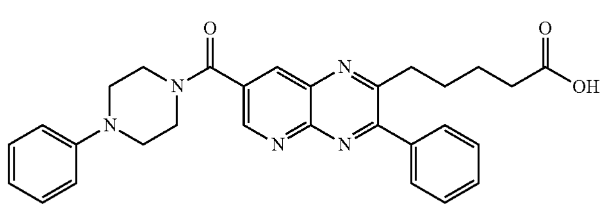 [SMILES: O=C(O)CCCCc1nc2cc(C(=O)N3CCN(c4ccccc4)CC3)cnc2nc1-c1ccccc1] | 5-{3-phenyl-7-[(4-phenylpiperazin-1-yl)carbonyl]pyrido[2,3-b]pyrazin-2-yl}pentanoic acid | 496 |

-continued

| No. | Reagent | Compound Structure | Name | M + H |
|---|---|---|---|---|
| 14H | 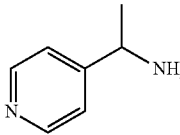 | 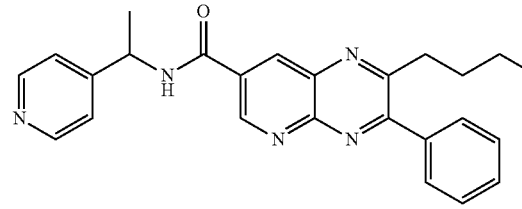 | 5-{3-phenyl-7-[(1-pyridin-4-ylethyl)carbamoyl]pyrido[2,3-b]pyrazin-2-yl}pentanoic acid | 456 |

Example 15

15

In a manner similar to that described for the synthesis of 3A, the following compounds were prepared by coupling acid 6D to the appropriate amine reagent followed by a TFA deprotection:

| No. | Reagent | Compound Structure | Name | M + H |
|---|---|---|---|---|
| 15A | 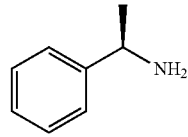 | 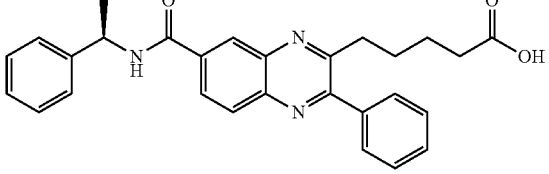 | 5-(3-phenyl-7-{[(1R)-1-phenylethyl]carbamoyl}quinoxalin-2-yl)pentanoic acid | 454 |
| 15B | 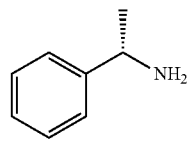 | 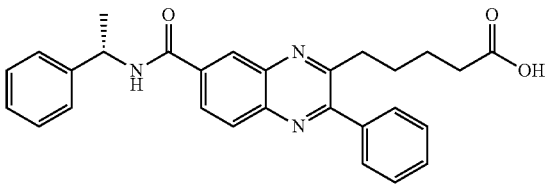 [SMILES: C[C@H](NC(=O)c1ccc2nc(-c3ccccc3)c(CCCCC(=O)O)nc2c1)c1ccccc1] | 5-(3-phenyl-7-{[(1S)-1-phenylethyl]carbamoyl}quinoxalin-2-yl)pentanoic acid | 454 |
| 15C | 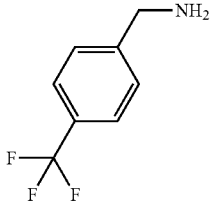 [SMILES: NCc1ccc(C(F)(F)F)cc1] | 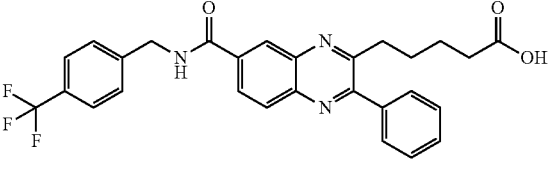 [SMILES: O=C(O)CCCCc1nc2cc(C(=O)NCc3ccc(C(F)(F)F)cc3)ccc2nc1-c1ccccc1] | 5-(3-phenyl-7-{[4-(trifluoromethyl)benzyl]carbamoyl}quinoxalin-2-yl)pentanoic acid | 508 |
| 15D | 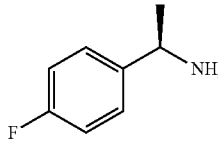 | 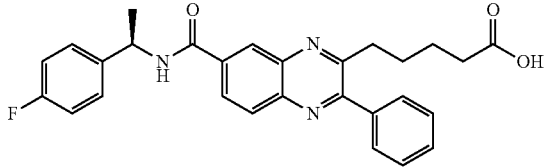 [SMILES: C[C@@H](NC(=O)c1ccc2nc(-c3ccccc3)c(CCCCC(=O)O)nc2c1)c1ccc(F)cc1] | 5-(7-{[(1R)-1-(4-fluorophenyl)ethyl]carbamoyl}-3-phenyl-quinoxalin-2-yl)pentanoic acid | 472 |
| 15E | 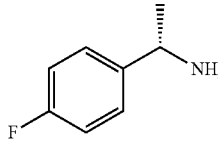 | 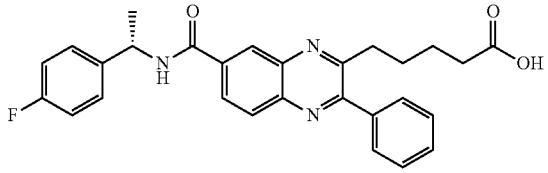 [SMILES: C[C@H](NC(=O)c1ccc2nc(-c3ccccc3)c(CCCCC(=O)O)nc2c1)c1ccc(F)cc1] | 5-(7-{[(1S)-1-(4-fluorophenyl)ethyl]carbamoyl}-3-phenylquinoxalin-2-yl)pentanoic acid | 472 |

-continued

| No. | Reagent | Compound Structure | Name | M + H |
|---|---|---|---|---|
| 15F | 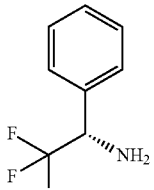 | 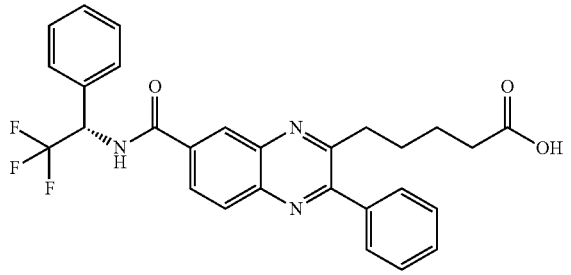 [SMILES: O=C(O)CCCCc1nc2cc(C(=O)N[C@@H](c3ccccc3)C(F)(F)F)ccc2nc1-c1ccccc1] | 5-(3-phenyl-7-{[(1S)-2,2,2-trifluoro-1-phenylethyl]carbamoyl}quinoxalin-2-yl)pentanoic acid | 508 |
| 15G | 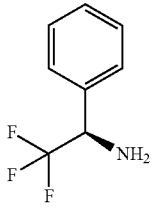 | 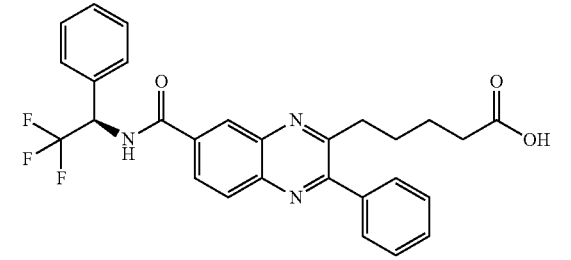 [SMILES: O=C(O)CCCCc1nc2cc(C(=O)N[C@H](c3ccccc3)C(F)(F)F)ccc2nc1-c1ccccc1] | 5-(3-phenyl-7-{[(1R)-2,2,2-trifluoro-1-phenylethyl]carbamoyl}quinoxalin-2-yl)pentanoic acid | 508 |
| 15H | 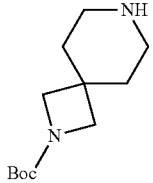 | 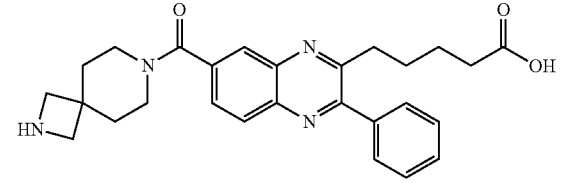 [SMILES: O=C(O)CCCCc1nc2cc(C(=O)N3CCC4(CC3)CNC4)ccc2nc1-c1ccccc1] | 5-[7-(2,7-diazaspiro[3.5]non-7-ylcarbonyl)-3-phenylquinoxalin-2-yl]pentanoic acid | 459 |
| 15i | 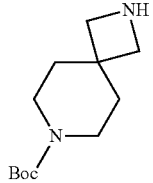 | 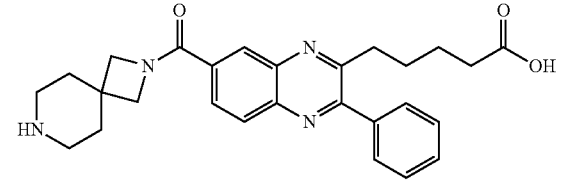 [SMILES: O=C(O)CCCCc1nc2cc(C(=O)N3CC4(CCNCC4)C3)ccc2nc1-c1ccccc1] | 5-[7-(2,7-diazaspiro[3.5]non-2-ylcarbonyl)-3-phenylquinoxalin-2-yl]pentanoic acid | 459 |
| 15J | 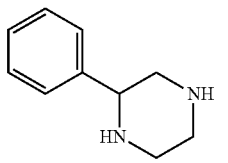 [SMILES: c1ccc(C2CNCCN2)cc1] | 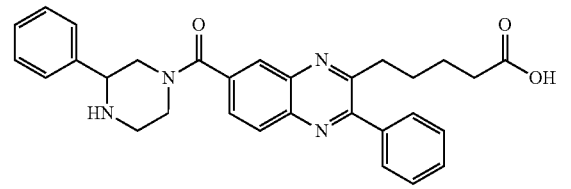 [SMILES: O=C(O)CCCCc1nc2cc(C(=O)N3CCNC(c4ccccc4)C3)ccc2nc1-c1ccccc1] | 5-{3-phenyl-7-[(3-phenylpiperazin-1-yl)carbonyl]quinoxalin-2-yl}pentanoic acid | 495 |
| 15K | 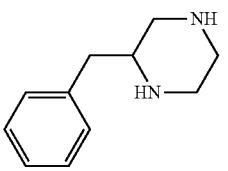 [SMILES: c1ccc(CC2CNCCN2)cc1] | 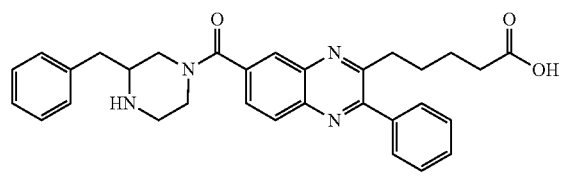 [SMILES: O=C(O)CCCCc1nc2cc(C(=O)N3CCNC(Cc4ccccc4)C3)ccc2nc1-c1ccccc1] | 5-{7-[(3-benzylpiperazin-1-yl)carbonyl]-3-phenyl-quinoxalin-2-yl}pentanoic acid | 509 |
| 15L | 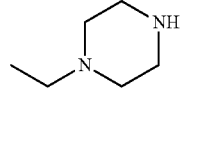 | 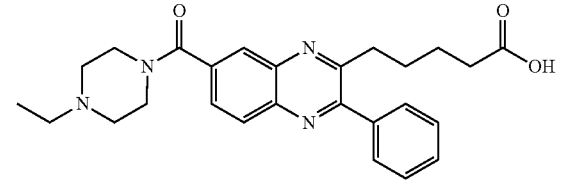 [SMILES: CCN1CCN(C(=O)c2ccc3nc(-c4ccccc4)c(CCCCC(=O)O)nc3c2)CC1] | 5-{7-[(4-ethylpiperazin-1-yl)carbonyl]-3-phenylquinoxalin-2-yl}pentanoic acid | 447 |

-continued

| No. | Reagent | Compound Structure | Name | M + H |
|---|---|---|---|---|
| 15M | | 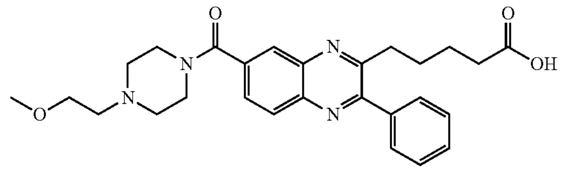 [SMILES: COCCN1CCN(C(=O)c2ccc3nc(-c4ccccc4)c(CCCCC(=O)O)nc3c2)CC1] | 5-(7-{[4-(2-methoxy-ethyl)piperazin-1-yl]-carbonyl}-3-phenyl-quinoxalin-2-yl) pentanoic acid | 477 |
| 15N | | 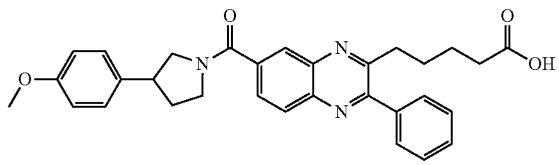 [SMILES: COc1ccc(C2CCN(C(=O)c3ccc4nc(-c5ccccc5)c(CCCCC(=O)O)nc4c3)C2)cc1] | 5-(7-{[3-(4-methoxy-phenyl)pyrrolidin-1-yl]-carbonyl}-3-phenyl-quinoxalin-2-yl) pentanoic acid | 510 |
| 15o | | 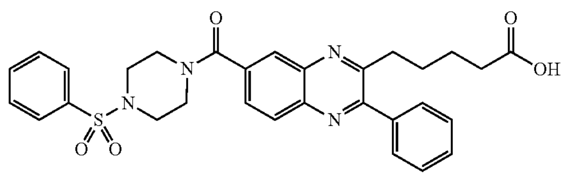 [SMILES: O=C(O)CCCCc1nc2cc(C(=O)N3CCN(S(=O)(=O)c4ccccc4)CC3)ccc2nc1-c1ccccc1] | 5-(3-phenyl-7-{[4-(phenylsulfonyl) piperazin-1-yl]carbonyl}quinoxalin-2-yl)pentanoic acid | 559 |
| 15P | | 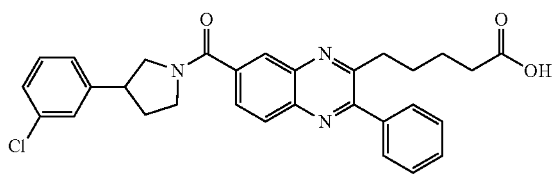 [SMILES: O=C(O)CCCCc1nc2cc(C(=O)N3CCC(c4cccc(Cl)c4)C3)ccc2nc1-c1ccccc1] | 5-(7-{[3-(3-chloro-phenyl)pyrrolidin-1-yl]-carbonyl}-3-phenyl-quinoxalin-2-yl) pentanoic acid | 514 |
| 15Q | | 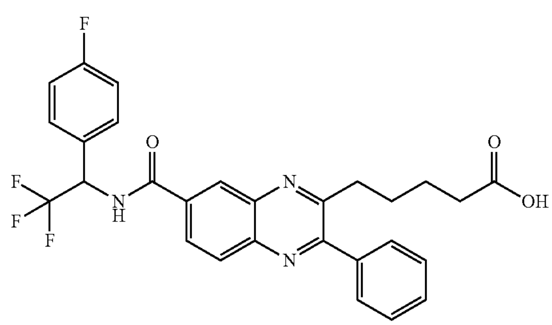 [SMILES: O=C(O)CCCCc1nc2cc(C(=O)NC(c3ccc(F)cc3)C(F)(F)F)ccc2nc1-c1ccccc1] | 5-(3-phenyl-7-{[2,2,2-trifluoro-1-(4-fluoro-phenyl)ethyl] carbamoyl}-quinoxalin-2-yl)pentanoic acid | 526 |
| 15R | | 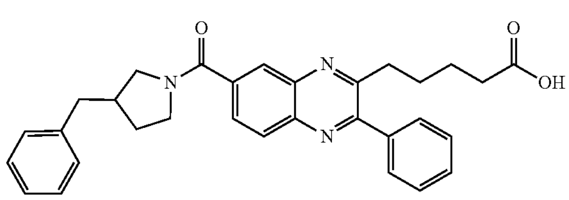 [SMILES: O=C(O)CCCCc1nc2cc(C(=O)N3CCC(Cc4ccccc4)C3)ccc2nc1-c1ccccc1] | 5-{7-[(3-benzylpyrrolidin-1-yl)carbonyl]-3-phenyl-quinoxalin-2-yl}pentanoic acid | 494 |

-continued

| No. | Reagent | Compound Structure | Name | M + H |
|---|---|---|---|---|
| 15S | | 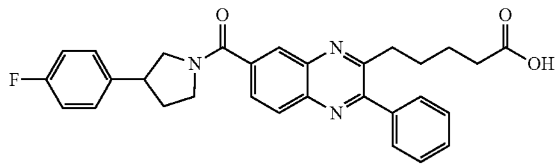 [SMILES: O=C(O)CCCCc1nc2cc(C(=O)N3CCC(c4ccc(F)cc4)C3)ccc2nc1-c1ccccc1] | 5-(7-{[3-(4-fluorophenyl)-pyrrolidin-1-yl]carbonyl}-3-phenylquinoxalin-2-yl)-pentanoic acid | 498 |
| 15T | | 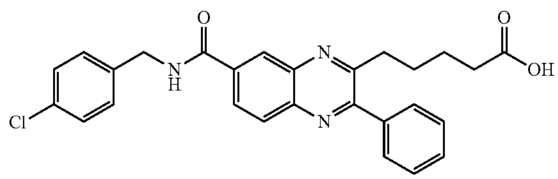 [SMILES: O=C(O)CCCCc1nc2cc(C(=O)NCc3ccc(Cl)cc3)ccc2nc1-c1ccccc1] | 5-{7-[(4-chlorobenzyl)-carbamoyl]-3-phenyl-quinoxalin-2-yl}pentanoic acid | 474 |
| 15U | | 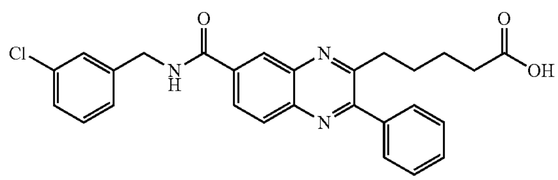 [SMILES: O=C(O)CCCCc1nc2cc(C(=O)NCc3cccc(Cl)c3)ccc2nc1-c1ccccc1] | 5-{7-[(3-chlorobenzyl)carbamoyl]-3-phenylquinoxalin-2-yl}pentanoic acid | 474 |
| 15V | | 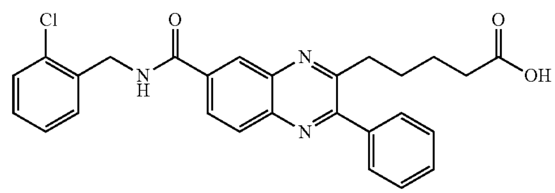 | 5-{7-[(2-chlorobenzyl)carbamoyl]-3-phenylquinoxalin-2-yl}pentanoic acid | 474 |
| 15X | | 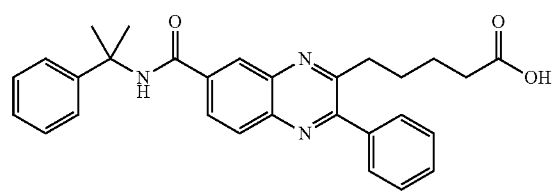 [SMILES: CC(C)(NC(=O)c1ccc2nc(-c3ccccc3)c(CCCCC(=O)O)nc2c1)c1ccccc1] | 5-{7-[(1-methyl-1-phenylethyl)carbamoyl]-3-phenylquinoxalin-2-yl}pentanoic acid | 468 |
| 15Y | | 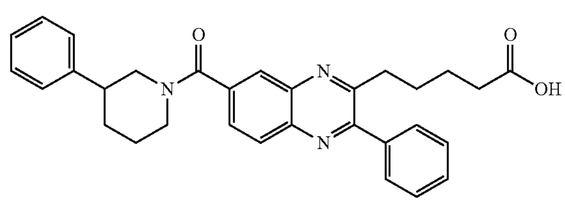 [SMILES: O=C(O)CCCCc1nc2cc(C(=O)N3CCCC(c4ccccc4)C3)ccc2nc1-c1ccccc1] | 5-{3-phenyl-7-[(3-phenylpiperidin-1-yl)carbonyl]quinoxalin-2-yl}pentanoic acid | 494 |
| 15Z | | 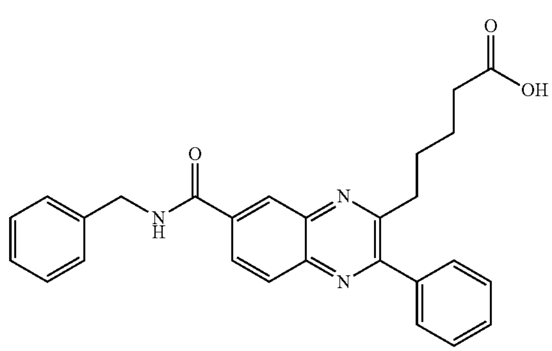 [SMILES: O=C(O)CCCCc1nc2cc(C(=O)NCc3ccccc3)ccc2nc1-c1ccccc1] | 5-[7-(benzylcarbamoyl)-3-phenylquinoxalin-2-yl]pentanoic acid | 440 |

-continued

| No. | Reagent | Compound Structure | Name | M + H |
|---|---|---|---|---|
| 15AA | aniline | 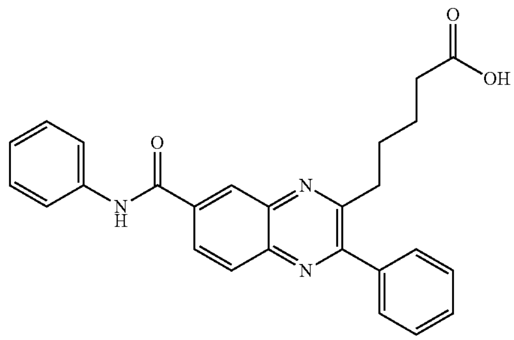 [SMILES: O=C(O)CCCCc1nc2cc(C(=O)Nc3ccccc3)ccc2nc1-c1ccccc1] | 5-[3-phenyl-7-(phenylcarbamoyl)quinoxalin-2-yl]pentanoic acid | 426 |
| 15AB | 2-fluorobenzylamine | 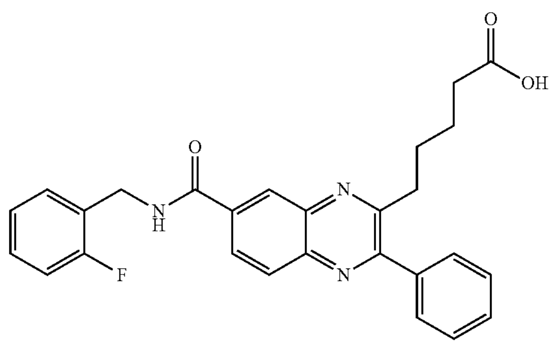 [SMILES: O=C(O)CCCCc1nc2cc(C(=O)NCc3ccccc3F)ccc2nc1-c1ccccc1] | 5-{7-[(2-fluorobenzyl)carbamoyl]-3-phenylquinoxalin-2-yl}pentanoic acid | 458 |
| 15AC | 3-fluorobenzylamine | 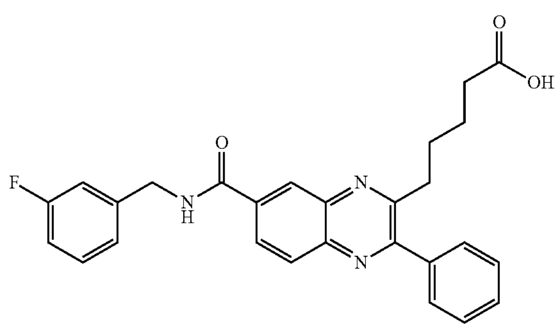 [SMILES: O=C(O)CCCCc1nc2cc(C(=O)NCc3cccc(F)c3)ccc2nc1-c1ccccc1] | 5-{7-[(3-fluorobenzyl)carbamoyl]-3-phenylquinoxalin-2-yl}pentanoic acid | 458 |
| 15AD | 4-fluorobenzylamine | 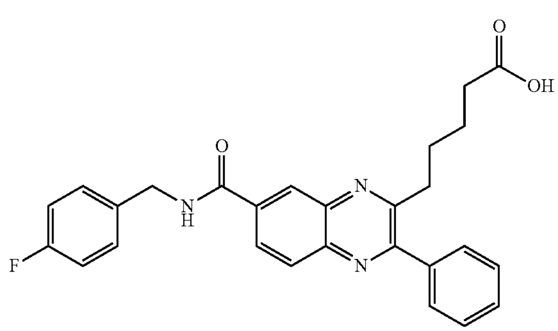 [SMILES: O=C(O)CCCCc1nc2cc(C(=O)NCc3ccc(F)cc3)ccc2nc1-c1ccccc1] | 5-{7-[(4-fluorobenzyl)carbamoyl]-3-phenylquinoxalin-2-yl}pentanoic acid | 458 |

-continued
| No. | Reagent | Compound Structure | Name | M + H |
|---|---|---|---|---|
| 15AE | 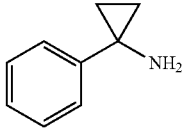 | 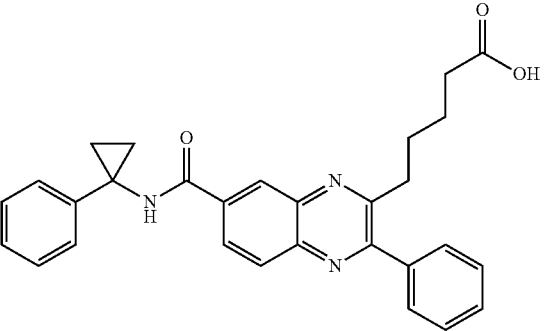 [SMILES: O=C(O)CCCCc1nc2cc(C(=O)NC3(c4ccccc4)CC3)ccc2nc1-c1ccccc1] | 5-{3-phenyl-7-[(1-phenylcyclopropyl)carbamoyl]quinoxalin-2-yl}pentanoic acid | 466 |
| 15AF | 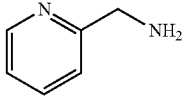 | 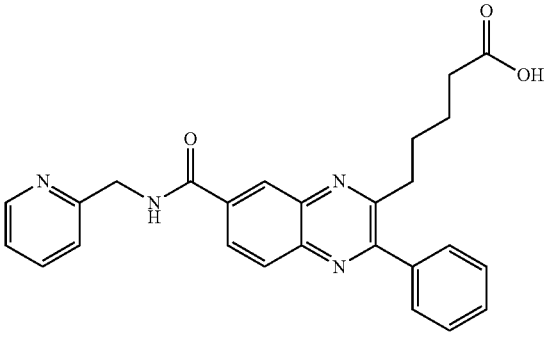 [SMILES: O=C(O)CCCCc1nc2cc(C(=O)NCc3ccccn3)ccc2nc1-c1ccccc1] | 5-{3-phenyl-7-[(pyridin-2-ylmethyl)carbamoyl]quinoxalin-2-yl}pentanoic acid | 441 |
| 15AG | 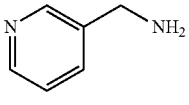 | 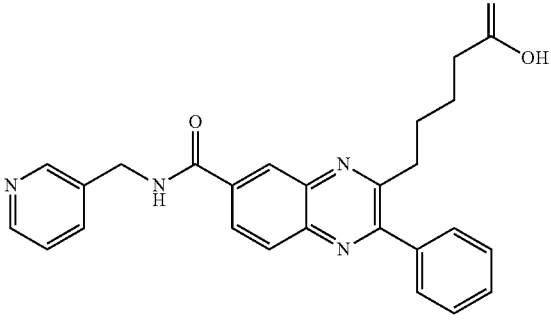 | 5-{3-phenyl-7-[(pyridin-3-ylmethyl)carbamoyl]quinoxalin-2-yl}pentanoic acid | 441 |
| 15AH | 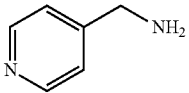 | 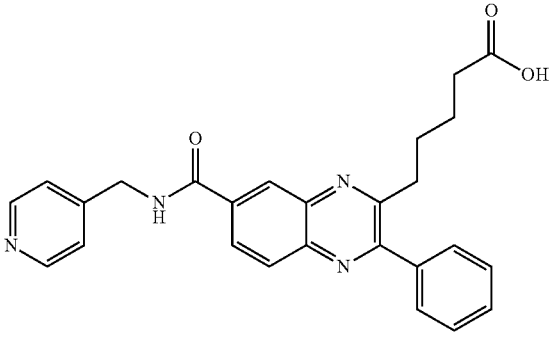 [SMILES: O=C(O)CCCCc1nc2cc(C(=O)NCc3ccncc3)ccc2nc1-c1ccccc1] | 5-{3-phenyl-7-[(pyridin-4-ylmethyl)carbamoyl]quinoxalin-2-yl}pentanoic acid | 441 |

-continued

| No. | Reagent | Compound Structure | Name | M + H |
|---|---|---|---|---|
| 15Ai | | 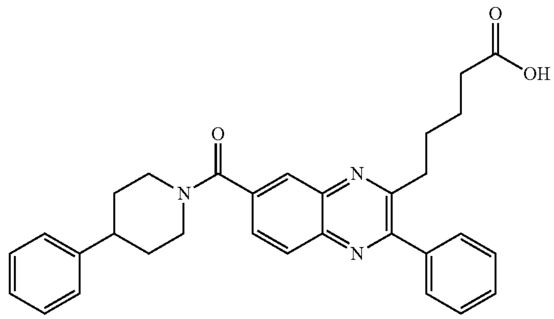 [SMILES: O=C(O)CCCCc1nc2cc(C(=O)N3CCC(c4ccccc4)CC3)ccc2nc1-c1ccccc1] | 5-{3-phenyl-7-[(4-phenylpiperidin-1-yl)carbonyl]quinoxalin-2-yl}pentanoic acid | 494 |
| 15AJ | | 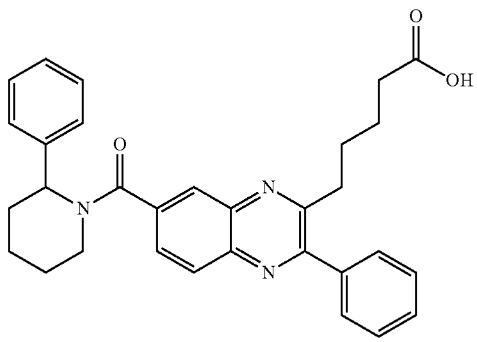 [SMILES: O=C(O)CCCCc1nc2cc(C(=O)N3CCCCC3c3ccccc3)ccc2nc1-c1ccccc1] | 5-{3-phenyl-7-[(2-phenylpiperidin-1-yl)carbonyl]quinoxalin-2-yl}pentanoic acid | 494 |
| 15AK | | 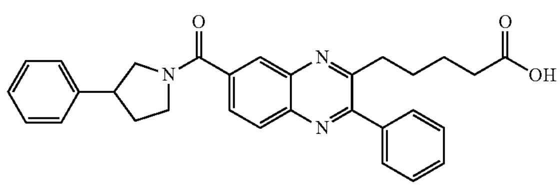 [SMILES: O=C(O)CCCCc1nc2cc(C(=O)N3CCC(c4ccccc4)C3)ccc2nc1-c1ccccc1] | 5-{3-phenyl-7-[(3-phenylpyrrolidin-1-yl)carbonyl]quinoxalin-2-yl}pentanoic acid | 480 |
| 15AL | | 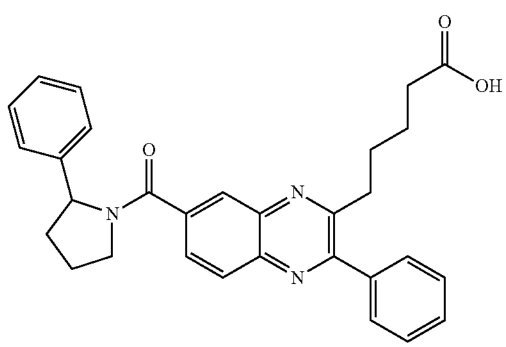 [SMILES: O=C(O)CCCCc1nc2cc(C(=O)N3CCCC3c3ccccc3)ccc2nc1-c1ccccc1] | 5-{3-phenyl-7-[(2-phenylpyrrolidin-1-yl)carbonyl]quinoxalin-2-yl}pentanoic acid | 480 |
| 15AM | | 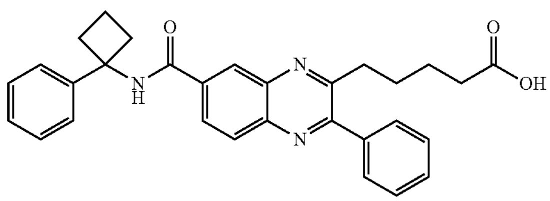 [SMILES: O=C(O)CCCCc1nc2cc(C(=O)NC3(c4ccccc4)CCC3)ccc2nc1-c1ccccc1] | 5-{3-phenyl-7-[(1-phenylcyclobutyl)carbamoyl]quinoxalin-2-yl}pentanoic acid | 480 |

-continued

| No. | Reagent | Compound Structure | Name | M + H |
|---|---|---|---|---|
| 15AN | | 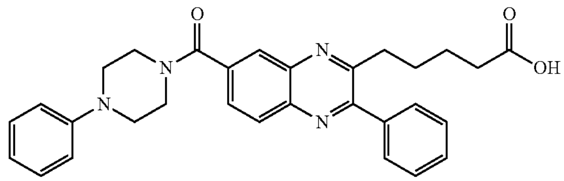 [SMILES: O=C(O)CCCCc1nc2cc(C(=O)N3CCN(c4ccccc4)CC3)ccc2nc1-c1ccccc1] | 5-{3-phenyl-7-[(4-phenylpiperazin-1-yl)carbonyl]quinoxalin-2-yl}pentanoic acid | 495 |
| 15Ao | | 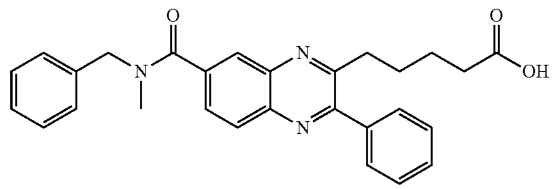 [SMILES: CN(Cc1ccccc1)C(=O)c1ccc2nc(-c3ccccc3)c(CCCCC(=O)O)nc2c1] | 5-{7-[benzyl(methyl)carbamoyl]-3-phenylquinoxalin-2-yl}pentanoic acid | 454 |
| 15AP | | 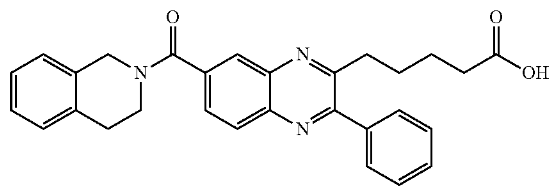 [SMILES: O=C(O)CCCCc1nc2cc(C(=O)N3CCc4ccccc4C3)ccc2nc1-c1ccccc1] | 5-[7-(3,4-dihydroisoquinolin-2(1H)-ylcarbonyl)-3-phenylquinoxalin-2-yl]pentanoic acid | 466 |
| 15AQ | | 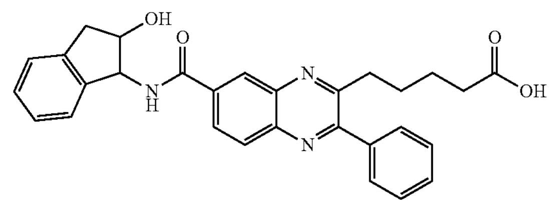 [SMILES: O=C(O)CCCCc1nc2cc(C(=O)NC3c4ccccc4CC3O)ccc2nc1-c1ccccc1] | 5-{7-[(2-hydroxy-2,3-dihydro-1H-inden-1-yl)carbamoyl]-3-phenylquinoxalin-2-yl}pentanoic acid | 482 |
| 15AR | | 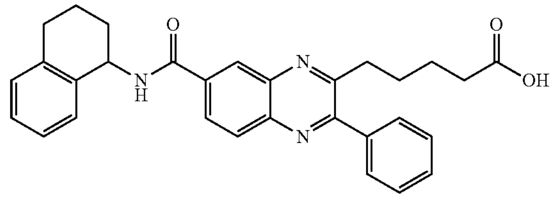 [SMILES: O=C(O)CCCCc1nc2cc(C(=O)NC3CCCc4ccccc43)ccc2nc1-c1ccccc1] | 5-[3-phenyl-7-(1,2,3,4-tetrahydronaphthalen-1-ylcarbamoyl)quinoxalin-2-yl]pentanoic acid | 480 |
| 15AS | | 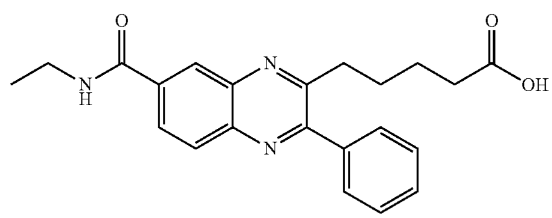 [SMILES: CCNC(=O)c1ccc2nc(-c3ccccc3)c(CCCCC(=O)O)nc2c1] | 5-[7-(ethylcarbamoyl)-3-phenylquinoxalin-2-yl]pentanoic acid | 378 |
| 15AT | | 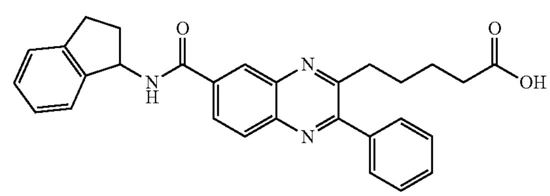 [SMILES: O=C(O)CCCCc1nc2cc(C(=O)NC3CCc4ccccc43)ccc2nc1-c1ccccc1] | 5-[7-(2,3-dihydro-1H-inden-1-ylcarbamoyl)-3-phenylquinoxalin-2-yl]pentanoic acid | 466 |
| 15AU | | 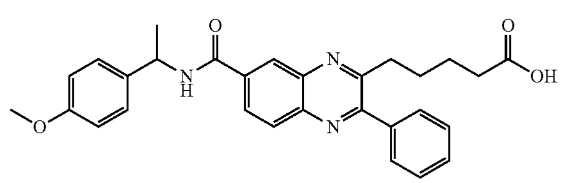 [SMILES: COc1ccc(C(C)NC(=O)c2ccc3nc(-c4ccccc4)c(CCCCC(=O)O)nc3c2)cc1] | 5-(7-{[1-(4-methoxyphenyl)ethyl]carbamoyl}-3-phenyl-quinoxalin-2-yl)pentanoic acid | 484 |

-continued

| No. | Reagent | Compound Structure | Name | M + H |
|---|---|---|---|---|
| 15AV | 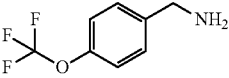 | 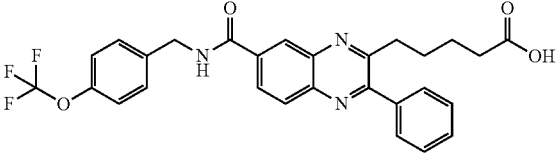 [SMILES: O=C(O)CCCCc1nc2cc(C(=O)NCc3ccc(OC(F)(F)F)cc3)ccc2nc1-c1ccccc1] | 5-(3-phenyl-7-{[4-(trifluoromethoxy)benzyl]carbamoyl}quinoxalin-2-yl)pentanoic acid | 524 |
| 15AW | 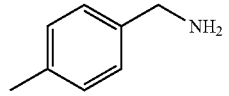 | 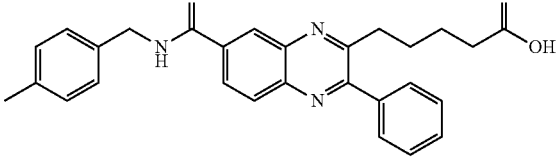 | 5-{7-[(4-methylbenzyl)carbamoyl]-3-phenylquinoxalin-2-yl}pentanoic acid | 454 |
| 15AX | 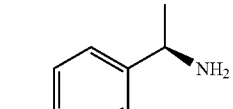 | 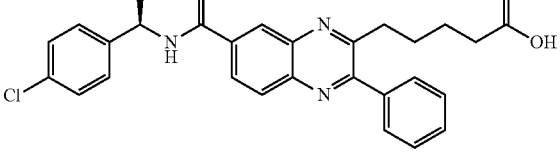 | 5-(7-{[(1R)-1-(4-chlorophenyl)ethyl]carbamoyl}-3-phenyl-quinoxalin-2-yl)pentanoic acid | 488 |
| 15AY | 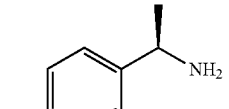 | 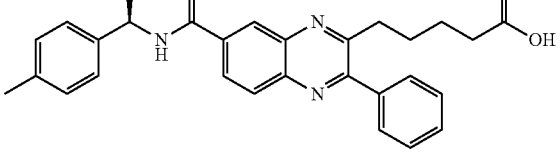 | 5-(7-{[(1R)-1-(4-methylphenyl)ethyl]carbamoyl}-3-phenyl-quinoxalin-2-yl)pentanoic acid | 468 |
| 15AZ | 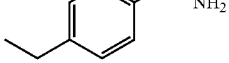 | 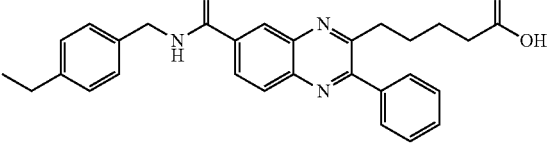 | 5-{7-[(4-ethylbenzyl)carbamoyl]-3-phenylquinoxalin-2-yl}pentanoic acid | 468 |
| 15AB | 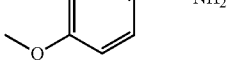 | 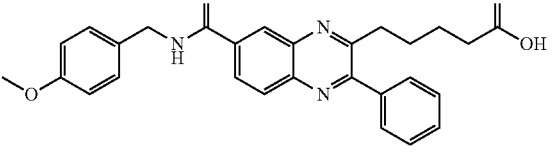 | 5-{7-[(4-methoxybenzyl)carbamoyl]-3-phenylquinoxalin-2-yl}pentanoic acid | 470 |
| 15BB | 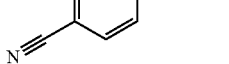 | 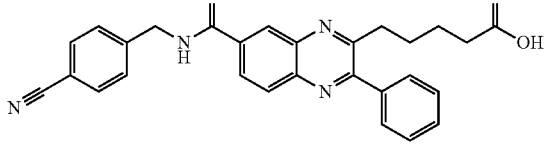 | 5-{7-[(4-cyanobenzyl)carbamoyl]-3-phenylquinoxalin-2-yl}pentanoic acid | 465 |
| 15BC | 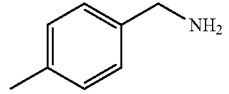 | 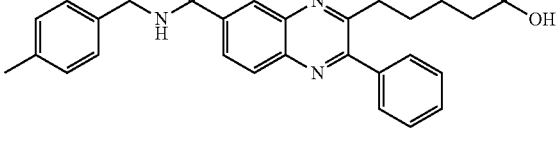 | 5-(7-{[(1S)-1-(4-methylphenyl)ethyl]carbamoyl}-3-phenylquinoxalin-2-yl)pentanoic acid | 468 |

-continued

| No. | Reagent | Compound Structure | Name | M + H |
|---|---|---|---|---|
| 15BD | | 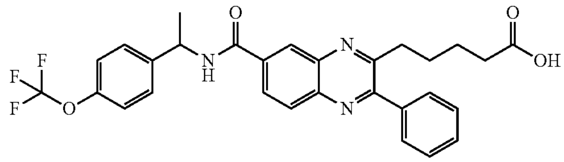 [SMILES: CC(NC(=O)c1ccc2nc(-c3ccccc3)c(CCCCC(=O)O)nc2c1)c1ccc(OC(F)(F)F)cc1] | 5-[3-phenyl-7-({1-[4-(trifluoromethoxy)phenyl]ethyl}carbamoyl)quinoxalin-2-yl]pentanoic acid | 538 |
| 15BE | | 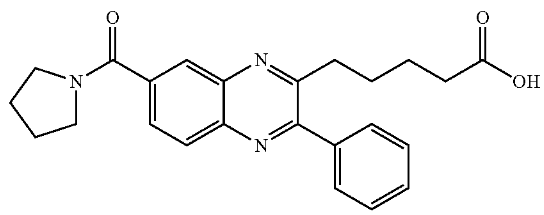 [SMILES: O=C(O)CCCCc1nc2cc(C(=O)N3CCCC3)ccc2nc1-c1ccccc1] | 5-[3-phenyl-7-(pyrrolidin-1-ylcarbonyl)quinoxalin-2-yl]pentanoic aicd | 404 |
| 15BF | | 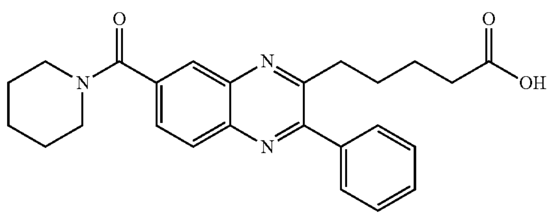 [SMILES: O=C(O)CCCCc1nc2cc(C(=O)N3CCCCC3)ccc2nc1-c1ccccc1] | 5-[3-phenyl-7-(piperidin-1-ylcarbonyl)quinoxalin-2-yl]pentanoic acid | 418 |
| 15BG | | 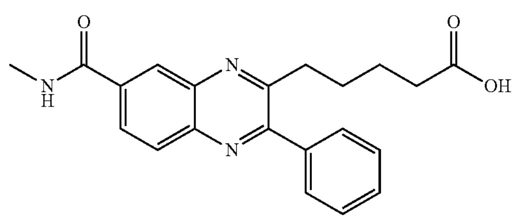 [SMILES: CNC(=O)c1ccc2nc(-c3ccccc3)c(CCCCC(=O)O)nc2c1] | 5-[7-(methylcarbamoyl)-3-phenylquinoxalin-2-yl]pentanoic acid | 364 |
| 15BH | | 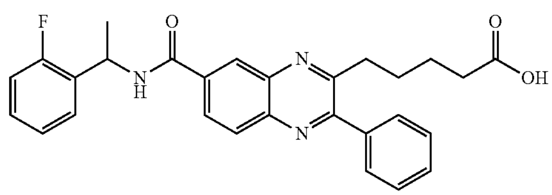 [SMILES: CC(NC(=O)c1ccc2nc(-c3ccccc3)c(CCCCC(=O)O)nc2c1)c1ccccc1F] | 5-(7-{[1-(2-fluorophenyl)ethyl]carbamoyl}-3-phenylquinoxalin-2-yl)pentanoic acid | 472 |
| 15Bi | | 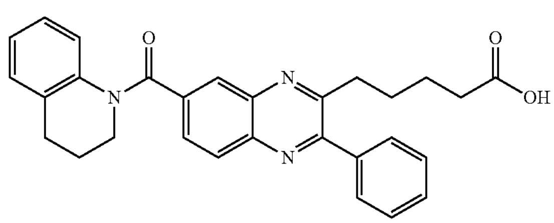 [SMILES: O=C(O)CCCCc1nc2cc(C(=O)N3CCCc4ccccc43)ccc2nc1-c1ccccc1] | 5-[7-(3,4-dihydroquinolin-1(2H)-ylcarbonyl)-3-phenylquinoxalin-2-yl]pentanoic acid | 466 |
| 15BJ | | 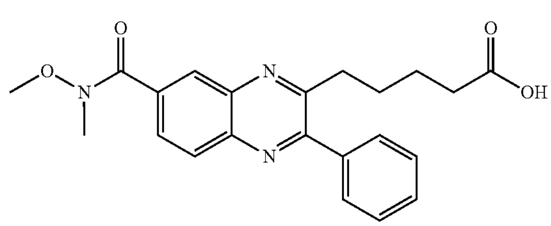 [SMILES: CON(C)C(=O)c1ccc2nc(-c3ccccc3)c(CCCCC(=O)O)nc2c1] | 5-{7-[methoxy(methyl)carbamoyl]-3-phenylquinoxalin-2-yl}pentanoic acid | 394 |

-continued

| No. | Reagent | Compound Structure | Name | M + H |
|---|---|---|---|---|
| 15BK | 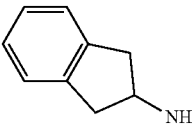 | 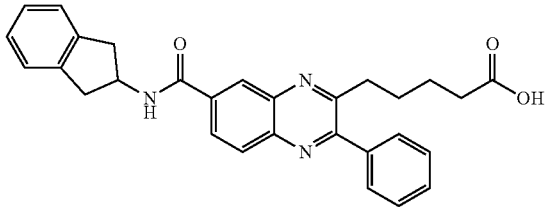 [SMILES: O=C(O)CCCCc1nc2cc(C(=O)NC3Cc4ccccc4C3)ccc2nc1-c1ccccc1] | 5-[7-(2,3-dihydro-1H-inden-2-ylcarbamoyl)-3-phenylquinoxalin-2-yl]pentanoic acid | 466 |
| 15BL | 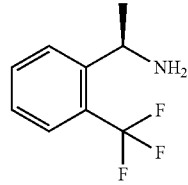 | 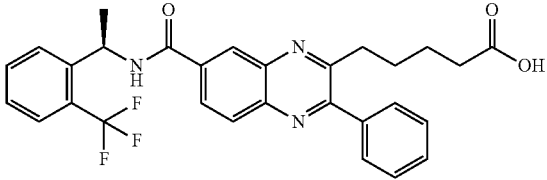 [SMILES: C[C@@H](NC(=O)c1ccc2nc(-c3ccccc3)c(CCCCC(=O)O)nc2c1)c1ccccc1C(F)(F)F] | 5-[3-phenyl-7-({(1R)-1-[2-(trifluoromethyl)phenyl]ethyl}carbamoyl)quinoxalin-2-yl]pentanoic acid | 522 |
| 15BM | 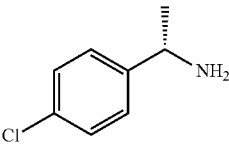 | 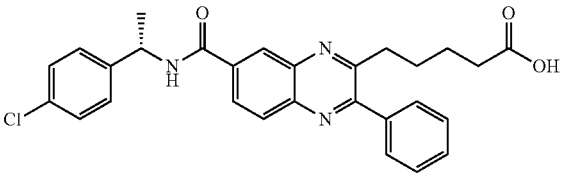 [SMILES: C[C@H](NC(=O)c1ccc2nc(-c3ccccc3)c(CCCCC(=O)O)nc2c1)c1ccc(Cl)cc1] | 5-(7-{[(1S)-1-(4-chlorophenyl)ethyl]carbamoyl}-3-phenylquinoxalin-2-yl)pentanoic acid | 488 |
| 15BN | 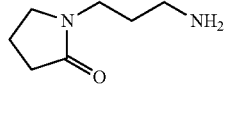 | 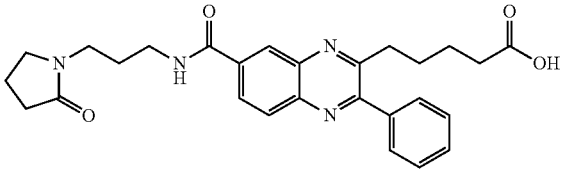 [SMILES: O=C(O)CCCCc1nc2cc(C(=O)NCCCN3CCCC3=O)ccc2nc1-c1ccccc1] | 5-(7-{[3-(2-oxopyrrolidin-1-yl)propyl]carbamoyl}-3-phenylquinoxalin-2-yl)pentanoic acid | 475 |
| 15Bo | 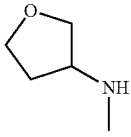 | 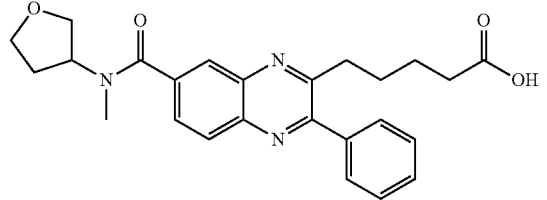 [SMILES: CN(C(=O)c1ccc2nc(-c3ccccc3)c(CCCCC(=O)O)nc2c1)C1CCOC1] | 5-{7-[methyl(tetrahydrofuran-3-yl)carbamoyl]-3-phenylquinoxalin-2-yl}pentanoic acid | 434 |
| 15BQ | 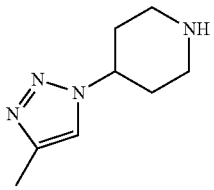 | 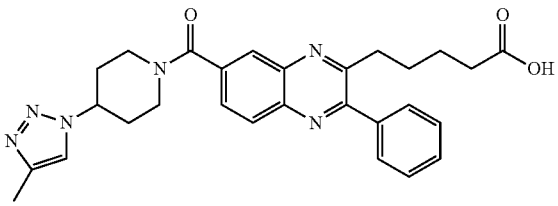 [SMILES: Cc1cn(C2CCN(C(=O)c3ccc4nc(-c5ccccc5)c(CCCCC(=O)O)nc4c3)CC2)nn1] | 5-(7-{[4-(4-methyl-1H-1,2,3-triazol-1-yl)piperidin-1-yl]carbonyl}-3-phenylquinoxalin-2-yl)pentanoic acid | 499 |
| 15BR | 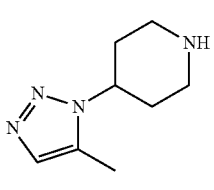 | 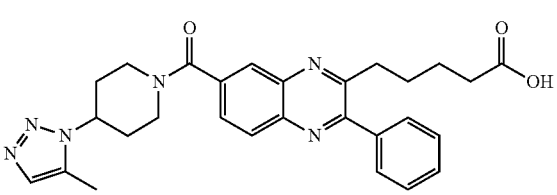 [SMILES: Cc1cnnn1C1CCN(C(=O)c2ccc3nc(-c4ccccc4)c(CCCCC(=O)O)nc3c2)CC1] | 5-(7-{[4-(5-methyl-1H-1,2,3-triazol-1-yl)piperidin-1-yl]carbonyl}-3-phenylquinoxalin-2-yl)pentanoic acid | 499 |

| No. | Reagent | Compound Structure | Name | M + H |
|---|---|---|---|---|
| 15BS | | 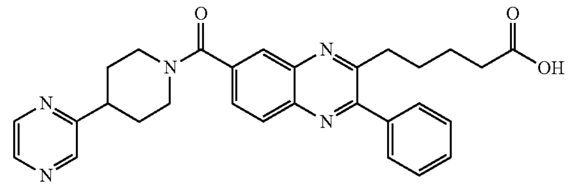 [SMILES: O=C(O)CCCCc1nc2cc(C(=O)N3CCC(c4cnccn4)CC3)ccc2nc1-c1ccccc1] | 5-{3-phenyl-7-[(4-pyrazin-2-ylpiperidin-1-yl)carbonyl]quinoxalin-2-yl}pentanoic acid | 496 |
| 15BT | | 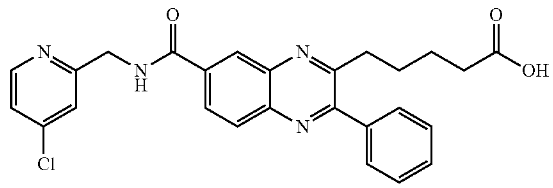 [SMILES: O=C(O)CCCCc1nc2cc(C(=O)NCc3cc(Cl)ccn3)ccc2nc1-c1ccccc1] | 5-(7-{[(4-chloropyridin-2-yl)methyl]carbamoyl}-3-phenylquinoxalin-2-yl)pentanoic acid | 475 |
| 15BU | | 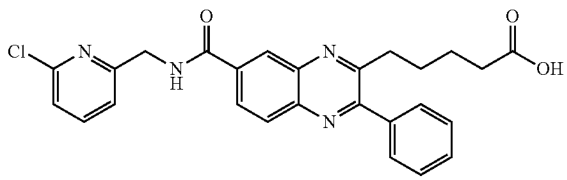 [SMILES: O=C(O)CCCCc1nc2cc(C(=O)NCc3cccc(Cl)n3)ccc2nc1-c1ccccc1] | 5-(7-{[(6-chloropyridin-2-yl)methyl]carbamoyl}-3-phenylquinoxalin-2-yl)pentanoic acid | 475 |
Preparative Example 16
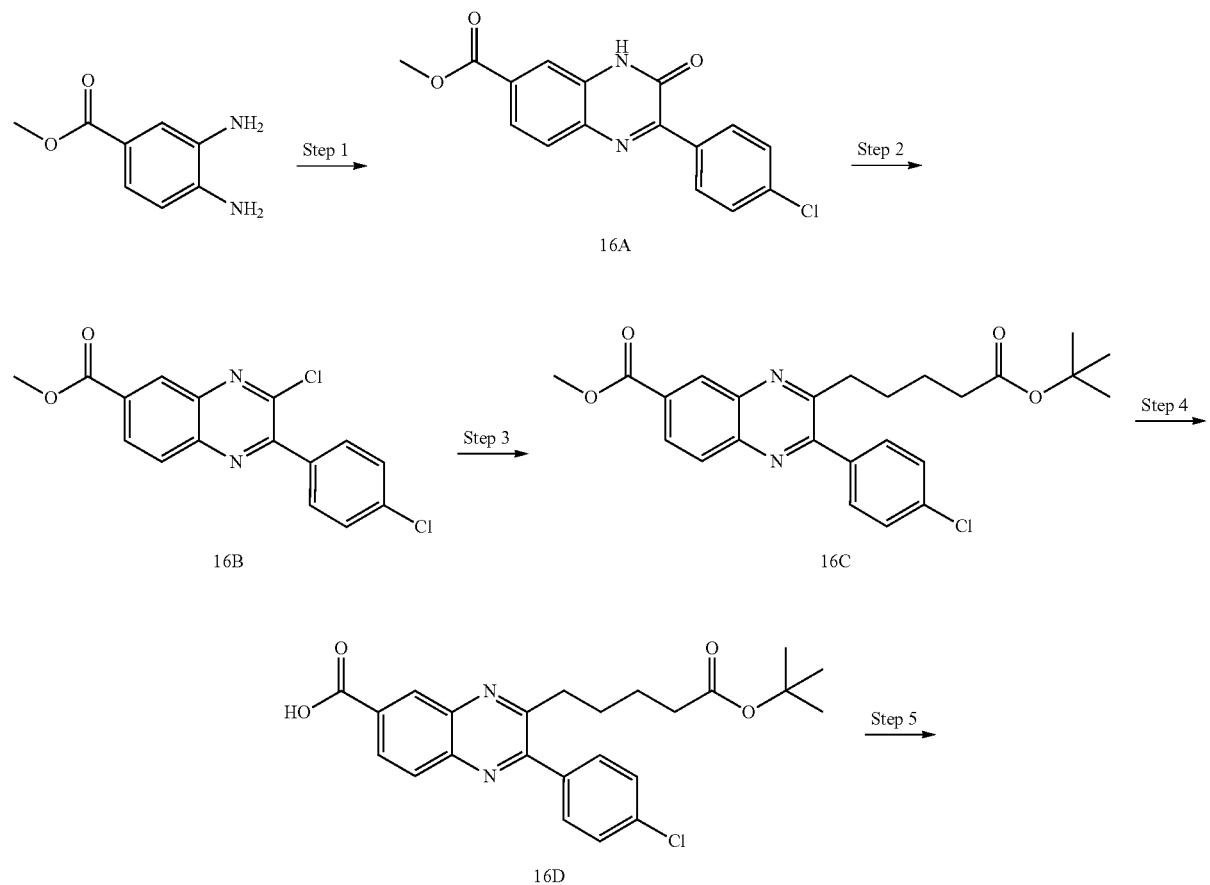

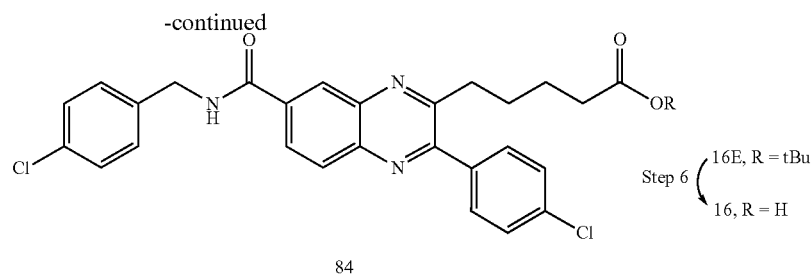

84

In a manner similar to that previously, methyl 3,4-diaminobenzoate was 2-(4-fluorophenyl)-2-oxoacetic acid (prepared from ethyl 2-(4-chlorophenyl)-2-oxoacetate as described in Example 2) to provide 16A (MS: M+H=315).

A mixture of 16A (13.43 g, 42.67 mmol), SOCK (70 mL, 1000 mmol), and DMF (0.4 mL, 5 mmol) was stirred at 80° C. for 4 h and then at 40° C. overnight.

The excess SOCl$_2$ was removed. The resulting residue was stirred with cold water for 2 h. The solid was then filtered and dried overnight in vacuo to give methyl 3-chloro-2-(4-chlorophenyl)quinoxaline-6-carboxylate (16B, 12.94 g; Yield=91.04%). LCMS (M+H)=333.

In a manner similar to that previously described, 16B was sequentially coupled with compound 1, hydrolyzed with LiOH (to afford 16D), coupled with 4-chlorobenzylamine, and deprotected with TFA to provide the title compound 16. LCMS (M+H)=508

16

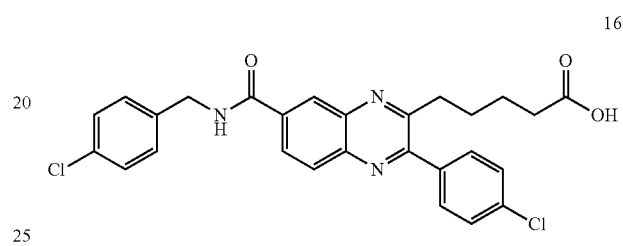

In a similar manner, the following compounds were prepared by coupling acid 16D to the appropriate amine reagent followed by a TFA deprotection:

| No. | Compound | Name | M + H |
|---|---|---|---|
| 16F | 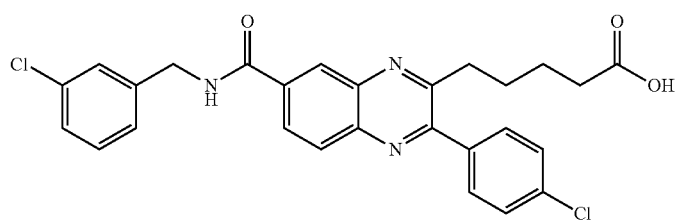 [SMILES: O=C(O)CCCCc1nc2cc(C(=O)NCc3cccc(Cl)c3)ccc2nc1-c1ccc(Cl)cc1] | 3-(4-chlorophenyl)-7-[[[(3-chlorophenyl)methyl]amino]carbonyl]-2-quinoxalinepentanoic acid | 508 |
| 16G | 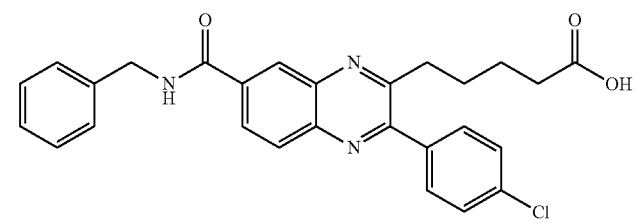 | 3-(4-chlorophenyl)-7-[[[(phenylmethyl)amino]carbonyl]-2-quinoxalinepentanoic acid | 474 |
| 16H | 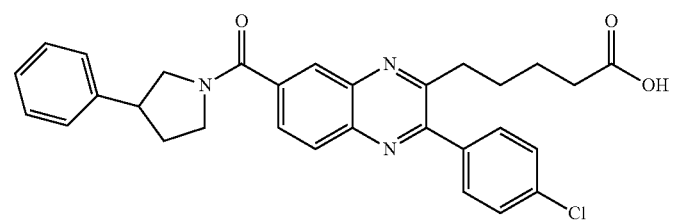 | 3-(4-chlorophenyl)-7-[(3-phenyl-1-pyrrolidinyl)carbonyl]-2-quinoxalinepentanoic acid | 514 |

-continued

| No. | Compound | Name | M + H |
|---|---|---|---|
| 16i | 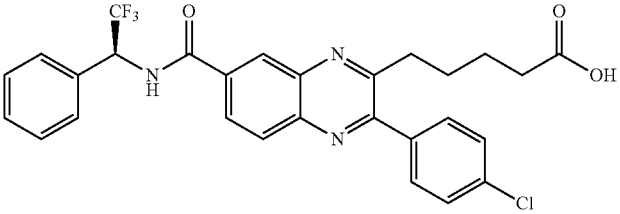 | 3-(4-chlorophenyl)-7-[[(2,2,2-trifluoro-1(s)-phenylethyl)amino]carbonyl]-2-quinoxalinepentanoic acid | 542 |
| 16J | 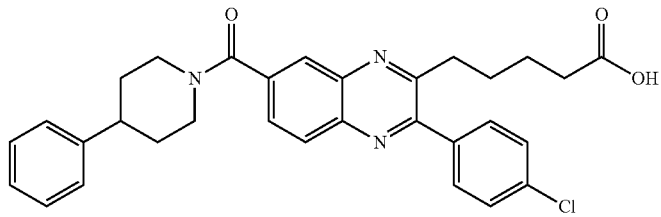 [SMILES: O=C(O)CCCCc1nc2cc(C(=O)N3CCC(c4ccccc4)CC3)ccc2nc1-c1ccc(Cl)cc1] | 3-(4-chlorophenyl)-7-[(4-phenyl-1-piperidinyl)carbonyl]-2-quinoxalinepentanoic acid | 528 |
| 16K | 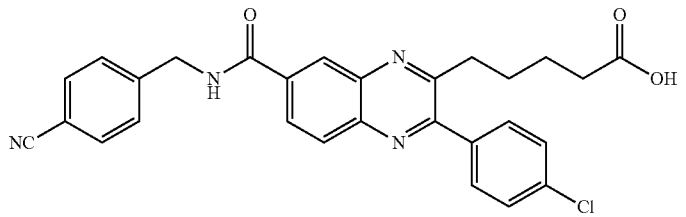 [SMILES: N#Cc1ccc(CNC(=O)c2ccc3nc(-c4ccc(Cl)cc4)c(CCCCC(=O)O)nc3c2)cc1] | 3-(4-chlorophenyl)-7-[[[(4-cyanophenyl)methyl]amino]carbonyl]-2-quinoxalinepentanoic acid | 499 |
| 16L | 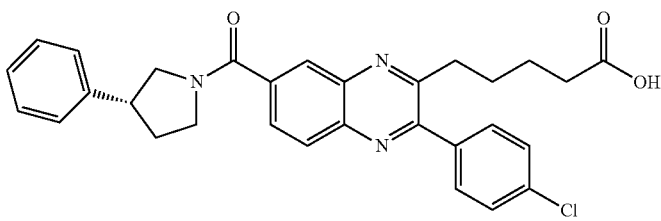 | 3-(4-chlorophenyl)-7-[(3(R)-phenyl-1-pyrrolidinyl)carbonyl]-2-quinoxalinepentanoic acid | 514 |
| 16M | 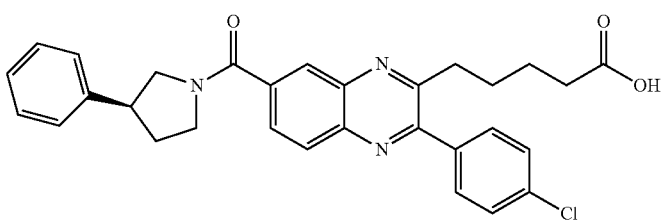 [SMILES: O=C(O)CCCCc1nc2cc(C(=O)N3CC[C@@H](c4ccccc4)C3)ccc2nc1-c1ccc(Cl)cc1] | 3-(4-chlorophenyl)-7-[(3(S)-phenyl-1-pyrrolidinyl)carbonyl]-2-quinoxalinepentanoic acid | 514 |
| 16N | 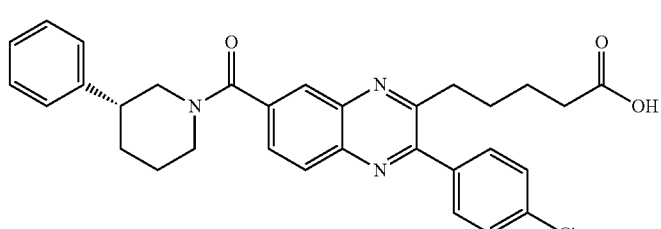 | 3-(4-chlorophenyl)-7-[(3(R)-phenyl-1-piperidinyl)carbonyl]-2-quinoxalinepentanoic acid | 528 |
| 16o | 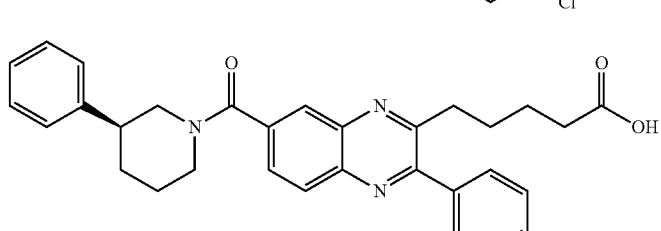 | 3-(4-chlorophenyl)-7-[(3(S)-phenyl-1-piperidinyl)carbonyl]-2-quinoxalinepentanoic acid | 528 |

-continued

| No. | Compound | Name | M + H |
|-----|----------|------|-------|
| 16P | | 3-(4-chlorophenyl)-7-[[[[4-(trifluoromethoxy)phenyl]methyl]amino]carbonyl]-2-quinoxalinepentanoic acid | 558 |
| 16Q | | 3-(4-chlorophenyl)-7-[[[(3,5-dichlorophenyl)methyl]amino]carbonyl]-2-quinoxalinepentanoic acid | 542 |
| 16R | | 3-(4-chlorophenyl)-7-[[[[(4-fluorophenyl)methyl]amino]carbonyl]-2-quinoxalinepentanoic acid | 492 |
| 16S | | 3-(4-chlorophenyl)-7-[[[1(R)-(4-fluorophenyl)ethyl]amino]carbonyl]-2-quinoxalinepentanoic acid | 506 |
| 16T | | 3-(4-chlorophenyl)-7-[[[1(S)-(4-fluorophenyl)ethyl]amino]carbonyl]-2-quinoxalinepentanoic acid | 506 |
| 16U | | 3-(4-chlorophenyl)-7-[[[[4-(trifluoromethyl)phenyl]methyl]amino]carbonyl]-2-quinoxalinepentanoic acid | 542 |
| 16V | | 3-(4-chlorophenyl)-7-[[[1(R)-(4-chlorophenyl)-2,2,2-trifluoroethyl]amino]carbonyl]-2-quinoxalinepentanoic acid | 576 |

-continued

| No. | Compound | Name | M + H |
|---|---|---|---|
| 16W | | 3-(4-chlorophenyl)-7-[[[(1(S)-(4-chlorophenyl)-2,2,2-trifluoro-ethyl]amino]carbonyl]-2-quinoxalinepentanoic acid | 576 |
| 16X | | 3-(4-chlorophenyl)-7-[[[2,2,2-trifluoro-1(R)-(4-fluorophenyl)ethyl]amino]carbonyl]-2-quinoxalinepentanoic acid | 560 |
| 16Y | | 3-(4-chlorophenyl)-7-[[[2,2,2-trifluoro-1(S)-(4-fluorophenyl)ethyl]amino]carbonyl]-2-quinoxalinepentanoic acid | 560 |
| 16Z | | 3-(4-chlorophenyl)-7-[[[1(S)-(2-pyridinyl)ethyl]amino]carbonyl]-2-quinoxalinepentanoic acid | 489 |
| 16AA | | 3-(4-chlorophenyl)-7-[[[1(S)-(2-pyridinyl)ethyl]amino]carbonyl]-2-quinoxalinepentanoic acid | 489 |
| 16AB | | 3-(4-chlorophenyl)-7-[[[[3-(trifluoromethyl)phenyl]methyl]amino]carbonyl]-2-quinoxalinepentanoic acid | 542 |
| 16AC | | 3-(4-chlorophenyl)-7-[[[[3-(trifluoromethoxy)phenyl]methyl]amino]carbonyl]-2-quinoxalinepentanoic acid | 558 |

-continued

| No. | Compound | Name | M + H |
|---|---|---|---|
| 16AD | | 3-(4-chlorophenyl)-7-[[[(R)-(4-chlorophenyl)ethyl]amino]carbonyl]-2-quinoxalinepentanoic acid | 522 |
| 16AE | | 3-(4-chlorophenyl)-7-[[[1(S)-(4-chlorophenyl)ethyl]amino]carbonyl]-2-quinoxalinepentanoic acid | 522 |
| 16AF | | 3-(4-chlorophenyl)-7-[(3-phenyl-1-azetidinyl)carbonyl]-2-quinoxalinepentanoic acid | 500 |
| 16AG | | 3-(4-chlorophenyl)-7-[(4-phenyl-1-piperazinyl)carbonyl]-2-quinoxalinepentanoic acid | 529 |
| 16AH | | 3-(4-chlorophenyl)-7-[[(2,2,2-trifluoro-1(R)-phenylethyl)amino]carbonyl]-2-quinoxalinepentanoic acid | 542 |
| 16Ai | | 3-(4-chlorophenyl)-7-[[[(1,2,3,4-tetrahydro-1-naphthalenyl)amino]carbonyl]-2-quinoxalinepentanoic acid | 514 |
| 16AJ | | 3-(4-chlorophenyl)-7-[(3,6-dihydro-4-phenyl-1(2H)-pyridinyl)carbonyl]-2-quinoxalinepentanoic acid | 526 |

-continued

| No. | Compound | Name | M + H |
|---|---|---|---|
| 16AK | | 3-(4-chlorophenyl)-7-[(4-cyano-4-phenyl-1-piperidinyl)carbonyl]-2-quinoxalinepentanoic acid | 553 |
| 16AL | | 3-(4-chlorophenyl)-7-[[(1(R)-phenylethyl)amino]carbonyl]-2-quinoxalinepentanoic acid | 488 |
| 16AM | | 3-(4-chlorophenyl)-7-[[(1-(S)-phenylethyl)amino]carbonyl]-2-quinoxalinepentanoic acid | 488 |
| 16AN | | 3-(4-chlorophenyl)-7-[[(1,2,3,4-tetrahydro-1(S)-naphthalenyl)amino]carbonyl]-2-quinoxalinepentanoic acid | 514 |
| 16Ao | | 3-(4-chlorophenyl)-7-[[(2,3-dihydro-1H-inden-1(R)-yl)amino]carbonyl]-2-quinoxalinepentanoic acid | 474 |
| 16AP | | 3-(4-chlorophenyl)-7-[[(2,3-dihydro-1H-inden-1(S)-yl)amino]carbonyl]-2-quinoxalinepentanoic acid | 500 |
| 16AQ | | 3-(4-chlorophenyl)-7-[[[(4-methylphenyl)methyl]amino]carbonyl]-2-quinoxalinepentanoic acid | 488 |

| No. | Compound | Name | M + H |
|---|---|---|---|
| 16AR | 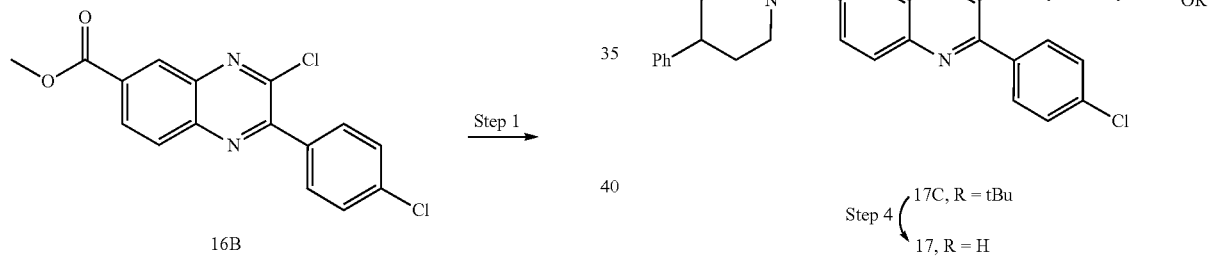 | 3-(4-chlorophenyl)-7-[[(3-hydroxy-1(S)-phenylpropyl)amino]carbonyl]-2-quinoxalinepentanoic acid | 518 |
| 16AS | 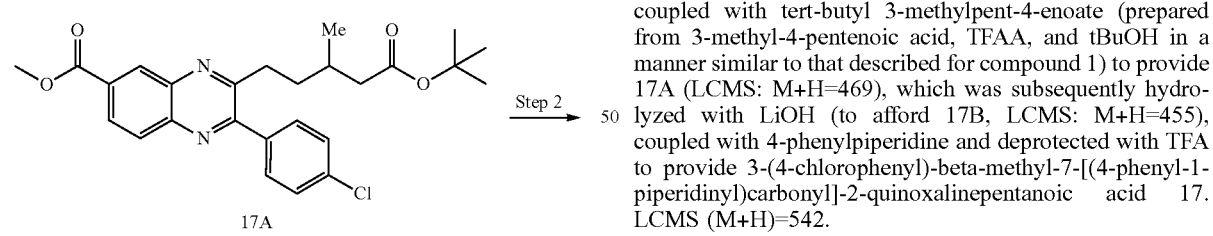 | 3-(4-chlorophenyl)-7-[[(2,3-dihydro-1H-inden-2-yl)amino]carbonyl]-2-quinoxalinepentanoic acid | 500 |

Example 17

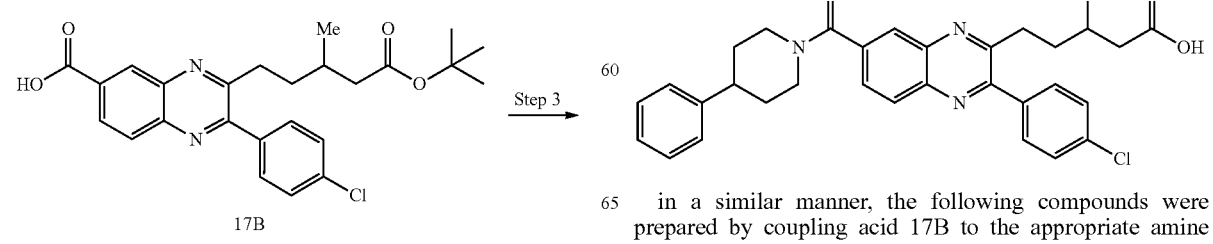

in a manner similar to that previously, methyl 3-chloro-2-(4-chlorophenyl)quinoxaline-6-carboxylate (16B) was coupled with tert-butyl 3-methylpent-4-enoate (prepared from 3-methyl-4-pentenoic acid, TFAA, and tBuOH in a manner similar to that described for compound 1) to provide 17A (LCMS: M+H=469), which was subsequently hydrolyzed with LiOH (to afford 17B, LCMS: M+H=455), coupled with 4-phenylpiperidine and deprotected with TFA to provide 3-(4-chlorophenyl)-beta-methyl-7-[(4-phenyl-1-piperidinyl)carbonyl]-2-quinoxalinepentanoic acid 17. LCMS (M+H)=542.

in a similar manner, the following compounds were prepared by coupling acid 17B to the appropriate amine reagent followed by a TFA deprotection:

| No. | Compound | Name | M + H |
|---|---|---|---|
| 17D | | 3-(4-chlorophenyl)-7-[[[1(S)-(4-chlorophenyl)ethyl]aminocarbonyl]-beta-methyl-2-quinoxaline pentanoic acid | 536 |
| 17E | | 3-(4-chlorophenyl)-7-[[[1(R)-(4-chlorophenyl)ethyl]amino]carbonyl]-beta-methyl-2-quinoxalinepentanoic acid | 536 |
| 17F | | 3-(4-chlorophenyl)-beta-methyl-7-[(3-phenyl-1-azetidinyl)carbonyl]-2-quinoxalinepentanoic acid | 514 |
| 17G | | 3-(4-chlorophenyl)-beta-methyl-7-[[[2,2,2-trifluoro-1(R)-(4-fluorophenyl)ethyl]aminocarbonyl]-2-quinoxalinepentanoic acid | 574 |
| 17H | | 3-(4-chlorophenyl)-7-[[[(4-methoxyphenyl)methyl]aminocarbonyl]-beta-methyl-2-quinoxaline pentanoic acid | 518 |
| 17i | | 3-(4-chlorophenyl)-beta-methyl-7-[(3(S)-phenyl-1-piperidinyl)carbonyl]-2-quinoxalinepentanoic acid | 542 |
| 17J | | 3-(4-chlorophenyl)-beta-methyl-7-[(3(R)-phenyl-1-piperidinyl)carbonyl]-2-quinoxalinepentanoic acid | 542 |

-continued

| No. | Compound | Name | M + H |
|---|---|---|---|
| 17K | | 3-(4-chlorophenyl)-beta-methyl-7-[(3(S)-phenyl-1-pyrrolidinyl)carbonyl]-2-quinoxalinepentanoic acid | 528 |
| 17L | | 3-(4-chlorophenyl)-beta-methyl-7-[(3(R)-phenyl-1-pyrrolidinyl)carbonyl]-2-quinoxalinepentanoic acid | 528 |
| 17M | | 3-(4-chlorophenyl)-beta-methyl-7-[[[2,2,2-trifluoro-(1S)-phenylethyl]amino]carbonyl]-2-quinoxaline pentanoic acid | 556 |
| 17N | | 3-(4-chlorophenyl)-beta-methyl-7-[[(2,2,2-trifluoro-1(R)-phenylethyl)amino]carbonyl]-2-quinoxalinepentanoic acid | 556 |
| 17o | | 3-(4-chlorophenyl)-7-[[[1(R)-(4-methoxyphenyl)ethyl]amino]carbonyl]-beta-methyl-2-quinoxaline pentanoic acid | 532 |
| 17P | | 3-(4-chlorophenyl)-7-[[[1(S)-(4-methoxyphenyl)ethyl]amino]carbonyl]-beta-methyl-2-quinoxaline pentanoic acid | 532 |

In a similar manner to that described above, the following compounds were prepared from methyl 3-chloro-2-(4-(trifluoromethyl)phenyl)quinoxaline-6-carboxylate (2i) and tert-butyl 3-methylpent-4-enoate, followed by sequential hydrolysis with LiOH, coupling with an appropriate amine and deprotection with TFA.

| No | Compound | Name | M + H |
|---|---|---|---|
| 17Q | | 7-[[[(3-chlorophenyl)methyl]amino]carbonyl]-beta-methyl-3-[4-(trifluoromethyl)phenyl]-2-quinoxalinepentanoic acid | 556 |
| 17R | | beta-methyl-7-[(4-phenyl-1-piperidinyl)carbonyl]-3-+4-(trifluoromethyl)phenyl]-2-quinolinepentanoic acid | 576 |
| 17S | | beta-methyl-3-[4-(trifluoromethyl)phenyl]-7-[(2,2,2-trifluoro-1(S)-phenylethyl)amino]carbonyl]-2-quinoxalinepentanoic acid | 590 |
| 17T | | 7-[[[(2,3-dihydro-1H-inden-2-yl)amino]carbonyl]-beta-methyl-3-[4-(trifluoromethyl)phenyl]-2-quinoxalinepentanoic acid | 548 |
| 17U | | beta-methyl-7-[(3(R)-phenyl-1-pyrrolidinyl)carbonyl]-3-[4-(trifluoromethyl)phenyl]-2-quinoxalinepentanoic acid | 562 |
| 17V | | beta-methyl-7-[(3(S)-phenyl-1-pyrrolidinyl)carbonyl]-3-[4-(trifluoromethyl)phenyl]-2-quinoxalinepentanoic acid | 562 |
| 17W | | beta-methyl-7-[(3-phenyl-1-azetidinyl)carbonyl]-3-[4-(trifluoromethyl)phenyl]-2-quinoxalinepentanoic acid | 548 |

| No | Compound | Name | M + H |
|---|---|---|---|
| 17X | | 7-[[[(4-chlorophenyl)methyl]amino]carbonyl]-beta-methyl-3-[4-(trifluoromethyl)phenyl]-2-quinoxalinepentanoic acid | 556 |
| 17Y | | beta-methyl-7-[[[[4-(trifluoromethoxy)phenyl]methyl]amino]carbonyl]-3-[4-(trifluoromethyl)phenyl]-2-quinoxalinepentanoic acid | 606 |
| 17Z | | 7-[[[(4-cyanophenyl)methyl]amino]carbonyl]-beta-methyl-3-[4-(trifluoromethyl)phenyl]-2-quinoxalinepentanoic acid | 547 |

Example 18

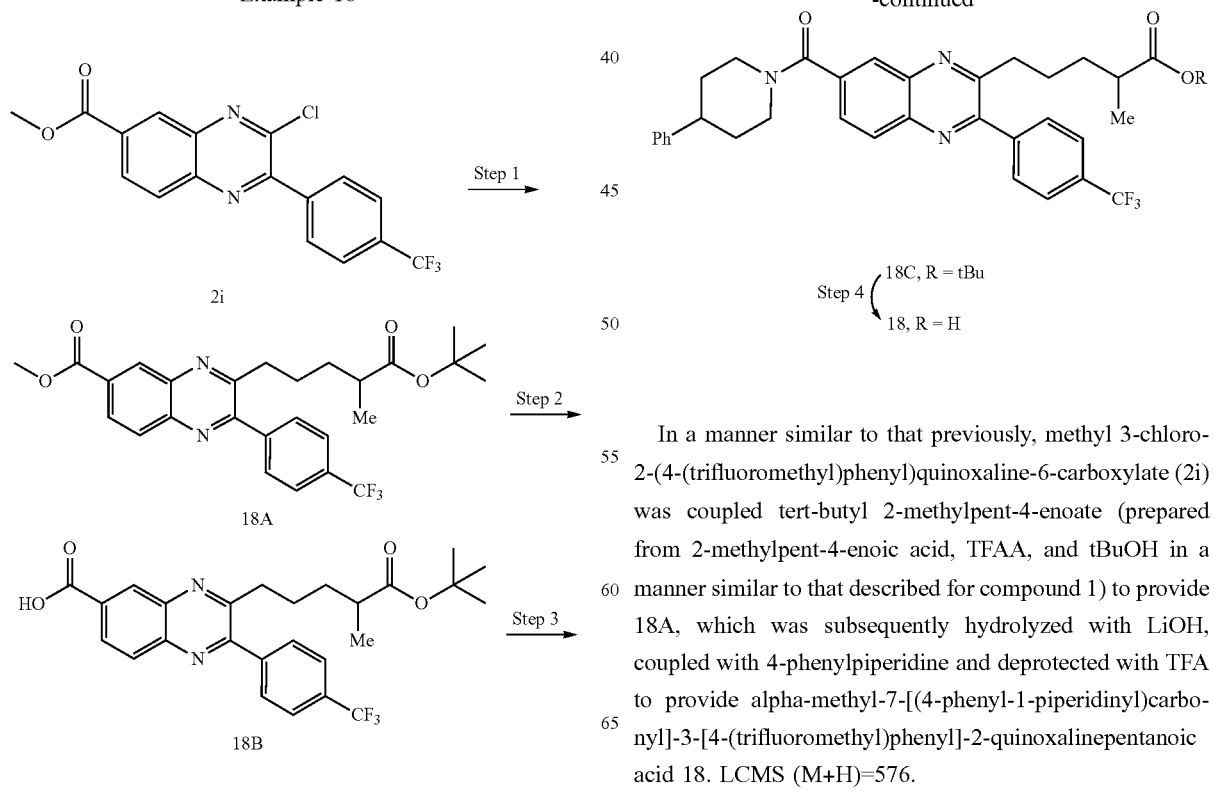

In a manner similar to that previously, methyl 3-chloro-2-(4-(trifluoromethyl)phenyl)quinoxaline-6-carboxylate (2i) was coupled tert-butyl 2-methylpent-4-enoate (prepared from 2-methylpent-4-enoic acid, TFAA, and tBuOH in a manner similar to that described for compound 1) to provide 18A, which was subsequently hydrolyzed with LiOH, coupled with 4-phenylpiperidine and deprotected with TFA to provide alpha-methyl-7-[(4-phenyl-1-piperidinyl)carbonyl]-3-[4-(trifluoromethyl)phenyl]-2-quinoxalinepentanoic acid 18. LCMS (M+H)=576.

Example 19

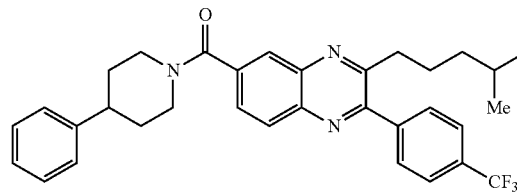

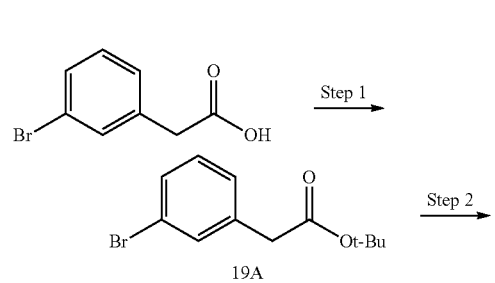

In a similar manner, the following compounds were prepared by coupling acid 18B to the appropriate amine reagent followed by a TFA deprotection:

| No. | Compound | Name | M + H |
|---|---|---|---|
| 18D | | 7-[[[(3-chlorophenyl)methyl]amino]carbonyl]-alpha-nethyl-3-[4-(trifluoromethyl)phenyl]-2-quinoxalinepentanoic acid | 556 |
| 18E | | alpha-methyl-7-[(3(S)-phenyl-1-pyrrolidinyl)carbonyl]-3-[4-(trifluoromethyl)phenyl]-2-quinoxalinepentanoic acid | 562 |
| 18F | | alpha-methyl-7-[(3(R)-phenyl-1-pyrrolidinyl)carbonyl]-3-[4-(trifluoromethyl)phenyl]-2-quinoxalinepentanoic acid | 562 |
| 18G | | 7-[[(2,3-dihydro-1H-inden-2-yl)amino]carbonyl]-alpha-methyl-3-[4-(trifluoromethyl)phenyl]-2-quinoxalinepentanoic acid | 548 |
| 18H | | alpha-methyl-3-[4-(trifluoromethyl)phenyl]-7-[[[(2,2,2-trifluoro-1(S)-phenylethyl)amino]carbonyl]-2-quinoxalinepentanoic acid | 590 |

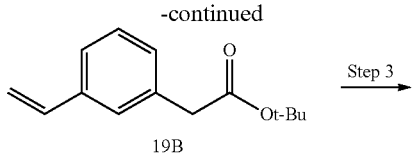

19B

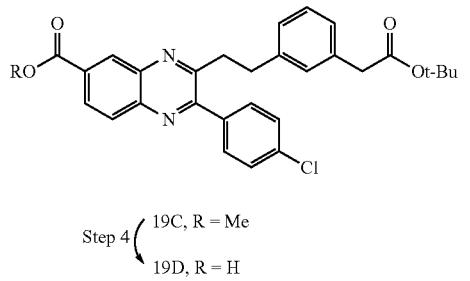

Step 4 ( 19C, R = Me
        ( 19D, R = H

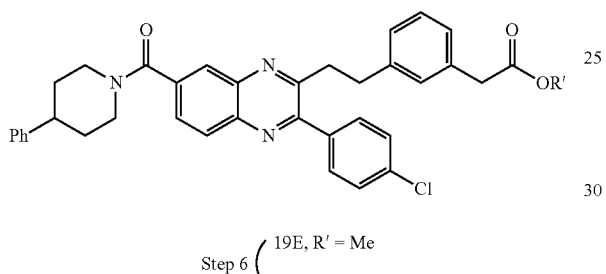

Step 6 ( 19E, R' = Me
        ( 19, R' = H

Steps 1-2 tert-Butyl 2-(3-Vinylphenyl)acetate

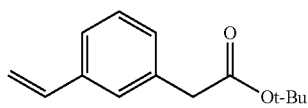

19A

In a manner similar to that described for compound 1, 2-(3-bromophenyl)acetic acid was reacted with TFAA and tBuOH to provide tert-butyl 2-(3-bromophenyl)acetate (19A).

A solution of 19A (600 mg, 2.21 mmol), potassium vinyltrifluoroborate (296 mg, 2.21 mmol), Pd(dppf)$_2$Cl$_2$·CH$_2$Cl$_2$ (180 mg, 0.221 mmol), and cesium carbonate (2.16 g, 6.63 mmol) in water (1 mL) and 1,4-dioxane (9 mL) under nitrogen was stirred at 90° C. for 18 h. After this time, the reaction was cooled to RT and diluted with water and DCM. The aqueous layer was separated and extracted with DCM. The combined organics were washed with brine, dried (Na$_2$SO$_4$), filtered, and concentrated. The residue was purified by flash chromatography (0% to 20% EtOAc/heptane) to yield 19B (268 mg, yield=56%): $^1$H NMR (500 MHz, CDCl$_3$) δ 7.32-7.24 (m, 3H), 7.18-7.15 (m, 1H), 6.70 (dd, J=23.5, 14.5 Hz, 1H), 5.75 (d, J=23.5 Hz, 1H), 5.24 (d, J=14.5 Hz, 1H), 3.52 (s, 2H), 1.44 (s, 9H).

Steps 3-6

2-(3-(2-(3-(4-chlorophenyl)-7-(4-phenylpiperidine-1-carbonyl)quinoxalin-2-yl)ethyl)phenyl)acetic acid

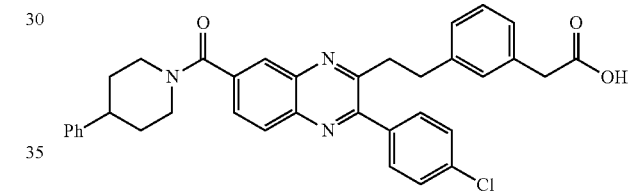

19

In a manner similar to that previously, tert-butyl 2-(3-vinylphenyl)acetate (19B) was sequentially coupled with methyl 3-chloro-2-(4-chlorophenyl)quinoxaline-6-carboxylate (16B) and hydrolyzed with LiOH. The resulting acid 19C (3-(3-(2-tert-butoxy-2-oxoethyl)phenethyl)-2-(4-chlorophenyl)quinoxaline-6-carboxylic acid) was coupled with 4-phenylpiperidine and deprotected with TFA to provide -[2-[3-(4-chlorophenyl)-7-[(4-phenyl-1-piperidinyl)carbonyl]-2-quinoxalinyl]ethyl]benzeneacetic acid 19. LCMS (M+H)=590.

In a similar manner, the following compounds were prepared by coupling acid 19C to the appropriate amine reagent followed by a TFA deprotection:

| No. | Compound | Name | M + H |
|---|---|---|---|
| 19F | | 3-[2-[3-(4-chlorophenyl)-7-[[[(4-cyanophenyl)methyl]amino]carbonyl]-2-quinoxalinyl]ethyl]benzeneacetic acid | 561 |

| No. | Compound | Name | M + H |
|---|---|---|---|
| 19G | | 3-[2-[3-(4-chlorophenyl)-7-[[[1(R)-(4-fluorophenyl)ethyl]amino]carbonyl]-2-quinaxalinyl]ethyl]benzeneacetic acid | 568 |
| 19H | | 3-[2-[3-(4-chlorophenyl)-7-[[[1(S)-(4-fluorophenyl)ethyl]amino]carbonyl]-2-quinoxalinyl]ethyl]benzeneacetic acid | 568 |
| 19i | | 3-[2-[3-(4-chlorophenyl)-7-[[[(3-chlorophenyl)methyl]amino]carbonyl]-2-quinoxalinyl]ethyl]benzeneacetic acid | 570 |
| 19J | | 3-[2-[3-(4-chlorophenyl)-7-[[[(2,2,2-trifluoro-1(S)-phenylethyl)amino]carbonyl]-2-quinoxalinyl]ethyl]benzeneacetic acid | 604 |
| 19K | | 3-[2-[3-(4-chlorophenyl)-7-[(3-phenyl-1-azetidinyl)carbonyl]-2-quinoxalinyl]ethyl]benzeneacetic acid | 562 |

Example 20

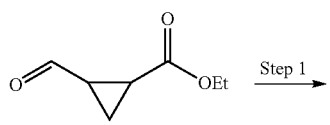

Step 1

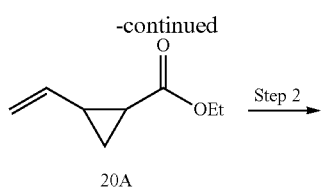

20A

-continued

Step 2

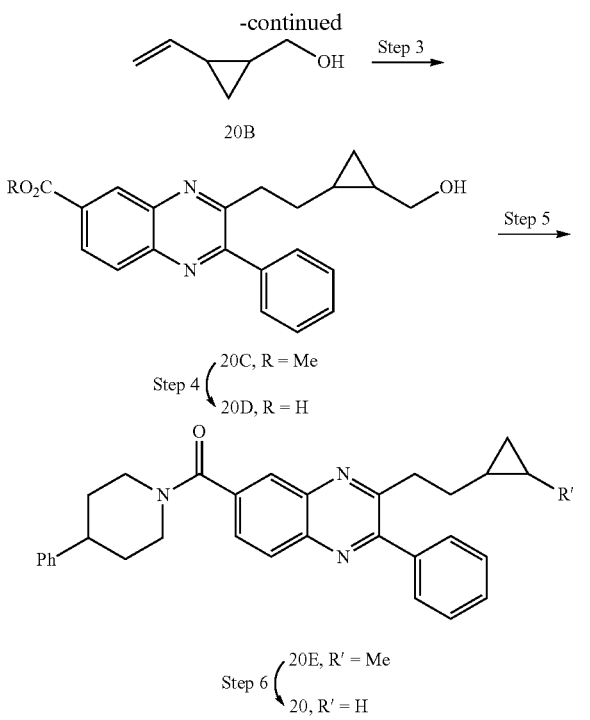

Step 1

Ethyl 2-vinylcyclopropanecarboxylate

20A

A mixture of methyltriphenyl-phosphonium bromide (60.3 g, 168.8 mmol, 2.4 eq) in 500 mL of THF was cooled down to ° C. and treated slowly with KOtBu (18.9 g, 168.8 mmol, 2.4 eq). The reaction was stirred at ° C. for 30 min, treated dropwise with ethyl 2-fomyl-1-cyclopropanecarboxylate (10 g, 70.34 mmol, 1.0 eq) in 200 mL THF, and then stirred for 2 h at RT. The mixture was then cooled to ° C., treated with water and extracted with ether (2×). The organic extracts were dried over $Na_2SO_4$, filtered and concentrated. Chromatography (*0 to 25% ether in pentane) afforded the olefin 20A (8.15 g).

Step 2

(2-Vinylcyclopropyl)methanol

20B

A solution of ethyl 2-vinylcyclopropanecarboxylate (20A, 4.26 g, 30.4 mmol, 1.0 eq) in THF (100 mL, anhydrous) was cooled to 0° C. and treated slowly with LAH (1.60 g, 38.0 mmol, 1.25 eq). The reaction was then slowly warmed to RT, stirred overnight, and then quenched with water. The precipitate was filtered and washed with THF. Chromatography of the filtrate (0 to 60% ether/hexanes) gave the alcohol 20B (2.0 g).

Step 3

Methyl 3-(2-(2-(hydroxymethyl)cyclopropyl)ethyl)-2-phenylquinoxaline-6-carboxylate

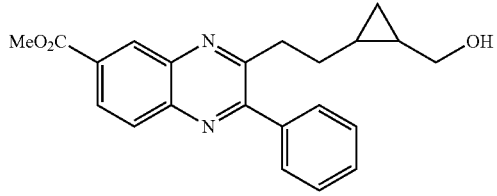

20C

To a solution of (2-vinylcyclopropyl)methanol (20B, 0.5 g, 5.10 mmol, 2.0 eq) in anhydrous THF (20 mL) was added 9-BBN (0.5 M in THF, 20 mL, 10.2 mmol, 4 eq) at 0° C. under nitrogen. The reaction was stirred at 0° C. for 30 min and warmed to RT for 4 h. methyl 3-chloro-2-phenylquinoxaline-6-carboxylate 6B (0.76 g, 2.55 mmol, 1.0 eq), $Pd(dppf)Cl_2 \cdot CH_2Cl_2$ (310 mg, 0.380 mmol, 0.15 eq), and $K_3PO_4$ (1.62 g, 7.65 mmol, 3.0 eq) were added. The suspension was degassed (3× vacuum/nitrogen) and heated at 68° C. overnight. The reaction was then cooled to RT and filtered. The filtrate was diluted with DCM and water. The aqueous layer was separated and extracted with DCM. The combined organics were dried ($Na_2SO_4$), filtered, and concentrated. The residue was purified by column chromatography (20%-50% EtOAc/hexane) to yield 20C (0.84 g). Further purification of the mixture (SFC chiral chromatography) provided the 4 stereoisomers, each in high purity.

Steps 4-6

2-(2-(3-phenyl-7-(4-phenylpiperidine-1-carbonyl) quinoxaline-2-yl)ethyl)cyclopropanecarboxylic acid

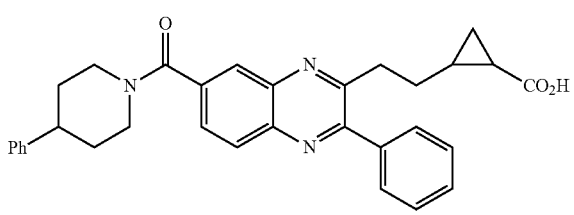

20

In a manner similar to that previously, each pure stereoisomer of 20C was individually hydrolyzed with LiOH and coupled with 4-phenylpiperidine to provide (3-(2-(2-(hydroxymethyl)cyclopropyl)ethyl)-2-phenylquinoxalin-6-yl) (4-phenylpiperidin-1-yl)methanone (20E). The first stereoisomer was then subjected to the following oxidation:

A mixture of the alcohol 20E (103 mg, 0.21 mmol, 1.0 eq), sodium periodate (135 mg, 0.629 mmol, 3.0 eq) and ruthenium chloride trihydrate (3 mg, 0.011 mmol, 0.05 eq) were combined in 3 mL $CCl_4$-4 mL $H_2O$-3 mL $CH_3CN$. The mixture was stirred at RT overnight, quenched with 10 mL sat. aq. NH₄Cl and filtered. The precipitate was filtered and washed with EtOAc. The aqueous layer was extracted with EtOAc (1×). The combined organic layers were dried (Na₂SO₄), filtered, and concentrated. Chromatography (0 to 10% MeOH/CH₂Cl₂) provided the title compound 20 (74 mg, LCMS: M+H 506).

The other three stereoisomers of 20E were similarly subjected to this oxidation to provide 20F (LCMS: M+H 506), 20G (LCMS: M+H 506), and 20H (LCMS: M+H 506).

Example 21

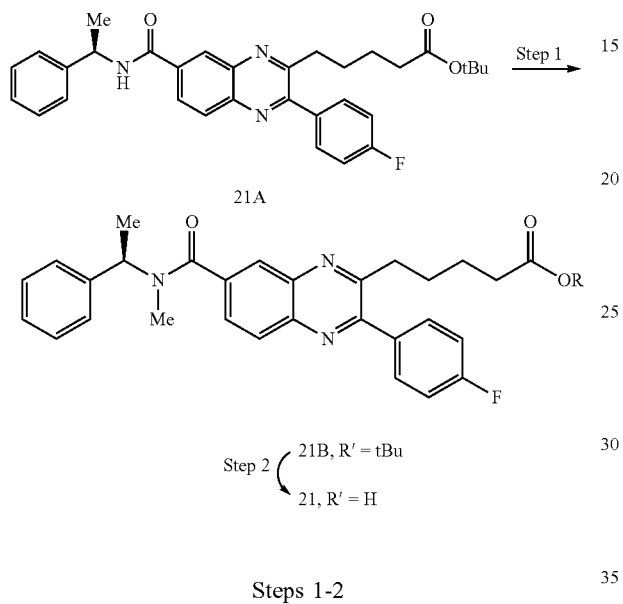

Steps 1-2

(R)-5-(3-(4-fluorophenyl)-7-(methyl(1-phenylethyl) carbamoyl)quinoxalin-2-yl)pentanoic acid A solution of (R)-tert-butyl 5-(3-(4-fluorophenyl)-7-(1-phenylethyl-carbamoyl)quinoxalin-2-yl)pentanoate (21A, 62 mg, 0.118 mmol; derived from the coupling of 5D and (R)-1-phenylethanamine as previously described) in 5 DMF (5 mL) was cooled to 0° C. and treated with NaH (60%, 7 mg, 0.176 mmol, 1.5 eq). After 20 min at 0° C., MeI (15 μL) was added and the reaction was warmed to RT for 2 h. The reaction was concentrated and then diluted with CH₂Cl₂ and H₂O. The H₂O layer was extracted with CH₂Cl₂ (1×). The combined organic layers were dried (Na₂SO₄), filtered, and concentrated. Chromatography (0 to 50% EtOAc/Hexane) provided the (R)-tert-butyl 5-(3-(4-fluorophenyl)-7-(methyl (1-phenylethyl)carbamoyl)-quinoxalin-2-yl)pentanoate (21B, 46 mg).

In a manner similar to that previously described, 21B was deprotected with TFA to provide 21. LCMS (M+H)=486.

The enantiomer -(4-fluorophenyl)-7-[[methyl(1(S)-phenylethyl)amino]carbonyl]-2-quinoxalinepentanoic acid 21C was synthesized in a similar fashion. LCMS (M+H)=486.

Example 22

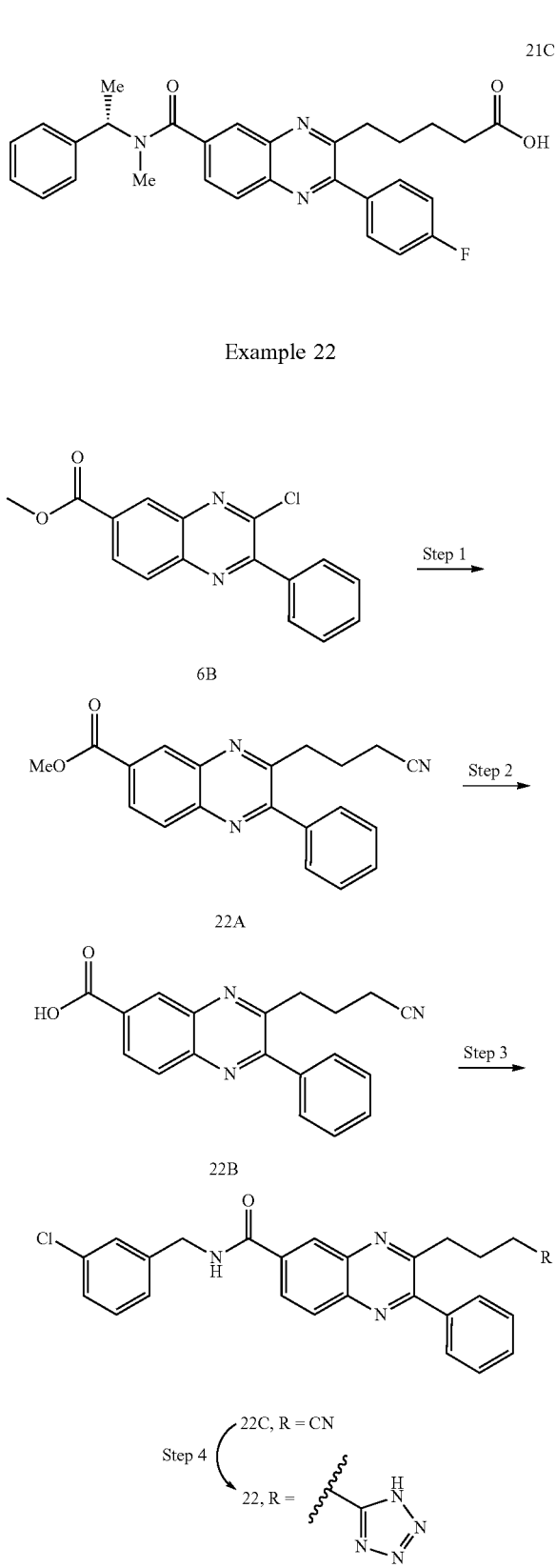

Step 1

Methyl 3-(3-cyanopropyl)-2-phenylquinoxaline-6-carboxylate

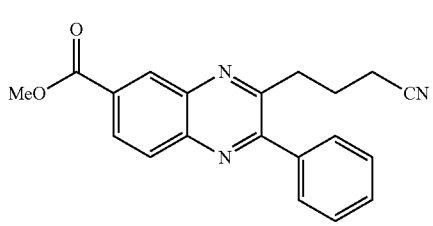

22A

In a manner similar to that described in Example 2, the following reaction was completed: To a solution of 3-butenenitrile in THF cooled to 0° C. was added 9-BBN. The reaction was stirred at 0° C. for 30 min and at RT for 3 h. To this solution was added methyl 3-chloro-2-phenylquinoxaline-6-carboxylate (6B), Pd(dppf)Cl$_2$.CH$_2$Cl$_2$ and K$_3$PO$_4$ The resulting solution was degassed and stirred at 60° C. for 16 h. The filtrate was diluted with DCM and water. The organic layer was removed and the aqueous phase was extracted with DCM (2×). The combined organics were dried (Na$_2$SO$_4$), filtered, and concentrated. The residue was purified by flash chromatography to provide 22A.

Steps 2-4

N-(3-chlorobenzyl)-3-(3-cyanopropyl)-2-phenylquinoxaline-6-carboxamide

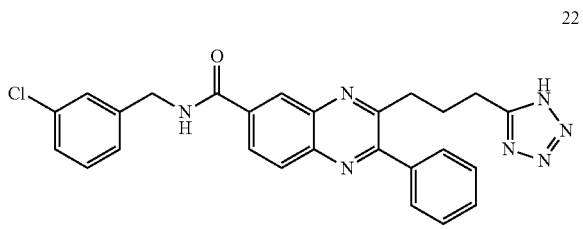 [SMILES: O=C(NCc1cccc(Cl)c1)c1ccc2nc(-c3ccccc3)c(CCCc3nnn[nH]3)nc2c1]

22

In a manner similar to that described previously (e.g., Examples 2-3), 22A was hydrolyzed with LiOH and then treated with 3-chlorobenzylamine, DIPEA, and Bop-Cl to provide 22C.

To a solution of the nitrile 22C and trimethylsilylazide in toluene was added dibutyltinoxide, and the reaction mixture was heated at 110 degree overnight until the nitrile was consumed. The mixture was concentrated down, dissolved in methanol and reconcentrated, then partitioned between EtOAc (20 mL) and 10% NaHCO$_3$ solution (20 mL). The organic layer was extracted with an additional portion of 10% NaHCO$_3$ solution (20 mL). The combined aqueous extracts were acidified to pH 2 with 10% HCl and then extracted with EtOAc (2×20 mL). The combined organic extracts were dried, concentrated, and purified by reverse-phase (C18, 5-95% MeCN—H$_2$O with 0.1% TFA) to give the 5-substituted tetrazole 22. LCMS (M+H)=484.

In a similar manner, N-[(3-chlorophenyl)methyl]-2-phenyl-3-[4-(1H-tetrazol-5-yl)butyl]-6-quinoxalinecarboxamide 22D was synthesized by using 4-pentenenitrile in Step 1, and then following the described sequence. LCMS (M+H)=498

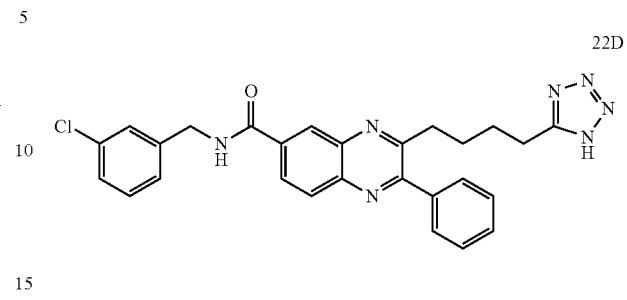

22D

Example 23

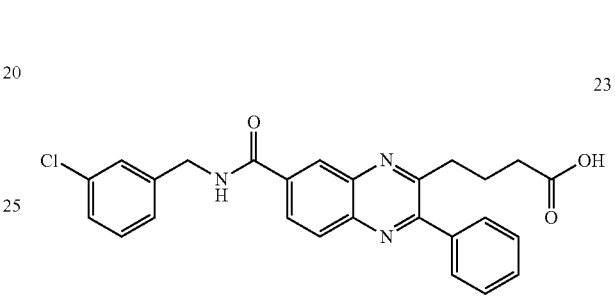

23

In a manner similar to that previously described in Examples 6 and 10, 7-[[[(3-chlorophenyl)methyl]amino]carbonyl]-3-phenyl-2-quinoxalinebutanoic acid 23 (LCMS, M+H=460) was synthesized by coupling tert-butyl 3-butenoate with 6B and then advancing the product through the described sequence.

Example 24

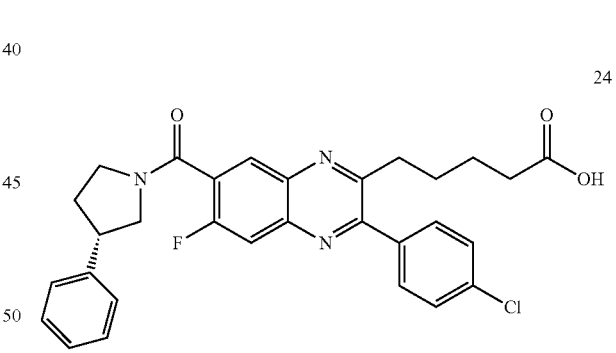

24

Step 1

Ammonium 4-amino-2-fluoro-5-nitrobenzoate

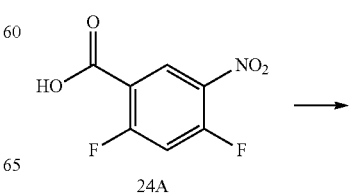

24A

-continued

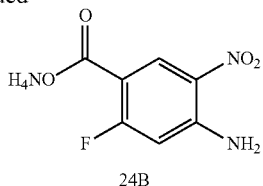

A solution of 2,4-difluoro-5-nitrobenzoic acid (24A, 10.0 g, 49.2 mmol) in 250 mL 0.5 NH₃/dioxane was heated in a sealed tube at 90° C. overnight. After the reaction mixture was cooled to RT, it was filtered and the solid collected was dried over the vacuum to provide the product as yellow solid 24B (8.3 g, 77%).

Step 2

Ammonium 4,5-diamino-2-fluorobenzoate

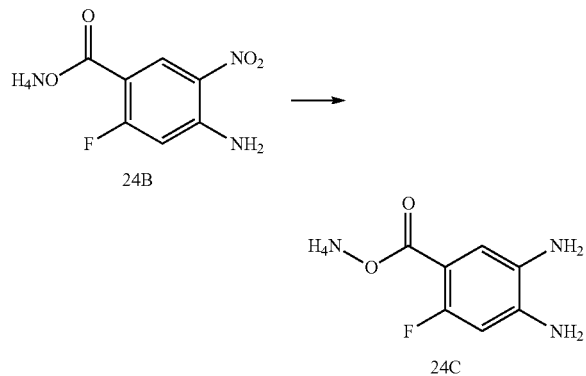

A suspension of 24B (3.5 g, 16.1 mmol) in MeOH/CH₂Cl₂ (4:1 v/v, 50 mL) was added with 10% Pd/C (wet, 0.88 g) and stirred under H₂ balloon overnight. The reaction mixture was then filtered and the filtrate was concentrated under vacuum to give crude product 24C (3.3 g) which was used in the next step without purification.

Step 3

3-(5-Ethoxy-5-oxopentyl)-7-fluoro-2-hydroxyquinoxaline-6-carboxylic acid

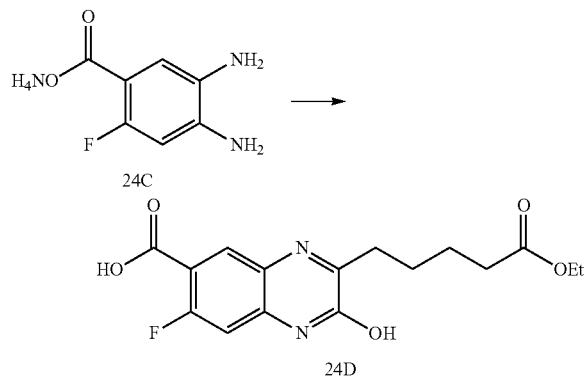

To the crude product 24C (3.3 g) in EtOH (50 mL) was added diethyl 2-oxoheptane-1,7-dicarboxylate (5.6 g, 24.2 mmol) and the mixture was heated at reflux overnight. It was then cooled to RT and acidified with 1N HCl to pH=5 and concentrated under vacuum. The resulting residue was purified by flash chromatography (CH₂Cl₂/MeOH) to provide 24D as gray solid (1.9 g, 35% over two steps).

Step 4

(S)-ethyl 5-(6-fluoro-3-hydroxy-7-(3-phenylpyrrolidine-1-carbonyl)-quinoxalin-2-yl)pentanoate

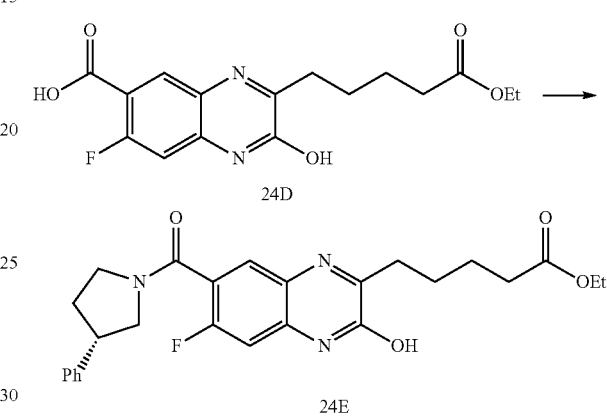

To a solution of 24D (509 mg, 1.4 mmol) in CH₂Cl₂ (10 mL) was added (S)-3-phenylpyrrolidine hydrochloride (220 mg, 1.2 mmol), HATU (912 mg, 2.4 mmol) and DIPEA (1.0 mL, 6.0 mmol) and the mixture was stirred at RT overnight. It was then diluted with CH₂Cl₂ and washed by H₂O, brine and dried over Na₂SO₄, then concentrated under vacuum. The resulting residue was purified by flash chromatography (EtOAc/hexane) to provide product 24E as colorless oil (500 mg, 90%).

Step 5

(S)-ethyl 5-(6-fluoro-7-(3-phenylpyrrolidine-1-carbonyl)-3-(trifluoromethyl-sulfonyloxy)quinoxalin-2-yl)pentanoate

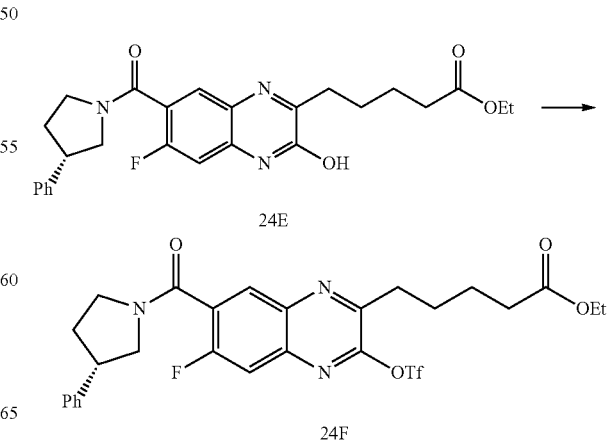

To a solution of 24E (700 mg, 1.5 mmol) in DMF (10 mL) was added PhNTf$_2$ (591 mg, 1.7 mmol) and DBU (252 mg, 1.7 mmol) and the mixture was stirred at RT overnight. Then it was diluted with EtOAc and washed by H$_2$O, brine and dried over Na$_2$SO$_4$, then concentrated over vacuum. The resulting residue was purified by flash chromatography (EtOAc/hexane) to provide product 24F as colorless oil (400 mg, 45%).

Step 6

(S)-ethyl 5-(3-(4-chlorophenyl)-6-fluoro-7-(3-phenylpyrrolidine-1-carbonyl)-quinoxalin-2-yl)pentanoate

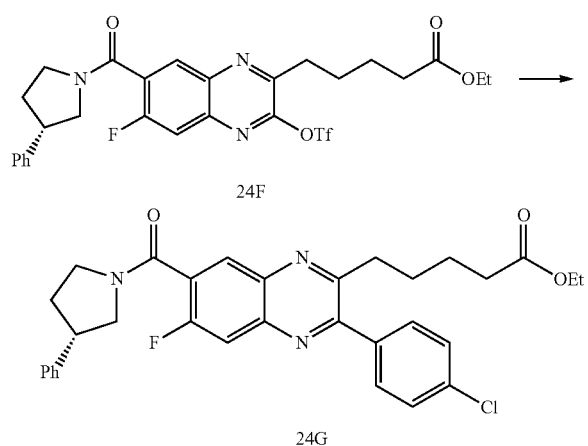

24F

24G

To a solution of 24F (100 mg, 0.17 mmol) in dioxane (10 mL) in a sealed tube was added 4-chlorophenylboronic acid (52 mg, 0.33 mmol), K$_3$PO$_4$ (71 mg, 0.33 mmol) and KBr (40 mg, 0.33 mmol) and the mixture was degassed for 5 min. Then Pd(PPh$_3$)$_4$ (53 mg, 0.046 mmol) was added and the resulting mixture was heated at 80° C. overnight. It was then taken into EtOAc and washed by H$_2$O, brine and dried over Na$_2$SO$_4$, then concentrated over vacuum. The resulting residue was purified by flash chromatography (EtOAc/hexane) to provide product 24G as colorless oil (90 mg, 95%).

Step 7

3-(4-chlorophenyl)-6-fluoro-7-[(3(S)-phenyl-1-pyrrolidinyl)carbonyl]-2-quinoxalinepentanoic acid

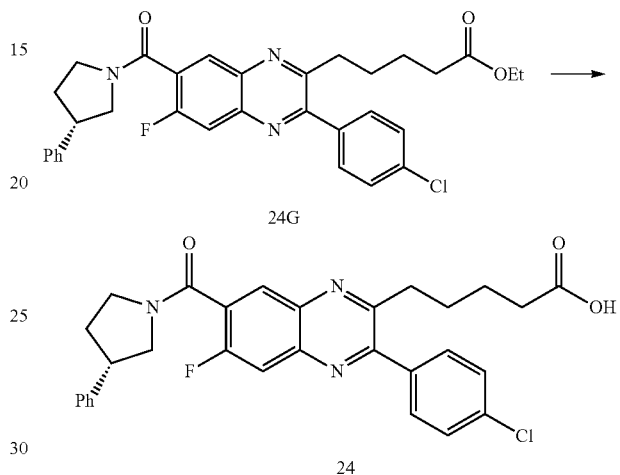

24G

24

A mixture of 24G (90 mg, 0.16 mmol) and LiOH.H$_2$O (10 mg, 0.24 mmol) in THF/H$_2$O (3:1 v/v, 4 mL) was stirred at RT overnight. Then it was acidified by 1N HCl to pH=5 and concentrated under vacuum. The resulting residue was purified by reverse phase HPLC to provide product 24 as colorless oil (50 mg, 59%). MS (M+H)=532.0.

In a similar manner, the following compounds were prepared by coupling the appropriate boronic acid to 24F followed by hydrolysis.

| No. | Compound | Name | M + H |
|---|---|---|---|
| 24H | | 6-fluoro-3-(4-fluorophenyl)-7-[(3(S)-phenyl-1-pyrrolidinyl)carbonyl]-2-quinoxalinepentanoic acid | 516 |
| 24i | | 6-fluoro-3-phenyl-7-[(3(S)-phenyl-1-pyrrolidinyl)carbonyl]-2-quinoxalinepentanoic acid | 498 |

Example 25

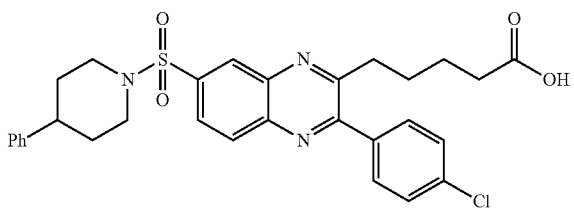

Step 1

3-(5-Ethoxy-5-oxopentyl)-2-oxo-1,2-dihydroquinoxaline-6-sulfonic acid

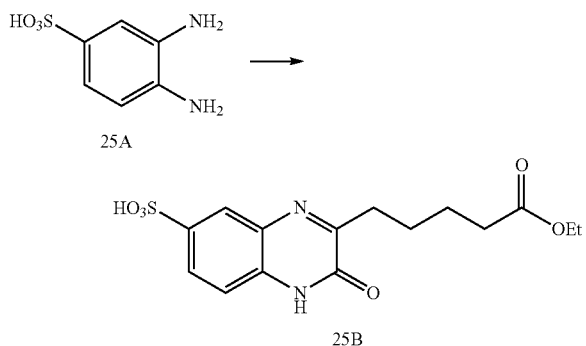

A mixture of 3,4-diaminobenzenesulfonic acid 25A (4.6 g, 24.6 mmol) and diethyl 2-oxoheptane-1,7-dicarboxylate (7.4 g, 32.0 mmol) in EtOH (100 mL) was heated at reflux overnight. Then it was concentrated under vacuum and the residue was purified by flash chromatography (CH$_2$Cl$_2$/MeOH) to provide 25B as brown solid (4.5 g, 52%).

Step 2

Ethyl 5-(3-oxo-7-(4-phenylpiperidin-4-ylsulfonyl)-3,4-dihydroquinoxalin-2-yl)pentanoate

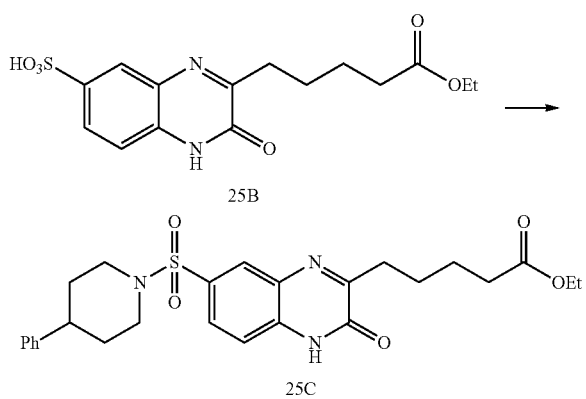

A solution of 25B (1.2 g, 3.45 mmol) in pyridine (10 mL) was stirred for 30 min and then concentrated under vacuum to give pyridine salt of 25B. In a different flask, to a solution of Ph$_3$PO (2.1 g, 7.6 mmol) in CH$_2$Cl$_2$ (20 mL) was added Tf$_2$O (0.58 mL, 3.45 mmol) and the mixture was stirred for 15 min. Then the above solution was cannulated into the pyridine salt of 25B and the resulting mixture was stirred for 30 min. A solution of 4-phenylpiperidine (1.1 g, 6.9 mmol) and Et$_3$N (4.2 mL, 15.2 mmol) in CH$_2$Cl$_2$ (3 mL) was then added into the above mixture slowly at 0° C. and stirred overnight. It was then diluted with CH$_2$Cl$_2$, washed by H$_2$O, brine, dried over Na$_2$SO$_4$ and concentrated under vacuum. The resulting residue was purified by flash chromatography (CH$_2$Cl$_2$/MeOH) to provide 25C as brownish oil (300 mg, 17%).

Step 3 ethyl 5-(7-(4-phenylpiperidin-1-ylsulfonyl)-3-(trifluoromethylsulfonyloxy)-quinoxalin-2-yl)pentanoate

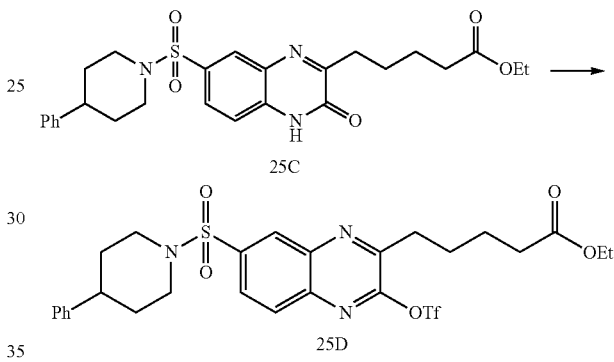

A mixture of 25C (300 mg, 0.6 mmol), PhNTf$_2$ (268 mg, 0.75 mmol) and DBU (114 mg, 0.75 mmol) in DMF (6 mL) was stirred overnight. Then it was diluted with EtOAc, washed by H$_2$O, brine, dried over Na$_2$SO$_4$ and concentrated under vacuum. The resulting residue was purified by flash chromatography (EtOAc/hexane) to provide 25D as colorless oil (170 mg, 45%).

Step 4 ethyl 5-(3-(4-chlorophenyl)-7-(4-phenylpiperidin-1-ylsulfonyl)quinoxalin-2-yl)pentanoate

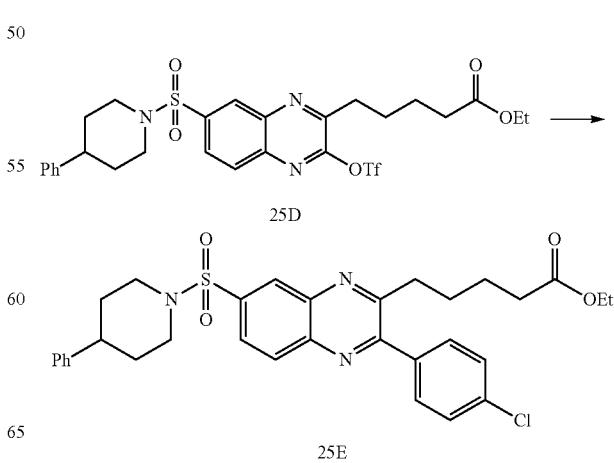

To a solution of 25D (170 mg, 0.27 mmol) in dioxane (6 mL) in a sealed tube was added 4-chlorophenylboronic acid (84 mg, 0.54 mmol), K₃PO₄ (115 mg, 0.54 mmol), and KBr (64 mg, 0.54 mmol) and the mixture was degassed for 5 min. Then Pd(PPh₃)₄ (94 mg, 0.08 mmol) was added and the mixture was heated at 80° C. overnight. It was then taken into EtOAc and washed by H₂O, brine and dried over Na₂SO₄, concentrated over vacuum. The resulting residue was purified by flash chromatography (EtOAc/hexane) to provide product 25E as colorless oil (40 mg, 25%).

Step 5

5-(3-(4-chlorophenyl)-7-(4-phenylpiperidin-1-ylsulfonyl)quinoxalin-2-yl)pentanoic acid

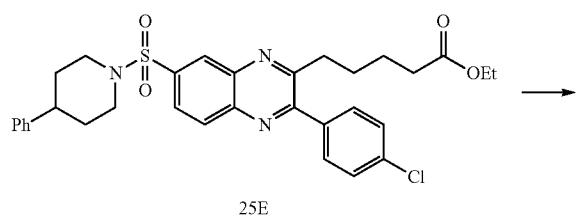

25E

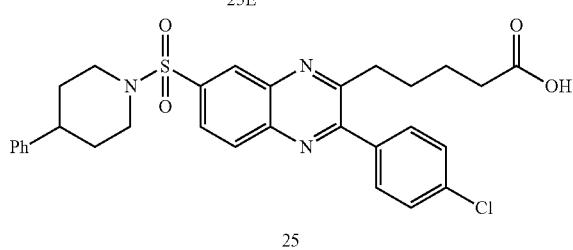

25

A mixture of 25E (34 mg, 0.057 mmol) and LiOH·H₂O (3.6 mg, 0.086 mmol) in THF/H₂O (3:1 v/v, 2.7 mL) was stirred at RT overnight. Then it was acidified by 1N HCl to PH=5 and concentrated under vacuum. The resulting residue was purified by reverse phase HPLC to provide product 25 as white solid (10 mg). MS (M+H)=564.

Example 26

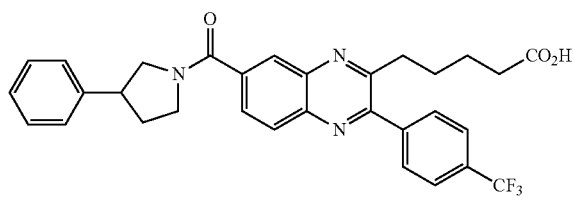

26

Step 1

3-(5-Ethoxy-5-oxopentyl)-2-hydroxyquinoxaline-6-carboxylic acid

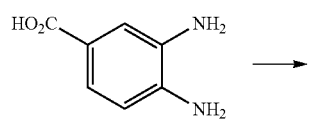

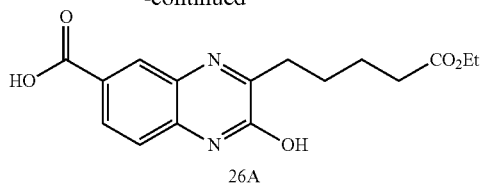

26A

A suspension of 3,4-diaminobenzoic acid (0.5 g, 3.29 mmol) and diethyl 2-oxoheptane-1,7-dicarboxylate (0.757 g, 3.29 mmol, 1.0 equiv) in 10 mL AcOH/EtOH (1:1) was heated to 100° C. After 2 h of heating, the reaction mixture was cooled to RT upon which some precipitation occurred. The solid precipitate was filtered, triturated with cold EtOH (2×5 mL) and dried to afford 0.35 g of the desired compound 26A as a brown solid.

Step 2

Ethyl 5-(3-hydroxy-7-(3-phenylpyrrolidine-1-carbonyl)quinoxalin-2-yl)-pentanoate

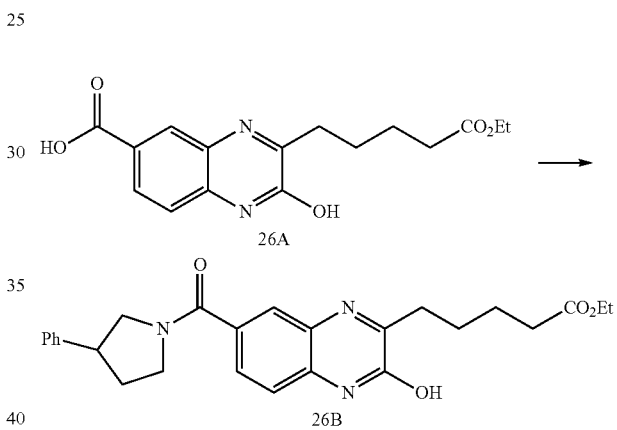

A mixture of 26A (0.25 g, 0.785 mmol), 3-phenylpyrrolidine HCl (0.144 g, 0.785 mmol), HATU (0.597 g, 1.57 mmol, 2.0 equiv), and DIPEA (0.273 mL, 1.57 mmol, 2.0 equiv) in 5 mL CH₂Cl₂ was allowed to stir at RT overnight. Upon completion, water (10 mL) was added. The mixture was extracted with CH₂Cl₂ (2×10 mL), dried over Na₂SO₄, filtered and concentrated. The crude product was purified by flash chromatography (3% MeOH/CH₂Cl₂) to yield 0.2 g of 26B.

Step 3

Ethyl 5-(7-(3-phenylpyrrolidine-1-carbonyl)-3-(trifluoromethylsulfonyloxy)-quinoxalin-2-yl)pentanoate

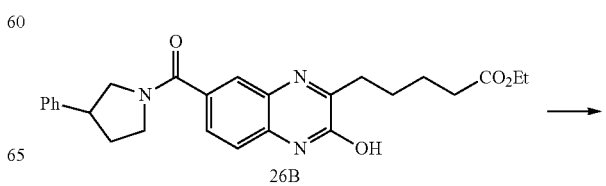

26B

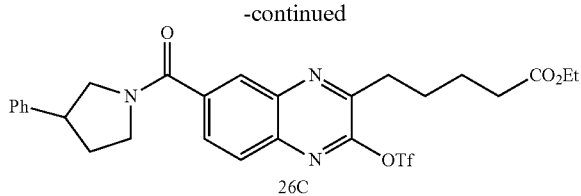

To a mixture of 26B (0.1 g, 0.22 mmol) in DMF (3 mL) at 0° C. was added DBU (37 µL, 0.25 mmol, 1.1 equiv). After stirring at that temperature for 30 min was added N-phenyl-bis(trifluoromethanesulfonimide) (0.094 g, 0.26 mmol, 1.2 equiv). The reaction was stirred at 0° C. for 1 h after which water (10 mL) was added. The reaction mixture was extracted with EtOAc (2×10 mL), washed with brine, dried over Na₂SO₄, filtered and evaporated to dryness. Purification of the crude product by flash chromatography (40% EtOAc/hexanes) afforded 0.1 g of the desired product 26C as a pale yellow solid.

Step 4

Ethyl 5-(7-(3-phenylpyrrolidine-1-carbonyl)-3-(4-(trifluoromethyl)phenyl)-quinoxalin-2-yl)pentanoate

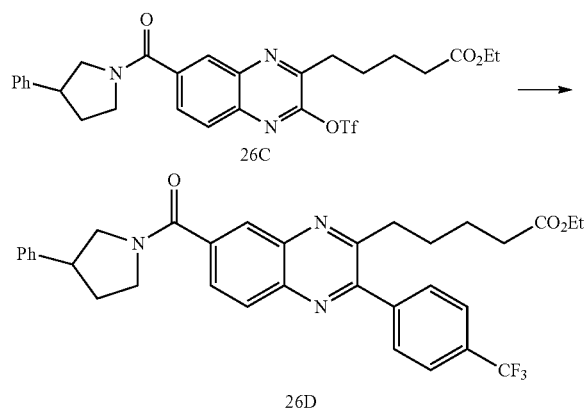

A mixture of 26C (100 mg, 0.17 mmol), 4-trifluoromethylbenzene boronic acid (49 mg, 0.26 mmol, 1.5 equiv), Pd(PPh₃)₄ (20 mg, 0.017 mmol, 10 mol %) and K₃PO₄ (55 mg, 0.26 mmol, 1.5 equiv) in 2.0 mL of 1,4-dioxane/H₂O (4:1) was heated to 90° C. for 2 h. After cooling, the reaction mixture was loaded onto a flash column and purified by eluting with 40% EtOAc/hexanes to yield 72 mg of compound 26D.

Step 5

5-(7-(3-Phenylpyrrolidine-1-carbonyl)-3-(4-(trifluoromethyl)phenyl)-quinoxalin-2-yl)pentanoic acid

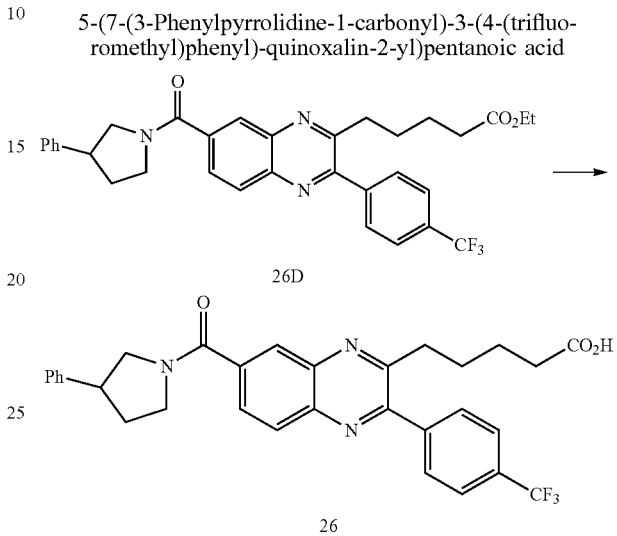

To a mixture of 26D (72 mg, 0.13 mmol) in 3 mL THF was added LiOH (22 mg, 0.25 mmol, 4.0 equiv) in 1 mL water. The reaction mixture was heated to 50° C. for 2 h after which another 11 mg of LiOH was added and stirred an additional 30 min. Upon completion, the reaction mixture was neutralized with 4 N HCl, extracted with EtOAc, dried over Na₂SO₄, filtered and concentrated to dryness. Purification by preparative TLC (60% CH₂Cl₂/30% hexanes/9% MeOH/1% AcOH) yielded 25 mg of the desired product 26 as an off white solid. MS (M+H)=548.

The following compounds were prepared in a similar manner to that described above:

| No. | Compound | Name | M + H |
|---|---|---|---|
| 26E | | 3-(3-fluorophenyl)-7-[(3-phenyl-1-pyrrolidinyl)carbonyl]-2-quinoxalinepentanoic acid | 498 |
| 26F | | 3-(3-chlorophenyl)-7-[(3-phenyl-1-pyrrolidinyl)carbonyl]-2-quinoxalinepentanoic acid | 514 |

-continued

| No. | Compound | Name | M + H |
|---|---|---|---|
| 26G | | 3-(3,5-dichlorophenyl)-7-[(3-phenyl-1-pyrrolidinyl)carbonyl]-2-quinoxalinepentanoic acid | 548 |
| 26H | | 3-(2,4-difluorophenyl)-7-[(3-phenyl-1-pyrrolidinyl)carbonyl]-2-quinoxalinepentanoic acid | 516 |
| 26i | | 3-(3,5-difluorophenyl)-7-[(3-phenyl-1-pyrrolidinyl)carbonyl]-2-quinoxalinepentanoic acid | 516 |
| 26J | | 3-(3-chlorophenyl)-7-[(4-phenyl-1-piperidinyl)carbonyl]-2-quinoxalinepentanoic acid | 528 |
| 26K | | 7-[(4-phenyl-1-piperidinyl)carbonyl]-3-[6-(trifluoromethyl)-3-pyridinyl]-2-quinoxalinepentanoic acid | 563 |
| 26L | | 3-(2-chlorophenyl)-7-[(4-phenyl-1-piperidinyl)carbonyl]-2-quinoxalinepentanoic acid | 528 |

| No. | Compound | Name | M + H |
|---|---|---|---|
| 26M | | 7-[(4-phenyl-1-piperidinyl)carbonyl]-3-(3-pyridinyl)-2-quinoxalinepentanoic acid | 495 |
| 26N | | 7-[(4-phenyl-1-piperidinyl)carbonyl]-3-[4-(trifluoromethoxy)phenyl]-2-quinoxalinepentanoic acid | 578 |
| 26o | | 3-(4-methoxyphenyl)-7-[(4-phenyl-1-piperidinyl)carbonyl]-2-quinoxalinepentanoic acid | 524 |
| 26P | | 3-(4-cyanophenyl)-7-[(4-phenyl-1-piperidinyl)carbonyl]-2-quinoxalinepentanoic acid | 519 |
| 26Q | | 7-[(4-phenyl-1-piperidinyl)carbonyl]-3-(5-pyrimidinyl)-2-quinoxalinepentanoic acid | 496 |
| 26R | | 3-(5-chloro-3-pyridinyl)-7-[(4-phenyl-1-piperidinyl)carbonyl]-2-quinoxalinepentanoic acid | 529 |
| 26S | | 7-[(4-phenyl-1-piperidinyl)carbonyl]-3-(3-thienyl)-2-quinoxalinepentanoic acid | 500 |

-continued

| No. | Compound | Name | M + H |
|---|---|---|---|
| 26T | | 3-(1-methyl-1H-pyrazol-4-yl)-7-[(4-phenyl-1-piperidinyl)carbonyl]-2-quinoxalinepentanoic acid | 498 |
| 26U | | 3-(2-acetylphenyl)-7-[(4-phenyl-1-piperidinyl)carbonyl]-2-quinoxalinepentanoic acid | 536 |
| 26V | | 3-[2-methoxy-4-(trifluoromethyl)phenyl]-7-[(4-phenyl-1-piperidinyl)carbonyl]-2-quinoxalinepentanoic acid | 592 |
| 26W | | 3-(2-chloro-4-methoxyphenyl)-7-[(4-phenyl-1-piperidinyl)carbonyl]-2-quinoxalinepentanoic acid | 558 |
| 26X | | 3-[4-methylsulfonyl)phenyl]-7-[(4-phenyl-1-piperidinyl)carbonyl]-2-quinoxalinepentanoic acid | 572 |
| 26Y | | 3-(2,4-dichlorophenyl)-7-[(4-phenyl-1-piperidinyl)carbonyl]-2-quinoxalinepentanoic acid | 562 |

-continued
| No. | Compound | Name | M + H |
|---|---|---|---|
| 26Z | | 3-(2,4-dimethoxyphenyl)-7-[(4-phenyl-1-piperidinyl)carbonyl]-2-quinoxalinepentanoic acid | 554 |
| 26AA | | 3-[2-chloro-4-(trifluoromethyl)phenyl]-7-[(4-phenyl-1-piperidinyl)carbonyl]-2-quinoxalinepentanoic acid | 596 |
| 26AB | | 3-(4-bromophenyl)-7-[(4-phenyl-1-piperidinyl)carbonyl]-2-quinoxalinepentanoic acid | 572 |
Example 27
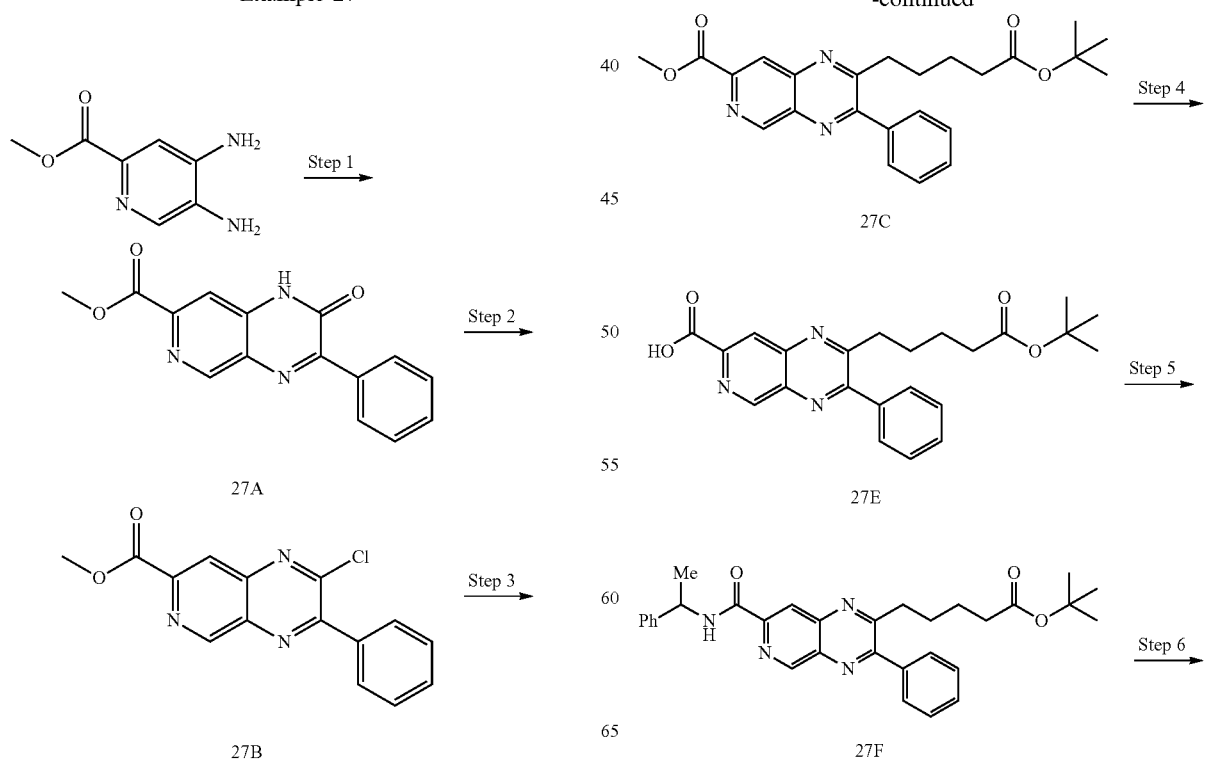

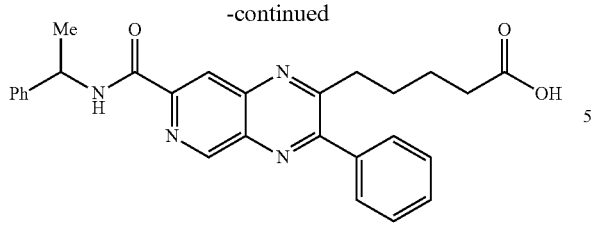

27

In a manner similar to that previously described (e.g., Example 5), 4,5-diaminopyridine-2-carboxylic acid methyl ester (available from 4-amino-5-nitropyridine-2-carboxylic acid methyl ester by hydrogenation on Pd—C) is reacted with 2-oxo-2-phenylacetic. The resulting product 27A is advanced through the sequence previously described (chlorination with POCl₃, coupling with tert-butyl pent-4-enoate, hydrolysis with LiOH, amide coupling with alpha-methyl-benzylamine, and deprotection with TFA) to give 27.

Example 28

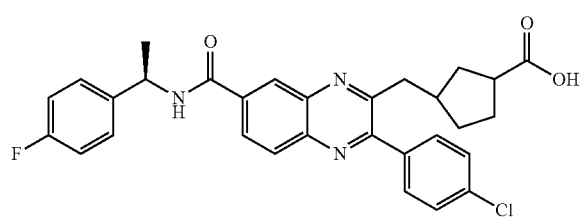

28

Step 1 tert-butyl 3-oxocyclopentanecarboxylate

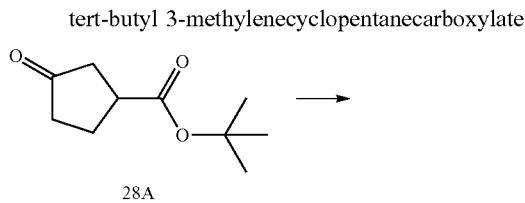

To a solution of 3-oxocyclopentanecarboxylic acid (11.0 g, 85.9 mmol) in CH₂Cl₂ (200 mL) was added TFAA (23.9 mL, 171.9 mmol) and stirred at RT for 3 h. Then t-BuOH (64.4 mL, 687.5 mmol) was added and the reaction was stirred overnight. The mixture was then diluted with CH₂Cl₂ and washed with H₂O and brine, dried (Na₂SO₄), concentrated and purified by flash chromatography to give product 28A as colorless liquid (10.8 g).

Step 2 tert-butyl 3-methylenecyclopentanecarboxylate

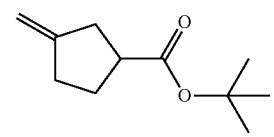

28B

A mixture of Ph₃PMeBr (35.7 g, 100 mmol) and KOtBu (11.2 g, 100 mmol) in THF (200 mL) was stirred at RT for 3 h, and then was treated with 28A (9.2 g, 50 mmol). The resulting mixture was stirred at RT overnight, then diluted with EtOAc and washed with H₂O and brine. The organic layer was dried (Na₂SO₄), concentrated and purified by flash chromatography to give product 28B as colorless liquid (9.5 g).

Step 3 methyl 3-((3-(tert-butoxycarbonyl)cyclopentyl)methyl)-2-(4-chlorophenyl)-quinoxaline-6-carboxylate

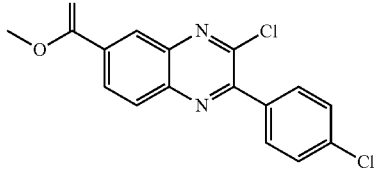

16B

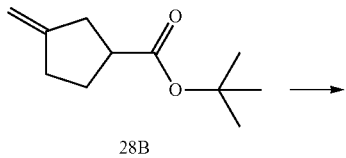

28B

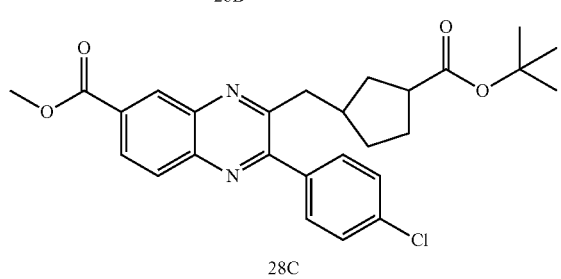

28C

To a solution of 28B (2.1 g, 11.3 mmol) in THF (12 mL) was added 9-BBN (28.2 mL, 0.4 M/hexane) and stirred for 3 h at RT. Compound 16B (1.5 g, 4.5 mmol), Pd₂(dba)₃ (103 mg, 0.11 mmol), cataCXium A (161 mg, 0.45 mmol), K₂CO₃ (1.24 g, 9.0 mmol) and H₂O (3 mL) were then added into the above mixture and heated at 80° C. overnight. The reaction was diluted with EtOAc, washed with H₂O, brine, dried (Na₂SO₄), concentrated and purified by flash chromatography to give product 28C as colorless oil (2.0 g, cis/trans=3:1).

Step 4

3-((3-(tert-butoxycarbonyl)cyclopentyl)methyl)-2-(4-chlorophenyl)-quinoxaline-6-carboxylic acid

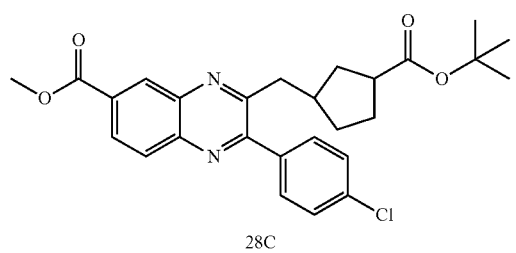

A mixture of 28C (440 mg, 0.92 mmol) and LiOH-$_2$O (46 mg, 1.10 mmol) was stirred at RT overnight. Then the reaction was acidified with 1N HCl to pH=5 and concentrated under reduced pressure to give crude residue, which was purified by HPLC to give product 28D as colorless oil (429 mg, cis/trans=3:1).

Step 5 tert-butyl 3-((3-(4-chlorophenyl)-7-((R)-1-(4-fluorophenyl)ethylcarbamoyl)-quinoxalin-2-yl)methyl)cyclopentanecarboxylate

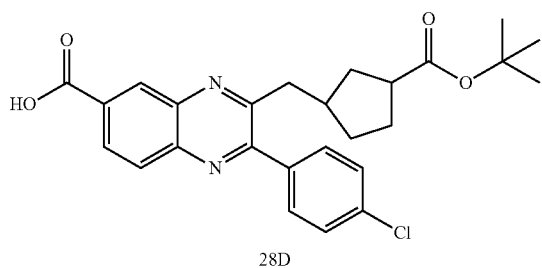

To a solution of 28D (429 mg, 0.92 mmol) in DMF (10 mL) was added (R)-1-(4-fluorophenyl)ethanamine (258 mg, 1.84 mmol), HATU (699 mg, 1.84 mmol) and DIPEA (0.32 mL, 1.84 mmol) and the mixture was stirred at RT overnight. Then the reaction was diluted with EtOAc and washed with H$_2$O, brine, dried (Na$_2$SO$_4$), concentrated and purified by flash chromatography to give product 28E as colorless oil (320 mg, cis/trans=3:1).

Step 6

3-((3-(4-chlorophenyl)-7-((R)-1-(4-fluorophenyl)ethylcarbamoyl)quinoxalin-2-yl)methyl)cyclopentanecarboxylic acid To a solution of 28E (320 mg, 0.54 mmol) in CH$_2$Cl$_2$ (10 mL) was added TFA (0.84 mL) and the mixture was stirred overnight. The reaction was concentrated under reduced pressure and the residue was purified by HPLC to give product 28 as off-white powder (170 mg, cis/trans=3:1). LCMS (M+H)=532.

Example 29

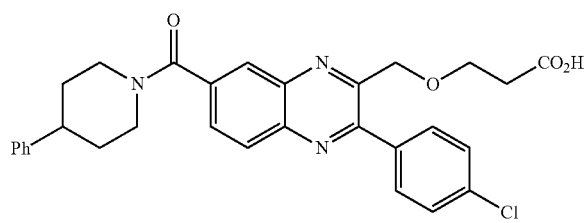

29

Step 1 methyl 2-hydroxy-3-methylquinoxaline-6-carboxylate

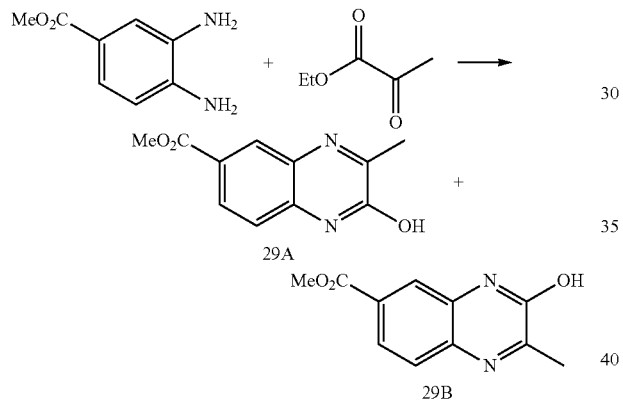

A suspension of methyl 3,4-diaminobenzoate (5.0 g, 30.09 mmol) and ethyl pyruvate (3.34 mL, 30.09 mmol, 1.0 equiv) in 60 mL AcOH/EtOH (1:1) was heated to 100° C. for 2 h of heating, the reaction mixture was cooled to RT upon which some precipitation occurred. The solid precipitate was filtered, triturated with cold EtOH (2×10 mL) followed by Et$_2$O (2×30 mL) and dried to afford 2.42 g of compound 29B as a brown solid. To the mother liquor was added 150 mL Et$_2$O upon which more precipitation occurred. The solid precipitate was filtered, triturated with Et$_2$O and dried to afford 1.16 g of the desired compound 29A as a brown solid.

Step 2 methyl 3-methyl-2-(trifluoromethylsulfonyloxy) quinoxaline-6-carboxylate

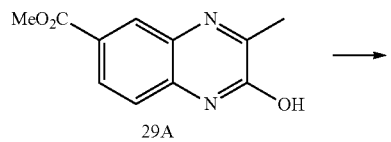

29A

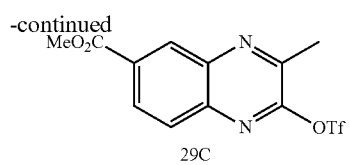

29C

To a mixture of 29A (1.81 g, 8.29 mmol) in DMF (30 mL) at 0° C. was added DBU (1.37 mL, 9.12 mmol, 1.1 equiv). After stirring at that temperature for 30 min, N-phenyl-bis (trifluoromethanesulfonimide) (3.56 g, 9.95 mmol, 1.2 equiv) was added. The reaction was stirred at 0° C. for 1 h after which water (50 mL) was added. The reaction mixture was extracted with EtOAc (2×30 mL), washed with brine, dried over Na$_2$SO$_4$, filtered and evaporated to dryness to yield 2.9 g of 29C as a brown solid. The product was used as such without further purification.

Step 3 methyl 2-(4-chlorophenyl)-3-methylquinoxaline-6-carboxylate

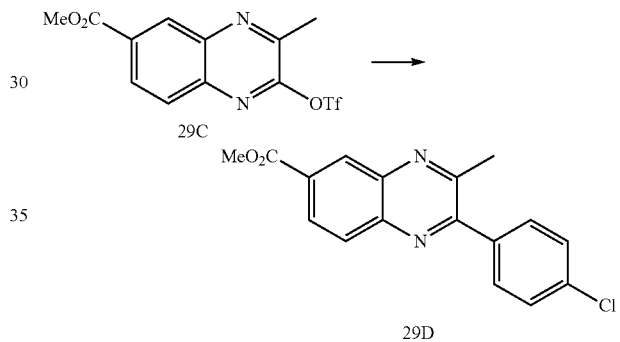

A mixture of 29C (2.9 g, 8.3 mmol), 4-chlorobenzeneboronic acid (1.95 g, 12.45 mmol, 1.5 equiv), Pd(PPh$_3$)$_4$ (958 mg, 0.83 mmol, 10 mol %) and K$_3$PO$_4$ (2.64 g, 12.45 mmol, 1.5 equiv) in 30 mL of 1,4-dioxane/H$_2$O (4:1) was heated to 90° C. for 2 h. After cooling, the reaction mixture was concentrated to half its volume, loaded onto a flash column and purified by eluting with 40% EtOAc/hexanes to yield 1.49 g of compound 29D.

Step 4 methyl 3-(bromomethyl)-2-(4-chlorophenyl)quinoxaline-6-carboxylate

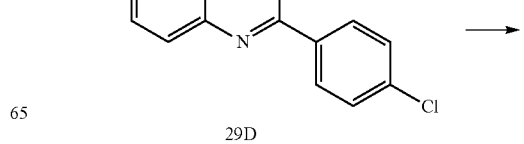

29D

-continued

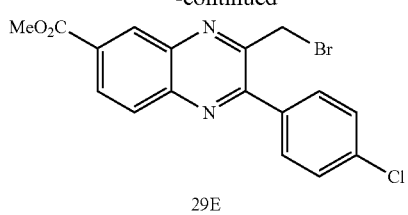

29E

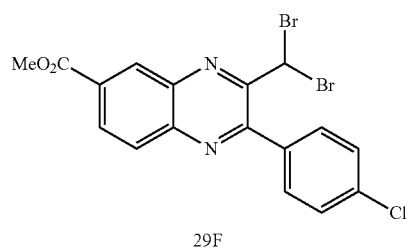

29F

To a mixture of 29D (1.39 g, 4.44 mmol) in 25 mL AcOH was added 1 mL HBr (33% in AcOH) followed by pyridinium tribromide (1.56 g, 4.88 mmol, 1.1 equiv). After all the starting material had been consumed, H$_2$O (30 mL) was added. The reaction mixture was extracted with Et$_2$O (2×20 mL), dried over Na$_2$SO$_4$, filtered and evaporated to dryness to yield a mixture of products. Purification by flash chromatography (5% EtOAc/hexanes) afforded 250 mg of the desired product 29E as a white powder and 120 mg of 29F.

Step 5 methyl 3-((3-tert-butoxy-3-oxopropoxy)methyl)-2-(4-chlorophenyl)-quinoxaline-6-carboxylate

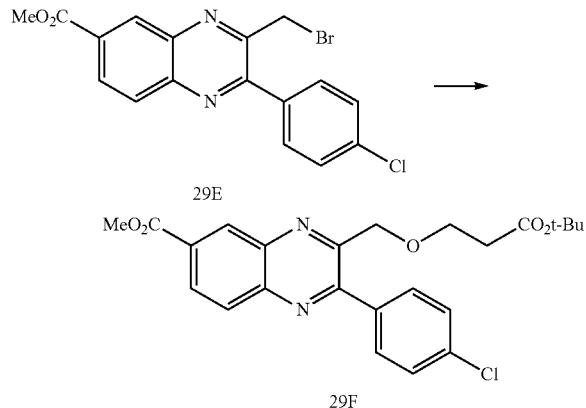

To a mixture of NaH (54 mg, 1.35 mmol, 3.0 equiv) in 5 mL THF at 0° C. was added tert-butyl 3-hydroxypropionate (200 µL, 1.35 mmol, 3.0 equiv) dropwise. After 30 min, 29E (175 mg, 0.45 mmol, 1.0 equiv) in THF (3 mL) was added dropwise and the reaction was gradually warmed to RT. After 3 h of stirring, 5 mL of a 0.5 N HCl solution was added. The reaction mixture was extracted with CH$_2$Cl$_2$ (2×5 mL), dried over Na$_2$SO$_4$, filtered and evaporated to dryness. Purification by preparative TLC (20% EtOAc/hexanes) afforded 30 mg of the desired product 29F.

Steps 6-8

3-((3-(4-chlorophenyl)-7-(4-phenylpiperidine-1-carbonyl)quinoxalin-2-yl)methoxy)propanoic acid

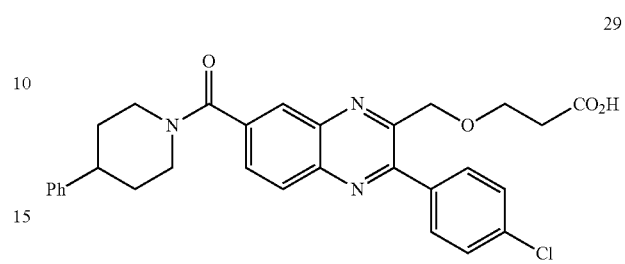

29

In a manner similar to that previously described, compound 29F was sequentially treated with LiOH (2 eq., THF—H$_2$O, 50° C., 2 h), coupled with 4-phenylpiperidine (HATU, DIPEA, DCM, RT overnight), and then deprotected with TFA to afford the title compound 29. LCMS (M+H)=530.

Example 30

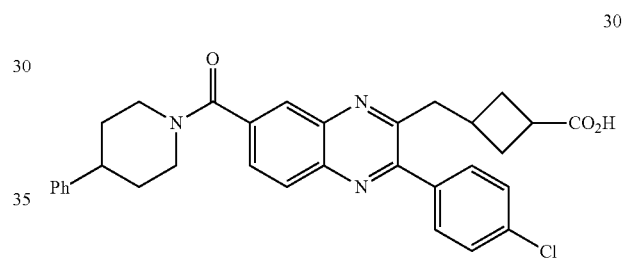

30

Step 1 methyl 2-(4-chlorophenyl)-3-((3-cyanocyclobutyl)methyl)quinoxaline-6-carboxylate

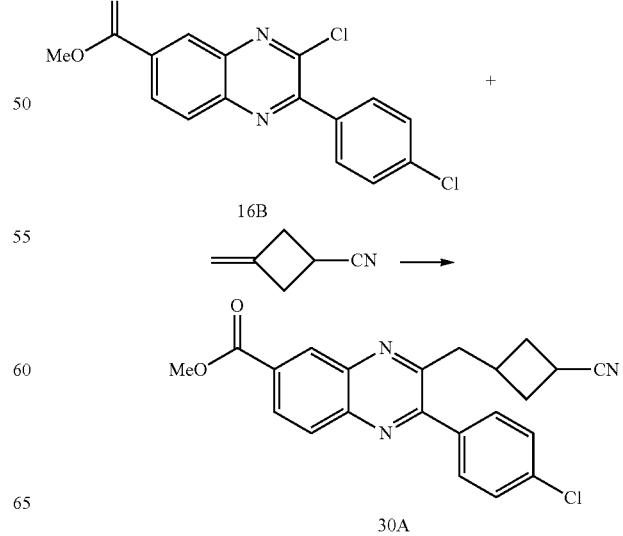

30A

A stirred solution of 3-methylenecyclobutanecarbonitrile (0.218 g, 2.34 mmol, 1.5 equiv) in THF (1 mL) under nitrogen was cooled to 0° C. 9-BBN (0.5 N in THF, 5.62 mL, 2.81 mmol, 1.8 equiv) was added and the solution was heated to 60° C. for 3 h. After this time, the reaction mixture was cooled to RT and methyl 3-chloro-2-(4-chlorophenyl) quinoxaline-6-carboxylate 16B (520 mg, 1.56 mmol), Pd(dppf)$_2$Cl$_2$.CH$_2$Cl$_2$ (255 mg, 0.312 mmol, 20 mol %) and K$_3$PO$_4$ (993 mg, 4.68 mmol, 3.0 equiv) were added. The reaction mixture was degassed and was heated at 60° C. under nitrogen for 12 h. After this time, the reaction was cooled to room temperature and diluted with water and CH$_2$Cl$_2$. The aqueous layer was separated and extracted with CH$_2$Cl$_2$ (2×15 mL), dried over Na$_2$SO$_4$, filtered and concentrated. The residue was purified by flash chromatography (10-15% EtOAc/hexanes) to yield 256 mg of the desired product 30A.

Steps 2-3

3-((3-(4-chlorophenyl)-7-(4-phenylpiperidine-1-carbonyl)quinoxalin-2-yl)methyl)cyclobutanecarbonitrile

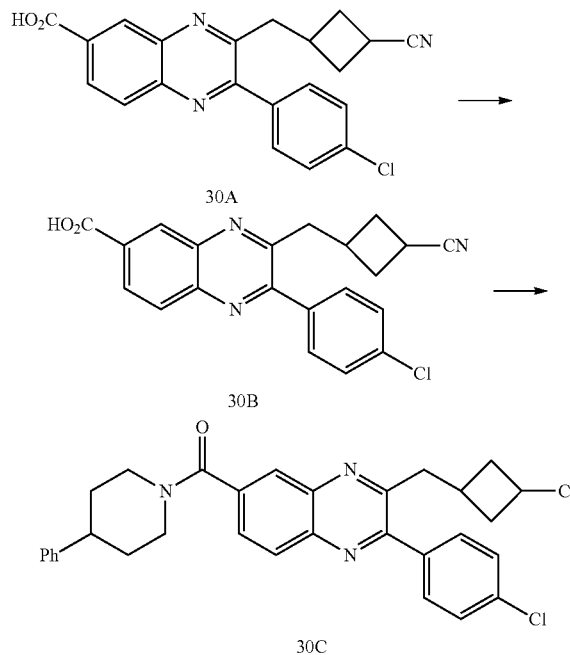

In a manner similar to that previously described, 30A was hydrolyzed with LiOH (2 eq, THF—H$_2$O, 3 h, RT) and then coupled with 4-phenylpiperidine (1 eq., 2 eq. HATU, 2 eq. DIPEA, DCM, overnight, RT) to provide 30C.

Steps 4-5

3-(((3-(4-chlorophenyl)-7-(4-phenylpiperidine-1-carbonyl)quinoxalin-2-yl)methyl)cyclobutanecarboxylic acid

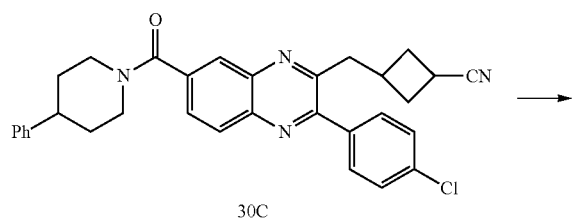

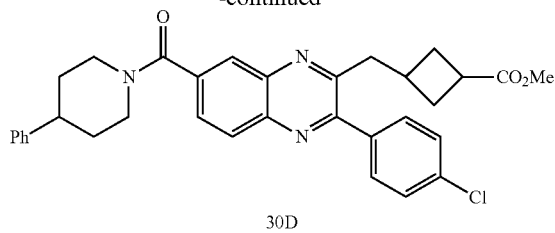

To a solution of 30C (150 mg, 0.29 mmol) in 5 mL MeOH was passed HCl (g) at 0° C. After 3 min of passing, the reaction mixture was allowed to stir at room temperature for 1 h. The excess solvent and HCl was concentrated, diluted with H$_2$O and extracted with CH$_2$Cl$_2$ (2×10 mL), dried over Na$_2$SO$_4$, filtered and concentrated. The crude product was purified by flash chromatography (20-30% EtOAc/hexanes) to yield 50 mg of the desired product 30D.

Step 6

3-((3-(4-chlorophenyl)-7-(4-phenylpiperidine-1-carbonyl)quinoxalin-2-yl)methyl)cyclobutanecarboxylic acid

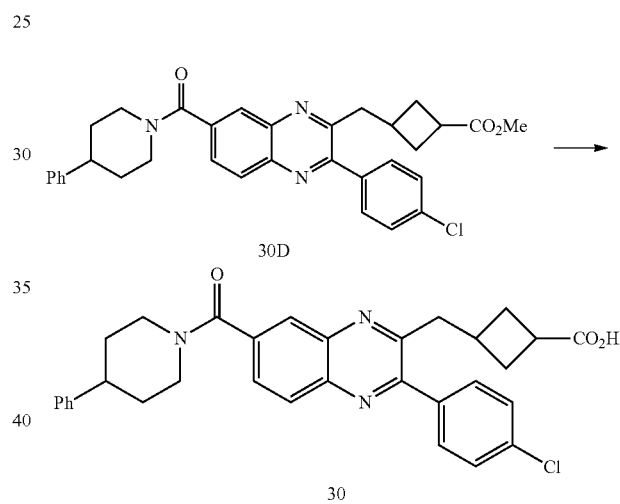

To a mixture of 30D (50 mg, 0.09 mmol) in 2 mL THF was added LiOH.H$_2$O (15 mg, 0.36 mmol, 4.0 equiv) in 1 mL water. The reaction mixture was heated to 50° C. for 2 h. Upon completion, the reaction mixture was neutralized with 2 N HCl, extracted with CH$_2$Cl$_2$ (2×5 mL), dried over Na$_2$SO$_4$, filtered and concentrated to dryness. The crude product was purified by preparative TLC (60% CH$_2$Cl$_2$/30% hexanes/9% MeOH/1% AcOH) to yield 44 mg of the desired product 30. LCMS (M+H)=540.

Compound 30E was prepared analogous manner using (R)-1-(4-fluorophenyl)ethanamine in Step 3. LCMS (M+H)=518.

Example 31

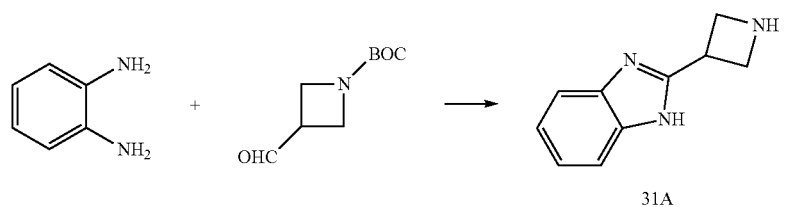

31A

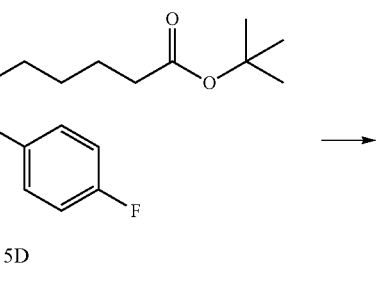

5D

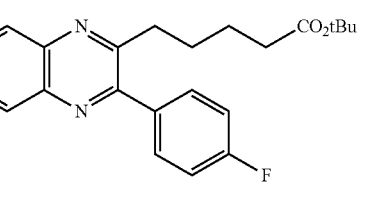

31B

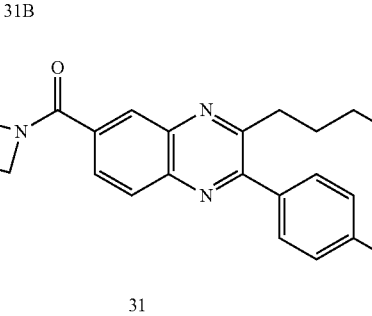

31

Step 1

2-(azetidin-3-yl)-1H-benzo[d]imidazole

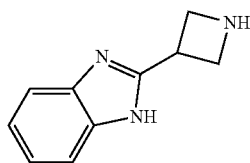

31A

To a solution of compound 1,2-phenylenediamine (1Mg, 9.25 mmol) and 1-Boc-3-azetidinecarboxaldehyde (2.1 g, 11.10 mmol) in 60 mL of IPA was added Pd/C (10%, 0.8 g). After heating at 80° C. for 2 h, the mixture was cooled down to RT, filtered through the CELITE, concentrated and purified (2.1 g). The product was treated with 4N HCl (8 mL) in 1,4-dioxane (20 mL) to give 2 g of compound 31A (Yield=83%).

Step 2

5-(7-(3-(1H-benzo[d]imidazol-2-yl)azetidine-1-carbonyl)-3-(4-fluorophenyl)quinoxalin-2-yl)pentanoic acid

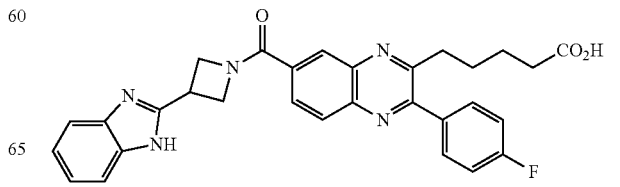

31

To a solution of compound 31A (0.11 g, 0.46 mmol) and 5D (0.13 g, 0.31 mmol) in 5 mL of DCM was added DEC (0.088 g, 0.46=1101), HOBT (0.062 g, 0.046 mmol), and DIEA (0.16 mL, 0.93 mmol). After stirring at RT for 20 h, the mixture was extracted with DCM and saturated NaHCO$_3$ (aq), dried over Na$_2$SO$_4$, concentrated and purified (0.063 g). The product 31B was deprotected with 0.5 mL of TFA in 5 mL of DCM to give the title compound 31 (0.051 g). MS (M+H)=524.

Compound 31C was prepared analogous manner using 2-aminophenol in Step 1. MS (M+H)=507.

31C

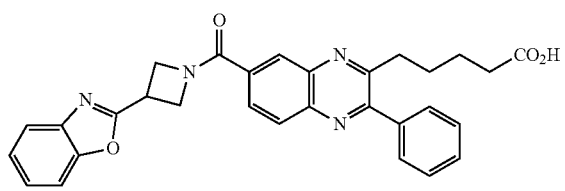

Example 32

Step 1 tert-Butyl 2-(3-allylphenyl)acetate

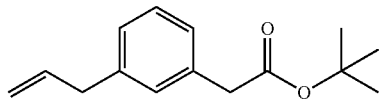

32A

To a solution of 19A (2.0 g, 7.38 mmol) in toluene (20 mL) was added allyltri-n-butyltin (2.382 mL, 9.59 mmol), and Pd(Ph$_3$P)$_4$ (0.852 g, 0.738 mmol). The reaction mixture was degassed and heated at 90° C. overnight under a nitrogen atmosphere. The mixture was diluted with EtOAc and washed with H$_2$O. Potassium fluoride (10 g, 172 mmol) and 200 mL of H$_2$O was added to the organic mixture and the mixture was stirred for 1.5 h. The layers were split and filtered the solids through CELITE, dried over MgSO$_4$, filtered and concentrated. The concentrate was purified by flash chromatography (over 120 g of silica gel) in 0-10% Et$_2$O in hexanes to yield 1.24 g (73% yield) of 19B.

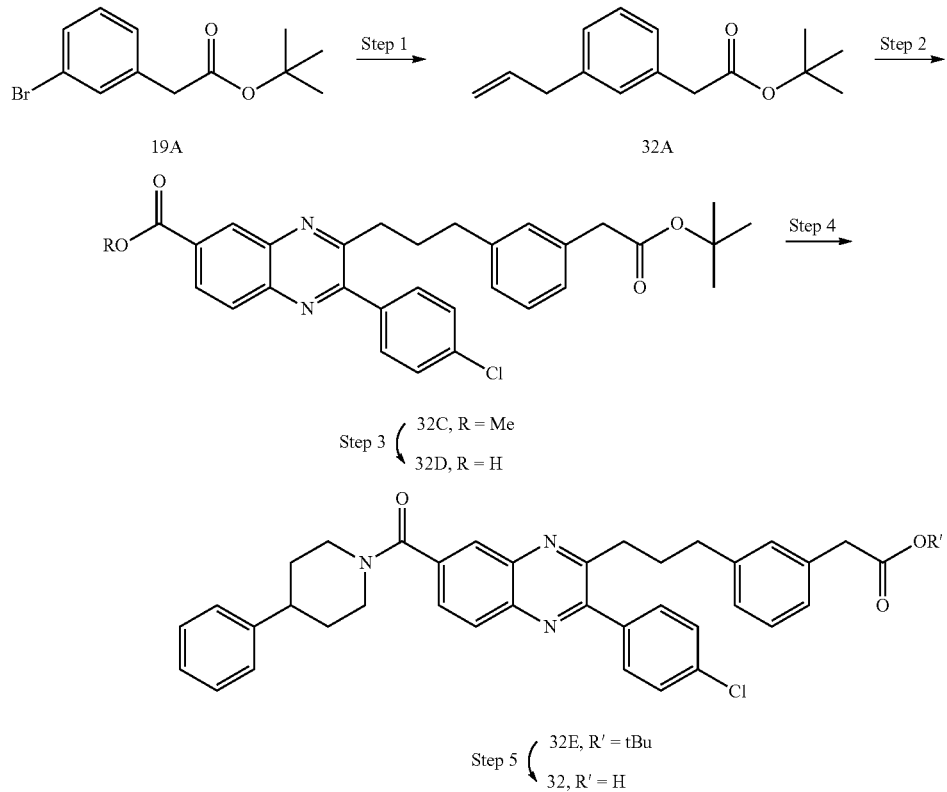

Step 2-5

2-(3-(3-(3-(4-chlorophenyl)-7-(4-phenylpiperidine-1-carbonyl)quinoxalin-2-yl)propyl)phenyl)acetic acid

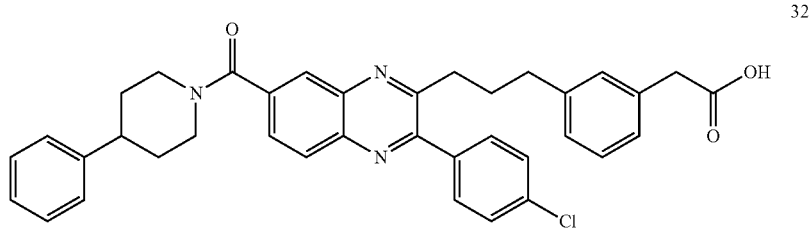 [SMILES: O=C(O)Cc1cccc(CCCc2nc3cc(C(=O)N4CCC(c5ccccc5)CC4)ccc3nc2-c2ccc(Cl)cc2)c1]

32

In a manner similar to that previously described, 19B was coupled with methyl 3-chloro-2-(4-chlorophenyl)quinoxaline-6-carboxylate (16B) and hydrolyzed with LiOH. The resulting acid 32D was coupled with 4-phenylpiperidine and deprotected with TFA to provide 32. MS (M+H)=604.

Example 33

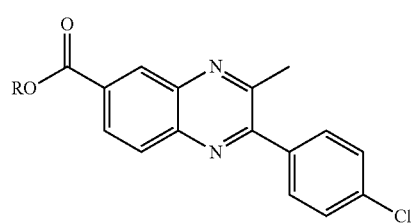

33A, R = Me
33B, R = H

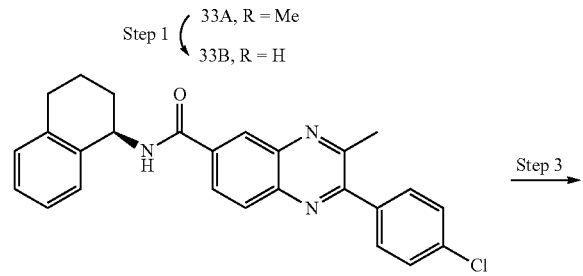

33C

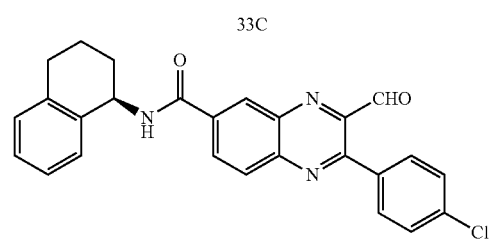

33D

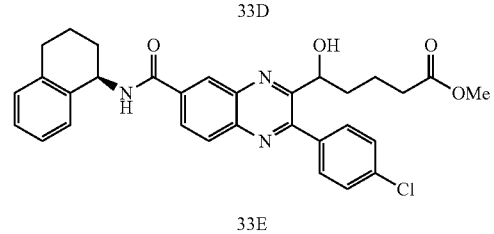

33E

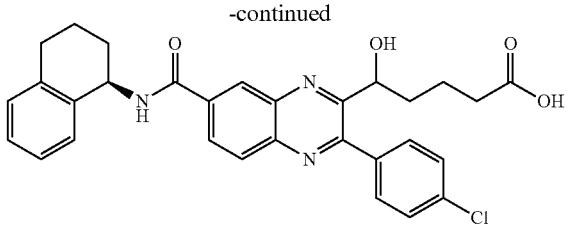

33

Step 1-2

(R)-2-(4-chlorophenyl)-3-methyl-N-(1,2,3,4-tetrahydronaphthalen-1-yl)quinoxaline-6-carboxamide In a manner similar to that previously described, 33A was hydrolyzed with LiOH and coupled with (R)-tetrahydronaphthalen-1-amine to provide 33C.

Step 3

(R)-2-(4-chlorophenyl)-3-formyl-N-(1,2,3,4-tetrahydronaphthalen-1-yl)quinoxaline-6-carboxamide To 33C (50 mg, 0.117 mmol) in dioxane (1 mL) was added selenium dioxide (19.45 mg, 0.175 mmol) in a sealed tube. The mixture was heated at 100° C. for 12 h. After cooling, the excess solvent was concentrated and the reaction mixture was purified by preparative TLC eluting with 3:1 Hex/EtOAc, then 2:1 Hex/EtOAc to yield 49 mg of 33D.

Step 4 methyl 5-(3-(4-chlorophenyl)-7-(((R)-1,2,3,4-tetrahydronaphthalen-1-yl)carbamoyl)quinoxalin-2-yl)-5-hydroxypentanoate To 33D (246 mg, 0.557 mmol) and CuCN (4.99 mg, 0.056 mmol) in DCM (5 mL) was added 4-ethoxy-4-oxobutylzinc bromide in THF (3.34 mL, 1.670 mmol). The reaction was stirred at 22° C. overnight, after which it was quenched with water and 1 N hydrochloric acid (1 mL) and extracted with ethyl acetate and with dichloromethane. The combined organics was dried over MgSO$_4$, filtered and concentrated.

Purification by flash chromatography (over 80 g of silica gel) in 0-25-50% EtOAc in hexanes afforded 59 mg (yield=19%) of 33E.

Step 5

5-(3-(4-chlorophenyl)-7-(((R)-1,2,3,4-tetrahydronaphthalen-1-yl) carbamoyl)quinoxalin-2-yl)-5-hydroxypentanoic acid To 33E (10.1 mg, 0.018 mmol) in THF (0.1 mL), Water (0.100 mL), and MeOH (0.100 mL) was added LiOH (3.04 mg, 0.072 mmol). The reaction was stirred at 22° C. for 3 h. The mixture was quenched with water, acidified with 1 N HCl to pH<1 and extracted with dichloromethane. The combined organics was dried over MgSO₄, filtered and concentrated. The mixture was purified by preparative TLC in 10:1 DCM/MeOH to obtain 3.0 mg (yield=29%) of desired product 2. MS (M+H)=530.

Example 34

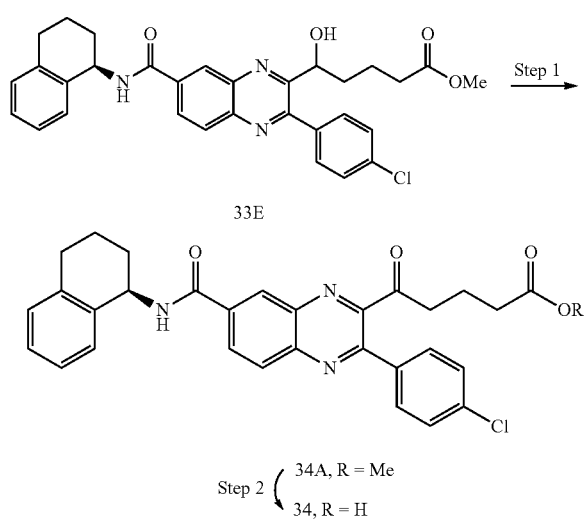

Step 1

(R)-methyl 5-(3-(4-chlorophenyl)-7-((1,2,3,4-tetrahydronaphthalen-1-yl)carbamoyl)quinoxalin-2-yl)-5-oxopentanoate To 33E (50 mg, 0.090 mmol) in DCM (1 mL) was added Dess-Martin periodinane (76 mg, 0.179 mmol). The reaction mixture was stirred at 22° C. overnight. After MS indicated the reaction was complete, the mixture was loaded on a 1 mm preparative TLC plate and eluted with 2:1 Hex/EtOAc twice to yield 13 mg (26% yield) of 34A.

Step 2

(R)-5-(3-(4-chlorophenyl)-7-((1,2,3,4-tetrahydronaphthalen-1-yl)carbamoyl)quinoxalin-2-yl)-5-oxopentanoic acid To 34A (13.0 mg, 0.023 mmol) in THF (0.3 mL), MeOH (0.300 mL), and water (0.300 mL) was added LiOH (3.92 mg, 0.094 mmol). The reaction was stirred at 22° C. and purified by preparative TLC in 10:1 DCM/MeOH to obtain 5.0 mg (41% yield) of product 34. MS (M+H)=528.

Example 35

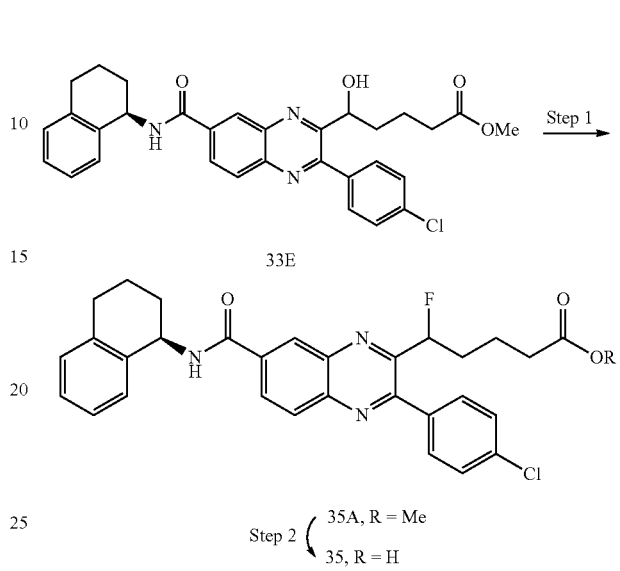

Step 1 methyl 5-(3-(4-chlorophenyl)-7-(((R)-1,2,3,4-tetrahydronaphthalen-1-yl)carbamoyl)quinoxalin-2-yl)-5-fluoropentanoate To 33E (40 mg, 0.072 mmol) in dichloroethane (1 mL) was added DAST (0.024 mL, 0.179 mmol). The reaction mixture was stirred at 22° C. overnight. The reaction was quenched with aqueous ammonium chloride and extracted with dichloromethane. The combined organics was dried over MgSO₄, filtered and concentrated. The mixture was purified on a 1 mm preparative TLC plate in 2:1 Hex/EtOAc to yield 38 mg of 35A.

Step 2

5-(3-(4-chlorophenyl)-7-(((R)-1,2,3,4-tetrahydronaphthalen-1-yl)carbamoyl)quinoxalin-2-yl)-5-fluoropentanoic acid To 35A (38.7 mg, 0.069 mmol) in THF (0.3 mL), MeOH (0.300 mL) and water (0.300 mL) was added LiOH (11.60 mg, 0.276 mmol). The mixture was stirred at 22° C. for 2 h. The reaction was quenched with water and hydrochloric acid and extracted with dichloromethane. The combined organics were dried over MgSO₄, filtered and concentrated. The mixture was purified by preparative TLC in 10:1 DCM/MeOH to yield 2.5 mg of 35. MS (M+H)=532.

Example 36

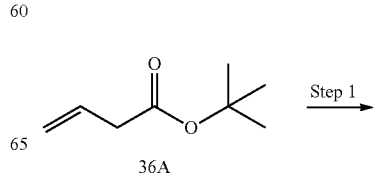

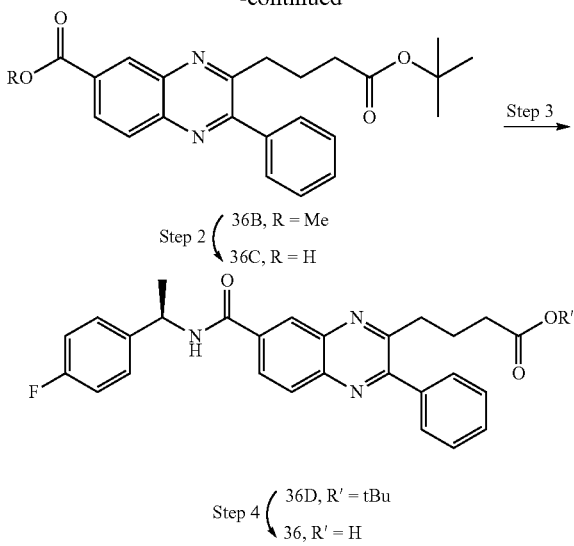

Steps 1-4

(R)-4-(7-((1-(4-fluorophenyl)ethyl)carbamoyl)-3-phenylquinoxalin-2-yl)butanoic acid In a manner similar to that previously described, 36A was coupled with methyl 3-chloro-2-phenylquinoxaline-6-carboxylate (6B) and hydrolyzed with LiOH. The resulting acid 36C was coupled with (R)-1-(4-fluorophenyl)ethanamine to provide 36D which was deprotected with TFA to provide 36.

Example 37

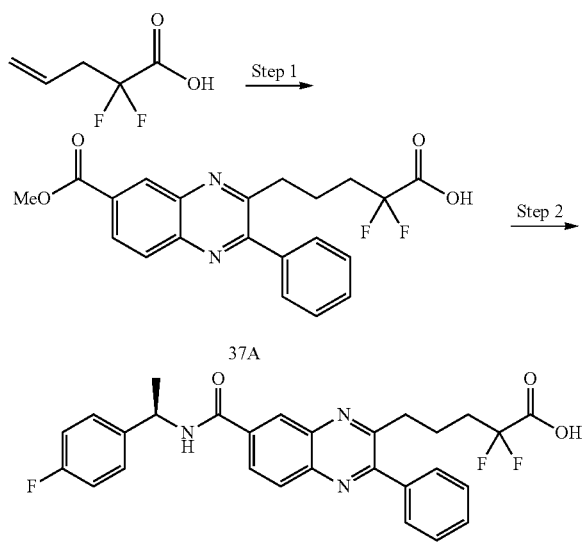

Step 1

2,2-difluoro-5-(7-(methoxycarbonyl)-3-phenylquinoxalin-2-yl)pentanoic acid

9-Borabicyclo[3.3.1]nonane (32.6 mL, 16.32 mmol) was added to a stirred, cooled 0° C. mixture of 2,2-difluoropent-4-enoic acid (1.110 g, 8.16 mmol) and the mixture was stirred at 0° C. for 30 min. before it was warmed to room temperature and stirred for overnight. Reactant 6B (1.4 g, 4.08 mmol), butyl di-1-adamantylphosphine (0.117 g, 0.326 mmol), potassium phosphate tribasic (1.732 g, 8.16 mmol) and tris(dibenzylideneacetone)dipalladium(0) chloroform adduct (0.084 g, 0.082 mmol) were dissolved in $H_2O$ (13.60 mL) and THF (27.2 mL). The solution was added to the 9-BBN adduct and stirred at 80° C. under nitrogen for 1 h. The mixture was cooled, diluted with ethyl acetate (30 mL), washed with hydrochloric acid (1 M, 1×20 mL), dried ($Na_2SO_4$), filtered and the solvent was evaporated under reduced pressure. The residue was purified by column chromatography on silica gel (50 g silica gel), eluting with EtOAc/Hexanes (10% to 80%) to give 37A as a yellow foam. MS (M+H)=508.

Step 2

(R)-2,2-difluoro-5-(7-((1-(4-fluorophenyl)ethyl)carbamoyl)-3-phenylquinoxalin-2-yl)pentanoic acid Isopropylmagnesium chloride (281 µl, 0.562 mmol) was added to a stirred, cooled 0° C. mixture of (R)-1-(4-fluorophenyl)ethylamine (31.3 mg, 0.225 mmol) and 6A (45 mg, 0.112 mmol) in THF (1124 µl) and the mixture was stirred at room temperature for overnight. The reaction was quenched by $NH_4Cl$ and worked up. The residue was purified by preparative HPLC Reverse phase (C-18), eluting with Acetonitrile/Water+0.1% TFA, to give 20 mg (34% yield) of 37 as an orange solid.

Example 38

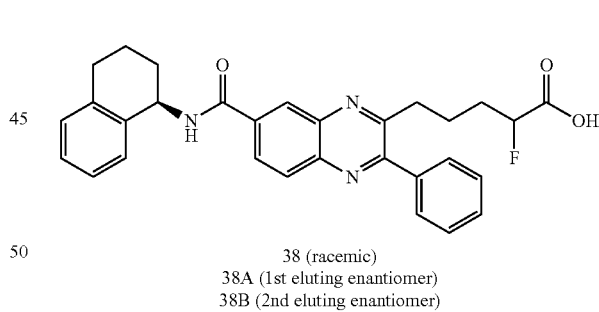

38 (racemic)
38A (1st eluting enantiomer)
38B (2nd eluting enantiomer)

In a manner similar to that described previously (Step 3), ethyl 2-fluoropent-4-enoate (prepared from allyl iodide of ethyl fluoroacetate, NaH, and allyl iodide in HMPA and benzene, 80° C., 12 h as described in *J. Am. Chem. Soc.* 2003, 125, 15521, S-21) was sequentially reacted with 9-BBN and 6B to provide the desired ethyl ester, which was subsequently treated with LiOH to afford 2-fluoro-5-(3-phenyl-7-(((R)-1,2,3,4-tetrahydronaphthalen-1-yl)carbamoyl)quinoxalin-2-yl)pentanoic acid (38, LCMS, M+H=498).

The enantiomers of 38 were separated by supercritical fluid chromatography (AD column, injected in MeOH, 55% MeOH co-solvent and 45% $CO_2$) to provide 38A (LCMS, M+H=498) and 38B. MS (M+H)=498.

Example 39

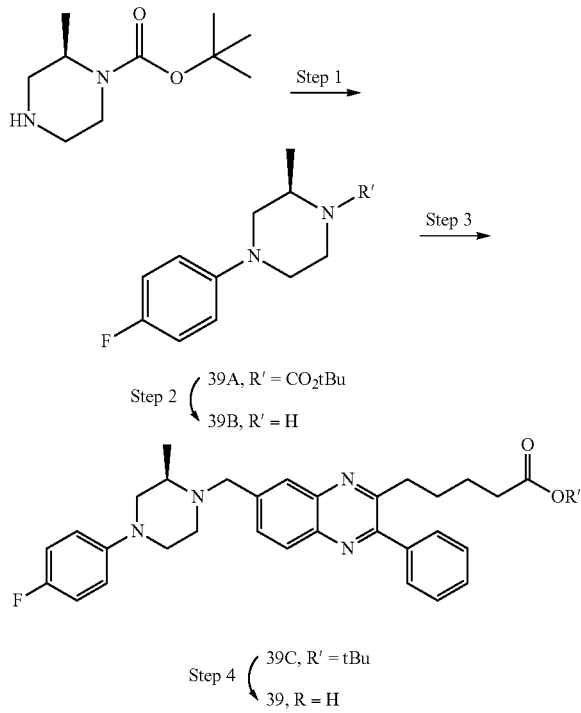

Step 1

(R)-tert-butyl 4-(4-fluorophenyl)-2-methylpiperazine-1-carboxylate

A mixture of (R)-tert-butyl 2-methylpiperazine-1-carboxylate (1.7 g, 8.49 mmol), 1-bromo-4-fluorobenzene (1.63 g, 9.34 mmol, 1.1 eq), $Pd_2(dba)_3$ (0.78 g, 0.85 mmol, 0.1 eq), $P(tBu)_3$ (0.343 g, 1.70 mmol, 0.2 eq) and t-BuOK (0.952 g, 8.49 mmol, 1.0 eq.) in toluene (8.0 mL) under nitrogen atmosphere was heated to 110° C. for 1 h in a microwave. After the reaction was complete, the mixture was diluted with water (100 mL) and extracted with $CH_2Cl_2$, dried over $Na_2SO_4$, filtered and evaporated to dryness. The crude reaction mixture was purified by column chromatography eluting with 10-20% EtOAc/hexanes to yield 1.9 g of 39A.

Step 2

(R)-1-(4-fluorophenyl)-3-methylpiperazine

To a solution of 39A (1.9 g, 6.45 mmol) in $CH_2Cl_2$ (10 mL) was added TFA (3.0 mL, 38.7 mmol, 6.0 eq) and the reaction was stirred at room temperature for 2 h. After reaction was complete, the excess TFA was concentrated to yield product 39B which was used as such without any further purification.

Step 3

(R)-tert-butyl 5-(7-(4-(4-fluorophenyl)-2-methylpiperazine-1-carbonyl)-3-phenylquinoxalin-2-yl)pentanoate To a flask containing the carboxylic acid 6D (2.2 g, 5.41 mmol) in $CH_2Cl_2$ (40 mL) was added (R)-1-(4-fluorophenyl)-3-methylpiperazine (1.16 g, 5.95 mmol, 1.1 eq), Hunig's base (3.75 mL, 21.65 mmol, 4.0 eq) and HATU (4.12 g, 10.82 mmol, 2.0 eq). The mixture was stirred at ambient temperature overnight after which the mixture was concentrated and purified by flash chromatography (10-30% EtOAc/hexanes) to yield 2.3 g of 39C (69% yield).

Step 4

(R)-5-(7-(4-(4-fluorophenyl)-2-methylpiperazine-1-carbonyl)-3-phenylquinoxalin-2-yl)pentanoic acid To a solution of 39C (2.3 g, 3.95 mmol) in $CH_2Cl_2$ (10 mL) was added TFA (1.83 mL, 23.68 mmol, 6.0 eq), and the reaction was stirred at room temperature for 2 h. After the reaction was complete, the excess TEA was concentrated to yield product 39 which was purified by column chromatography eluting with 2-4% MeOH/$CH_2Cl_2$ to yield 1.9 g of desired product 39. $^1$H NMR (DMSO, 500 MHz) δ 8.16 (d, 1H, J=8.5 Hz), 8.08 (s, 1H), 7.82 (dd, 1H, J=1.5 Hz, J=8.5 Hz), 7.71-7.69 (m, 2H), 7.60-7.57 (m, 3H), 7.08 (t, 2H, J=9 Hz), 7.00-6.97 (m, 2H), 3.61-3.36 (m, 3H), 3.03 (1, 2 H, J=7.5 Hz), 2.91 (d, 1H, J=9.5 Hz), 2.72 (dt, 1H, J=2.5 Hz, J=11.5 Hz, J=14.5 Hz), 2.47 (m, 2H), 2.16 (t, 2H, J=7 Hz), 1.74-1.70 (m, 2H), 1.51-1.46 (m, 2H), 1.42-1.32 (m, 3H). MS (M+H)=527.

Example 40

(R)-5-(7-((6-fluoro-1,2,3,4-tetrahydronaphthalen-1-yl)carbamoyl)-3-phenylquinoxalin-2-yl)pentanoic acid

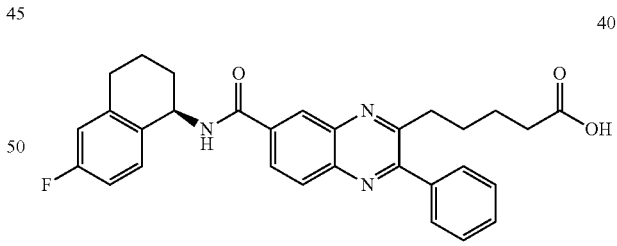

In a manner similar to that previously described, 6C was hydrolyzed with LiOH. The resulting acid 6D was coupled with (R)-6-fluoro-1,2,3,4-tetrahydronaphthalen-1-amine and deprotected with TFA to provide 40. $^1$H NMR (DMSO, 500 MHz) δ 11.97 (s, 1H), 9.17 (d, 1H, J=8.5 Hz), 8.65 (d, 1H, J=2 Hz), 8.28 (dd, 1H, J=1.5 Hz, J=8.5 Hz), 8.13 (d, 1H, J=9 Hz), 7.71-7.69 (m, 2H), 7.58-7.56 (m, 2H), 7.30 (t, 1H, J=7 Hz), 7.02-6.98 (m, 2H), 5.28 (q, 1H, J=7 Hz, J=12 Hz), 3.02 (t, 2H, J=7.5 Hz), 2.86-2.75 (m, 2H), 2.15 (t, 2H, J=7 Hz), 2.03-1.97 (m, 2H), 1.94-1.87 (m, 1H), 1.80-1.71 (m, 3H), 1.51-1.45 (m, 2H). MS (M+H)=498.

Example 41

(R)-5-(7-(2-methyl-4-phenylpiperazine-1-carbonyl)-3-phenylquinoxalin-2-yl)pentanoic acid

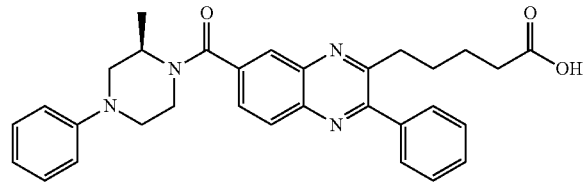

41

In a manner similar to that previously described, 6C was hydrolyzed with LiOH. The resulting acid 6D was coupled with (R)-3-methyl-1-phenylpiperazine and deprotected with TFA to provide 41. $^1$H NMR (DMSO, 500 MHz) δ 8.16 (d, 1H, J=8.5 Hz), 8.08 (d, 1H, J=1.5 Hz), 7.82 (dd, 1H, J=2 Hz, J=8.5 Hz), 7.71-7.69 (m, 2H), 7.59-7.57 (m, 3H), 7.26-7.22 (m, 2H), 6.96 (d, 2H, J=8 Hz), 6.82 (t, 1H, J=7 Hz), 3.71-3.49 (m, 3H), 3.03 (t, 2H, J=7.5 Hz), 2.98-2.92 (m, 1H), 2.76 (dt, 1H, J=3.5 Hz, J=12 Hz, J=15.5 Hz), 2.44 (m, 2H), 2.16 (t, 2H, J=7.5 Hz), 1.76-1.70 (m, 2H), 1.51-1.45 (m, 2H), 1.43-1.30 (m, 3H). MS (M+H)=509.

Example 42

2-(3-(2-(3-(4-chlorophenyl)-7-(4-phenylpiperidine-1-carbonyl)quinoxalin-2-yl)ethyl)-5-fluorophenyl)acetic acid

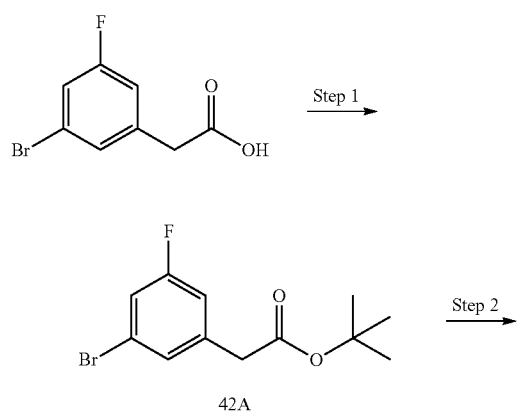

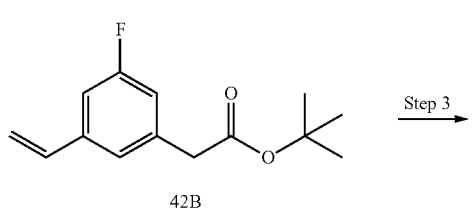

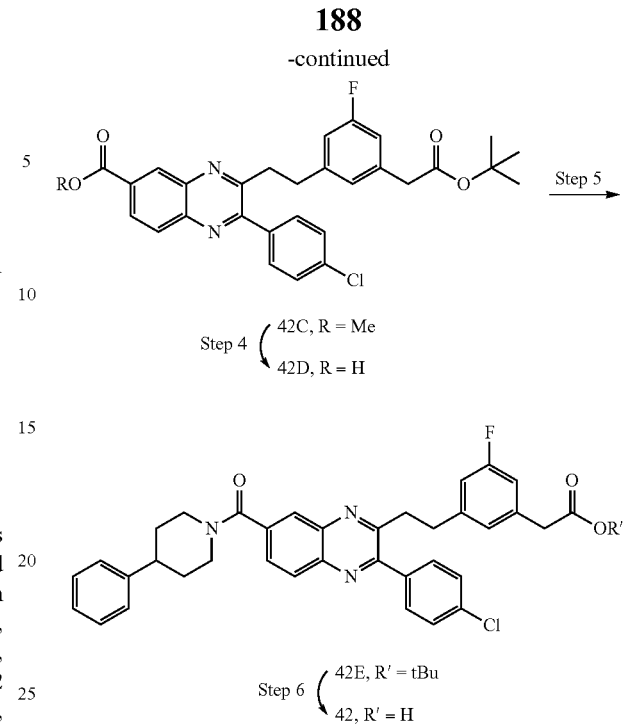

In a manner similar to that previously described for compound 19, 3-bromo-5-fluorophenylacetic acid was reacted with TFAA and t-BuOH to provide tert-butyl 2-(3-bromo-5-fluorophenyl)acetate 42A and coupled with potassium vinyltrifluoroborate to afford 42B. The resulting vinyl compound 42B was coupled with methyl 3-chloro-2-(4-chlorophenyl)quinoxaline-6-carboxylate (16B) and hydrolyzed with LiOH. The resulting acid 42D was coupled with 4-phenylpiperidine and deprotected with TFA to provide 42 (LCMS, M+H=608).

Example 43

Parallel Preparation of Compounds Bearing a 4-Chlorophenyl R$^2$ Substituent from Compound 16C

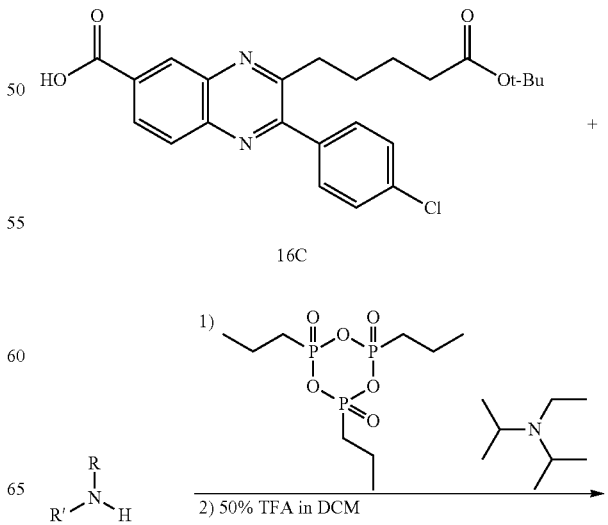

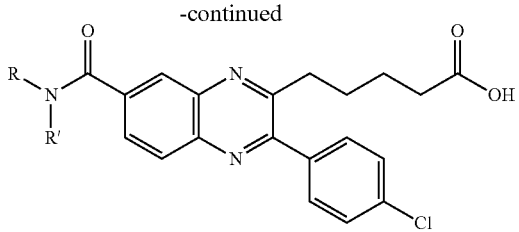

Into twenty-four 2 dram vials were added the amines (R')(R)NH (0.044 mmol), followed by a DCM (1.0 mL) solution of 3-(5-tert-butoxy-5-oxopentyl)-2-(4-chlorophenyl)quinoxaline-6-carboxylic acid 16C (15.0 mg, 0.034 mmol) and DIBA (24 µL, 0.137 mmol). The mixtures shaken at room temperature for 5 min., then 1-propanephosphonic acid cyclic anhydride (50% w/w in EtOAc) (30.0 µL, 0.050 mmol) was added, and then the vials were capped and shaken at room temperature overnight.

Trifluoroacetic acid (50%) in DCM (1.0 mL, 6.49 mmol) was then added to each of the vials. The vials were then recapped and shaken at room temperature for 2 hrs. The solvent was then concentrated in vacuo from each vial.

DMSO (1.0 mL) was then added to each of the vials. The vials were sonicated until all were in solution, and the DMSO solutions passed through a filter plate under vacuum into a deep-well plate and purified by reverse-phase chromatography.

Example 44

Step 1

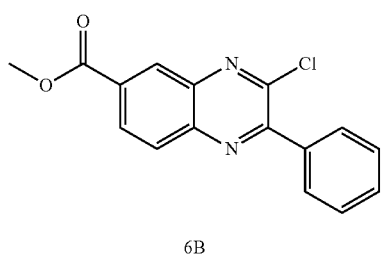

6B

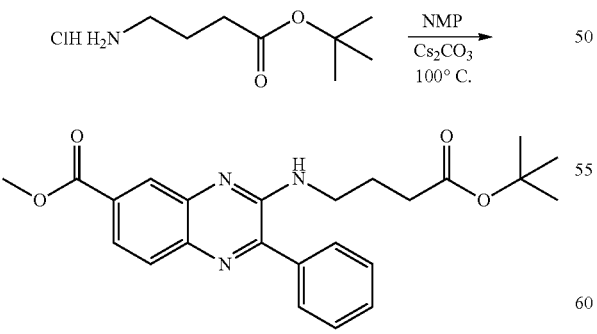

44A

To the mixture of compound 6B (8.6 g, 28.8 mmol) in N-methyl-2-pyrrolidinone (50 mL), H-gamma-ABU-OtBu HCl salt (7.04 g, 36.0 mmol), and Cs₂CO₃ (23.45 g, 72.0 mmol) was stirred and heated to 100° C. for 16 hours. The reaction mixture was worked up with ethyl acetate (200 mL) and brine (150 mL×3) to give a brown paste. The paste was separated by flash chromatography (220 g silica gel) eluting with 10~20% EtOAc/Hexanes to give compound 44A (10.5 g, 82%).

Step 2

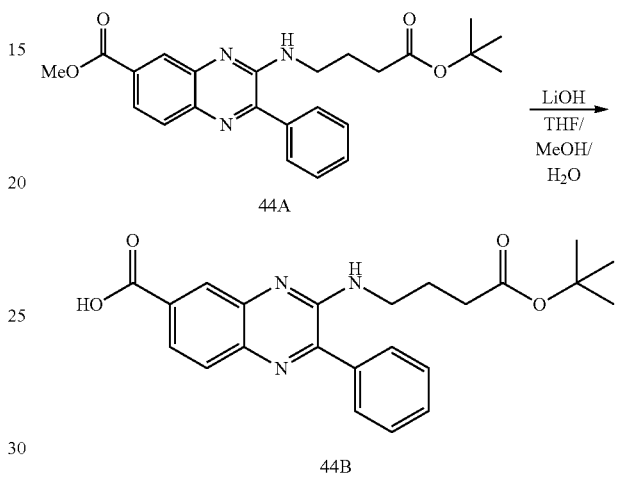

The mixture of 44A (10.3 g, 24.4 mmol) in THF/MeOH/H₂O (50 mL, 2:2:1) and LiOH—H₂O (2.05 g, 48.9 mmol) was stirred at RT for 2 hours. The reaction mixture was neutralized with 1 N HCl, extracted with CH₂Cl₂ (100 mL×2). The organic solution was dried (Na₂SO₄) and concentrated to give compound 44B (9.4 g, 76%).

Step 3

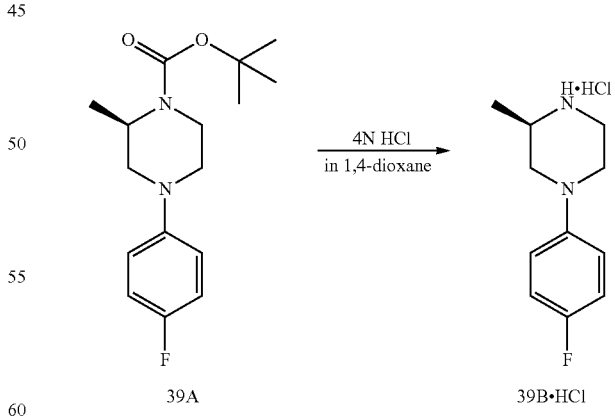

A mixture of 39A (0.95 g, 3.23 mmol) in dichloromethane (2 mL) and 4 N HCl in 1,4-dioxane (4.03 mL. 16.14 mmol) was stirred at room temperature for 2 hours. The excess HCl and solvents were removed in vacuo to give 0.74 g compound 39B.HCl (0.74 g, 99%).

Step 4

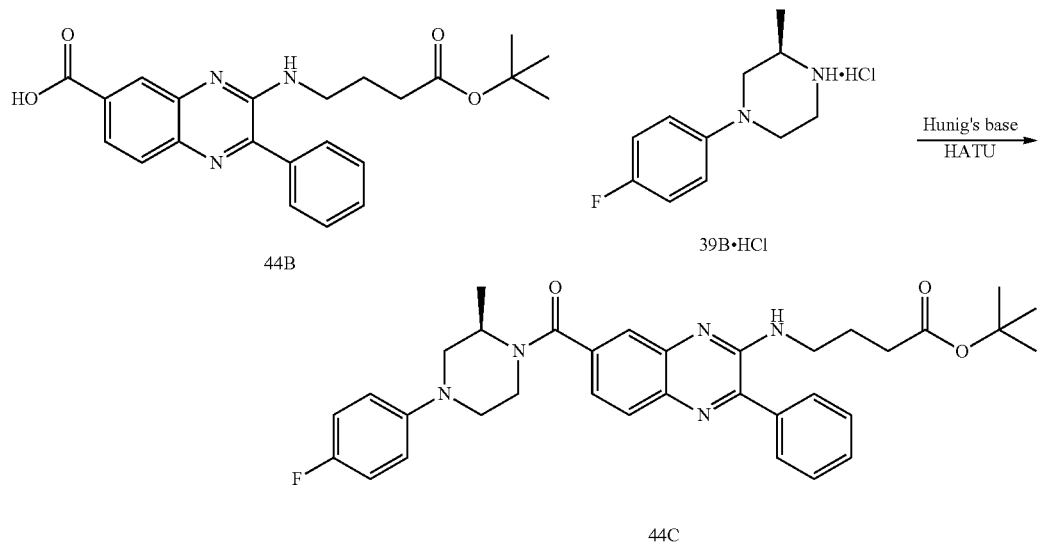

The mixture of compound 44B (2.0 g, 4.91 mmol) in dichloromethane (20 mL), compound 39B.HCl (1.13 g, 4.91 mmol), Hunig's base (1.59 g, 12.27 mmol) and HATU (2.80 g, 7.36 mmol) was stirred at room temperature for 16 h. The reaction mixture was worked up with dichloromethane (100 mL)/water (40 mL), and purified by flash chromatography (120 g silica gel) eluting with 20~30% EtOAc/Hexanes to give compound 44C (1.6 g, 51%).

Step 5

(R)-4-((7-(4-(4-fluorophenyl)-2-methylpiperazine-1-carbonyl)-3-phenylquinoxalin-2-yl)amino)butanoic acid

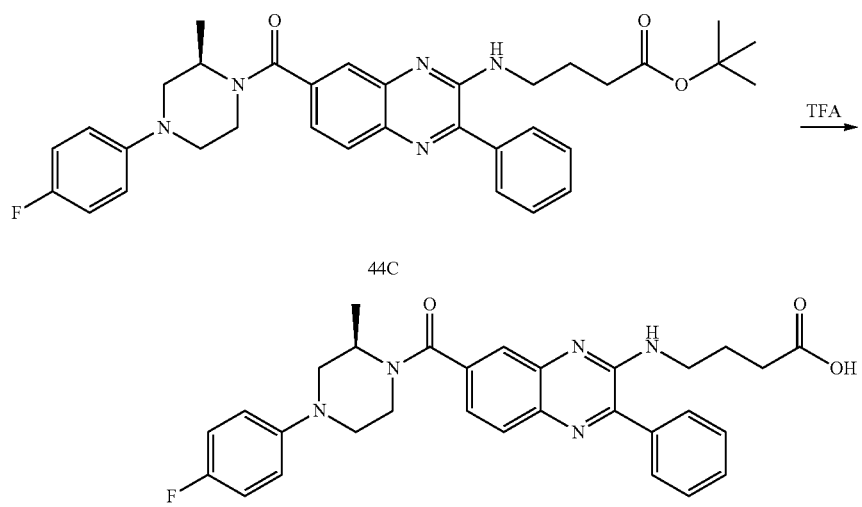

A mixture of compound 44C (1.4 g, 2.40 mmol) in dichloromethane (2 mL) and TFA (2.73 g, 23.99 mmol) was stirred at room temperature for 2 h. The excess TFA and the solvent were removed to give a brown gum. The gum was neutralized with 2 N NaOH and purified by flash column chromatography (40 g silica gel) eluting with 40~60% EtOAc/hexanes to give compound 44 (1.15 g, 86%). MS (M+H)=528.

Compound 44H, shown below, was prepared in a similar manner. $^1$H NMR (DMSO, 500 MHz) δ 7.84 (d, 1H, J=8.5 Hz), 7.74-7.72 (m, 2H), 7.61 (d, 1H, J=1.5 Hz), 7.60-7.57 (m, 2H), 7.36 (dd, 1H, J=1.5 Hz, J=8 Hz), 7.10-7.05 (m, 2H), 7.02-6.99 (m, 2H), 6.95-6.88 (m, 1H), 3.88-3.74 (m, 2H), 3.63-3.5 (m, 2H), 3.46 (q, 2H, J=6.5 Hz, J=12.5 Hz), 3.38-3.05 (m, 4H), 2.29 (t, 2H, J=7 Hz), 1.86 (t, 2H, J=6.5 Hz).

The following compounds were prepared in a similar manner to that described above in Example 44:

| No. | Structure | Name | M + H |
|---|---|---|---|
| 44D | 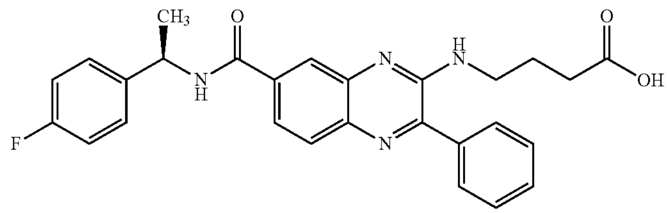 [SMILES: C[C@@H](NC(=O)c1ccc2nc(-c3ccccc3)c(NCCCC(=O)O)nc2c1)c1ccc(F)cc1] | (R)-4-((7-((1-(4-fluorophenyl)ethyl)carbamoyl)-3-phenylquinoxalin-2-yl)amino)butanoic acid | 473 |
| 44E | 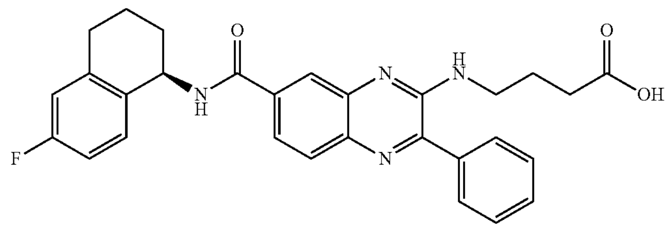 [SMILES: O=C(O)CCCNc1nc2cc(C(=O)N[C@@H]3CCCc4cc(F)ccc43)ccc2nc1-c1ccccc1] | (R)-4-((7-((6-fluoro-1,2,3,4-tetrahydronaphthalen-1-yl)carbamoyl)-3-phenylquinoxalin-2-yl)amino)butanoic acid | 499 |
| 44F | 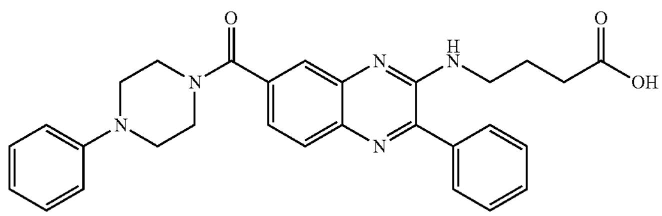 [SMILES: O=C(O)CCCNc1nc2cc(C(=O)N3CCN(c4ccccc4)CC3)ccc2nc1-c1ccccc1] | 4-((3-phenyl-7-(4-phenylpiperazine-1-carbonyl)quinoxalin-2-yl)amino)butanoic acid | 496 |
| 44G | 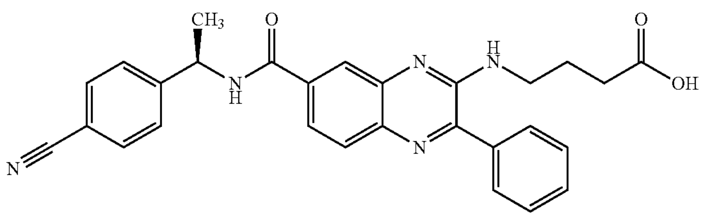 [SMILES: C[C@@H](NC(=O)c1ccc2nc(-c3ccccc3)c(NCCCC(=O)O)nc2c1)c1ccc(C#N)cc1] | (R)-4-(((7-((1-(4-cyanophenyl)ethyl)carbamoyl)-3-phenylquinoxalin-2-yl)amino)butanoic acid | 480 |
| 44H | 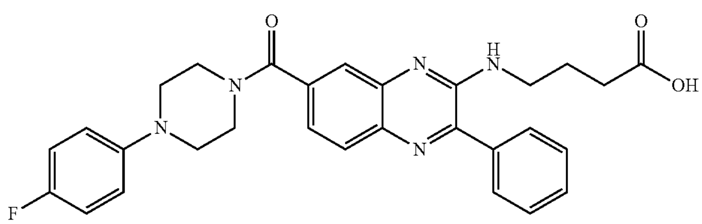 [SMILES: O=C(O)CCCNc1nc2cc(C(=O)N3CCN(c4ccc(F)cc4)CC3)ccc2nc1-c1ccccc1] | 4-((7-(4-(4-fluorophenyl)piperazine-1-carbonyl)-3-phenylquinoxalin-2-yl)amino)butanoic acid | 514 |
| 44i | 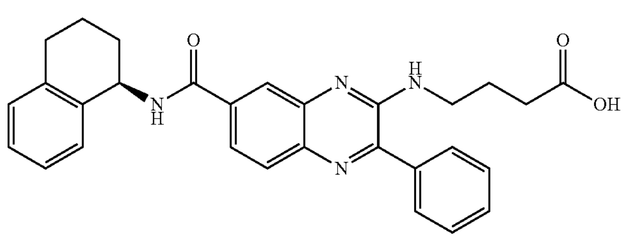 [SMILES: O=C(O)CCCNc1nc2cc(C(=O)N[C@@H]3CCCc4ccccc43)ccc2nc1-c1ccccc1] | (R)-4-((3-phenyl-7-((1,2,3,4-tetrahydronaphthalen-1-yl)carbamoyl)quinoxalin-2-yl)amino)butanoic acid | 481 |
| 44J | 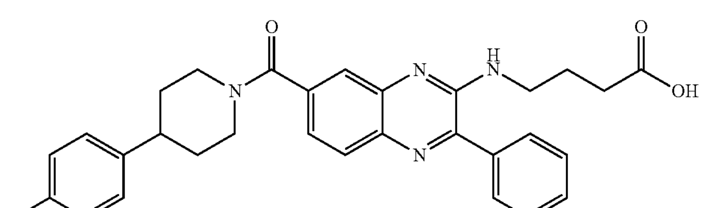 | 4-((7-(4-(4-fluorophenyl)piperidine-1-carbonyl)-3-phenylquinoxalin-2-yl)amino)butanoic acid | 513 |

| No. | Structure | Name | M + H |
|---|---|---|---|
| 44K | 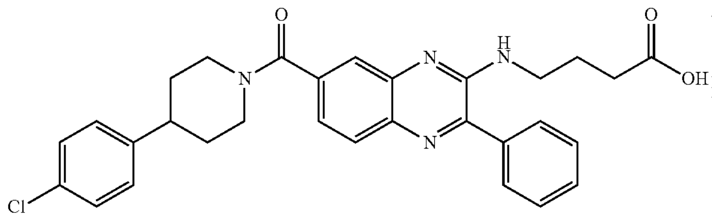 [SMILES: O=C(O)CCCNc1nc2cc(C(=O)N3CCC(c4ccc(Cl)cc4)CC3)ccc2nc1-c1ccccc1] | 4-((7-(4-(4-chlorophenyl)piperidine-1-carbonyl)-3-phenylquinoxalin-2-yl)amino)butanoic acid | 513 |
| 44L | 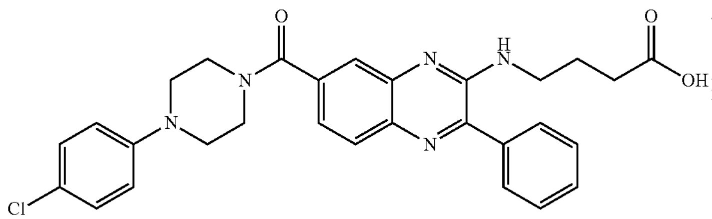 [SMILES: O=C(O)CCCNc1nc2cc(C(=O)N3CCN(c4ccc(Cl)cc4)CC3)ccc2nc1-c1ccccc1] | 4-((7-(4-(4-chlorophenyl)piperazine-1-carbonyl)-3-phenylquinoxalin-2-yl)amino)butanoic acid | 529 |
| 44M | 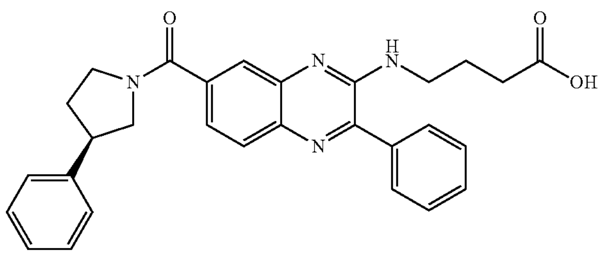 [SMILES: O=C(O)CCCNc1nc2cc(C(=O)N3CC[C@H](c4ccccc4)C3)ccc2nc1-c1ccccc1] | (R)-4-((3-phenyl-7-(3-phenylpyrrolidine-1-carbonyl)quinoxalin-2-yl)amino)butanoic acid | 481 |
| 44N | 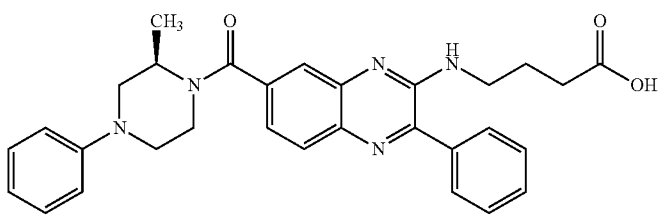 [SMILES: C[C@@H]1CN(c2ccccc2)CCN1C(=O)c1ccc2nc(-c3ccccc3)c(NCCCC(=O)O)nc2c1] | (R)-4-((7-(2-methyl-4-phenylpiperazine-1-carbonyl)-3-phenylquinoxalin-2-yl)amino)butanoic acid | 510 |

The following compounds were prepared following procedures similar to those exemplified in the examples above.

| No. | Structure | Name | M + H |
|---|---|---|---|
| 100 | 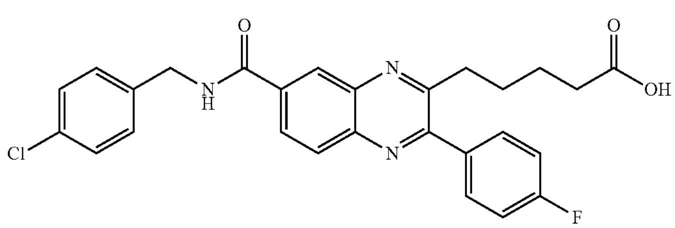 [SMILES: O=C(O)CCCCc1nc2cc(C(=O)NCc3ccc(Cl)cc3)ccc2nc1-c1ccc(F)cc1] | 7-[[[(4-chlorophenyl)methyl]carbonyl]-3-(4-fluorophenyl)-2-quinoxalinepentanoic acid | 492 |
| 101 | 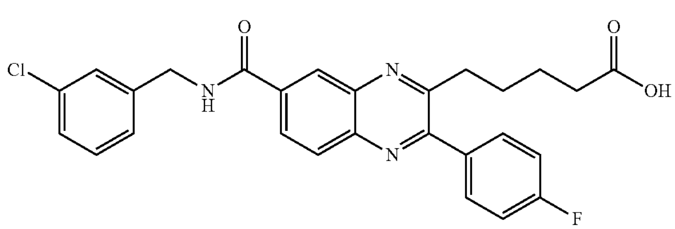 [SMILES: O=C(O)CCCCc1nc2cc(C(=O)NCc3cccc(Cl)c3)ccc2nc1-c1ccc(F)cc1] | 7-[[[(3-chlorophenyl)methyl]amino]carbonyl]-3-(4-fluorophenyl)-2-quinoxalinepentanoic acid | 492 |

-continued

| No. | Structure | Name | M + H |
|---|---|---|---|
| 102 | 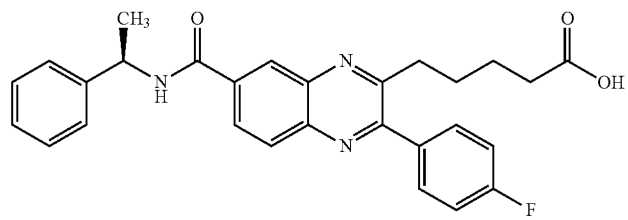 [SMILES: C[C@@H](NC(=O)c1ccc2nc(-c3ccc(F)cc3)c(CCCCC(=O)O)nc2c1)c1ccccc1] | 3-(4-fluorophenyl)-7-[[(2,2,2-trifluoro-1(S)-phenylethyl)amino]carbonyl]-2-quinoxalinepentanoic acid | 526 |
| 103 | 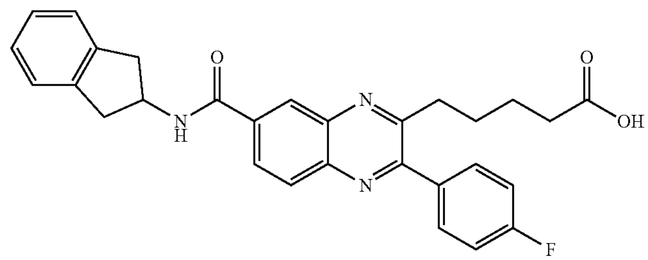 [SMILES: O=C(O)CCCCc1nc2cc(C(=O)NC3Cc4ccccc4C3)ccc2nc1-c1ccc(F)cc1] | 7-[[[(2,3-dihydro-1H-inden-2-yl)amino]carbonyl]-3-(4-fluorophenyl)-2-quinoxalinepentanoic acid | 484 |
| 104 | 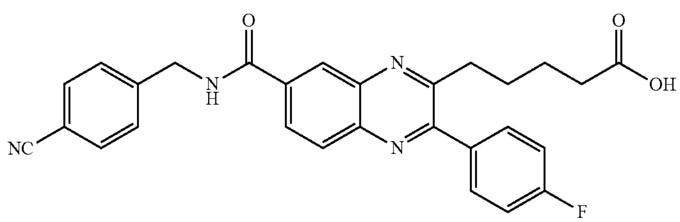 [SMILES: N#Cc1ccc(CNC(=O)c2ccc3nc(-c4ccc(F)cc4)c(CCCCC(=O)O)nc3c2)cc1] | 7-[[[(4-cyanophenyl)methyl]amino]carbonyl]-3-(4-fluorophenyl)-2-quinoxalinepentanoic acid | 483 |
| 105 | 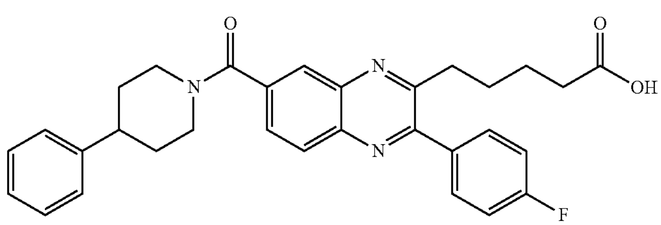 [SMILES: O=C(O)CCCCc1nc2cc(C(=O)N3CCC(c4ccccc4)CC3)ccc2nc1-c1ccc(F)cc1] | 3-(4-fluorophenyl)-7-[(4-phenyl-1-piperidinyl)carbonyl]-2-quinoxalinepentanoic acid | 512 |
| 106 | 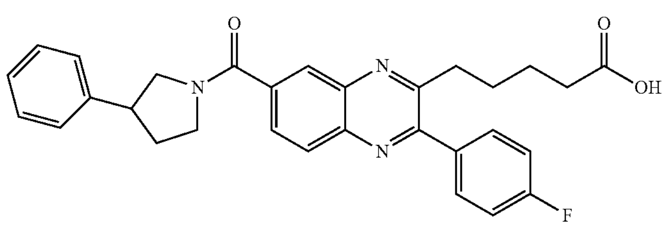 [SMILES: O=C(O)CCCCc1nc2cc(C(=O)N3CCC(c4ccccc4)C3)ccc2nc1-c1ccc(F)cc1] | 3-(4-fluorophenyl)-7-[(3-phenyl-1-pyrrolidinyl)carbonyl]-2-quinoxalinepentanoic acid | 498 |
| 107 | 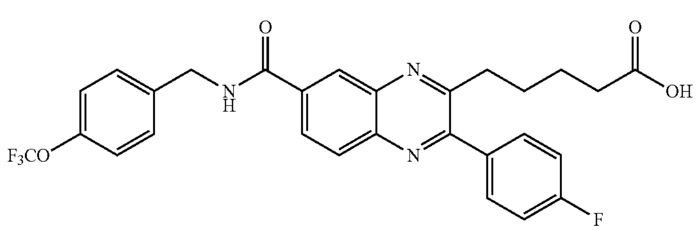 [SMILES: O=C(O)CCCCc1nc2cc(C(=O)NCc3ccc(OC(F)(F)F)cc3)ccc2nc1-c1ccc(F)cc1] | 3-(4-fluorophenyl)-7-[[[[4-(trifluoromethoxy)phenyl]methyl]amino]carbonyl]-2-quinoxalinepentanoic acid | 542 |

| No. | Structure | Name | M + H |
|---|---|---|---|
| 108 | 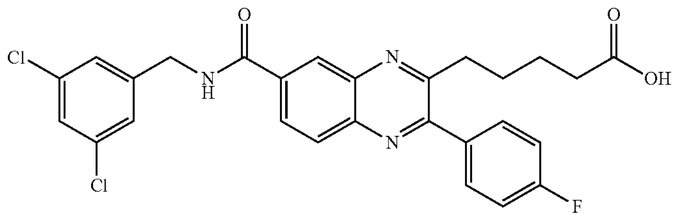 [SMILES: O=C(O)CCCCc1nc2cc(C(=O)NCc3cc(Cl)cc(Cl)c3)ccc2nc1-c1ccc(F)cc1] | 7-[[[(3,5-dichlorophenyl)methyl]amino]carbonyl]-3-(4-fluorophenyl)-2-quinoxalinepentanoic acid | 526 |
| 109 | 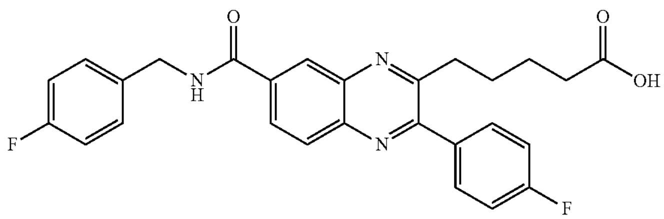 [SMILES: O=C(O)CCCCc1nc2cc(C(=O)NCc3ccc(F)cc3)ccc2nc1-c1ccc(F)cc1] | 3-(4-fluorophenyl)-7-[[[(4-fluorophenyl)methyl]amino]carbonyl]-2-quinoxalinepentanoic acid | 476 |
| 110 | 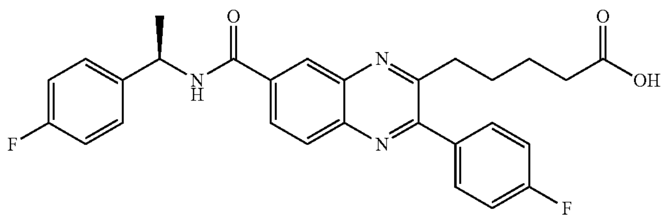 | 3-(4-fluorophenyl)-7-[[[1(R)-(4-fluorophenyl)ethyl]amino]carbonyl]-2-quinoxalinepentanoic acid | 490 |
| 111 | 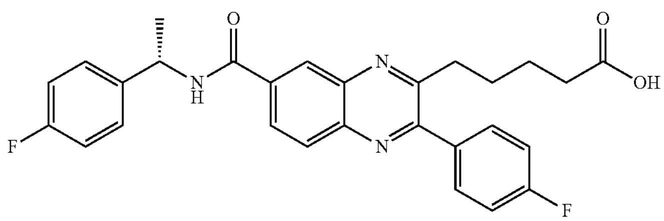 [SMILES: C[C@H](NC(=O)c1ccc2nc(-c3ccc(F)cc3)c(CCCCC(=O)O)nc2c1)c1ccc(F)cc1] | 3-(4-fluorophenyl)-7-[[[1(S)-(4-fluorophenyl)ethyl]amino]carbonyl]-2-quinoxalinepentanoic acid | 490 |
| 112 | 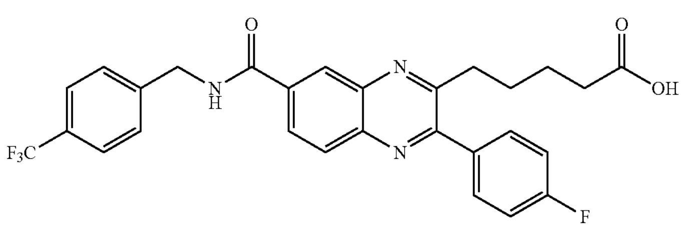 [SMILES: O=C(O)CCCCc1nc2cc(C(=O)NCc3ccc(C(F)(F)F)cc3)ccc2nc1-c1ccc(F)cc1] | 3-(4-fluorophenyl)-7-[[[[4-(trifluoromethyl)phenyl]methyl]amino]carbonyl]-2-quinoxalinepentanoic acid | 526 |
| 113 | 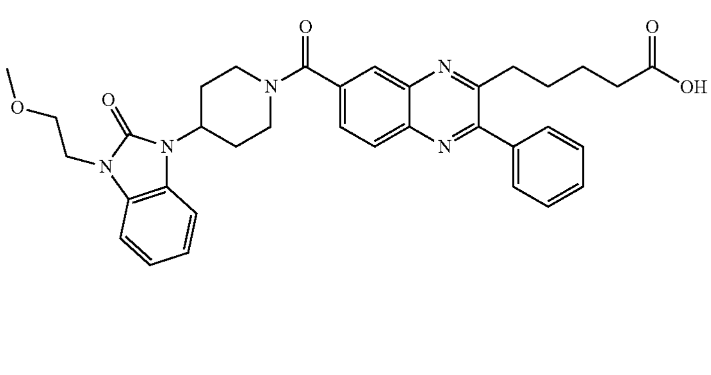 [SMILES: COCCn1c(=O)n(C2CCN(C(=O)c3ccc4nc(-c5ccccc5)c(CCCCC(=O)O)nc4c3)CC2)c2ccccc21] | 7-[[4-[2,3-dihydro-3-(2-methoxyethyl)-2-oxo-1H-benzimidazol-1-yl]-1-piperidinyl]carbonyl]-3-phenyl-2-quinoxalinepentanoic acid | 608 |

-continued

| No. | Structure | Name | M + H |
|---|---|---|---|
| 114 | 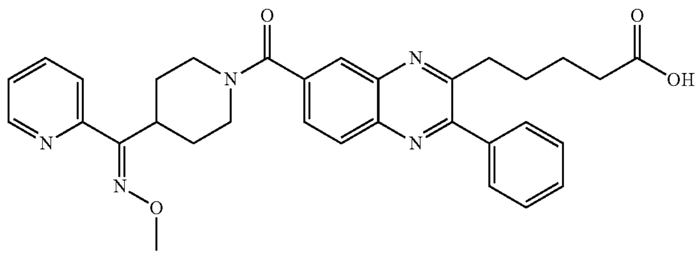 [SMILES: CO/N=C(/c1ccccn1)C1CCN(C(=O)c2ccc3nc(-c4ccccc4)c(CCCCC(=O)O)nc3c2)CC1] | 7-[[4-[(E)-(methoxyimino)-2-pyridinylmethyl]-1-piperidinyl]carbonyl]-3-phenyl-2-quinoxalinepentanoic acid | 552 |
| 115 | 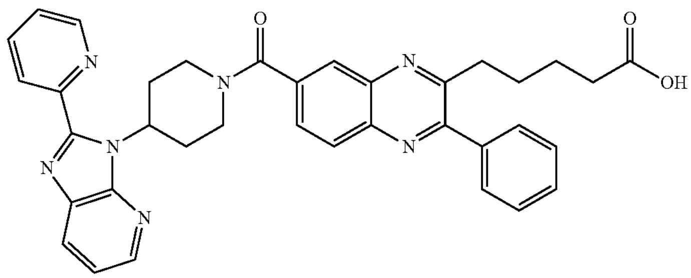 [SMILES: O=C(O)CCCCc1nc2cc(C(=O)N3CCC(n4c(-c5ccccn5)nc5cccnc54)CC3)ccc2nc1-c1ccccc1] | 3-phenyl-7-[[4-[2-(2-pyridinyl)-1H-benzimidazol-1-yl]-1-piperidinyl]carbonyl]-2-quinoxalinepentanoic acid | 612 |
| 116 | 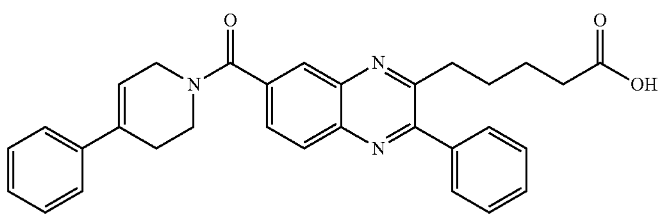 [SMILES: O=C(O)CCCCc1nc2cc(C(=O)N3CC=C(c4ccccc4)CC3)ccc2nc1-c1ccccc1] | 7-(4-phenyl-1,2,3,6-tetrahydropyridine-1-carbonyl)-3-phenyl-2-quinoxalinepentanoic acid | 492 |
| 117 | 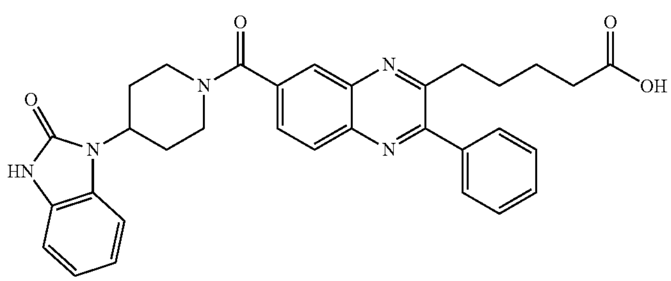 [SMILES: O=C(O)CCCCc1nc2cc(C(=O)N3CCC(n4c(=O)[nH]c5ccccc54)CC3)ccc2nc1-c1ccccc1] | 7-[[4-(2,3-dihydro-2-oxo-1H-benzimidazol-1-yl)-1-piperidinyl]carbonyl]-3-phenyl-2-quinoxalinepentanoic acid | 550 |
| 118 | 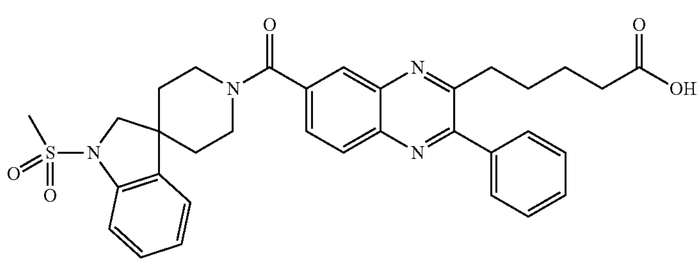 [SMILES: CS(=O)(=O)N1CC2(CCN(C(=O)c3ccc4nc(-c5ccccc5)c(CCCCC(=O)O)nc4c3)CC2)c2ccccc21] | 7-[[1,2-dihydro-1-(methylsulfonyl)spiro[3H-indole-3,4'-piperidin]-1'-yl]carbonyl]-3-phenyl-2-quinoxalinepentanoic acid | 599 |
| 119 | 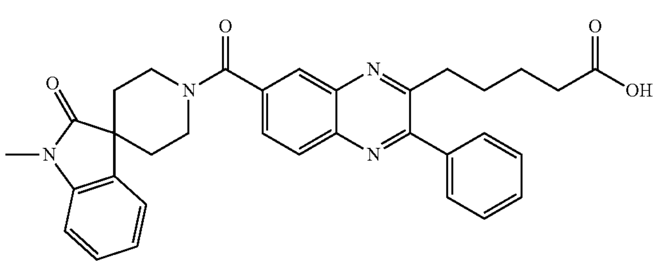 [SMILES: CN1C(=O)C2(CCN(C(=O)c3ccc4nc(-c5ccccc5)c(CCCCC(=O)O)nc4c3)CC2)c2ccccc21] | 7-[(1,2-dihydro-1-methyl-2-oxospiro 3H-indole-3,4'-piperidin]-1'-yl)carbonyl]-3-phenyl-2-quinoxalinepentanoic acid | 549 |

-continued

| No. | Structure | Name | M + H |
|---|---|---|---|
| 120 | 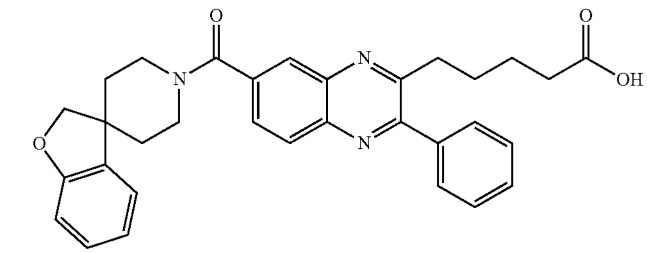 [SMILES: O=C(O)CCCCc1nc2cc(C(=O)N3CCC4(CC3)COc3ccccc34)ccc2nc1-c1ccccc1] | 3-phenyl-7-(spiro[benzofuran-3(2H),4'-piperidin]-1'-ylcarbonyl)-2-quinoxalinepentanoic acid | 522 |
| 121 | 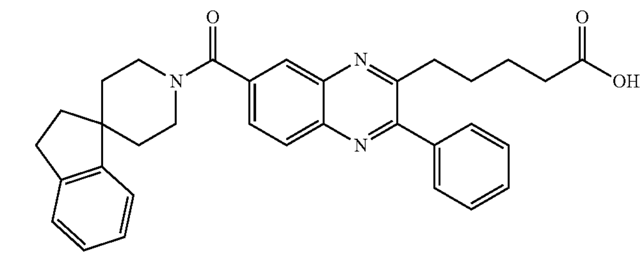 [SMILES: O=C(O)CCCCc1nc2cc(C(=O)N3CCC4(CCc5ccccc54)CC3)ccc2nc1-c1ccccc1] | 7-[(2,3-dihydrospiro [1H-indene-1,4'-piperidin]-1'-yl)carbonyl]-3-phenyl-2-quinoxalinepentanoic acid | 520 |
| 122 | 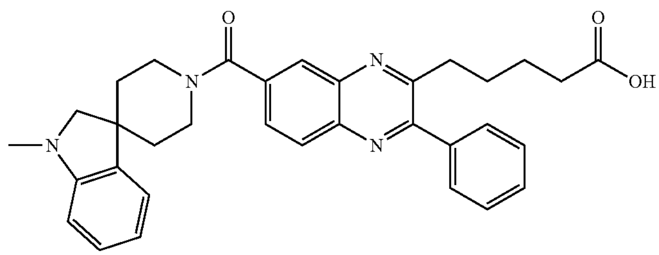 [SMILES: CN1CC2(CCN(C(=O)c3ccc4nc(-c5ccccc5)c(CCCCC(=O)O)nc4c3)CC2)c2ccccc21] | 7-[(1,2-dihydro-1-methylspiro[3H-indole-3,4'-piperidin]-1'-yl)carbonyl]-3-phenyl-2-quinoxalinepentanoic acid | 535 |
| 123 | 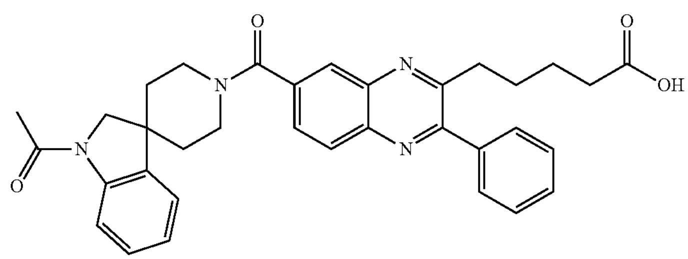 [SMILES: CC(=O)N1CC2(CCN(C(=O)c3ccc4nc(-c5ccccc5)c(CCCCC(=O)O)nc4c3)CC2)c2ccccc21] | 7-[(1-acetyl-1,2-dihydrospiro[3H-indole-3,4'-piperidin]-1'-yl)carbonyl]-3-phenyl-2-quinoxalinepentanoic acid | 563 |
| 124 | 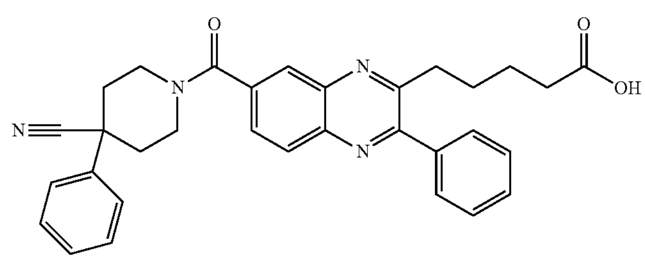 [SMILES: N#CC1(c2ccccc2)CCN(C(=O)c2ccc3nc(-c4ccccc4)c(CCCCC(=O)O)nc3c2)CC1] | 7-[(4-cyano-4-phenyl-1-piperidinyl)carbonyl]-3-phenyl-2-quinolaxinepentanoic acid | 519 |
| 125 | 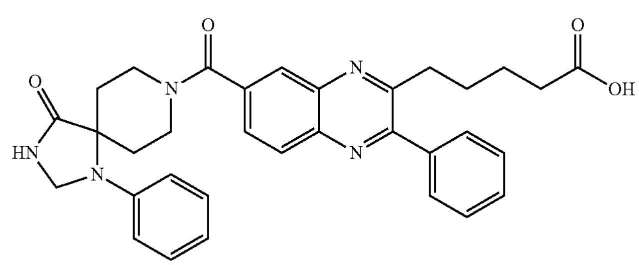 [SMILES: O=C(O)CCCCc1nc2cc(C(=O)N3CCC4(CC3)C(=O)NCN4c3ccccc3)ccc2nc1-c1ccccc1] | 7-[(4-oxo-l-phenyl-1,3,8-triazaspiro[4.5]dec-8-yl)carbonyl]-3-phenyl-2-quinoxalinepentanoic acid | 564 |

-continued

| No. | Structure | Name | M + H |
|-----|-----------|------|-------|
| 126 | 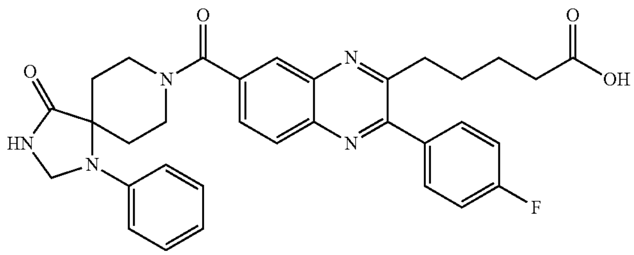 [SMILES: O=C(O)CCCCc1nc2cc(C(=O)N3CCC4(CC3)C(=O)NCN4c3ccccc3)ccc2nc1-c1ccc(F)cc1] | 3-(4-fluorophenyl)-7-[(4-oxo-1-phenyl-1,3,8-triazaspiro[4.5]dec-8-yl)carbonyl]-2-quinoxalinepentanoic acid | 582 |
| 127 | 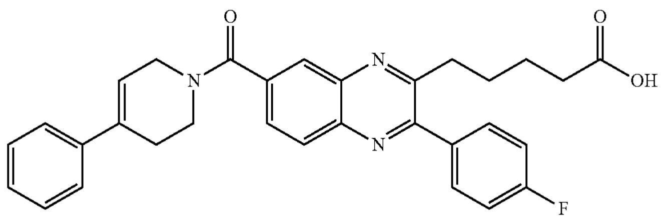 | 5-(3-(4-fluorophenyl)-7-(4-phenyl-1,2,3,6-tetrahydropyridine-1-carbonyl)quinoxalin-2-yl)pentanoic acid | 510 |
| 128 | 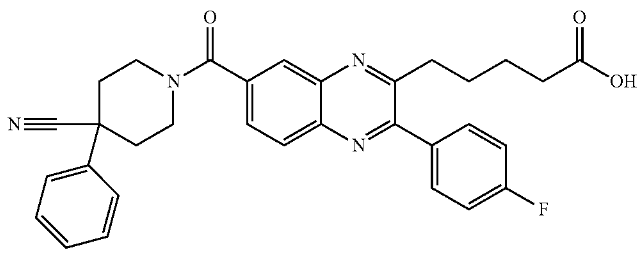 [SMILES: N#CC1(c2ccccc2)CCN(C(=O)c2ccc3nc(-c4ccc(F)cc4)c(CCCCC(=O)O)nc3c2)CC1] | 7-[(4-cyano-4-phenyl-1-piperidinyecarbonyl]-3-(4-fluorophenyl)-2-quinoxalinepentanoic acid | 537 |
| 129 | 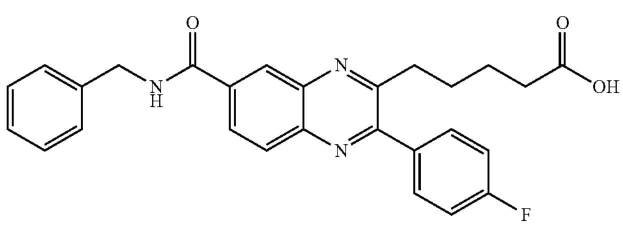 [SMILES: O=C(O)CCCCc1nc2cc(C(=O)NCc3ccccc3)ccc2nc1-c1ccc(F)cc1] | 3-(4-fluorophenyl)-7-[[(phenylmethyl)amino]carbonyl]-2-quinoxalinepentanoic acid | 458 |
| 130 | 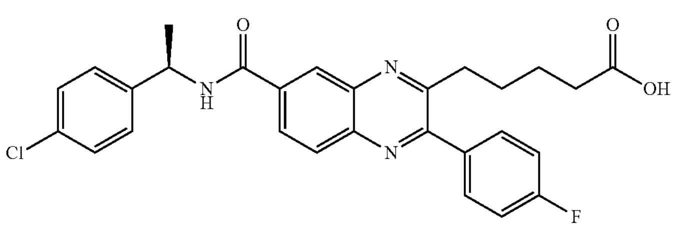 [SMILES: C[C@@H](NC(=O)c1ccc2nc(-c3ccc(F)cc3)c(CCCCC(=O)O)nc2c1)c1ccc(Cl)cc1] | 7-[[[1(R)-(4-chlorophenyl)ethyl]amino]carbonyl]-3-(4-fluorophenyl)-2-quinoxalinepentanoic acid | 506 |
| 131 | 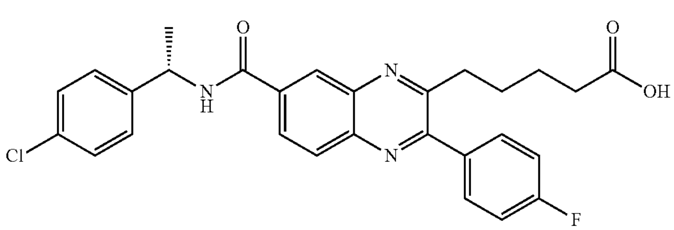 [SMILES: C[C@H](NC(=O)c1ccc2nc(-c3ccc(F)cc3)c(CCCCC(=O)O)nc2c1)c1ccc(Cl)cc1] | 7-[[[1(S)-(4-chlorophenyl)ethyl]amino]carbonyl]-3-(4-fluorophenyl)-2-quinoxalinepentanoic acid | 506 |

-continued

| No. | Structure | Name | M + H |
|---|---|---|---|
| 132 | 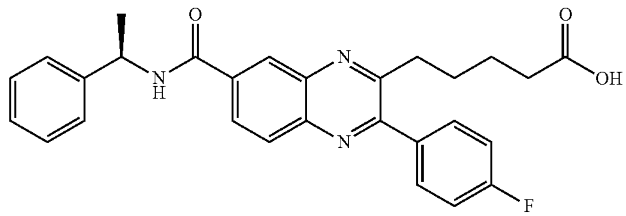 [SMILES: C[C@@H](NC(=O)c1ccc2nc(-c3ccc(F)cc3)c(CCCCC(=O)O)nc2c1)c1ccccc1] | 3-(4-fluorophenyl)-7-[[(1(R)-phenylethyl)amino]carbonyl]-2-quinoxalinepentanoic acid | 472 |
| 133 | 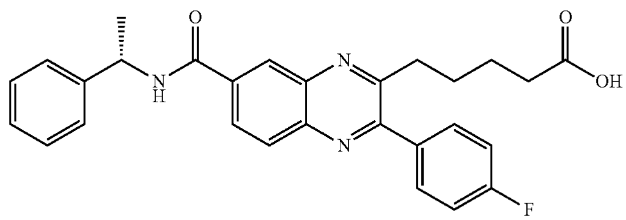 [SMILES: C[C@H](NC(=O)c1ccc2nc(-c3ccc(F)cc3)c(CCCCC(=O)O)nc2c1)c1ccccc1] | 3-(4-fluorophenyl)-7-[[(1(S)-phenylethyl)amino]carbonyl]-2-quinoxalinepentanoic acid | 472 |
| 134 | 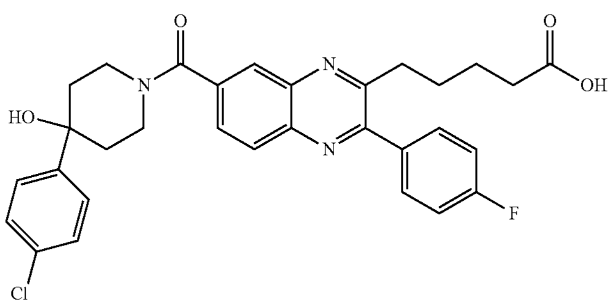 [SMILES: O=C(O)CCCCc1nc2cc(C(=O)N3CCC(O)(c4ccc(Cl)cc4)CC3)ccc2nc1-c1ccc(F)cc1] | 7-[[4-(4-chlorophenyl)-4-hydroxy-1-piperidinyl]carbonyl]-3-(4-fluorophenyl)-2-quinoxalinepentanoic acid | 562 |
| 135 | 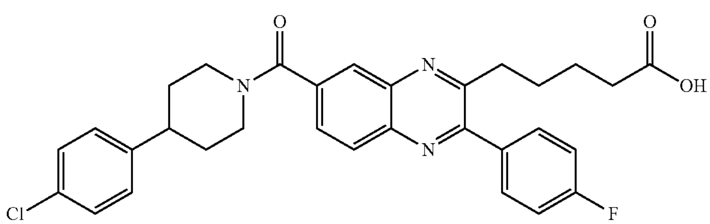 [SMILES: O=C(O)CCCCc1nc2cc(C(=O)N3CCC(c4ccc(Cl)cc4)CC3)ccc2nc1-c1ccc(F)cc1] | 7-[[4-(4-chlorophenyl)-1-piperidinyl carbonyl]-3-(4-fluorophenyl)-2-quinoxalinepentanoic acid | 546 |
| 136 | 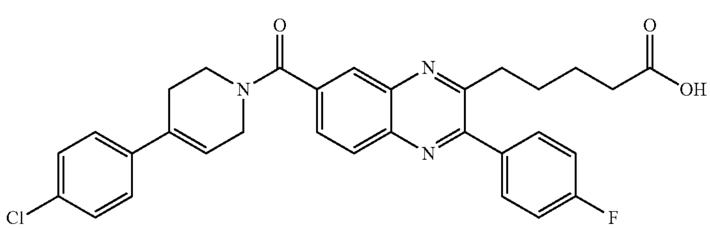 [SMILES: O=C(O)CCCCc1nc2cc(C(=O)N3CC=C(c4ccc(Cl)cc4)CC3)ccc2nc1-c1ccc(F)cc1] | 7-[[4-(4-chlorophenyl)]-3,6-dihydro-1(2H)-pyridinyl]carbonyl]-3-(4-fluorophenyl)-2-quinoxalinepentanoic acid | 544 |
| 137 | 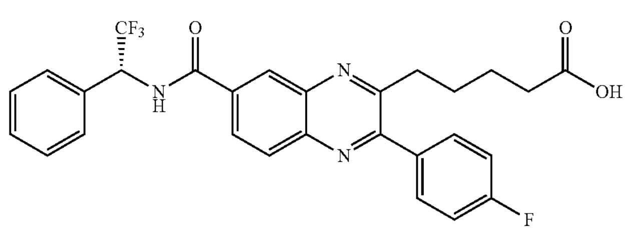 [SMILES: O=C(O)CCCCc1nc2cc(C(=O)N[C@H](c3ccccc3)C(F)(F)F)ccc2nc1-c1ccc(F)cc1] | 3-(4-fluorophenyl)-7-[[[2,2,2-trifluoro-1(R)-phenylethyl)amino]carbonyl]-2-quinoxalinepentanoic acid | 526 |

-continued

| No. | Structure | Name | M + H |
|---|---|---|---|
| 138 | 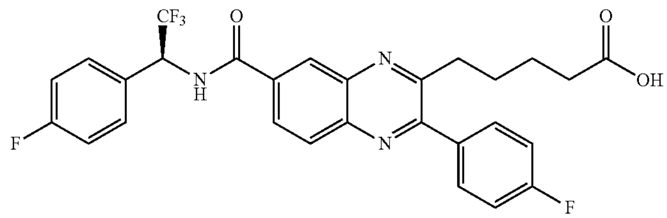 [SMILES: O=C(O)CCCCc1nc2cc(C(=O)N[C@@H](c3ccc(F)cc3)C(F)(F)F)ccc2nc1-c1ccc(F)cc1] | 3-(4-fluorophenyl)-7-[[[2,2,2-trifluoro-1(S)-(4-fluorophenyl)ethyl]amino]carbonyl]-2-quinoxalinepentanoic acid | 544 |
| 139 | 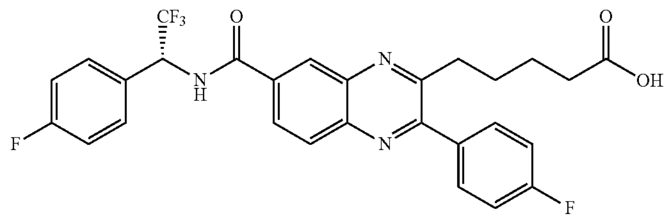 [SMILES: O=C(O)CCCCc1nc2cc(C(=O)N[C@H](c3ccc(F)cc3)C(F)(F)F)ccc2nc1-c1ccc(F)cc1] | 3-(4-fluorophenyl)-7-[[[(1R)-2,2,2-trifluoro-1-(4-fluorophenyl)ethyl]amino]carbonyl]-2-quinoxalinepentanoic acid | 544 |
| 140 | 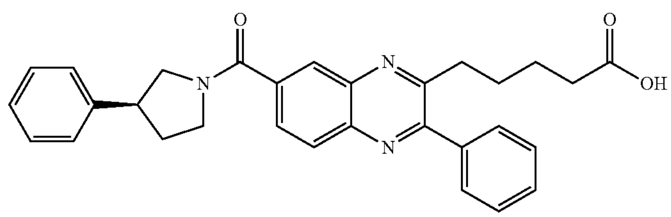 [SMILES: O=C(O)CCCCc1nc2cc(C(=O)N3CC[C@@H](c4ccccc4)C3)ccc2nc1-c1ccccc1] | 3-phenyl-7-[(3(S)-phenyl-1-pyrrolidinyl)carbonyl]-2-quinoxalinepentanoic acid | 480 |
| 141 | 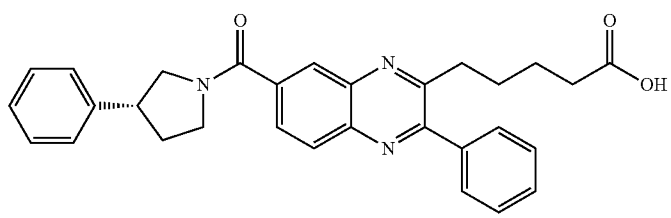 [SMILES: O=C(O)CCCCc1nc2cc(C(=O)N3CC[C@H](c4ccccc4)C3)ccc2nc1-c1ccccc1] | 3-phenyl-7-[(3(R)-phenyl-1-pyyrolidinyl)carbonyl]-2-quinoxalinepentanoic acid | 480 |
| 142 | 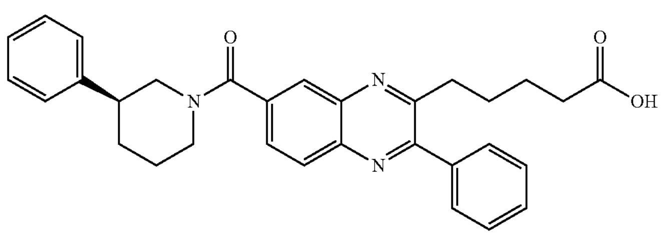 [SMILES: O=C(O)CCCCc1nc2cc(C(=O)N3CCC[C@@H](c4ccccc4)C3)ccc2nc1-c1ccccc1] | 3-phenyl-7-[(3(S)-phenyl-1-piperidinyl)carbonyl]-2-quinoxalinepentanoic acid | 494 |
| 143 | 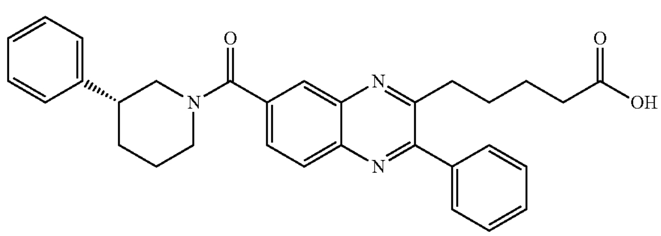 [SMILES: O=C(O)CCCCc1nc2cc(C(=O)N3CCC[C@H](c4ccccc4)C3)ccc2nc1-c1ccccc1] | 3-phenyl-7-[(3(R)-phenyl-1-piperidinyl)carbonyl]-2-quinooxalinepentanoic acid | 494 |
| 144 | 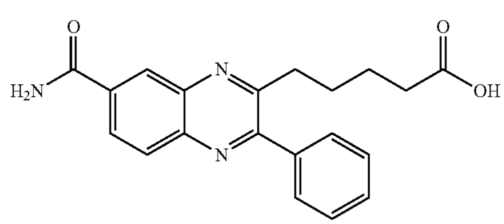 [SMILES: NC(=O)c1ccc2nc(-c3ccccc3)c(CCCCC(=O)O)nc2c1] | 5-(7-carbamoyl-3-phenylquinoxalin-2-yl)pentanoic acid | 350 |

-continued

| No. | Structure | Name | M + H |
|---|---|---|---|
| 145 | 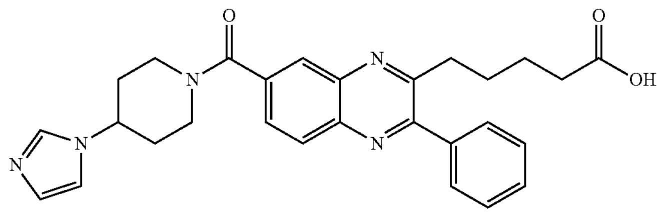 [SMILES: O=C(O)CCCCc1nc2cc(C(=O)N3CCC(n4ccnc4)CC3)ccc2nc1-c1ccccc1] | 5-(7-(4-(1H-imidazol-1-yl)piperidine-1-carbonyl)-3-phenylquinoxalin-2-yl)pentanoic acid | 484 |
| 146 | 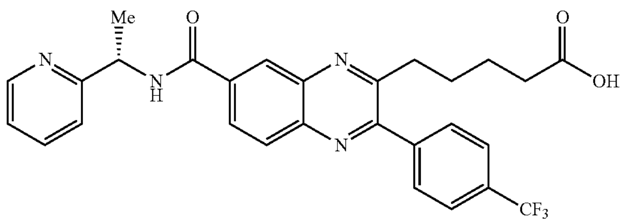 | 7-[[[1(S)-(2-pyridinyl)ethyl]amino]carbonyl]-3-[4-(trifluoromethyl)phenyl]-2-quinoxalinepentanoic acid | 523 |
| 147 | 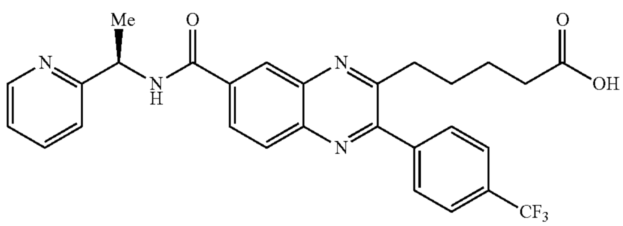 | 7-[[[1(R)-(2-pyridinyl)ethyl]amino]carbonyl]-3-[4-(trifluoromethyl)phenyl]-2-quinoxalinepentanoic acid | 523 |
| 148 | 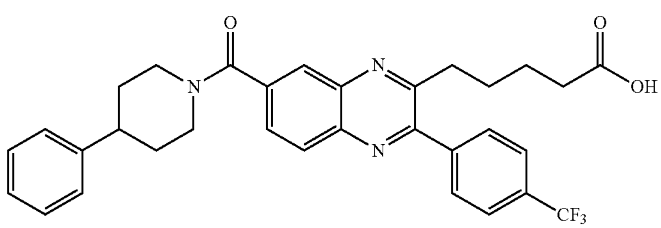 [SMILES: O=C(O)CCCCc1nc2cc(C(=O)N3CCC(c4ccccc4)CC3)ccc2nc1-c1ccc(C(F)(F)F)cc1] | 7-[(4-phenyl-1-piperidinyl)carbonyl]-3-[4-(trifluoromethyl)phenyl]-2-quinoxalinepentanoic acid | 562 |
| 149 | 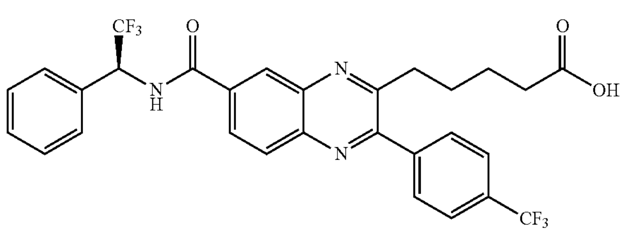 | 3-[4-(trifluoromethyl)phenyl]-7-[[(2,2,2-trifluoro-1(S)-phenylethyl)amino]carbonyl]-2-quinoxalinepentanoic acid | 576 |
| 150 | 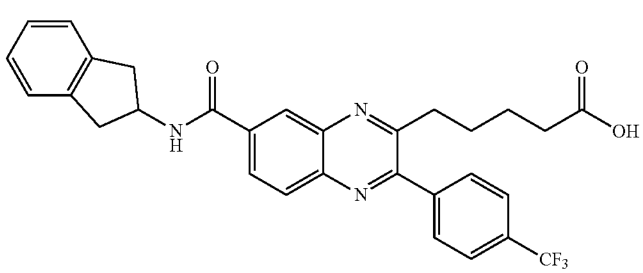 [SMILES: O=C(O)CCCCc1nc2cc(C(=O)NC3Cc4ccccc4C3)ccc2nc1-c1ccc(C(F)(F)F)cc1] | 7-[[(2,3-dihydro-1H-inden-2-yl)amino]carbonyl]-3-[4-(trifluoromethyl)phenyl]-2-quinoxalinepentanoic acid | 534 |

-continued

| No. | Structure | Name | M + H |
|---|---|---|---|
| 151 | 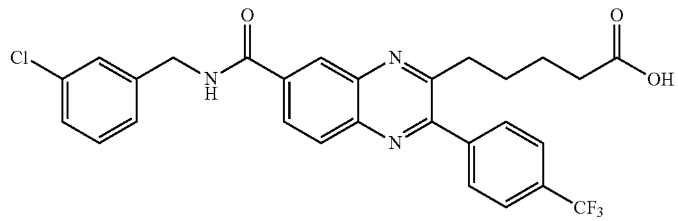 [SMILES: O=C(O)CCCCc1nc2cc(C(=O)NCc3cccc(Cl)c3)ccc2nc1-c1ccc(C(F)(F)F)cc1] | 7-[[[(3-chlorophenyl)methyl]amino]carbonly]-3-[4-(trifluoromethyl)phenyl]-2-quinoxalinepentanoic acid | 542 |
| 152 | 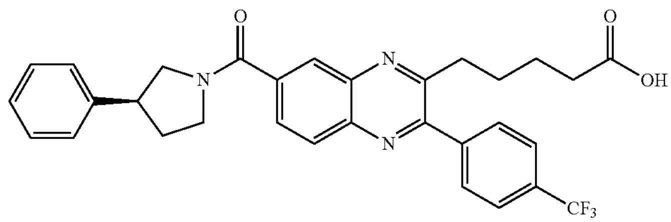 [SMILES: O=C(O)CCCCc1nc2cc(C(=O)N3CC[C@@H](c4ccccc4)C3)ccc2nc1-c1ccc(C(F)(F)F)cc1] | 7-[(3R)-phenyl-1-pyrrolidinyl]carbonyl]-3-[4-(trifluoromethyl)phenyl]-2-quinoxalinepentanoic acid | 548 |
| 153 | 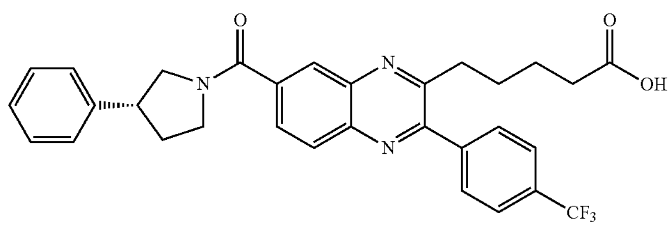 [SMILES: O=C(O)CCCCc1nc2cc(C(=O)N3CC[C@H](c4ccccc4)C3)ccc2nc1-c1ccc(C(F)(F)F)cc1] | 7-[(3(S)-phenyl-1-pyrrolidinyl]carbonyl]-3-[4-(trifluoromethyl)phenyl]-2-quinoxalinepentanoic acid | 548 |
| 154 | 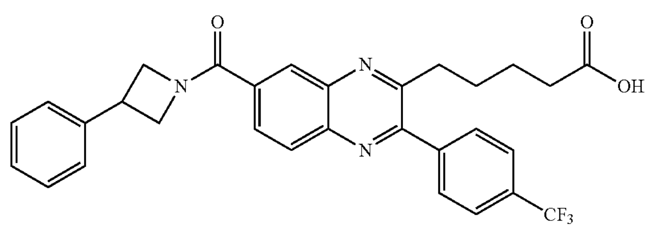 [SMILES: O=C(O)CCCCc1nc2cc(C(=O)N3CC(c4ccccc4)C3)ccc2nc1-c1ccc(C(F)(F)F)cc1] | 7-[(3-phenyl-1-azetidinyl)carbonyl]-3-[4-(trifluoromethyl)phenyl]-2-quinoxalinepentanoic acid | 534 |
| 155 | 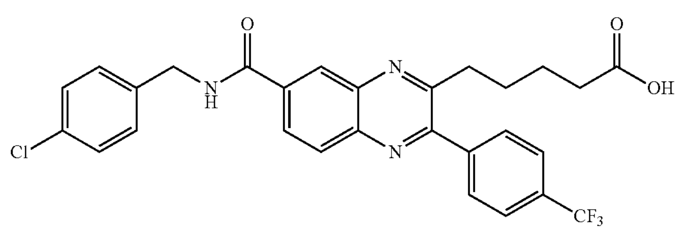 [SMILES: O=C(O)CCCCc1nc2cc(C(=O)NCc3ccc(Cl)cc3)ccc2nc1-c1ccc(C(F)(F)F)cc1] | 7-[[[(4-chlorophenyl)methyl]amino]carbonyl]-3-[4-(trifluoromethyl)phenyl]-2-quinoxalinepentanoic acid | 542 |
| 156 | 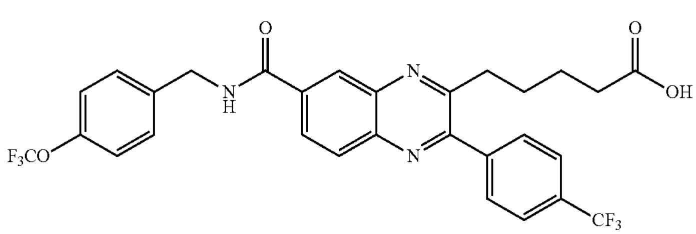 [SMILES: O=C(O)CCCCc1nc2cc(C(=O)NCc3ccc(OC(F)(F)F)cc3)ccc2nc1-c1ccc(C(F)(F)F)cc1] | 7-[[[[4-(trifluoromethoxy)phenyl]methyl]amino]carbonyl]-3-[4-(trifluoromethyl)phenyl]-2-quinoxalinepentanoic acid | 592 |

-continued

| No. | Structure | Name | M + H |
|---|---|---|---|
| 157 | 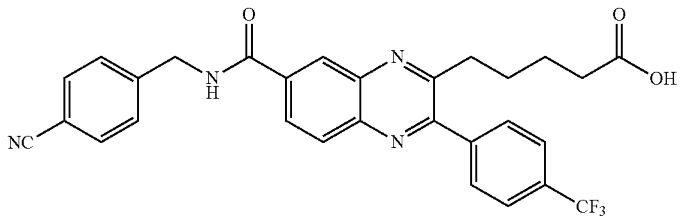 [SMILES: N#Cc1ccc(CNC(=O)c2ccc3nc(-c4ccc(C(F)(F)F)cc4)c(CCCCC(=O)O)nc3c2)cc1] | 7-[[[(4-cyanophenyl)methyl]amino]carbonyl]-3-[4-(trifluoromethyl)phenyl]-2-quinoxalinepentanoic acid | 533 |
| 158 | 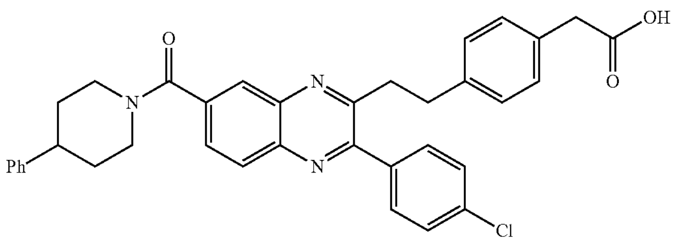 [SMILES: O=C(O)Cc1ccc(CCc2nc3cc(C(=O)N4CCC(c5ccccc5)CC4)ccc3nc2-c2ccc(Cl)cc2)cc1] | 4-[2-[3-(4-chlorophenyl)-7-[(4-phenyl-1-piperidinyl)carbonyl]-2-quinoxalinyl]ethyl]benzeneacetic acid | 590 |
| 159 | 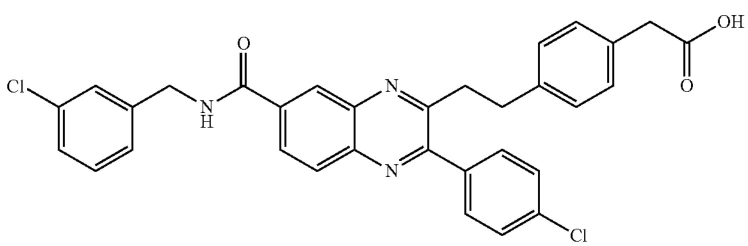 [SMILES: O=C(O)Cc1ccc(CCc2nc3cc(C(=O)NCc4cccc(Cl)c4)ccc3nc2-c2ccc(Cl)cc2)cc1] | 4-[2-[3-(4-chlorophenyl)-7-[[[(3-chlorophenyl)methyl]amino]carbonyl]-2-quinoxalinyl]ethyl]benzeneacetic acid | 570 |
| 160 | 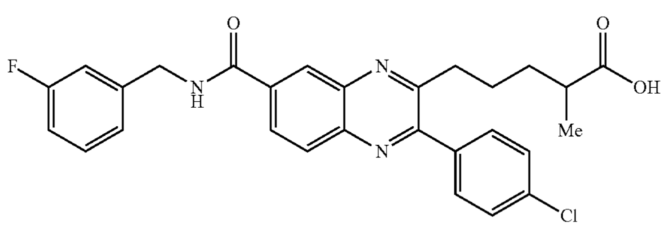 [SMILES: CC(CCCc1nc2cc(C(=O)NCc3cccc(F)c3)ccc2nc1-c1ccc(Cl)cc1)C(=O)O] | 3-(4-chlorophenyl)-7-[[[(3-fluorophenyl)methyl]amino]carbonyl]-alpha-methyl-2-quinoxalinepentanoic acid | 506 |
| 161 | 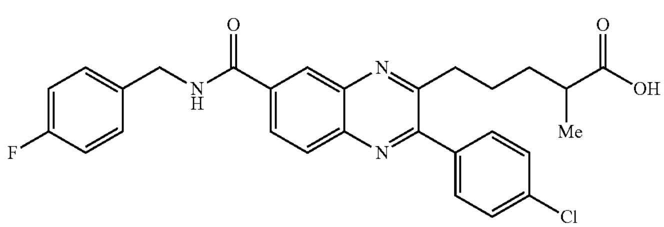 [SMILES: CC(CCCc1nc2cc(C(=O)NCc3ccc(F)cc3)ccc2nc1-c1ccc(Cl)cc1)C(=O)O] | 3-(4-chlorophenyl)-7-[[[(4-fluorophenyl)methyl]amino]carbonyl-alpha-methyl-2-quinoxalinepentanoic acid | 506 |
| 162 | 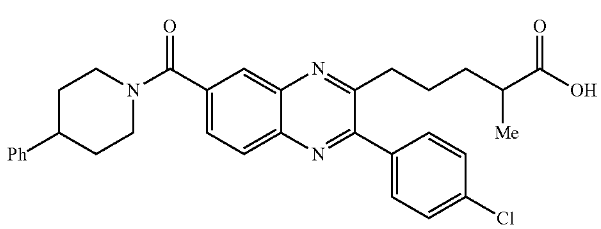 [SMILES: CC(CCCc1nc2cc(C(=O)N3CCC(c4ccccc4)CC3)ccc2nc1-c1ccc(Cl)cc1)C(=O)O] | 3-(4-chlorophenyl)-alpha-methyl-7-[(4-phenyl-1-piperidinyl)carbonyl]-2-quinoxalinepentanoic acid | 542 |

-continued

| No. | Structure | Name | M + H |
|---|---|---|---|
| 163 | 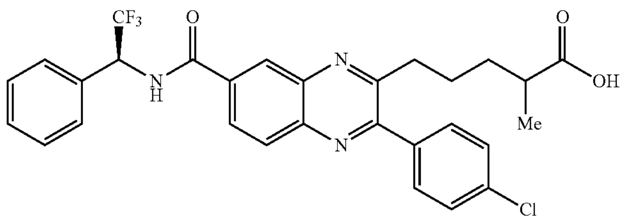 [SMILES: CC(CCCc1nc2cc(C(=O)N[C@@H](c3ccccc3)C(F)(F)F)ccc2nc1-c1ccc(Cl)cc1)C(=O)O] | 3-(4-chlorophenyl)-alpha-methyl-7-[[(2,2,2-trifluoro-1(S)-phenylethyl)amino]carbonyl]-2-2-quinoxalinepentanoic acid | 556 |
| 164 | 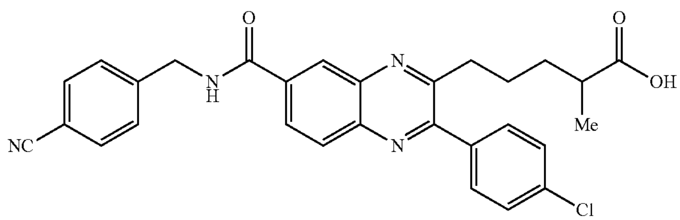 [SMILES: CC(CCCc1nc2cc(C(=O)NCc3ccc(C#N)cc3)ccc2nc1-c1ccc(Cl)cc1)C(=O)O] | 3-(4-chlorophenyl)-7-[[[(4-cyanophenyl)methyl]amino]carbonyl]-alpha-methyl-2-quinoxalinepentanoic acid | 513 |
| 165 | 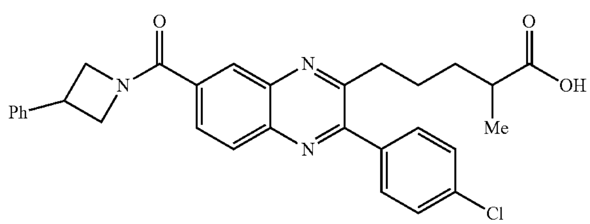 [SMILES: CC(CCCc1nc2cc(C(=O)N3CC(c4ccccc4)C3)ccc2nc1-c1ccc(Cl)cc1)C(=O)O] | 3-(4-chlorophenyl)-alpha-methyl-7-[(3-phenyl-1-azetidinyl)carbonyl]-2-quinoxalinepentanoic acid | 514 |
| 166 | 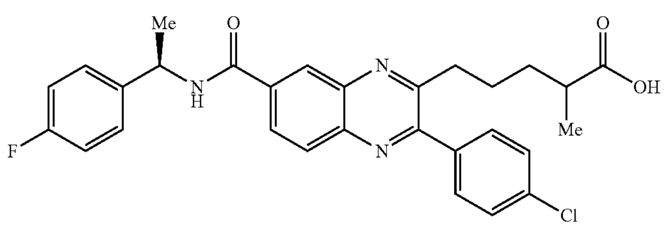 [SMILES: CC(CCCc1nc2cc(C(=O)N[C@H](C)c3ccc(F)cc3)ccc2nc1-c1ccc(Cl)cc1)C(=O)O] | 3(4-chlorophenyl)-7-[[[1(R)-(4-fluorophenyl)ethyl]amino]carbonyl]-alpha-methyl-2-quinoxalinepentanoic acid | 520 |
| 167 | 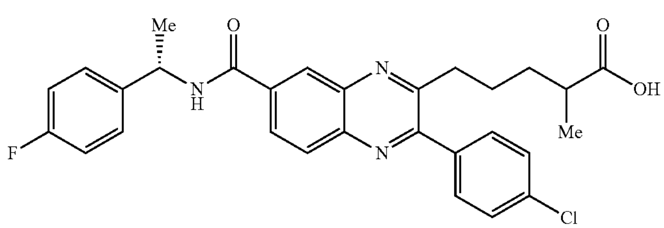 [SMILES: CC(CCCc1nc2cc(C(=O)N[C@@H](C)c3ccc(F)cc3)ccc2nc1-c1ccc(Cl)cc1)C(=O)O] | 3-(4-chlorophenyl)-7-[[[1(S)-(4-fluorophenyl)ethyl]amino]carbonyl]-alpha-methyl-2-quinoxalinepentanoic acid | 520 |
| 168 | 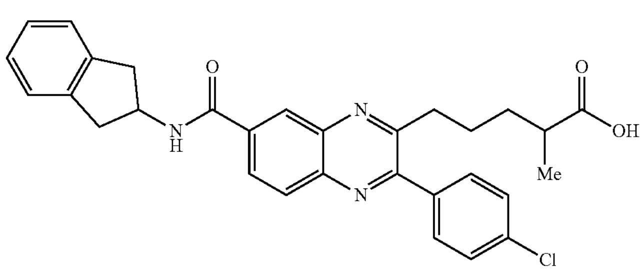 [SMILES: CC(CCCc1nc2cc(C(=O)NC3Cc4ccccc4C3)ccc2nc1-c1ccc(Cl)cc1)C(=O)O] | 3-(4-chlorophenyl)-7-[[(2,3-dihydro-1H-inden-2-yl)amino]carbonyl]-alpha-methyl-2-quinoxalinepentanoic acid | 514 |

-continued

| No. | Structure | Name | M + H |
|---|---|---|---|
| 169 | 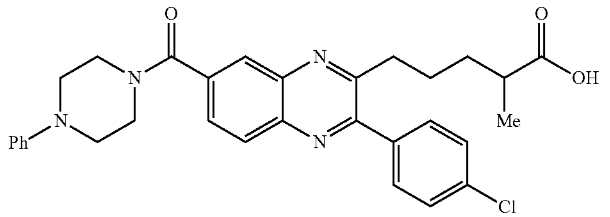 [SMILES: CC(CCCc1nc2cc(C(=O)N3CCN(c4ccccc4)CC3)ccc2nc1-c1ccc(Cl)cc1)C(=O)O] | 3-(4-chlorophenyl)-alpha-methyl-7-[(4-phenyl-1-piperazinyl)carbonyl]-2-quinoxalinepentanoic acid | 543 |
| 170* | 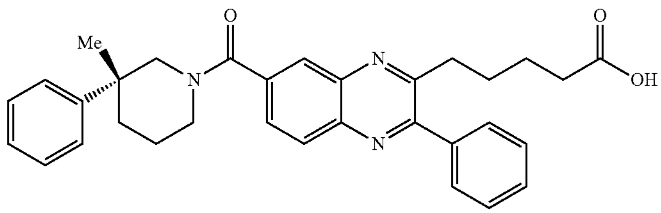 [SMILES: C[C@]1(c2ccccc2)CCCN(C(=O)c2ccc3nc(-c4ccccc4)c(CCCCC(=O)O)nc3c2)C1] | 7-[(3(R)-methyl-3-phenyl-1-piperidinyl)carbonyl]-3-phenyl-2-quinoxalinepentanoic acid | 508 |
| 171* | 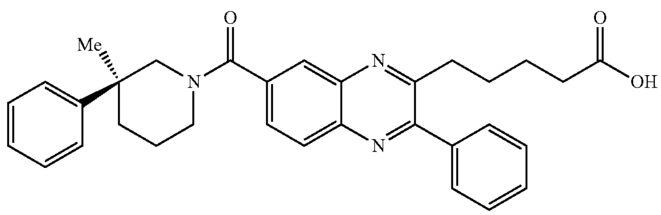 [SMILES: C[C@@]1(c2ccccc2)CCCN(C(=O)c2ccc3nc(-c4ccccc4)c(CCCCC(=O)O)nc3c2)C1] | 7-[(3(S)-methyl-3-phenyl-1-piperidinyl)carbonyl]-3-phenyl-2-quinoxalinepentanoic acid | 508 |
| 172 | 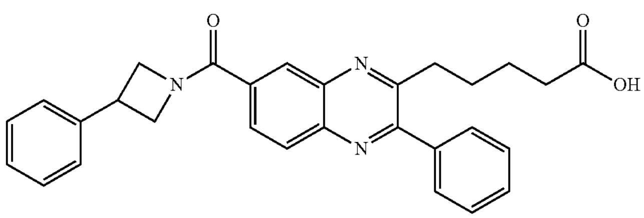 [SMILES: O=C(O)CCCCc1nc2cc(C(=O)N3CC(c4ccccc4)C3)ccc2nc1-c1ccccc1] | 3-phenyl-7-[(3-phenyl-1-azetidinyl)carbonyl]-2-quinoxalinepentanoic acid | 466 |
| 173 | 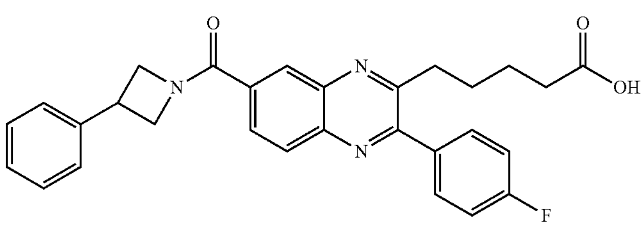 [SMILES: O=C(O)CCCCc1nc2cc(C(=O)N3CC(c4ccccc4)C3)ccc2nc1-c1ccc(F)cc1] | 3-(4-fluorophenyl)--7-[(3-phenyl-1-azetidinyl)carbonyl]-2-quinoxalinepentanoic acid | 484 |
| 174 | 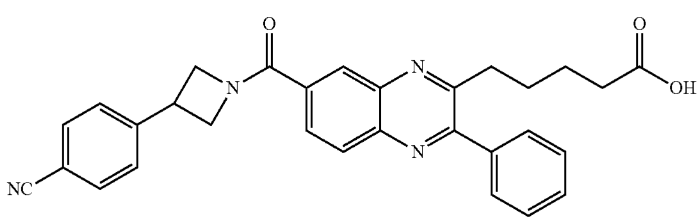 [SMILES: N#Cc1ccc(C2CN(C(=O)c3ccc4nc(-c5ccccc5)c(CCCCC(=O)O)nc4c3)C2)cc1] | 7-[[3-(4-cyanophenyl)-1-azetidinyl]carbonyl]-3-phenyl-2-quinoxalinepentanoic acid | 491 |
| 175 | 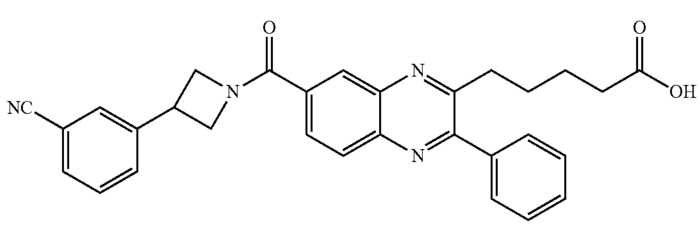 [SMILES: N#Cc1cccc(C2CN(C(=O)c3ccc4nc(-c5ccccc5)c(CCCCC(=O)O)nc4c3)C2)c1] | 7-[[3-(3-cyanophenyl)-1-azetidinyl]carbonyl]-3-phenyl-2-quinoxalinepentanoic acid | 491 |

-continued

| No. | Structure | Name | M + H |
|-----|-----------|------|-------|
| 176 | 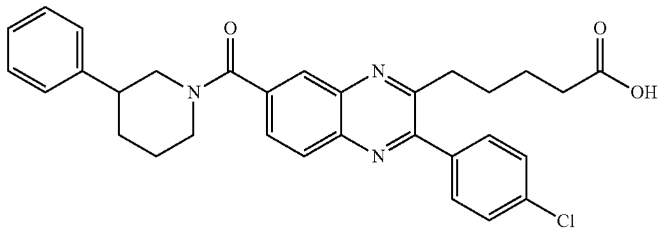 [SMILES: O=C(O)CCCCc1nc2cc(C(=O)N3CCCC(c4ccccc4)C3)ccc2nc1-c1ccc(Cl)cc1] | 3-(4-chlorophenyl)-7-[(3-phenyl-1-piperidinyl)carbonyl]-2-quinoxalinepentanoic acid | 528 |
| 177 | 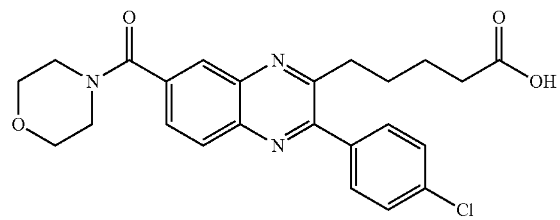 [SMILES: O=C(O)CCCCc1nc2cc(C(=O)N3CCOCC3)ccc2nc1-c1ccc(Cl)cc1] | 3-(4-chlorophenyl)-7-(4-morpholinylcarbonyl)-2-quinoxalinepentanoic acid | 454 |
| 178 | 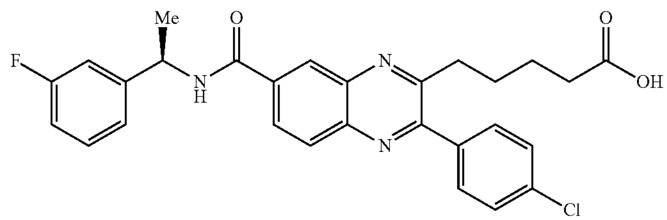 [SMILES: C[C@@H](NC(=O)c1ccc2nc(-c3ccc(Cl)cc3)c(CCCCC(=O)O)nc2c1)c1cccc(F)c1] | 3-(4-chlorophenyl)-7-[[[1(R)-(3-fluorophenyl)ethyl]amino]carbonyl]-2-quinoxalinepentanoic acid | 506 |
| 179 | 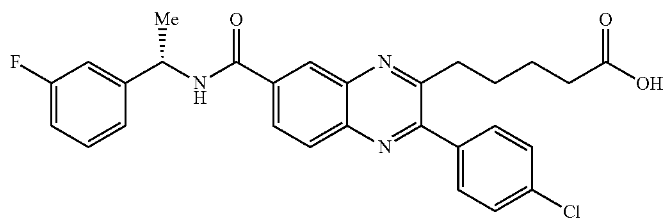 [SMILES: C[C@H](NC(=O)c1ccc2nc(-c3ccc(Cl)cc3)c(CCCCC(=O)O)nc2c1)c1cccc(F)c1] | 3-(4-chlorophenyl)-7-[[[1(S)-(3-fluorophenyl)ethyl]amino]carbonyl]-2-quinoxalinepentanoic acid | 506 |
| 180 | 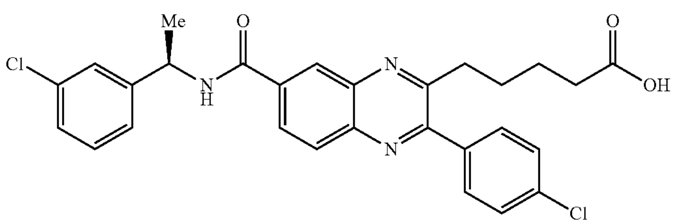 [SMILES: C[C@@H](NC(=O)c1ccc2nc(-c3ccc(Cl)cc3)c(CCCCC(=O)O)nc2c1)c1cccc(Cl)c1] | 3-(4-chlorophenyl)-7-[[[1(R)-(3-chlorophenyl)ethyl]amino]carbonyl]-2-quinoxalinepentanoic acid | 522 |
| 181 | 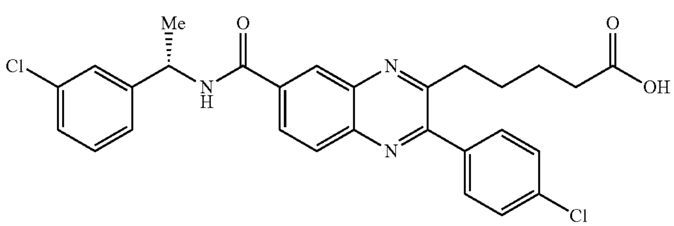 [SMILES: C[C@H](NC(=O)c1ccc2nc(-c3ccc(Cl)cc3)c(CCCCC(=O)O)nc2c1)c1cccc(Cl)c1] | 3-(4-chlorophenyl)-7-[[[1(S)-(3-chlorophenyl)ethyl]amino]carbonyl]-2-quinoxalinepentanoic acid | 522 |
| 182 | 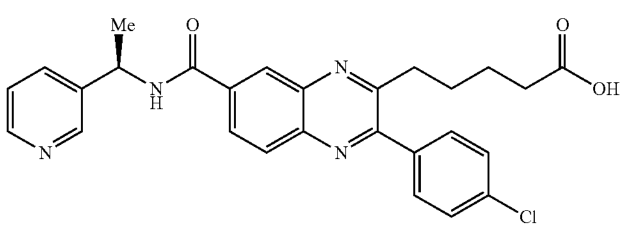 [SMILES: C[C@@H](NC(=O)c1ccc2nc(-c3ccc(Cl)cc3)c(CCCCC(=O)O)nc2c1)c1cccnc1] | 3-(4-chlorophenyl)-7-[[[1(R)-(3-pyridinyl)ethyl]amino]carbonyl]-2-quinoxalinepentanoic acid | 489 |

-continued

| No. | Structure | Name | M + H |
|---|---|---|---|
| 183 | 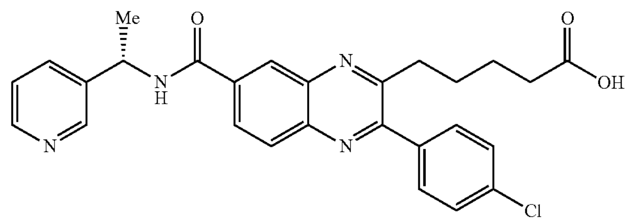 [SMILES: C[C@H](NC(=O)c1ccc2nc(-c3ccc(Cl)cc3)c(CCCCC(=O)O)nc2c1)c1cccnc1] | 3-(4-chlorophenyl)-7-[[[1(S)-pyridinyl)ethyl]amino]carbonyl]-2-quinoxalinepentanoic acid | 489 |
| 184 | 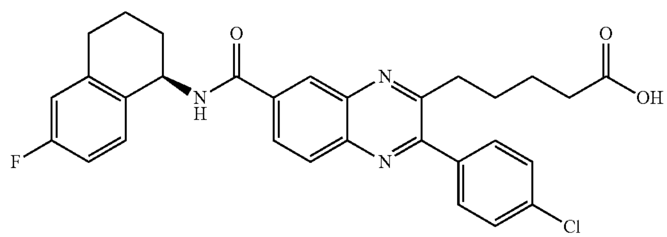 [SMILES: O=C(O)CCCCc1nc2cc(C(=O)N[C@@H]3CCCc4cc(F)ccc43)ccc2nc1-c1ccc(Cl)cc1] | 3-(4-chlorophenyl)-7-[[(6-fluoro-1,2,3,4-tetrahydro-1(R)-naphthalenyl)amino]carbonyl]-2-quinoxalinepentanoic acid | 532 |
| 185 | 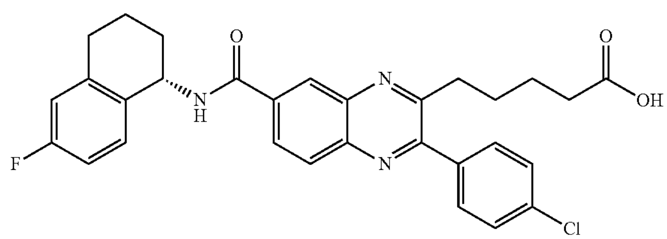 [SMILES: O=C(O)CCCCc1nc2cc(C(=O)N[C@H]3CCCc4cc(F)ccc43)ccc2nc1-c1ccc(Cl)cc1] | 3-(4-chlorophenyl)-7-[[(6-fluoro-1,2,3,4-tetrahydro-1(S)-naphthalenyl)amino]carbonyl]2-quinoxalinepentanoic acid | 532 |
| 186 | 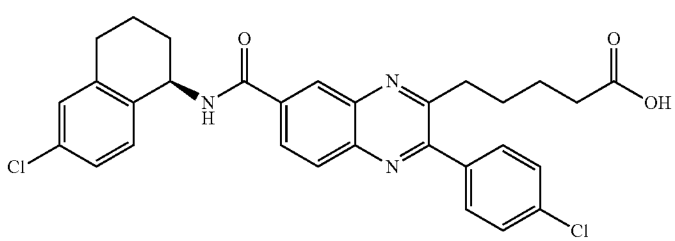 | 3-(4-chlorophenyl)-7-[[(6-chloro-1,2,3,4-tetrahydro-1(R)-naphthalenyl)amino]carbonyl]-2-quinoxalinepentanoic acid | 548 |
| 187 | 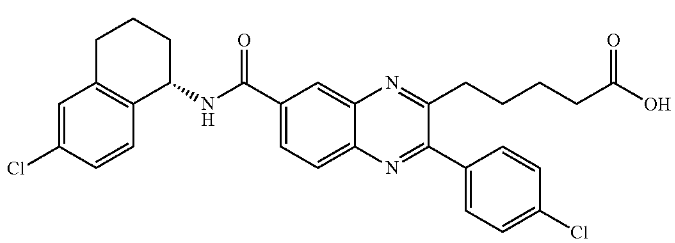 [SMILES: O=C(O)CCCCc1nc2cc(C(=O)N[C@H]3CCCc4cc(Cl)ccc43)ccc2nc1-c1ccc(Cl)cc1] | 3-(4-chlorophenyl)-7-[[(6-chloro-1,2,3,4-tetrahydro-1(S)-naphthalenyl)amino]carbonyl]-2-quinoxalinepentanoic acid | 548 |
| 188 | 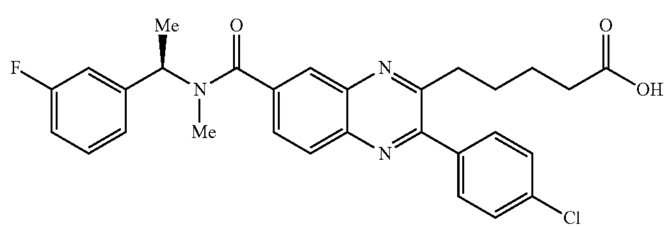 [SMILES: C[C@H](c1cccc(F)c1)N(C)C(=O)c1ccc2nc(-c3ccc(Cl)cc3)c(CCCCC(=O)O)nc2c1] | 3-(4-chlorophenyl)-7-[[[1(R)-(4-fluorophenyl)ethyl]methylamino]carbonyl]-2-quinoxalinepentanoic acid | 520 |

| No. | Structure | Name | M + H |
|---|---|---|---|
| 189 | 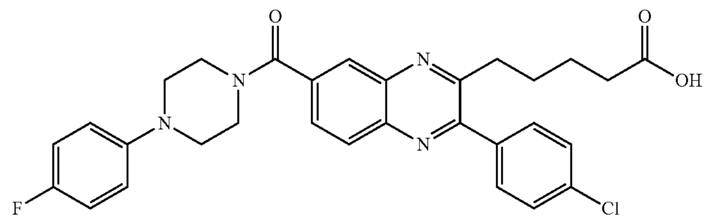 [SMILES: O=C(O)CCCCc1nc2cc(C(=O)N3CCN(c4ccc(F)cc4)CC3)ccc2nc1-c1ccc(Cl)cc1] | 3-(4-chlorophenyl)-7-[[4-(4-fluorophenyl)-1-piperazinyl]carbonyl]-2-quinoxalinepentanoic acid | 547 |
| 190 | 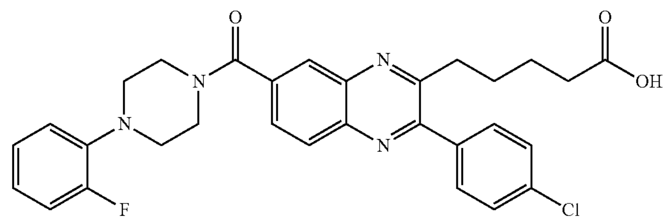 [SMILES: O=C(O)CCCCc1nc2cc(C(=O)N3CCN(c4ccccc4F)CC3)ccc2nc1-c1ccc(Cl)cc1] | 3-(4-chlorophenyl)-7-[[4-(2-fluorophenyl)-1-piperazinyl]carbonyl]-2-quinoxalinepentanoic acid | 547 |
| 191 | 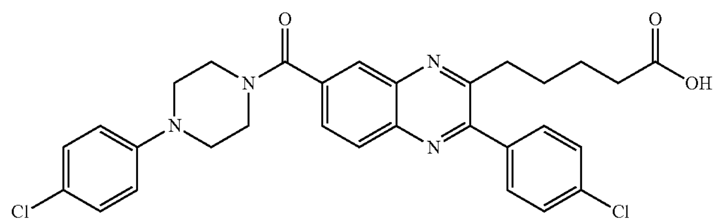 | 3-(4-chlorophenyl)-7-[[4-(4-chlorophenyl)-1-piperazinyl]carbonyl]-2-quinoxalinepentanoic acid | 563 |
| 192 | 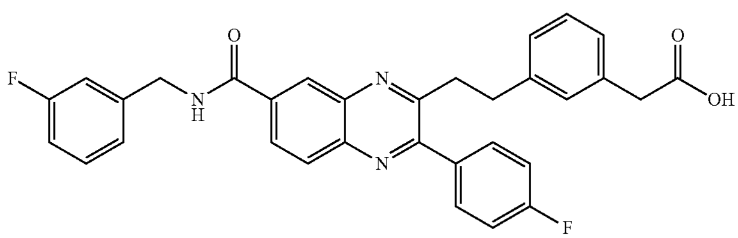 [SMILES: O=C(O)Cc1cccc(CCc2nc3cc(C(=O)NCc4cccc(F)c4)ccc3nc2-c2ccc(F)cc2)c1] | 3-[2-[3-(4-fluorophenyl)-7-[[[(3-fluorophenyl)methyl]amino]carbonyl]-2-quinoxalinyl]ethyl]benzencacetic acid | 538 |
| 193 | 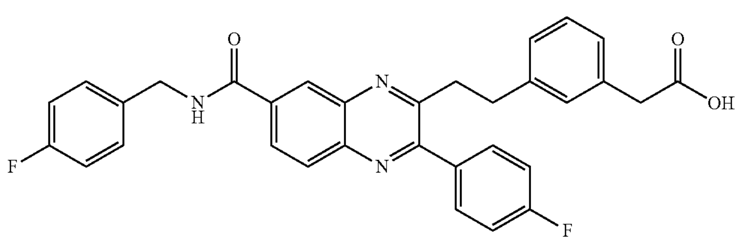 [SMILES: O=C(O)Cc1cccc(CCc2nc3cc(C(=O)NCc4ccc(F)cc4)ccc3nc2-c2ccc(F)cc2)c1] | 3-[2-[3-(4-fluorophenyl)-7-[[[(4-fluorophenyl)methyl]amino]carbonyl]-2-quinoxalinyl]ethyl]benzeneacetic acid | 538 |
| 194 | 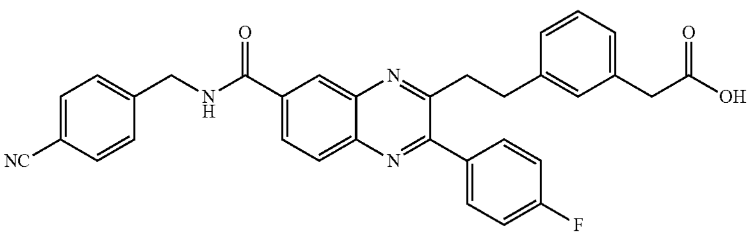 [SMILES: N#Cc1ccc(CNC(=O)c2ccc3nc(-c4ccc(F)cc4)c(CCc4cccc(CC(=O)O)c4)nc3c2)cc1] | 3-[2-[7-[[[(4-cyanophenyl)methyl]amino]carbonyl]-3-(4-fluorophenyl-2-quinoxalinyl]ethyl]benzeneacetic acid | 545 |

-continued

| No. | Structure | Name | M + H |
|---|---|---|---|
| 195 | 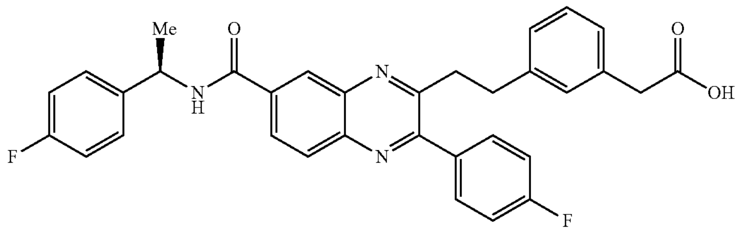 [SMILES: C[C@@H](NC(=O)c1ccc2nc(-c3ccc(F)cc3)c(CCc3cccc(CC(=O)O)c3)nc2c1)c1ccc(F)cc1] | 3-[2-[3-(4-fluorophenyl)-7-[[[1(R)-(4-fluorophenyl)ethyl]amino]carbonyl]-2-quinoxalinyl]ethyl]benzeneacetic acid | 552 |
| 196 | 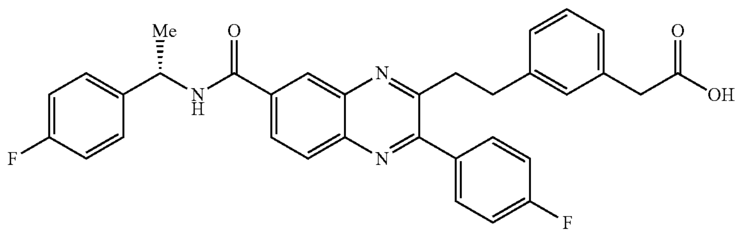 [SMILES: C[C@H](NC(=O)c1ccc2nc(-c3ccc(F)cc3)c(CCc3cccc(CC(=O)O)c3)nc2c1)c1ccc(F)cc1] | 3-[2-[3-(4-fluorophenyl)-7-[[[1(S)-(4-fluorophenyl)ethyl]amino]carbonyl]-2-quinoxalinyl]ethylbenzeneacetic acid | 552 |
| 197 | 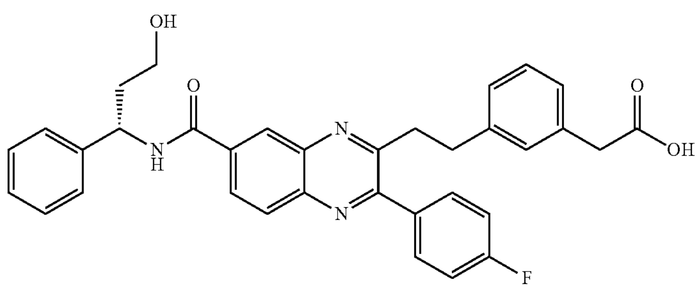 [SMILES: O=C(O)Cc1cccc(CCc2nc3cc(C(=O)N[C@@H](CCO)c4ccccc4)ccc3nc2-c2ccc(F)cc2)c1] | 3-[2-[3-(4-fluorophenyl)-7-[[(3-hydroxy-1(S)-phenylpropyl)amino]carbonyl]-2-quinoxalinyl]ethyl]benzeneacetic acid | 564 |
| 198 | 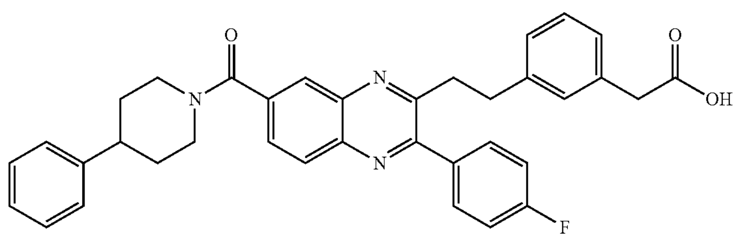 [SMILES: O=C(O)Cc1cccc(CCc2nc3cc(C(=O)N4CCC(c5ccccc5)CC4)ccc3nc2-c2ccc(F)cc2)c1] | 3-[2-[3-(4-fluorophenyl)-7-[(4-phenyl-1-piperidinyl)carbonyl]-2-quinoxalinyl]ethyl]benzeneacetic acid | 574 |
| 199 | 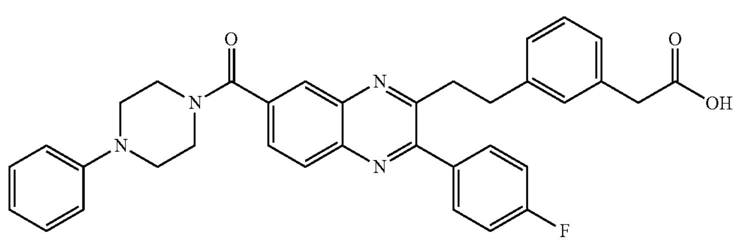 [SMILES: O=C(O)Cc1cccc(CCc2nc3cc(C(=O)N4CCN(c5ccccc5)CC4)ccc3nc2-c2ccc(F)cc2)c1] | 3-[2-[3-(4-fluorophenyl)-7-[(4-phenyl-1-piperazinyl)carbonyl]-2-quinoxalinyl]ethyl]benzeneacetic acid | 575 |
| 200 | 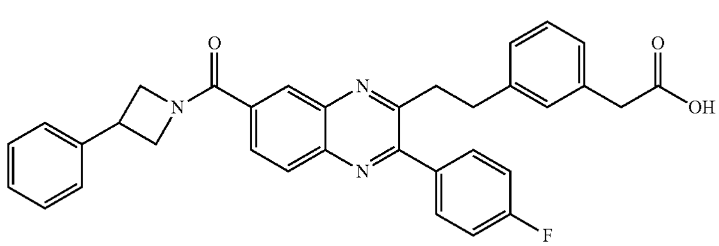 [SMILES: O=C(O)Cc1cccc(CCc2nc3cc(C(=O)N4CC(c5ccccc5)C4)ccc3nc2-c2ccc(F)cc2)c1] | 3-[2-[3-(4-fluorophenyl)-7-[(3-phenyl-1-azetidinyl)carbonyl]-2-quinoxalinyl]ethyl]benzeneacetic acid | 546 |

| No. | Structure | Name | M + H |
|---|---|---|---|
| 201 | 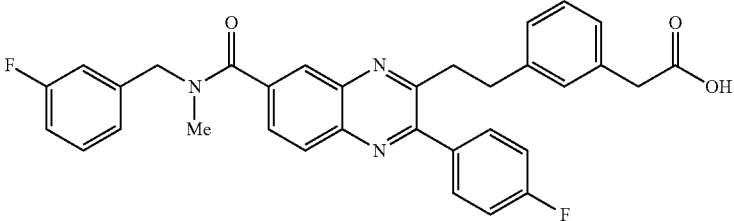 [SMILES: CN(Cc1cccc(F)c1)C(=O)c1ccc2nc(-c3ccc(F)cc3)c(CCc3cccc(CC(=O)O)c3)nc2c1] | 3-[2-[3-(3-fluorophenyl)-7-[[[(4-fluorophenyl)methyl]methylamino]carbonyl]-2-quinoxalinyl]ethyl]benzeneacetic acid | 552 |
| 202 | 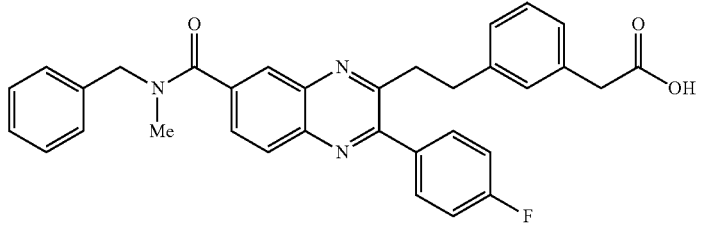 [SMILES: CN(Cc1ccccc1)C(=O)c1ccc2nc(-c3ccc(F)cc3)c(CCc3cccc(CC(=O)O)c3)nc2c1] | 3-[2-[3-(4-fluorophenyl)-7-[[methyl(phenylmethyl)amino]carbonyl]-2-quinoxalinyl]ethyl]benzeneacetic acid | 534 |
| 203 | 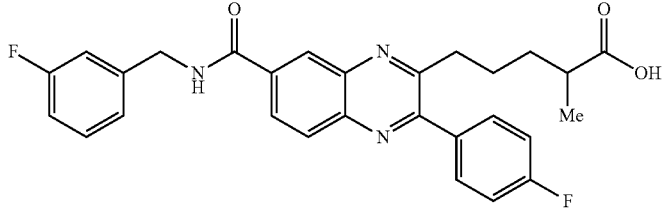 [SMILES: CC(CCCc1nc2cc(C(=O)NCc3cccc(F)c3)ccc2nc1-c1ccc(F)cc1)C(=O)O] | 3-(4-fluorophenyl)-7-[[[(3-fluorophenyl)methyl]amino]carbonyl]-alpha-methyl-2-quinoxalinepentanoic acid | 490 |
| 204 | 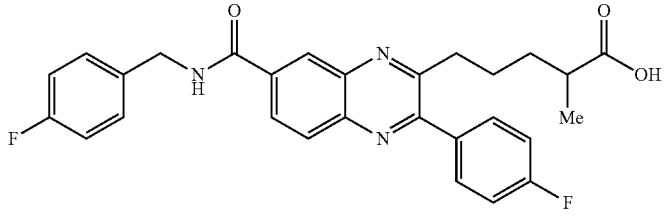 [SMILES: CC(CCCc1nc2cc(C(=O)NCc3ccc(F)cc3)ccc2nc1-c1ccc(F)cc1)C(=O)O] | 3-(4-fluorophenyl)-7-[[[(4-fluorophenyl)methyl]amino]carbonyl]-alpha-methyl-2-quinoxalinepentanoic acid | 490 |
| 205 | 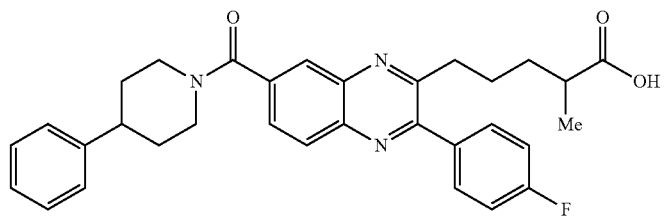 [SMILES: CC(CCCc1nc2cc(C(=O)N3CCC(c4ccccc4)CC3)ccc2nc1-c1ccc(F)cc1)C(=O)O] | 3-(4-fluorophenyl)-alpha-methyl-7-[(4-phenyl-1-piperidinyl)carbonyl]-2-quinoxalinepentanoic acid | 526 |
| 206 | 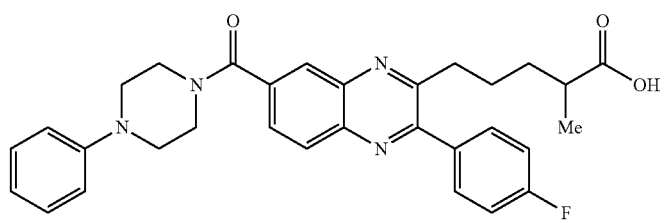 [SMILES: CC(CCCc1nc2cc(C(=O)N3CCN(c4ccccc4)CC3)ccc2nc1-c1ccc(F)cc1)C(=O)O] | 3-(4-fluorophenyl)-alpha-methyl-7-[(4-phenyl-1-piperazinyl)carbonyl]-2-quinoxalinepentanoic acid | 527 |

-continued

| No. | Structure | Name | M + H |
|---|---|---|---|
| 207 | 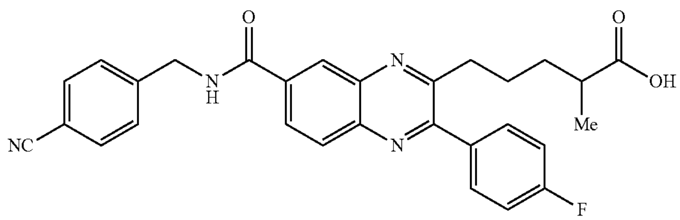 [SMILES: CC(CCCc1nc2cc(C(=O)NCc3ccc(C#N)cc3)ccc2nc1-c1ccc(F)cc1)C(=O)O] | 7-[[[(4-cyanophenyl)methyl]amino]carbonyl]-3-(4-fluorophenyl)-alpha-methyl-2-quinoxalinepentanoic acid | 497 |
| 208 | 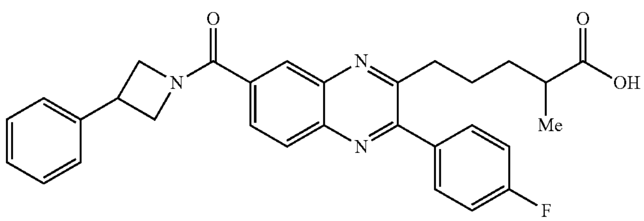 [SMILES: CC(CCCc1nc2cc(C(=O)N3CC(c4ccccc4)C3)ccc2nc1-c1ccc(F)cc1)C(=O)O] | 3-(4-fluorophenyl)-alpha-methyl-7-[(3-phenyl-1-azetidinyl)carbonyl]-2-quinoxalinepentanoic acid | 498 |
| 209 | 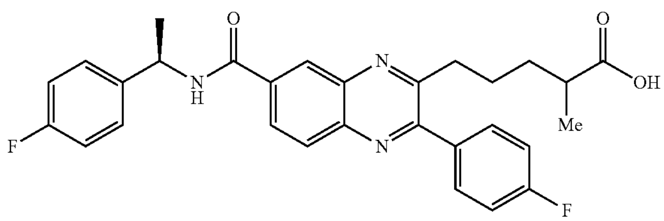 [SMILES: CC(CCCc1nc2cc(C(=O)N[C@H](C)c3ccc(F)cc3)ccc2nc1-c1ccc(F)cc1)C(=O)O] | 3-(4-fluorophenyl)-7-[[[1(R)-(4-fluorophenyl)ethyl]amino]carbonyl]-alpha-methyl-2-quinoxalinepentanoic acid | 504 |
| 210 | 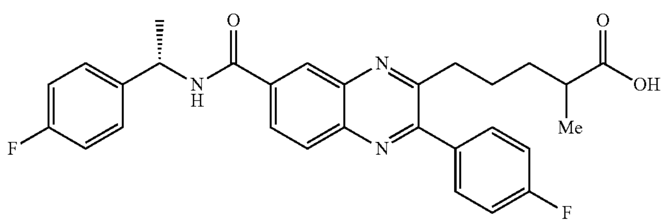 [SMILES: CC(CCCc1nc2cc(C(=O)N[C@@H](C)c3ccc(F)cc3)ccc2nc1-c1ccc(F)cc1)C(=O)O] | 3-(4-fluorophenyl)-7-[[[1(S)-(4-fluorophenyl)ethyl]amino]carbonyl]-alpha-methyl-2-quinoxalinepentanoic acid | 504 |
| 211 | 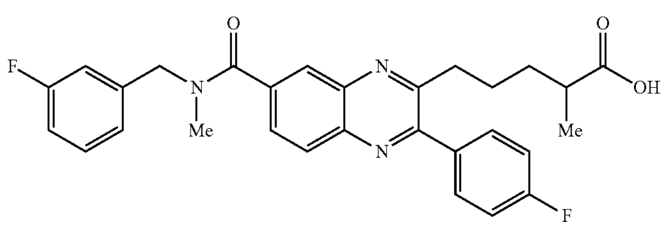 [SMILES: CC(CCCc1nc2cc(C(=O)N(C)Cc3cccc(F)c3)ccc2nc1-c1ccc(F)cc1)C(=O)O] | 3-(4-fluorophenyl)-7-[[[(3-fluorophenyl)methyl]methylamino]carbonyl]-alpha-methyl-2-quinoxalinepentanoic acid | 504 |
| 212 | 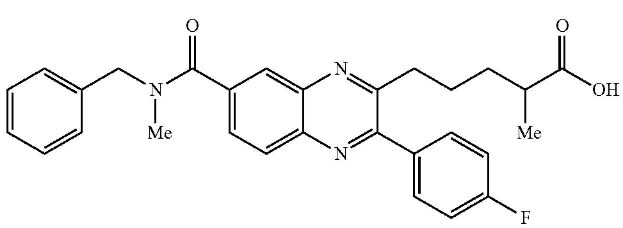 [SMILES: CC(CCCc1nc2cc(C(=O)N(C)Cc3ccccc3)ccc2nc1-c1ccc(F)cc1)C(=O)O] | 3-(4-fluorophenyl)-alpha-methyl-7-[[methyl(phenylmethyl)amino]carbonyl]-2-quinoxalinepentanoic acid | 486 |

-continued

| No. | Structure | Name | M + H |
|---|---|---|---|
| 213 | 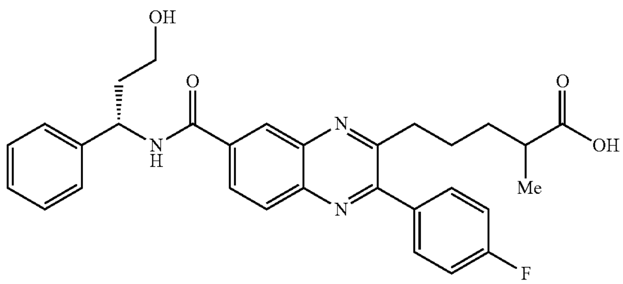 [SMILES: CC(CCCc1nc2cc(C(=O)N[C@@H](CCO)c3ccccc3)ccc2nc1-c1ccc(F)cc1)C(=O)O] | 3-(4-fluorophenyl)-7-[[(3-hydroxy-1(S)-phenylpropyl)amino]carbonyl]-alpha-methyl-2-quinoxalinepentanoic acid | 516 |
| 214 | 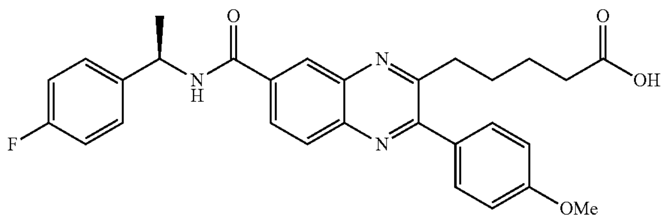 [SMILES: COc1ccc(-c2nc3ccc(C(=O)N[C@H](C)c4ccc(F)cc4)cc3nc2CCCCC(=O)O)cc1] | 7-[[[1(R)-(4-fluorophenyl)ethyl]amino]carbonyl]-3-(4-methoxyphenyl)-2-quinoxalinepentanoic acid | 502 |
| 215 | 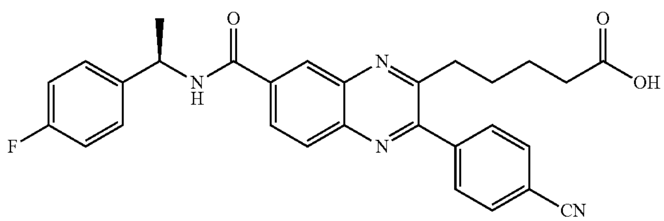 [SMILES: C[C@@H](NC(=O)c1ccc2nc(-c3ccc(C#N)cc3)c(CCCCC(=O)O)nc2c1)c1ccc(F)cc1] | 3-(4-cyanophenyl)-7-[[[1(R)-(4-fluorophenyl)ethyl]amino]carbonyl]-2-quinoxalinepentanoic acid | 497 |
| 216 | 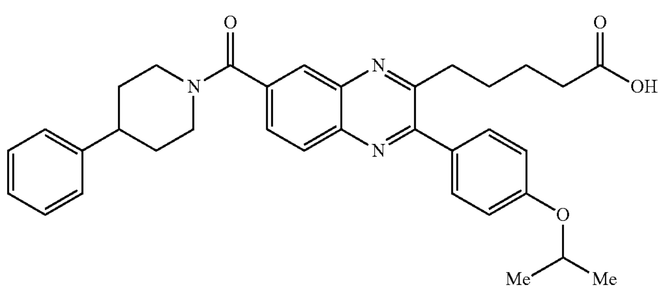 [SMILES: CC(C)Oc1ccc(-c2nc3ccc(C(=O)N4CCC(c5ccccc5)CC4)cc3nc2CCCCC(=O)O)cc1] | 3-[4-(1-methyl-ethoxy)phenyl]-7-[(4-phenyl-1-piperidinyl)carbonyl]-2-quinoxalinepentanoic acid | 552 |
| 217 | 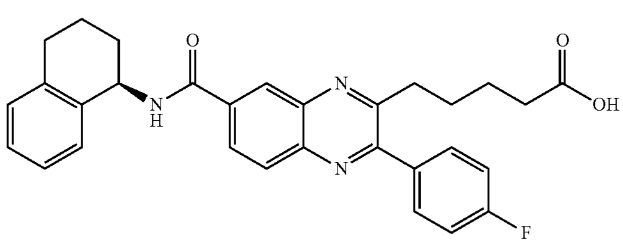 [SMILES: O=C(O)CCCCc1nc2cc(C(=O)N[C@@H]3CCCc4ccccc43)ccc2nc1-c1ccc(F)cc1] | 3-(4-fluorophenyl)-7-[[(1,2,3,4-tetrahydro-1(R)-naphthalenyl)amino]carbonyl]-2-quinoxalinepentanoic acid | 498 |
| 218 | 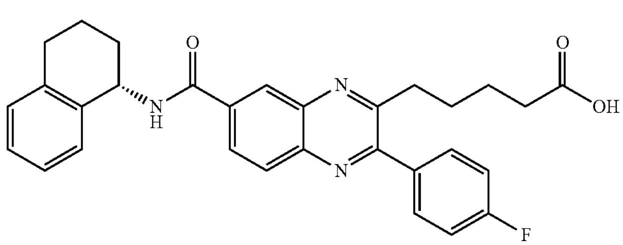 [SMILES: O=C(O)CCCCc1nc2cc(C(=O)N[C@H]3CCCc4ccccc43)ccc2nc1-c1ccc(F)cc1] | 3-(4-fluorophenyl)-7-[[(1,2,3,4-tetrahydro-1(S)-naphthalenyl)amino]carbonyl]-2-quinoxalinepentanoic acid | 498 |

| No. | Structure | Name | M + H |
|---|---|---|---|
| 219 | 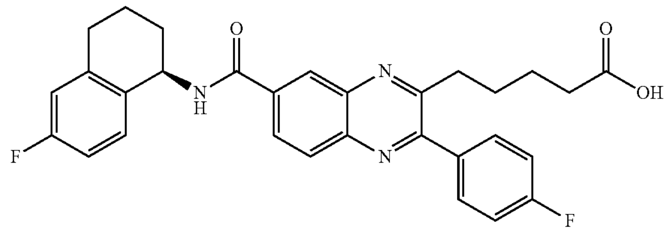 [SMILES: O=C(O)CCCCc1nc2cc(C(=O)N[C@@H]3CCCc4cc(F)ccc43)ccc2nc1-c1ccc(F)cc1] | 3-(4-fluorophenyl)-7-[[(6-fluoro-1,2,3,4-tetrahydro-1(R)-naphthalenyl)amino]carbonyl]-2-quinoxalinepentanoic acid | 516 |
| 220 | 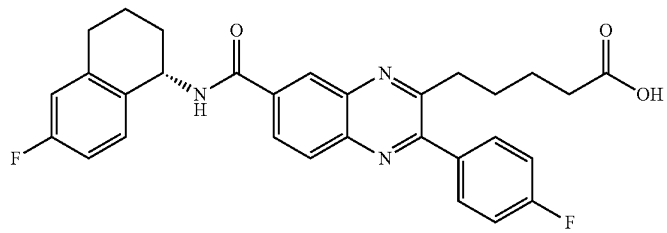 [SMILES: O=C(O)CCCCc1nc2cc(C(=O)N[C@H]3CCCc4cc(F)ccc43)ccc2nc1-c1ccc(F)cc1] | 3-(4-fluorophenyl)-7-[[(6-fluoro-1,2,3,4-tetrahydro-1(S)-naphthalenyl)amino]carbonyl]-2-quinoxalinepentanoic acid | 516 |
| 221 | 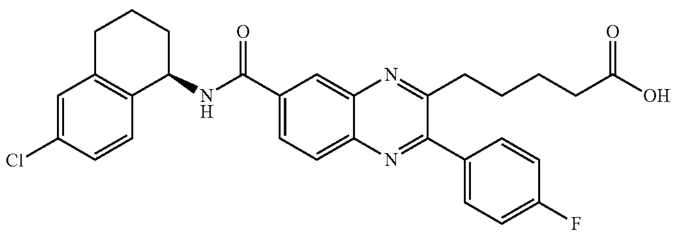 [SMILES: O=C(O)CCCCc1nc2cc(C(=O)N[C@@H]3CCCc4cc(Cl)ccc43)ccc2nc1-c1ccc(F)cc1] | 7-[[(6-chloro-1,2,3,4-tetrahydro-1(R)-naphthalenyl)amino]carbonyl]-3-(4-fluorophenyl)-2-quinoxalinepentanoic acid | 532 |
| 222 | 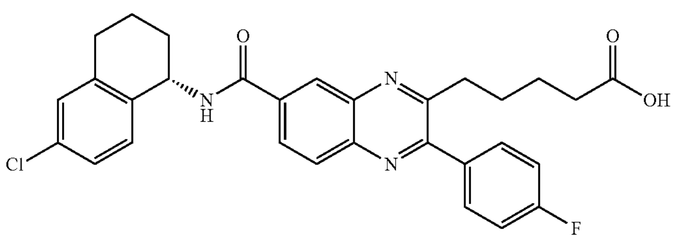 [SMILES: O=C(O)CCCCc1nc2cc(C(=O)N[C@H]3CCCc4cc(Cl)ccc43)ccc2nc1-c1ccc(F)cc1] | 7-[[(6-chloro-1,2,3,4-tetrahydro-1(S)-naphthalenyl)amino]carbonyl]-3-(4-fluorophenyl)-2-quinoxalinepentanoic acid | 532 |
| 223 | 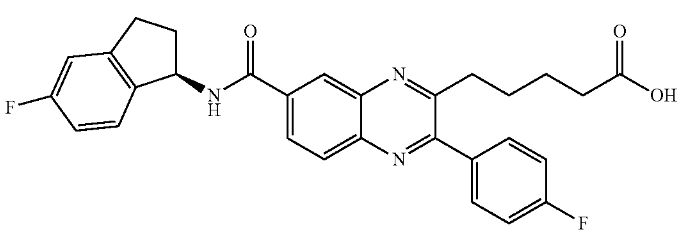 [SMILES: O=C(O)CCCCc1nc2cc(C(=O)N[C@@H]3CCc4cc(F)ccc43)ccc2nc1-c1ccc(F)cc1] | 7-[[(5-fluoro-2,3-dihydro-1H-inden-1(R)-yl)amino]carbonyl]-3-(4-fluorophenyl)-2-quinoxalinepentanoic acid | 502 |
| 224 | 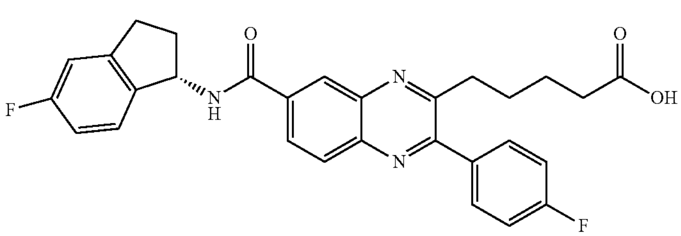 [SMILES: O=C(O)CCCCc1nc2cc(C(=O)N[C@H]3CCc4cc(F)ccc43)ccc2nc1-c1ccc(F)cc1] | 7-[[(5-fluoro-2,3-dihydro-1H-inden-1(S)-yl)amino]carbonyl]-3-(4-fluorophenyl)-2-quinoxalinepentanoic acid | 502 |

-continued

| No. | Structure | Name | M + H |
|---|---|---|---|
| 225 | 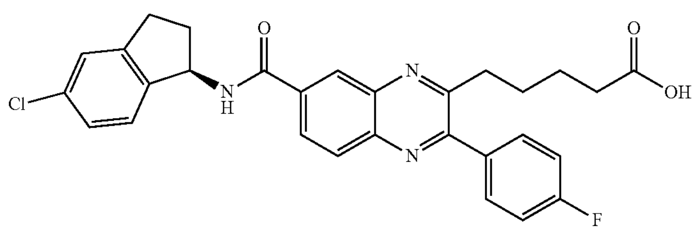 [SMILES: O=C(O)CCCCc1nc2cc(C(=O)N[C@@H]3CCc4cc(Cl)ccc43)ccc2nc1-c1ccc(F)cc1] | 7-[[(5-chloro-2,3-dihydro-1H-inden-1(R)-yl)amino]carbonyl]-3-(4-fluorophenyl)-2-quinoxalinepentanoic acid | 518 |
| 226 | 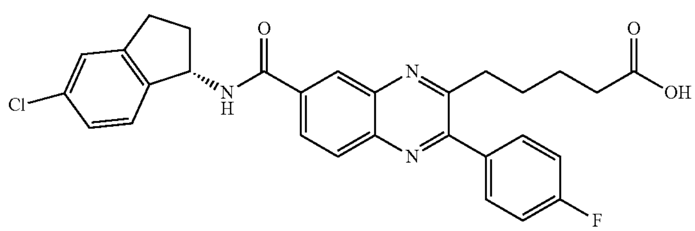 [SMILES: O=C(O)CCCCc1nc2cc(C(=O)N[C@H]3CCc4cc(Cl)ccc43)ccc2nc1-c1ccc(F)cc1] | 7-[[(5-chloro-2,3-dihydro-1H-inden-1(S)-yl)amino]carbonyl]-3-(4-fluorophenyl)-2-quinoxalinepentanic acid | 518 |
| 227 | 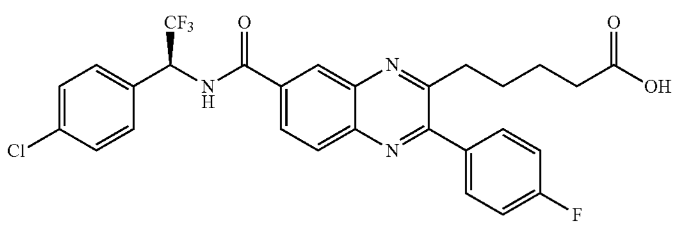 [SMILES: O=C(O)CCCCc1nc2cc(C(=O)N[C@@H](c3ccc(Cl)cc3)C(F)(F)F)ccc2nc1-c1ccc(F)cc1] | 7-[[[1(S)-(4-chlorophenyl)-2,2,2-trifluoroethyl]amino]carbonyl]-3-(4-fluorophenyl)-2-quinoxalinepentanoic acid | 560 |
| 228 | 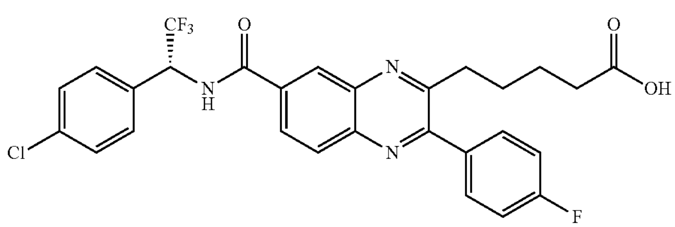 [SMILES: O=C(O)CCCCc1nc2cc(C(=O)N[C@H](c3ccc(Cl)cc3)C(F)(F)F)ccc2nc1-c1ccc(F)cc1] | 7-[[[1(R)-(4-chlorophenyl)-2,2,2-trifluoroethyl]amino]carbonyl]-3-(4-fluorophenyl)-2-quinoxalinepentanoic acid | 560 |
| 229 | 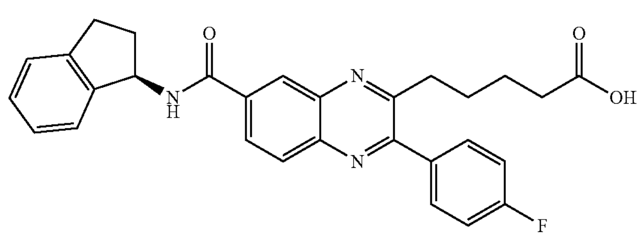 [SMILES: O=C(O)CCCCc1nc2cc(C(=O)N[C@@H]3CCc4ccccc43)ccc2nc1-c1ccc(F)cc1] | 7-[[(2,3-dihydro-1H-inden-1(R)-yl)amino]carbonyl]-3-(4-fluorophenyl)-2-quinoxalinepentanoic acid | 484 |
| 230 | 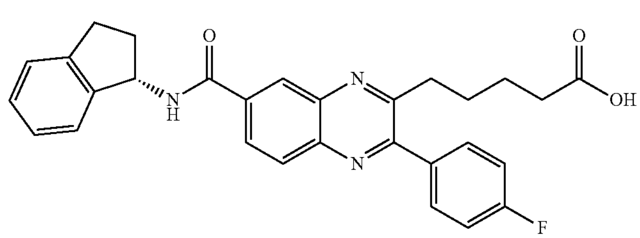 [SMILES: O=C(O)CCCCc1nc2cc(C(=O)N[C@H]3CCc4ccccc43)ccc2nc1-c1ccc(F)cc1] | 7-[[(2,3-dihydro-1H-inden-1(S)-yl)amino]carbonyl]-3-(4-fluorophenyl)-2-quinoxalinepentanoic acid | 484 |

-continued

| No. | Structure | Name | M + H |
|---|---|---|---|
| 231 | 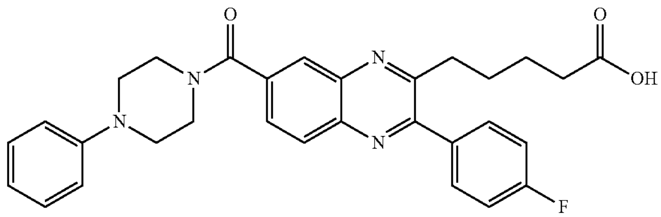 [SMILES: O=C(O)CCCCc1nc2cc(C(=O)N3CCN(c4ccccc4)CC3)ccc2nc1-c1ccc(F)cc1] | 3-(4-fluorophenyl)-7-[(4-phenyl-1-piperazinyl)carbonyl]-2-quinoxalinepentanoic acid | 513 |
| 232 | 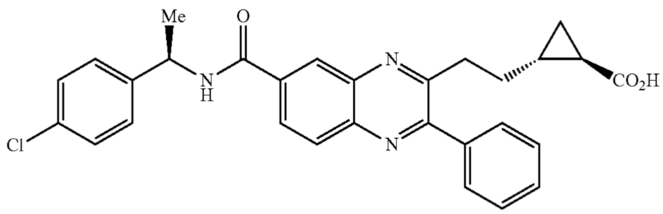 [SMILES: C[C@@H](NC(=O)c1ccc2nc(-c3ccccc3)c(CC[C@@H]3C[C@H]3C(=O)O)nc2c1)c1ccc(Cl)cc1] | trans-2-[2-[7-[[[1(R)-(4-chlorophenyl)ethyl]amino]carbonyl]-3-phenyl-2-quinoxalinyl]ethyl]cyclopropanecarboxylic acid | 500 |
| 233 | 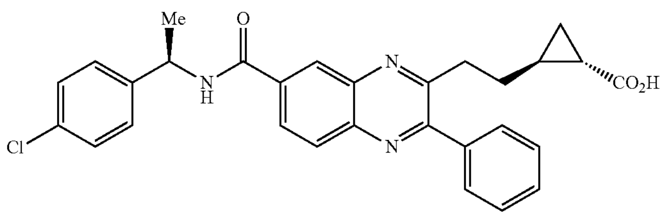 [SMILES: C[C@@H](NC(=O)c1ccc2nc(-c3ccccc3)c(CC[C@H]3C[C@@H]3C(=O)O)nc2c1)c1ccc(Cl)cc1] | trans-2-[2-[7-[[[1(R)-(4-chlorophenyl)ethyl]amino]carbonyl]-3-phenyl-2-quinexalinyl]ethyl]cyclopropanecarboxylic acid | 500 |
| 234 | 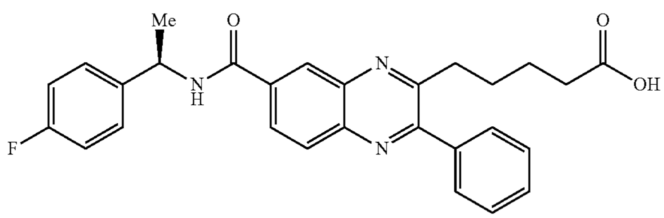 [SMILES: C[C@@H](NC(=O)c1ccc2nc(-c3ccccc3)c(CCCCC(=O)O)nc2c1)c1ccc(F)cc1] | 7-[[[1(R)-(4-fluorophenyl)ethyl]amino]carbonyl]-3-phenyl-2-quinoxalinepentanoic acid | 472 |
| 235 | 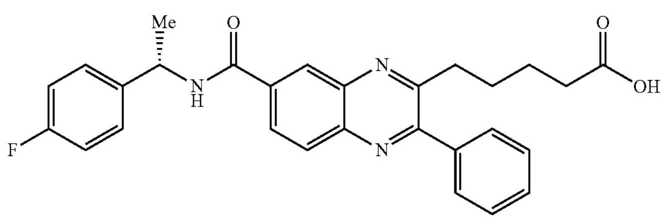 [SMILES: C[C@H](NC(=O)c1ccc2nc(-c3ccccc3)c(CCCCC(=O)O)nc2c1)c1ccc(F)cc1] | 7-[[[1(S)-(4-fluorophenyl)ethyl]amino]carbonyl]-3-phenyl-2-quinoxalinepentanoic acid | 472 |
| 236 | 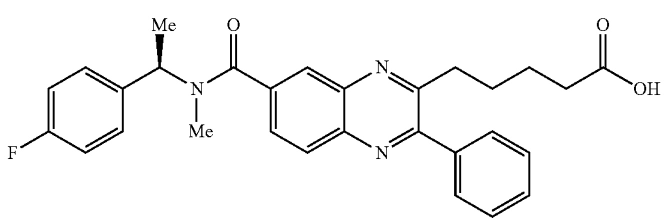 [SMILES: C[C@H](c1ccc(F)cc1)N(C)C(=O)c1ccc2nc(-c3ccccc3)c(CCCCC(=O)O)nc2c1] | 7-[[[1(R)-(4-fluorophenyl)ethyl]methylamino]carbonyl]-3-phenyl-2-quinoxalinepentanoic acid | 486 |
| 237 | 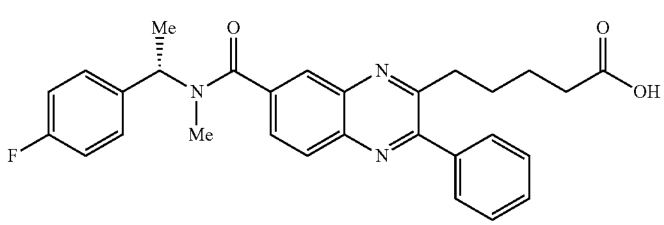 [SMILES: C[C@@H](c1ccc(F)cc1)N(C)C(=O)c1ccc2nc(-c3ccccc3)c(CCCCC(=O)O)nc2c1] | 7-[[[1(S)-(4-fluorophenyl)ethyl]methylamino]carbonyl]-3-phenyl-2-quinoxalinepentanoic acid | 486 |

-continued

| No. | Structure | Name | M + H |
|---|---|---|---|
| 238 | 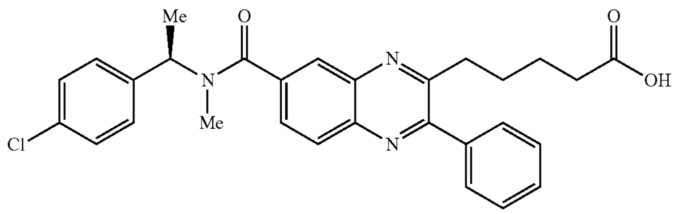 [SMILES: C[C@H](c1ccc(Cl)cc1)N(C)C(=O)c1ccc2nc(-c3ccccc3)c(CCCCC(=O)O)nc2c1] | 7-[[[1(R)-(4-chlorophenyl)ethyl]methylamino]carbonyl]-3-phenyl-2-quinoxalinepentanoic acid | 502 |
| 239 | 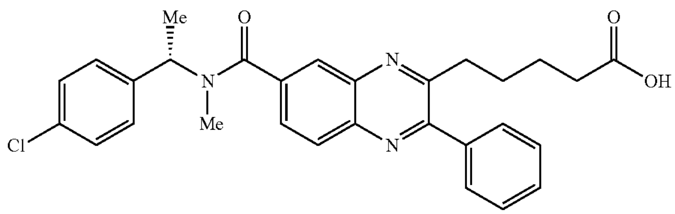 [SMILES: C[C@@H](c1ccc(Cl)cc1)N(C)C(=O)c1ccc2nc(-c3ccccc3)c(CCCCC(=O)O)nc2c1] | 7-[[[1(S)-(4-chlorophenyl)ethyl]methylamino]carbonyl]-3-phenyl-2-quinoxalinepentanoic acid | 502 |
| 240 | 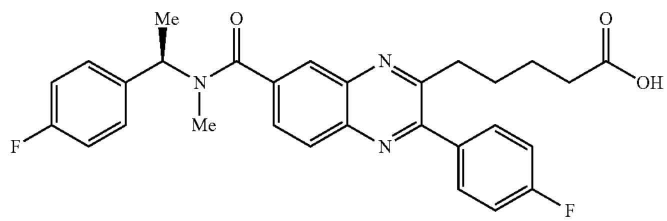 [SMILES: C[C@H](c1ccc(F)cc1)N(C)C(=O)c1ccc2nc(-c3ccc(F)cc3)c(CCCCC(=O)O)nc2c1] | 3-(4-fluorophenyl)-7-[[[1(R)-(4-fluorophenyl)ethyl]methylamino]carbonyl]-2-quinoxalinepentanoic acid | 504 |
| 241 | 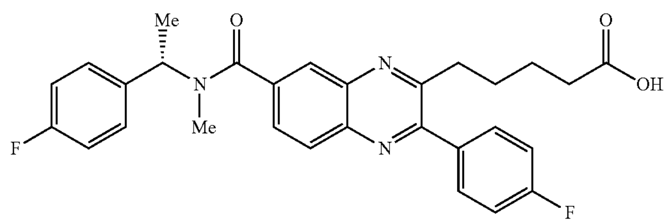 [SMILES: C[C@@H](c1ccc(F)cc1)N(C)C(=O)c1ccc2nc(-c3ccc(F)cc3)c(CCCCC(=O)O)nc2c1] | 3-(4-fluorophenyl)-7-[[[1(S)-(4-fluorophenyl)ethyl]methylamino]carbonyl]-2-quinoxalinepentanoic acid | 504 |
| 242 | 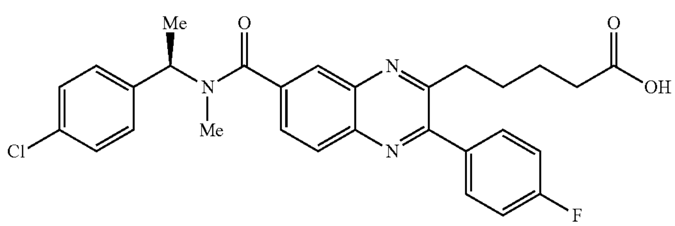 [SMILES: C[C@H](c1ccc(Cl)cc1)N(C)C(=O)c1ccc2nc(-c3ccc(F)cc3)c(CCCCC(=O)O)nc2c1] | 7-[[[1(R)-(4-chlorophenyl)ethyl]methylamino]carbonyl]-3-(4-fluorophenyl)-2-quinoxalinepentanoic acid | 520 |
| 243 | 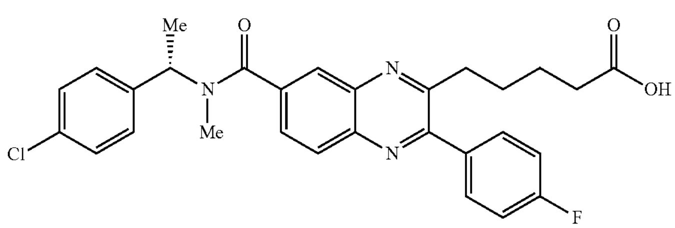 [SMILES: C[C@@H](c1ccc(Cl)cc1)N(C)C(=O)c1ccc2nc(-c3ccc(F)cc3)c(CCCCC(=O)O)nc2c1] | 7-[[[1(S)-(4-chlorophenyl)ethyl]methylamino]carbonyl]-3-(4-fluorophenyl)-2-quinoxalinepentanoic acid | 520 |
| 244 | 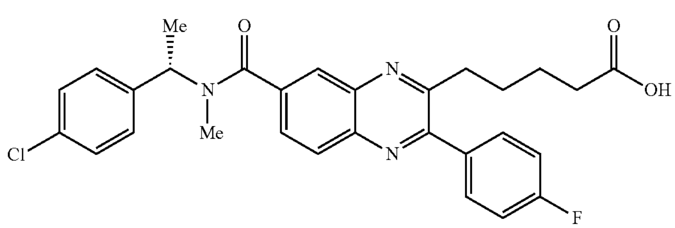 [SMILES: C[C@@H](c1ccc(Cl)cc1)N(C)C(=O)c1ccc2nc(-c3ccc(F)cc3)c(CCCCC(=O)O)nc2c1] | 3-(4-fluorophenyl)-7-[[4-(2-pyrimidinyl)-1-piperidinyl]carbonyl]-2-quinoxalinepentanoic acid | 514 |

-continued

| No. | Structure | Name | M + H |
|---|---|---|---|
| 245 | 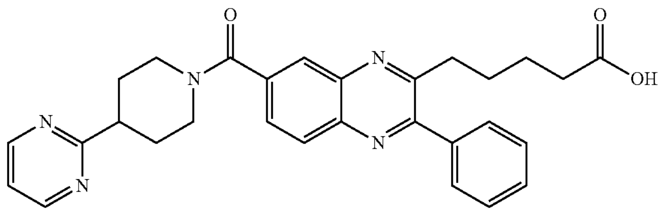 [SMILES: O=C(O)CCCCc1nc2cc(C(=O)N3CCC(c4ncccn4)CC3)ccc2nc1-c1ccccc1] | 3-phenyl-7-[[4-(2-pyrimidinyl)-1-piperidinyl]carbonyl]-2-quinoxalinepentanoic acid | 496 |
| 246 | 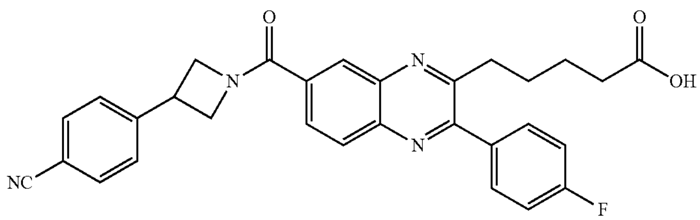 [SMILES: N#Cc1ccc(C2CN(C(=O)c3ccc4nc(-c5ccc(F)cc5)c(CCCCC(=O)O)nc4c3)C2)cc1] | 7-[[3-(4-cyanophenyl)-1-azetidinyl]carbonyl]-3-(4-fluorophenyl)-2-quinoxalinepentanoic acid | 509 |
| 247 | 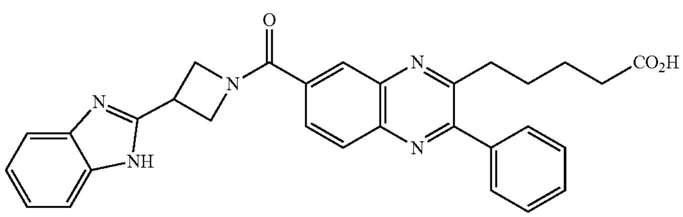 [SMILES: O=C(O)CCCCc1nc2cc(C(=O)N3CC(c4nc5ccccc5[nH]4)C3)ccc2nc1-c1ccccc1] | 7-[[3-(1H-benzimidazol-2-yl)-1-azetidinyl]carbonyl]-3-phenyl-2-quinoxalinepentanoic acid | 506 |
| 248 | 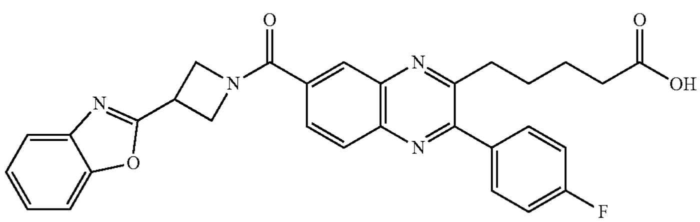 [SMILES: O=C(O)CCCCc1nc2cc(C(=O)N3CC(c4nc5ccccc5o4)C3)ccc2nc1-c1ccc(F)cc1] | 7-[[3-(2-benzoxazolyl)-1-azetidinyl]carbonyl]-3-(4-fluorophenyl)-2-quinoxalinepentanoic acid | 525 |
| 249 | 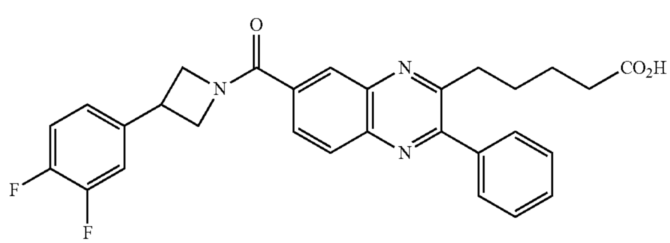 [SMILES: O=C(O)CCCCc1nc2cc(C(=O)N3CC(c4ccc(F)c(F)c4)C3)ccc2nc1-c1ccccc1] | 7-[[3-(3,4-difluorophenyl)-1-azetidinyl]carbonyl]-3-phenyl-2-quinoxalinepentanoic acid | 502 |
| 250 | 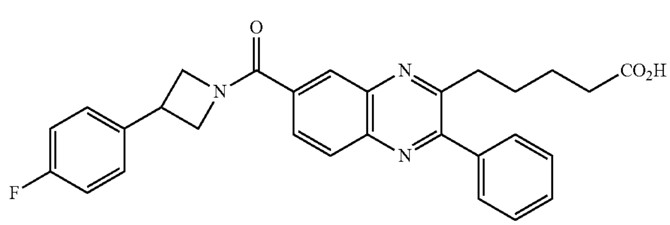 [SMILES: O=C(O)CCCCc1nc2cc(C(=O)N3CC(c4ccc(F)cc4)C3)ccc2nc1-c1ccccc1] | 7-[[3-(4-fluorophenyl)-1-azetidinyl]carbonyl]-3-phenyl-2-quinoxalinepentanoic acid | 484 |
| 251 | 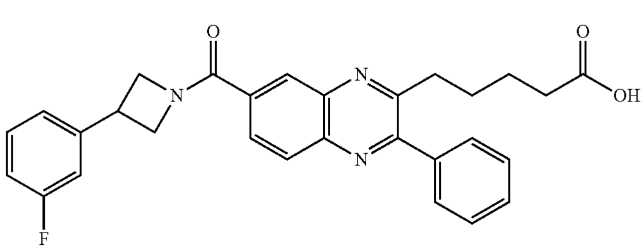 [SMILES: O=C(O)CCCCc1nc2cc(C(=O)N3CC(c4cccc(F)c4)C3)ccc2nc1-c1ccccc1] | 7-[[3-(3-fluorophenyl)-1-azetidinyl]carbonyl]-3-phenyl-2-quinoxalinepentanoic acid | 484 |

-continued

| No. | Structure | Name | M + H |
|---|---|---|---|
| 252 | 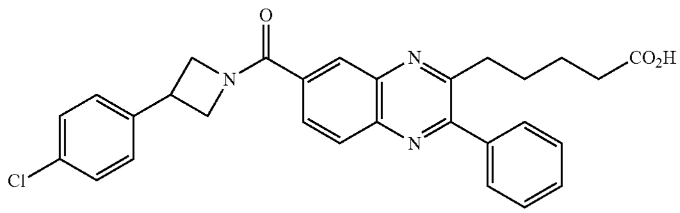 [SMILES: O=C(O)CCCCc1nc2cc(C(=O)N3CC(c4ccc(Cl)cc4)C3)ccc2nc1-c1ccccc1] | 7-[[3-(4-chlorophenyl)-1-azetidinyl]carbonyl]-3-phenyl-2-quinoxalinepentanoic acid | 500 |
| 253 | 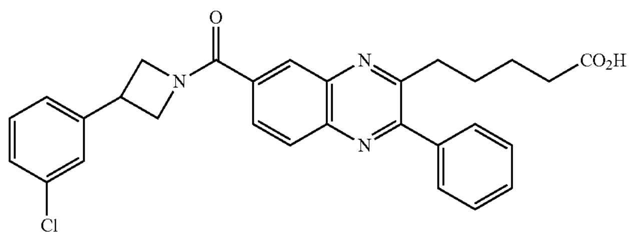 [SMILES: O=C(O)CCCCc1nc2cc(C(=O)N3CC(c4cccc(Cl)c4)C3)ccc2nc1-c1ccccc1] | 7-[[3-(3-chlorophenyl)-1-azetidinyl]carbonyl]-3-phenyl-2-quinoxalinepentanoic acid | 500 |
| 254 | 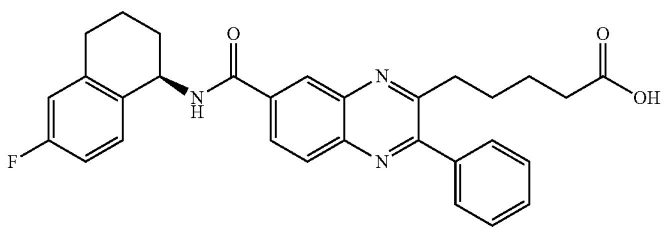 [SMILES: O=C(O)CCCCc1nc2cc(C(=O)N[C@@H]3CCCc4cc(F)ccc43)ccc2nc1-c1ccccc1] | 7-[[(6-fluoro-1,2,3,4-tetrahydro-1(R)-naphthalenyl)amino]carbonyl]-3-phenyl-2-quinoxalinepentanoic acid | 498 |
| 255 | 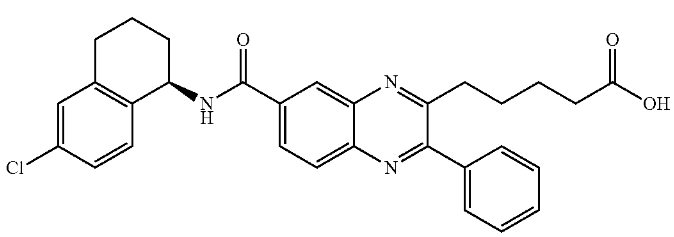 [SMILES: O=C(O)CCCCc1nc2cc(C(=O)N[C@@H]3CCCc4cc(Cl)ccc43)ccc2nc1-c1ccccc1] | 7-[[(6-chloro-1,2,3,4-tetrahydro-1(R)-naphthalenyl)amino)carbonyl]-3-phenyl-2-quinoxalinepentanoic acid | 514 |
| 256 | 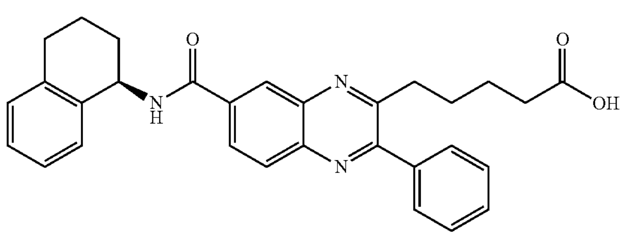 [SMILES: O=C(O)CCCCc1nc2cc(C(=O)N[C@@H]3CCCc4ccccc43)ccc2nc1-c1ccccc1] | (R)-5-(3-phenyl-7-((1,2,3,4-tetrahydronaphthalen-1-yl)carbamoyl)quinoxalin-2-yl)pentanoic acid | 480 |
| 257 | 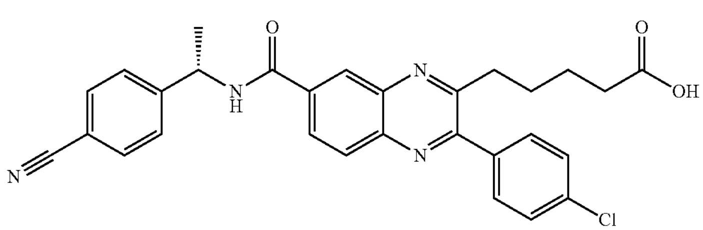 [SMILES: C[C@H](NC(=O)c1ccc2nc(-c3ccc(Cl)cc3)c(CCCCC(=O)O)nc2c1)c1ccc(C#N)cc1] | (S)-5-(3-(4-chlorophenyl)-7-((1-(4-cyanophenyl)ethyl)carbamoyl)quinoxalin-2-pentanoic acid | 513 |

-continued

| No. | Structure | Name | M + H |
|---|---|---|---|
| 258 | 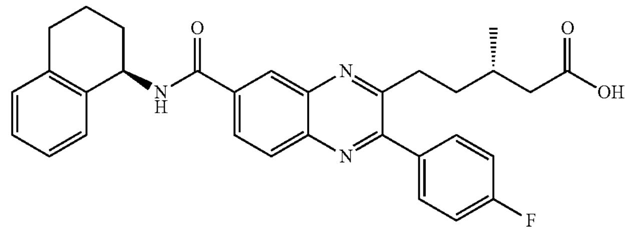 [SMILES: C[C@@H](CCc1nc2cc(C(=O)N[C@@H]3CCCc4ccccc43)ccc2nc1-c1ccc(F)cc1)CC(=O)O] | (S)-5-(3-(4-fluorophenyl)-7-(((R)-1,2,3,4-tetrahydronaphthalen-1-yl)carbamoyl)quinoxalin-2-yl)-3-methylpentanoic acid | 512 |
| 259 | 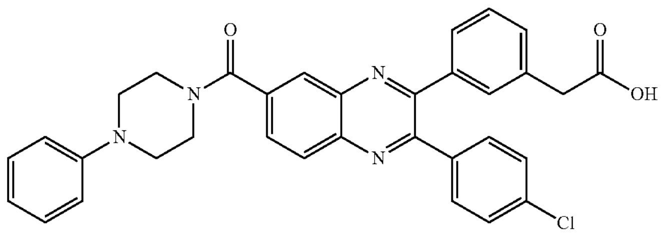 [SMILES: O=C(O)Cc1cccc(-c2nc3cc(C(=O)N4CCN(c5ccccc5)CC4)ccc3nc2-c2ccc(Cl)cc2)c1] | 2-(3-(3-(4-chlorophenyl)-7-(4-phenylpiperazine-1-carbonyl)quinoxalin-2-yl)phenyl)acetic acid | 563 |
| 260 | 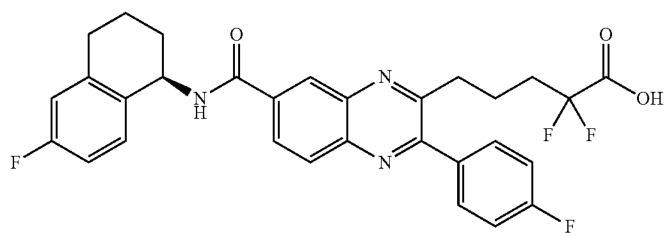 [SMILES: O=C(N[C@@H]1CCCc2cc(F)ccc21)c1ccc2nc(-c3ccc(F)cc3)c(CCCC(F)(F)C(=O)O)nc2c1] | (R)-2,2-difluoro-5-(7-((6-fluoro-1,2,3,4-tetrahydronaphthalen-1-yl)carbamoyl)-3-(4-fluorophenyl)quinoxalin-2-yl)pentanoic acid | 552 |
| 261 | 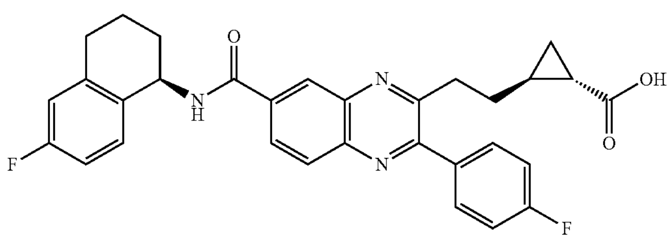 [SMILES: O=C(N[C@@H]1CCCc2cc(F)ccc21)c1ccc2nc(-c3ccc(F)cc3)c(CC[C@H]3C[C@@H]3C(=O)O)nc2c1] | (1S,2S)-2-(2-(7-(((R)-6-fluoro-1,2,3,4-tetrahydronaphthalen-1-yl)carbamoyl)-3-(4-fluorophenyl)quinoxalin-2-yl)ethyl)cyclopropanecarboxylic acid | 528 |
| 262 | 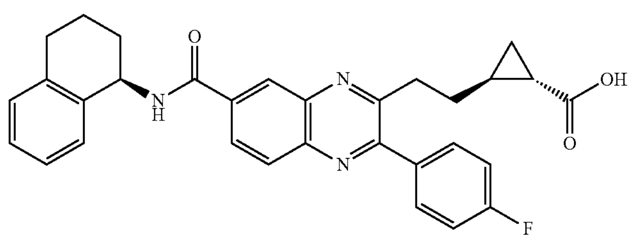 [SMILES: O=C(N[C@@H]1CCCc2ccccc21)c1ccc2nc(-c3ccc(F)cc3)c(CC[C@H]3C[C@@H]3C(=O)O)nc2c1] | (1S,2S)-2-(2-(3-(4-fluorophenyl)-7-(((R)-1,2,3,4-tetrahydronaphthalen-1-yl)carbamoyl)quinoxalin-2-yl)ethyl)cyclopropanecarboxylic acid | 510 |
| 263 | 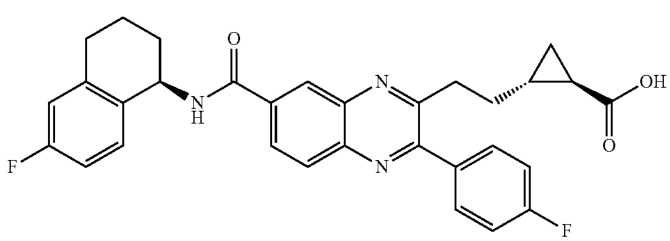 [SMILES: O=C(N[C@@H]1CCCc2cc(F)ccc21)c1ccc2nc(-c3ccc(F)cc3)c(CC[C@@H]3C[C@H]3C(=O)O)nc2c1] | (1R,2R)-2-(2-(7-(((R)-6-fluoro-1,2,3,4-tetrahydronaphthalen-1-yl)carbamoyl)-3-(4-fluorophenyl)quinoxalin-2-yl)ethyl)cyclopropanecarboxylic acid | 528 |

| No. | Structure | Name | M + H |
|---|---|---|---|
| 264 | 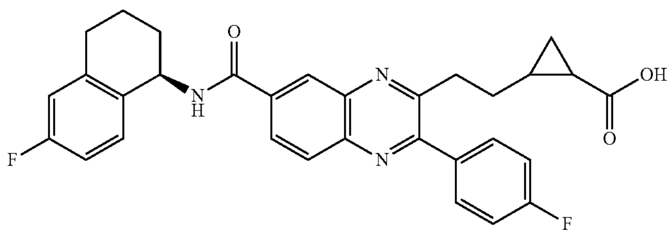 [SMILES: O=C(N[C@@H]1CCCc2cc(F)ccc21)c1ccc2nc(-c3ccc(F)cc3)c(CCC3CC3C(=O)O)nc2c1] | 2-(2-(7-(((R)-6-fluoro-1,2,3,4-tetrahydronaphthalen-1-yl)carbamoyl)-3-(4-fluorophenyl)quinoxalin-2-yl)ethyl)cyclopropanecarboxylic acid | 528 |
| 265 | 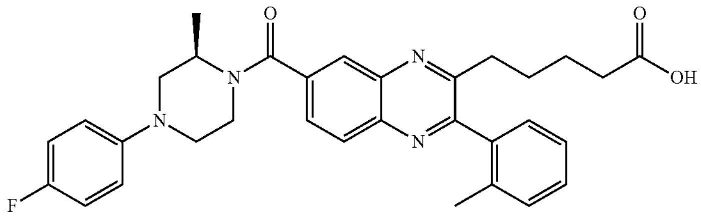 [SMILES: Cc1ccccc1-c1nc2ccc(C(=O)N3CCN(c4ccc(F)cc4)C[C@H]3C)cc2nc1CCCCC(=O)O] | (R)-5-(7-(4-(4-fluorophenyl)-2-methylpiperazine-1-carbonyl)-3-phenylquinoxalin-2-yl)pentanoic acid | 527 |
| 266 | 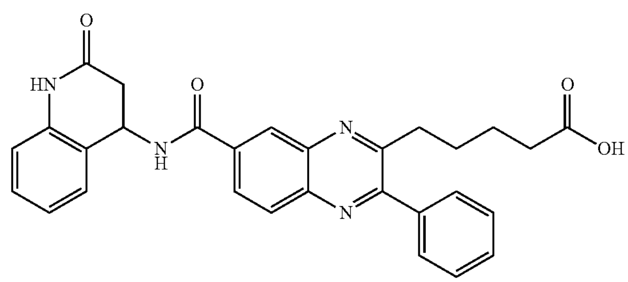 [SMILES: O=C(O)CCCCc1nc2cc(C(=O)NC3CC(=O)Nc4ccccc43)ccc2nc1-c1ccccc1] | 5-(7-((2-oxo-1,2,3,4-tetrahydroquinolin-4-yl)carbamoyl)-3-phenylquinoxalin-2-yl)pentanoic acid | 495 |
| 267 | 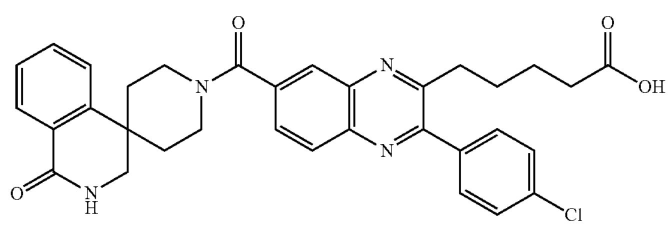 [SMILES: O=C(O)CCCCc1nc2cc(C(=O)N3CCC4(CC3)CNC(=O)c3ccccc34)ccc2nc1-c1ccc(Cl)cc1] | 5-(3-(4-chlorophenyl)-7-(1-oxo-2,3-dihydro-1H-spiro[isoquinoline-4,4'-piperidin]-1'-ylcarbonyl)quinoxalin-2-yl)pentanoic acid | 583.3 |
| 268 | 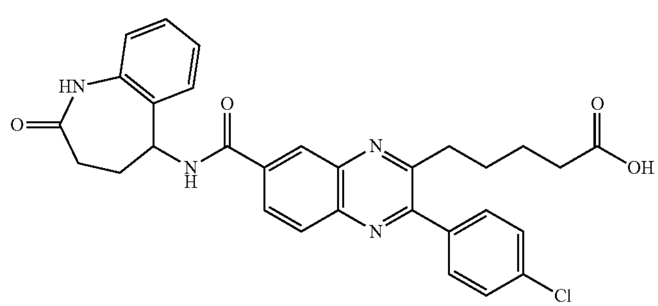 [SMILES: O=C(O)CCCCc1nc2cc(C(=O)NC3CCC(=O)Nc4ccccc43)ccc2nc1-c1ccc(Cl)cc1] | 5-(3-(4-chlorophenyl)-7-((2-oxo-2,3,4,5-tetrahydro-1H-benzo[b]azepin-5-yl)carbamoyl)quinoxalin-2-yl)pentanoic acid | 543.3 |
| 269 | 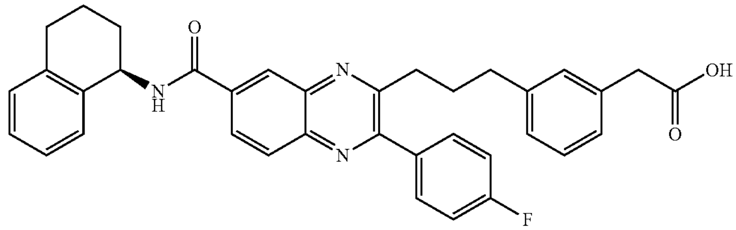 [SMILES: O=C(O)Cc1cccc(CCCc2nc3cc(C(=O)N[C@@H]4CCCc5ccccc54)ccc3nc2-c2ccc(F)cc2)c1] | (R)-2-(3-(3-(3-(4-fluorophenyl)-7-((1,2,3,4-tetrahydronaphthalen-1-yl)carbamoyl)quinoxalin-2-yl)propyl)phenyl)acetic acid | 574.4 |

| No. | Name | M + H |
|---|---|---|
| 270 | (S)-2-(3-(3-(3-(4-fluorophenyl)-7-((1,2,3,4-tetrahydronaphthalen-1-yl)carbamoyl)quinoxalin-2-yl)propyl)phenyl)acetic acid | 574.4 |
| 271 | (R)-2-(3-(3-(3-(4-fluorophenyl)-7-((1-(4-fluorophenyl)ethyl)carbamoyl)quinoxalin-2-yl)propyl)phenyeacetic acid | 566.3 |
| 272 | 2-(3-(3-(3-(4-fluorophenyl)-7-(4-phenylpiperazine-1-carbonyl)quinoxalin-2-yl)propyl)phenyl)acetic acid | 589.4 |
| 273 | 2-(3-(3-(3-(4-fluorophenyl)-7-(3-(3-fluorophenyl)azetidine-1-carbonyl)quinoxalin-2-yl)propyl)phenyl)acetic acid | 578.4 |
| 274 | (S)-2-(3-(3-(3-(4-fluorophenyl)-7-(3-phenylpyrrolidine-1-carbonyl)quinoxalin-2-yl)propyl)phenyl)acetic acid | 574.4 |
| 275 | 2-(3-(3-(7-((4-fluorobenzyl)(methyl)carbamoyl)-3-(4-fluorophenyl)quinoxalin-2-yl)propyl)phenyl)acetic acid | 566.4 |

-continued

| No. | Structure | Name | M + H |
|---|---|---|---|
| 276 | 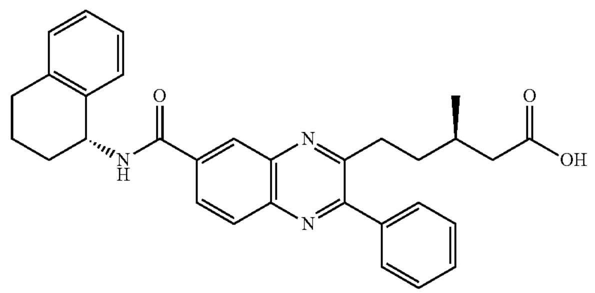 [SMILES: C[C@H](CCc1nc2cc(C(=O)N[C@@H]3CCCc4ccccc43)ccc2nc1-c1ccccc1)CC(=O)O] | (R)-3-methyl-5-(3-phenyl-7-(((R)-1,2,3,4-tetrahydronaphthalen-1-yl)carbamoyl)quinoxalin-2-yl)pentanoic acid | 494.4 |
| 277 | 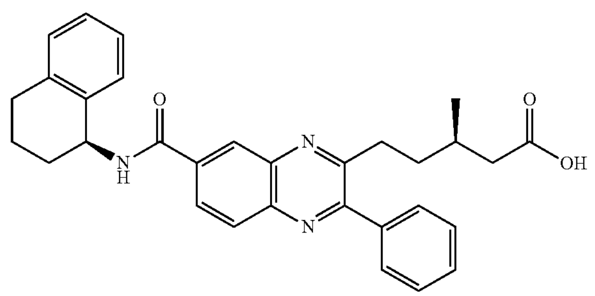 [SMILES: C[C@H](CCc1nc2cc(C(=O)N[C@H]3CCCc4ccccc43)ccc2nc1-c1ccccc1)CC(=O)O] | (R)-3-methyl-5-(3-phenyl-7-(((S)-1,2,3,4-tetrahydronaphthalen-1-yl)carbamoyl)quinoxalin-2-yl)pentanoic acid | 494.4 |
| 278 | 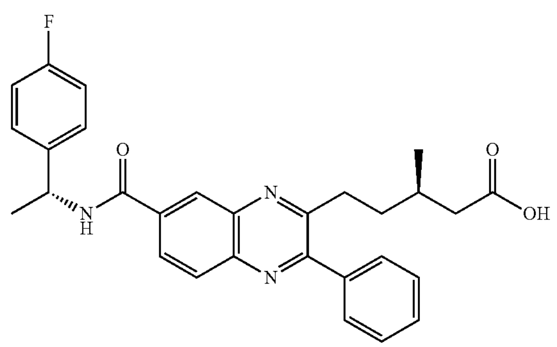 [SMILES: C[C@H](CCc1nc2cc(C(=O)N[C@H](C)c3ccc(F)cc3)ccc2nc1-c1ccccc1)CC(=O)O] | (R)-5-(7-(((R)-1-(4-fluorophenyl)ethyl)carbamoyl)-3-phenylquinoxalin-2-yl)-3-methylpentanoic acid | 486.4 |
| 279 | 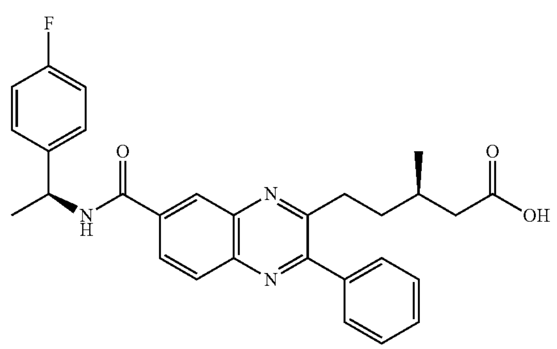 [SMILES: C[C@H](CCc1nc2cc(C(=O)N[C@@H](C)c3ccc(F)cc3)ccc2nc1-c1ccccc1)CC(=O)O] | (R)-5-(7-(((S)-1-(4-fluorophenyl)ethyl)carbamoyl)-3-phenylquinoxalin-2-yl)-3-methylpentanoic acid | 486.4 |
| 280 | 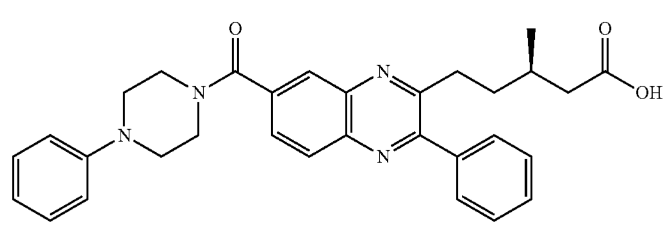 [SMILES: C[C@H](CCc1nc2cc(C(=O)N3CCN(c4ccccc4)CC3)ccc2nc1-c1ccccc1)CC(=O)O] | (R)-3-methyl-5-(3-phenyl-7-(4-phenylpiperazine-1-carbonyl)quinoxalin-2-yl)pentanoic acid | 509.4 |

-continued

| No. | Structure | Name | M + H |
|---|---|---|---|
| 281 | 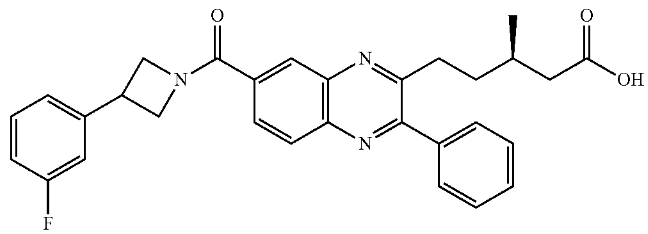 [SMILES: C[C@H](CCc1nc2cc(C(=O)N3CC(c4cccc(F)c4)C3)ccc2nc1-c1ccccc1)CC(=O)O] | (R)-5-(7-(3-(3-fluorophenyl)azetidine-1-carbonyl)-3-phenylquinoxalin-2-yl)-3-methylpentanoic acid | 498.4 |
| 282 | 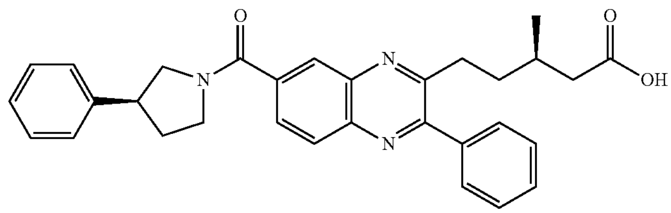 [SMILES: C[C@H](CCc1nc2cc(C(=O)N3CC[C@@H](c4ccccc4)C3)ccc2nc1-c1ccccc1)CC(=O)O] | (R)-3-methyl-5-(3-phenyl-7-((S)-3-phenylpyrrolidine-1-carbonyl)quinoxalin-2-yl)pentannic acid | 494.4 |
| 283 | 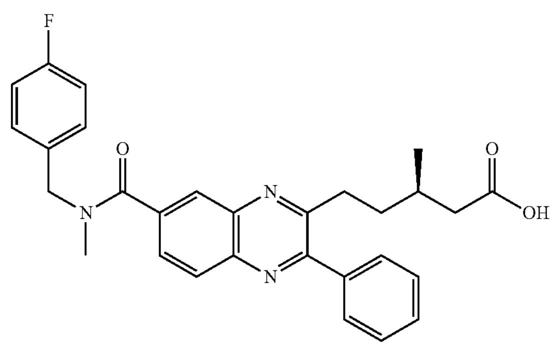 [SMILES: C[C@H](CCc1nc2cc(C(=O)N(C)Cc3ccc(F)cc3)ccc2nc1-c1ccccc1)CC(=O)O] | (R)-5-(7-((4-fluorobenzyl)(methyl)carbamoyl)-3-phenylquinoxalin-2-yl)-3-methylpentanoic acid | 486.4 |
| 284 | 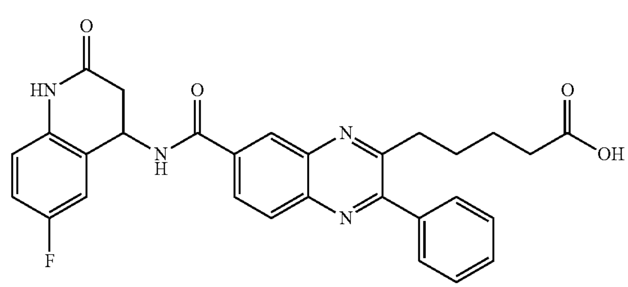 [SMILES: O=C(O)CCCCc1nc2cc(C(=O)NC3CC(=O)Nc4ccc(F)cc43)ccc2nc1-c1ccccc1] | 5-(7-((6-fluoro-2-oxo-1,2,3,4-tetrahydroquinolin-4-yl)carbamoyl)-3-phenylquinoxalin-2-yl)pentanoic acid | 513 |
| 285 | 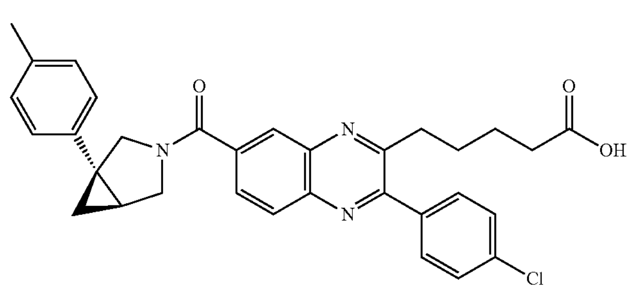 [SMILES: Cc1ccc([C@@]23C[C@@H]2CN(C(=O)c2ccc4nc(-c5ccc(Cl)cc5)c(CCCCC(=O)O)nc4c2)C3)cc1] | 5-(3-(4-chlorophenyl)-7-((1R,5S)-1-(p-tolyl)-3-azabicyclo[3.1.0]hexane-3-carbonyl)quinoxalin-2-yl)pentanoic acid | 540.4 |

-continued

| No. | Structure | Name | M + H |
|---|---|---|---|
| 286 | 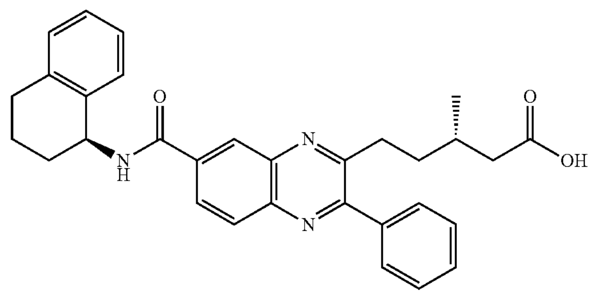 [SMILES: C[C@@H](CCc1nc2cc(C(=O)N[C@H]3CCCc4ccccc43)ccc2nc1-c1ccccc1)CC(=O)O] | (S)-3-methyl-5-(3-phenyl-7-(((S)-1,2,3,4-tetrahydronaphthalen-1-yl)carbamoyl)quinoxalin-2-yl)pentanoic acid | 494.4 |
| 287 | 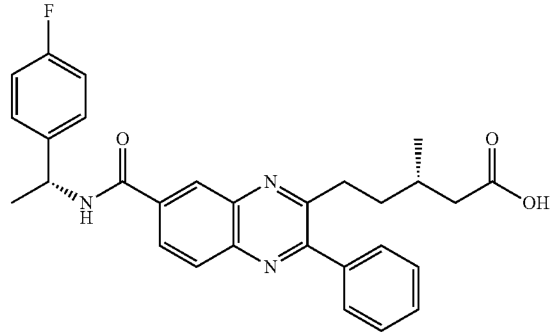 [SMILES: C[C@@H](CCc1nc2cc(C(=O)N[C@H](C)c3ccc(F)cc3)ccc2nc1-c1ccccc1)CC(=O)O] | (S)-5-(7-(((R)-1-(4-fluorophenyl)ethyl)carbamoyl)-3-phenylquinoxalin-2-yl)-3-methylpentanoic acid | 486.3 |
| 288 | 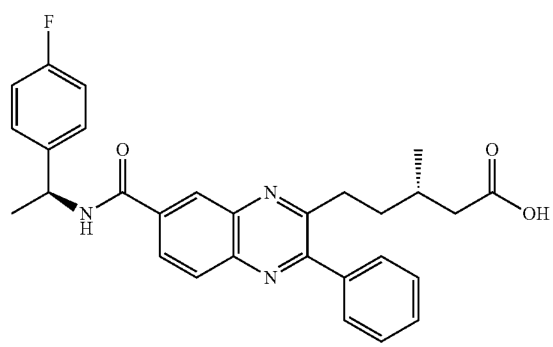 [SMILES: C[C@@H](CCc1nc2cc(C(=O)N[C@@H](C)c3ccc(F)cc3)ccc2nc1-c1ccccc1)CC(=O)O] | (S)-5-(7-(((S)-1-(4-fluorophenyl)ethyl)carbamoyl)-3-3-phenylquinoxalin-2-yl)-3-methylpentanoic acid | 486.3 |
| 289 | 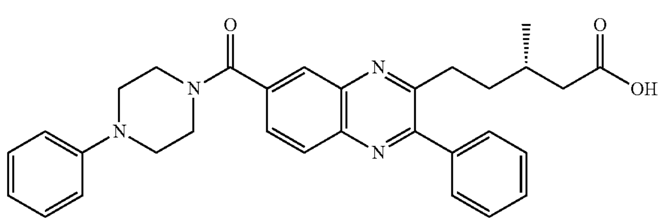 [SMILES: C[C@@H](CCc1nc2cc(C(=O)N3CCN(c4ccccc4)CC3)ccc2nc1-c1ccccc1)CC(=O)O] | (S)-3-methyl-5-(3-phenyl-7-(4-phenylpiperazine-1-carbonyl)quinoxalin-2-yl)pentanoic acid | 509.4 |
| 290 | 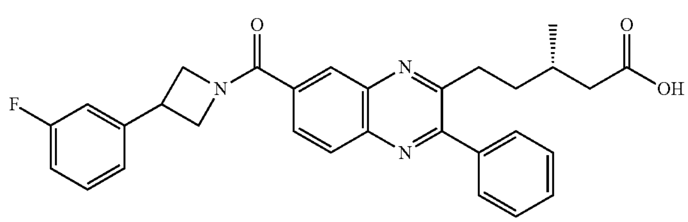 [SMILES: C[C@@H](CCc1nc2cc(C(=O)N3CC(c4cccc(F)c4)C3)ccc2nc1-c1ccccc1)CC(=O)O] | (S)-5-(7-(3-(3-fluorophenyl)azetidine-1-carbonyl)-3-phenylquinoxalin-2-yl)-3-methylpentanoic acid | 498.4 |

-continued

| No. | Structure | Name | M + H |
|---|---|---|---|
| 291 | 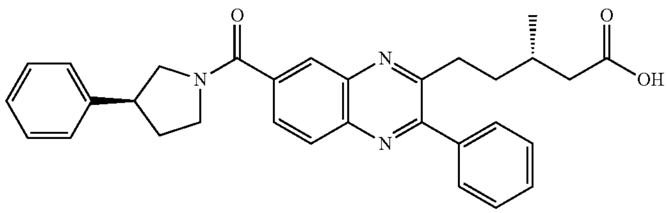 [SMILES: C[C@@H](CCc1nc2cc(C(=O)N3CC[C@@H](c4ccccc4)C3)ccc2nc1-c1ccccc1)CC(=O)O] | (S)-3-methyl-5-(3-phenyl-7-((S)-3-phenylpyrrolidine-1-carbonyl)quinoxalin-2-yl)pentanoic acid | 494.4 |
| 292 | 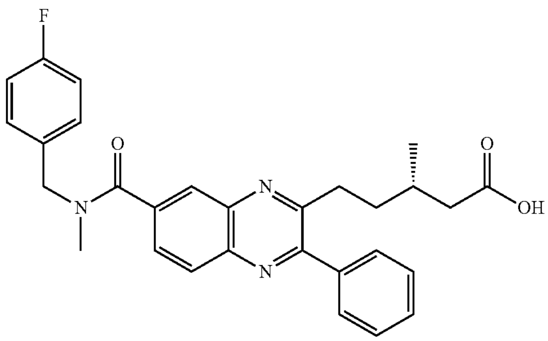 [SMILES: C[C@@H](CCc1nc2cc(C(=O)N(C)Cc3ccc(F)cc3)ccc2nc1-c1ccccc1)CC(=O)O] | (S)-5-(7-((4-fluorobenzyl(methyl)carbamoyl)-3-phenylquinoxalin-2-yl)-3-methylpentanoic acid | 486.3 |
| 293 | 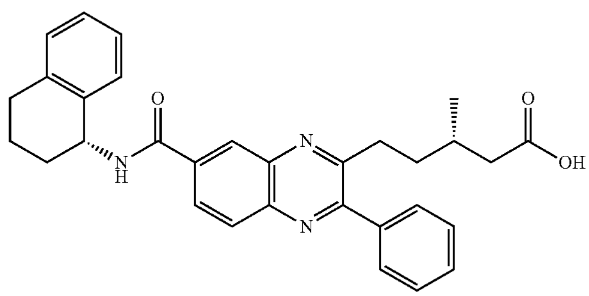 [SMILES: C[C@@H](CCc1nc2cc(C(=O)N[C@@H]3CCCc4ccccc43)ccc2nc1-c1ccccc1)CC(=O)O] | (S)-3-methyl-S-(3-phenyl-7-(((R)-1,2,3,4-tetrahydronaphthalen-1-yl)carbamoyl)quinoxalin-2-yl)pentanoic acid | 494.4 |
| 294 | 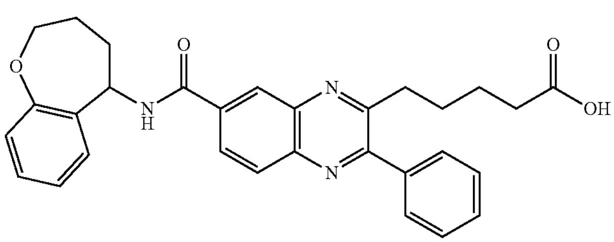 [SMILES: O=C(O)CCCCc1nc2cc(C(=O)NC3CCCOc4ccccc43)ccc2nc1-c1ccccc1] | 5-(3-phenyl-7-((2,3,4,5-tetrahydrobenzo[b]oxepin-5-yl)carbamoyl)quinoxalin-2-yl)pentanoic acid | 496.4 |
| 295 | 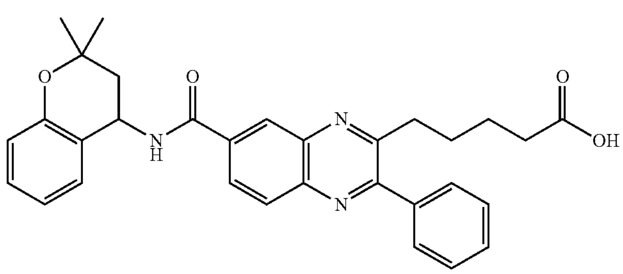 [SMILES: CC1(C)CC(NC(=O)c2ccc3nc(-c4ccccc4)c(CCCCC(=O)O)nc3c2)c2ccccc2O1] | 5-(7((2,2-dimethylchroman-4-yl)carbamoyl)-3-phenylquinoxalin-2-yl)pentanoic acid | 510.4 |

| No. | Structure | Name | M + H |
|---|---|---|---|
| 296 | 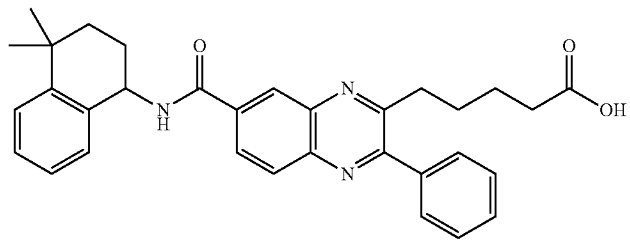 [SMILES: CC1(C)CCC(NC(=O)c2ccc3nc(-c4ccccc4)c(CCCCC(=O)O)nc3c2)c2ccccc21] | 5-(7-((4,4-dimethyl-1,2,3,4-tetrahydronaphthalen-1-yl)carbamoyl)-3-phenylquinoxalin-2-yl)pentanoic acid | 508.4 |
| 297 | 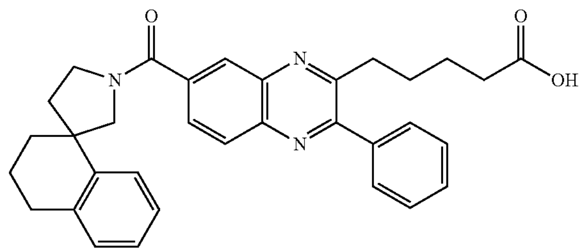 [SMILES: O=C(O)CCCCc1nc2cc(C(=O)N3CCC4(CCCc5ccccc54)C3)ccc2nc1-c1ccccc1] | 5-(7-(3,4-dihydro-2H-spiro[naphthalene-1,3'-pyrrolidin]-1'-ylcarbonyl)-3-phenylquinoxalin-2-yl)pentanoic acid | 520.4 |
| 298 | 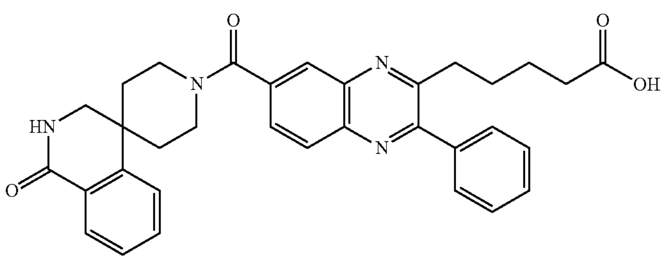 [SMILES: O=C(O)CCCCc1nc2cc(C(=O)N3CCC4(CC3)CNC(=O)c3ccccc34)ccc2nc1-c1ccccc1] | 5-(7-(i-oxo-2,3-dihydro-1H-spiro[isoquinoline-4,4'-piperidin]-1'-ylcarbonyl)-3-phenylquinoxalin-2-yl)pentanoic acid | 549.4 |
| 299 | 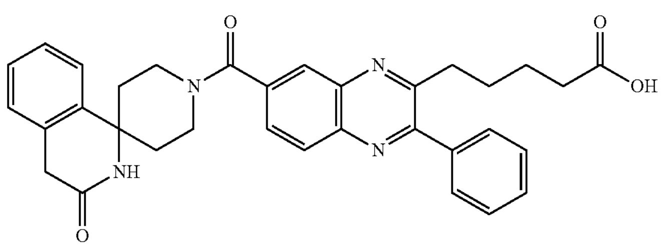 [SMILES: O=C(O)CCCCc1nc2cc(C(=O)N3CCC4(CC3)NC(=O)Cc3ccccc34)ccc2nc1-c1ccccc1] | 5-(7-(3-oxo-3,4-dihydro-2H-spiro[isoquinoline-1,4'-piperidin]-1'-ylcarbonyl)-3-phenylquinoxalin-2-yl)pentanoic acid | 549.4 |
| 300 | 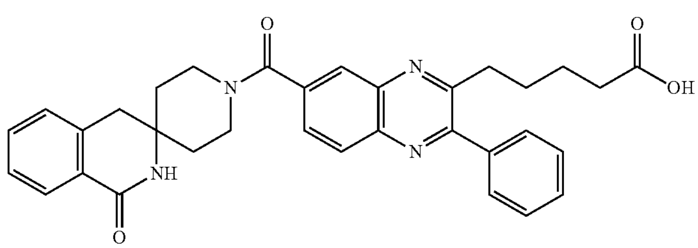 [SMILES: O=C(O)CCCCc1nc2cc(C(=O)N3CCC4(CC3)Cc3ccccc3C(=O)N4)ccc2nc1-c1ccccc1] | 5-(7-(1-oxo-2,4-dihydro-1H-spiro[isoquinoline-3,4'-piperidin]-1'-ylcarbonyl)-3-phenylquinoxalin-2-yl)pentanoic acid | 549.4 |
| 301 | 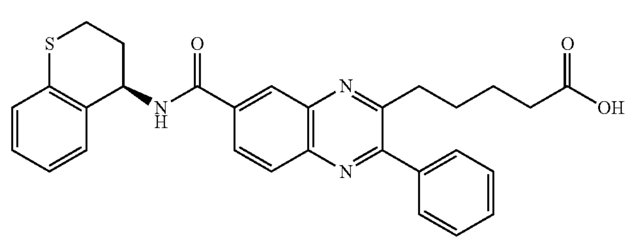 [SMILES: O=C(O)CCCCc1nc2cc(C(=O)N[C@@H]3CCSc4ccccc43)ccc2nc1-c1ccccc1] | (R)-5-(3-phenyl-7-(thiochroman-4-ylcarbamoyl)quinoxalin-2-yl)pentanoic acid | 498.3 |

-continued

| No. | Structure | Name | M + H |
|---|---|---|---|
| 302 | 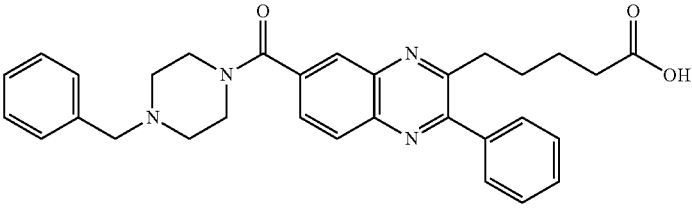 [SMILES: O=C(O)CCCCc1nc2cc(C(=O)N3CCN(Cc4ccccc4)CC3)ccc2nc1-c1ccccc1] | 5-(7-(4-benzylpiperazine-1-carbonyl)-3-phenylquinoxalin-2-yl)pentanoic acid | 509.4 |
| 303 | 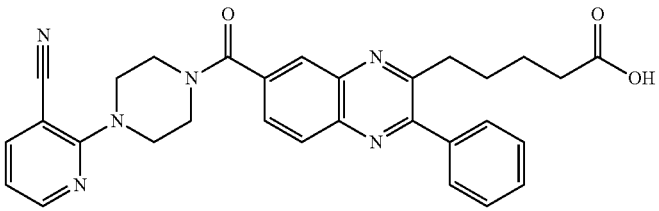 [SMILES: N#Cc1cccnc1N1CCN(C(=O)c2ccc3nc(-c4ccccc4)c(CCCCC(=O)O)nc3c2)CC1] | 5-(7-(4-(3-cyanopyridin-2-yl)piperazine-1-carbonyl)-3-phenylquinoxalin-2-yl)pentanoic acid | 521.4 |
| 304 | 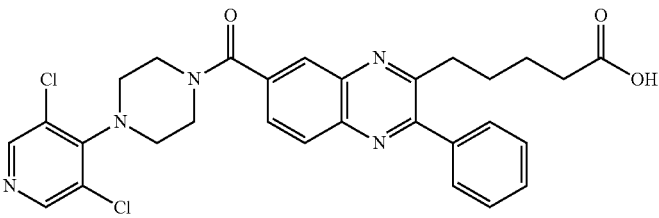 [SMILES: O=C(O)CCCCc1nc2cc(C(=O)N3CCN(c4c(Cl)cncc4Cl)CC3)ccc2nc1-c1ccccc1] | 5-(7-(4-(3,5-dichloropyridin-4-yl)piperazine-1-carbonyl)-3-phenylquinoxalin-2-yl)pentanoic acid | 564.3 |
| 305 | 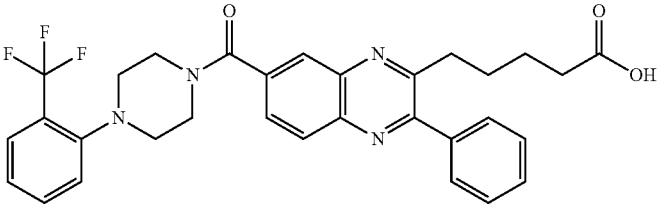 [SMILES: O=C(O)CCCCc1nc2cc(C(=O)N3CCN(c4ccccc4C(F)(F)F)CC3)ccc2nc1-c1ccccc1] | 5-(3-phenyl-7-(4-(2-(trifluoromethyl)phenyl)piperazine-1-carbonyl)quinoxalin-2-yl)pentanoic acid | 563.3 |
| 306 | 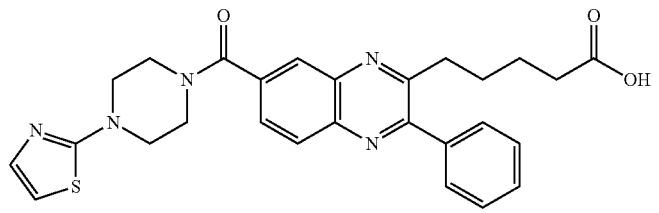 [SMILES: O=C(O)CCCCc1nc2cc(C(=O)N3CCN(c4nccs4)CC3)ccc2nc1-c1ccccc1] | 5-(3-phenyl-7-(4-(thiazol-2-yl)piperazine-1-carbonyl)quinoxalin-2-yl)pentanoic acid | 502.3 |
| 307 | 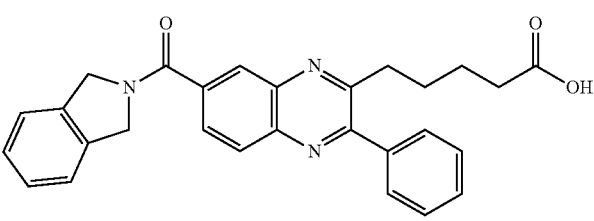 [SMILES: O=C(O)CCCCc1nc2cc(C(=O)N3Cc4ccccc4C3)ccc2nc1-c1ccccc1] | 5-(7-(isoindoline-2-carbonyl)-3-phenylquinoxalin-2-yl)pentanoic acid | 452.3 |
| 308 | 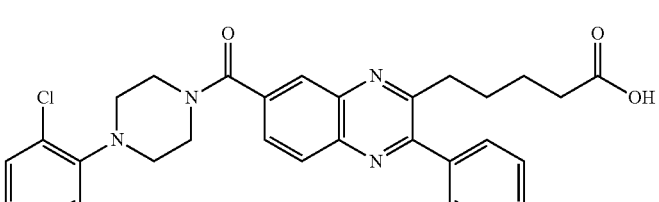 | 5-(7-(4-(2-chlorophenyl)piperazine-1-carbonyl)-3-phenylquinoxalin-2-yl)pentanoic acid | 529.3 |

| No. | Structure | Name | M + H |
|---|---|---|---|
| 309 | 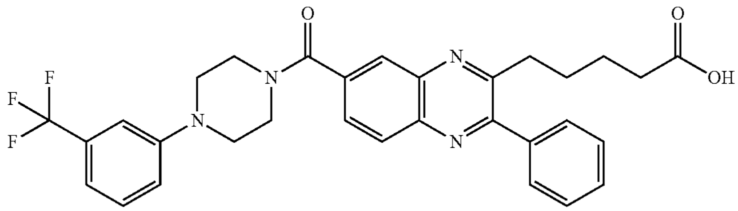 [SMILES: O=C(O)CCCCc1nc2cc(C(=O)N3CCN(c4cccc(C(F)(F)F)c4)CC3)ccc2nc1-c1ccccc1] | 5-(3-phenyl-7-(4-(3-(trifluoromethyl)phenyl)piperazine-1-carbonyl)quinoxalin-2-yl)pentanoic acid | 563.4 |
| 310 | 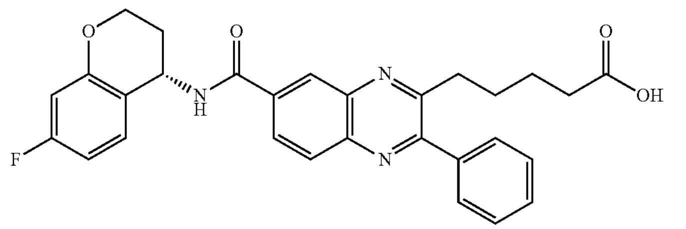 [SMILES: O=C(O)CCCCc1nc2cc(C(=O)N[C@H]3CCOc4cc(F)ccc43)ccc2nc1-c1ccccc1] | (S)-5-(7((7-fluorochroman-4-yl)carbamoyl)-3-phenylquinoxalin-2-yl)pentanoic acid | 500.3 |
| 311 | 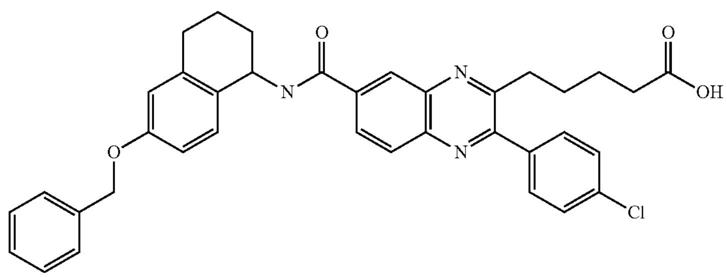 [SMILES: O=C(O)CCCCc1nc2cc(C(=O)NC3CCCc4cc(OCc5ccccc5)ccc43)ccc2nc1-c1ccc(Cl)cc1] | 5-(7-((6-(benzyloxy)-1,2,3,4-tetrahydronaphthalen-1-yl)carbamoyl)-3-(4-chlorophenyl)quinoxalin-2-yl)pentanoic acid | 620.6 |
| 312 | 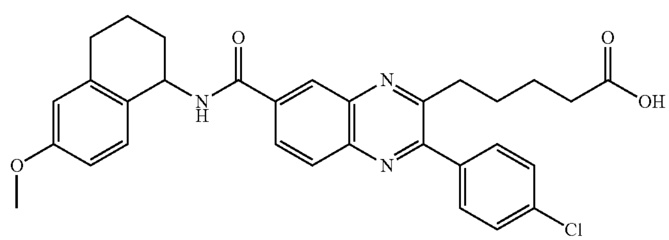 [SMILES: COc1ccc2c(c1)CCCC2NC(=O)c1ccc2nc(-c3ccc(Cl)cc3)c(CCCCC(=O)O)nc2c1] | 5-(3-(4-chlorophenyl)-7-((6-methoxy-1,2,3,4-tetrahydronaphthalen-1-yl)carbamoyl)quinoxalin-2-yl)pentanoic acid | 544.5 |
| 313 | 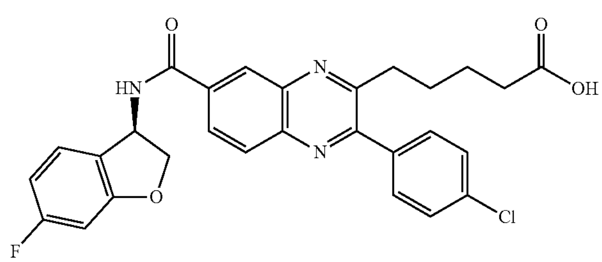 [SMILES: O=C(O)CCCCc1nc2cc(C(=O)N[C@H]3COc4cc(F)ccc43)ccc2nc1-c1ccc(Cl)cc1] | (R)-5-(3-(4-chlorophenyl)-7-((6-fluoro-2,3-dihydrobenzofuran-3-yl)carbamoyl)quinoxalin-2-yl)pentanoic acid | 520.4 |
| 314 | 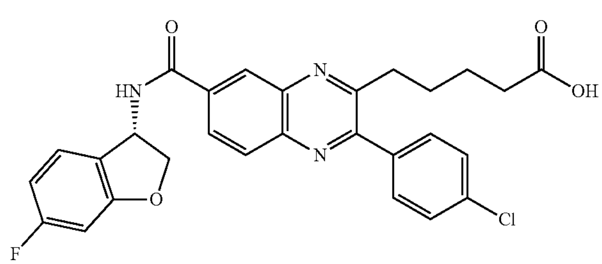 [SMILES: O=C(O)CCCCc1nc2cc(C(=O)N[C@@H]3COc4cc(F)ccc43)ccc2nc1-c1ccc(Cl)cc1] | (S)-5-(3-(4-chlorophenyl)-7-((6-fluoro-2,3-dihydrobenzofuran-3-yl)carbamoyl)quinoxalin-2-yl)pentanoic acid | 520.4 |

-continued

| No. | Structure | Name | M + H |
|---|---|---|---|
| 315 | 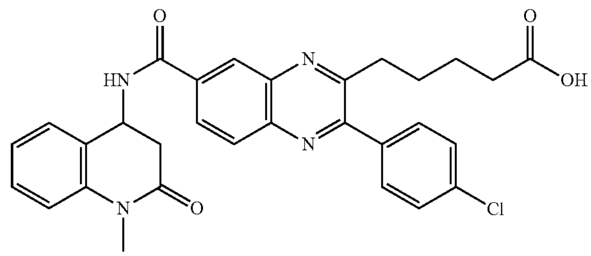 [SMILES: CN1C(=O)CC(NC(=O)c2ccc3nc(-c4ccc(Cl)cc4)c(CCCCC(=O)O)nc3c2)c2ccccc21] | 5-(3-(4-chlorophenyl)-7-((1-methyl-2-oxo-1,2,3,4-tetrahydroquinolin-4-yl)carbamoyl)quinoxalin-2-yl)pentanoic acid | 543.3 |
| 316 | 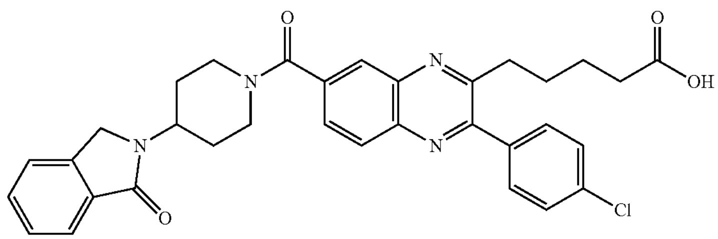 [SMILES: O=C(O)CCCCc1nc2cc(C(=O)N3CCC(N4Cc5ccccc5C4=O)CC3)ccc2nc1-c1ccc(Cl)cc1] | 5-(3-(4-chlorophenyl)-7-(4-(1-oxoisoindolin-2-yl)piperidine-1-carbonyl)quinoxalin-2-yl)pentanoic acid | 583.5 |
| 317 | 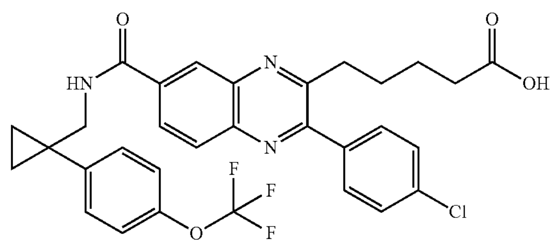 [SMILES: O=C(O)CCCCc1nc2cc(C(=O)NCC3(c4ccc(OC(F)(F)F)cc4)CC3)ccc2nc1-c1ccc(Cl)cc1] | 5-(3-(4-chlorophenyl)-7-(((1-(4-(trifluoromethoxy)phenyl)cyclopropyl)methyl)carbamoyl)quinoxalin-2-yl)pentanoic acid | 598.5 |
| 318 | 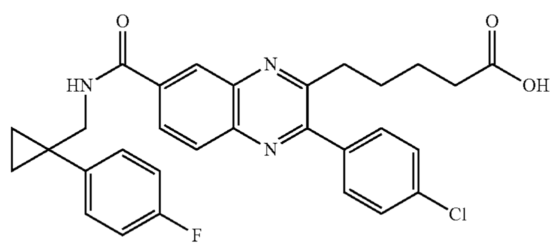 [SMILES: O=C(O)CCCCc1nc2cc(C(=O)NCC3(c4ccc(F)cc4)CC3)ccc2nc1-c1ccc(Cl)cc1] | 5-(3-(4-chlorophenyl)-7-(((1-(4-fluorophenyl)cyclopropyl)methyl)carbamoyl)quinoxalin-2-yl)pentanoic acid | 532.5 |
| 319 | 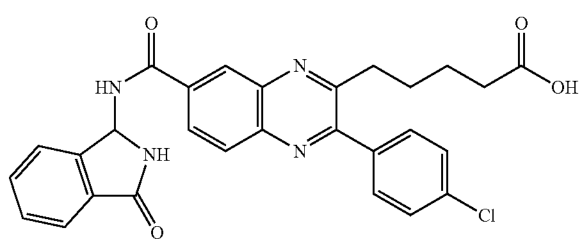 [SMILES: O=C(O)CCCCc1nc2cc(C(=O)NC3NC(=O)c4ccccc43)ccc2nc1-c1ccc(Cl)cc1] | 5-(3-(4-chlorophenyl)-7-((3-oxoisoindolin-1-yl)carbamoyl)quinoxalin-2-yl)pentanoic acid | 515.4 |
| 320 | 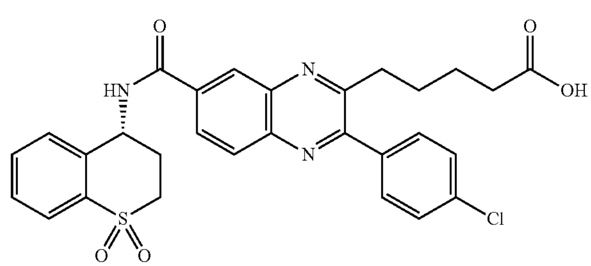 [SMILES: O=C(O)CCCCc1nc2cc(C(=O)N[C@@H]3CCS(=O)(=O)c4ccccc43)ccc2nc1-c1ccc(Cl)cc1] | (R)-5-(3-(4-chlorophenyl)-7-((1,1-dioxidothiochroman-4-yl)carbamoyl)quinoxalin-2-yl)pentanoic acid | 564.4 |

-continued

| No. | Structure | Name | M + H |
|---|---|---|---|
| 321 | 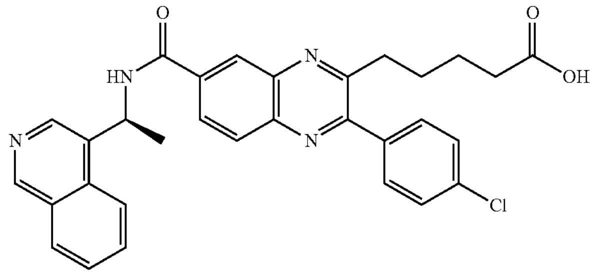 [SMILES: C[C@H](NC(=O)c1ccc2nc(-c3ccc(Cl)cc3)c(CCCCC(=O)O)nc2c1)c1cncc2ccccc12] | (S)-5-(3-(4-chlorophenyl)-7-((1-(isoquinolin-4-yl)ethyl)carbamoyl)quinoxalin-2-yl)pentanoic acid | 539.5 |
| 322 | 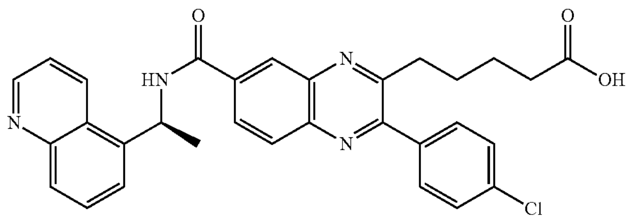 [SMILES: C[C@H](NC(=O)c1ccc2nc(-c3ccc(Cl)cc3)c(CCCCC(=O)O)nc2c1)c1cccc2ncccc12] | (S)-5-(3-(4-chlorophenyl)-7-((1-(quinolin-5-yl)ethyl)carbamoyl)quinoxalin-2-yl)pentanoic acid | 539.5 |
| 323 | 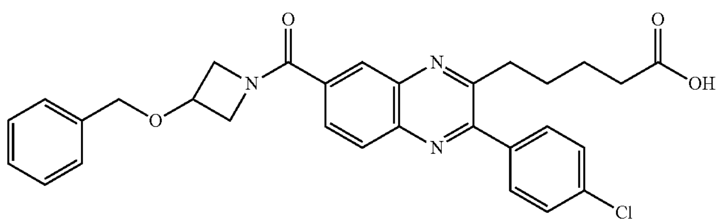 [SMILES: O=C(O)CCCCc1nc2cc(C(=O)N3CC(OCc4ccccc4)C3)ccc2nc1-c1ccc(Cl)cc1] | 5-(7-(3-(benzyloxy)azetidine-1-carbonyl)-3-(4-chlorophenyl)quinoxalin-2-yl)pentanoic acid | 530.5 |
| 324 | 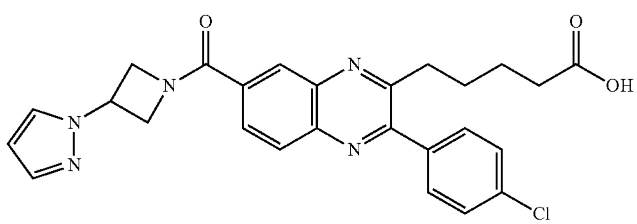 [SMILES: O=C(O)CCCCc1nc2cc(C(=O)N3CC(n4cccn4)C3)ccc2nc1-c1ccc(Cl)cc1] | 5-(7-(3-(1H-pyrazol-1-yl)azetidine-1-carbonyl)-3-(4-chlorophenyl)quinoxalin-2-yl)pentanoic acid | 490.4 |
| 325 | 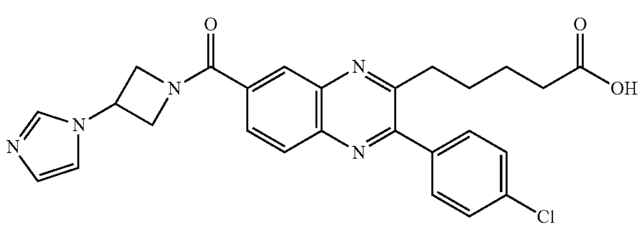 [SMILES: O=C(O)CCCCc1nc2cc(C(=O)N3CC(n4ccnc4)C3)ccc2nc1-c1ccc(Cl)cc1] | 5-(7-(3-(1H-imidazol-1-yl)azetidine-1-carbonyl)-3-(4-chlorophenyl)quinoxalin-2-yl)pentanoic acid | 490.4 |
| 326 | 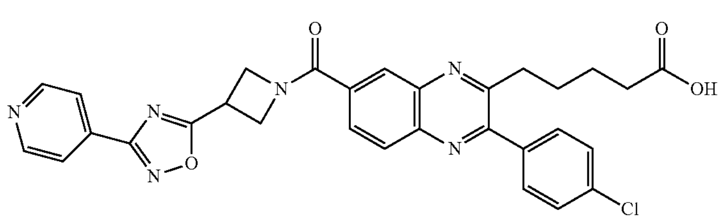 [SMILES: O=C(O)CCCCc1nc2cc(C(=O)N3CC(c4nc(-c5ccncc5)no4)C3)ccc2nc1-c1ccc(Cl)cc1] | 5-(3-(4-chlorophenyl)-7-(3-(3-(pyridin-4-yl)-1,2,4-oxadiazol-5-yl)azetidine-1-carbonyl)quinoxalin-2-yl)pentanoic acid | 569.5 |

-continued

| No. | Structure | Name | M + H |
|---|---|---|---|
| 327 | 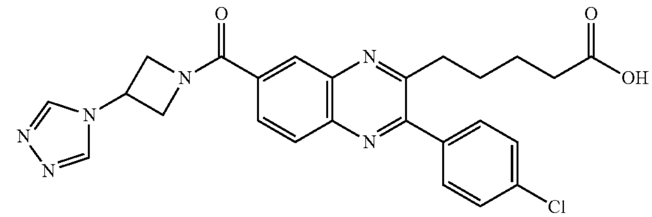 [SMILES: O=C(O)CCCCc1nc2cc(C(=O)N3CC(n4cnnc4)C3)ccc2nc1-c1ccc(Cl)cc1] | 5-(7-(3-(4H-1,2,4-triazol-4-yl)azetidine-1-carbonyl)-3-(4-chlorophenyl)quinoxalin-2-yl)pentanoic acid | 491.4 |
| 328 | 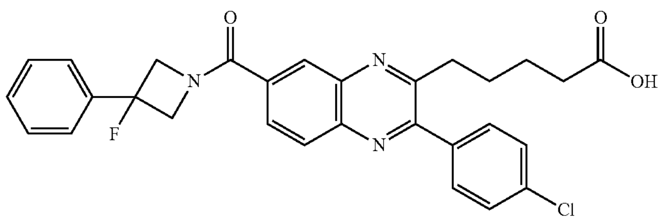 [SMILES: O=C(O)CCCCc1nc2cc(C(=O)N3CC(F)(c4ccccc4)C3)ccc2nc1-c1ccc(Cl)cc1] | 5-(3-(4-chlorophenyl)-7-(3-fluoro-3-phenylazetidine-1-carbonyl)quinoxalin-2-yl)pentanoic acid | 518.4 |
| 329 | 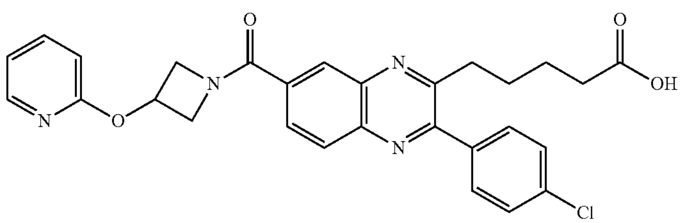 [SMILES: O=C(O)CCCCc1nc2cc(C(=O)N3CC(Oc4ccccn4)C3)ccc2nc1-c1ccc(Cl)cc1] | 5-(3-(4-chlorophenyl)-7-(3-(pyridin-2-yloxy)azetidine-1-carbonyl)quinoxalin-2-yl)pentanoic acid | 517.5 |
| 330 | 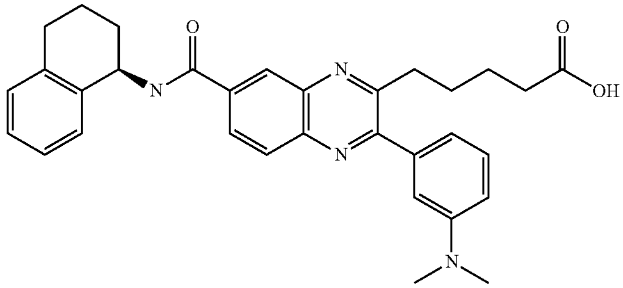 [SMILES: CN(C)c1cccc(-c2nc3ccc(C(=O)N[C@@H]4CCCc5ccccc54)cc3nc2CCCCC(=O)O)c1] | (R)-5-(3-(3-(dimethylamino)phenyl)-7-((1,2,3,4-tetrahydronaphthalen-1-yl)carbamoyl)quinoxalin-2-yl)pentanoic acid | 523.4 |
| 331 | 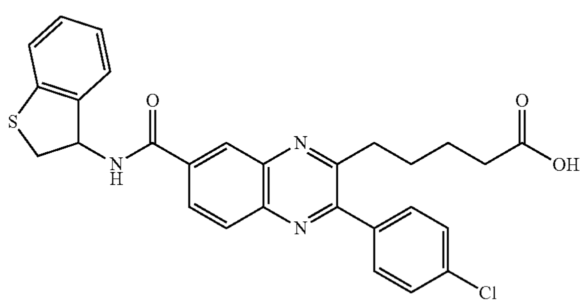 [SMILES: O=C(O)CCCCc1nc2cc(C(=O)NC3CSc4ccccc43)ccc2nc1-c1ccc(Cl)cc1] | 5-(3-(4-chlorophenyl)-7-((2,3-dihydrobenzo[b]thiophen-3-yl)carbamoyl)quinoxalin-2-yl)pentanoic acid | 518.2 |
| 332 | 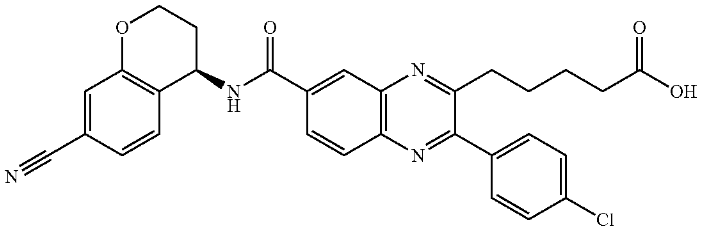 [SMILES: N#Cc1ccc2c(c1)OCC[C@H]2NC(=O)c1ccc2nc(-c3ccc(Cl)cc3)c(CCCCC(=O)O)nc2c1] | (R)-5-(3-(4-chlorophenyl)-7-((7-cyanochroman-4-yl)carbamoyl)quinoxalin-2-yl)pentanoic acid | 541.2 |

-continued

| No. | Structure | Name | M + H |
|---|---|---|---|
| 333 | 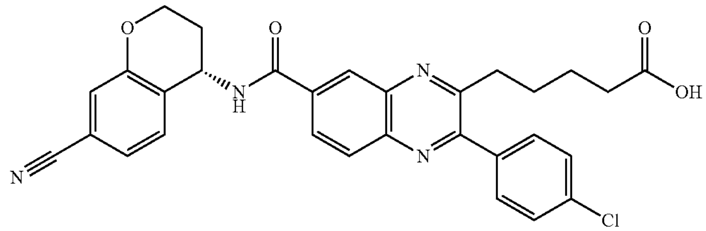 [SMILES: N#Cc1ccc2c(c1)OCC[C@@H]2NC(=O)c1ccc2nc(-c3ccc(Cl)cc3)c(CCCCC(=O)O)nc2c1] | (S)-5-(3-(4-chlorophenyl)-7-((7-cyanochroman-4-yl)carbamoyl)quinoxalin-2-yl)pentanoic acid. | 541.2 |
| 334 | 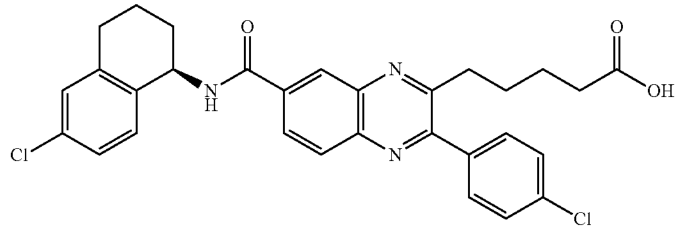 [SMILES: O=C(O)CCCCc1nc2cc(C(=O)N[C@@H]3CCCc4cc(Cl)ccc43)ccc2nc1-c1ccc(Cl)cc1] | (R)-5-(7-((7-chlorochroman-4-yl)carbamoyl)-3-(4-chlorophenyl)quinoxalin-2-yl)pentanoic acid | 550.2 |
| 335 | 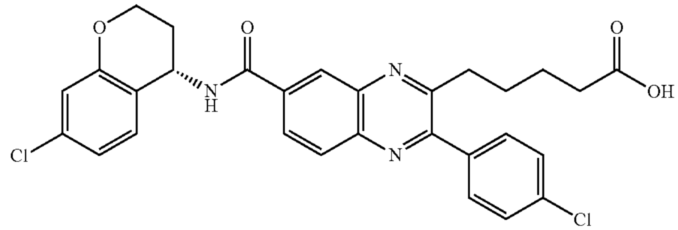 [SMILES: O=C(O)CCCCc1nc2cc(C(=O)N[C@H]3CCOc4cc(Cl)ccc43)ccc2nc1-c1ccc(Cl)cc1] | (S)-5-(7-((7-chlorochroman-4-yl)carbamoyl)-3-(4-chlorophenyl)quinoxalin-2-yl)pentanoic acid | 550.2 |
| 336 | 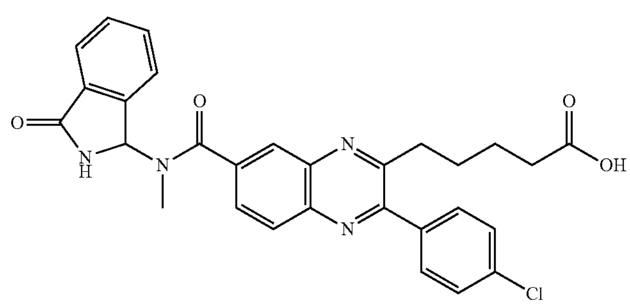 [SMILES: CN(C(=O)c1ccc2nc(-c3ccc(Cl)cc3)c(CCCCC(=O)O)nc2c1)C1NC(=O)c2ccccc21] | 5-(3-(4-chlorophenyl)-7-(methyl(3-oxoisoindolin-1-yl)carbamoyl)quinoxalin-2-yl)pentanoic acid | 529.2 |
| 337 | 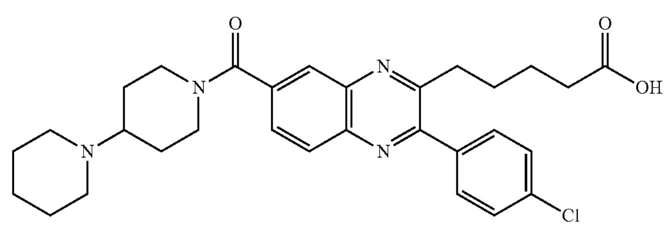 [SMILES: O=C(O)CCCCc1nc2cc(C(=O)N3CCC(N4CCCCC4)CC3)ccc2nc1-c1ccc(Cl)cc1] | 5-(7-([1,4'-bipiperidine]-1'-carbonyl)-3 (4-chlorophenyl)quinoxalin-2-yl)pentanoic acid | 535.3 |
| 338 | 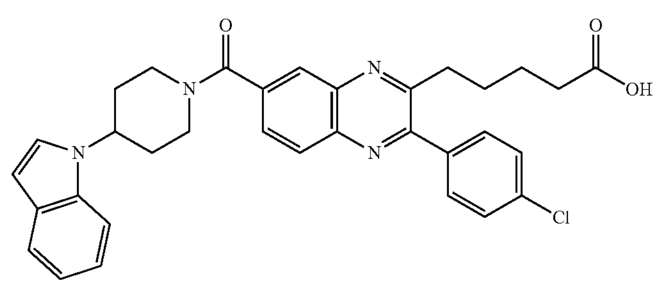 [SMILES: O=C(O)CCCCc1nc2cc(C(=O)N3CCC(n4ccc5ccccc54)CC3)ccc2nc1-c1ccc(Cl)cc1] | 5-(7-(4-(1H-indol-1-yl)piperidine-1-carbonyl)-3-(4-chlorophenyl)quinoxalin-2-yl)pentanoic acid | 567.3 |

-continued

| No. | Structure | Name | M + H |
|---|---|---|---|
| 339 | 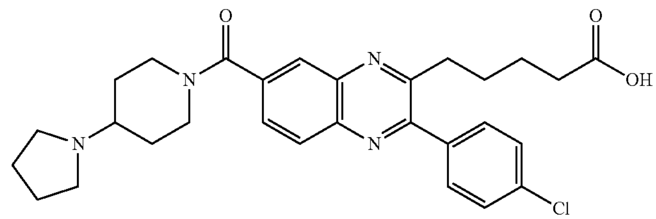 [SMILES: O=C(O)CCCCc1nc2cc(C(=O)N3CCC(N4CCCC4)CC3)ccc2nc1-c1ccc(Cl)cc1] | 5-(3-(4-chlorophenyl)-7-(4-(pyrrolidin-1-yl)piperidine-1-carbonyl)quinoxalin-2-yl)pentanoic acid | 521.3 |
| 340 | 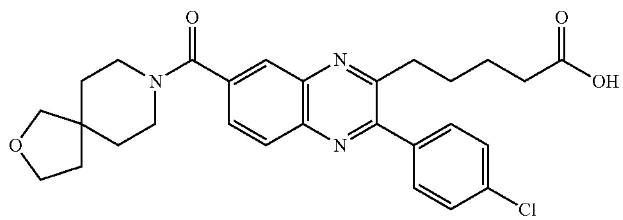 [SMILES: O=C(O)CCCCc1nc2cc(C(=O)N3CCC4(CCOC4)CC3)ccc2nc1-c1ccc(Cl)cc1] | 5-(3-(4-chlorophenyl)-7-(2-oxa-8-azaspiro[4.5]decane-8-carbonyl)quinoxalin-2-yl)pentanoic acid | 508.3 |
| 341 | 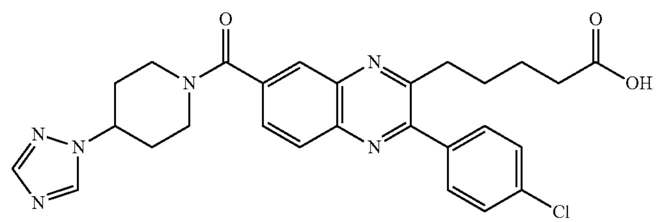 [SMILES: O=C(O)CCCCc1nc2cc(C(=O)N3CCC(n4cncn4)CC3)ccc2nc1-c1ccc(Cl)cc1] | 5-(7-(4-(1H-1,2,4-triazol-yl)piperidine-1-carbonyl)-3-(4-chlorophenyl)quinoxalin-2-yl)pentanoic acid | 519.3 |
| 342 | 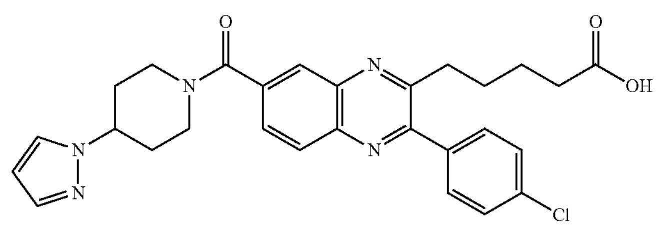 [SMILES: O=C(O)CCCCc1nc2cc(C(=O)N3CCC(n4cccn4)CC3)ccc2nc1-c1ccc(Cl)cc1] | 5-(7-(4-(1H-pyrazol-1-yl)piperidine-1-carbonyl)-3-(4-chlorophenyl)quinoxalin-2-yl)pentanoic acid | 518.3 |
| 343 | 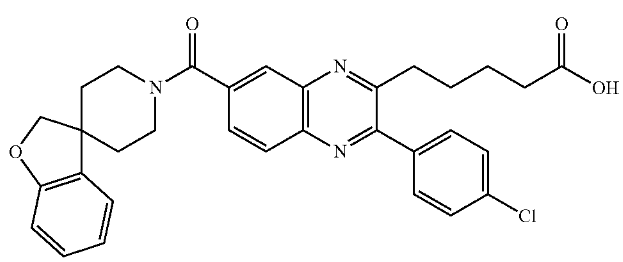 [SMILES: O=C(O)CCCCc1nc2cc(C(=O)N3CCC4(CC3)COc3ccccc34)ccc2nc1-c1ccc(Cl)cc1] | 5-(3--(4-chlorophenyl)-7-(2H-spiro[benzofuran-3,4'-piperidin]-1'-ylcarbonyl)quinoxalin-2-yl)pentanoic acid | 556.3 |
| 344 | 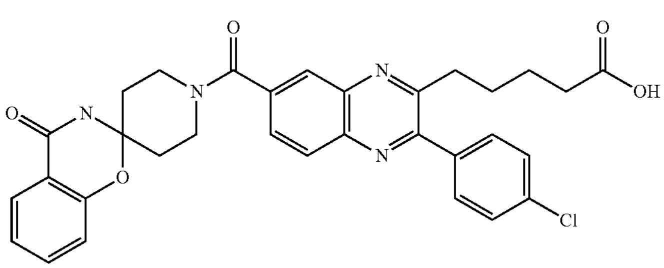 [SMILES: O=C(O)CCCCc1nc2cc(C(=O)N3CCC4(CC3)NC(=O)c3ccccc3O4)ccc2nc1-c1ccc(Cl)cc1] | 5-(3-(4-chlorophenyl)-7-(4-oxo-3,4-dihydrospiro[benzo[e][1,3]oxazine-2,4'-piperidin]-1'-ylcarbonyl)quinoxalin-2-yl)pentanoic acid | 585.3 |

US 9,469,615 B2

| No. | Structure | Name | M + H |
|---|---|---|---|
| 345 | 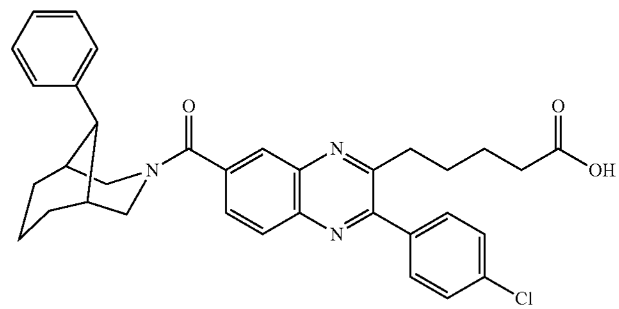 [SMILES: O=C(O)CCCCc1nc2cc(C(=O)N3CC4CCCC(C3)C4c3ccccc3)ccc2nc1-c1ccc(Cl)cc1] | 5-(3-(4-chlorophenyl)-7-((1R,5S,9r)-9-phenyl-3-azabicyclo[3.3.1]nonane-3-carbonyl)quinoxalin-2-yl)pentanoic acid | 568.3 |
| 346 | 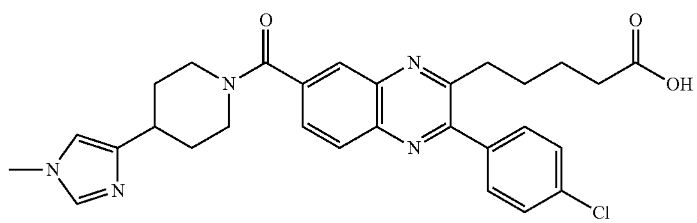 [SMILES: Cn1cnc(C2CCN(C(=O)c3ccc4nc(-c5ccc(Cl)cc5)c(CCCCC(=O)O)nc4c3)CC2)c1] | 5-(3-(4-chlorophenyl)-7-(4-(1-methyl-1H-imidazol-4-yl)piperidine-1-carbonyl)quinoxalin-2-yl)pentanoic acid | 532.3 |
| 347 | 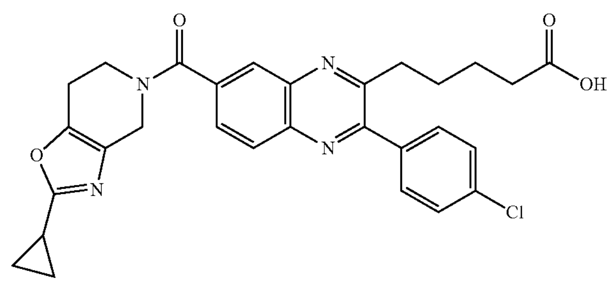 [SMILES: O=C(O)CCCCc1nc2cc(C(=O)N3CCc4oc(C5CC5)nc4C3)ccc2nc1-c1ccc(Cl)cc1] | 5-(3-(4-chlorophenyl)-7-(2-cyclopropyl-4,5,6,7-tetrahydrooxazolo[4,5-c]pyridine-5-carbonyl)quinoxalin-2-yl)pentanoic acid | 531.2 |
| 348 | 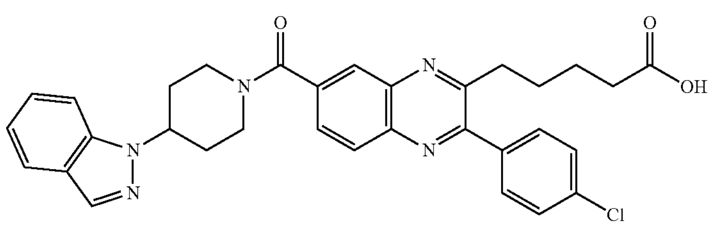 [SMILES: O=C(O)CCCCc1nc2cc(C(=O)N3CCC(n4ncc5ccccc54)CC3)ccc2nc1-c1ccc(Cl)cc1] | 5-(7-(4-(1H-indazol-1-yl)piperidine-1-carbonyl)-3-(4-chlorophenyl)quinoxalin-2-yl)pentanoic acid | 568.3 |
| 349 | 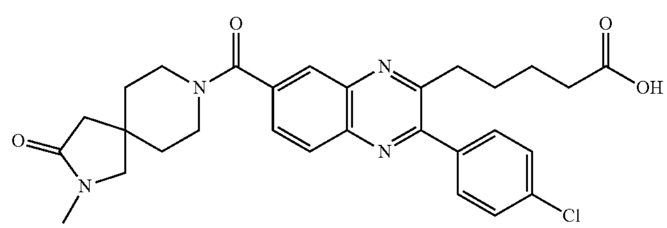 [SMILES: CN1CC2(CCN(C(=O)c3ccc4nc(-c5ccc(Cl)cc5)c(CCCCC(=O)O)nc4c3)CC2)CC1=O] | 5-(3-(4-chlorophenyl)-7-(2-methyl-3-oxo-2,8-diazaspiro[4.5]decane-8-carbonyl)quinoxalin-2-yl)pentanoic acid | 535.3 |
| 350 | 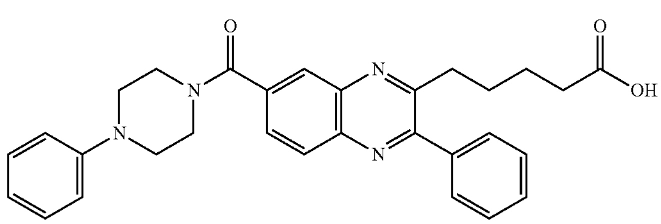 [SMILES: O=C(O)CCCCc1nc2cc(C(=O)N3CCN(c4ccccc4)CC3)ccc2nc1-c1ccccc1] | 5-(7-(3-oxo-4-phenylpiperazine-1-carbonyl)-3-phenylquinoxalin-2-yl)pentanoic acid | 509.3 |

-continued

| No. | Structure | Name | M + H |
|---|---|---|---|
| 351 | 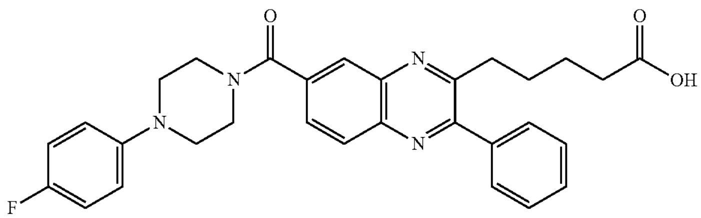 [SMILES: O=C(O)CCCCc1nc2cc(C(=O)N3CCN(c4ccc(F)cc4)CC3)ccc2nc1-c1ccccc1] | 5-(7-(4-(4-fluorophenyl)piperazine-1-carbonyl)-3-phenylquinoxalin-2-yl)pentanoic acid | 513.3 |
| 352 | 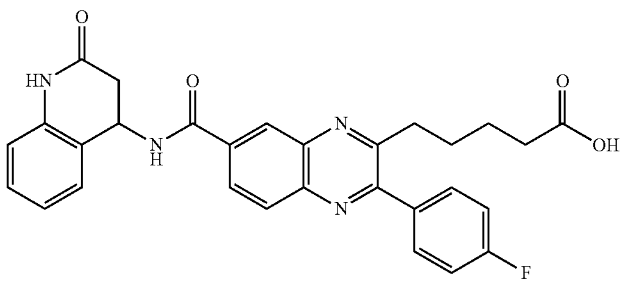 [SMILES: O=C(O)CCCCc1nc2cc(C(=O)NC3CC(=O)Nc4ccccc43)ccc2nc1-c1ccc(F)cc1] | 5-(3-(4-fluorophenyl)-7-((2-oxo-1,2,3,4-tetrahydroquinolin-4-yl)carbamoyl)quinoxalin-2-yl)pentanoic acid | 513.3 |
| 353 | 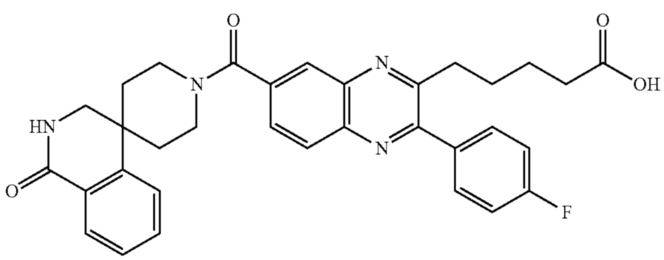 [SMILES: O=C(O)CCCCc1nc2cc(C(=O)N3CCC4(CC3)CNC(=O)c3ccccc34)ccc2nc1-c1ccc(F)cc1] | 5-(3-(4-fluorophenyl)-7-(1-oxo-2,3-dihydro-1H-spiro[isoquinoline-4,4'-piperidin]-1'-ylcarbonyl)quinoxalin-2-yl)pentanoic acid | 567.3 |
| 354 | 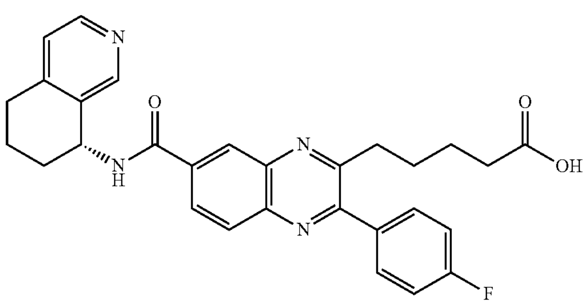 [SMILES: O=C(O)CCCCc1nc2cc(C(=O)N[C@@H]3CCCc4ccncc43)ccc2nc1-c1ccc(F)cc1] | (R)-5-(3-(4-fluorophenyl)-7-((5,6,7,8-tetrahydroisoquinolin-8-yl)carbamoyl)quinoxalin-2-yl)pentanoic acid | 499.3 |
| 355 | 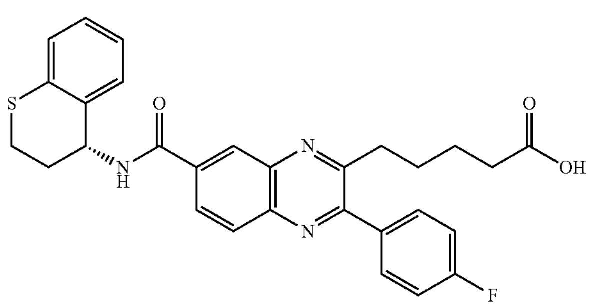 [SMILES: O=C(O)CCCCc1nc2cc(C(=O)N[C@@H]3CCSc4ccccc43)ccc2nc1-c1ccc(F)cc1] | (R)-5-(3-(4-fluorophenyl)-7-(thiochroman-4-ylcarbamoyl)quinoxalin-2-yl)pentanoic acid | 516.3 |

-continued

| No. | Structure | Name | M + H |
|---|---|---|---|
| 356 | 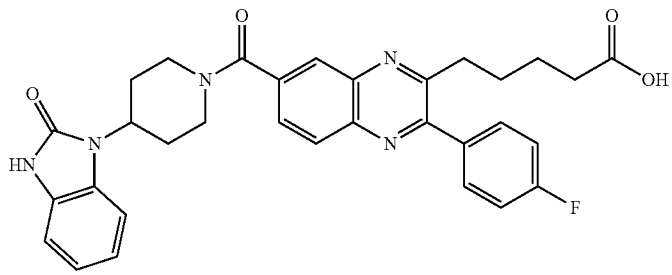 [SMILES: O=C(O)CCCCc1nc2cc(C(=O)N3CCC(n4c(=O)[nH]c5ccccc54)CC3)ccc2nc1-c1ccc(F)cc1] | 5-(3-(4-fluorophenyl)-7-(4-(2-oxo-2,3-dihydro-1H-benzo[d]imidazol-1-yl)piperidine-1-carbonyl)quinoxalin-2-yl)pentanoic acid | 568.3 |
| 357 | 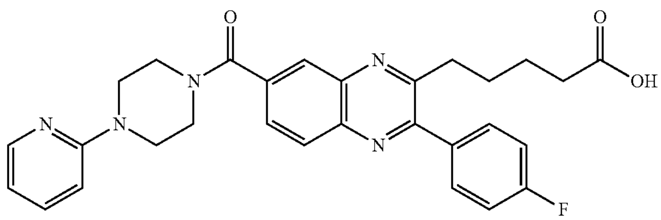 [SMILES: O=C(O)CCCCc1nc2cc(C(=O)N3CCN(c4ccccn4)CC3)ccc2nc1-c1ccc(F)cc1] | 5-(3-(4-fluorophenyl)-7-(4-(pyridin-2-yl)piperazine-1-carbonyl)quinoxalin-2-yl)pentanoic acid | 514.3 |
| 358 | 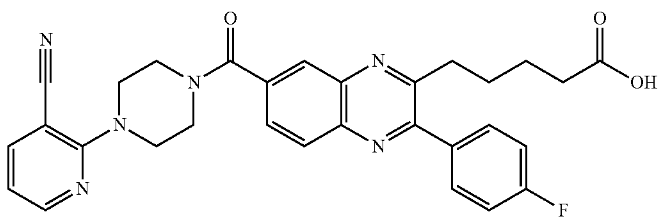 [SMILES: N#Cc1cccnc1N1CCN(C(=O)c2ccc3nc(-c4ccc(F)cc4)c(CCCCC(=O)O)nc3c2)CC1] | 5-(7-(4-(3-cyanopyridin-2-yl)piperazine-1-carbonyl)-3-(4-fluorophenyl)quinoxalin-2-yl)pentanoic acid | 539.3 |
| 359 | 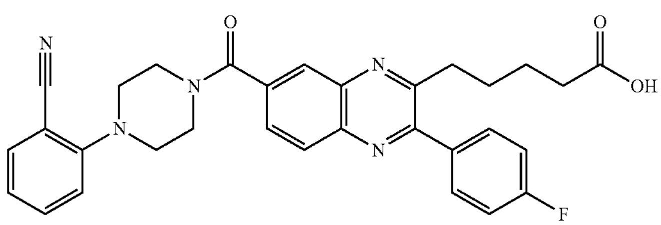 [SMILES: N#Cc1ccccc1N1CCN(C(=O)c2ccc3nc(-c4ccc(F)cc4)c(CCCCC(=O)O)nc3c2)CC1] | 5-(7-(4-(2-cyanophenyl)piperazine-1-carbonyl)-3-(4-fluorophenyl)quinoxalin-2-yl)pentanoic acid | 538.3 |
| 360 | 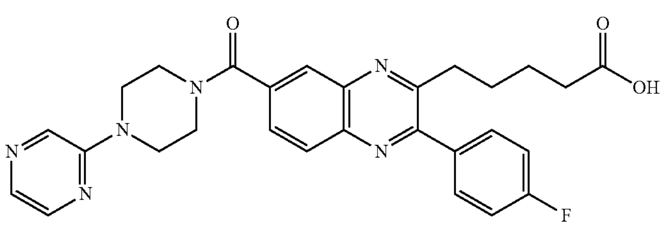 [SMILES: O=C(O)CCCCc1nc2cc(C(=O)N3CCN(c4cnccn4)CC3)ccc2nc1-c1ccc(F)cc1] | 5-(3-(4-fluorophenyl) 7-(4-(pyrazin-2-yl)piperazine-1-carbonyl)quinoxalin-2-yl)pentanoic acid | 515.3 |
| 361 | 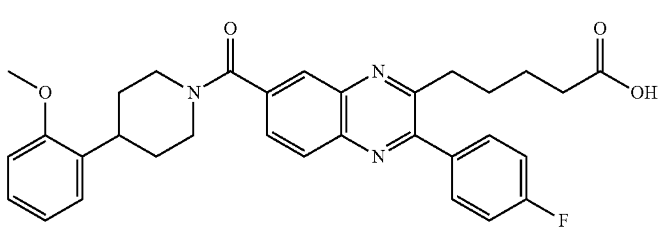 [SMILES: COc1ccccc1C1CCN(C(=O)c2ccc3nc(-c4ccc(F)cc4)c(CCCCC(=O)O)nc3c2)CC1] | 5-(3-(4-fluorophenyl)-7-(4-(2-methoxyphenyl)piperidine-1-carbonyl)quinoxalin-2-yl)pentanoic acid | 542.3 |

| No. | Name | M + H |
|---|---|---|
| 362 | 5-(3-(4-fluorophenyl)-7-(3H-spiro[isobenzofuran-1,4'-piperidin]-1'-ylcarbonyl)quinoxalin-2-yl)pentanoic acid | 540.3 |
| 363 | 5-(3-(4-fluorophenyl)-7-(4-(2-(trifluoromethyl)phenyl)piperazine-1-carbonyl)quinoxalin-2-yl)pentanoic acid | 581.3 |
| 364 | 5-(7-(4-(2-chlorophenyl)piperazine-1-carbonyl)-3-(4-fluorophenyl)quinoxalin-2-yl)pentanoic acid | 547.3 |
| 365 | 5-(3-(4-fluorophenyl)-7-(4-(o-tolyl)piperazine-1-carbonyl)quinoxalin-2-yl)pentanoic acid | 527.3 |
| 366 | 5-(3-(4-fluorophenyl)-7-(4-(m-tolyl)piperazine-1-carbonyl)quinoxalin-2-yl)pentanoic acid | 527.3 |
| 367 | 5-(3-(4-fluorophenyl)-7-(4-(4-methoxyphenyl)piperazine-1-carbonyl)quinoxalin-2-yl)pentanoic acid | 543.3 |

| No. | Structure | Name | M + H |
|---|---|---|---|
| 368 | 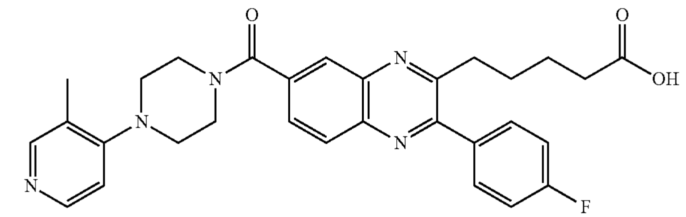 [SMILES: Cc1cnccc1N1CCN(C(=O)c2ccc3nc(-c4ccc(F)cc4)c(CCCCC(=O)O)nc3c2)CC1] | 5-(3-(4-fluorophenyl)-7-(4-(3-methylpyridin-4-yl)piperazine-1-carbonyl)quinoxalin-2-yl)pentanoic acid | 528.3 |
| 369 | 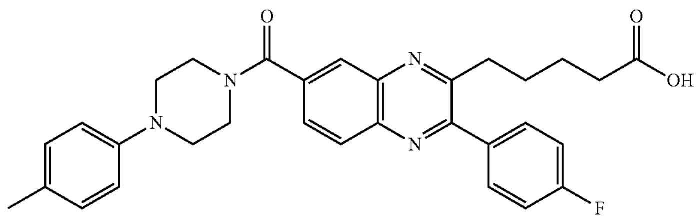 | 5-(3-(4-fluorophenyl)-7-(4-(p-tolyl)piperazine-1-carbonyl)quinoxalin-2-yl)pentanoic acid | 527.3 |
| 370 | 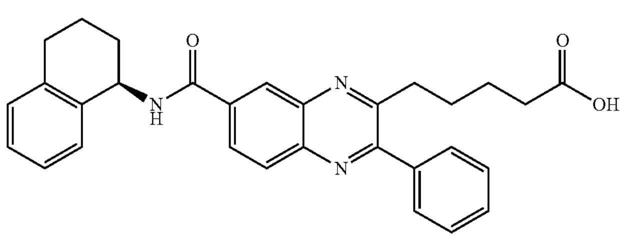 [SMILES: O=C(O)CCCCc1nc2cc(C(=O)N[C@@H]3CCCc4ccccc43)ccc2nc1-c1ccccc1] | (R)-8-(3-(4-carboxybutyl)-2-phenylquinoxaline-6-carboxamido)-5,6,7,8-tetrahydroquinolin-1-ium 2,2,2-trifluoroacetic acid | 481 |
| 371 | 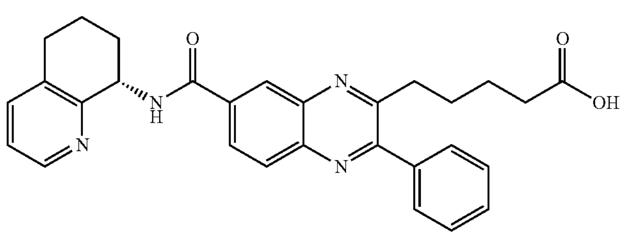 [SMILES: O=C(O)CCCCc1nc2cc(C(=O)N[C@H]3CCCc4cccnc43)ccc2nc1-c1ccccc1] | (S)-8-(3-(4-carboxybutyl)-2-phenylquinoxaline-6-carboxamido)-5,6,7,8-tetrahydroquinolin-1-ium 2,2,2-trifluoroacetic acid | 481 |
| 372 | 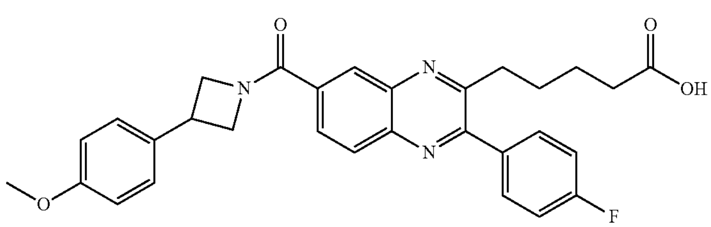 [SMILES: COc1ccc(C2CN(C(=O)c3ccc4nc(-c5ccc(F)cc5)c(CCCCC(=O)O)nc4c3)C2)cc1] | 5-(3-(4-fluorophenyl)-7-(3-(4-methoxyphenyl)azetidine-1-carbonyl)quinoxalin-2-yl)pentanoic acid | 514 |
| 373 | 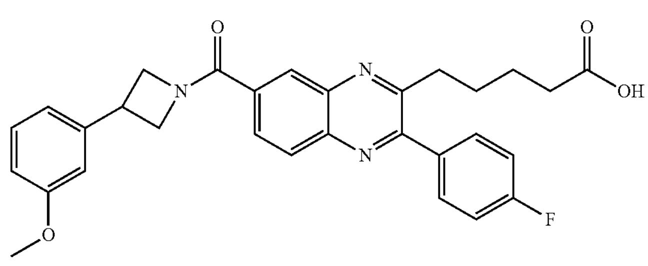 [SMILES: COc1cccc(C2CN(C(=O)c3ccc4nc(-c5ccc(F)cc5)c(CCCCC(=O)O)nc4c3)C2)c1] | 5-(3-(4-fluorophenyl)-7-(3-(3-methoxyphenyl)azetidine-1-carbonyl)quinoxalin-2-yl)pentanoic acid | 514 |

-continued

| No. | Structure | Name | M + H |
|---|---|---|---|
| 374 | 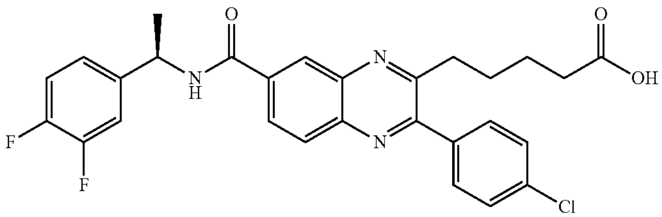 [SMILES: C[C@@H](NC(=O)c1ccc2nc(-c3ccc(Cl)cc3)c(CCCCC(=O)O)nc2c1)c1ccc(F)c(F)c1] | (R)-5-(3-(4-chlorophenyl)-7-((1-(3,4-difluorophenyl)ethyl)carbamoyl)quinoxalin-2-yl)pentanoic acid | 524 |
| 375 | 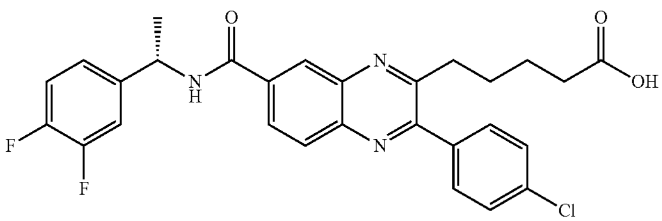 [SMILES: C[C@H](NC(=O)c1ccc2nc(-c3ccc(Cl)cc3)c(CCCCC(=O)O)nc2c1)c1ccc(F)c(F)c1] | (S)-5-(3-(4-chlorophenyl)-7-((1-(3,4-difluorophenyl)ethyl)carbamoyl)quinoxalin-2-yl)pentanoic acid | 524 |
| 376 | 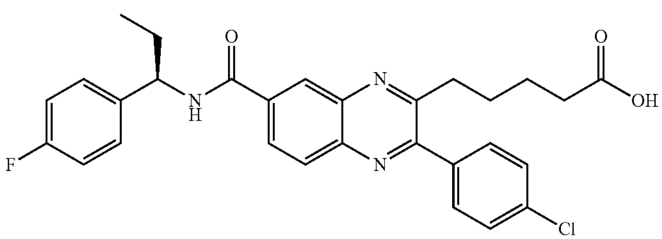 [SMILES: CC[C@@H](NC(=O)c1ccc2nc(-c3ccc(Cl)cc3)c(CCCCC(=O)O)nc2c1)c1ccc(F)cc1] | (R)-5-(3-(4-chlorophenyl)-7-((1-(4-fluorophenyl)propyl)carbamoyl)quinoxalin-2-yl)pentanoic acid | 522 |
| 377 | 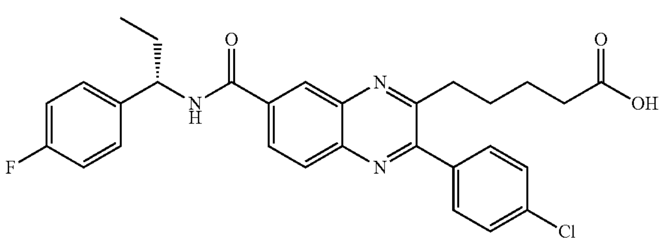 [SMILES: CC[C@H](NC(=O)c1ccc2nc(-c3ccc(Cl)cc3)c(CCCCC(=O)O)nc2c1)c1ccc(F)cc1] | (S)-5-(3-(4-chlorophenyl)-7-((1-4-fluorophenyl)propyl)carbamoyl)quinoxalin-2-yl)pentanoic acid | 522 |
| 378 | 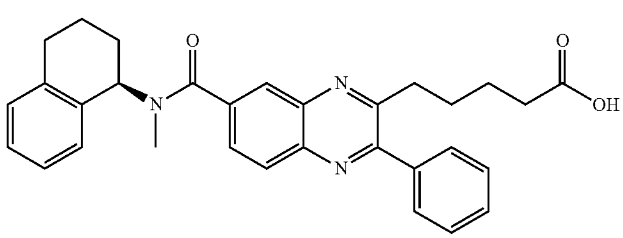 [SMILES: CN(C(=O)c1ccc2nc(-c3ccccc3)c(CCCCC(=O)O)nc2c1)[C@@H]1CCCc2ccccc21] | (R)-5-(7-(methyl(1,2,3,4-tetrahydronaphthalen-1-yl)carbamoyl)-3-phenylquinoxalin-2-yl)pentanoic acid | 494 |
| 379 | 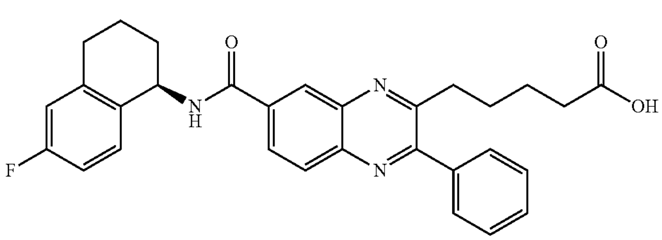 [SMILES: O=C(O)CCCCc1nc2cc(C(=O)N[C@@H]3CCCc4cc(F)ccc43)ccc2nc1-c1ccccc1] | (R)-5-(7-((6-fluoro-1,2,3,4-tetrahydronaphthalen-1-yl)(methyl)carbamoyl)-3-phenylquinoxalin-2-yl)pentanoic acid | 512 |

-continued

| No. | Structure | Name | M + H |
|---|---|---|---|
| 380 | 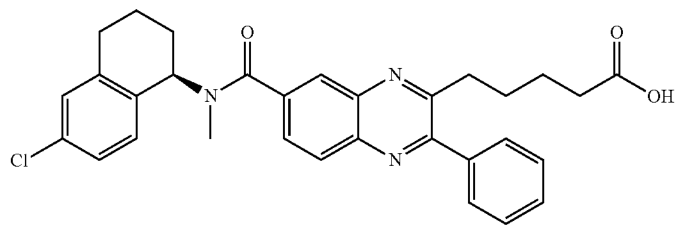 [SMILES: CN(C(=O)c1ccc2nc(-c3ccccc3)c(CCCCC(=O)O)nc2c1)[C@@H]1CCCc2cc(Cl)ccc21] | (R)-5-(7-(((6-chloro-1,2,3,4-tetrahydronaphthalen-1-yl)(methyl)carbamoyl)-3-phenylquinoxalin-2-yl)pentanoic acid | 528 |
| 381 | 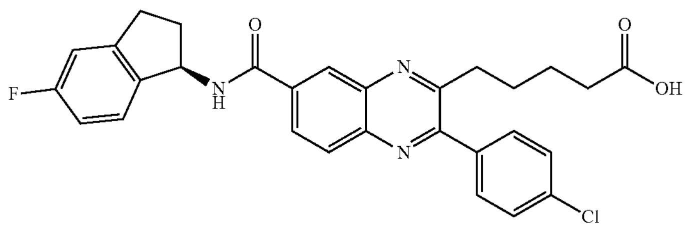 | (R)-5-(3-(4-chlorophenyl)-7-((5-fluoro-2,3-dihydro-1H-inden-1-yl)carbamoyl)quinoxalin-2-yl)pentanoic acid | 518 |
| 382 | 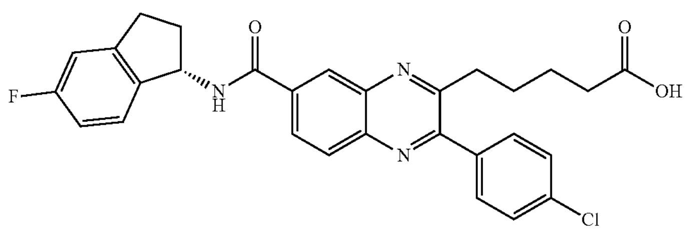 | (S)-5-(3-(4-chlorophenyl)-7-((5-fluoro-2,3-dihydro-1H-inden-1-yl)carbamoyl)quinoxalin-2-yl)pentanoic acid | 518 |
| 383 | 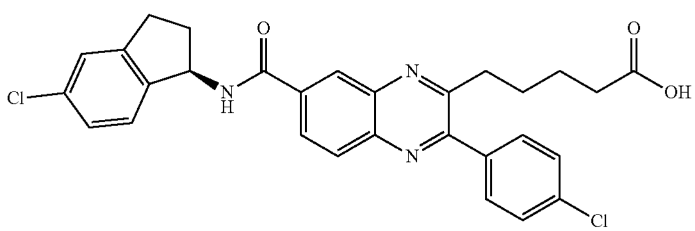 [SMILES: O=C(O)CCCCc1nc2cc(C(=O)N[C@@H]3CCc4cc(Cl)ccc43)ccc2nc1-c1ccc(Cl)cc1] | (R)-5-(7-((5-chloro-2,3-dihydro-1H-inden-1-yl)carbamoyl)-3-(4-chlorophenyl)quinoxalin-2-yl)pentanoic acid | 534 |
| 384 | 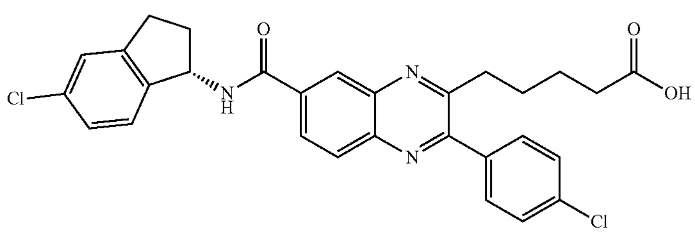 [SMILES: O=C(O)CCCCc1nc2cc(C(=O)N[C@H]3CCc4cc(Cl)ccc43)ccc2nc1-c1ccc(Cl)cc1] | (S)-5-(7-((5-chloro-2,3-dihydro-1H-inden-1-yl)carbamoyl)-3-(4-chlorophenyl)quinoxalin-2-yl)pentanoic acid | 534 |
| 385 | 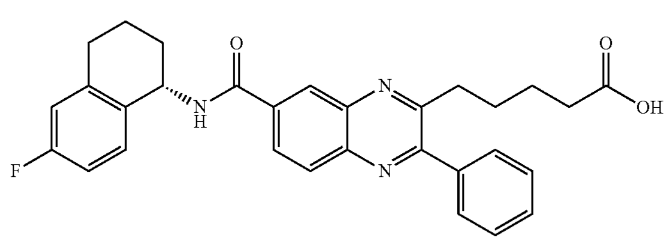 [SMILES: O=C(O)CCCCc1nc2cc(C(=O)N[C@H]3CCCc4cc(F)ccc43)ccc2nc1-c1ccccc1] | (S)-5-(7-(((6-fluoro-1,2,3,4-tetrahydronaphthalen-1-yl)carbamoyl)-3-phenylquinoxalin-2-yl)pentanoic acid | 498 |

| No. | Structure | Name | M + H |
|---|---|---|---|
| 386 | 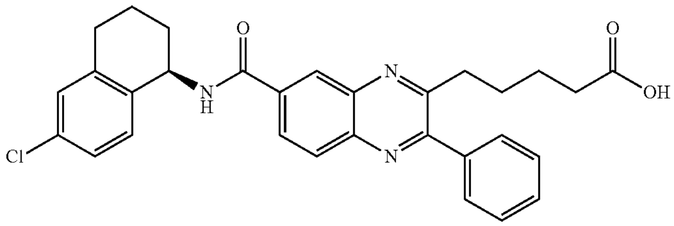 [SMILES: O=C(O)CCCCc1nc2cc(C(=O)N[C@@H]3CCCc4cc(Cl)ccc43)ccc2nc1-c1ccccc1] | (R)-5-(7-((6-chloro-1,2,3,4-tetrahydronaphthalen-1-yl)carbamoyl)-3-phenylquinoxalin-2-yl)pentanoic acid | 514 |
| 387 | 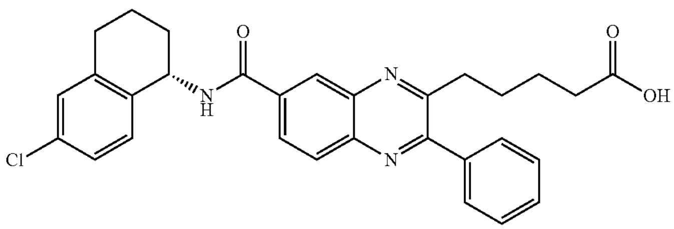 [SMILES: O=C(O)CCCCc1nc2cc(C(=O)N[C@H]3CCCc4cc(Cl)ccc43)ccc2nc1-c1ccccc1] | (S)-5-(7-((6-chloro-1,2,3,4-tetrahydronaphthalen-1-yl)carbamoyl)-3-phenylquinoxalin-2-yl)pentanoic acid | 514 |
| 388 | 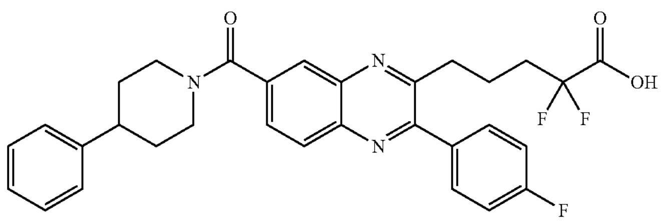 [SMILES: O=C(c1ccc2nc(-c3ccc(F)cc3)c(CCCC(F)(F)C(=O)O)nc2c1)N1CCC(c2ccccc2)CC1] | (S)-5-(3-phenyl-7-((1,2,3,4-tetrahydronaphthalen-1-yl)carbamoyl)quinoxalin-2-yl)pentanoic acid | 480 |
| 389 | 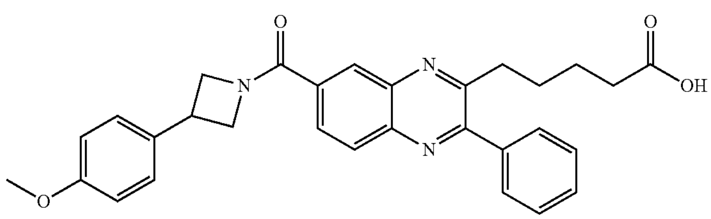 [SMILES: COc1ccc(C2CN(C(=O)c3ccc4nc(-c5ccccc5)c(CCCCC(=O)O)nc4c3)C2)cc1] | 5-(7-(3-(4-methoxyphenyl)azetidine-1-carbonyl)-3-phenylquinoxalin-2-yl)pentanoic acid | 496 |
| 390 | 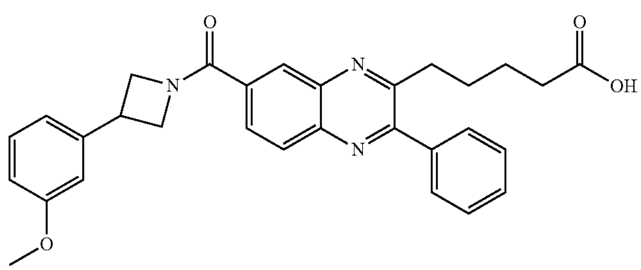 [SMILES: COc1cccc(C2CN(C(=O)c3ccc4nc(-c5ccccc5)c(CCCCC(=O)O)nc4c3)C2)c1] | 5-(7-(3-(3-methoxyphenyl)azetidine-1-carbonyl)-3-phenylquinoxalin-2-yl)pentanoic acid | 496 |
| 391 | 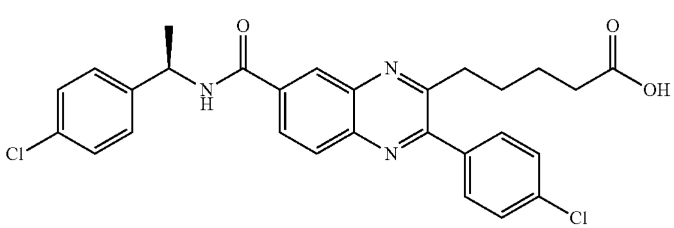 [SMILES: C[C@@H](NC(=O)c1ccc2nc(-c3ccc(Cl)cc3)c(CCCCC(=O)O)nc2c1)c1ccc(Cl)cc1] | 5-(3-(4-chlorophenyl)-7-(((R)-1-(4-chlorophenyl)ethyl)carbamoyl)quinoxalin-2-yl)-2-methylpentanoic acid | 536 |

| No. | Structure | Name | M + H |
|---|---|---|---|
| 392 | 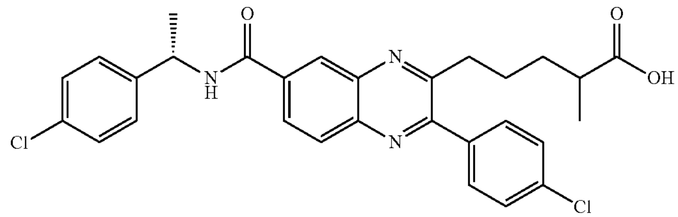 [SMILES: CC(CCCc1nc2cc(C(=O)N[C@@H](C)c3ccc(Cl)cc3)ccc2nc1-c1ccc(Cl)cc1)C(=O)O] | 5-(3-(4-chlorophenyl)-7-(((S)-1-(4-chlorophenyl)ethyl)carbamoyl)quinoxalin-2-yl)-2-methylpentanoic acid | 536 |
| 393 | 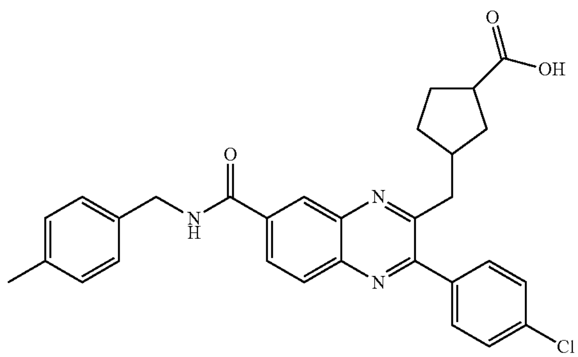 [SMILES: Cc1ccc(CNC(=O)c2ccc3nc(-c4ccc(Cl)cc4)c(CC4CCC(C(=O)O)C4)nc3c2)cc1] | 3-((3-(4-chlorophenyl)-7-((4-methylbenzyl)carbamoyl)quinoxalin-2-yl)methyl)cyclopentanecarboxylic acid | |
| 394 | 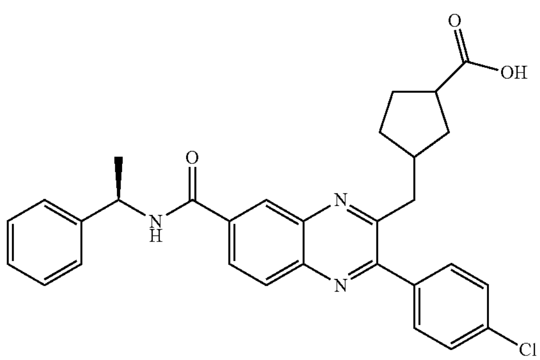 [SMILES: C[C@@H](NC(=O)c1ccc2nc(-c3ccc(Cl)cc3)c(CC3CCC(C(=O)O)C3)nc2c1)c1ccccc1] | 3-((3-(4-chlorophenyl)-7-(((R)-1-phenylethyl)carbamoyl)quinoxalin-2-yl)methyl)cyclopentanecarboxylic acid | 514 |
| 395 | 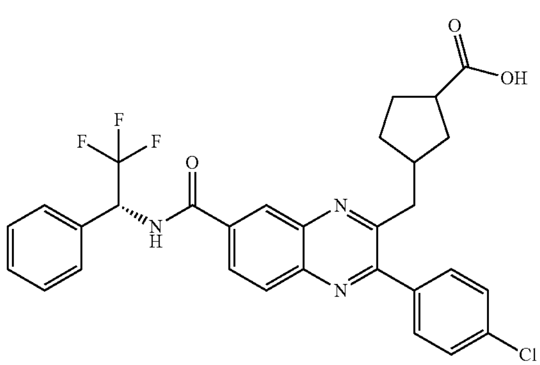 [SMILES: O=C(N[C@H](c1ccccc1)C(F)(F)F)c1ccc2nc(-c3ccc(Cl)cc3)c(CC3CCC(C(=O)O)C3)nc2c1] | 3-((3-(4-chlorophenyl)-7-(((R)-2,2,2-trifluoro-1-phenylethyl)carbamoyl)quinoxalin-2-yl)methyl)cyclopentanecarboxylic acid | 568 |

| No. | Structure | Name | M + H |
|---|---|---|---|
| 396 | 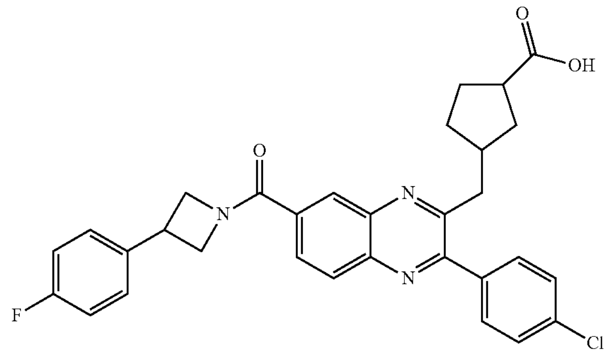 [SMILES: O=C(O)C1CCC(Cc2nc3cc(C(=O)N4CC(c5ccc(F)cc5)C4)ccc3nc2-c2ccc(Cl)cc2)C1] | 3-((3-(4-chlorophenyl)-7-(3-(4-fluorophenyl)azetidine-1-carbonyl)quinoxalin-2-yl)methyl)cyclopentanecarboxylic acid | 544 |
| 397 | 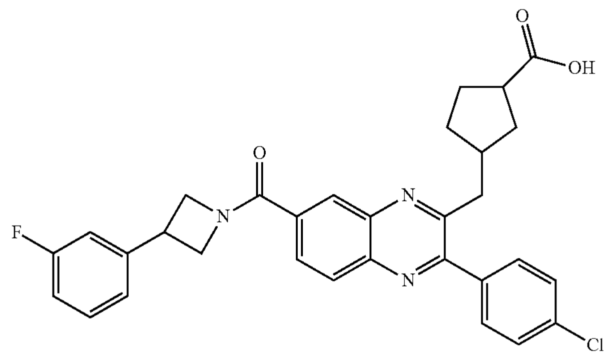 [SMILES: O=C(O)C1CCC(Cc2nc3cc(C(=O)N4CC(c5cccc(F)c5)C4)ccc3nc2-c2ccc(Cl)cc2)C1] | 3-((3-(4-chlorophenyl)-7-(3-(3-fluorophenyl)azetidine-1-carbonyl)quinoxalin-2-yl)methyl)cyclopentane-carboxylic acid | 544 |
| 398 | 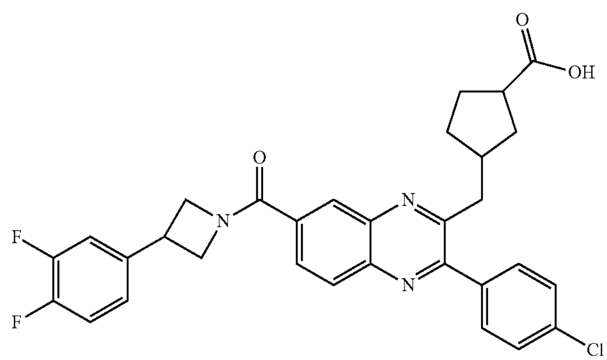 | 3-((3-(4-chlorophenyl)-7-(3-(3,4-difluorophenyl)azetidine-1-carbonyl)quinoxalin-2-yl)methyl)cyclopentane-carboxylic acid | 562 |
| 399 | 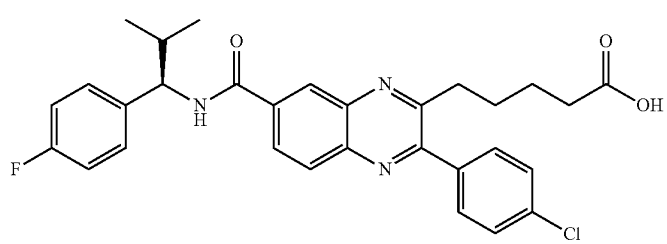 [SMILES: CC(C)[C@@H](NC(=O)c1ccc2nc(-c3ccc(Cl)cc3)c(CCCCC(=O)O)nc2c1)c1ccc(F)cc1] | (R)-5-(3-(4-chlorophenyl)-7-((1-(4-fluorophenyl)-2-methylpropyl)carbamoyl)quinoxalin-2-yl)pentanoic acid | 534 |

| No. | Structure | Name | M + H |
|---|---|---|---|
| 400 | 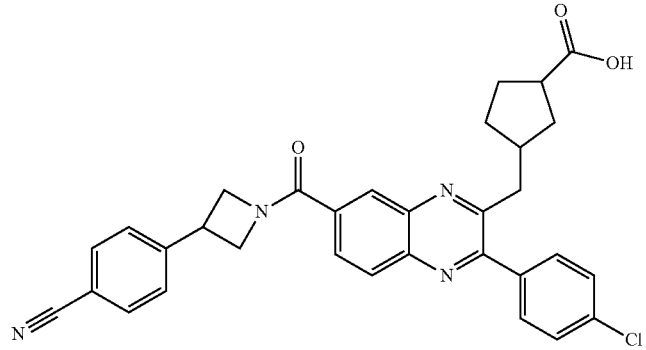 [SMILES: N#Cc1ccc(C2CN(C(=O)c3ccc4nc(-c5ccc(Cl)cc5)c(CC5CCC(C(=O)O)C5)nc4c3)C2)cc1] | 3-((3-(4-chlorophenyl)-7-(3-(4-cyanophenyl)azetidine-1-carbonyl)quinoxalin-2-yl)methyl)cyclopentane-carboxylic acid | |
| 401 | 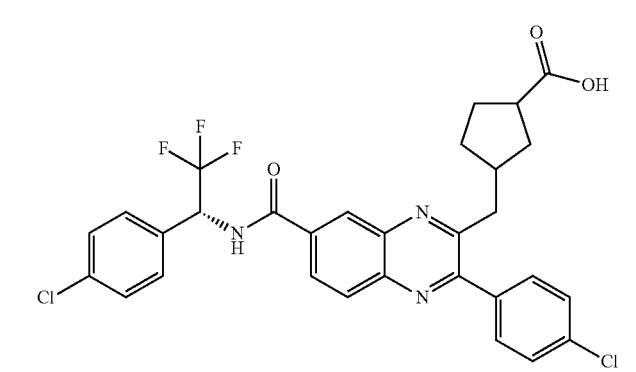 [SMILES: O=C(N[C@H](c1ccc(Cl)cc1)C(F)(F)F)c1ccc2nc(-c3ccc(Cl)cc3)c(CC3CCC(C(=O)O)C3)nc2c1] | 3-((3-(4-chlorophenyl)-7-((R)-1-(4-chlorophenyl)-2,2,2-trifluoroethyl)carbamoyl)quinoxalin-2-yl)methyl)cyclopentane-carboxylic acid | 603 |
| 402 | 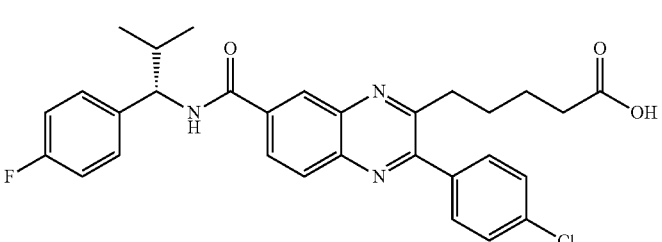 | (S)-5-(3-(4-chlorophenyl)-7-((1-(4-fluorophenyl)-2-methylpropyl)carbamoyl)quinoxalin-2-yl)pentanoic acid | 534 |
| 403 | 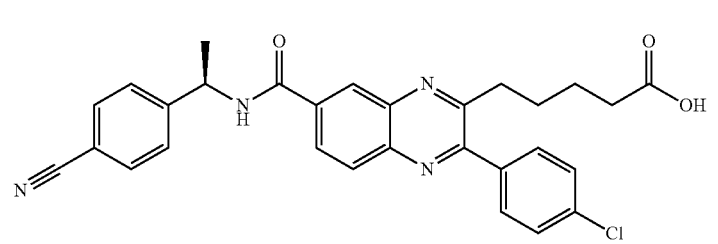 [SMILES: C[C@@H](NC(=O)c1ccc2nc(-c3ccc(Cl)cc3)c(CCCCC(=O)O)nc2c1)c1ccc(C#N)cc1] | (R)-5-(3-(4-chlorophenyl)-7-((1-(4-cyanophenyl)ethyl)carbamoyl)quinoxalin-2-yl)pentanoic acid | 513 |
| 404 | 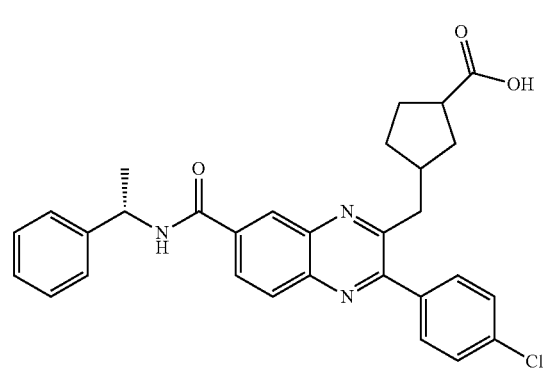 [SMILES: C[C@H](NC(=O)c1ccc2nc(-c3ccc(Cl)cc3)c(CC3CCC(C(=O)O)C3)nc2c1)c1ccccc1] | 3-((3-(4-chlorophenyl)-7-(((S)-1-phenylethyl)carbamoyl)quinoxalin-2-yl)methyl)cyclopentane-carboxylic acid | 514 |

| No. | Structure | Name | M + H |
|---|---|---|---|
| 405 | 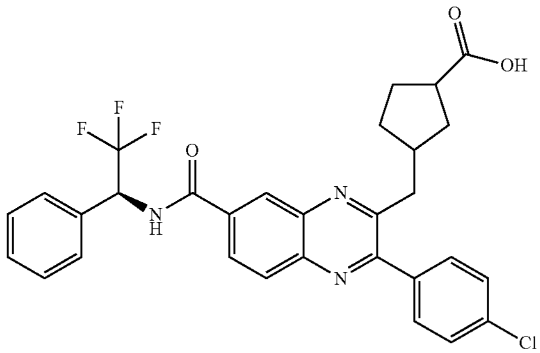 [SMILES: O=C(N[C@@H](c1ccccc1)C(F)(F)F)c1ccc2nc(-c3ccc(Cl)cc3)c(CC3CCC(C(=O)O)C3)nc2c1] | 3-((3-(4-chlorophenyl)-7-(((S)-2,2,2-trifluoro-1-phenylethyl)carbamoyl)quinoxalin-2-yl)methyl)cyclopentanecarboxylic acid | 568 |
| 406 | 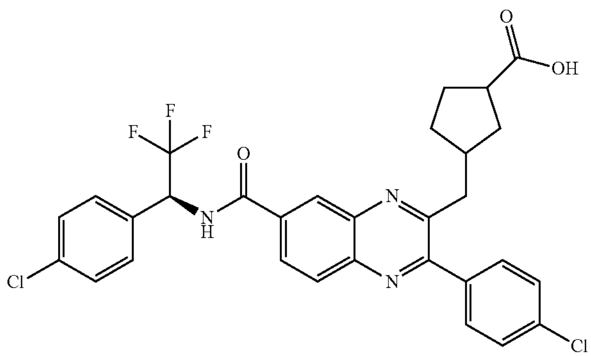 [SMILES: O=C(N[C@@H](c1ccc(Cl)cc1)C(F)(F)F)c1ccc2nc(-c3ccc(Cl)cc3)c(CC3CCC(C(=O)O)C3)nc2c1] | 3-((3-(4-chlorophenyl)-7-(((S)-1-(4-chlorophenyl)-2,2,2-trifluoroethyl)carbamoyl)quinoxalin-2-yl)methyl)cyclopentanecarboxylic acid | 603 |
| 407 | 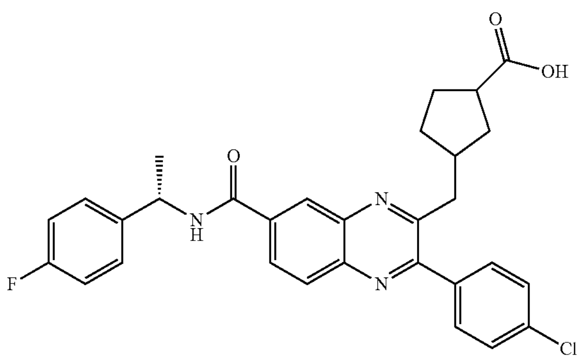 [SMILES: C[C@H](NC(=O)c1ccc2nc(-c3ccc(Cl)cc3)c(CC3CCC(C(=O)O)C3)nc2c1)c1ccc(F)cc1] | 3-((3-(4-chlorophenyl)-7-(((S)-1-(4-fluorophenyl)ethyl)carbamoyl)quinoxalin-2-yl)methyl)cyclopentanecarboxylic acid | 532 |
| 408 | 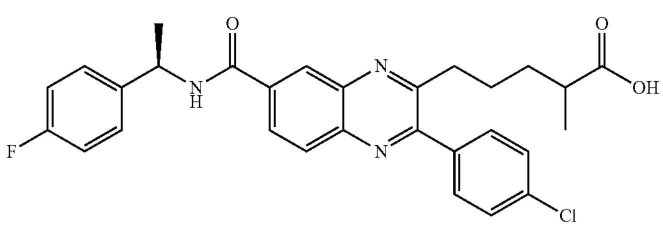 [SMILES: CC(CCCc1nc2cc(C(=O)N[C@H](C)c3ccc(F)cc3)ccc2nc1-c1ccc(Cl)cc1)C(=O)O] | 5-(3-(4-chlorophenyl)-7-(((R)-1-(4-fluorophenyl)ethyl)carbamoyl)quinoxalin-2-yl)-2-methylpentanoic acid | 520 |
| 409 | 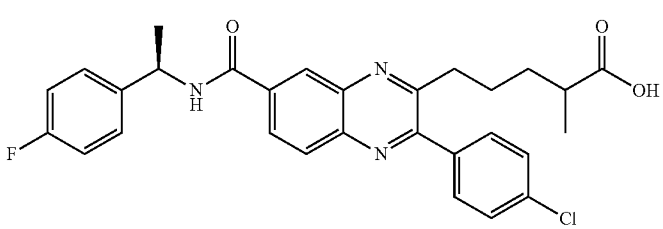 [SMILES: CC(CCCc1nc2cc(C(=O)N[C@H](C)c3ccc(F)cc3)ccc2nc1-c1ccc(Cl)cc1)C(=O)O] | 5-(3-(4-chlorophenyl)-7-(((R)-1-(4-fluorophenyl)ethyl)carbamoyl)quinoxalin-2-yl)-2-methylpentanoic acid | 520 |

-continued

| No. | Structure | Name | M + H |
|---|---|---|---|
| 410 | 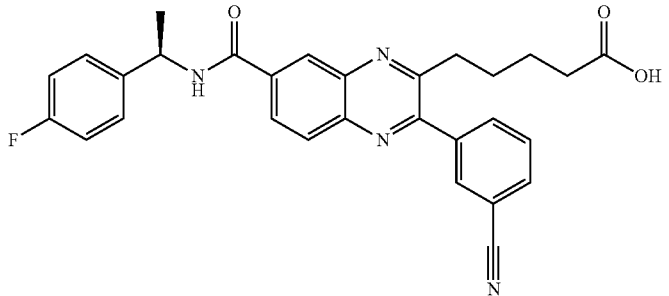 [SMILES: C[C@@H](NC(=O)c1ccc2nc(-c3cccc(C#N)c3)c(CCCCC(=O)O)nc2c1)c1ccc(F)cc1] | (R)-5-(3-(3-cyanophenyl)-7-((1-(4-fluorophenyl)ethyl)carbamoyl)quinoxalin-2-yl)pentanoic acid | 497 |
| 411 | 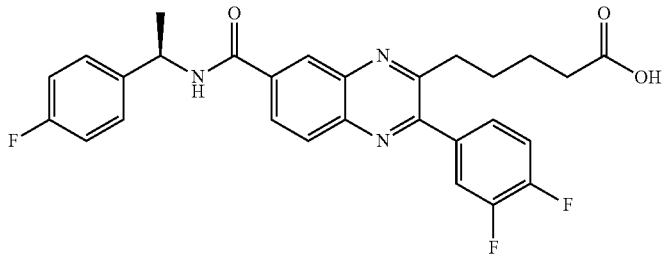 [SMILES: C[C@@H](NC(=O)c1ccc2nc(-c3ccc(F)c(F)c3)c(CCCCC(=O)O)nc2c1)c1ccc(F)cc1] | (R)-5-(3-(3,4-difluarophenyl)-7-(((1-(4-fluorophenyl)ethyl)carbamoyl)quinoxalin-2-yl)pentanoic acid | 508 |
| 412 | 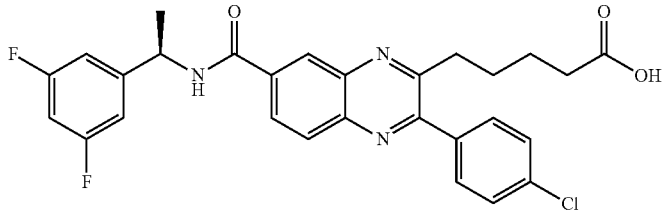 [SMILES: C[C@@H](NC(=O)c1ccc2nc(-c3ccc(Cl)cc3)c(CCCCC(=O)O)nc2c1)c1cc(F)cc(F)c1] | (R)-5-(3-(4-chlorophenyl)-7-((1-(3,5-difluorophenyl)ethyl)carbamoyl)quinoxalin-2-yl)pentanoic acid | 524 |
| 413 | 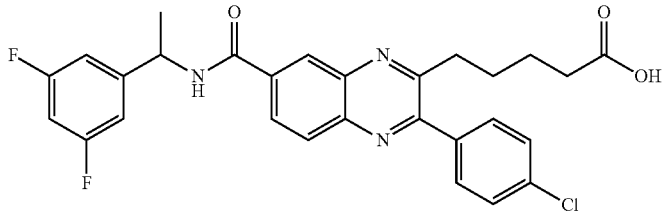 [SMILES: CC(NC(=O)c1ccc2nc(-c3ccc(Cl)cc3)c(CCCCC(=O)O)nc2c1)c1cc(F)cc(F)c1] | (S)-5-(3-(4-chlorophenyl)-7-((1-(3,5-difluorophenyl)ethyl)carbamoyl)quinoxalin-2-yl)pentanoic acid | 524 |
| 414 | 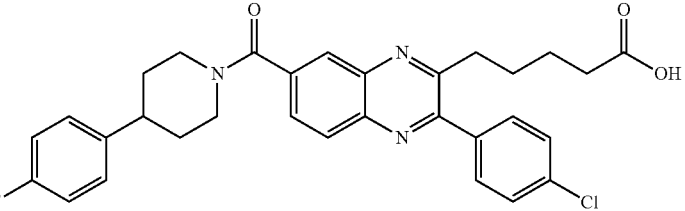 | 5-(3-(4-chlorophenyl)-7-(4-(4-fluorophenyl)piperidine-1-carbonyl)quinoxalin-2-yl)pentanoic acid | 546 |
| 415 | 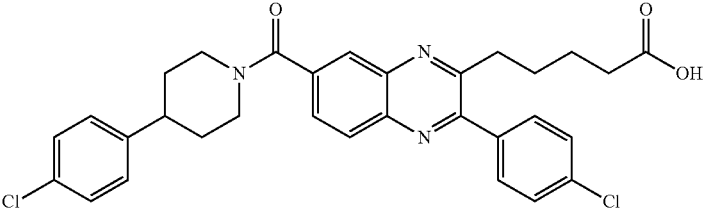 [SMILES: O=C(O)CCCCc1nc2cc(C(=O)N3CCC(c4ccc(Cl)cc4)CC3)ccc2nc1-c1ccc(Cl)cc1] | 5-(3-(4-chlorophenyl)-7-(4-(4-chlorophenyl)piperidine-1-carbonyl)quinoxalin-2-yl)pentanoic acid | 562 |

-continued

| No. | Structure | Name | M + H |
|---|---|---|---|
| 416 | 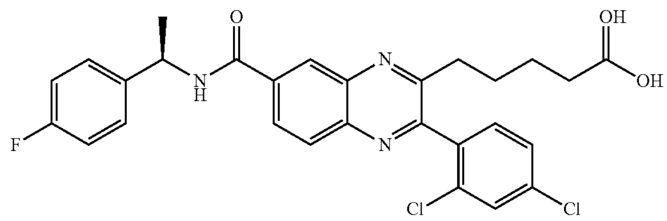 [SMILES: C[C@@H](NC(=O)c1ccc2nc(-c3ccc(Cl)cc3Cl)c(CCCCC(=O)O)nc2c1)c1ccc(F)cc1] | (R)-5-(3-(2,4-dichlorophenyl)-7-((1-(4-fluorophenyl)ethyl)carbamoyl)quinoxalin-2-yl)pentanoic acid | 540 |
| 417 | 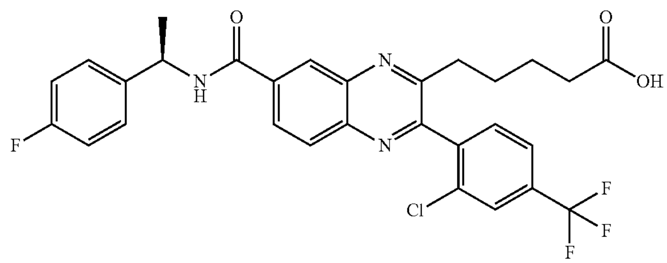 [SMILES: C[C@@H](NC(=O)c1ccc2nc(-c3ccc(C(F)(F)F)cc3Cl)c(CCCCC(=O)O)nc2c1)c1ccc(F)cc1] | (R)-5-(3-(2-chloro-4-(trifluoromethyl)phenyl)-7-((1-(4-fluorophenyl)ethyl)carbamoyl)quinoxalin-2-yl) pentanoic acid | 574 |
| 418 | 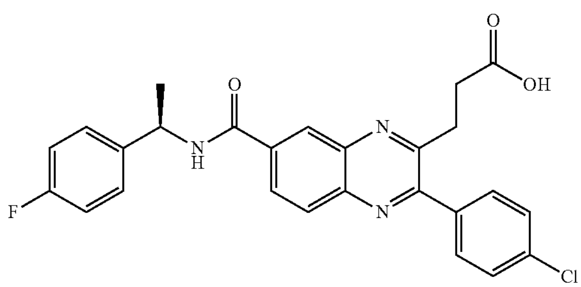 [SMILES: C[C@@H](NC(=O)c1ccc2nc(-c3ccc(Cl)cc3)c(CCC(=O)O)nc2c1)c1ccc(F)cc1] | (R)-3-(3-(4-chlorophenyl)-7-((1-(4-fluorophenyl)ethyl)carbamoyl)quinoxalin-2-yl) propanoic acid | 478 |
| 419 | 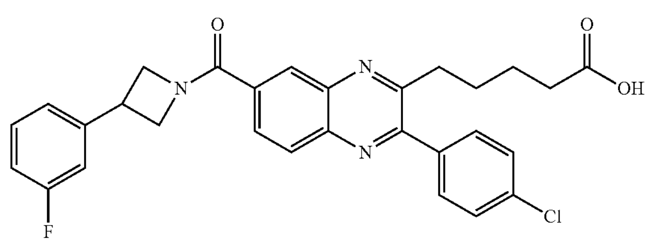 [SMILES: O=C(O)CCCCc1nc2cc(C(=O)N3CC(c4cccc(F)c4)C3)ccc2nc1-c1ccc(Cl)cc1] | 5-(3-(4-chlorophenyl)-7-(3-(3-fluorophenyl)azetidine-1-carbonyl)quinoxalin-2-yl)pentanoic acid | 518 |
| 420 | 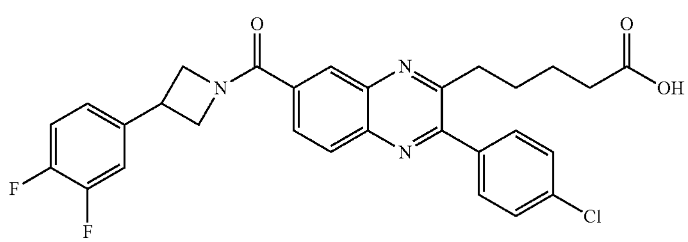 [SMILES: O=C(O)CCCCc1nc2cc(C(=O)N3CC(c4ccc(F)c(F)c4)C3)ccc2nc1-c1ccc(Cl)cc1] | 5-(3-(4-chlorophenyl)-7-(3-(3,4-difluorophenyl)azetidine-1-carbonyl)quinoxalin-2-yl)pentanoic acid | 536 |
| 421 | 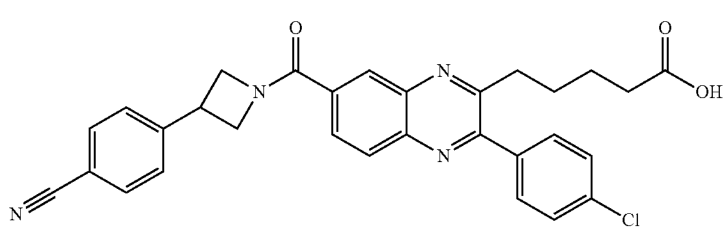 [SMILES: N#Cc1ccc(C2CN(C(=O)c3ccc4nc(-c5ccc(Cl)cc5)c(CCCCC(=O)O)nc4c3)C2)cc1] | 5-(3-(4-chlorophenyl)-7-(3-(4-cyanophenyl)azetidine-1-carbonyl)quinoxalin-2-yl)pentanoic acid | 525 |

-continued

| No. | Structure | Name | M + H |
|---|---|---|---|
| 422 | 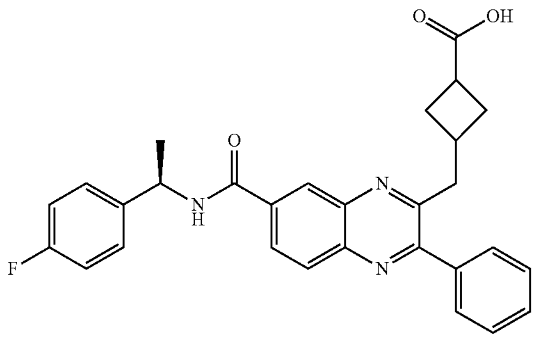 [SMILES: C[C@@H](NC(=O)c1ccc2nc(-c3ccccc3)c(CC3CC(C(=O)O)C3)nc2c1)c1ccc(F)cc1] | (R)-3-((7-((1-(4-fluorophenyl)ethyl)carbamoyl)-3-phenylquinoxalin-2-yl)methyl)cyclobutanecarboxylic acid | 484 |
| 423 | 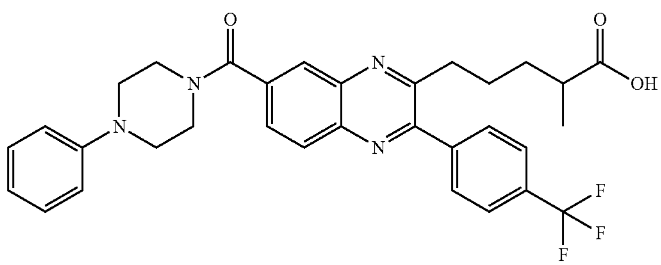 [SMILES: CC(CCCc1nc2cc(C(=O)N3CCN(c4ccccc4)CC3)ccc2nc1-c1ccc(C(F)(F)F)cc1)C(=O)O] | 2-methyl-5-(7-(4-phenylpperazine-1-carbonyl)-3-(4-(trifluoromethyl)phenyl)quinoxalin-2-yl)pentanoic acid | 577 |
| 424 | 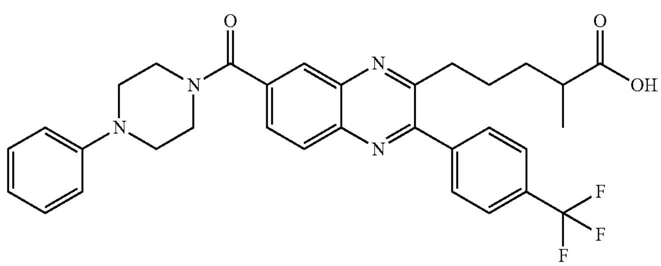 [SMILES: CC(CCCc1nc2cc(C(=O)N3CCN(c4ccccc4)CC3)ccc2nc1-c1ccc(C(F)(F)F)cc1)C(=O)O] | 3-methyl-5-(7-(4-phenylpiperazine-1-carbonyl)-3-(4-(trifluoromethyl)phenyl)quinoxalin-2-yl)pentanoic acid | 577 |
| 425 | 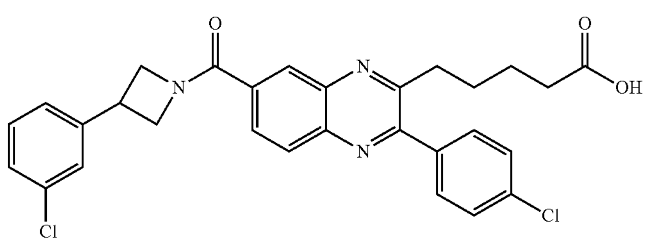 [SMILES: O=C(O)CCCCc1nc2cc(C(=O)N3CC(c4cccc(Cl)c4)C3)ccc2nc1-c1ccc(Cl)cc1] | 5-(3-(4-chlorophenyl)-7-(3-(3-chlorophenyl)azetidine-1-carbonyl)quinoxalin-2-yl)pentanoic acid | 534 |
| 426 | 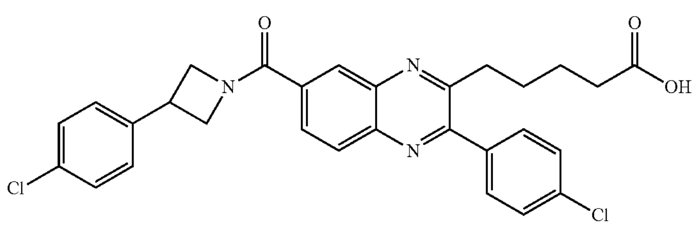 [SMILES: O=C(O)CCCCc1nc2cc(C(=O)N3CC(c4ccc(Cl)cc4)C3)ccc2nc1-c1ccc(Cl)cc1] | 5-(3-(4-chlorophenyl)-7-(3-(4-chlorophenyl)azetidine-1-carbonyl)quinoxalin-2-yl)pentanoic acid | 534 |
| 427 | 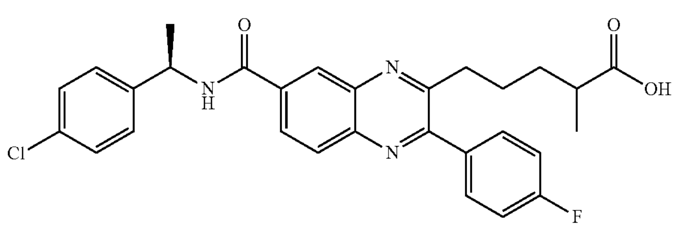 [SMILES: CC(CCCc1nc2cc(C(=O)N[C@H](C)c3ccc(Cl)cc3)ccc2nc1-c1ccc(F)cc1)C(=O)O] | 5-(7-(((R)-1-(4-chlorophenyl)ethyl)carbamoyl)-3-(4-fluorophenyl)quinoxalin-2-yl)-2-methylpentanoic acid | 520 |

-continued

| No. | Structure | Name | M + H |
|---|---|---|---|
| 428 | 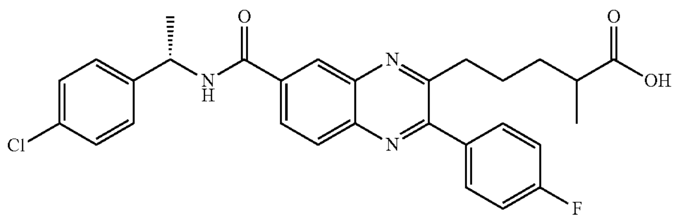 [SMILES: CC(CCCc1nc2cc(C(=O)N[C@@H](C)c3ccc(Cl)cc3)ccc2nc1-c1ccc(F)cc1)C(=O)O] | 5-(7-(((S)-1-(4-chlorophenyl)ethyl)carbamoyl)-3-3-(4-fluorophenyl)quinoxalin-2-yl)-2-methylpentanoic acid | 520 |
| 429 | 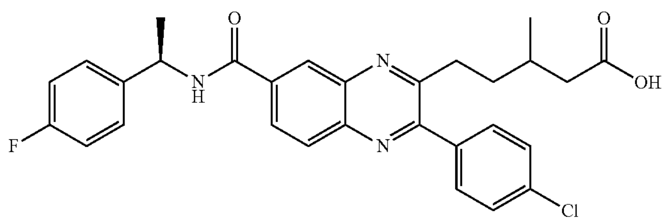 [SMILES: CC(CCc1nc2cc(C(=O)N[C@H](C)c3ccc(F)cc3)ccc2nc1-c1ccc(Cl)cc1)CC(=O)O] | 5-(3-(4-chlorophenyl)-7-(((R)-1-(4-fluorophenyl)ethyl)carbamoyl)quinoxalin-2-yl)-3-methylpentanoic acid | 520 |
| 430 | 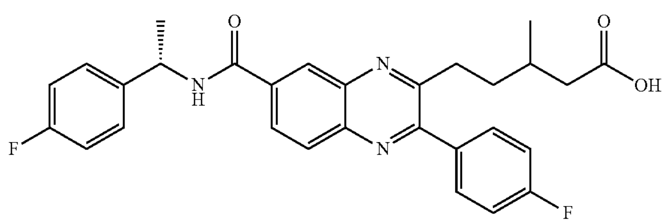 [SMILES: CC(CCc1nc2cc(C(=O)N[C@@H](C)c3ccc(F)cc3)ccc2nc1-c1ccc(F)cc1)CC(=O)O] | 5-(3-(4-fluorophenyl)-7-(((S)-1-(4-fluorophenyl)ethyl)carbamoyl)quinoxalin-2-yl)-3-methylpentanoic acid | 504 |
| 431 | 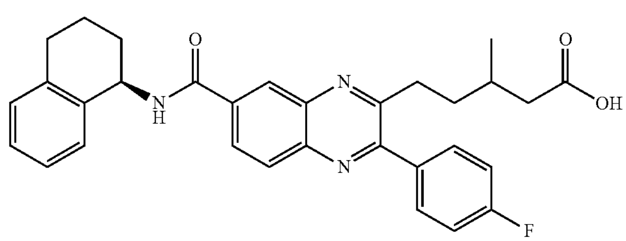 | 5-(3-(4-fluorophenyl)-7-(((R)-1,2,3,4-tetrahydronaphthalen-1-yl)carbamoyl)quinoxalin-2-yl)-3-methylpentanoic acid | 512 |
| 432 | 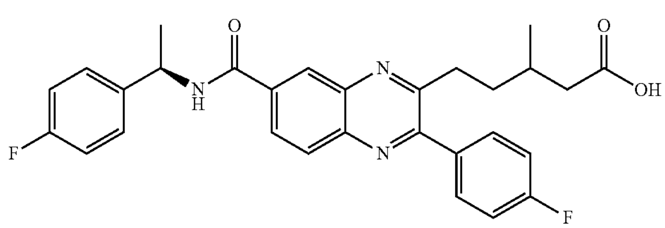 [SMILES: CC(CCc1nc2cc(C(=O)N[C@H](C)c3ccc(F)cc3)ccc2nc1-c1ccc(F)cc1)CC(=O)O] | 5-(3-(4-fluorophenyl)-7-(((R)-1-(4-fluorophenyl)ethyl)carbamoyl)quinoxalin-2-yl)-3-methylpentanoic acid | 504 |
| 433 | 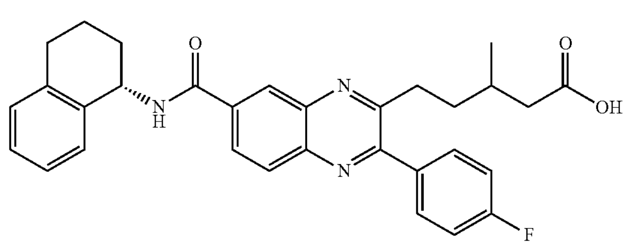 [SMILES: CC(CCc1nc2cc(C(=O)N[C@H]3CCCc4ccccc43)ccc2nc1-c1ccc(F)cc1)CC(=O)O] | 5-(3-(4-fluorophenyl)-7-(((S)-1,2,3,4-tetrahydronaphthalen-1-yl)carbamoyl)quinoxalin-2-yl)-3-methylpentanoic acid | 512 |

-continued

| No. | Structure | Name | M + H |
|---|---|---|---|
| 434 | 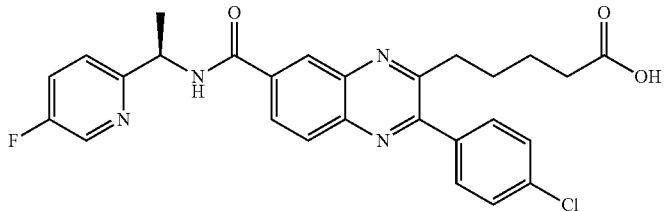 | (R)-5-(3-(4-chlorophenyl)-7-((1-(5-fluoropyridin-2-yl)ethyl)carbamoyl)quinoxalin-2-yl)pentanoic acid | 507 |
| 435 | 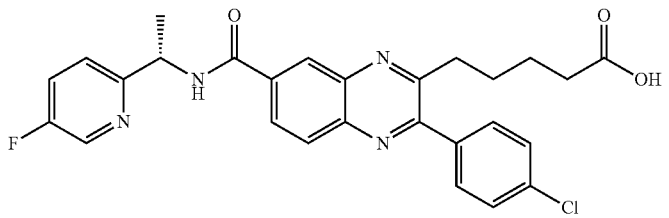 | (S)-5-(3-(4-chlorophenyl)-7-((1-(5-fluoropyridin-2-yl)ethyl)carbamoyl)quinoxalin-2-yl)pentanoic acid | 507 |
| 436 | 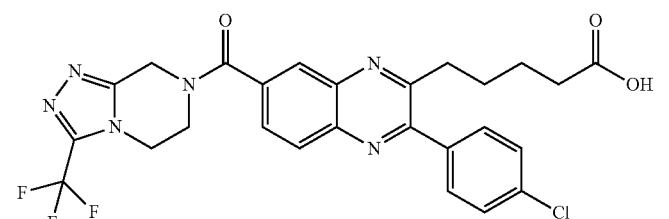 | 5-(3-(4-chlorophenyl)-7-(3-(trifluoromethyl)-5,6,7,8-tetrahydro-[1,2,4]triazolo[4,3-a]pyrazine-7-carbonyl)quinoxalin-2-yl)pentanoic acid | 559 |
| 437 | 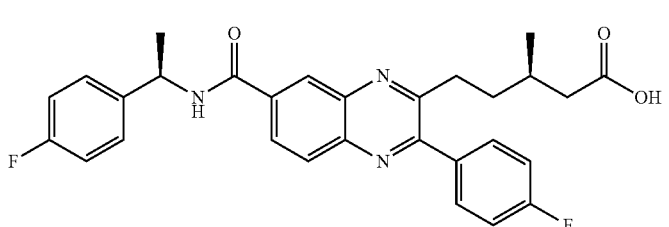 | (R)-5-(3-(4-fluorophenyl)-7-(((R)-1-(4-fluorophenyl)ethyl)carbamoyl)quinoxalin-2-yl)-3-methylpentanoic acid | 504 |
| 438 | 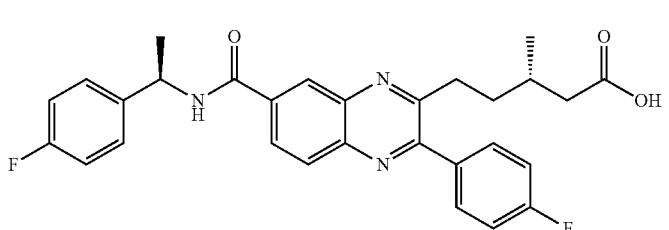 | (S)-5-(3-(4-fluorophenyl)-7-(((R)-1-(4- fluorophenyl)ethyl)carbamoyl)quinoxalin-2-yl)-3-methylpentanoic acid | 504 |
| 439 | 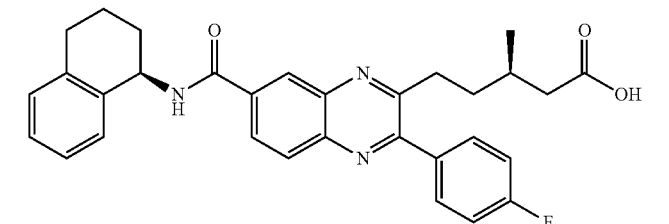 | (R)-5-(3-(4-fluorophenyl)-7-(((R)-1,2,3,4-tetrahydronaphthalen-1-yl)carbamoyl)quinoxalin-2-yl)-3-methylpentanoic acid | 512 |

| No. | Structure | Name | M + H |
|---|---|---|---|
| 440 | 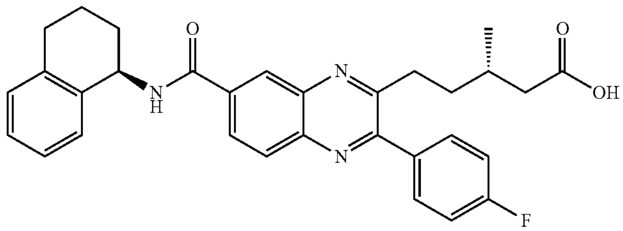 [SMILES: C[C@@H](CCc1nc2cc(C(=O)N[C@@H]3CCCc4ccccc43)ccc2nc1-c1ccc(F)cc1)CC(=O)O] | (S)-5-(3-(4-fluorophenyl)-7-(((R)-1,2,3,4-tetrahydronaphthalen-1-yl)carbamoyl)quinoxalin-2-yl)-3-methylpentanoic acid | 512 |
| 441 | 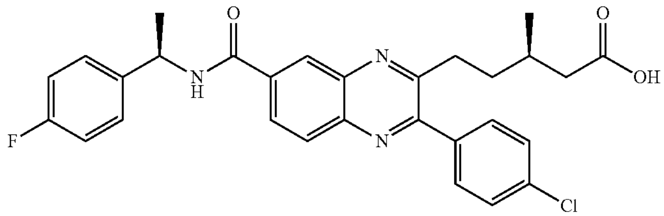 [SMILES: C[C@H](CCc1nc2cc(C(=O)N[C@H](C)c3ccc(F)cc3)ccc2nc1-c1ccc(Cl)cc1)CC(=O)O] | (R)-5-(3-(4-chlorophenyl)-7-(((R)-1-(4-fluorophenyl)ethyl)carbamoyl)quinoxalin-2-yl)-3-methylpentanoic acid | 520 |
| 442 | 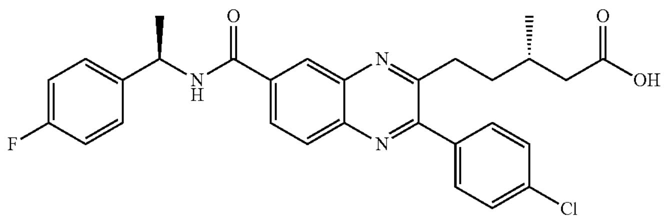 | (S)-5-(3-(4-chlorophenyl)-fluorophenyl)ethyl)carbamoyl)quinoxalin-2-yl)-3-methylpentanoic acid | 520 |
| 443 | 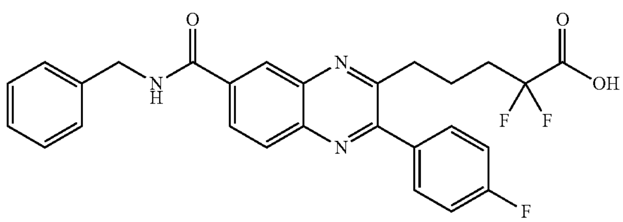 [SMILES: O=C(NCc1ccccc1)c1ccc2nc(-c3ccc(F)cc3)c(CCCC(F)(F)C(=O)O)nc2c1] | 5-(7-(benzylcarbamoyl)-3-(4-fluorophenyl)quinoxalin-2-yl)-2,2-difluoropentanoic acid | 494 |
| 444 | 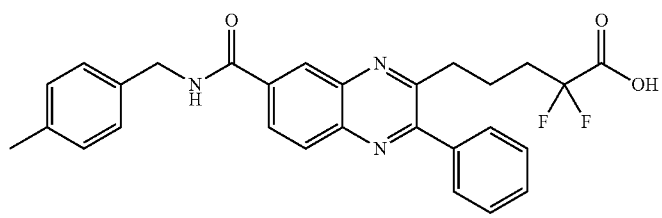 [SMILES: Cc1ccc(CNC(=O)c2ccc3nc(-c4ccccc4)c(CCCC(F)(F)C(=O)O)nc3c2)cc1] | 2,2-difluoro-5-(7-(4-((4-methylbenzyl)carbamoyl)-3-phenylquinoxalin-2-yl)pentanoic acid | 490 |
| 445 | 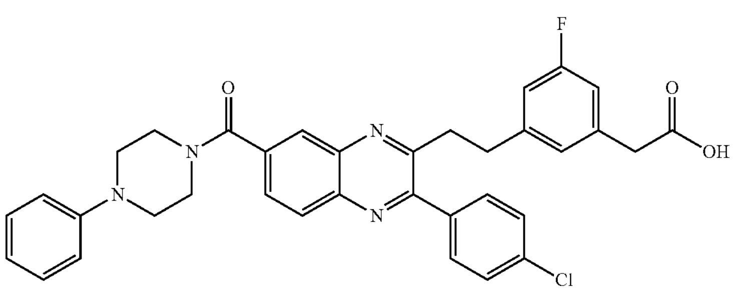 [SMILES: O=C(O)Cc1cc(F)cc(CCc2nc3cc(C(=O)N4CCN(c5ccccc5)CC4)ccc3nc2-c2ccc(Cl)cc2)c1] | 2-(3-(4-chlorophenyl)-7-(4-phenylpiperazine-1-carbonyl)quinoxalin-2-yl)ethyl)-5-fluorophenyl)acetic acid | 610 |

| No. | Structure | Name | M + H |
|---|---|---|---|
| 446 | 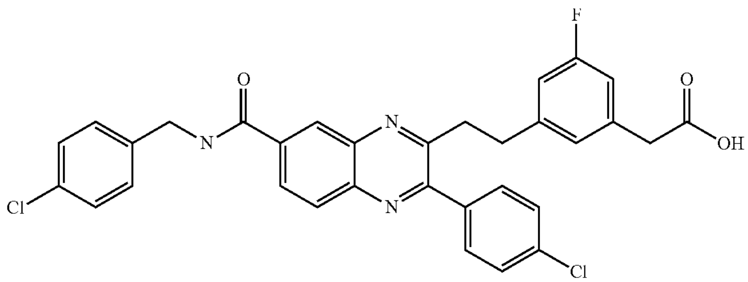 [SMILES: O=C(O)Cc1cc(F)cc(CCc2nc3cc(C(=O)NCc4ccc(Cl)cc4)ccc3nc2-c2ccc(Cl)cc2)c1] | 2-(3-(2-(7-((4-chlorobenzyl)carbamoyl)-3-(4-chlorophenyl)quinoxalin-2-yl)ethyl)-5-fluorophenyl)acetic acid | 589 |
| 447 | 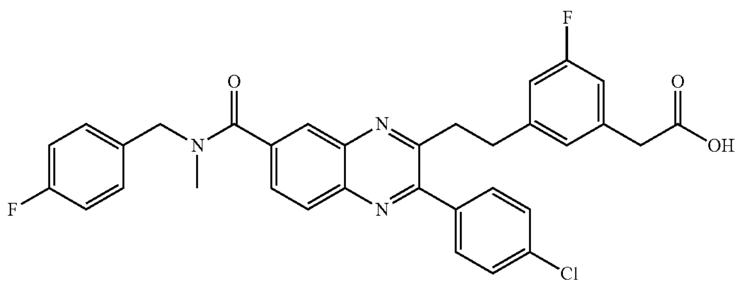 [SMILES: CN(Cc1ccc(F)cc1)C(=O)c1ccc2nc(-c3ccc(Cl)cc3)c(CCc3cc(F)cc(CC(=O)O)c3)nc2c1] | 2-(3-(2-(3-(4-chlorophenyl)-7-((4-fluorobenzyl)(methyl)carbamoyl)quinoxalin-2-yl)ethyl)-5-fluorophenyl)acetic acid | 586 |
| 448 | 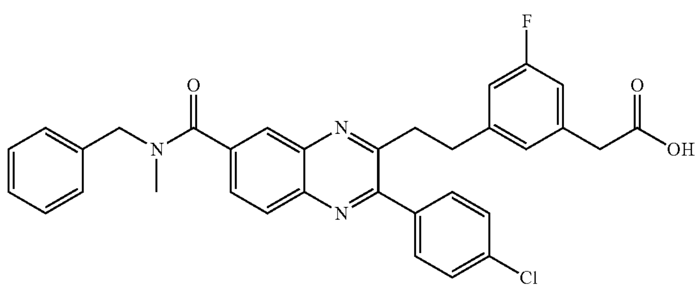 [SMILES: CN(Cc1ccccc1)C(=O)c1ccc2nc(-c3ccc(Cl)cc3)c(CCc3cc(F)cc(CC(=O)O)c3)nc2c1] | 2-(3-(2-(7-(benzyl(methyl)carbamoyl)-3-(4-chlorophenyl)quinoxalin-2-yl)ethyl)-5-fluorophenyl)acetic acid | 568 |
| 449 | 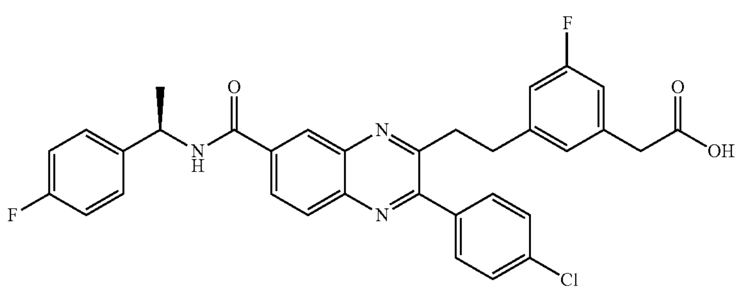 [SMILES: C[C@@H](NC(=O)c1ccc2nc(-c3ccc(Cl)cc3)c(CCc3cc(F)cc(CC(=O)O)c3)nc2c1)c1ccc(F)cc1] | (R)-2-(3-2-(3-(4-chlorophenyl)-7-(1-(4-fluorophenyl)ethyl)carbamoyl)quinoxalin-2-yl)ethyl)-5-fluorophenyl)acetic acid | 586 |
| 450 | 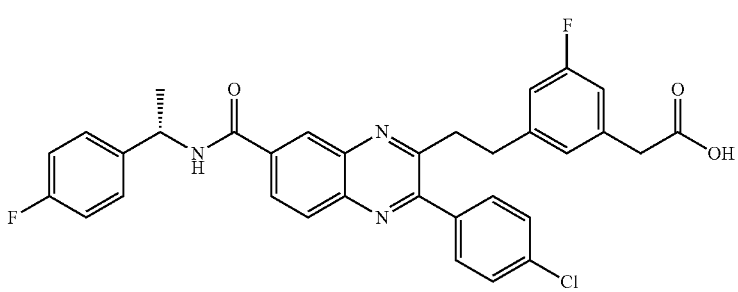 [SMILES: C[C@H](NC(=O)c1ccc2nc(-c3ccc(Cl)cc3)c(CCc3cc(F)cc(CC(=O)O)c3)nc2c1)c1ccc(F)cc1] | (S)-2-(3-(2-(3-(4-chlorophenyl)-7-((1-(4-fluorophenyl)ethyl)carbamoyl)quinoxalin-2-yl)ethyl)-5-fluorophenyl)acetic acid | 586 |

-continued

| No. | Structure | Name | M + H |
|---|---|---|---|
| 451 | 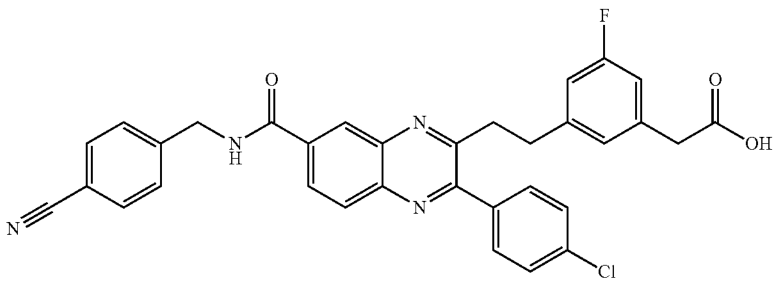 [SMILES: N#Cc1ccc(CNC(=O)c2ccc3nc(-c4ccc(Cl)cc4)c(CCc4cc(F)cc(CC(=O)O)c4)nc3c2)cc1] | 2-(3-(2-(3-(4-chlorophenyl)-7-(((4-cyanobenzyl)carbamoyl)quinoxalin-2-yl)ethyl)-5-fluorophenyl)acetio acid | 579 |
| 452 | 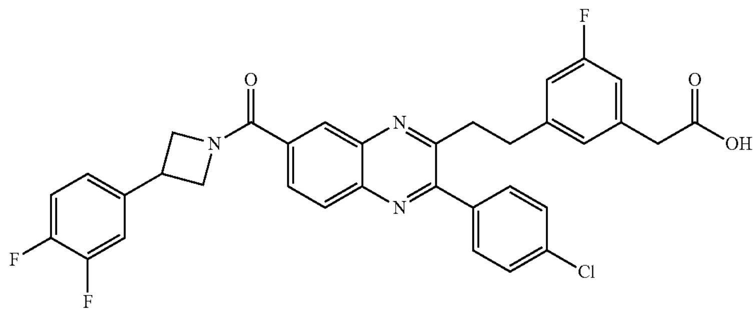 [SMILES: O=C(O)Cc1cc(F)cc(CCc2nc3cc(C(=O)N4CC(c5ccc(F)c(F)c5)C4)ccc3nc2-c2ccc(Cl)cc2)c1] | 2-(3-(2-(3-(4-chlorophenyl)-7-(3-(3,4-difluorophenyl)azetidine-1-carbonyl)quinoxalin-2-yl)ethyl)-5-fluorophenyl)aceticacid | 616 |
| 453 | 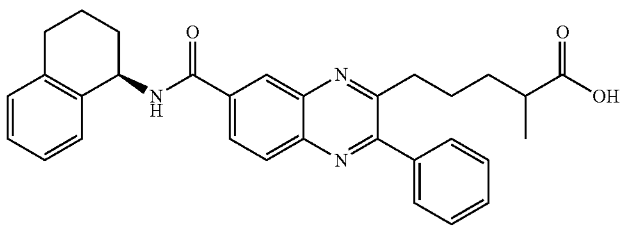 [SMILES: CC(CCCc1nc2cc(C(=O)N[C@@H]3CCCc4ccccc43)ccc2nc1-c1ccccc1)C(=O)O] | 2-methyl-5-(3-phenyl-7-(((R)-1-yl)carbamoyl)quinoxalin-2-yl)pentanoic acid | 494 |
| 454 | 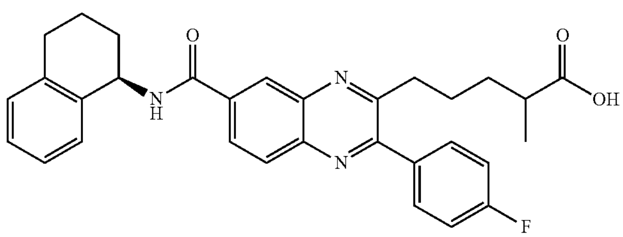 [SMILES: CC(CCCc1nc2cc(C(=O)N[C@@H]3CCCc4ccccc43)ccc2nc1-c1ccc(F)cc1)C(=O)O] | 5-(3-(4-fluorophenyl)-7-(((R)-1,2,3,4-tetrahydronaphthalen-1-yl)carbamoyl)quinoxalin-2-yl)-2-methy)pentanoic acid | 512 |
| 455 | 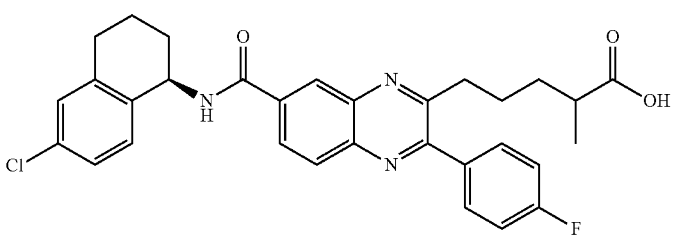 [SMILES: CC(CCCc1nc2cc(C(=O)N[C@@H]3CCCc4cc(Cl)ccc43)ccc2nc1-c1ccc(F)cc1)C(=O)O] | 5-(7-(((R)-6-chloro-1,2,3,4-tetrahydronaphthalen-1-yl)carbamoyl)-3-(4-fluorophenyl)quinoxalin-2-yl)-2-methylpentanoic acid | 546 |
| 456 | 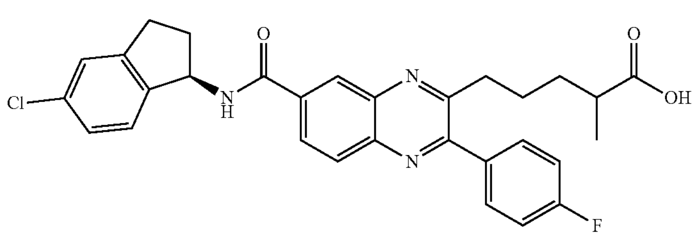 [SMILES: CC(CCCc1nc2cc(C(=O)N[C@@H]3CCc4cc(Cl)ccc43)ccc2nc1-c1ccc(F)cc1)C(=O)O] | 5-(7-(((R)-5-chloro-2,3-dihydro-1H-inden-1-yl)carbamoyl)-3-(4-fluorophenyl)quinoxalin-2-yl)-2-methylpentanoic acid | 532 |

-continued

| No. | Structure | Name | M + H |
|---|---|---|---|
| 457 | 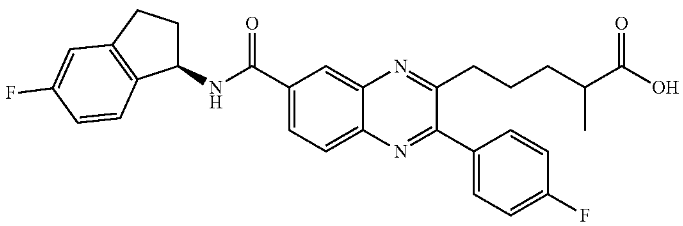 [SMILES: CC(CCCc1nc2cc(C(=O)N[C@@H]3CCc4cc(F)ccc43)ccc2nc1-c1ccc(F)cc1)C(=O)O] | 5-(7-(((R)-5-fluoro-2,3-dihydro-1H-inden-1-yl)carbamoyl)-3-(4-fluorophenyl)quinoxalin-2-yl)-2-methylpentanoic acid | 516 |
| 458 | 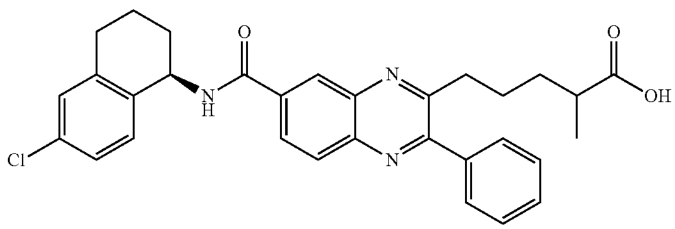 [SMILES: CC(CCCc1nc2cc(C(=O)N[C@@H]3CCCc4cc(Cl)ccc43)ccc2nc1-c1ccccc1)C(=O)O] | 5-(7-(((R)-6-chloro-1,2,3,4-tetrahydronaphthalen-1-yl)carbamoyl)-3-phenylquinoxalin-2-yl)-2-methylpentanoic acid | 528 |
| 459 | 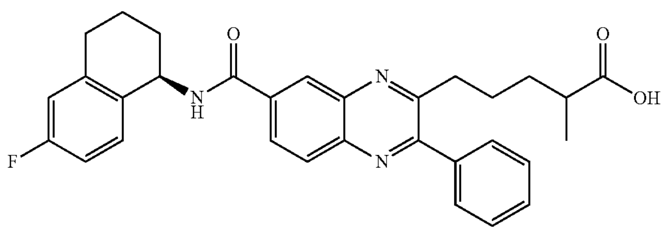 [SMILES: CC(CCCc1nc2cc(C(=O)N[C@@H]3CCCc4cc(F)ccc43)ccc2nc1-c1ccccc1)C(=O)O] | 5-(7-(((R)-6-fluoro-1,2,3,4-tetrahydronaphthalen-1-yl)carbamoyl)-3-phenylquinoxalin-2-yl)-2-methylpentanoic acid | 512 |
| 460 | 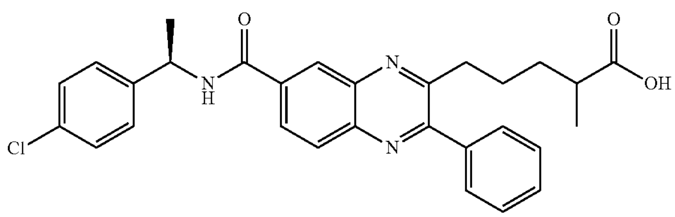 [SMILES: CC(CCCc1nc2cc(C(=O)N[C@H](C)c3ccc(Cl)cc3)ccc2nc1-c1ccccc1)C(=O)O] | 5-(7-(((R)-1-(4-chlorophenyl)ethyl)carbamoyl)-3-3-phenylquinoxalin-2-yl)-2-methylpentanoic acid | 502 |
| 461 | 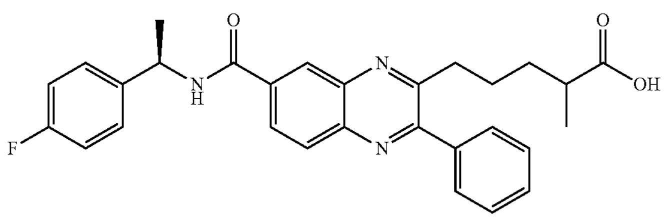 [SMILES: CC(CCCc1nc2cc(C(=O)N[C@H](C)c3ccc(F)cc3)ccc2nc1-c1ccccc1)C(=O)O] | 5-(7-(((R)-1-(4-fluorophenyl)ethyl)carbamoyl)-3-phenylquinoxalin-2-yl)-2-methylpentanoic acid | 486 |
| 462 | 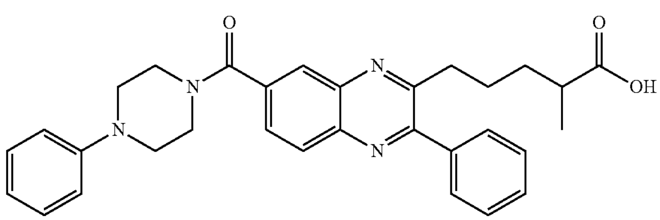 [SMILES: CC(CCCc1nc2cc(C(=O)N3CCN(c4ccccc4)CC3)ccc2nc1-c1ccccc1)C(=O)O] | 2-methyl-5-(3-phenyl-7-(4-phenylpiperazine-1-carbonyl)quinoxalin-2-yl)pentanoic acid | 509 |
| 463 | 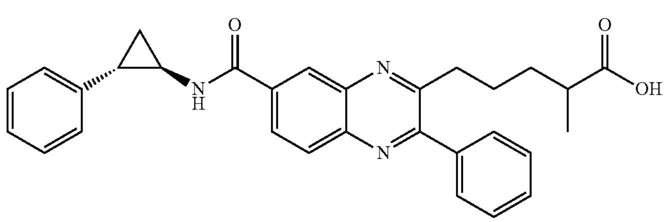 [SMILES: CC(CCCc1nc2cc(C(=O)N[C@@H]3C[C@H]3c3ccccc3)ccc2nc1-c1ccccc1)C(=O)O] | 2-methyl-5-(3-phenyl-7-((((1R,2S)-2-phenylcyclopropyl)carbamoyl)quinoxalin-2-yl)pentanoic acid | 480 |

US 9,469,615 B2

-continued

| No. | Structure | Name | M + H |
|---|---|---|---|
| 464 | 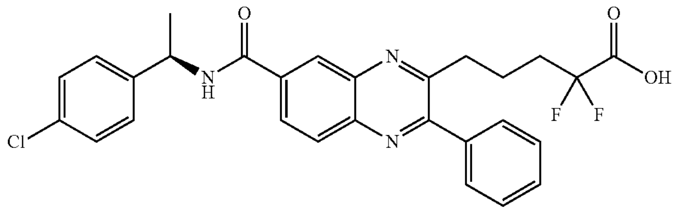 [SMILES: C[C@@H](NC(=O)c1ccc2nc(-c3ccccc3)c(CCCC(F)(F)C(=O)O)nc2c1)c1ccc(Cl)cc1] | (R)-5-(7-((1-(4-chlorophenyl)ethyl)carbamoyl)-3-phenylquinoxalin-2-yl)-2,2-difluoropentanoic acid | 524 |
| 465 | 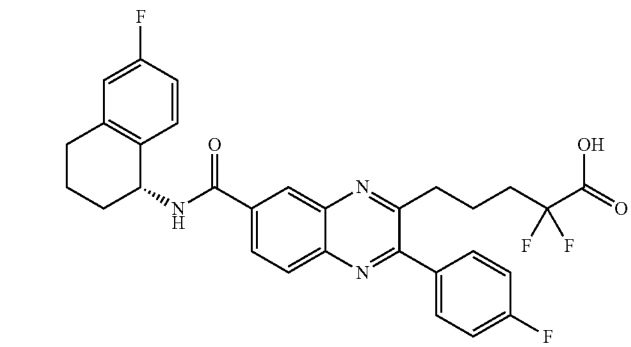 [SMILES: O=C(N[C@@H]1CCCc2cc(F)ccc21)c1ccc2nc(-c3ccc(F)cc3)c(CCCC(F)(F)C(=O)O)nc2c1] | (R)-2,2-difluoro-5-(7-((6-fluoro-1,2,3,4-tetrahydronaphthalen-1-yl)carbamoyl)-3-(4-fluorophenyl)quinoxalin-2-yl)pentanoic acid | 552 |
| 466 | 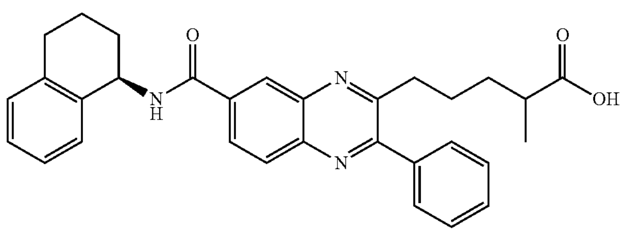 [SMILES: CC(CCCc1nc2cc(C(=O)N[C@@H]3CCCc4ccccc43)ccc2nc1-c1ccccc1)C(=O)O] | (R)-2,2-difluoro-5-(3-phenyl-7-((1,2,3,4-tetahydronaphthalen-1-yl)carbamoyl)quinoxalin-2-yl)pentanoic acid | 516 |
| 467 | 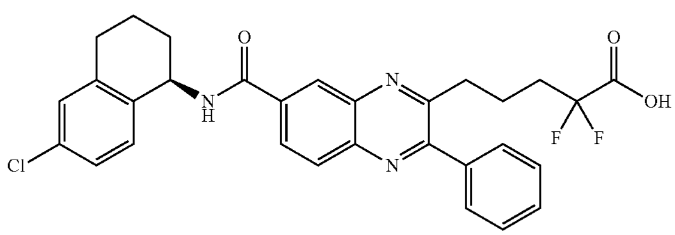 [SMILES: O=C(N[C@@H]1CCCc2cc(Cl)ccc21)c1ccc2nc(-c3ccccc3)c(CCCC(F)(F)C(=O)O)nc2c1] | (R)-5-(7-((6-chloro-1,2,3,4-tetrahydronaphthalen-1-yl)carbamoyl)-3-phenylquinoxalin-2-yl)-2,2-difluoropentanoic acid | 550 |
| 468 | 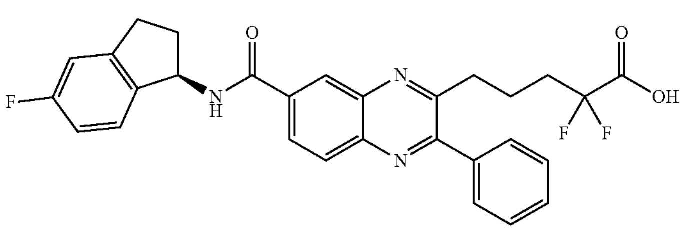 [SMILES: O=C(N[C@@H]1CCc2cc(F)ccc21)c1ccc2nc(-c3ccccc3)c(CCCC(F)(F)C(=O)O)nc2c1] | (R)-2,2-difluoro-5-(7-((5-fluoro-2,3-dihydro-1H-inden-1-yl)carbamoyl)-3-phenylquinoxalin-2-yl)pentanoic acid | 520 |

| No. | Structure | Name | M + H |
|---|---|---|---|
| 469 | 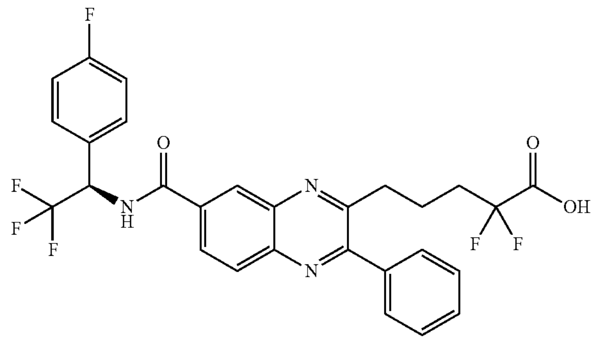 [SMILES: O=C(N[C@H](c1ccc(F)cc1)C(F)(F)F)c1ccc2nc(-c3ccccc3)c(CCCC(F)(F)C(=O)O)nc2c1] | (R)-2,2-difluoro-5-(3-phenyl-7-((2,2,2-trifluoro-1-(4-fluorophenyl)ethyl)carbamoyl)quinoxalin-2-yl)pentanoic acid | 562 |
| 470 | 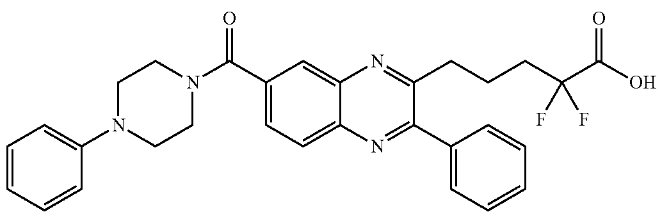 [SMILES: O=C(c1ccc2nc(-c3ccccc3)c(CCCC(F)(F)C(=O)O)nc2c1)N1CCN(c2ccccc2)CC1] | 2,2-difluoro-5-(3-phenyl-7-(4-phenylpiperazine-1-carbonyl)quinoxalin-2-yl)pentanoic acid | 531 |
| 471 | 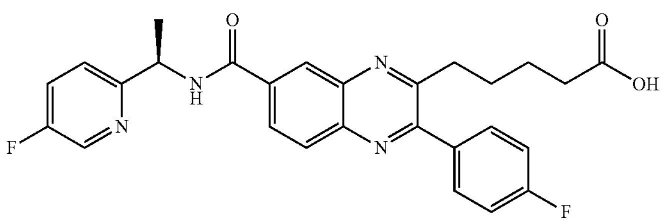 [SMILES: C[C@@H](NC(=O)c1ccc2nc(-c3ccc(F)cc3)c(CCCCC(=O)O)nc2c1)c1ccc(F)cn1] | (R)-5-(3-(4-fluorophenyl)-7-((1-(5-fluoropyridin-2-yl)ethyl)carbamoyl)quinoxalin-2-yl)pentanoic acid | 491 |
| 472 | 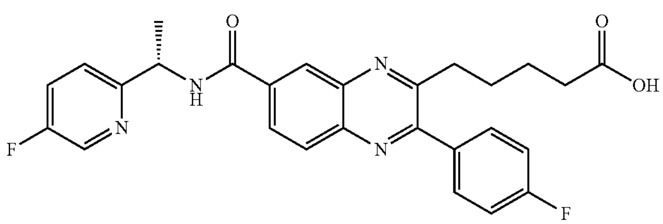 [SMILES: C[C@H](NC(=O)c1ccc2nc(-c3ccc(F)cc3)c(CCCCC(=O)O)nc2c1)c1ccc(F)cn1] | (S)-5-(3-(4-fluorophenyl)-7-((1-(5-fluoropyridin-2-yl)ethyl)carbamoyl)quinoxalin-2-yl)pentanoic acid | 491 |
| 473 | 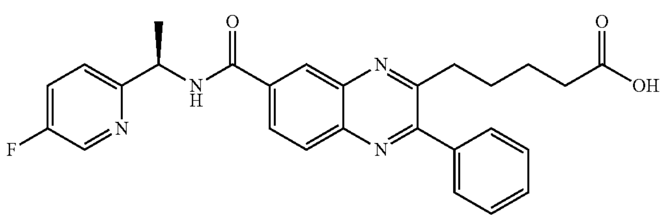 [SMILES: C[C@@H](NC(=O)c1ccc2nc(-c3ccccc3)c(CCCCC(=O)O)nc2c1)c1ccc(F)cn1] | (R)-5-(7-((1-(5-fluoropyridin-2-yl)ethyl)carbamoyl)-3-phenylquinoxalin-2-yl)pentanoic acid | 473 |
| 474 | 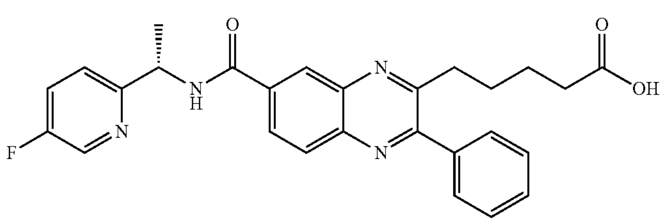 [SMILES: C[C@H](NC(=O)c1ccc2nc(-c3ccccc3)c(CCCCC(=O)O)nc2c1)c1ccc(F)cn1] | (S)-5-(7-((1-(5-fluoropyridin-2-yl)ethyl)carbamoyl)-3-phenylquinoxalin-2-yl)pentanoic acid | 473 |

-continued

| No. | Structure | Name | M + H |
|---|---|---|---|
| 475 | 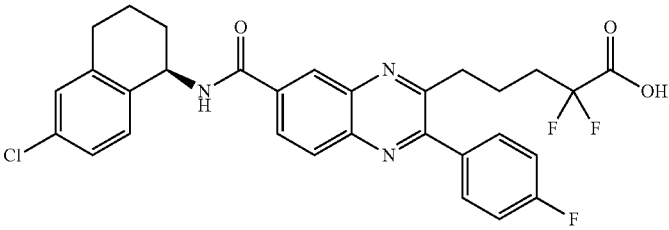 [SMILES: O=C(N[C@@H]1CCCc2cc(Cl)ccc21)c1ccc2nc(-c3ccc(F)cc3)c(CCCC(F)(F)C(=O)O)nc2c1] | (R)-5-(7-((6-chloro-1,2,3,4-tetrahydronaphthalen-1-yl)carbamoyl)-3-(4-fluorophenyl)quinoxalin-2-yl)-2,2-difluoropentanoic acid | 568 |
| 476 | 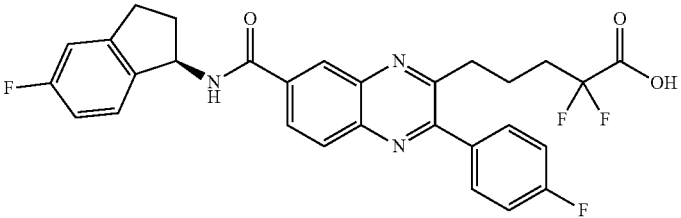 [SMILES: O=C(N[C@@H]1CCc2cc(F)ccc21)c1ccc2nc(-c3ccc(F)cc3)c(CCCC(F)(F)C(=O)O)nc2c1] | (R)-2,2-difluoro-5-(7-((5-fluoro-2,3-dihydro-1H-inden-1-yl)carbamoyl)-3-(4-fluorophenyl)quinoxalin-2-yl)pentanoic acid | 538 |
| 477 | 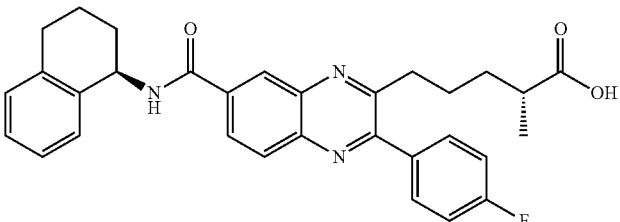 | (R)-5-(3-(4-fluorophenyl)-7-(((R)-1,2,3,4-tetrahydronaphthalen-1-yl)carbamoyl)quinoxalin-2-yl)-2-methylpentanoic acid | 512 |
| 478 | 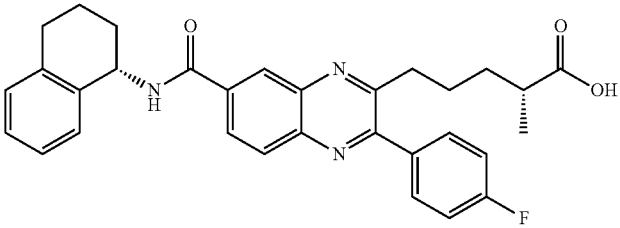 [SMILES: C[C@H](CCCc1nc2cc(C(=O)N[C@H]3CCCc4ccccc43)ccc2nc1-c1ccc(F)cc1)C(=O)O] | (R)-5-(3-(4-fluorophenyl)-7-(((S)-1,2,3,4-tetrahydronaphthalen-1-yl)carbamoyl)quinoxalin-2-yl)-2-methylpentanoic acid | 512 |
| 479 | 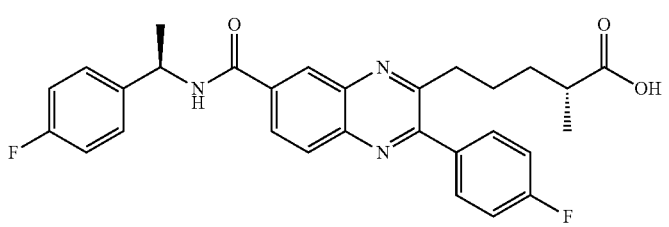 [SMILES: C[C@H](CCCc1nc2cc(C(=O)N[C@H](C)c3ccc(F)cc3)ccc2nc1-c1ccc(F)cc1)C(=O)O] | (R)-5-(3-(4-fluorophenyl)-7-fluorophenyl)ethyl)carbamoyl)quinoxalin-2-yl)-2-methylpentanoic acid | 504 |
| 480 | 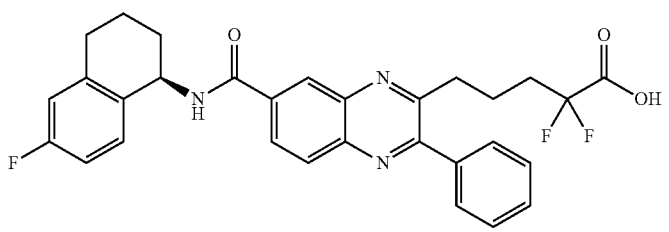 [SMILES: O=C(N[C@@H]1CCCc2cc(F)ccc21)c1ccc2nc(-c3ccccc3)c(CCCC(F)(F)C(=O)O)nc2c1] | (R)-2,2-difluoro-5-(7-((6-fluoro-1,2,3,4-tetrahydronaphthalen-1-yl)carbamoyl)-3-phenylquinoxalin-2-yl)pentanoic acid | 534 |

| No. | Structure | Name | M + H |
|-----|-----------|------|-------|
| 481 | 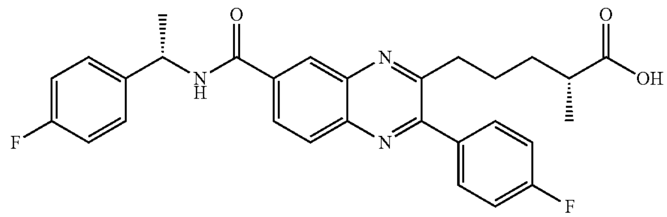 [SMILES: C[C@H](CCCc1nc2cc(C(=O)N[C@@H](C)c3ccc(F)cc3)ccc2nc1-c1ccc(F)cc1)C(=O)O] | (R)-5-(3-(4-fluorophenyl)-7-(((S)-1-(4-fluorophenyl)ethyl)carbamoyl)quinoxalin-2-yl)-2-methylpentanoic acid | 504 |
| 482 | 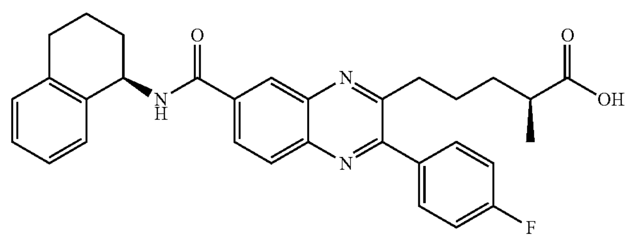 [SMILES: C[C@@H](CCCc1nc2cc(C(=O)N[C@@H]3CCCc4ccccc43)ccc2nc1-c1ccc(F)cc1)C(=O)O] | (S)-5-(3-(4-fluorophenyl)-7-(((R)-1,2,3,4-tetrahydronaphthalen-1-yl)carbamoyl)quinoxalin-2-yl)-2-methylpentanoic acid | 512 |
| 483 | 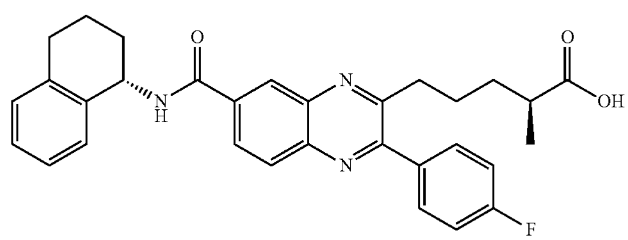 [SMILES: C[C@@H](CCCc1nc2cc(C(=O)N[C@H]3CCCc4ccccc43)ccc2nc1-c1ccc(F)cc1)C(=O)O] | (S)-5-(3-(4-fluorophenyl)-7-(((S)-1,2,3,4-tetrahydronaphthalen-1-yl)carbamoyl)quinoxalin-2-yl)-2-methylpentanoic acid | 512 |
| 484 | 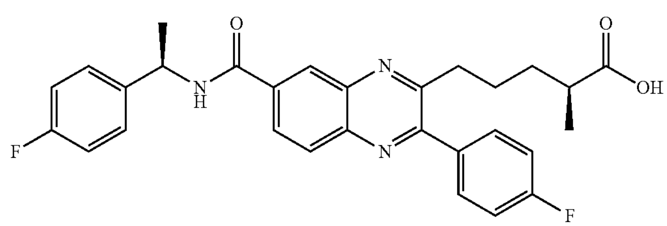 [SMILES: C[C@@H](CCCc1nc2cc(C(=O)N[C@H](C)c3ccc(F)cc3)ccc2nc1-c1ccc(F)cc1)C(=O)O] | (S)-5-(3-(4-fluorophenyl)-7-(((R)-1-(4-fluorophenyl)ethyl)carbamoyl)quinoxalin-2-yl)-2-methylpentanoic acid | 504 |
| 485 | 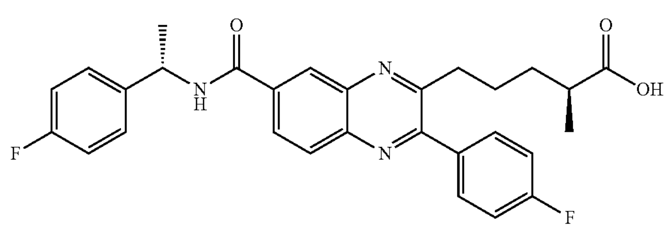 [SMILES: C[C@H](NC(=O)c1ccc2nc(-c3ccc(F)cc3)c(CCC[C@H](C)C(=O)O)nc2c1)c1ccc(F)cc1] | (S)-5-(3-(4-fluorophenyl)-7-(((S)-1-(4-fluorophenyl)ethyl)carbamoyl)quinoxalin-2-yl)-2-methylpentanoic acid | 504 |
| 486 | 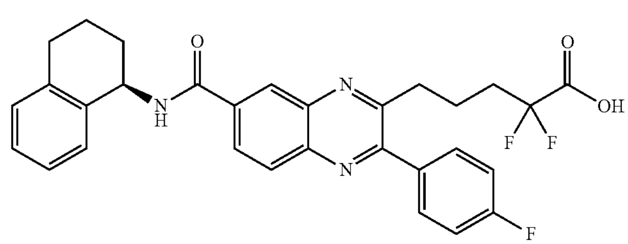 | (R)-2,2-difluoro-5-(3-(4-fluorophenyl)-7-((1,2,3,4-tetrahydronaphthalen-1-yl)carbamoyl)quinoxalin-2-yl)pentanoic acid | 534 |

-continued

| No. | Structure | Name | M + H |
|---|---|---|---|
| 487 | 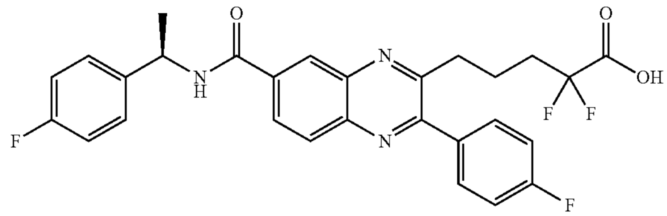 [SMILES: C[C@@H](NC(=O)c1ccc2nc(-c3ccc(F)cc3)c(CCCC(F)(F)C(=O)O)nc2c1)c1ccc(F)cc1] | (R)-2,2-difluoro-5-(3-(4-fluorophenyl)-7-((1-(4-fluorophenyl)ethyl)carbamoyl)quinoxalin-2-yl)pentanoic acid | 526 |
| 488 | 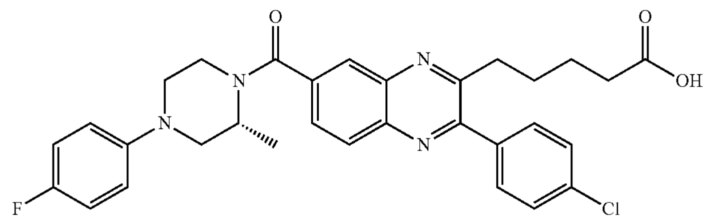 [SMILES: C[C@@H]1CN(c2ccc(F)cc2)CCN1C(=O)c1ccc2nc(-c3ccc(Cl)cc3)c(CCCCC(=O)O)nc2c1] | (R)-5-(3-(4-chlorophenyl)-7-(4-(4-fluorophenyl)-2-methylpiperazine-1-carbonyl)quinoxalin-2-yl)pentanoic acid | 561 |
| 489 | 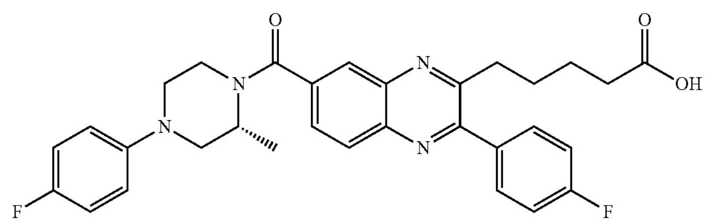 [SMILES: C[C@@H]1CN(c2ccc(F)cc2)CCN1C(=O)c1ccc2nc(-c3ccc(F)cc3)c(CCCCC(=O)O)nc2c1] | (R)-5-(3-(4-fluorophenyl)-7-(4-(4-fluorophenyl)-2-methylpiperazine-1-carbonyl)quinoxalin-2-yl)pentanoic acid | 545 |
| 490 | 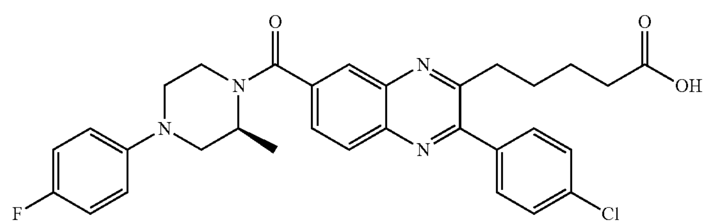 [SMILES: C[C@H]1CN(c2ccc(F)cc2)CCN1C(=O)c1ccc2nc(-c3ccc(Cl)cc3)c(CCCCC(=O)O)nc2c1] | (S)-5-(3-(4-chlorophenyl)-7-(4-(4-fluorophenyl)-2-methylpiperazine-1-carbonyl)quinoxalin-2-yl)pentanoic acid | 561 |
| 491 | 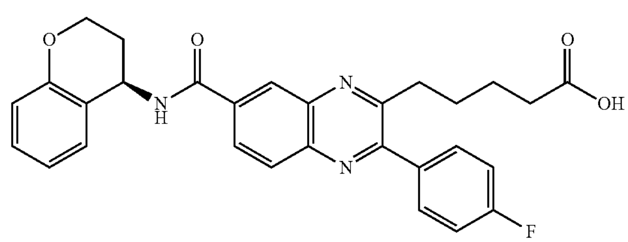 [SMILES: O=C(O)CCCCc1nc2cc(C(=O)N[C@@H]3CCOc4ccccc43)ccc2nc1-c1ccc(F)cc1] | (R)-5-(7-(chroman-4-ylcarbamoyl)-3-(4-fluorophenyl)quinoxalin-2-yl)pentanoic acid | 500 |
| 492 | 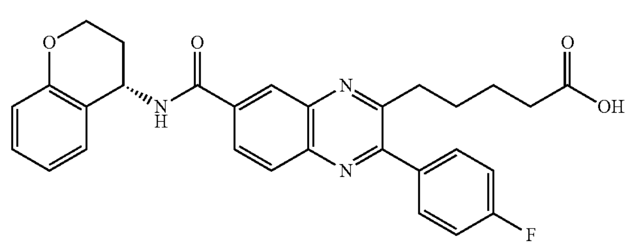 [SMILES: O=C(O)CCCCc1nc2cc(C(=O)N[C@H]3CCOc4ccccc43)ccc2nc1-c1ccc(F)cc1] | (S)-5-(7-(chroman-4-ylcarbamoyl)-3-(4-fluorophenyl)quinoxalin-2-yl)pentanoic acid | 500 |

-continued

| No. | Structure | Name | M + H |
|---|---|---|---|
| 493 | 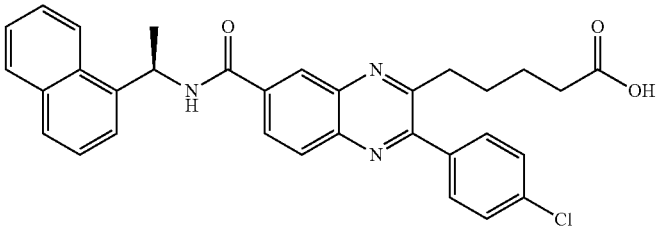 [SMILES: C[C@@H](NC(=O)c1ccc2nc(-c3ccc(Cl)cc3)c(CCCCC(=O)O)nc2c1)c1cccc2ccccc12] | (R)-5-(3-(4-chlorophenyl)-7-((1-(naphthalen-1-yl)ethyl)carbamoyl)quinoxalin-2-yl)pentanoic acid | 539 |
| 494 | 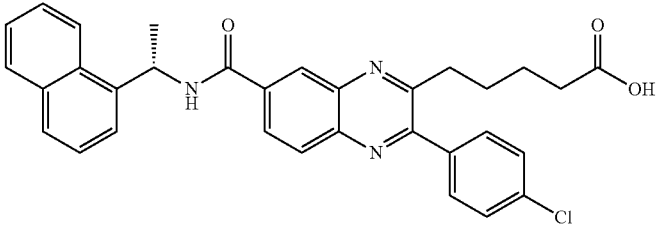 [SMILES: C[C@H](NC(=O)c1ccc2nc(-c3ccc(Cl)cc3)c(CCCCC(=O)O)nc2c1)c1cccc2ccccc12] | (S)-5-(3-(4-chlorophenyl)-7-((1-(naphthalen-1-yl)ethyl)carbamoyl)quinoxalin-2-yl)pentanoic acid | 539 |
| 495 | 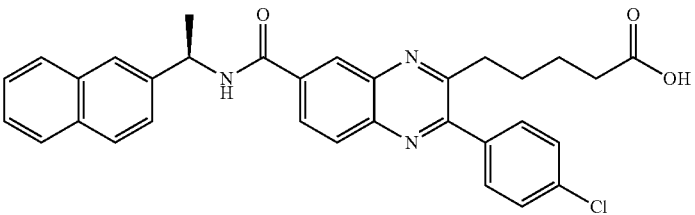 [SMILES: C[C@@H](NC(=O)c1ccc2nc(-c3ccc(Cl)cc3)c(CCCCC(=O)O)nc2c1)c1ccc2ccccc2c1] | (R)-5-(3-(4-chlorophenyl)-7-((1-(naphthalen-2-yl)ethyl)carbamoyl)quinoxalin-2-yl)pentanoic acid | 539 |
| 496 | 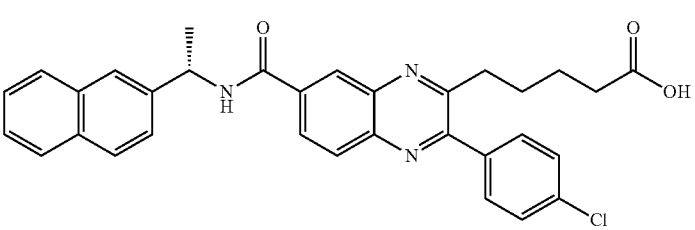 [SMILES: C[C@H](NC(=O)c1ccc2nc(-c3ccc(Cl)cc3)c(CCCCC(=O)O)nc2c1)c1ccc2ccccc2c1] | (S)-5-(3-(4-chlorophenyl)-7-((1-(naphthalen-2-yl)ethyl)carbamoyl)quinoxalin-2-yl)pentanoic acid | 539 |
| 497 | 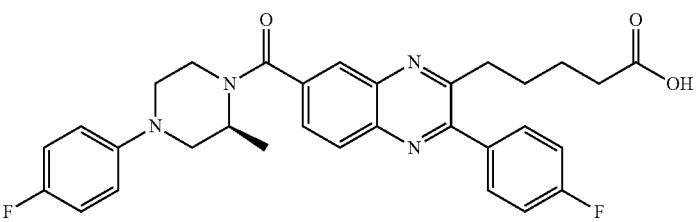 [SMILES: C[C@H]1CN(c2ccc(F)cc2)CCN1C(=O)c1ccc2nc(-c3ccc(F)cc3)c(CCCCC(=O)O)nc2c1] | (S)-5-(3-(4-fluoro-phenyl)-7-(4-(4-fluorophenyl)-2-methylpiperazine-1-carbonyl)quinoxalin-2-yl)pentanoic acid | 545 |
| 498 | 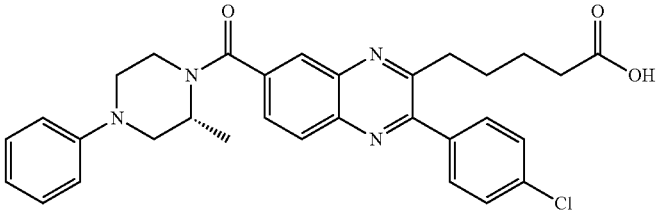 [SMILES: C[C@@H]1CN(c2ccccc2)CCN1C(=O)c1ccc2nc(-c3ccc(Cl)cc3)c(CCCCC(=O)O)nc2c1] | (R)-5-(3-(4-chlorophenyl)-7-(2-methyl-4-phenyl-piperazine-1-carbonyl)quinoxalin-2-yl)pentanoic acid | 543 |

-continued

| No. | Structure | Name | M + H |
|---|---|---|---|
| 499 | 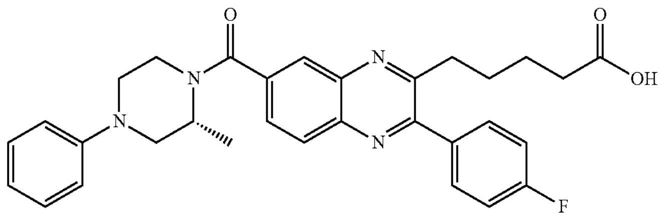 [SMILES: C[C@@H]1CN(c2ccccc2)CCN1C(=O)c1ccc2nc(-c3ccc(F)cc3)c(CCCCC(=O)O)nc2c1] | (R)-5-(3-(4-fluorophenyl)-7-(2-methyl-4-phenyl-piperazine-1-carbonyl)quinoxalin-2-yl)pentanoic acid | 527 |
| 500 | 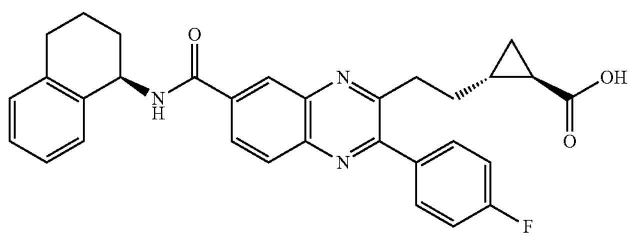 [SMILES: O=C(N[C@@H]1CCCc2ccccc21)c1ccc2nc(-c3ccc(F)cc3)c(CC[C@@H]3C[C@H]3C(=O)O)nc2c1] | (1R,2R)-2-(2-(3-(4-fluorophenyl)-7-(((R)-1,2,3,4-tetrahydronaphthalen-1-yl)carbamoyl)quinoxalin-2-yl)ethyl)cyclopropane-carboxylic acid | 510 |
| 501 | 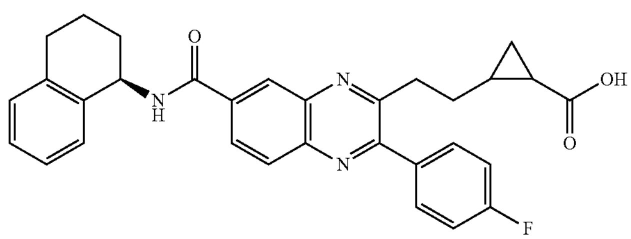 [SMILES: O=C(N[C@@H]1CCCc2ccccc21)c1ccc2nc(-c3ccc(F)cc3)c(CCC3CC3C(=O)O)nc2c1] | 2-(2-(3-(4-fluorophenyl)-7-(((R)-1,2,3,4-tetrahydronaphthalen-1-yl)carbamoyl)quinoxalin-2-yl)ethyl)cyclopropane-carboxylic acid | 510 |
| 502 | 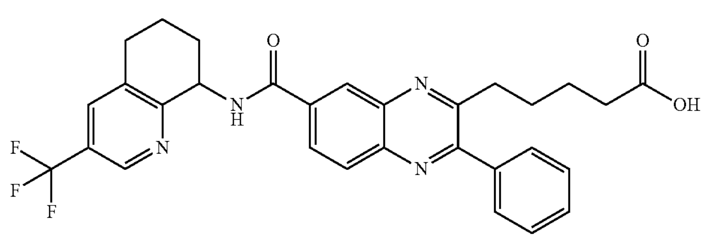 [SMILES: O=C(O)CCCCc1nc2cc(C(=O)NC3CCCc4cc(C(F)(F)F)cnc43)ccc2nc1-c1ccccc1] | 5-(3-phenyl-7-((3-(trifluoromethyl)-5,6,7,8-tetrahydroquinolin-8-yl)carbamoyl)quinoxalin-2-yl)pentanoic acid | 549 |
| 503 | 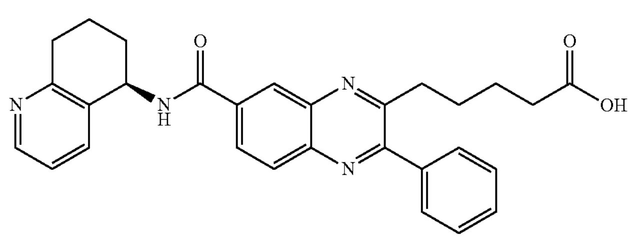 [SMILES: O=C(O)CCCCc1nc2cc(C(=O)N[C@@H]3CCCc4ncccc43)ccc2nc1-c1ccccc1] | (R)-5-(3-phenyl-7-((5,6,7,8-tetrahydroquinolin-5-yl)carbamoyl)quinoxalin-2-yl)pentanoic acid | 481 |
| 504 | 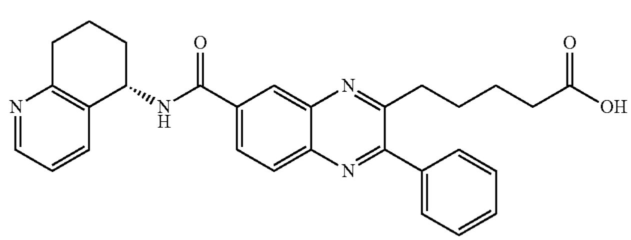 [SMILES: O=C(O)CCCCc1nc2cc(C(=O)N[C@H]3CCCc4ncccc43)ccc2nc1-c1ccccc1] | (S)-5-(3-phenyl-7-((5,6,7,8-tetrahydroquinolin-5-yl)carbamoyl)quinoxalin-2-yl)pentanoic acid | 481 |

-continued

| No. | Structure | Name | M + H |
|---|---|---|---|
| 505 | 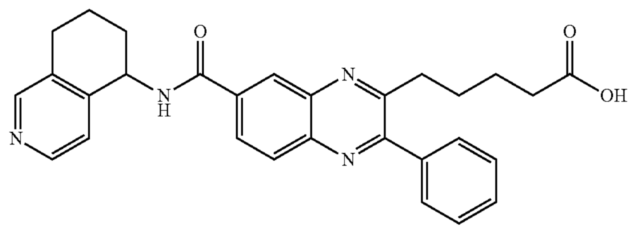 [SMILES: O=C(O)CCCCc1nc2cc(C(=O)NC3CCCc4cnccc43)ccc2nc1-c1ccccc1] | 5-(3-phenyl-7-((5,6,7,8-tetrahydroisoquinolin-5-yl)carbamoyl)quinoxalin-2-yl)pentanoic acid | 481 |
| 506 | 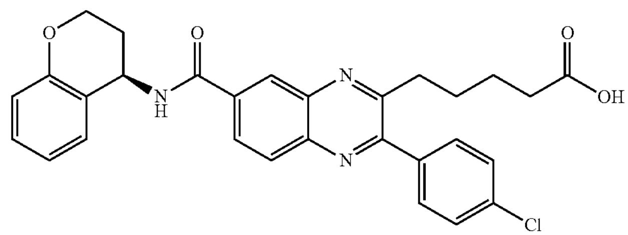 [SMILES: O=C(O)CCCCc1nc2cc(C(=O)N[C@@H]3CCOc4ccccc43)ccc2nc1-c1ccc(Cl)cc1] | (R)-5-(3-(4-chlorophenyl)-7-(chroman-4-ylcarbamoyl)quinoxalin-2-yl)pentanoic acid | 516 |
| 507 | 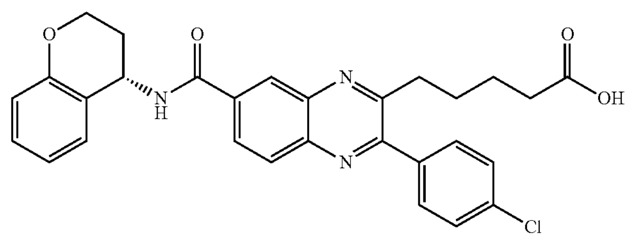 | (S)-5-(3-(4-chlorophenyl)-7-(chroman-4-ylcarbamoyl)quinoxalin-2-yl)pentanoic acid | 516.3 |
| 508 | 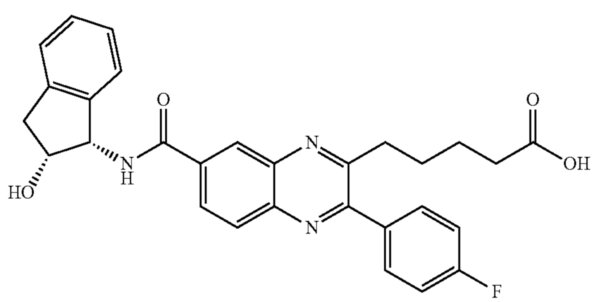 [SMILES: O=C(O)CCCCc1nc2cc(C(=O)N[C@H]3c4ccccc4C[C@H]3O)ccc2nc1-c1ccc(F)cc1] | 5-(3-(4-fluorophenyl)-7-((((1S,2R)-2-hydroxy-2,3-dihydro-1H-inden-1-yl)carbamoyl)quinoxalin-2-yl)pentanoic acid | 500 |
| 509 | 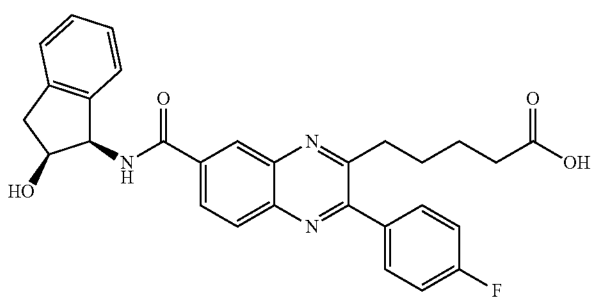 [SMILES: O=C(O)CCCCc1nc2cc(C(=O)N[C@@H]3c4ccccc4C[C@@H]3O)ccc2nc1-c1ccc(F)cc1] | 5-(3-(4-fluorophenyl)-7-((((1R,2S)-2-hydroxy-2,3-dihydro-1H-inden-1-yl)carbamoyl)quinoxalin-2-yl)pentanoic acid | 500 |
| 510 | 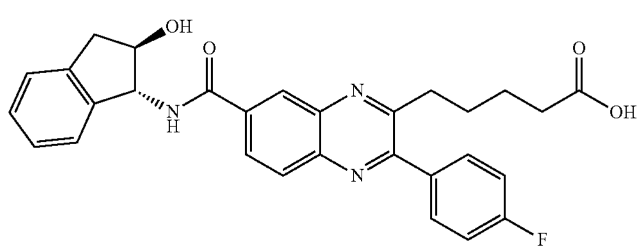 [SMILES: O=C(O)CCCCc1nc2cc(C(=O)N[C@@H]3c4ccccc4C[C@H]3O)ccc2nc1-c1ccc(F)cc1] | 5-(3-(4-fluorophenyl)-7-((((1R,2R)-2-hydroxy-2,3-dihydro-1H-inden-1-yl)carbamoyl)quinoxalin-2-yl)pentanoic acid | 500 |

| No. | Structure | Name | M + H |
|---|---|---|---|
| 511 | 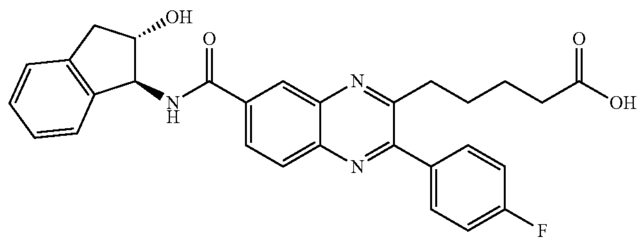 [SMILES: O=C(O)CCCCc1nc2cc(C(=O)N[C@H]3c4ccccc4C[C@@H]3O)ccc2nc1-c1ccc(F)cc1] | 5-(3-(4-fluorophenyl)-7-(((1S,2S)-2-hydroxy-2,3-dihydro-1H-inden-1-yl)carbamoyl)quinoxalin-2-yl)pentanoic acid | 500 |
| 512 | 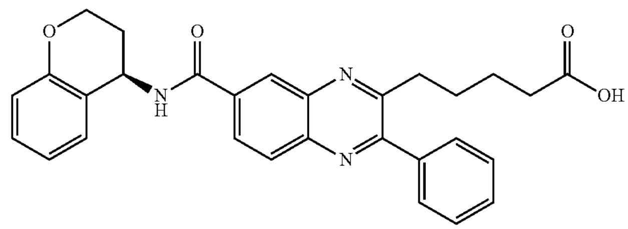 [SMILES: O=C(O)CCCCc1nc2cc(C(=O)N[C@@H]3CCOc4ccccc43)ccc2nc1-c1ccccc1] | (R)-5-(7-(chroman-4-ylcarbamoyl)-3-phenylquinoxalin-2-yl)pentanoic acid | 482 |
| 513 | 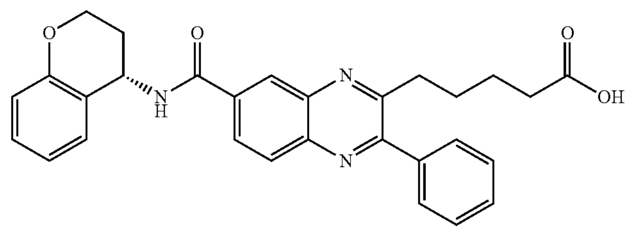 [SMILES: O=C(O)CCCCc1nc2cc(C(=O)N[C@H]3CCOc4ccccc43)ccc2nc1-c1ccccc1] | (S)-5-(7-(chroman-4-ylcarbamoyl)-3-phenylquinoxalin-2-yl)pentanoic acid | 482 |
| 514 | 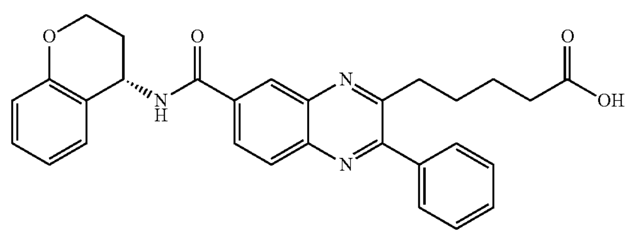 [SMILES: O=C(O)CCCCc1nc2cc(C(=O)N[C@H]3CCOc4ccccc43)ccc2nc1-c1ccccc1] | (S)-5-(3-(4-chlorophenyl)-7-(2-methyl-4-phenyl-piperazine-1-carbonyl)quinoxalin-2-yl)pentanoic acid | 543 |
| 515 | 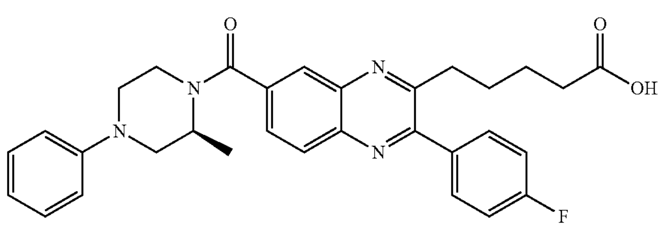 [SMILES: C[C@H]1CN(c2ccccc2)CCN1C(=O)c1ccc2nc(-c3ccc(F)cc3)c(CCCCC(=O)O)nc2c1] | (S)-5-(3-(4-fluorophenyl)-7-(2-methyl-4-phenylpiperazine-1-carbonyl)quinoxalin-2-yl)pentanoic acid | 527 |
| 516 | 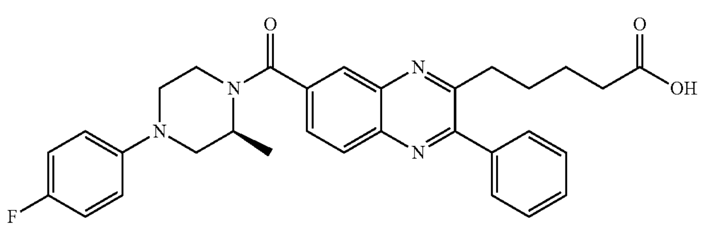 [SMILES: C[C@H]1CN(c2ccc(F)cc2)CCN1C(=O)c1ccc2nc(-c3ccccc3)c(CCCCC(=O)O)nc2c1] | (S)-5-(7-(4-(4-fluorophenyl)-2-methylpiperazine-1-carbonyl)-3-phenylquinoxalin-2-yl)pentanoic acid | 527 |

| No. | Structure | Name | M + H |
|---|---|---|---|
| 517 | 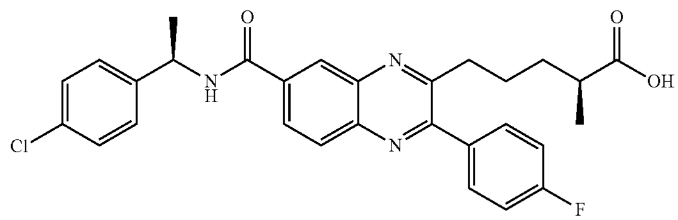 [SMILES: C[C@@H](CCCc1nc2cc(C(=O)N[C@H](C)c3ccc(Cl)cc3)ccc2nc1-c1ccc(F)cc1)C(=O)O] | (S)-5-(7-(((R)-1-(4-chlorophenyl)ethyl)carbamoyl)-3-(4-fluorophenyl)quinoxalin-2-yl)-2-methylpentanoic acid | 520 |
| 518 | 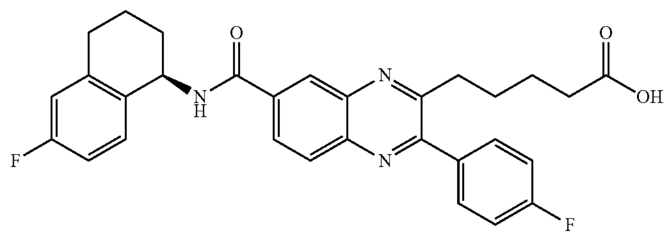 [SMILES: O=C(O)CCCCc1nc2cc(C(=O)N[C@@H]3CCCc4cc(F)ccc43)ccc2nc1-c1ccc(F)cc1] | (S)-5-(7-(((R)-6-fluoro-1,2,3,4-tetrahydronaphthalen-1-yl)carbamoyl)-3-(4-fluorophenyl)quinoxalin-2-yl)-2-methylpentanoic acid | 530 |
| 519 | 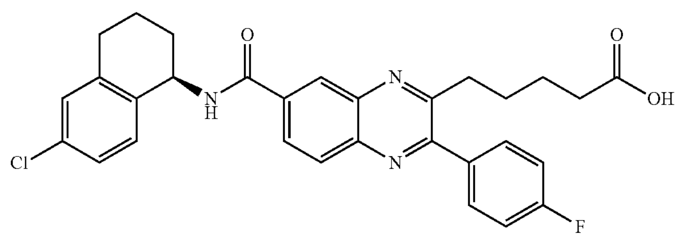 [SMILES: O=C(O)CCCCc1nc2cc(C(=O)N[C@@H]3CCCc4cc(Cl)ccc43)ccc2nc1-c1ccc(F)cc1] | (S)-5-(7-(((R)-6-chloro-1,2,3,4-tetrahydronaphthalen-1-yl)carbamoyl)-3-(4-fluorophenyl)quinoxalin-2-yl)-2-methylpentanoic acid | 546 |
| 520 | 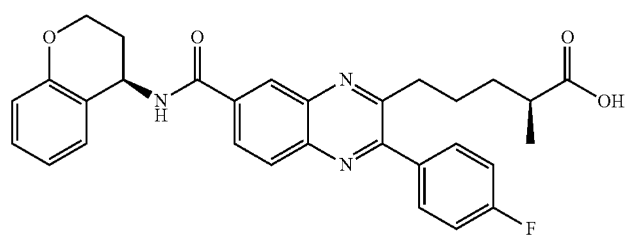 [SMILES: C[C@@H](CCCc1nc2cc(C(=O)N[C@@H]3CCOc4ccccc43)ccc2nc1-c1ccc(F)cc1)C(=O)O] | (S)-5-(7-((R)-chroman-4-ylcarbamoyl)-3-(4-fluorophenyl)quinoxalin-2-yl)-2-methylpentanoic acid | 514 |
| 521 | 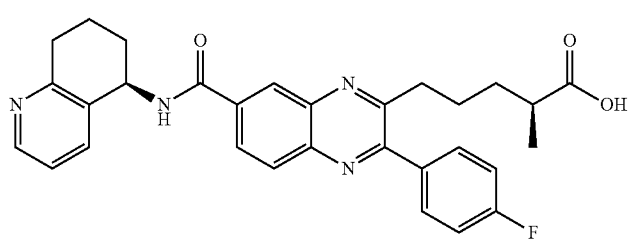 [SMILES: C[C@@H](CCCc1nc2cc(C(=O)N[C@@H]3CCCc4ncccc43)ccc2nc1-c1ccc(F)cc1)C(=O)O] | (S)-5-(3-(4-fluorophenyl)-7-(((R)-5,6,7,8-tetrahydroquinolin-5-yl)carbamoyl)quinoxalin-2-yl)-2-methylpentanoic acid | 513 |
| 522 | 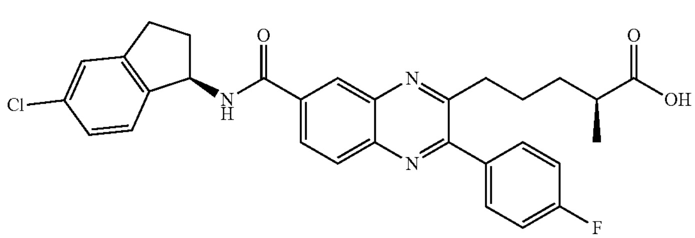 [SMILES: C[C@@H](CCCc1nc2cc(C(=O)N[C@@H]3CCc4cc(Cl)ccc43)ccc2nc1-c1ccc(F)cc1)C(=O)O] | (S)-5-(7-(((R)-5-chloro-2,3-dihydro-1H-inden-1-yl)carbamoyl)-3-(4-fluorophenyl)quinoxalin-2-yl)-2-methylpentanoic acid | 532 |

| No. | Structure | Name | M + H |
|---|---|---|---|
| 523 | 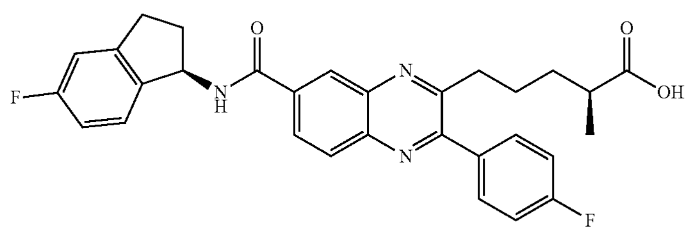 [SMILES: C[C@@H](CCCc1nc2cc(C(=O)N[C@@H]3CCc4cc(F)ccc43)ccc2nc1-c1ccc(F)cc1)C(=O)O] | (S)-5-(7-(((R)-5-fluoro-2,3-dihydro-1H-inden-1-yl)carbamoyl)-3-(4-fluorophenyl)quinoxalin-2-yl)-2-methylpentanoic acid | 516 |
| 524 | 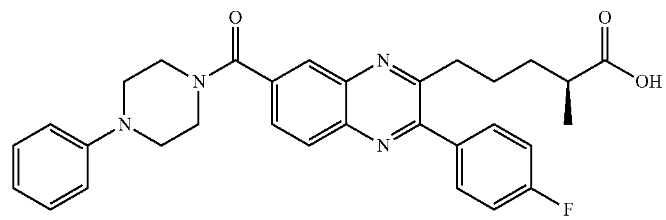 [SMILES: C[C@@H](CCCc1nc2cc(C(=O)N3CCN(c4ccccc4)CC3)ccc2nc1-c1ccc(F)cc1)C(=O)O] | (S)-5-(3-(4-fluorophenyl)-7-(4-phenylpiperazine-1-carbonyl)quinoxalin-2-yl)-2-methylpentanoic acid | 527 |
| 525 | 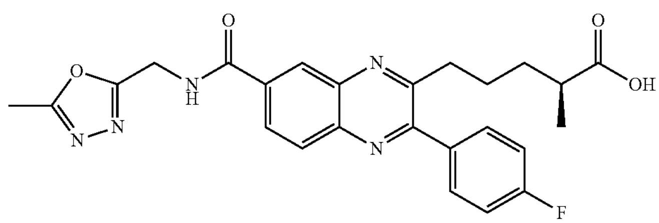 [SMILES: Cc1nnc(CNC(=O)c2ccc3nc(-c4ccc(F)cc4)c(CCC[C@H](C)C(=O)O)nc3c2)o1] | 5-(3-(4-fluorophenyl)-7-(((5-methyl-1,3,4-oxadiazol-2-yl)methyl)carbamoyl)quinoxalin-2-yl)pentanoic acid | 464 |
| 526 | 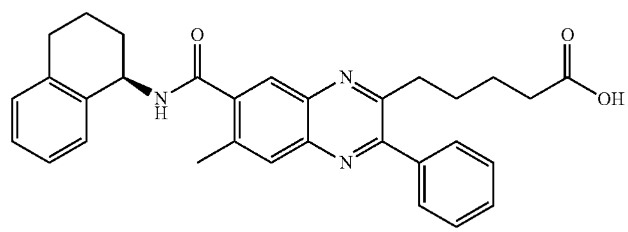 [SMILES: Cc1cc2nc(-c3ccccc3)c(CCCCC(=O)O)nc2cc1C(=O)N[C@@H]1CCCc2ccccc21] | (R)-5-(6-methyl-3-phenyl-7-((1,2,3,4-tetrahydronaphthalen-1-yl)carbamoyl)quinoxalin-2-yl)pentanoic acid | 494 |
| 527 | 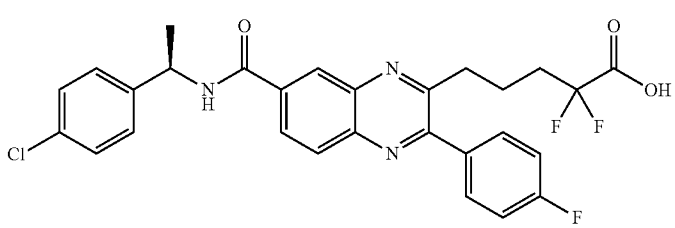 [SMILES: C[C@@H](NC(=O)c1ccc2nc(-c3ccc(F)cc3)c(CCCC(F)(F)C(=O)O)nc2c1)c1ccc(Cl)cc1] | (R)-5-(7-((1-(4-chlorophenyl)ethyl)carbamoyl)-3-(4-fluorophenyl)quinoxalin-2-yl)-2,2-difluoropentanoic acid | 542 |
| 528 | 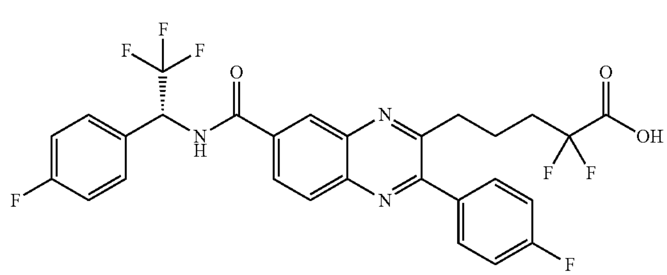 [SMILES: O=C(N[C@H](c1ccc(F)cc1)C(F)(F)F)c1ccc2nc(-c3ccc(F)cc3)c(CCCC(F)(F)C(=O)O)nc2c1] | (R)-2,2-difluoro-5-(3-(4-fluorophenyl)-7-((2,2,2-trifluoro-1-(4-fluorophenyl)ethyl)carbamoyl)quinoxalin-2-yl)pentanoic acid | 580 |

-continued

| No. | Structure | Name | M + H |
|---|---|---|---|
| 529 | 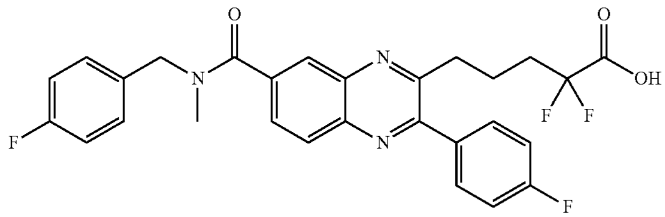 [SMILES: CN(Cc1ccc(F)cc1)C(=O)c1ccc2nc(-c3ccc(F)cc3)c(CCCC(F)(F)C(=O)O)nc2c1] | 2,2-difluoro-5-(7-((4-fluorobenzyl)(methyl)carbamoyl)-3-(4-fluorophenyl)quinoxalin-2-yl)pentanoic acid | 526 |
| 530 | 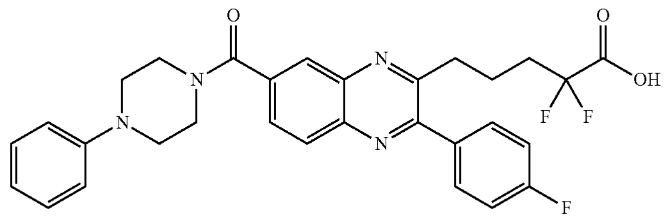 [SMILES: O=C(c1ccc2nc(-c3ccc(F)cc3)c(CCCC(F)(F)C(=O)O)nc2c1)N1CCN(c2ccccc2)CC1] | 2,2-difluoro-5-(3-(4-fluorophenyl)-7-(4-phenylpiperazine-1-yl)pentanoic acid | 549 |
| 531 | 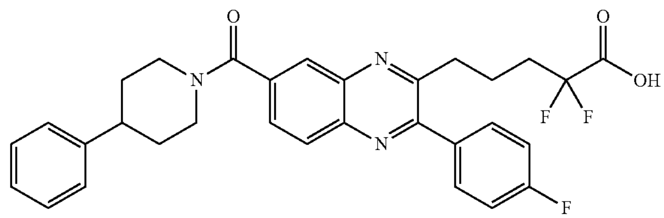 [SMILES: O=C(c1ccc2nc(-c3ccc(F)cc3)c(CCCC(F)(F)C(=O)O)nc2c1)N1CCC(c2ccccc2)CC1] | 2,2-difluoro-5-(3-(4-fluorophenyl)-7-(4-phenylpiperidine-1-carbonyl)quinoxalin-2-yl)pentanoic acid | 548 |
| 532 | 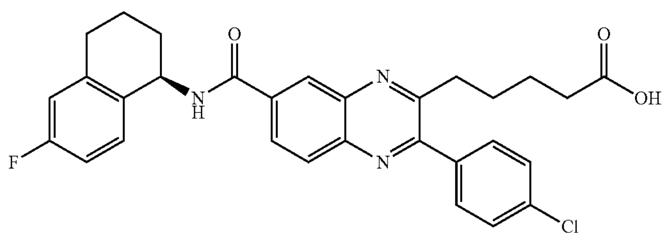 | (R)-5-(3-(4-chlorophenyl)-7-((7-fluorochroman-4-yl)carbamoyl)quinoxalin-2-yl)pentanoic acid | 534 |
| 533 | 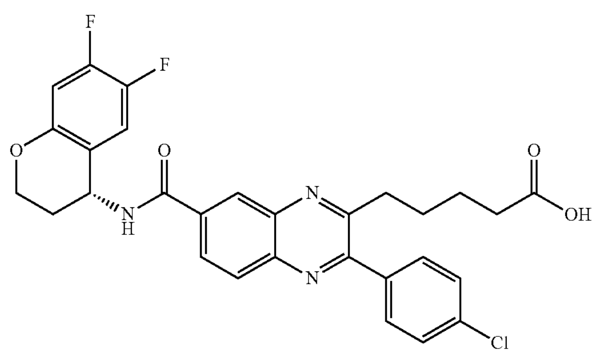 [SMILES: O=C(O)CCCCc1nc2cc(C(=O)N[C@@H]3CCOc4cc(F)c(F)cc43)ccc2nc1-c1ccc(Cl)cc1] | (R)-5-(3-(4-chlorophenyl)-7-((6,7-difluorochroman-4-yl)carbamoyl)quinoxalin-2-yl)pentanoic acid | 552 |
| 534 | 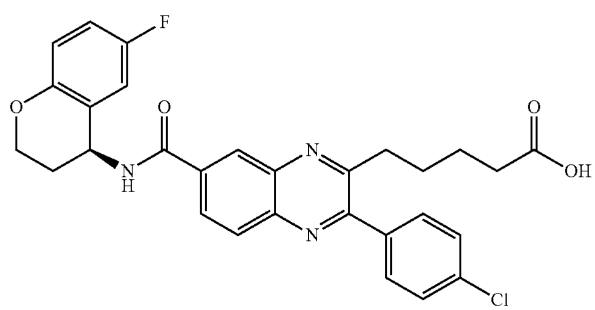 [SMILES: O=C(O)CCCCc1nc2cc(C(=O)N[C@H]3CCOc4ccc(F)cc43)ccc2nc1-c1ccc(Cl)cc1] | (S)-5-(3-(4-chlorophenyl)-7-((6-fluorochroman-4-yl)carbamoyl)quinoxalin-2-yl)pentanoic acid | 534 |

-continued

| No. | Structure | Name | M + H |
|---|---|---|---|
| 535 | 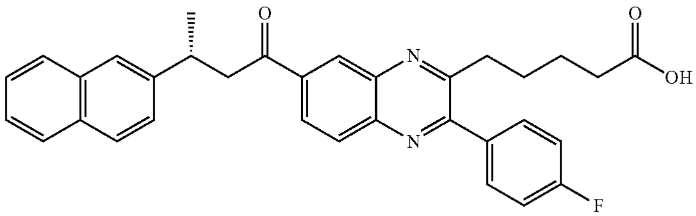 [SMILES: C[C@H](CC(=O)c1ccc2nc(-c3ccc(F)cc3)c(CCCCC(=O)O)nc2c1)c1ccc2ccccc2c1] | (S)-5-(3-(4-fluorophenyl)-7-((1-(naphthalen-2-yl)ethyl)carbamoyl)quinoxalin-2-yl)pentanoic acid | 522 |
| 536 | 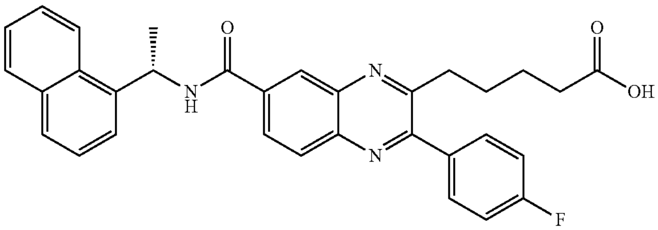 [SMILES: C[C@H](NC(=O)c1ccc2nc(-c3ccc(F)cc3)c(CCCCC(=O)O)nc2c1)c1cccc2ccccc12] | (S)-5-(3-(4-fluorophenyl)-7-((1-(naphthalen-1-yl)ethyl)carbamoyl)quinoxalin-2-yl)pentanoic acid | 522 |
| 537 | 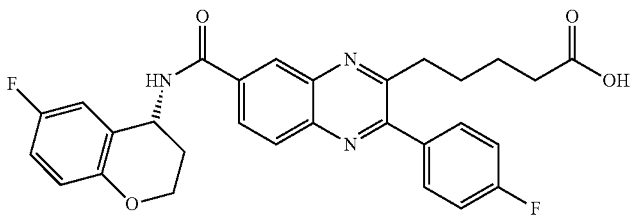 | (R)-5-(7((6-fluorochroman-4-yl)carbamoyl)-3-(4-fluorophenyl)quinoxalin-2-yl)pentanoic acid | 518 |
| 538 | 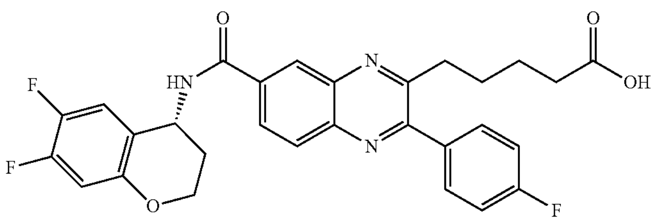 [SMILES: O=C(O)CCCCc1nc2cc(C(=O)N[C@@H]3CCOc4cc(F)c(F)cc43)ccc2nc1-c1ccc(F)cc1] | (R)-5-(7-((6,7-difluorochroman-4-yl)carbamoyl)-3-(4-fluorophenyl)quinoxalin-2-yl)pentanoic acid | 536 |
| 539 | 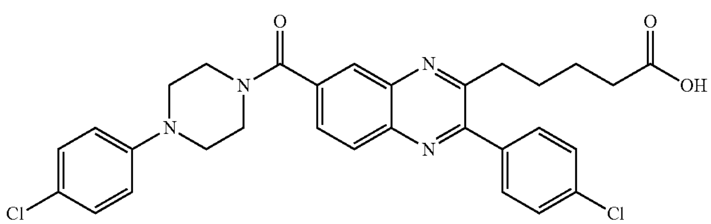 [SMILES: O=C(O)CCCCc1nc2cc(C(=O)N3CCN(c4ccc(Cl)cc4)CC3)ccc2nc1-c1ccc(Cl)cc1] | (R)-5-(3-(4-chlorophenyl)-7-(4-(4-chlorophenyl)-2-methylpiperazine-1-carbonyl)quinoxalin-2-yl)pentanoic acid | 577 |
| 540 | 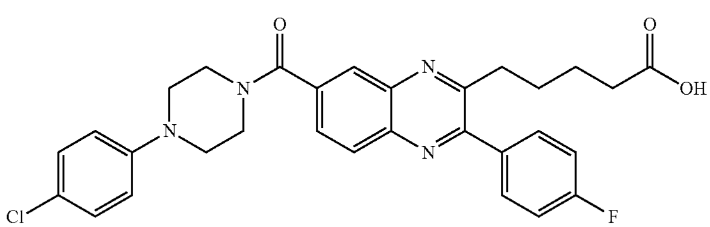 [SMILES: O=C(O)CCCCc1nc2cc(C(=O)N3CCN(c4ccc(Cl)cc4)CC3)ccc2nc1-c1ccc(F)cc1] | (R)-5-(7-(4-(4-chlorophenyl)-2-methylpiperazine-1-carbonyl)-3-(4-fluorophenyl)quinoxalin-2-yl)pentanoic acid | 561 |
| 541 | 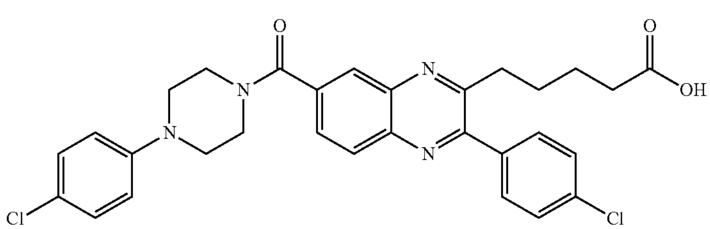 [SMILES: O=C(O)CCCCc1nc2cc(C(=O)N3CCN(c4ccc(Cl)cc4)CC3)ccc2nc1-c1ccc(Cl)cc1] | (S)-5-(3-(4-chlorophenyl)-7-(4-(4-chlorophenyl)-2-methylpiperazine-1-carbonyl)quinoxalin-2-yl)pentanoic acid | 577 |

| No. | Structure | Name | M + H |
|---|---|---|---|
| 542 | 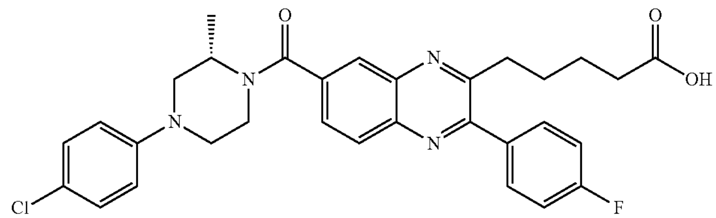 [SMILES: C[C@H]1CN(c2ccc(Cl)cc2)CCN1C(=O)c1ccc2nc(-c3ccc(F)cc3)c(CCCCC(=O)O)nc2c1] | (S)-5-(7-(4-(4-chlorophenyl)-2-methylpiperazine-1-carbonyl)-3-(4-fluorophenyl)quinoxalin-2-yl)pentanoic acid | 561 |
| 543 | 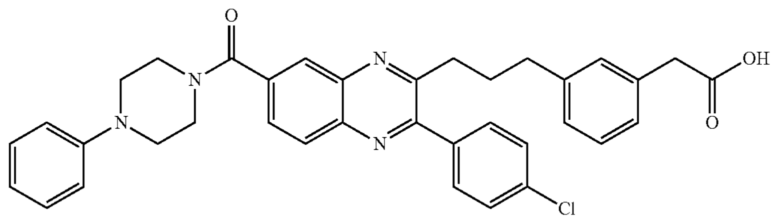 [SMILES: O=C(O)Cc1cccc(CCCc2nc3cc(C(=O)N4CCN(c5ccccc5)CC4)ccc3nc2-c2ccc(Cl)cc2)c1] | 2-(3-(3-(3-(4-chlorophenyl)-7-(4-phenylpiperazine-1-carbonyl)quinoxalin-2-yl)propyl)phenyl)acetic acid | 601 |
| 544 | 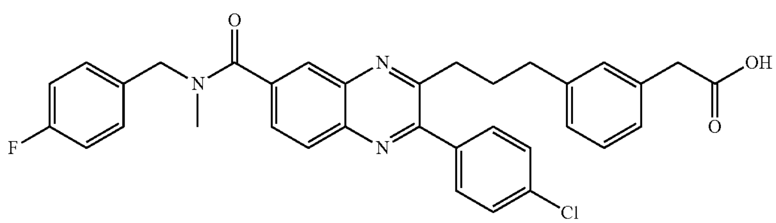 [SMILES: CN(Cc1ccc(F)cc1)C(=O)c1ccc2nc(-c3ccc(Cl)cc3)c(CCCc3cccc(CC(=O)O)c3)nc2c1] | 2-(3-(3-(3-(4-chlorophenyl)-7-((4-fluorobenzyl)(methyl)carbamoyl)quinoxalin-2-yl)propyl)phenyl)acetic acid | 582 |
| 545 | 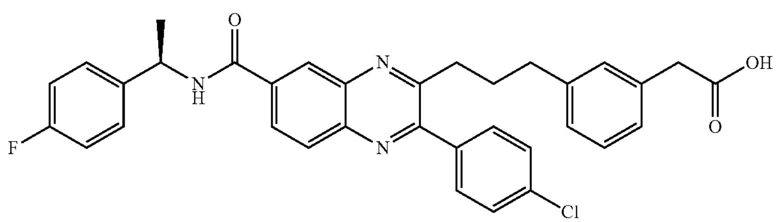 [SMILES: C[C@@H](NC(=O)c1ccc2nc(-c3ccc(Cl)cc3)c(CCCc3cccc(CC(=O)O)c3)nc2c1)c1ccc(F)cc1] | (R)-2-(3-(3-(3-(4-chlorophenyl)-7-((1-(4-fluorophenyl)ethyl)carbamoyl)quinoxalin-2-yl)propyl)phenyl)acetic acid | 582 |
| 546 | 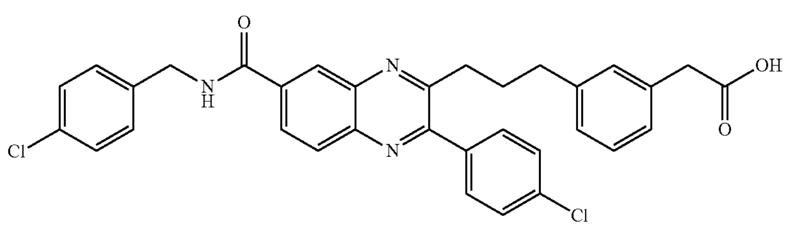 [SMILES: O=C(O)Cc1cccc(CCCc2nc3cc(C(=O)NCc4ccc(Cl)cc4)ccc3nc2-c2ccc(Cl)cc2)c1] | 2-(3-(3-(7-((4-chlorobenzyl)carbamoyl)-3-(4-chlorophenyl)quinoxalin-2-yl)propyl)phenyl)acetic acid | 586 |
| 547 | 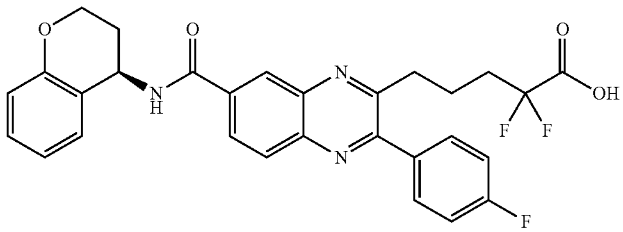 [SMILES: O=C(N[C@@H]1CCOc2ccccc21)c1ccc2nc(-c3ccc(F)cc3)c(CCCC(F)(F)C(=O)O)nc2c1] | (R)-5-(7-chroman-4-ylcarbamoyl)-3-(4-fluorophenyl)quinoxalin-2-yl)-2,2-difluoro-pentanoic acid | 536 |

| No. | Structure | Name | M + H |
|---|---|---|---|
| 548 | 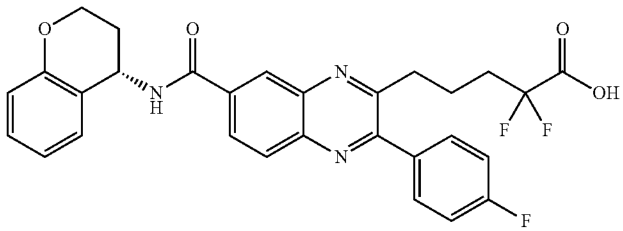 [SMILES: O=C(N[C@H]1CCOc2ccccc21)c1ccc2nc(-c3ccc(F)cc3)c(CCCC(F)(F)C(=O)O)nc2c1] | (S)-5-(7-(chroman-4-ylcarbamoyl)-3-(4-fluorophenyl)quinoxalin-2-yl)-2,2-difluoro-pentanoic acid | 536 |
| 549 | 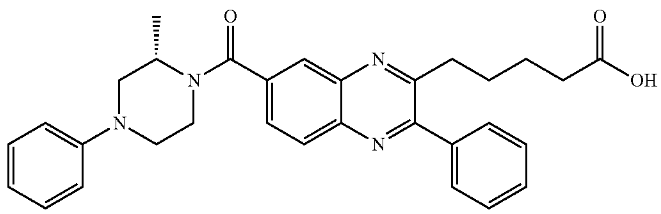 [SMILES: C[C@H]1CN(c2ccccc2)CCN1C(=O)c1ccc2nc(-c3ccccc3)c(CCCCC(=O)O)nc2c1] | (S)-5-(7-(2-methyl-4-phenylpiperazine-1-carbonyl)-3-phenylquinoxalin-2-yl)pentanoic acid | 509 |
| 550 | 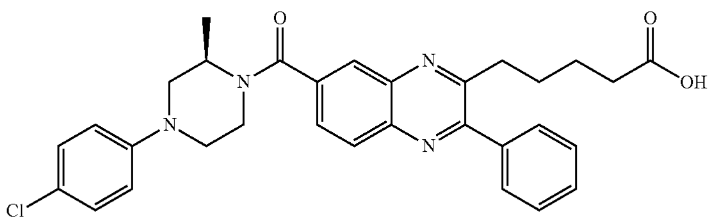 [SMILES: C[C@@H]1CN(c2ccc(Cl)cc2)CCN1C(=O)c1ccc2nc(-c3ccccc3)c(CCCCC(=O)O)nc2c1] | (R)-5-(7-(4-(4-chlorophenyl)-2-methylpiperazine-1-carbonyl)-3-phenyl-quinoxalin-2-yl)pentanoic acid | 543 |
| 551 | 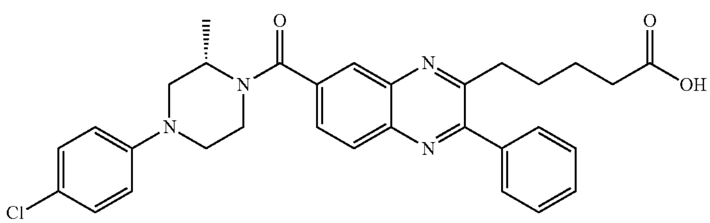 [SMILES: C[C@H]1CN(c2ccc(Cl)cc2)CCN1C(=O)c1ccc2nc(-c3ccccc3)c(CCCCC(=O)O)nc2c1] | (S)-5-(7-(4-(4-chlorophenyl)-2-methylpiperazine-1-carbonyl)-3-phenyl-quinoxalin-2-yl)pentanoic acid | 543 |
| 552 | 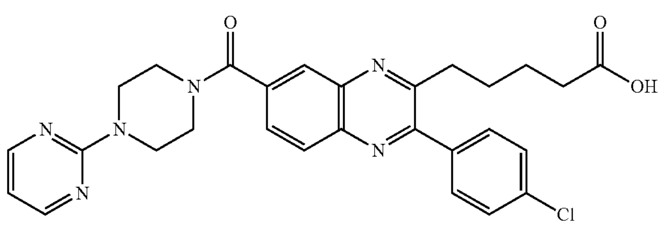 [SMILES: O=C(O)CCCCc1nc2cc(C(=O)N3CCN(c4ncccn4)CC3)ccc2nc1-c1ccc(Cl)cc1] | 5-(3-(4-chlorophenyl)-7-(4-(pyrimidin-2-yl)piperazine-1-carbonyl)quinoxalin-2-yl)pentanoic acid | 531.3 |
| 553 | 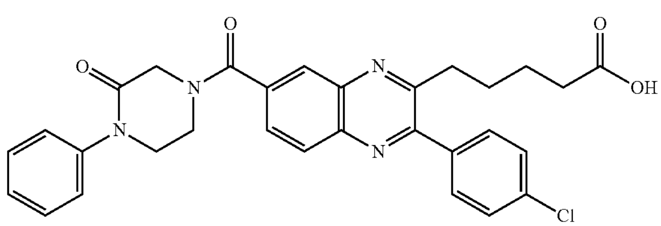 [SMILES: O=C(O)CCCCc1nc2cc(C(=O)N3CCN(c4ccccc4)C(=O)C3)ccc2nc1-c1ccc(Cl)cc1] | 5-(3-(4-chlorophenyl)-7-(3-oxo-4-phenylpiperazine-1-carbonyl)quinoxalin-2-yl)pentanoic acid | 543.3 |
| 554 | 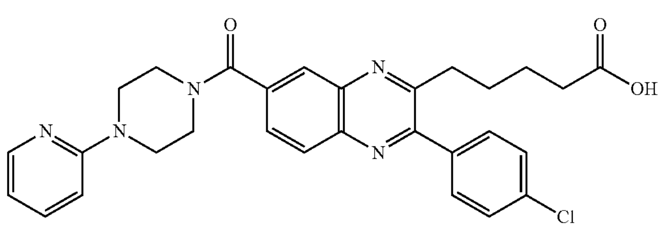 [SMILES: O=C(O)CCCCc1nc2cc(C(=O)N3CCN(c4ccccn4)CC3)ccc2nc1-c1ccc(Cl)cc1] | 5-(3-(4-chlorophenyl)-7-(4-(pyridin-2-yl)piperazine-1-carbonyl)quinoxalin-2-yl)pentanoic acid | 530.3 |

-continued

| No. | Structure | Name | M + H |
|---|---|---|---|
| 555 | 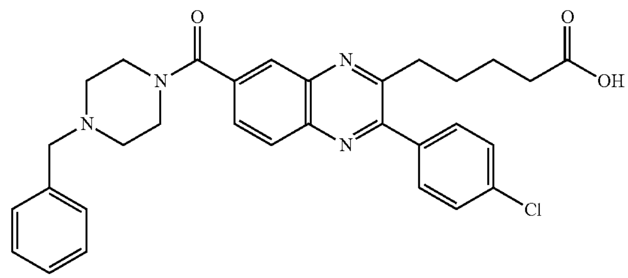 [SMILES: O=C(O)CCCCc1nc2cc(C(=O)N3CCN(Cc4ccccc4)CC3)ccc2nc1-c1ccc(Cl)cc1] | 5-(7-(4-benzylpiperazine-1-carbonyl)-3-(4-chlorophenyl)quinoxalin-2-yl)pentanoic acid | 543.3 |
| 556 | 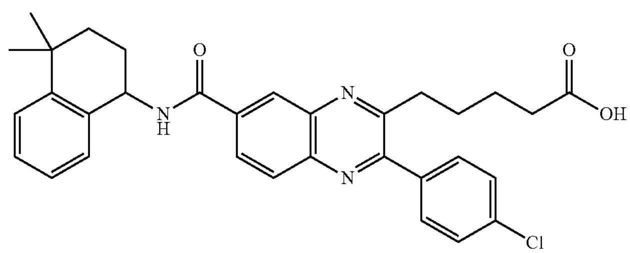 [SMILES: CC1(C)CCC(NC(=O)c2ccc3nc(-c4ccc(Cl)cc4)c(CCCCC(=O)O)nc3c2)c2ccccc21] | 5-(3-(4-chlorophenyl)-7-(4,4-dimethyl-1,2,3,4-tetrahydronaphthalen-1-yl)carbamoyl)quinoxalin-2-yl)pentanoic acid | 542.3 |
| 557 | 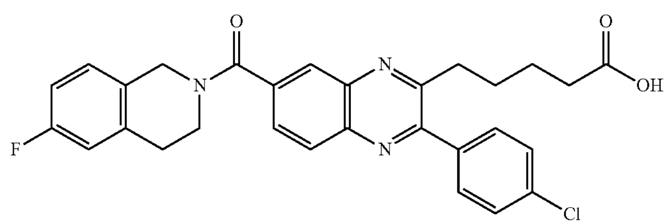 [SMILES: O=C(O)CCCCc1nc2cc(C(=O)N3CCc4cc(F)ccc4C3)ccc2nc1-c1ccc(Cl)cc1] | 5-(3-(4-chlorophenyl)-7-(6-fluoro-1,2,3,4-tetrahydroisoquinoline-2-carbonyl)quinoxalin-2-yl)pentanoic acid | 518.2 |
| 558 | 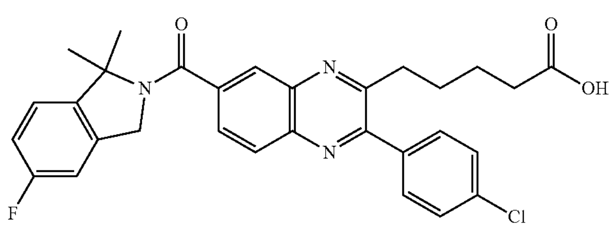 [SMILES: CC1(C)c2ccc(F)cc2CN1C(=O)c1ccc2nc(-c3ccc(Cl)cc3)c(CCCCC(=O)O)nc2c1] | 5-(3-(4-chlorophenyl)-7-(5-fluoro-1,1-dimethylisoindoline-2-carbonyl)quinoxalin-2-yl)pentanoic acid | 532.3 |
| 559 | 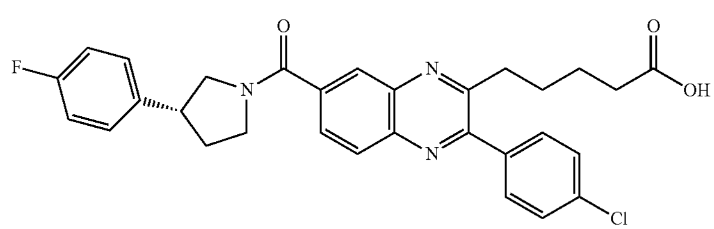 [SMILES: O=C(O)CCCCc1nc2cc(C(=O)N3CC[C@H](c4ccc(F)cc4)C3)ccc2nc1-c1ccc(Cl)cc1] | (R)-5-(3-(4-chlorophenyl)-7-(3-(4-fluorophenyl)pyrrolidine-1-carbonyl)quinoxalin-2-yl)pentanoic acid | 532.3 |
| 560 | 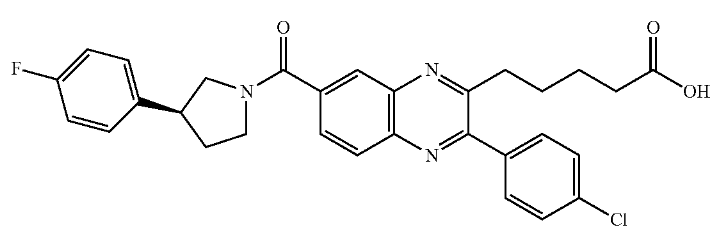 [SMILES: O=C(O)CCCCc1nc2cc(C(=O)N3CC[C@@H](c4ccc(F)cc4)C3)ccc2nc1-c1ccc(Cl)cc1] | (S)-5-(3-(4-chlorophenyl)-7-(3-(4-fluorophenyl)pyrrolidine-1-carbonyl)quinoxalin-2-yl)pentanoic acid | 532.3 |

-continued

| No. | Structure | Name | M + H |
|---|---|---|---|
| 561 | 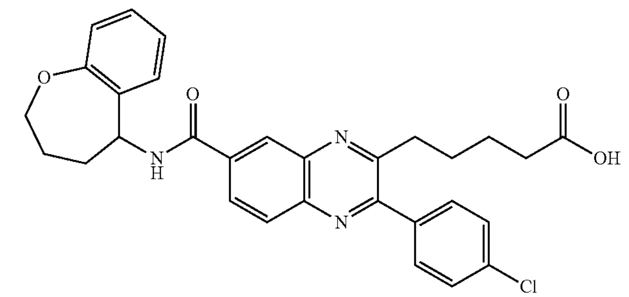 [SMILES: O=C(O)CCCCc1nc2cc(C(=O)NC3CCCOc4ccccc43)ccc2nc1-c1ccc(Cl)cc1] | 5-(3-(4-chlorophenyl)-7-((2,3,4,5-tetrahydrobenzo[b]oxepin-5-yl)carbamoyl)quinoxalin-2-yl)pentanoic acid | 530.3 |
| 562 | 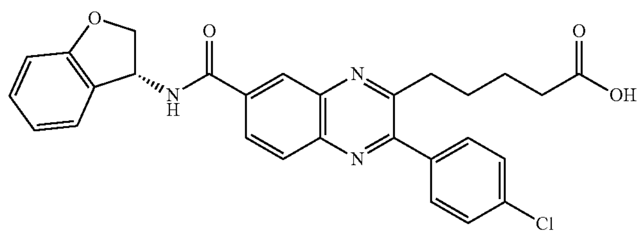 [SMILES: O=C(O)CCCCc1nc2cc(C(=O)N[C@H]3COc4ccccc43)ccc2nc1-c1ccc(Cl)cc1] | (R)-5-(3-(4-chlorophenyl)-7-((2,3-dihydrobenzofuran-3-yl)carbamoyl)quinoxalin-2-yl)pentanoic acid | 502.2 |
| 563 | 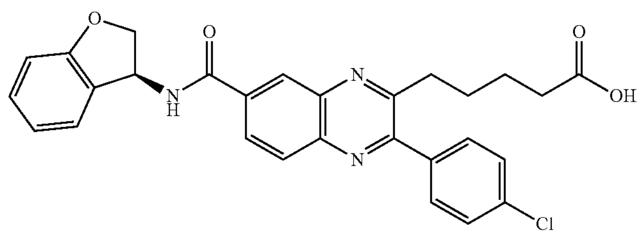 [SMILES: O=C(O)CCCCc1nc2cc(C(=O)N[C@@H]3COc4ccccc43)ccc2nc1-c1ccc(Cl)cc1] | (S)-5-(3-(4-chlorophenyl)-7-((2,3-dihydrobenzofuran-3-yl)carbamoyl)quinoxalin-2-yl)pentanoic acid | 502.2 |
| 564 | 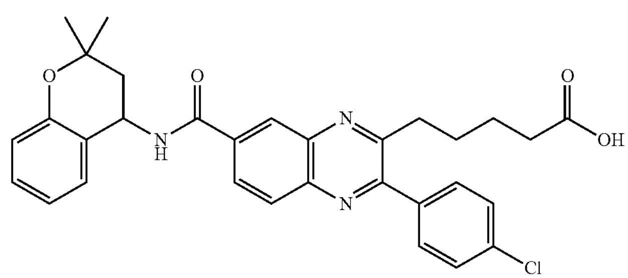 [SMILES: CC1(C)CC(NC(=O)c2ccc3nc(-c4ccc(Cl)cc4)c(CCCCC(=O)O)nc3c2)c2ccccc2O1] | 5-(3-(4-chlorophenyl)-7-((2,2-dimethylchroman-4-yl)carbamoyl)quinoxalin-2-yl)pentanoic acid | 544.3 |
| 565 | 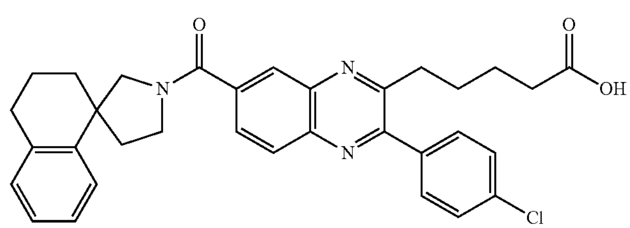 [SMILES: O=C(O)CCCCc1nc2cc(C(=O)N3CCC4(CCCc5ccccc54)C3)ccc2nc1-c1ccc(Cl)cc1] | 5-(3-(4-chlorophenyl)-7-(3,4-dihydro-2H-spiro[naphthalene-1,3'-pyrrolidin]-1'-ylcarbonyl)quinoxalin-2-yl)pentanoic acid | 554.3 |
| 566 | 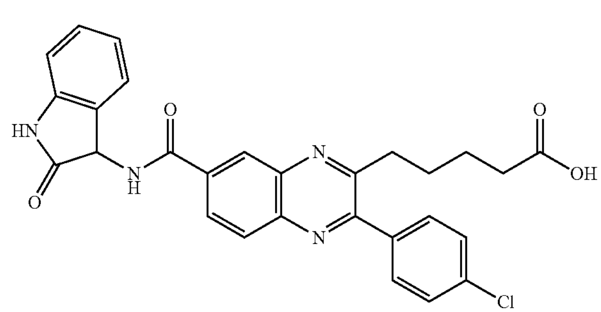 [SMILES: O=C(O)CCCCc1nc2cc(C(=O)NC3C(=O)Nc4ccccc43)ccc2nc1-c1ccc(Cl)cc1] | 5-(3-(4-chlorophenyl)-7-((2-oxoindolin-3-yl)carbamoyl)quinoxalin-2-yl)pentanoic acid | 515.2 |

-continued

| No. | Structure | Name | M + H |
|---|---|---|---|
| 567 | 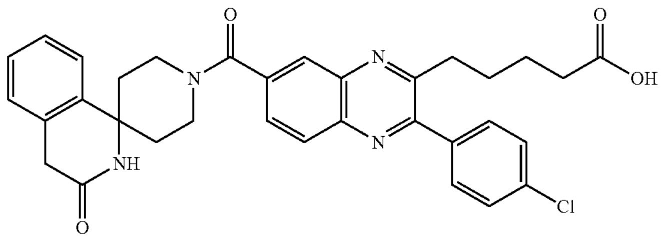 [SMILES: O=C(O)CCCCc1nc2cc(C(=O)N3CCC4(CC3)NC(=O)Cc3ccccc34)ccc2nc1-c1ccc(Cl)cc1] | 5-(3-(4-chlorophenyl)-7-(3-oxo-3,4-dihydro-2H-spiro[isoquinoline-1,4'-piperidin+9-1'-ylcarbonyl)quinoxalin-2-yl)pentanoic acid | 583.3 |
| 568 | 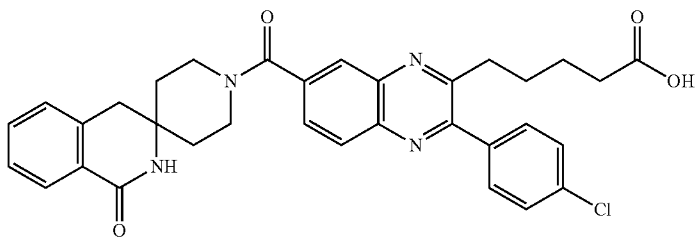 [SMILES: O=C(O)CCCCc1nc2cc(C(=O)N3CCC4(CC3)Cc3ccccc3C(=O)N4)ccc2nc1-c1ccc(Cl)cc1] | 5-(3-(4-chlorophenyl)-7-(1-oxo-2,4-dihydro-1H-spiro[isoquinoline-3,4'-piperidin]-1'-ylcarbonyl)quinoxalin-2-yl)pentanoic acid | 583.3 |
| 569 | 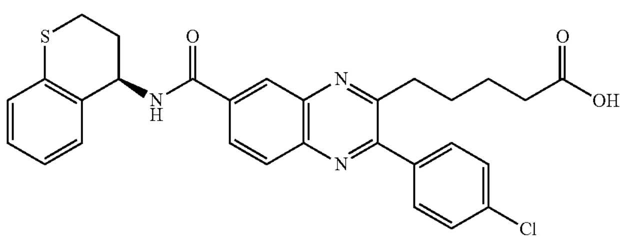 | (R)-5-(3-(4-chlorophenyl)-7-(thiochroman-4-ylcarbamoyl)quinoxalin-2-yl)pentanoic acid | 532.3 |
| 570 | 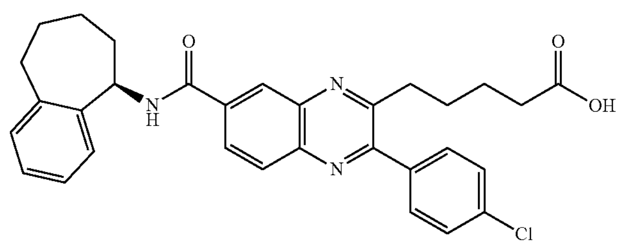 [SMILES: O=C(O)CCCCc1nc2cc(C(=O)N[C@@H]3CCCCc4ccccc43)ccc2nc1-c1ccc(Cl)cc1] | (R)-5-(3-(4-chlorophenyl)-7-((6,7,8,9-tetrahydro-5H-benzo[7]annulen-5-yl)carbamoyl)quinoxalin-2-yl)pentanoic acid | 528.3 |
| 571 | 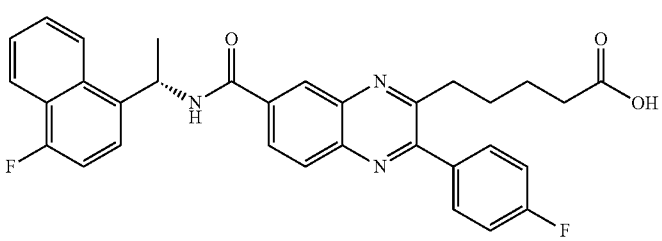 [SMILES: C[C@H](NC(=O)c1ccc2nc(-c3ccc(F)cc3)c(CCCCC(=O)O)nc2c1)c1ccc(F)c2ccccc12] | (S)-5-(7-((1-(4-fluoronaphthalen-1-yl)ethyl)carbamoyl)-3-(4-fluorophenyl)quinoxalin-2-yl)pentanoic acid | 540 |
| 572 | 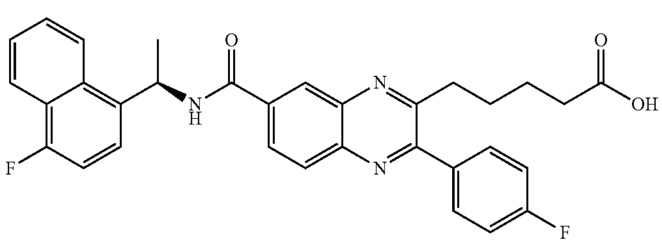 [SMILES: C[C@@H](NC(=O)c1ccc2nc(-c3ccc(F)cc3)c(CCCCC(=O)O)nc2c1)c1ccc(F)c2ccccc12] | (R)-5-(7-((1-(4-fluoronaphthalen-1-yl)ethyl)carbamoyl)-3-(4-fluorophenyl)quinoxalin-2-yl)pentanoic acid | 540 |

| No. | Structure | Name | M + H |
|-----|-----------|------|-------|
| 573 | 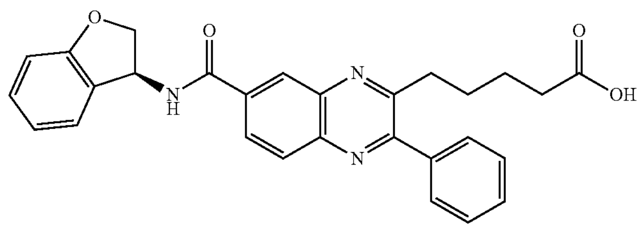 [SMILES: O=C(O)CCCCc1nc2cc(C(=O)N[C@@H]3COc4ccccc43)ccc2nc1-c1ccccc1] | (S)-5-(7-((2,3-dihydrobenzofuran-3-yl)carbamoyl)-3-phenylquinoxalin-2-yl)pentanoic acid | 468 |
| 574 | 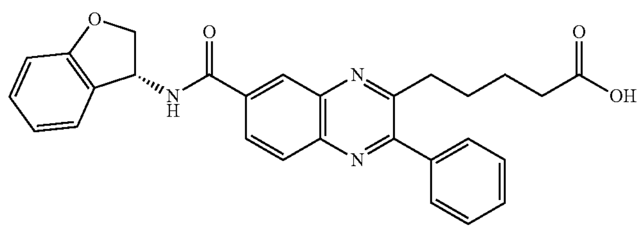 [SMILES: O=C(O)CCCCc1nc2cc(C(=O)N[C@H]3COc4ccccc43)ccc2nc1-c1ccccc1] | (R)-5-(7-((2,3-dihydrobenzofuran-3-yl)carbamoyl)-3-phenylquinoxalin-2-yl)pentanoic acid | 468 |
| 575 | 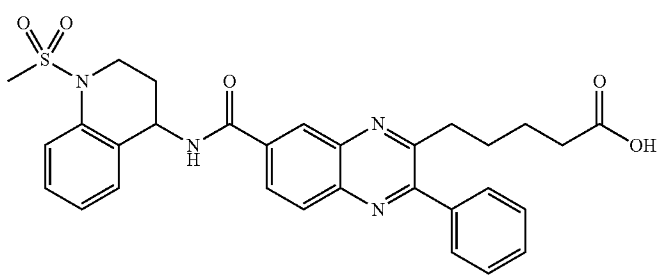 [SMILES: CS(=O)(=O)N1CCC(NC(=O)c2ccc3nc(-c4ccccc4)c(CCCCC(=O)O)nc3c2)c2ccccc21] | 5-(7-((1-(methylsulfonyl)-1,2,3,4-tetrahydroquinolin-4-yl)carbamoyl)-3-phenylquinoxalin-2-yl)pentanoic acid | 559 |
| 576 | 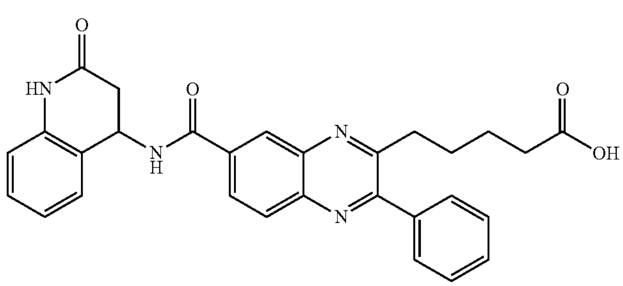 | 5-(7-((2-oxo-1,2,3,4-tetrahydroquinolin-4-yl)carbamoyl)-3-phenylquinoxalin-2-yl)pentanoic acid | 495 |
| 577 | 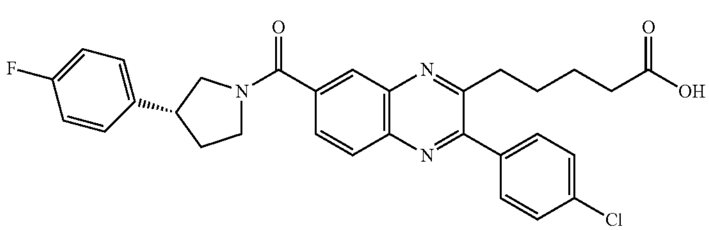 [SMILES: O=C(O)CCCCc1nc2cc(C(=O)N3CC[C@H](c4ccc(F)cc4)C3)ccc2nc1-c1ccc(Cl)cc1] | (R)-5-(3-(4-chlorophenyl)-7-(3-(4-fluorophenyl)pyrrolidine-1-carbonyl)quinoxalin-2-yl)pentanoic acid | 532.3 |
| 578 | 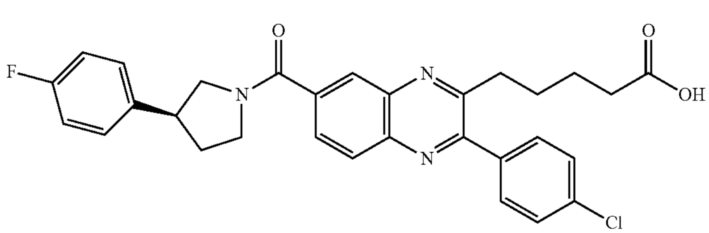 [SMILES: O=C(O)CCCCc1nc2cc(C(=O)N3CC[C@@H](c4ccc(F)cc4)C3)ccc2nc1-c1ccc(Cl)cc1] | (S)-5-(3-(4-chlorophenyl)-7-(3-(4-fluorophenyl)pyrrolidine-1-carbonyl)quinoxalin-2-yl)pentanoic acid | 532.3 |

| No. | Structure | Name | M + H |
|---|---|---|---|
| 579 | 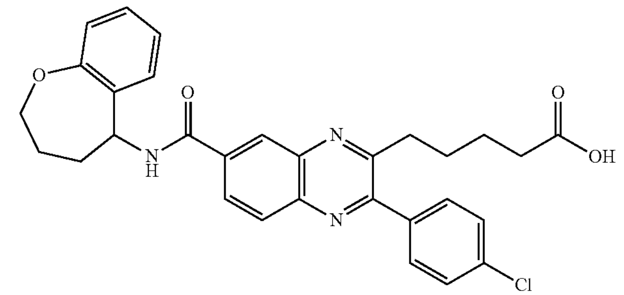 [SMILES: O=C(O)CCCCc1nc2cc(C(=O)NC3CCCOc4ccccc43)ccc2nc1-c1ccc(Cl)cc1] | 5-(3-(4-chlorophenyl)-7-((2,3,4,5-tetralaydrobenzo[b]oxepin-5-yl)carbamoyl)quinoxalin-2-yl)pentanoic acid | 530.3 |
| 580 | 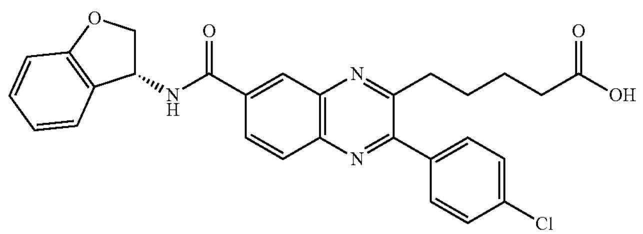 [SMILES: O=C(O)CCCCc1nc2cc(C(=O)N[C@H]3COc4ccccc43)ccc2nc1-c1ccc(Cl)cc1] | (R)-5-(3-(4-chlorophenyl)-7-((2,3-dihydrobenzofuran-3-yl)carbamoyl)quinoxalin-2-yl)pentanoic acid | 502.2 |
| 581 | 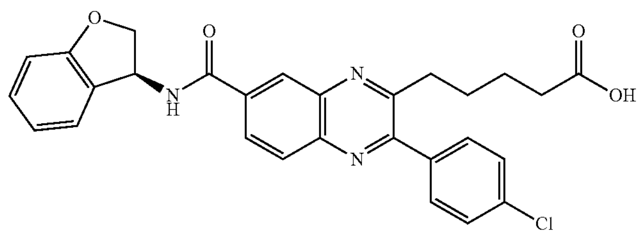 [SMILES: O=C(O)CCCCc1nc2cc(C(=O)N[C@@H]3COc4ccccc43)ccc2nc1-c1ccc(Cl)cc1] | (S)-5-(3-(4-chlorophenyl)-7-((2,3-dihydrobenzofuran-3-yl)carbatnoyl)quinoxalin-2-yl)pentanoic acid | 502.2 |
| 582 | 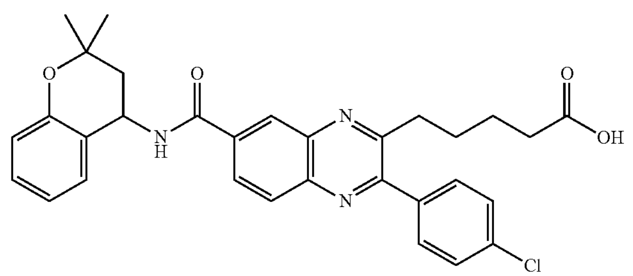 [SMILES: CC1(C)CC(NC(=O)c2ccc3nc(-c4ccc(Cl)cc4)c(CCCCC(=O)O)nc3c2)c2ccccc2O1] | 5-(3-(4-chlorophenyl)-7-((2,2-dimethylchroman-4-yl)carbamoyl)quinoxalin-2-yl)pentanoic acid | 544.3 |
| 583 | 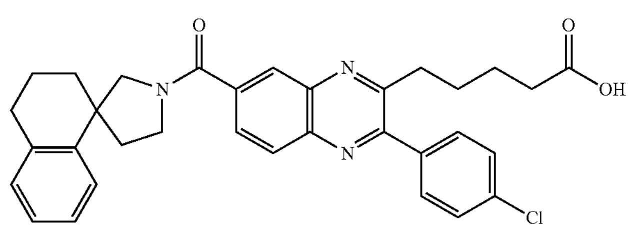 [SMILES: O=C(O)CCCCc1nc2cc(C(=O)N3CCC4(CCCc5ccccc54)C3)ccc2nc1-c1ccc(Cl)cc1] | 5-(3-(4-chlorophenyl)-7-(3,4-dihydro-2H-spiro[naphthalene-1,3'-pyrrolidin]-1'-ylcarbonyl)quinoxalin-2-yl)pentanoic acid | 554.3 |
| 584 | 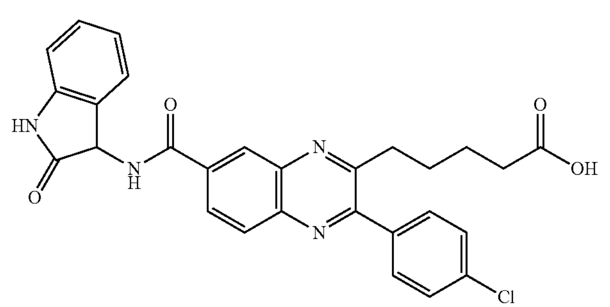 [SMILES: O=C(O)CCCCc1nc2cc(C(=O)NC3C(=O)Nc4ccccc43)ccc2nc1-c1ccc(Cl)cc1] | 5-(3-(4-chlorophenyl)-7-((2-oxoindolin-3-yl)carbamoyl)quinoxalin-2-yl)pentanoic acid | 515.2 |

-continued

| No. | Structure | Name | M + H |
|---|---|---|---|
| 585 | 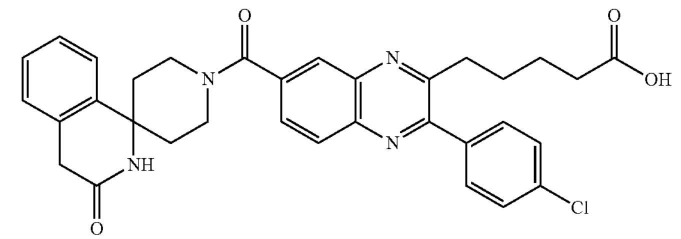 [SMILES: O=C(O)CCCCc1nc2cc(C(=O)N3CCC4(CC3)NC(=O)Cc3ccccc34)ccc2nc1-c1ccc(Cl)cc1] | 5-(3-(4-chlorophenyl)-7-(3-oxo-3,4-dihydro-2H-spiro[isoquinoline-1,4'-piperidin]-1'-ylcarbonyl)quinoxalin-2-yl)pentanoic acid | 583.3 |
| 586 | 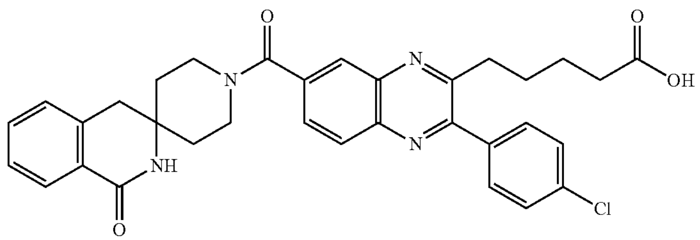 [SMILES: O=C(O)CCCCc1nc2cc(C(=O)N3CCC4(CC3)Cc3ccccc3C(=O)N4)ccc2nc1-c1ccc(Cl)cc1] | 5-(3-(4-chlorophenyl)-7-(1-oxo-2,4-dihydro-1H-spiro[isoquinotine-3,4'-piperidin]-1'-ylcarbonyl)quinoxalin-2-yl)pentanoic acid | 583.3 |
| 587 | 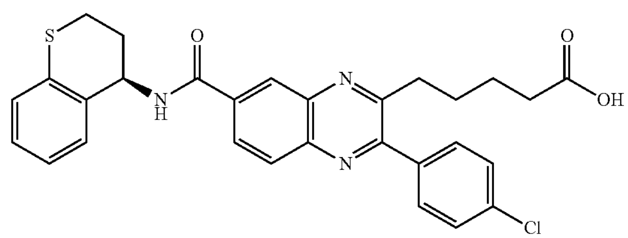 | (R)-5-(3-(4-chlorophenyl)-7-(thiochroman-4-ylcarbamoyl)quinoxalin-2-yl)pentanoic acid | 532.3 |
| 588 | 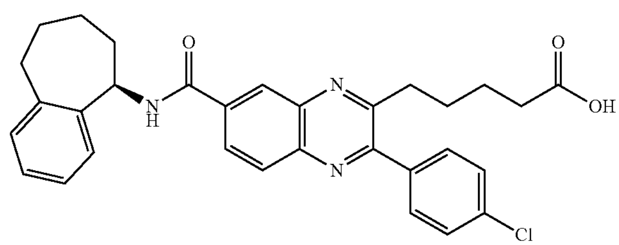 [SMILES: O=C(O)CCCCc1nc2cc(C(=O)N[C@@H]3CCCCc4ccccc43)ccc2nc1-c1ccc(Cl)cc1] | (R)-5-(3-(4-chlorophenyl)-7-((6,7,8,9-tetrahydro-5H-benzo[7]annulen-5-yl)carbamoyl)quinoxalin-2-yl)pentanoic acid. | 528.3 |
| 589 | 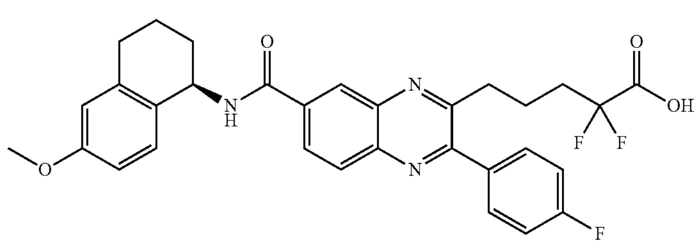 [SMILES: COc1ccc2c(c1)CCC[C@H]2NC(=O)c1ccc2nc(-c3ccc(F)cc3)c(CCCC(F)(F)C(=O)O)nc2c1] | (R)-2,2-difluoro-5-(3-(4-fluorophenyl)-7-((6-methoxy-1,2,3,4-tetrahydro-naphthalen-1-yl)carbamoyl)quinoxalin-2-yl)pentanoic acid | 564 |
| 590 | 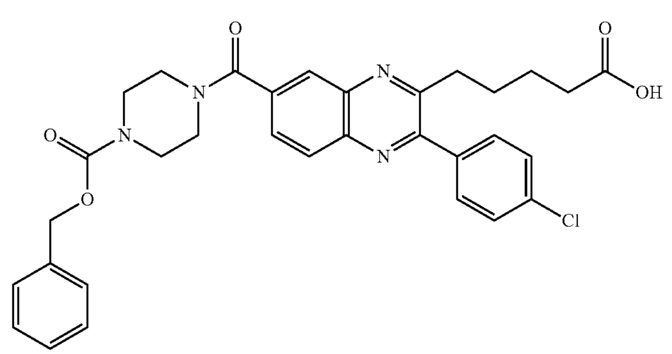 [SMILES: O=C(O)CCCCc1nc2cc(C(=O)N3CCN(C(=O)OCc4ccccc4)CC3)ccc2nc1-c1ccc(Cl)cc1] | 5-(7-(4-((benzyloxy)carbonyl)piperazine-1-carbonyl)-3-(4-chlorophenyl)quinoxalin-2-yl)pentanoic acid | 587.4 |

-continued

| No. | Structure | Name | M + H |
|---|---|---|---|
| 591 | 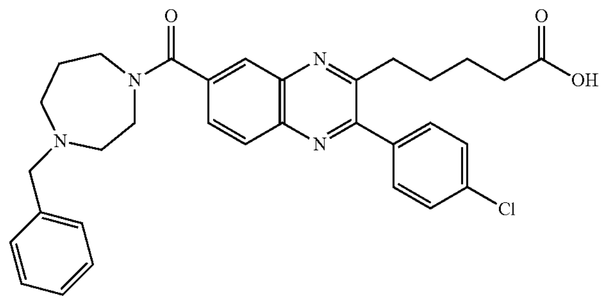 [SMILES: O=C(O)CCCCc1nc2cc(C(=O)N3CCCN(Cc4ccccc4)CC3)ccc2nc1-c1ccc(Cl)cc1] | 5-(7-(4-benzyl-1,4-diazepane-1-carbonyl)-3-(4-chlorophenyl)quinoxalin-2-yl)pentanoic acid | 557.3 |
| 592 | 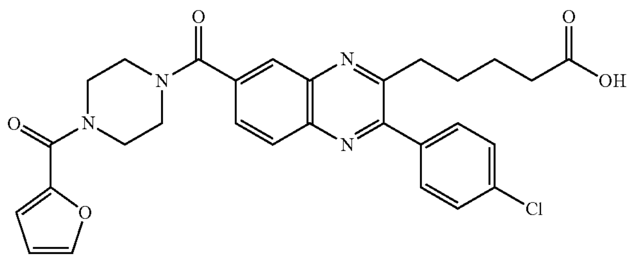 [SMILES: O=C(O)CCCCc1nc2cc(C(=O)N3CCN(C(=O)c4ccco4)CC3)ccc2nc1-c1ccc(Cl)cc1] | 5-(3-(4-chlorophenyl)-7-(4-(furan-2-carbonyl)piperazine-1-carbonyl)quinoxalin-2-yl)pentanoic acid | 547.3 |
| 593 | 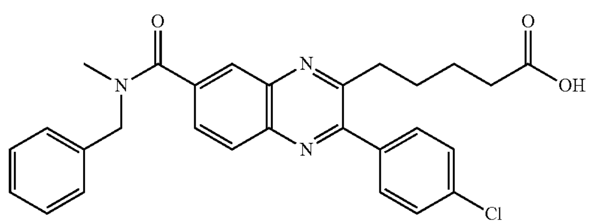 [SMILES: CN(Cc1ccccc1)C(=O)c1ccc2nc(-c3ccc(Cl)cc3)c(CCCCC(=O)O)nc2c1] | 5-(7-(benzyl(methyl)carbamoyl)-3-(4-chlorophenyl)quinoxalin-2-yl)pentanoic acid | 488.2 |
| 594 | 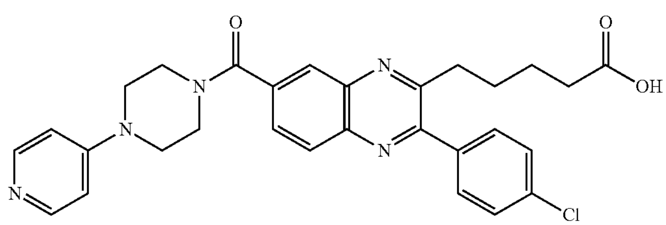 [SMILES: O=C(O)CCCCc1nc2cc(C(=O)N3CCN(c4ccncc4)CC3)ccc2nc1-c1ccc(Cl)cc1] | 5-(3-(4-chlorophenyl)-7-(4-(pyridin-4-yl)piperazine-1-carbonyl)quinoxalin-2-yl)pentanoic acid | 530.3 |
| 595 | 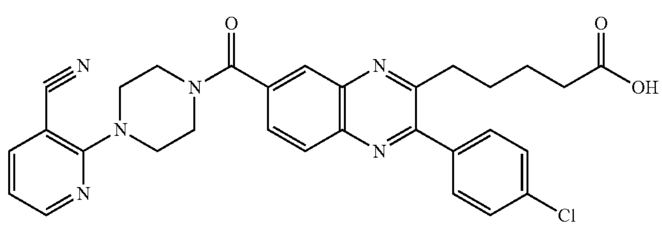 [SMILES: N#Cc1cccnc1N1CCN(C(=O)c2ccc3nc(-c4ccc(Cl)cc4)c(CCCCC(=O)O)nc3c2)CC1] | 5-(3-(4-chlorophenyl)-7-(4-(3-cyanopyridin-2-yl)piperazine-1-carbonyl)quinoxalin-2-yl)pentanoic acid | 555.3 |
| 596 | 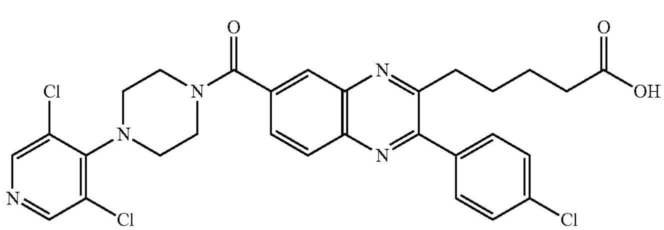 [SMILES: O=C(O)CCCCc1nc2cc(C(=O)N3CCN(c4c(Cl)cncc4Cl)CC3)ccc2nc1-c1ccc(Cl)cc1] | 5-(3-(4-chlorophenyl)-7-(4-(3,5-dichloropyridin-4-yl)piperazine-1-carbonyl)quinoxalin-2-yl)pentanoic acid | 600.2 |

-continued

| No. | Structure | Name | M + H |
|---|---|---|---|
| 597 | 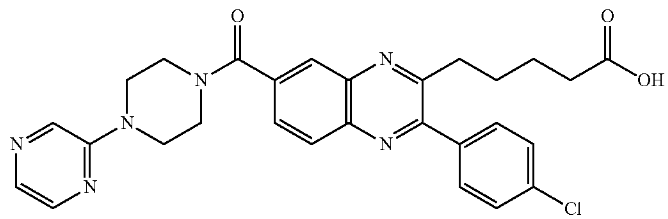 | 5-(3-(4-chlorophenyl)-7-(4-(pyrazin-2-yl)piperazine-1-carbonyl)quinoxalin-2-yl)pentanoic acid | 531.3 |
| 598 | 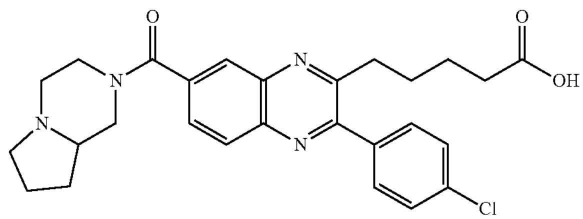 [SMILES: O=C(O)CCCCc1nc2cc(C(=O)N3CCN4CCCC4C3)ccc2nc1-c1ccc(Cl)cc1] | 5-(3-(4-chlorophenyl)-7-(octahydropyrrolo[1,2-a]pyrazine-2-carbonyl)quinoxalin-2-yl)pentanoic acid | 493.3 |
| 599 | 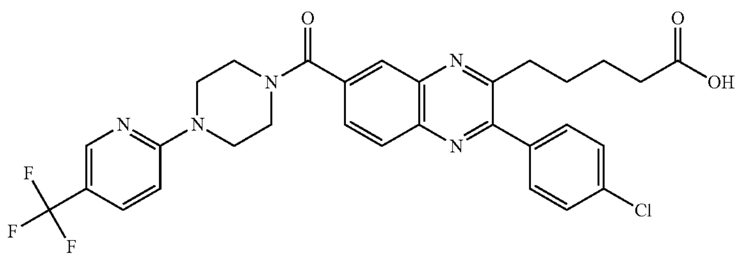 [SMILES: O=C(O)CCCCc1nc2cc(C(=O)N3CCN(c4ccc(C(F)(F)F)cn4)CC3)ccc2nc1-c1ccc(Cl)cc1] | 5-(3-(4-chlorophenyl)-7-(4-(5-yl)piperazine-1-carbonyl)quinoxalin-2-yl)pentanoic acid | 599.3 |
| 600 | 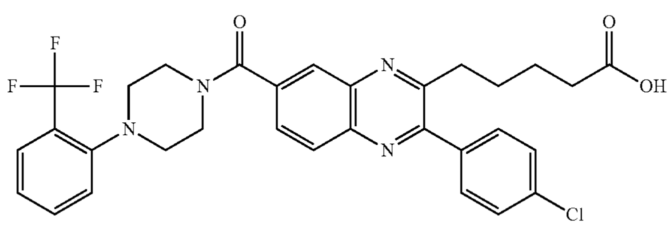 [SMILES: O=C(O)CCCCc1nc2cc(C(=O)N3CCN(c4ccccc4C(F)(F)F)CC3)ccc2nc1-c1ccc(Cl)cc1] | 5-(3-(4-chlorophenyl)-7-(4-(2-(trifluoromethyl)phenyl)piperazine-1-carbonyl)quinoxalin-2-yl)pentanoic acid | 597.3 |
| 601 | 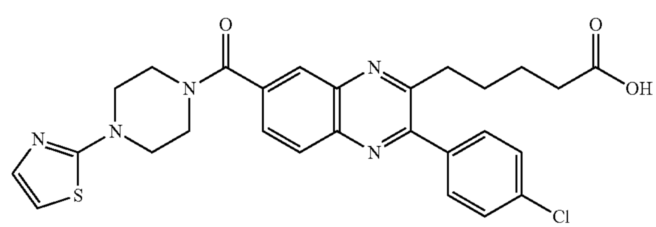 [SMILES: O=C(O)CCCCc1nc2cc(C(=O)N3CCN(c4nccs4)CC3)ccc2nc1-c1ccc(Cl)cc1] | 5-(3-(4-chlorophenyl)-7-(4-(thiazol-2-yl)piperazine-1-carbonyl) quinoxalin-2-yl)pentanoic acid | 536.2 |
| 602 | 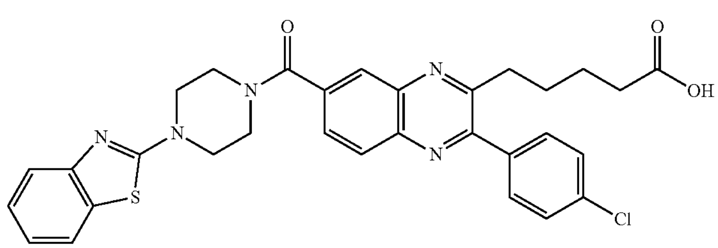 [SMILES: O=C(O)CCCCc1nc2cc(C(=O)N3CCN(c4nc5ccccc5s4)CC3)ccc2nc1-c1ccc(Cl)cc1] | 5-(7-(4-(benzo[d]thiazol-2-yl)piperazine-1-carbonyl)-3-(4-chlorophenyl)quinoxalin-2-yl)pentanoic acid | 586.3 |

| No. | Structure | Name | M + H |
|---|---|---|---|
| 603 | 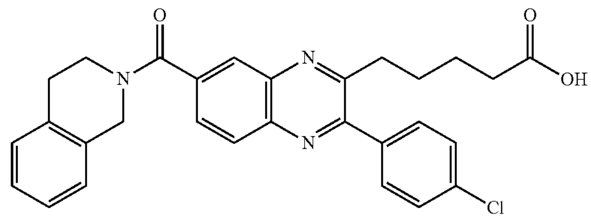 [SMILES: O=C(O)CCCCc1nc2cc(C(=O)N3CCc4ccccc4C3)ccc2nc1-c1ccc(Cl)cc1] | 5-(3-(4-chlorophenyl)-7-(1,2,3,4-tetrahydroisoquinoline-2-carbonyl)quinoxalin-2-yl)pentanoic acid | 500.3 |
| 604 | 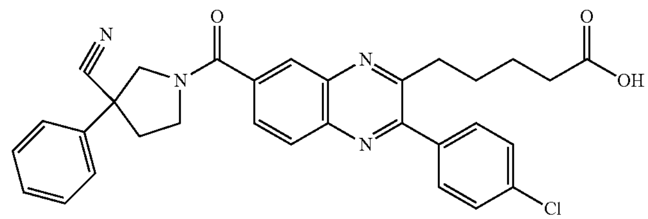 [SMILES: N#CC1(c2ccccc2)CCN(C(=O)c2ccc3nc(-c4ccc(Cl)cc4)c(CCCCC(=O)O)nc3c2)C1] | 5-(3-(4-chlorophenyl)-7-(3-cyano-3-phenyl-pyrrolidine-1-carbonyl)quinoxalin-2-yl)pentanoic acid | 539.3 |
| 605 | 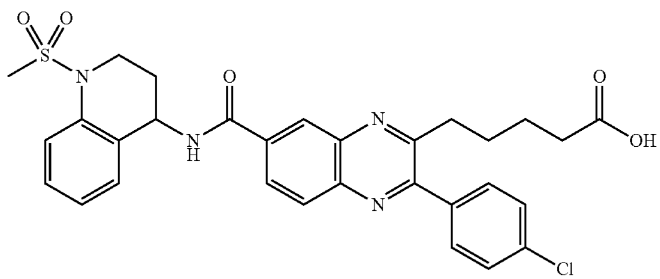 [SMILES: CS(=O)(=O)N1CCC(NC(=O)c2ccc3nc(-c4ccc(Cl)cc4)c(CCCCC(=O)O)nc3c2)c2ccccc21] | 5-(3-(4-chlorophenyl)-7-((1-(methylsulfonyl)-1,2,3,4-tetrahydroquinolin-4-yl)carbamoyl)quinoxalin-2-yl)pentanoic acid | 539.3 |
| 606 | 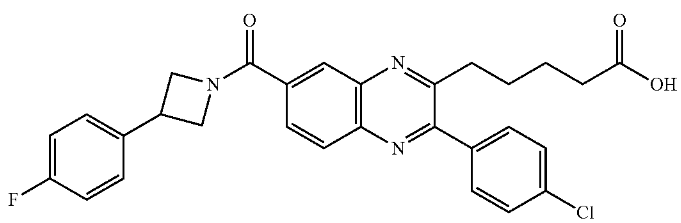 [SMILES: O=C(O)CCCCc1nc2cc(C(=O)N3CC(c4ccc(F)cc4)C3)ccc2nc1-c1ccc(Cl)cc1] | 5-(3-(4-chlorophenyl)-7-(3-(4-fluorophenyl)azetidine-1-carbonyl)quinoxalin-2-yl)pentanoic acid | 518.3 |
| 607 | 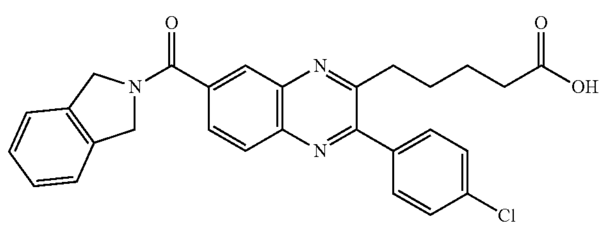 [SMILES: O=C(O)CCCCc1nc2cc(C(=O)N3Cc4ccccc4C3)ccc2nc1-c1ccc(Cl)cc1] | 5-(3-(4-chlorophenyl)-7-(isoindoline-2-carbonyl)quinoxalin-2-yl)pentanoic acid | 486.3 |
| 608 | 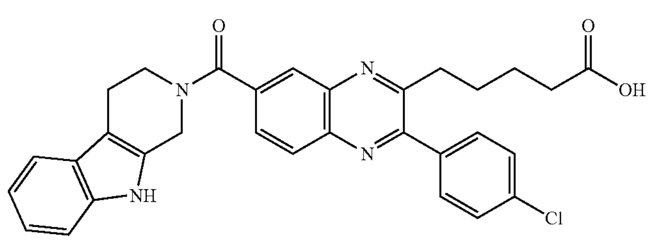 [SMILES: O=C(O)CCCCc1nc2cc(C(=O)N3CCc4c([nH]c5ccccc45)C3)ccc2nc1-c1ccc(Cl)cc1] | 5-(3-(4-chlorophenyl)-7-(2,3,4,9-tetrahydro-1H-pyrido[3,4-b]indole-2-carbonyl)quinoxalin-2-yl)pentanoic acid | 539.3 |

-continued

| No. | Structure | Name | M + H |
|---|---|---|---|
| 609 | 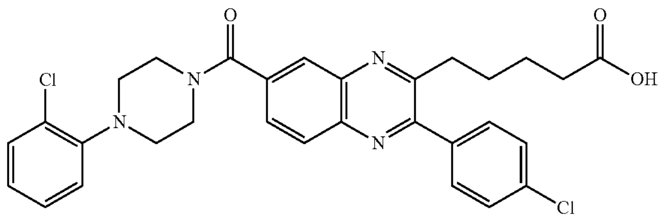 [SMILES: O=C(O)CCCCc1nc2cc(C(=O)N3CCN(c4ccccc4Cl)CC3)ccc2nc1-c1ccc(Cl)cc1] | 5-(3-(4-chlorophenyl)-7-(4-(2-chlorophenyl)piperazine-1-carbonyl)quinoxalin-2-yl)pentanoic acid | 563.3 |
| 610 | 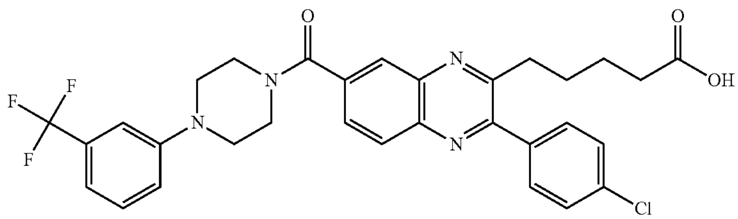 [SMILES: O=C(O)CCCCc1nc2cc(C(=O)N3CCN(c4cccc(C(F)(F)F)c4)CC3)ccc2nc1-c1ccc(Cl)cc1] | 5-(3-(4-chlorophenyl)-7-(4-(3-(trifluoromethyl)phenyl)piperazine-1-carbonyl)quinoxalin-2-yl)pentanoic acid | 597.7 |
| 611 | 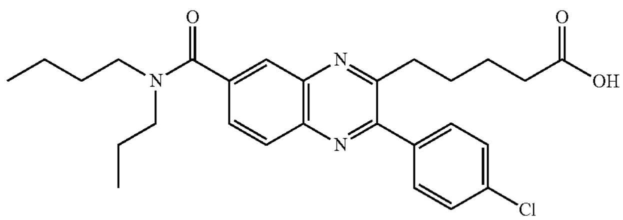 [SMILES: CCCCN(CCC)C(=O)c1ccc2nc(-c3ccc(Cl)cc3)c(CCCCC(=O)O)nc2c1] | 5-(7-(butyl(propyl)carbamoyl)-3-(4-chlorophenyl)quinoxalin-2-yl)pentanoic acid | 492.3 |
| 612 | 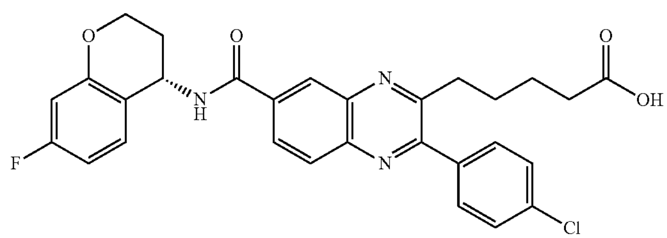 [SMILES: O=C(O)CCCCc1nc2cc(C(=O)N[C@H]3CCOc4cc(F)ccc43)ccc2nc1-c1ccc(Cl)cc1] | (S)-5-(3-(4-chlorophenyl)-7-((7-fluorochroman-4-yl)carbamoyl)quinoxalin-2-yl)pentanoic acid | 534.3 |
| 613 | 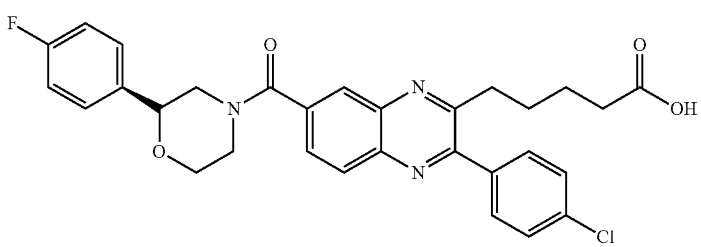 | (S)-5-(3-(4-chlorophenyl)-7-(2-(4-fluorophenyl)morpholine-4-carbonyl)quinoxalin-2-yl)pentanoic acid | 548 |
| 614 | 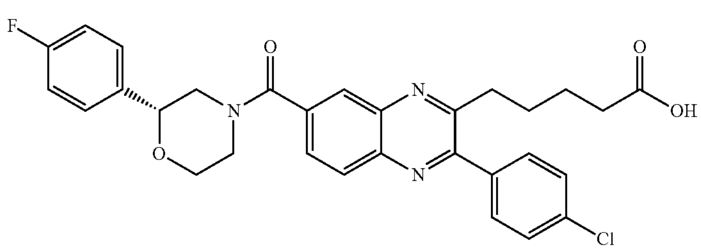 [SMILES: O=C(O)CCCCc1nc2cc(C(=O)N3CCO[C@H](c4ccc(F)cc4)C3)ccc2nc1-c1ccc(Cl)cc1] | (R)-5-(3-(4-chlorophenyl)-7-(2-(4-fluorophenyl)morpholine-4-carbonyl)quinoxalin-2-yl)pentanoic acid | 548 |

-continued

| No. | Structure | Name | M + H |
|---|---|---|---|
| 615 | 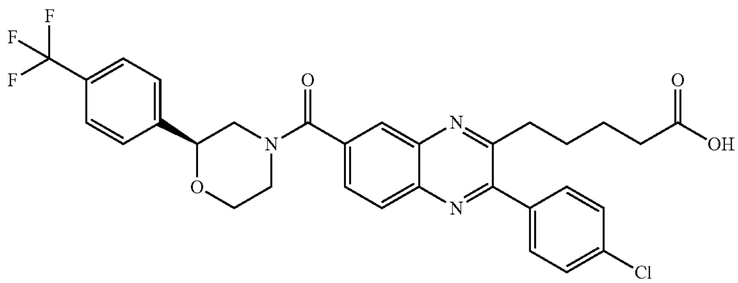 [SMILES: O=C(O)CCCCc1nc2cc(C(=O)N3CCO[C@@H](c4ccc(C(F)(F)F)cc4)C3)ccc2nc1-c1ccc(Cl)cc1] | (S)-5-(3-(4-chlorophenyl)-7-(2-(4-(trifluoromethyl)phenyl)morpholine-4-carbonyl)quinoxalin-2-yl)pentanoic acid | 598 |
| 616 | 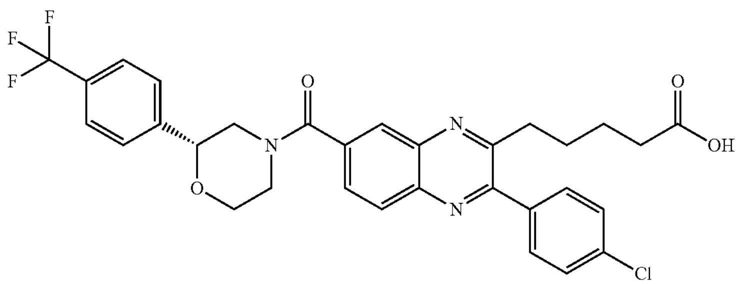 [SMILES: O=C(O)CCCCc1nc2cc(C(=O)N3CCO[C@H](c4ccc(C(F)(F)F)cc4)C3)ccc2nc1-c1ccc(Cl)cc1] | (R)-5-(3-(4-chlorophenyl)-7-(2-(4-(trifluoromethyl)phenyl)morpholine-4-carbonyl)quinoxalin-2-yl)pentanoic acid | 598 |
| 617 | 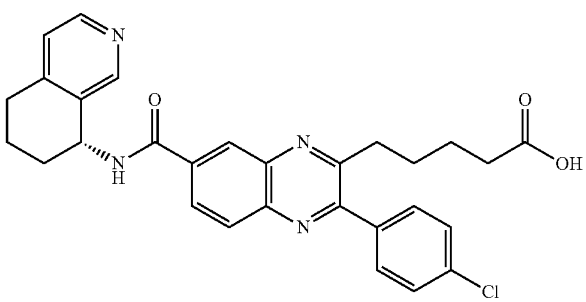 [SMILES: O=C(O)CCCCc1nc2cc(C(=O)N[C@@H]3CCCc4ccncc43)ccc2nc1-c1ccc(Cl)cc1] | (R)-5-(3-(4-chlorophenyl)-7-(5,6,7,8-tetrahydroisoquinolin-8-yl)carbamoyl)quinoxalin-2-yl)pentanoic acid | 515.4 |
| 618 | 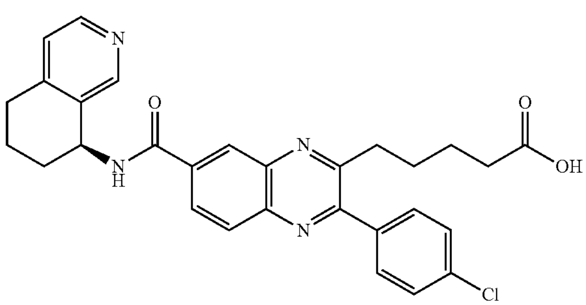 [SMILES: O=C(O)CCCCc1nc2cc(C(=O)N[C@H]3CCCc4ccncc43)ccc2nc1-c1ccc(Cl)cc1] | (S)-5-(3-(4-chlorophenyl)-7-((5,6,7,8-tetrahydroisoquinolin-8-yl)carbamoyl)quinoxalin-2-yl)pentanoic acid | 515.4 |
| 619 | 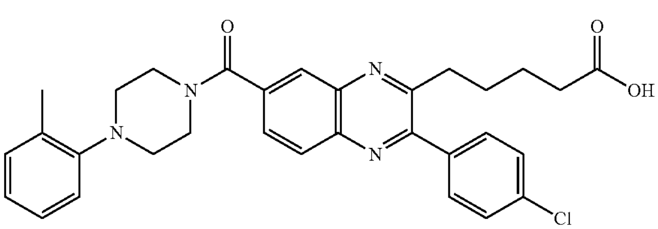 [SMILES: Cc1ccccc1N1CCN(C(=O)c2ccc3nc(-c4ccc(Cl)cc4)c(CCCCC(=O)O)nc3c2)CC1] | 5-(3-(4-chlorophenyl)-7-(4-(o-tolyl)piperazine-1-carbonyl)quinoxalin-2-yl)pentanoic acid | 543.3 |

-continued

| No. | Structure | Name | M + H |
|---|---|---|---|
| 620 | 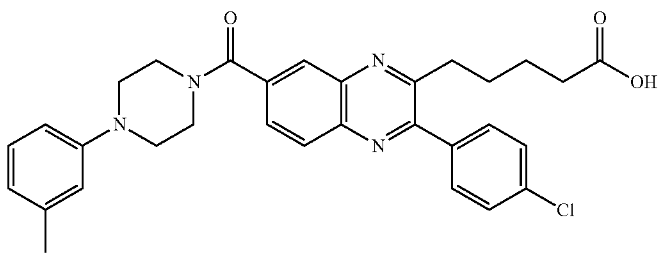 [SMILES: Cc1cccc(N2CCN(C(=O)c3ccc4nc(-c5ccc(Cl)cc5)c(CCCCC(=O)O)nc4c3)CC2)c1] | 5-(3-(4-chlorophenyl)-7-(4-(m-tolyl)piperazine-1-carbonyl)quinoxalin-2-yl)pentanoic acid | 543.3 |
| 621 | 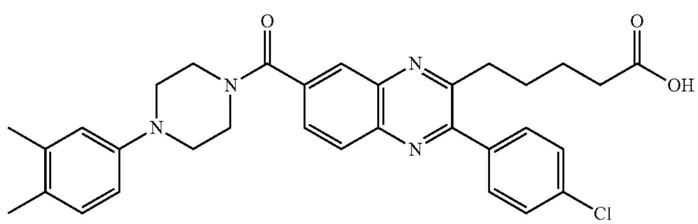 [SMILES: Cc1ccc(N2CCN(C(=O)c3ccc4nc(-c5ccc(Cl)cc5)c(CCCCC(=O)O)nc4c3)CC2)cc1C] | 5-(3-(4-chlorophenyl)-7-(4-(3,4-dimethylphenyl)piperazine-1-carbonyl)quinoxalin-2-yl)pentanoic acid | 557.4 |
| 622 | 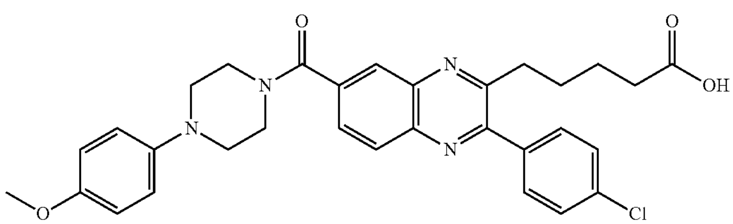 [SMILES: COc1ccc(N2CCN(C(=O)c3ccc4nc(-c5ccc(Cl)cc5)c(CCCCC(=O)O)nc4c3)CC2)cc1] | 5-(3-(4-chlorophenyl)-7-(4-(4-methoxyphenyl)piperazine-1-carbonyl)quinoxalin-2-yl)pentanoic acid | 559.4 |
| 623 | 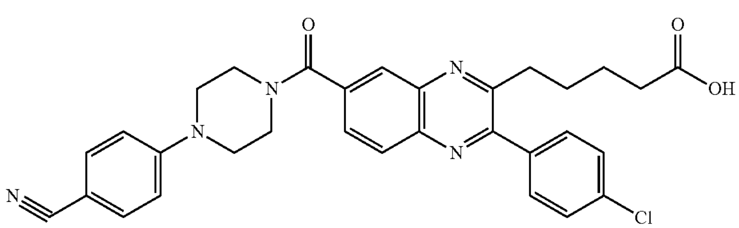 [SMILES: N#Cc1ccc(N2CCN(C(=O)c3ccc4nc(-c5ccc(Cl)cc5)c(CCCCC(=O)O)nc4c3)CC2)cc1] | 5-(3-(4-chlorophenyl)-7-(4-(4-cyanophenyl)piperazine-1-carbonyl)quinoxalin-2-yl)pentanoic acid | 554.4 |
| 624 | 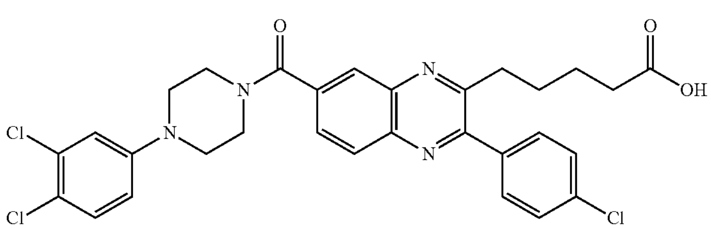 [SMILES: O=C(O)CCCCc1nc2cc(C(=O)N3CCN(c4ccc(Cl)c(Cl)c4)CC3)ccc2nc1-c1ccc(Cl)cc1] | 5-(3-(4-chlorophenyl)-7-(4-(3,4-dichlorophenyl)piperazine-1-carbonyl)quinoxalin-2-yl)pentanoic acid | 597.3 |
| 625 | 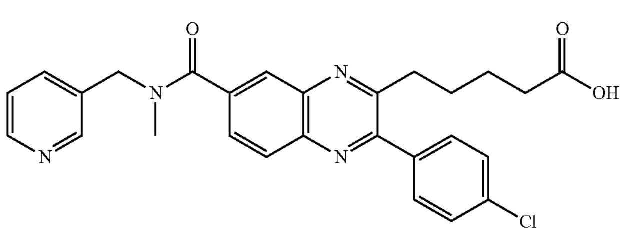 [SMILES: CN(Cc1cccnc1)C(=O)c1ccc2nc(-c3ccc(Cl)cc3)c(CCCCC(=O)O)nc2c1] | 5-(3-(4-chlorophenyl)-7-(methyl(pyridin-3-ylmethyl)carbamoyl)quinoxalin-2-yl)pentanoic acid | 489.3 |

-continued

| No. | Structure | Name | M + H |
|---|---|---|---|
| 626 | 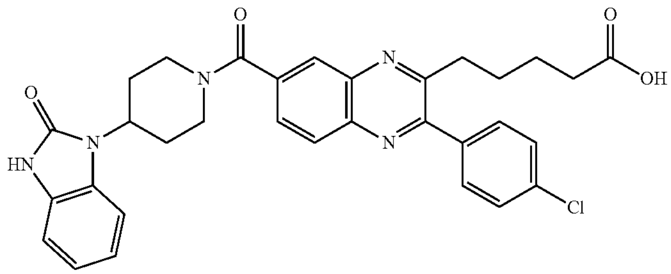 [SMILES: O=C(O)CCCCc1nc2cc(C(=O)N3CCC(n4c(=O)[nH]c5ccccc54)CC3)ccc2nc1-c1ccc(Cl)cc1] | 5-(3-(4-chlorophenyl)-7-(4-(2-oxo-2,3-dihydro-1H-benzo[d]imidazol-1-yl)piperidine-1-carbonyl)quinoxalin-2-yl)pentanoic acid | 584.4 |
| 627 | 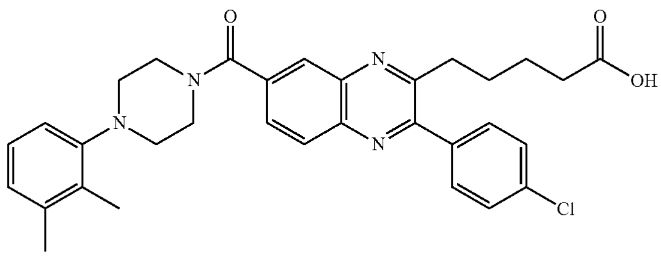 [SMILES: Cc1cccc(N2CCN(C(=O)c3ccc4nc(-c5ccc(Cl)cc5)c(CCCCC(=O)O)nc4c3)CC2)c1C] | 5-(3-(4-chlorophenyl)-7-(4-(2,3-dimethylphenyl)piperazine-1-carbonyl)quinoxalin-2-yl)pentanoic acid | 557.4 |
| 628 | 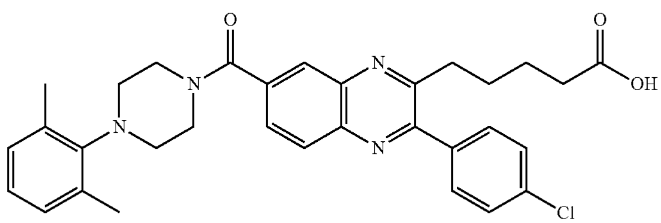 [SMILES: Cc1cccc(C)c1N1CCN(C(=O)c2ccc3nc(-c4ccc(Cl)cc4)c(CCCCC(=O)O)nc3c2)CC1] | 5-(3-(4-chlorophenyl)-7-(4-(2,6-dimethylphenyl)piperazine-1-carbonyl)quinoxalin-2-yl)pentanoic acid | 557.4 |
| 629 | 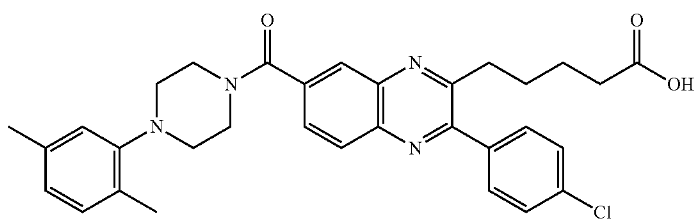 [SMILES: Cc1ccc(C)c(N2CCN(C(=O)c3ccc4nc(-c5ccc(Cl)cc5)c(CCCCC(=O)O)nc4c3)CC2)c1] | 5-(3-(4-chlorophenyl)-7-(4-(2,5-dimethylphenyl)piperazine-1-carbonyl)quinoxalin-2-yl)pentanoic acid | 557.4 |
| 630 | 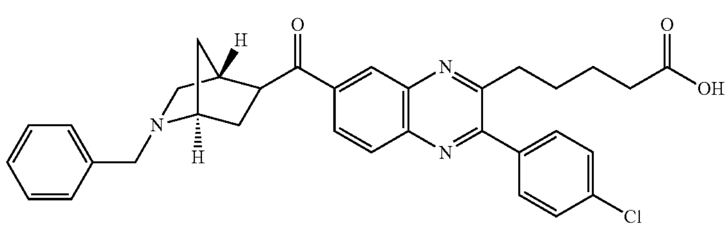 [SMILES: O=C(O)CCCCc1nc2cc(C(=O)C3C[C@@H]4C[C@H]3CN4Cc3ccccc3)ccc2nc1-c1ccc(Cl)cc1] | 5-(7-(1S,4S)-5-benzyl-2,5-diazabicyclo[2.2.1]heptane-2-carbonyl)-3-(4-chlorophenyl)quinoxalin-2-yl)pentanoic acid | 555.4 |
| 631 | 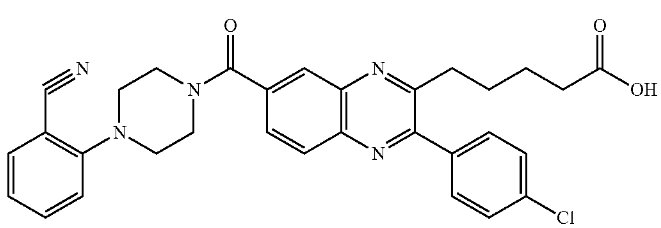 [SMILES: N#Cc1ccccc1N1CCN(C(=O)c2ccc3nc(-c4ccc(Cl)cc4)c(CCCCC(=O)O)nc3c2)CC1] | 5-(3-(4-chlorophenyl)-7-(4-(2-cyanophenyl)piperazine-1-carbonyl)quinoxalin-2-yl)pentanoic acid | 554.4 |

| No. | Structure | Name | M + H |
|---|---|---|---|
| 632 | 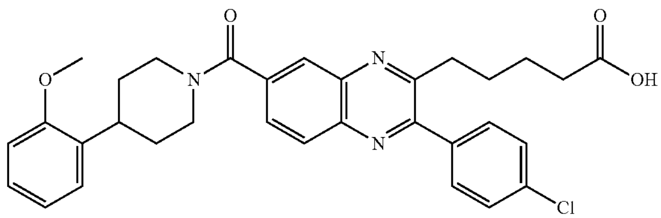 [SMILES: COc1ccccc1C1CCN(C(=O)c2ccc3nc(-c4ccc(Cl)cc4)c(CCCCC(=O)O)nc3c2)CC1] | 5-(3-(4-chlorophenyl)-7-(4-(2-methoxyphenyl)piperidine-1-carbonyl)quinoxalin-2-yl)pentanoic acid | 558.4 |
| 633 | 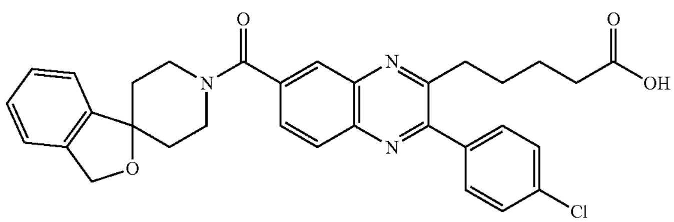 [SMILES: O=C(O)CCCCc1nc2cc(C(=O)N3CCC4(CC3)OCc3ccccc34)ccc2nc1-c1ccc(Cl)cc1] | 5-(3-(4-chlorophenyl)-7-(3H-spiro[isobenzofuran-1,4'-piperidin]-1'-ylcarbonyl)quinoxalin-2-yl)pentanoic acid | 556.4 |
| 634 | 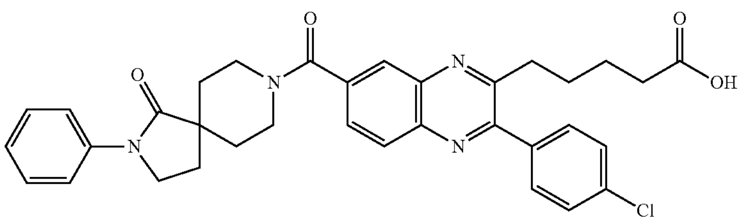 [SMILES: O=C(O)CCCCc1nc2cc(C(=O)N3CCC4(CC3)CCN(c3ccccc3)C4=O)ccc2nc1-c1ccc(Cl)cc1] | 5-(3-(4-chlorophenyl)-7-(1-oxo-2-phenyl-2,8-diazaspiro[4.5]decane-8-carbonyl)quinoxalin-2-yl)pentanoic acid | 597.5 |
| 635 | 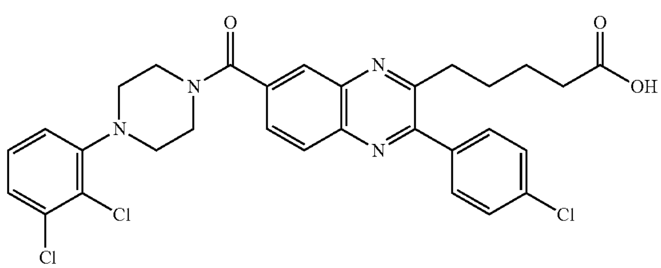 [SMILES: O=C(O)CCCCc1nc2cc(C(=O)N3CCN(c4cccc(Cl)c4Cl)CC3)ccc2nc1-c1ccc(Cl)cc1] | 5-(3-(4-chlorophenyl)-7-(4-(2,3-dichlorophenyl)piperazine-1-carbonyl)quinoxalin-2-yl)pentanoic acid | 597.3 |
| 636 | 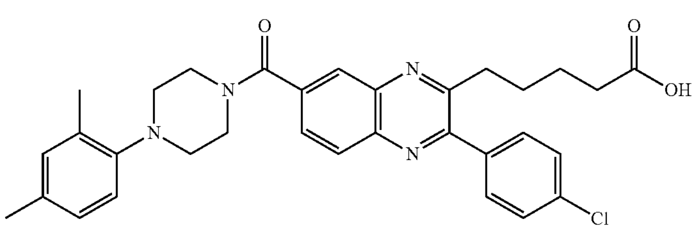 [SMILES: Cc1ccc(N2CCN(C(=O)c3ccc4nc(-c5ccc(Cl)cc5)c(CCCCC(=O)O)nc4c3)CC2)c(C)c1] | 5-(3-(4-chlorophenyl)-7-(4-(2,4-dimethylphenyl)piperazine-1-carbonyl)quinoxalin-2-yl)pentanoic acid | 557.4 |
| 637 | 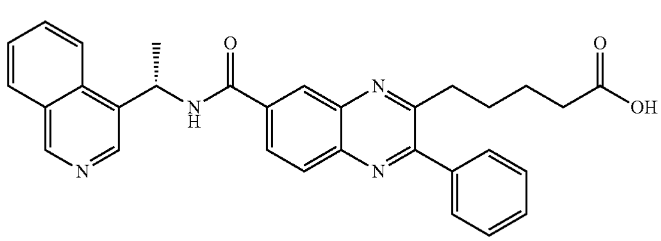 [SMILES: C[C@H](NC(=O)c1ccc2nc(-c3ccccc3)c(CCCCC(=O)O)nc2c1)c1cncc2ccccc12] | (S)-5-(7-((1-(isoquinolin-4-yl)ethyl)carbamoyl)-3-phenylquinoxalin-2-yl)pentanoic acid | 505 |

-continued

| No. | Structure | Name | M + H |
|---|---|---|---|
| 638 | 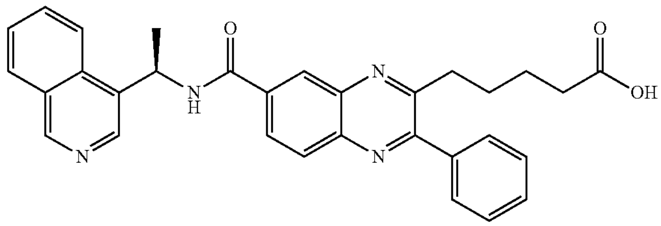 [SMILES: C[C@@H](NC(=O)c1ccc2nc(-c3ccccc3)c(CCCCC(=O)O)nc2c1)c1cncc2ccccc12] | (R)-5-(7-((1-(isoquinolin-4-yl)ethyl)carbamoyl)-3-phenylquinoxalin-2-yl)pentanoic acid | 505 |
| 639 | 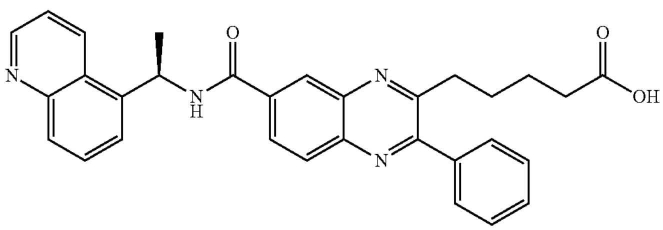 [SMILES: C[C@@H](NC(=O)c1ccc2nc(-c3ccccc3)c(CCCCC(=O)O)nc2c1)c1cccc2ncccc12] | (R)-5-(3-phenyl-7-((1-(quinolin-5-yl)ethyl)carbamoyl)quinoxalin-2-yl)pentanoic acid | 505 |
| 640 | 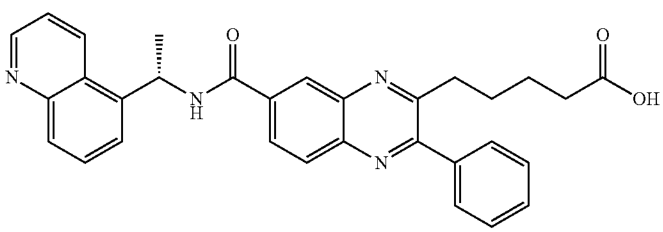 [SMILES: C[C@H](NC(=O)c1ccc2nc(-c3ccccc3)c(CCCCC(=O)O)nc2c1)c1cccc2ncccc12] | (S)-5-(3-phenyl-7-((1-(quinolin-5-yl)ethyl)carbamoyl)quinoxalin-2-yl)pentanoic acid | 505 |
| 641 | 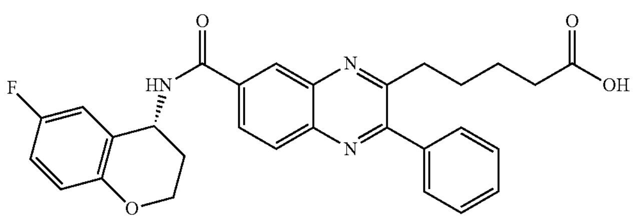 [SMILES: O=C(O)CCCCc1nc2cc(C(=O)N[C@@H]3CCOc4ccc(F)cc43)ccc2nc1-c1ccccc1] | (R)-5-(7-((6-fluoro-chroman-4-yl)carbamoyl)-3-phenylquinoxalin-2-yl)pentanoic acid | 500 |
| 642 | 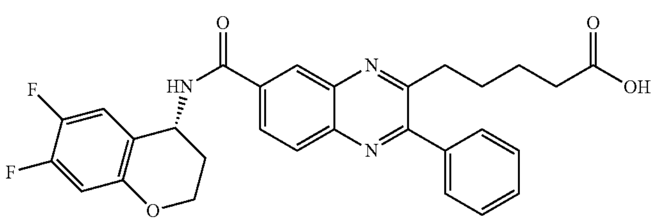 [SMILES: O=C(O)CCCCc1nc2cc(C(=O)N[C@@H]3CCOc4cc(F)c(F)cc43)ccc2nc1-c1ccccc1] | (R)-5-(7-((6,7-difluorochroman-4-yl)carbamoyl)-3-phenylquinoxalin-2-yl)pentanoic acid | 518 |
| 643 | 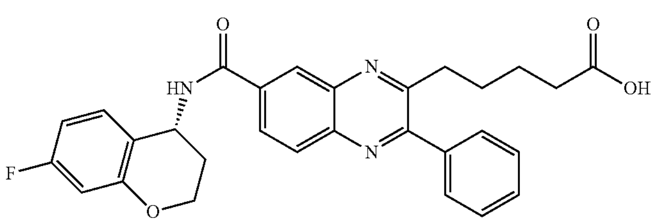 [SMILES: O=C(O)CCCCc1nc2cc(C(=O)N[C@@H]3CCOc4cc(F)ccc43)ccc2nc1-c1ccccc1] | (R)-5-(7-((7-fluoro-chroman-4-yl)carbamoyl)-3-phenylquinoxalin-2-yl)pentanoic acid | 500 |
| 644 | 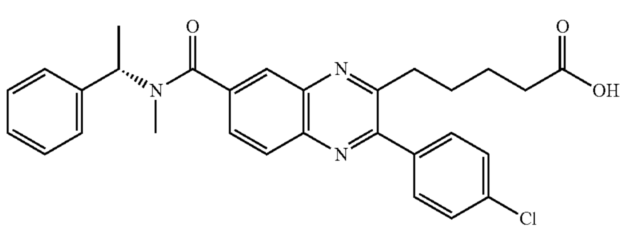 [SMILES: C[C@@H](c1ccccc1)N(C)C(=O)c1ccc2nc(-c3ccc(Cl)cc3)c(CCCCC(=O)O)nc2c1] | (S)-5-(3-(4-chloro-phenyl)-7-(methyl(1-phenylethyl)carbamoyl)quinoxalin-2-yl)pentanoic acid | 502.3 |

-continued

| No. | Structure | Name | M + H |
|---|---|---|---|
| 645 | 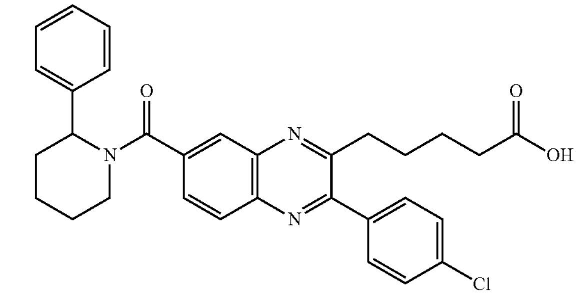 [SMILES: O=C(O)CCCCc1nc2cc(C(=O)N3CCCCC3c3ccccc3)ccc2nc1-c1ccc(Cl)cc1] | 5-(3-(4-chlorophenyl)-7-(2-phenylpiperidine-1-carbonyl)quinoxalin-2-yl)pentanoic acid | 528.3 |
| 646 | 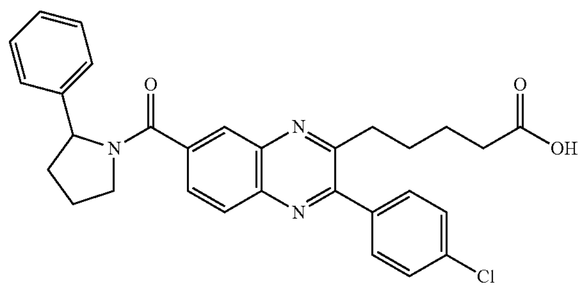 [SMILES: O=C(O)CCCCc1nc2cc(C(=O)N3CCCC3c3ccccc3)ccc2nc1-c1ccc(Cl)cc1] | 5-(3-(4-chlorophenyl)-7-(2-phenylpyrrolidine-1-carbonyl)quinoxalin-2-yl)pentanoic acid | 514.3 |
| 647 | 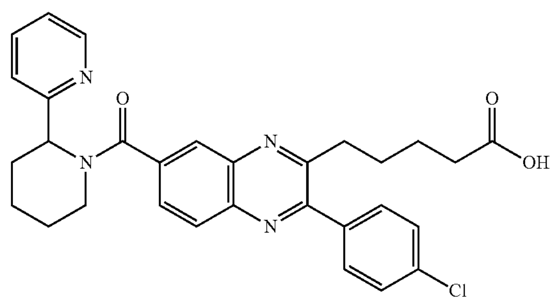 [SMILES: O=C(O)CCCCc1nc2cc(C(=O)N3CCCCC3c3ccccn3)ccc2nc1-c1ccc(Cl)cc1] | 5-(3-(4-chlorophenyl)-7-(2-(pyridin-2-yl)piperidine-1-carbonyl)quinoxalin-2-yl)pentanoic acid | 529.3 |
| 648 | 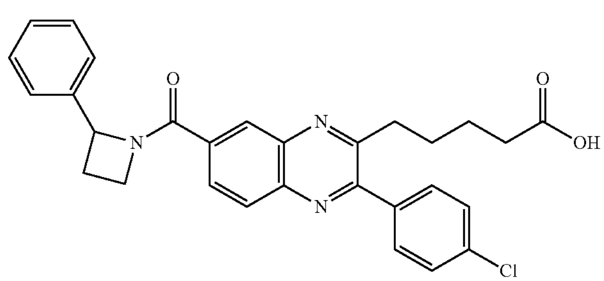 [SMILES: O=C(O)CCCCc1nc2cc(C(=O)N3CCC3c3ccccc3)ccc2nc1-c1ccc(Cl)cc1] | 5-(3-(4-chlorophenyl)-7-(2-phenylazetidine-1-carbonyl)quinoxalin-2-yl)pentanoic acid | 500.3 |
| 649 | 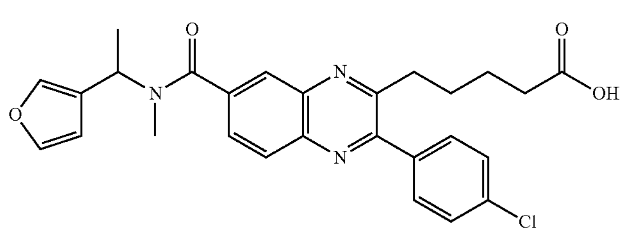 [SMILES: CC(c1ccoc1)N(C)C(=O)c1ccc2nc(-c3ccc(Cl)cc3)c(CCCCC(=O)O)nc2c1] | 5-(3-(4-chlorophenyl)-7-((1-(furan-3-yl)ethyl)(methyl)carbamoyl)quinoxalin-2-yl)pentanoic acid | 492.3 |

-continued

| No. | Structure | Name | M + H |
|---|---|---|---|
| 650 | 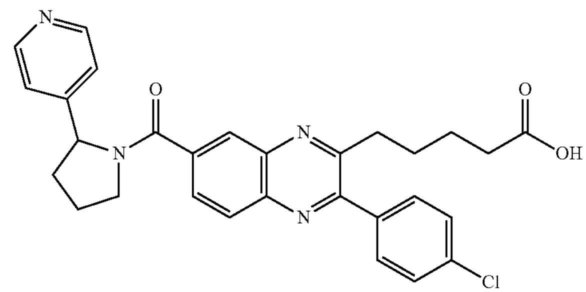 [SMILES: O=C(O)CCCCc1nc2cc(C(=O)N3CCCC3c3ccncc3)ccc2nc1-c1ccc(Cl)cc1] | 5-(3-(4-chlorophenyl)-7-(2-(pyridin-4-yl)pyrrolidine-1-carbonyl)quinoxalin-2-yl)pentanoic acid | 515.3 |
| 651 | 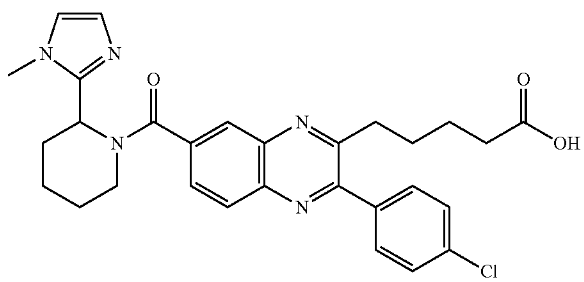 [SMILES: Cn1ccnc1C1CCCCN1C(=O)c1ccc2nc(-c3ccc(Cl)cc3)c(CCCCC(=O)O)nc2c1] | 5-(3-(4-chlorophenyl)-7-(2-(1-methyl-1H-imidazol-2-yl)piperidine-1-carbonyl)quinoxalin-2-yl)pentanoic acid | 532.3 |
| 652 | 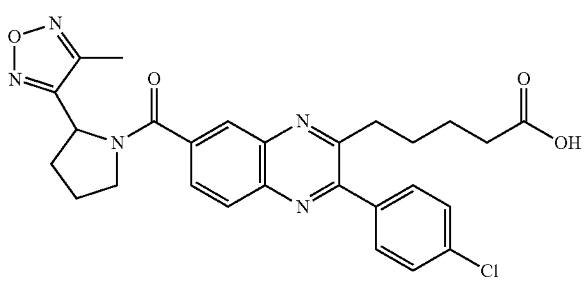 [SMILES: Cc1nonc1C1CCCN1C(=O)c1ccc2nc(-c3ccc(Cl)cc3)c(CCCCC(=O)O)nc2c1] | 5-(3-(4-chlorophenyl)-7-(2-(4-methyl-1,2,5-oxadiazol-3-yl)pyrrolidine-1-carbonyl)quinoxalin-2-yl)pentanoic acid | 520.3 |
| 653 | 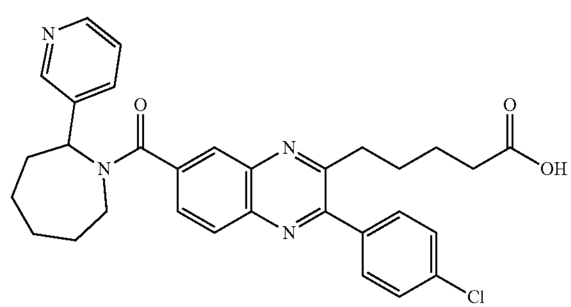 [SMILES: O=C(O)CCCCc1nc2cc(C(=O)N3CCCCCC3c3cccnc3)ccc2nc1-c1ccc(Cl)cc1] | 5-(3-(4-chlorophenyl)-7-(2-(pyridin-3-yl)azepane-1-carbonyl)quinoxalin-2-yl)pentanoic acid | 543.3 |
| 654 | 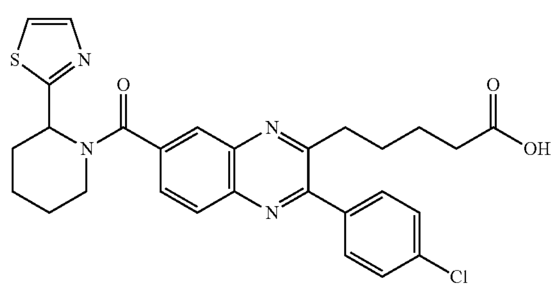 [SMILES: O=C(O)CCCCc1nc2cc(C(=O)N3CCCCC3c3nccs3)ccc2nc1-c1ccc(Cl)cc1] | 5-(3-(4-chlorophenyl)-7-(2-(thiazol-2-yl)piperidine-1-carbonyl)quinoxalin-2-yl)pentanoic acid | 535.3 |

| No. | Structure | Name | M + H |
|---|---|---|---|
| 655 | 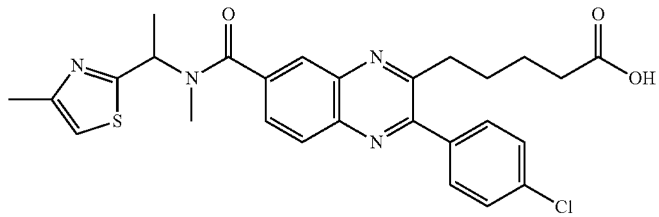 [SMILES: Cc1csc(C(C)N(C)C(=O)c2ccc3nc(-c4ccc(Cl)cc4)c(CCCCC(=O)O)nc3c2)n1] | 5-(3-(4-chlorophenyl)-7-(methyl(1-(4-methylthiazol-2-yl)ethyl)carbamoyl)quinoxalin-2-yl)pentanoic acid | 523.3 |
| 656 | 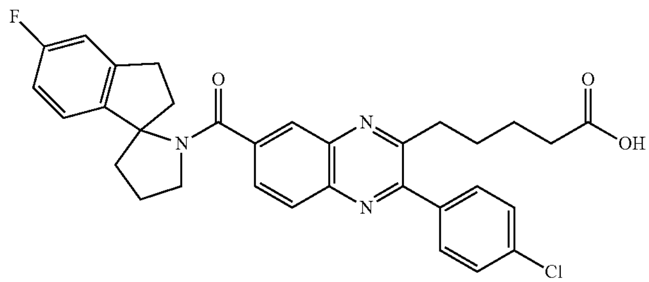 [SMILES: O=C(O)CCCCc1nc2cc(C(=O)N3CCCC34CCc3cc(F)ccc34)ccc2nc1-c1ccc(Cl)cc1] | 5-(3-(4-chlorophenyl)-7-(5-fluoro-2,3-dihydrospiro[indene-1,2'-pyrrolidin]-1'-ylcarbonyl)quinoxalin-2-yl)pentanoic acid | 558.3 |
| 657 | 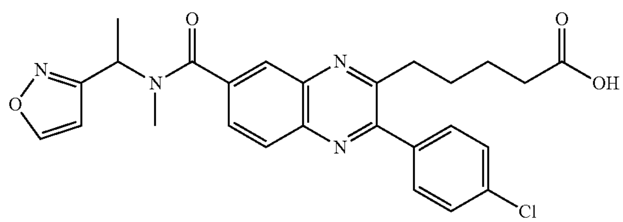 [SMILES: CC(c1ccon1)N(C)C(=O)c1ccc2nc(-c3ccc(Cl)cc3)c(CCCCC(=O)O)nc2c1] | 5-(3-(4-chlorophenyl)-7-((1-(isoxazol-3-yl)ethyl)(methyl)carbamoyl)quinoxalin-2-yl)pentanoic acid | 493.3 |
| 658 | 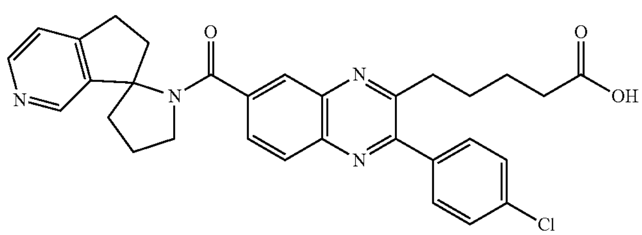 [SMILES: O=C(O)CCCCc1nc2cc(C(=O)N3CCCC34CCc3ccncc34)ccc2nc1-c1ccc(Cl)cc1] | 5-(3-(4-chlorophenyl)-7-(5,6-dihydrospiro[cyclopenta[c]pyridine-7,2'-pyrrolidin]-1'-ylcarbonyl)quinoxalin-2-yl)pentanoic acid | 541.3 |
| 659 | 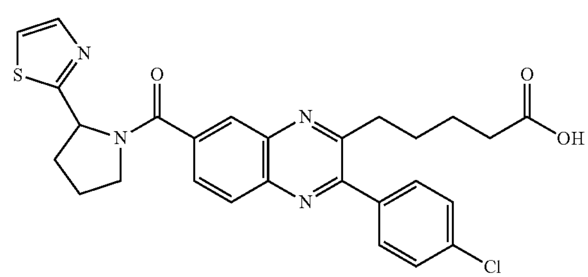 [SMILES: O=C(O)CCCCc1nc2cc(C(=O)N3CCCC3c3nccs3)ccc2nc1-c1ccc(Cl)cc1] | 5-(3-(4-chlorophenyl)-7-(2-(thiazol-2-yl)pyrrolidine-1-carbonyl)quinoxalin-2-yl)pentanoic acid | 521.2 |
| 660 | 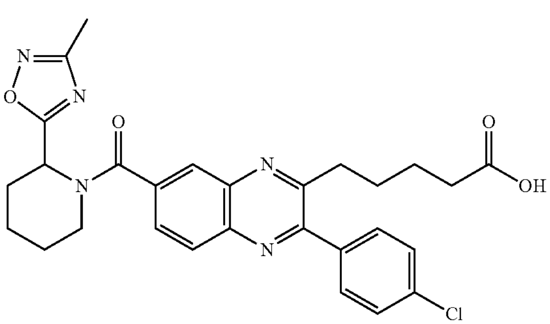 [SMILES: Cc1noc(C2CCCCN2C(=O)c2ccc3nc(-c4ccc(Cl)cc4)c(CCCCC(=O)O)nc3c2)n1] | 5-(3-(4-chlorophenyl)-7-(2-(3-methyl-1,2,4-oxadiazol-5-yl)piperidine-1-carbonyl)quinoxalin-2-yl)pentanoic acid | 534.3 |

-continued

| No. | Structure | Name | M + H |
|---|---|---|---|
| 661 | 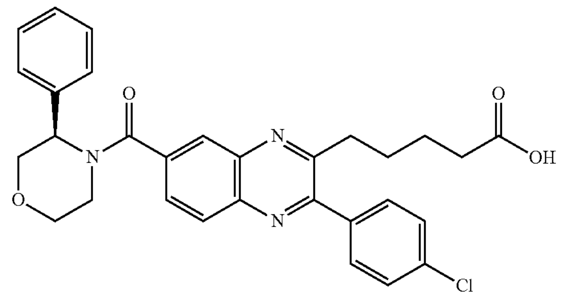 [SMILES: O=C(O)CCCCc1nc2cc(C(=O)N3CCOC[C@H]3c3ccccc3)ccc2nc1-c1ccc(Cl)cc1] | (R)-5-(3-(4-chlorophenyl)-7-(3-phenylmorphohne-4-carbonyl)quinoxalin-2-yl)pentanoic acid | 530.3 |
| 662 | 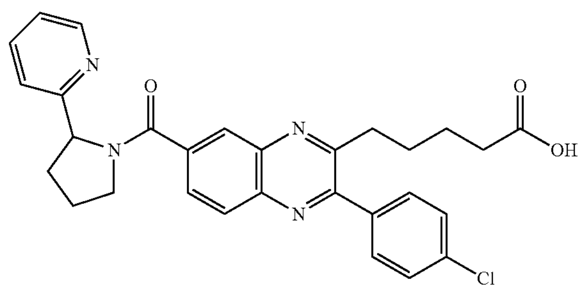 [SMILES: O=C(O)CCCCc1nc2cc(C(=O)N3CCCC3c3ccccn3)ccc2nc1-c1ccc(Cl)cc1] | 5-(3-(4-chlorophenyl)-7-(2-(pyridin-2-yl)pyrrolidine-1-carbonyl)quinoxalin-2-yl)pentanoic acid | 515.3 |
| 663 | 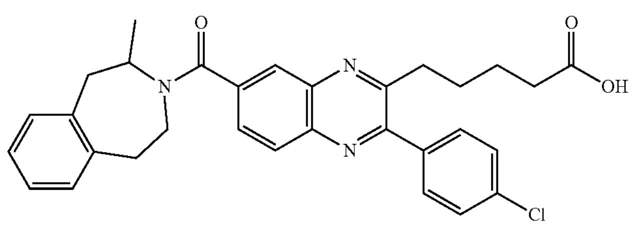 [SMILES: CC1Cc2ccccc2CCN1C(=O)c1ccc2nc(-c3ccc(Cl)cc3)c(CCCCC(=O)O)nc2c1] | 5-(3-(4-chlorophenyl)-7-(2-methyl-2,3,4,5-tetrahydro-1H-benzo[d]azepine-3-carbonyl)quinoxalin-2-yl)pentanoic acid | 528.3 |
| 664 | 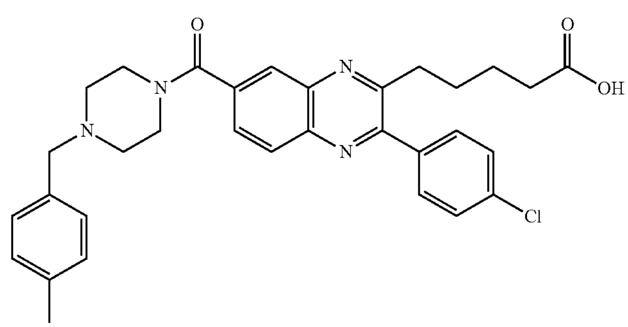 [SMILES: Cc1ccc(CN2CCN(C(=O)c3ccc4nc(-c5ccc(Cl)cc5)c(CCCCC(=O)O)nc4c3)CC2)cc1] | 5-(3-(4-chlorophenyl)-7-(4-(4-methylbenzyl)piperazine-1-carbonyl)quinoxalin-2-yl)pentanoic acid | 557.4 |
| 665 | 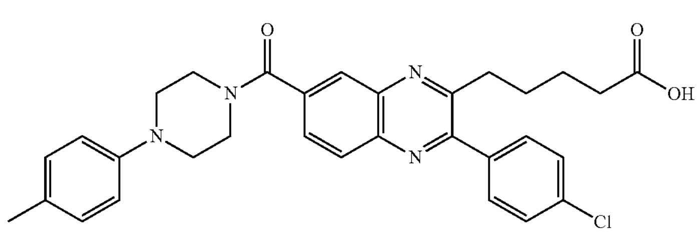 [SMILES: Cc1ccc(N2CCN(C(=O)c3ccc4nc(-c5ccc(Cl)cc5)c(CCCCC(=O)O)nc4c3)CC2)cc1] | 5-(3-(4-chlorophenyl)-7-(4-(p-tolyl)piperazine-1-carbonyl)quinoxalin-2-yl)pentanoic acid | 543.3 |

| No. | Structure | Name | M + H |
|---|---|---|---|
| 666 | 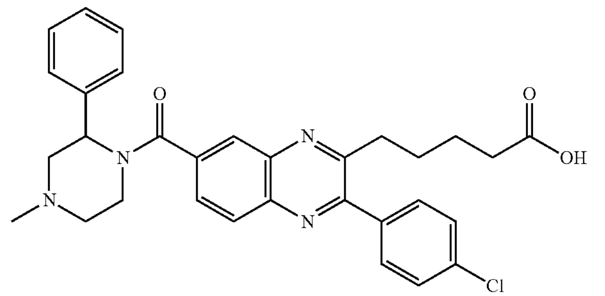 [SMILES: CN1CCN(C(=O)c2ccc3nc(-c4ccc(Cl)cc4)c(CCCCC(=O)O)nc3c2)C(c2ccccc2)C1] | 5-(3-(4-chlorophenyl)-7-(4-methyl-2-phenylpiperazine-1-carbonyl)quinoxalin-2-yl)pentanoic acid | 543.3 |
| 667 | 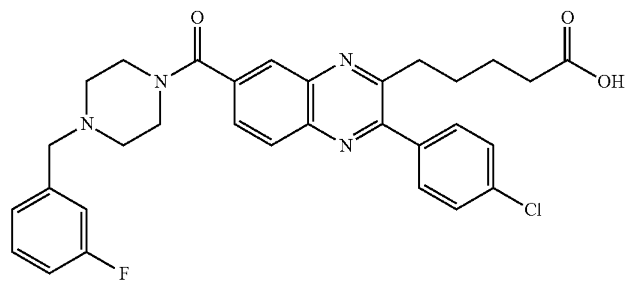 [SMILES: O=C(O)CCCCc1nc2cc(C(=O)N3CCN(Cc4cccc(F)c4)CC3)ccc2nc1-c1ccc(Cl)cc1] | 5-(3-(4-chlorophenyl)-7-(4-(3-fluorobenzyl)piperazine-1-carbonyl)quinoxalin-2-yl)pentanoic acid | 561.3 |
| 668 | 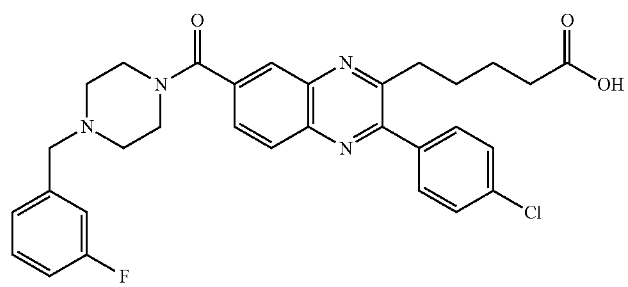 [SMILES: O=C(O)CCCCc1nc2cc(C(=O)N3CCN(Cc4cccc(F)c4)CC3)ccc2nc1-c1ccc(Cl)cc1] | 5-(3-(4-chlorophertyl)-7-(2-(trifluoromethyl)-5,6,7,8-tetrahydroimidazo[1,2-a]pyrazine-7-carbonyl)quinoxalin-2-yl)pentanoic acid | 558.3 |
| 669 | 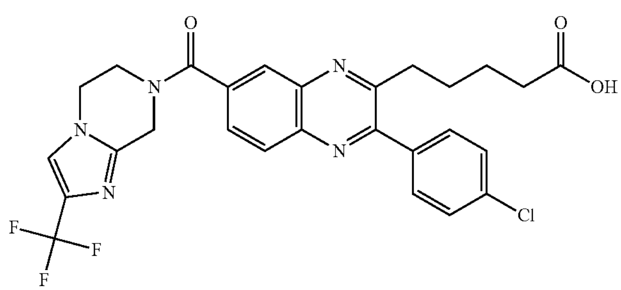 [SMILES: O=C(O)CCCCc1nc2cc(C(=O)N3CCn4cc(C(F)(F)F)nc4C3)ccc2nc1-c1ccc(Cl)cc1] | 5-(3-(4-chlorophenyl)-7-(4-(5-chloropyridin-2-yl)piperazine-1-carbonyl)quinoxalin-2-yl)pentanoic acid | 564.3 |
| 670 | 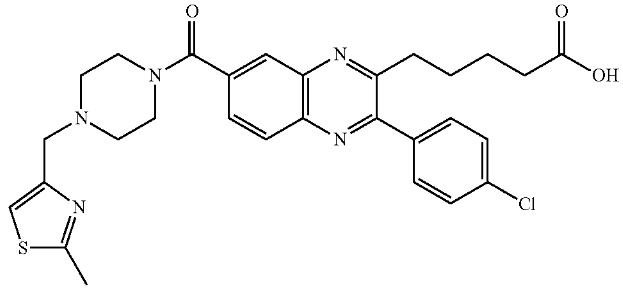 [SMILES: Cc1nc(CN2CCN(C(=O)c3ccc4nc(-c5ccc(Cl)cc5)c(CCCCC(=O)O)nc4c3)CC2)cs1] | 5-(3-(4-chlorophenyl)-7-(4-((2-methylthiazol-4-yl)methyl)piperazine-1-carbonyl)quinoxalin-2-yl)pentanoic acid | 564.3 |

-continued

| No. | Structure | Name | M + H |
|---|---|---|---|
| 671 | 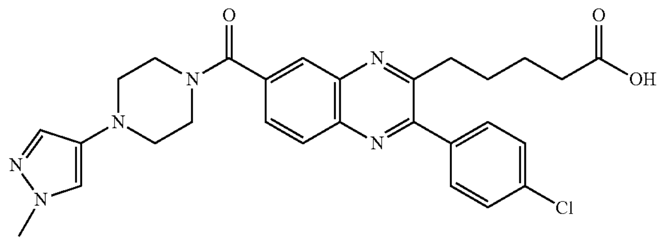 [SMILES: Cn1cc(N2CCN(C(=O)c3ccc4nc(-c5ccc(Cl)cc5)c(CCCCC(=O)O)nc4c3)CC2)cn1] | 5-(3-(4-chlorophenyl)-7-(4-(1-methyl-1H-pyrazol-4-yl)piperazine-1-carbonyl)quinoxalin-2-yl)pentanoic acid | 533.3 |
| 672 | 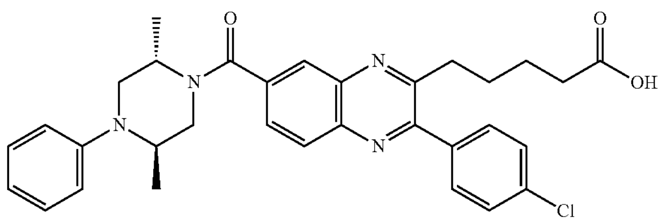 [SMILES: C[C@@H]1CN(C(=O)c2ccc3nc(-c4ccc(Cl)cc4)c(CCCCC(=O)O)nc3c2)[C@@H](C)CN1c1ccccc1] | 5-(3-(4-chlorophenyl)-7-((2S,5R)-2,5-dimethyl-4-phenylpiperazine-1-carbonyl)quinoxalin-2-yl)pentanoic acid | 557.4 |
| 673 | 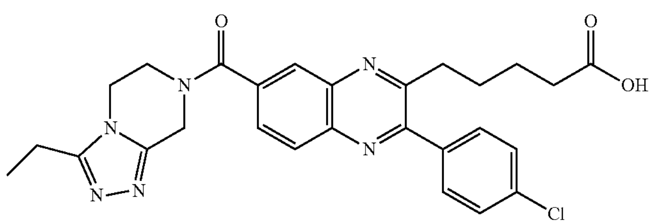 [SMILES: CCc1nnc2n1CCN(C(=O)c1ccc3nc(-c4ccc(Cl)cc4)c(CCCCC(=O)O)nc3c1)C2] | 5-(3-(4-chlorophenyl)-7-(3-ethyl-5,6,7,8-tetrahydro-[1,2,4]triazolo[4,3-a]pyrazine-7-carbonyl)quinoxalin-2-yl)pentanoic acid | 519.3 |
| 674 | 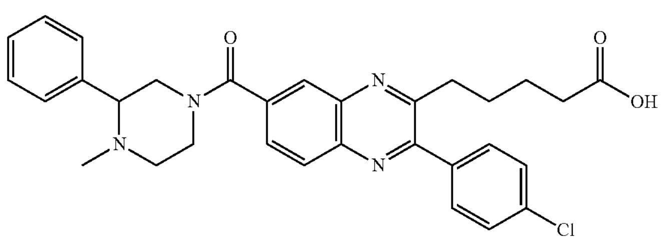 [SMILES: CN1CCN(C(=O)c2ccc3nc(-c4ccc(Cl)cc4)c(CCCCC(=O)O)nc3c2)CC1c1ccccc1] | 5-(3-(4-chlorophenyl)-7-(4-methyl-3-phenylpiperazine-1-carbonyl)quinoxalin-2-yl)pentanoic acid | 543.3 |
| 675 | 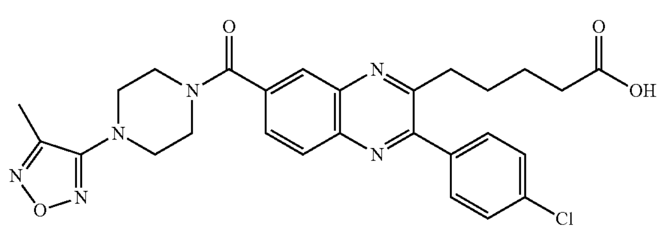 [SMILES: Cc1nonc1N1CCN(C(=O)c2ccc3nc(-c4ccc(Cl)cc4)c(CCCCC(=O)O)nc3c2)CC1] | 5-(3-(4-chlorophenyl)-7-(4-(4-methyl-1,2,5-oxadiazol-3-yl)piperazine-1-carbonyl)quinoxalin-2-yl)pentanoic acid | 535.3 |
| 676 | 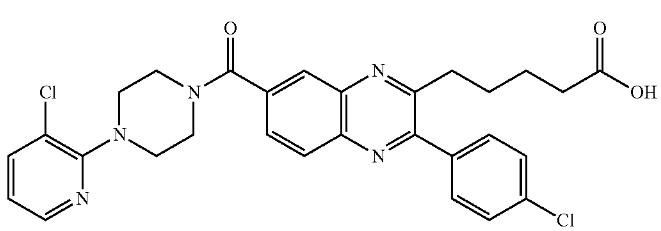 [SMILES: O=C(O)CCCCc1nc2cc(C(=O)N3CCN(c4ncccc4Cl)CC3)ccc2nc1-c1ccc(Cl)cc1] | 5-(3-(4-chlorophenyl)-7-(4-(3-chloropyridin-2-yl)piperazine-1-carbonyl)quinoxalin-2-yl)pentanoic acid | 564.3 |

-continued

| No. | Structure | Name | M + H |
|---|---|---|---|
| 677 | 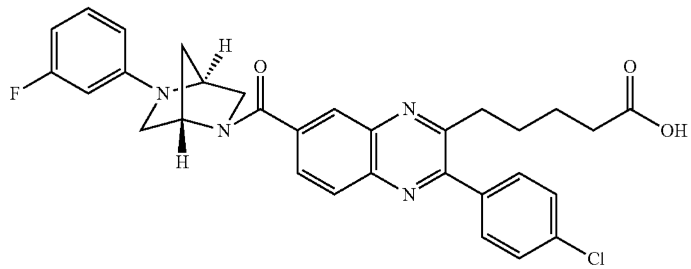 [SMILES: O=C(O)CCCCc1nc2cc(C(=O)N3C[C@@H]4C[C@H]3CN4c3cccc(F)c3)ccc2nc1-c1ccc(Cl)cc1] | 5-(3-(4-chlorophenyl)-7-((1S,4S)-5-(3-fluorophenyl)-2,5-diazabicyclo[2.2.1]heptane-2-carbonyl)quinoxalin-2-yl)pentanoic acid | 559.3 |
| 678 | 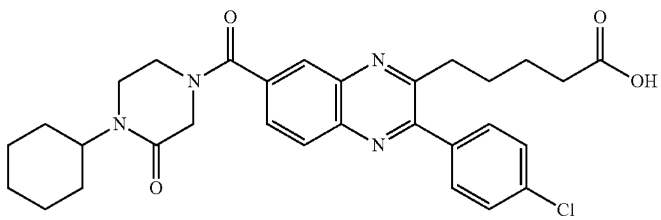 [SMILES: O=C(O)CCCCc1nc2cc(C(=O)N3CCN(C4CCCCC4)C(=O)C3)ccc2nc1-c1ccc(Cl)cc1] | 5-(3-(4-chlorophenyl)-7-(4-cyclohexyl-3-oxo-piperazine-1-carbonyl)quinoxalin-2-yl)pentanoic acid | 549.4 |
| 679 | 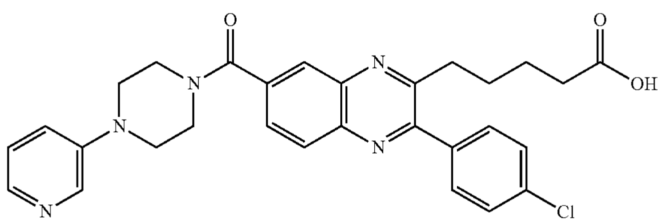 [SMILES: O=C(O)CCCCc1nc2cc(C(=O)N3CCN(c4cccnc4)CC3)ccc2nc1-c1ccc(Cl)cc1] | 5-(3-(4-chlorophenyl)-7-(4-(pyridin-3-y)piperazine-1-carbonyl)quinoxalin-2-yl)pentanoic acid | 530.3 |
| 680 | 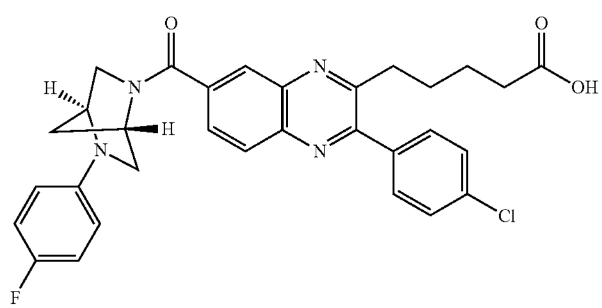 [SMILES: O=C(O)CCCCc1nc2cc(C(=O)N3C[C@@H]4C[C@H]3CN4c3ccc(F)cc3)ccc2nc1-c1ccc(Cl)cc1] | 5-(3-(4-chlorophenyl)-7-((1S,4S)-5-(4-fluorophenyl)-2,5-diazabicyclo[2.2.1]heptane-2-carbonyl)quinoxalin-2-yl)pentanoic acid | 559.3 |
| 681 | 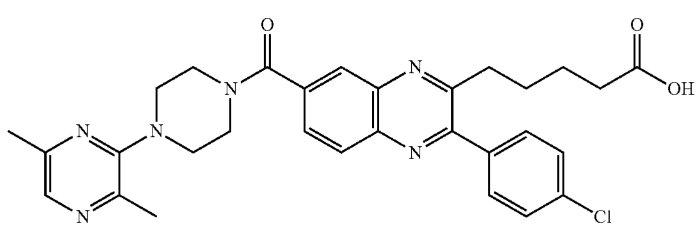 [SMILES: Cc1cnc(C)c(N2CCN(C(=O)c3ccc4nc(-c5ccc(Cl)cc5)c(CCCCC(=O)O)nc4c3)CC2)n1] | 5-(3-(4-chlorophenyl)-7-(4-(3,6-dimethylpyrazin-2-yl)piperazine-1-carbonyl)quinoxalin-2-yl)pentanoic acid | 559.4 |
| 682 | 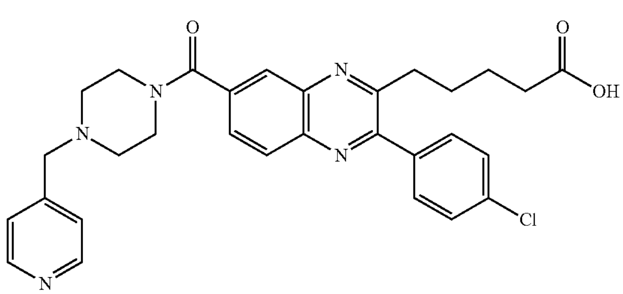 [SMILES: O=C(O)CCCCc1nc2cc(C(=O)N3CCN(Cc4ccncc4)CC3)ccc2nc1-c1ccc(Cl)cc1] | 5-(3-(4-chlorophenyl)-7-(4-(pyridin-4-ylmethyl)piperazine-1-carbonyl)quinoxalin-2-yl)pentanoic acid | 544.3 |

| No. | Structure | Name | M + H |
|---|---|---|---|
| 683 | 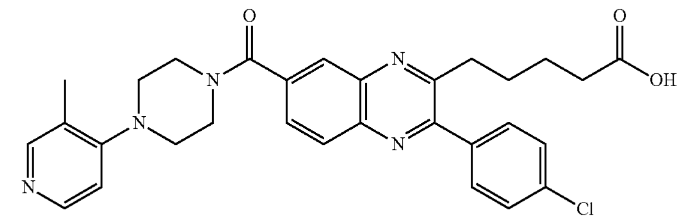 [SMILES: Cc1cnccc1N1CCN(C(=O)c2ccc3nc(-c4ccc(Cl)cc4)c(CCCCC(=O)O)nc3c2)CC1] | 5-(3-(4-chlorophenyl)-7-(4-(3-methylpyridin-4-yl)piperazine-1-carbonyl)quinoxalin-2-yl)pentanoic acid | 544.3 |
| 684 | 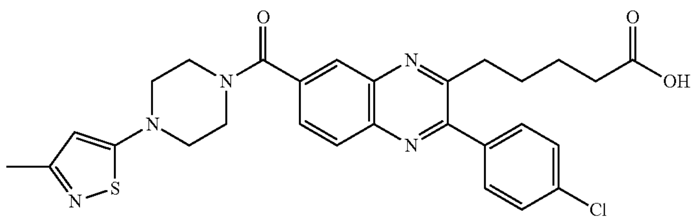 [SMILES: Cc1cc(N2CCN(C(=O)c3ccc4nc(-c5ccc(Cl)cc5)c(CCCCC(=O)O)nc4c3)CC2)sn1] | 5-(3-(4-chlorophenyl)-7-(4-(3-methylisothiazol-5-yl)piperazine-1-carbonyl)quinoxalin-2-yl)pentanoic acid | 550.3 |
| 685 | 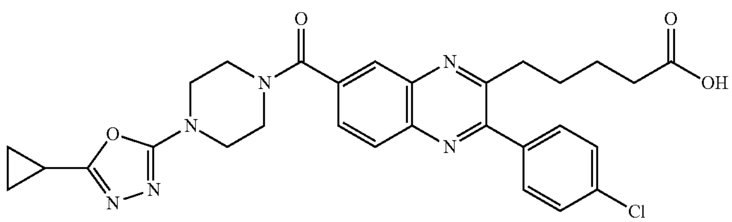 [SMILES: O=C(O)CCCCc1nc2cc(C(=O)N3CCN(c4nnc(C5CC5)o4)CC3)ccc2nc1-c1ccc(Cl)cc1] | 5-(3-(4-chlorophenyl)-7-(4-(5-cyclopropyl-1,3,4-oxadiazol-2-yl)piperazine-1-carbonyl)quinoxalin-2-yl)pentanoic acid | 561.4 |
| 686 | 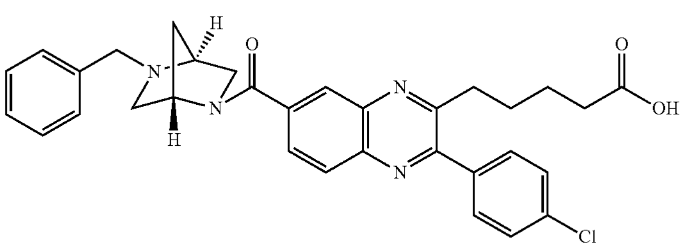 [SMILES: O=C(O)CCCCc1nc2cc(C(=O)N3C[C@@H]4C[C@H]3CN4Cc3ccccc3)ccc2nc1-c1ccc(Cl)cc1] | 5-(7-((1S,4S)-5-benzyl-2,5-diazabicyclo[2.2.1]heptane-2-carbonyl)-3-(4-chlorophenyl)quinoxalin-2-yl)pentanoic acid | 555.4 |
| 687 | 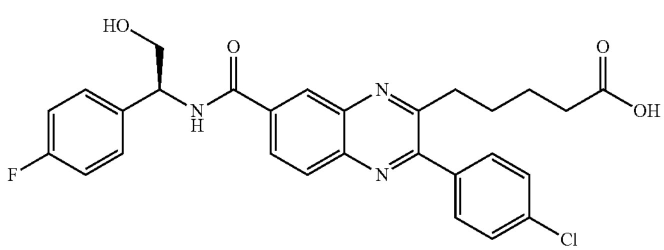 [SMILES: O=C(O)CCCCc1nc2cc(C(=O)N[C@H](CO)c3ccc(F)cc3)ccc2nc1-c1ccc(Cl)cc1] | (S)-5-(3-(4-chlorophenyl)-7-((1-(4-fluorophenyl)-2-hydroxyethyl)carbamoyl)quinoxalin-2-yl)pentanoic acid | 522 |
| 688 | 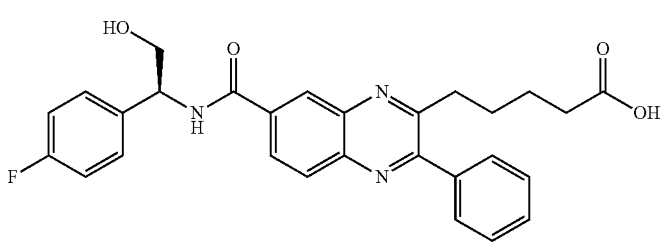 [SMILES: O=C(O)CCCCc1nc2cc(C(=O)N[C@H](CO)c3ccc(F)cc3)ccc2nc1-c1ccccc1] | (S)-5-(7-((1-(4-fluorophenyl)-2-hydroxyethyl)carbamoyl)-3-phenylquinoxalin-2-yl)pentanoic acid | 488 |

-continued

| No. | Structure | Name | M + H |
|---|---|---|---|
| 689 | 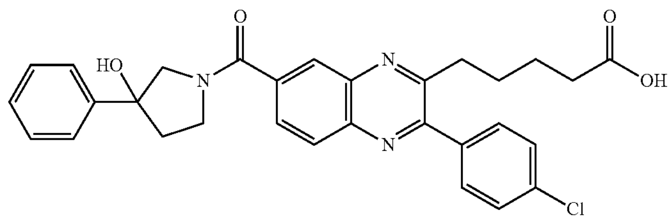 [SMILES: O=C(O)CCCCc1nc2cc(C(=O)N3CCC(O)(c4ccccc4)C3)ccc2nc1-c1ccc(Cl)cc1] | 5-(3-(4-chlorophenyl)-7-(3-hydroxy-3-phenylpyrrolidine-1-carbonyl)quinoxalin-2-yl)pentanoic acid | 530.4 |
| 690 | 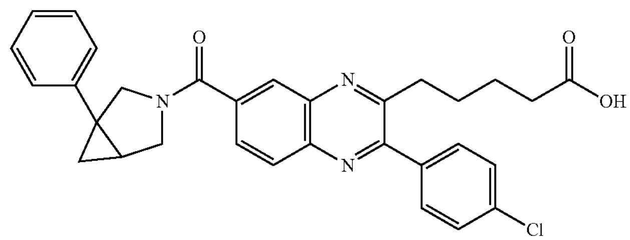 [SMILES: O=C(O)CCCCc1nc2cc(C(=O)N3CC4CC4(c4ccccc4)C3)ccc2nc1-c1ccc(Cl)cc1] | 5-(3-(4-chlorophenyl)-7-(1-phenyl-3-azabicyclo[3.1.0]hexane-3-carbonyl)quinoxalin-2-yl)pentanoic acid | 526.4 |
| 691 | 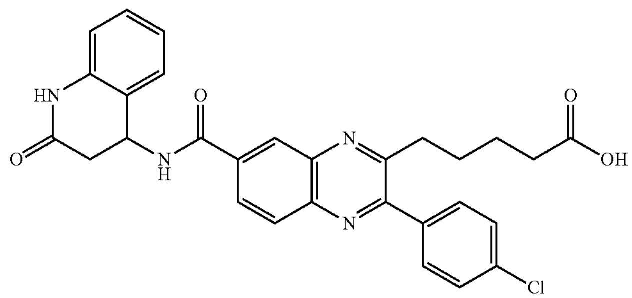 [SMILES: O=C(O)CCCCc1nc2cc(C(=O)NC3CC(=O)Nc4ccccc43)ccc2nc1-c1ccc(Cl)cc1] | 5-(3-(4-chlorophenyl)-7-((2-oxo-1,2,3,4-tetrahydroquinolin-4-yl)carbamoyl)quinoxalin-2-yl)pentanoic acid | 529.4 |
| 692 | 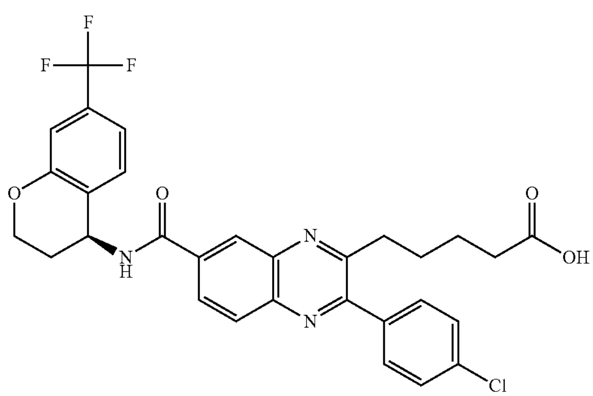 [SMILES: O=C(O)CCCCc1nc2cc(C(=O)N[C@H]3CCOc4cc(C(F)(F)F)ccc43)ccc2nc1-c1ccc(Cl)cc1] | (S)-5-(3-(4-chlorophenyl)-7-((7-(trifluoromethyl)chroman-4-yl)carbamoyl)quinoxalin-2-yl)pentanoic acid | 584.4 |
| 693 | 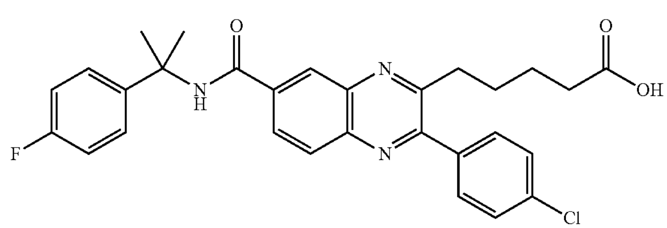 [SMILES: CC(C)(NC(=O)c1ccc2nc(-c3ccc(Cl)cc3)c(CCCCC(=O)O)nc2c1)c1ccc(F)cc1] | 5-(3-(4-chlorophenyl)-7-((2-(4-fluorophenyl)propan-2-yl)carbamoyl)quinoxalin-2-yl)pentanoic acid | 520.4 |

| No. | Structure | Name | M + H |
|---|---|---|---|
| 694 | 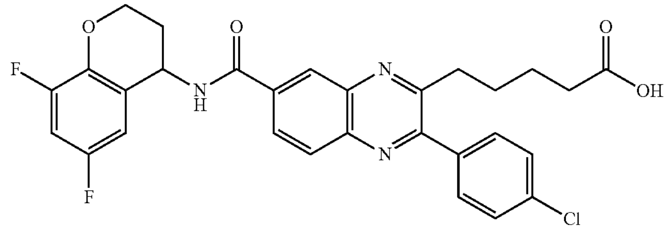 [SMILES: O=C(O)CCCCc1nc2cc(C(=O)NC3CCOc4c(F)cc(F)cc43)ccc2nc1-c1ccc(Cl)cc1] | 5-(3-(4-chlorophenyl)-7-((6,8-difluorochroman-4-yl)carbamoyl)quinoxalin-2-yl)pentanoic acid | 552.4 |
| 695 | 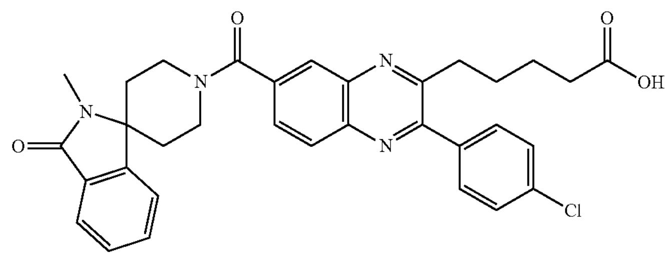 [SMILES: CN1C(=O)c2ccccc2C12CCN(C(=O)c1ccc3nc(-c4ccc(Cl)cc4)c(CCCCC(=O)O)nc3c1)CC2] | 5-(3-(4-chlorophenyl)-7-(2-methyl-3-oxospiro[isoindoline-1,4'-piperidin]-1'-ylcarbonyl)quinoxalin-2-yl)pentanoic acid | 583.5 |
| 696 | 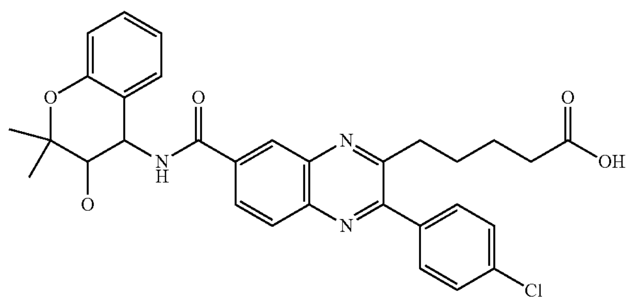 [SMILES: CC1(C)Oc2ccccc2C(NC(=O)c2ccc3nc(-c4ccc(Cl)cc4)c(CCCCC(=O)O)nc3c2)C1O] | 5-(3-(4-chlorophenyl)-7-((3-hydroxy-2,2-dimethylchroman-4-yl)carbamoyl)quinoxalin-2-yl)pentanoic acid | 560.4 |
| 697 | 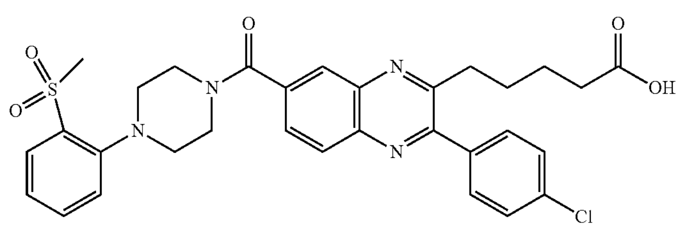 [SMILES: CS(=O)(=O)c1ccccc1N1CCN(C(=O)c2ccc3nc(-c4ccc(Cl)cc4)c(CCCCC(=O)O)nc3c2)CC1] | 5-(3-(4-chlorophenyl)-7-(4-(2-(methylsulfonyl)phenyl)piperazine-1-carbonyl)quinoxalin-2-yl)pentanoic acid | 607.5 |
| 698 | 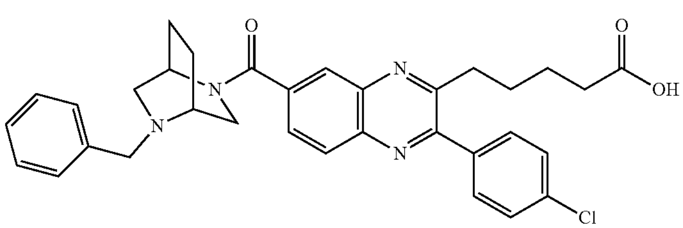 [SMILES: O=C(O)CCCCc1nc2cc(C(=O)N3CC4CCC3CN4Cc3ccccc3)ccc2nc1-c1ccc(Cl)cc1] | 5-(7-((1R,4R)-5-benzyl-2,5-diazabicyclo[2.2.2]octane-2-carbonyl)-3-(4-chlorophenyl)quinoxalin-2-yl)pentanoic acid | 569.5 |
| 699 | 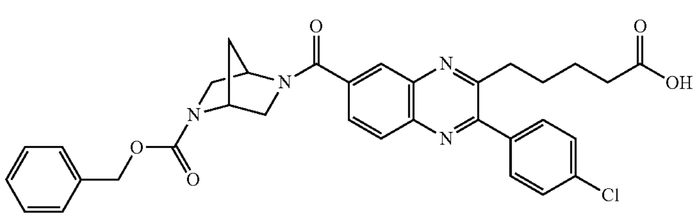 [SMILES: O=C(O)CCCCc1nc2cc(C(=O)N3CC4CC3CN4C(=O)OCc3ccccc3)ccc2nc1-c1ccc(Cl)cc1] | 5-(7-((1R,4R)-5-((benzyloxy)carbonyl)-2,5-diazabicyclo[2.2.1]heptane-2-carbonyl)-3-(4-chlorophenyl)quinoxalin-2-yl)pentanoic acid | 599.5 |

| No. | Structure | Name | M + H |
|---|---|---|---|
| 700 | 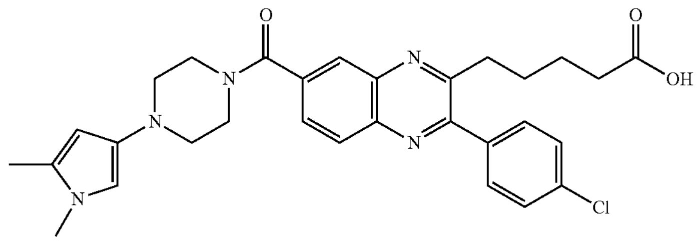 [SMILES: Cc1cc(N2CCN(C(=O)c3ccc4nc(-c5ccc(Cl)cc5)c(CCCCC(=O)O)nc4c3)CC2)cn1C] | 5-(3-(4-chlorophenyl)-7-(4-(1,2-dimethyl-1H-imidazol-4-yl)piperazine-1-carbonyl)quinoxalin-2-yl)pentanoic acid | 547.5 |
| 701 | 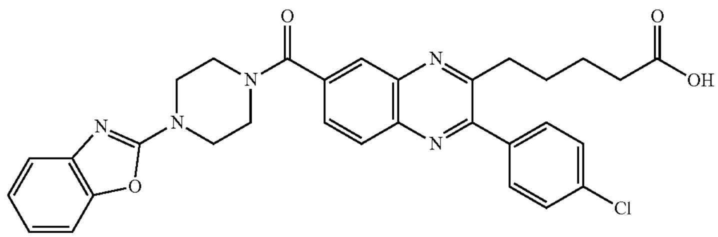 | 5-(7-(4-(benzo[d]oxazol-2-yl)piperazine-1-carbonyl)-3-(4-chlorophenyl)quinoxalin-2-yl)pentanoic acid | 570.5 |
| 702 | 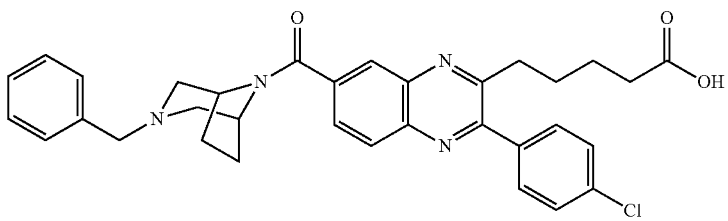 [SMILES: O=C(O)CCCCc1nc2cc(C(=O)N3C4CCC3CN(Cc3ccccc3)C4)ccc2nc1-c1ccc(Cl)cc1] | 5-(7-(1R,5S)-3-benzyl-3,8-diazabicyclo[3.2.1]octane-8-carbonyl)-3-(4-chloropheayl)quinoxalin-2-yl)pentanoic acid | 569.5 |
| 703 | 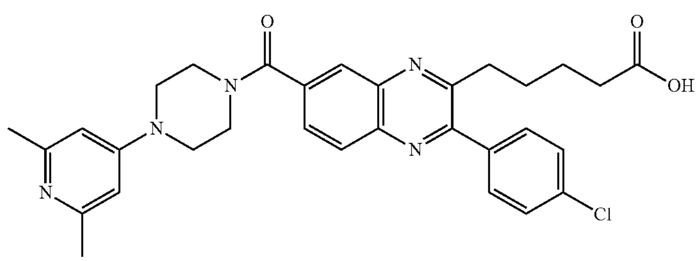 [SMILES: Cc1cc(N2CCN(C(=O)c3ccc4nc(-c5ccc(Cl)cc5)c(CCCCC(=O)O)nc4c3)CC2)cc(C)n1] | 5-(3-(4-chlorophenyl)-7-(4-(2,6-dimethylpyridin-4-yl)piperazine-1-carbonyl)quinoxalin-2-yl)pentanoic acid | 558.5 |
| 704 | 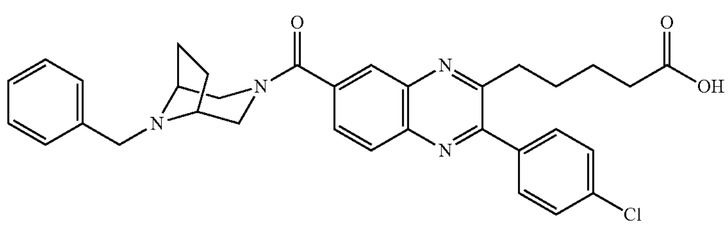 [SMILES: O=C(O)CCCCc1nc2cc(C(=O)N3CC4CCC(C3)N4Cc3ccccc3)ccc2nc1-c1ccc(Cl)cc1] | 5-(7-((1R,5S)-8-benzyl-3,8-diazabicyclo[3.2.1]octane-3-carbonyl)-3-(4-chlorophenyl)quinoxalin-2-yl)pentanoic acid | 569.5 |
| 705 | 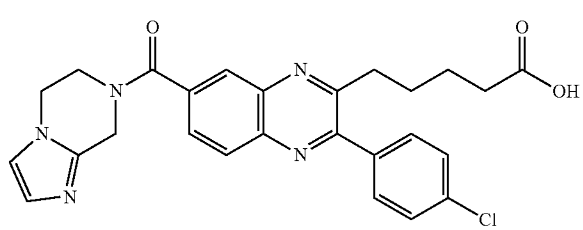 [SMILES: O=C(O)CCCCc1nc2cc(C(=O)N3CCn4ccnc4C3)ccc2nc1-c1ccc(Cl)cc1] | 5-(3-(4-chlorophenyl)-7-(5,6,7,8-tetrahydroimidazo[1,2-a]pyrazine-7-carbonyl)quinoxalin-2-yl)pentanoic acid | 490.3 |

| No. | Structure | Name | M + H |
|---|---|---|---|
| 706 | 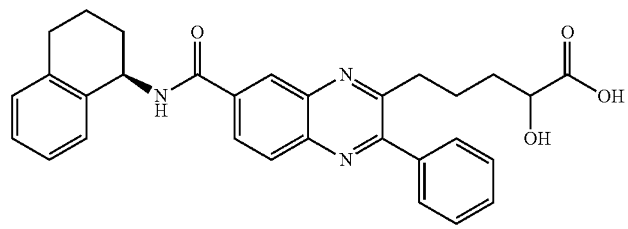 [SMILES: O=C(N[C@@H]1CCCc2ccccc21)c1ccc2nc(-c3ccccc3)c(CCCC(O)C(=O)O)nc2c1] | 2-hydroxy-5-(3-phenyl-7-(((R)-1,2,3,4-tetrahydronaphthalen-1-yl)carbamoyl)quinoxalin-2-yl)pentanoic acid | 496 |
| 707 | 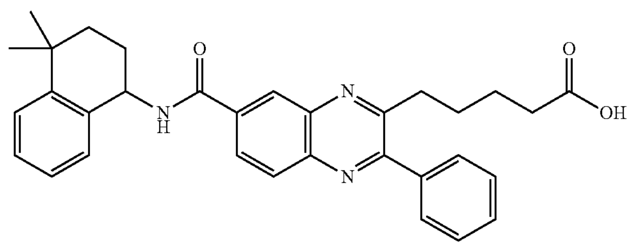 [SMILES: CC1(C)CCC(NC(=O)c2ccc3nc(-c4ccccc4)c(CCCCC(=O)O)nc3c2)c2ccccc21] | 5-(7-((4,4-dimethyl-1,2,3,4-tetrahydronaphthalen-1-yl)carbamoyl)-3-phenylquinoxalin-2-yl)pentatioic acid | 508 |
| 708 | 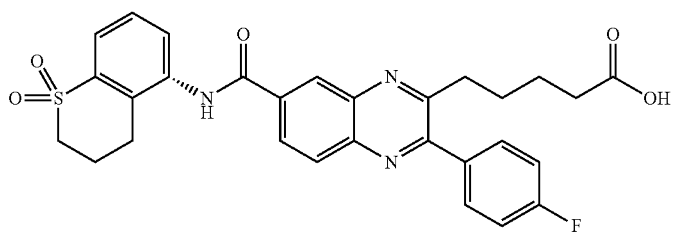 | (R)-5-(7-((1,1-dioxidothiochroman-4-yl)carbamoyl)-3-(4-fluorophenyl)quinoxalin-2-yl)pentanoic acid | 548 |
| 709 | 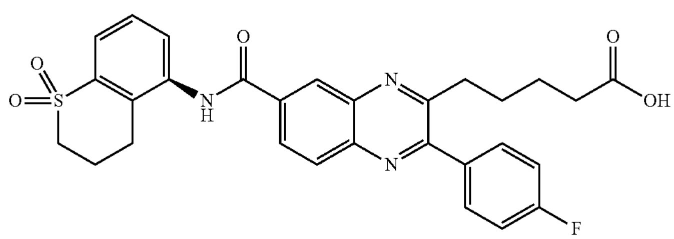 | (S)-5-(7-((1,1-dioxidothiochroman-4-yl)carbamoyl)-3-(4-fluorophenyl)quinoxalin-2-yl)pentanoic acid | 548 |
| 710 | 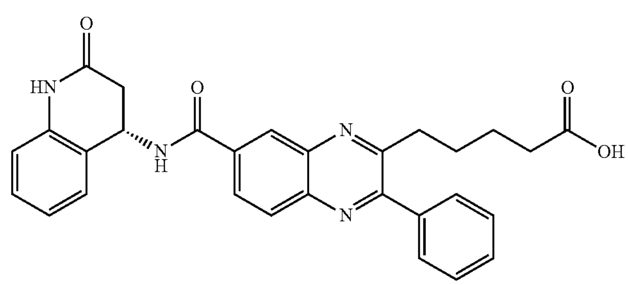 [SMILES: O=C(O)CCCCc1nc2cc(C(=O)N[C@H]3CC(=O)Nc4ccccc43)ccc2nc1-c1ccccc1] | (S)-5-(7-((2-oxo-1,2,3,4-tetrahydroquinolin-4-yl)carbamoyl)-3-phenylquinoxalin-2-yl)pentanoic acid | 495 |
| 711 | 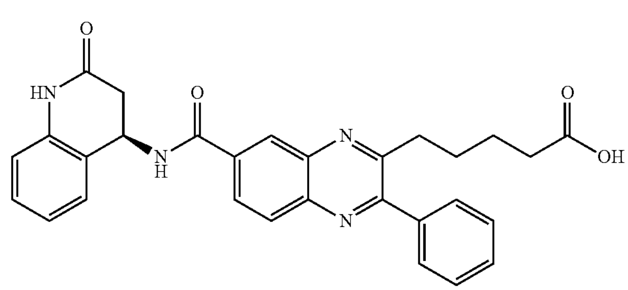 [SMILES: O=C(O)CCCCc1nc2cc(C(=O)N[C@@H]3CC(=O)Nc4ccccc43)ccc2nc1-c1ccccc1] | (R)-5-(7-((2-oxo-1,2,3,4-tetrahydroquinolin-4-yl)carbamoyl)-3-phenylquinoxalin-2-yl)pentanoic acid | 495 |

-continued

| No. | Structure | Name | M + H |
|---|---|---|---|
| 712 | 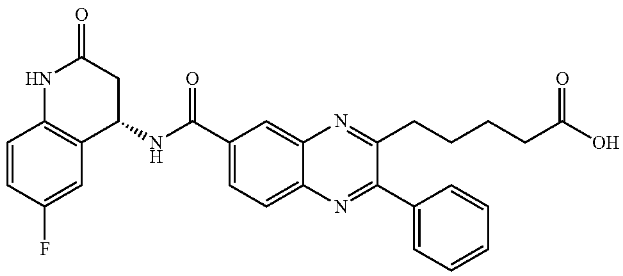 [SMILES: O=C(O)CCCCc1nc2cc(C(=O)N[C@H]3CC(=O)Nc4ccc(F)cc43)ccc2nc1-c1ccccc1] | (S)-5-(7-((6-fluoro-2-oxo-1,2,3,4-tetrahydroquinolin-4-yl)carbamoyl)-3-phenylquinoxalin-2-yl)pentanoic acid | 513 |
| 713 | 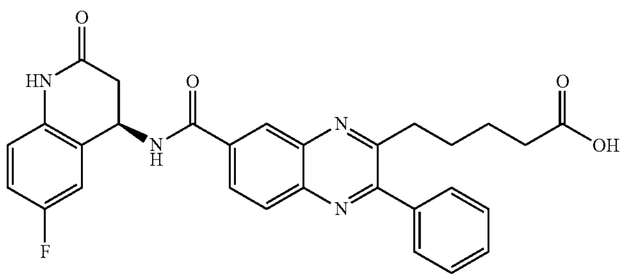 [SMILES: O=C(O)CCCCc1nc2cc(C(=O)N[C@@H]3CC(=O)Nc4ccc(F)cc43)ccc2nc1-c1ccccc1] | (R)-5-(7-((6-fluoro-2-oxo-1,2,3,4-tetrahydroquinolin-4-yl)carbamoyl)-3-phenylquinoxalin-2-yl)pentanoic acid | 513 |
| 714 | 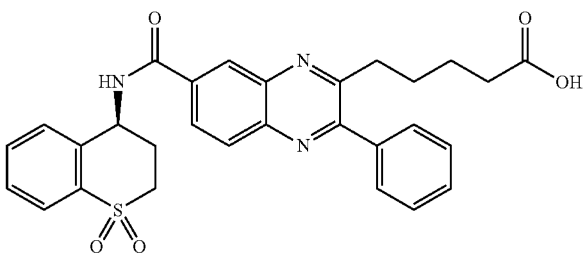 [SMILES: O=C(O)CCCCc1nc2cc(C(=O)N[C@H]3CCS(=O)(=O)c4ccccc43)ccc2nc1-c1ccccc1] | (S)-5-(7-((1,1-dioxidothiochroman-4-yl)carbamoyl)-3-phenylquinoxalin-2-yl)pentanoic acid | 530 |
| 715 | 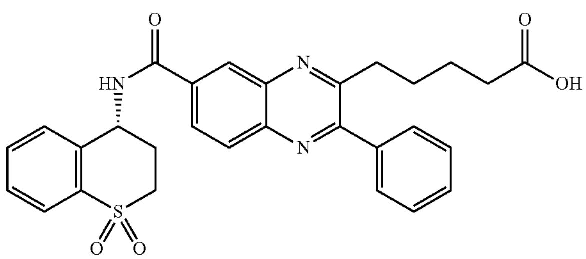 [SMILES: O=C(O)CCCCc1nc2cc(C(=O)N[C@@H]3CCS(=O)(=O)c4ccccc43)ccc2nc1-c1ccccc1] | (R)-5-(7-((1,1-dioxidothiochroman-4-yl)carbamoyl)-3-phenylquinoxalin-2-yl)pentanoic acid | 530 |
| 716 | 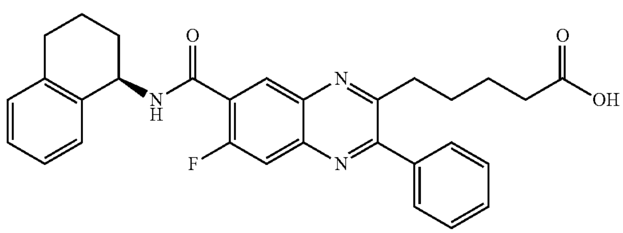 [SMILES: O=C(O)CCCCc1nc2cc(C(=O)N[C@@H]3CCCc4ccccc43)c(F)cc2nc1-c1ccccc1] | (R)-5-(6-fluoro-3-phenyl-7-((1,2,3,4-tetrahydro-naphthalen-1-yl)carbamoyl)quinoxalin-2-yl)pentanoic acid | 498 |
| 717 | 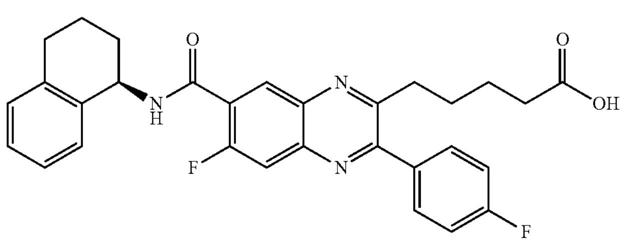 [SMILES: O=C(O)CCCCc1nc2cc(C(=O)N[C@@H]3CCCc4ccccc43)c(F)cc2nc1-c1ccc(F)cc1] | (R)-5-(6-fluoro-3-(4-fluorophenyl)-7-((1,2,3,4-tetrahydronaphthalen-1-yl)carbamoyl)quinoxalin-2-yl)pentanoic acid | 516 |

-continued

| No. | Structure | Name | M + H |
|---|---|---|---|
| 718 | 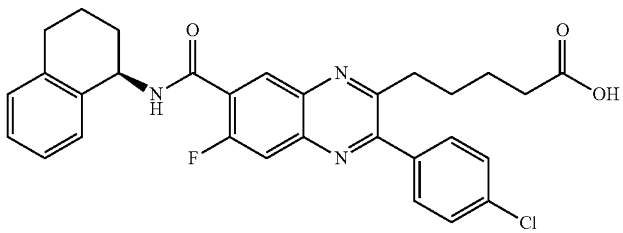 [SMILES: O=C(O)CCCCc1nc2cc(C(=O)N[C@@H]3CCCc4ccccc43)c(F)cc2nc1-c1ccc(Cl)cc1] | (R)-5-(3-(4-chlorophenyl)-6-fluoro-7-((1,2,3,4-tetrahydronaphthalen-1-yl)carbamoyl)quinoxalin-2-yl)pentanoic acid | 532 |
| 719 | 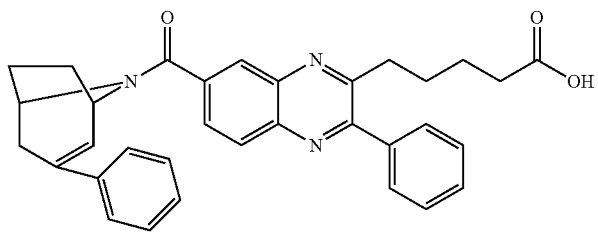 [SMILES: O=C(O)CCCCc1nc2cc(C(=O)N3C4C=C(c5ccccc5)CC3CC4)ccc2nc1-c1ccccc1] | 5-(3-phenyl-7-(3-phenyl-8-azabicyclo[3.2.1]oct-2-ene-8-carbonyl)quinoxalin-2-yl)pentanoic acid | 518.4 |
| 720 | 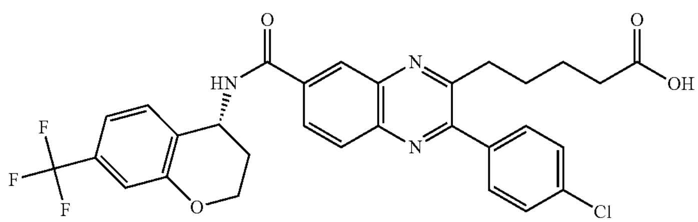 [SMILES: O=C(O)CCCCc1nc2cc(C(=O)N[C@@H]3CCOc4cc(C(F)(F)F)ccc43)ccc2nc1-c1ccc(Cl)cc1] | (R)-5-(3-(4-chlorophenyl)-7-((7-(trifluoromethyl)chroman-4-yl)carbamoyl)quinoxalin-2-yl)pentanoic acid | 584.5 |
| 721 | 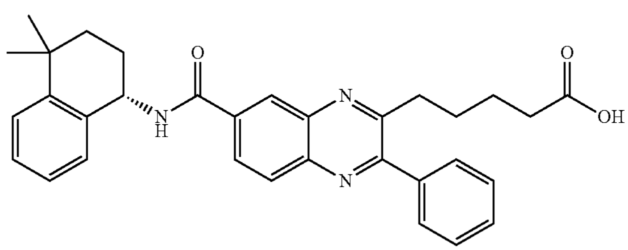 [SMILES: CC1(C)CC[C@H](NC(=O)c2ccc3nc(-c4ccccc4)c(CCCCC(=O)O)nc3c2)c2ccccc21] | (S)-5-(7-((4,4-dimethyl-1,2,3,4-tetrahydronaphthalen-1-yl)carbamoyl)-3-phenylquinoxalin-2-yl)pentanoic acid | 508 |
| 722 | 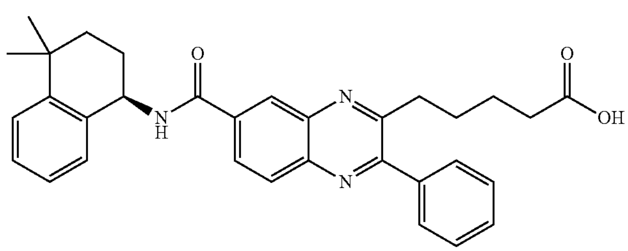 [SMILES: CC1(C)CC[C@@H](NC(=O)c2ccc3nc(-c4ccccc4)c(CCCCC(=O)O)nc3c2)c2ccccc21] | (R)-5-(7-((4,4-dimethyl-1,2,3,4-tetrahydronaphthalen-1-yl)carbamoyl)-3-phenylquinoxalin-2-yl)pentanoic acid | 508 |
| 723 | 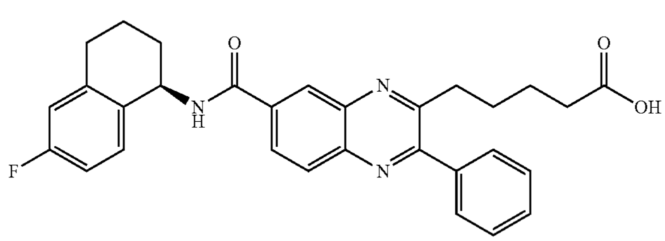 [SMILES: O=C(O)CCCCc1nc2cc(C(=O)N[C@@H]3CCCc4cc(F)ccc43)ccc2nc1-c1ccccc1] | (R)-4-(7-((6-fluoro-1,2,3,4-tetrahydronaphthalen-1-yl)carbamoyl)-3-phenylquinoxalin-2-yl)butanoic acid | 484 |

| No. | Structure | Name | M + H |
|---|---|---|---|
| 724 | 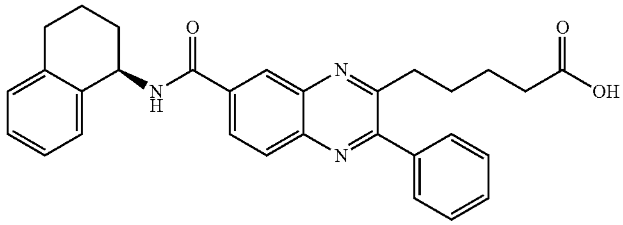 [SMILES: O=C(O)CCCCc1nc2cc(C(=O)N[C@@H]3CCCc4ccccc43)ccc2nc1-c1ccccc1] | (R)-4-(3-phenyl-7-((1,2,3,4-tetrahydronaphthalen-1-yl)carbamoyl)quinoxalin-2-yl)butanoic acid | 466 |
| 725 | 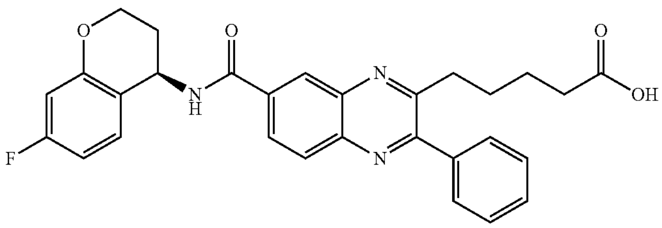 | (R)-4-(7-((7-fluorochroman-4-yl)carbamoyl)-3-phenylquinoxalin-2-yl)butanoic acid | 486 |
| 726 | 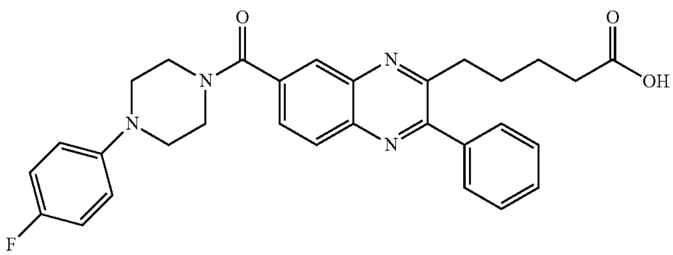 [SMILES: O=C(O)CCCCc1nc2cc(C(=O)N3CCN(c4ccc(F)cc4)CC3)ccc2nc1-c1ccccc1] | 4-(7-(4-(4-fluorophenyl)piperazine-1-carbonyl)-3-phenylquinoxalin-2-yl)butanoic acid | 500 |
| 727 | 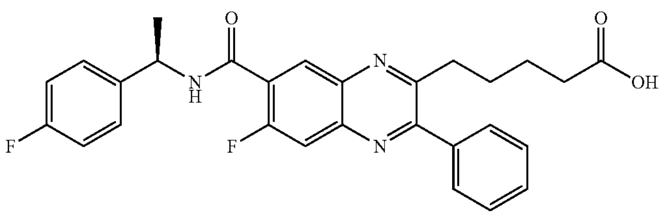 [SMILES: C[C@@H](NC(=O)c1cc2nc(CCCCC(=O)O)c(-c3ccccc3)nc2cc1F)c1ccc(F)cc1] | (R)-5-(6-fluoro-7-((1-(4-fluorophenyl)ethyl)carbamoyl)-3-phenylquinoxalin-2-yl)pentanoic acid | 490 |
| 728 | 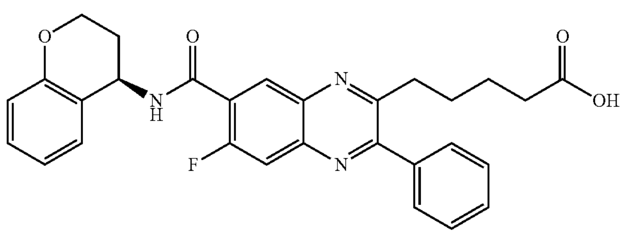 | (R)-5-(7-(chroman-4-ylcarbamoyl)-6-fluoro-3-phenylquinoxalin-2-yl)pentanoic acid | 500 |

*The left side 3-methyl-3-phenylpiperidine used to synthesize compounds 170 and 171 was prepared according to *J. Org. Chem.* 2007, 72, 4431

Biological Assays
Radioligand Binding Assay.

Radioligand binding assays were performed at room temperature in 50 mM Tris-HCl pH 7.4, 1 mM EDTA containing 2 mM $MnCl_2$ and 3.0 nM [$^3$H]$PGD_2$ (New England Nuclear, Boston, Mass.) (171 Ci $mmol^{-1}$), in a final volume of 0.2 mL. Competing ligands were diluted in dimethylsulfoxide ($Me_2SO$) that was kept constant at 1% (v/v) of the final incubation volume. The reaction was initiated by the addition of 8-20 μg of membrane protein prepared from a human embryonic kidney (HEK)-$hCRTH_2$ cell line. Total and non-specific binding were determined in the absence and the presence of 10 μM $PGD_2$, respectively. Under these conditions, specific binding (total minus non-specific) of the radioligand to the receptor reached equilibrium within 50 min and was stable up to 180 min. The reaction was routinely conducted for 60 min at room temperature and terminated by rapid filtration through prewetted (0.3% polyethyleneimine) 96-well printed Filtermate™ (Wallac) using a Tomtec® harvester (Hamden, Conn.). After washing with cold buffer, the filter was dried for 2 minutes in microwave, and Meltilex Scintillator sheet (Wallac) was melted on for 2 min. The radioactivity was measured with Betaplate model 1205 (Wallac). Tables A and B below list representative compounds of the invention with binding data whereby the Ki values are rated "A", "B," "C," "D," or "E." The Ki values are rated "A" for Ki values in the range of 0.1 to 2.0 nM, "B" for Ki values in the range from 2.1-20 nM, "C" for Ki values in the range from 20.1-200 nM, "D" for Ki values in the range from 201-700 nM, and "E" for Ki values in the range from 701-2300 nM. The designation "NT" indicates that the compound in the entry was not tested in this binding assay.

TABLE A

| No. | Ki (nM) |
|---|---|
| 3 | B |
| 3T | C |
| 3U | C |
| 3V | D |
| 3W | B |
| 3X | B |
| 3Y | A |
| 3Z | A |
| 3AA | B |
| 3AB | B |
| 3AC | B |
| 3AD | B |
| 3AE | B |
| 3AF | B |
| 3AG | B |
| 4 | B |
| 4D | C |
| 4E | A |
| 4F | B |
| 4G | B |
| 5 | A |
| 5G | A |
| 5N | C |
| 5O | C |
| 5P | D |
| 5Q | C |
| 5R | B |
| 5S | B |
| 6 | A |
| 6F | NT |
| 6G | A |
| 6H | B |
| 7 | B |
| 7C | A |
| 8 | C |
| 8G | C |
| 9 | B |
| 10 | B |
| 10C | A |
| 10D | B |
| 10E | A |
| 10F | B |
| 11 | C |
| 11D | D |
| 11E | D |
| 11F | D |
| 12 | D |
| 13 | C |
| 14 | B |
| 14C | C |
| 14D | B |
| 14E | C |
| 14F | C |
| 14G | A |
| 14H | C |
| 15A | B |
| 15B | B |
| 15C | A |
| 15D | A |
| 15E | A |
| 15F | B |
| 15G | B |
| 15H | C |
| 15i | D |
| 15J | B |
| 15K | B |
| 15L | C |
| 15M | C |
| 15N | B |
| 15o | B |
| 15P | A |

TABLE A-continued

| No. | Ki (nM) |
|---|---|
| 15Q | A |
| 15R | A |
| 15S | A |
| 15T | A |
| 15U | B |
| 15V | A |
| 15X | A |
| 15Y | A |
| 15Z | A |
| 15AA | C |
| 15AB | A |
| 15AC | A |
| 15AD | B |
| 15AE | B |
| 15AF | B |
| 15AG | B |
| 15AH | C |
| 15Ai | A |
| 15AJ | B |
| 15AK | B |
| 15AL | A |
| 15AM | B |
| 15AN | B |
| 15Ao | A |
| 15AP | B |
| 15AQ | B |
| 15AR | A |
| 15AS | B |
| 15AT | A |
| 15AU | B |
| 15AV | A |
| 15AW | A |
| 15AX | B |
| 15AY | B |
| 15AZ | B |
| 15BA | A |
| 15BB | B |
| 15BC | B |
| 15BD | B |
| 15BE | B |
| 15BF | B |
| 15BG | B |
| 15BH | B |
| 15Bi | A |
| 15BJ | B |
| 15BK | A |
| 15BL | C |
| 15BM | B |
| 15BN | B |
| 15Bo | C |
| 15BQ | B |
| 15BR | A |
| 15BS | B |
| 15BT | A |
| 15BU | A |
| 16 | A |
| 16F | A |
| 16G | A |
| 16H | A |
| 16i | A |
| 16J | B |
| 16K | A |
| 16L | B |
| 16M | A |
| 16N | A |
| 16o | A |
| 16P | A |
| 16Q | A |
| 16R | A |
| 16S | A |
| 16T | A |
| 16U | A |
| 16V | A |
| 16W | A |
| 16X | B |
| 16Y | A |
| 16Z | B |
| 16AA | A |

TABLE A-continued

| No. | Ki (nM) |
|---|---|
| 16AB | A |
| 16AC | A |
| 16AD | A |
| 16AE | A |
| 16AF | A |
| 16AG | A |
| 16AH | B |
| 16Ai | A |
| 16AJ | A |
| 16AK | A |
| 16AL | A |
| 16AM | A |
| 16AN | A |
| 16Ao | A |
| 16AP | A |
| 16AQ | A |
| 16AR | B |
| 16AS | A |
| 17 | B |
| 17D | A |
| 17E | B |
| 17F | A |
| 17G | B |
| 17H | B |
| 17i | B |
| 17J | B |
| 17K | A |
| 17L | B |
| 17M | B |
| 17N | B |
| 17o | A |
| 17P | B |
| 17Q | B |
| 17R | A |
| 17S | B |
| 17T | A |
| 17U | B |
| 17V | A |
| 17W | A |
| 17X | B |
| 17Y | B |
| 17Z | B |
| 18 | B |
| 18D | B |
| 18E | A |
| 18F | B |
| 18G | A |
| 18H | B |
| 19 | B |
| 19F | B |
| 19G | B |
| 19H | B |
| 19i | B |
| 19J | C |
| 19K | B |
| 20 | C |
| 20F | B |
| 20G | B |
| 20H | B |
| 21 | A |
| 21C | B |
| 22 | C |
| 22D | C |
| 23 | C |
| 24 | B |
| 24H | B |
| 24i | B |
| 25 | D |
| 26 | A |
| 26E | B |
| 26F | B |
| 26G | B |
| 26H | B |
| 26i | B |
| 26J | A |
| 26K | B |
| 26L | B |
| 26M | B |

TABLE A-continued

| No. | Ki (nM) |
|---|---|
| 26N | A |
| 26o | A |
| 26P | B |
| 26Q | C |
| 26R | C |
| 26S | A |
| 26T | B |
| 26U | B |
| 26V | A |
| 26W | A |
| 26X | C |
| 26Y | A |
| 26Z | A |
| 26AA | A |
| 26AB | A |
| 28 | B |
| 29 | B |
| 30 | B |
| 30E | B |
| 31 | B |
| 31C | B |
| 32 | B |
| 33 | C |
| 34 | D |
| 35 | C |
| 36 | E |
| 37 | C |
| 38 | C |
| 38A | C |
| 38B | C |
| 39 | B |
| 40 | B |
| 41 | B |
| 42 | B |
| 44 | B |
| 44D | B |
| 44E | B |
| 44F | B |
| 44G | C |
| 44H | B |
| 44i | A |
| 44J | B |
| 44K | A |
| 44L | B |
| 44M | B |
| 44N | B |
| 100 | A |
| 101 | B |
| 102 | B |
| 103 | A |
| 104 | B |
| 105 | B |
| 106 | A |
| 107 | B |
| 108 | B |
| 109 | B |
| 110 | B |
| 111 | B |
| 112 | B |
| 113 | B |
| 114 | B |
| 115 | C |
| 116 | B |
| 117 | B |
| 118 | B |
| 119 | B |
| 120 | B |
| 121 | B |
| 122 | B |
| 123 | B |
| 124 | B |
| 125 | B |
| 126 | B |
| 127 | B |
| 128 | B |
| 129 | A |
| 130 | A |
| 131 | B |

TABLE A-continued

| No. | Ki (nM) |
|-----|---------|
| 132 | B |
| 133 | B |
| 134 | A |
| 135 | B |
| 136 | B |
| 137 | C |
| 138 | B |
| 139 | B |
| 140 | A |
| 141 | B |
| 142 | B |
| 143 | B |
| 144 | C |
| 145 | B |
| 146 | C |
| 147 | B |
| 148 | A |
| 149 | B |
| 150 | A |
| 151 | A |
| 152 | B |
| 153 | A |
| 154 | A |
| 155 | B |
| 156 | B |
| 157 | B |
| 158 | D |
| 159 | D |
| 160 | B |
| 161 | B |
| 162 | A |
| 163 | B |
| 164 | B |
| 165 | B |
| 166 | B |
| 167 | B |
| 168 | B |
| 169 | B |
| 170 | B |
| 171 | B |
| 172 | A |
| 173 | A |
| 174 | A |
| 175 | B |
| 176 | B |
| 177 | B |
| 178 | A |
| 179 | A |
| 180 | A |
| 181 | A |
| 182 | B |
| 183 | B |
| 184 | A |
| 185 | B |
| 186 | A |
| 187 | B |
| 188 | A |
| 189 | A |
| 190 | A |
| 191 | A |
| 192 | B |
| 193 | B |
| 194 | C |
| 195 | C |
| 196 | C |
| 197 | D |
| 198 | B |
| 199 | B |
| 200 | B |
| 201 | A |
| 202 | A |
| 203 | B |
| 204 | B |
| 205 | B |
| 206 | B |
| 207 | B |
| 208 | B |
| 209 | B |

TABLE A-continued

| No. | Ki (nM) |
|-----|---------|
| 210 | B |
| 211 | B |
| 212 | B |
| 213 | C |
| 214 | A |
| 215 | B |
| 216 | C |
| 217 | A |
| 218 | A |
| 219 | A |
| 220 | A |
| 221 | A |
| 222 | B |
| 223 | A |
| 224 | A |
| 225 | A |
| 226 | A |
| 227 | A |
| 228 | A |
| 229 | A |
| 230 | A |
| 231 | B |
| 232 | B |
| 233 | B |
| 234 | B |
| 235 | B |
| 236 | B |
| 237 | B |
| 238 | B |
| 239 | B |
| 240 | B |
| 241 | B |
| 242 | B |
| 243 | B |
| 244 | B |
| 245 | B |
| 246 | A |
| 247 | B |
| 248 | B |
| 249 | A |
| 250 | A |
| 251 | A |
| 252 | A |
| 253 | A |
| 254 | A |
| 255 | A |

TABLE B

| No. | Ki (nM) |
|-----|---------|
| 256 | A |
| 257 | B |
| 258 | B |
| 259 | D |
| 260 | B |
| 261 | B |
| 262 | B |
| 263 | B |
| 264 | B |
| 265 | B |
| 266 | B |
| 267 | B |
| 268 | B |
| 269 | D |
| 270 | D |
| 271 | D |
| 272 | C |
| 273 | C |
| 274 | B |
| 275 | C |
| 276 | B |
| 277 | B |
| 278 | C |
| 279 | C |

TABLE B-continued

| No. | Ki (nM) |
|-----|---------|
| 280 | E |
| 281 | C |
| 282 | D |
| 283 | D |
| 284 | B |
| 285 | B |
| 286 | C |
| 287 | C |
| 288 | C |
| 289 | C |
| 290 | B |
| 291 | B |
| 292 | C |
| 293 | B |
| 294 | B |
| 295 | B |
| 296 | B |
| 297 | B |
| 298 | B |
| 299 | B |
| 300 | B |
| 301 | B |
| 302 | B |
| 303 | B |
| 304 | B |
| 305 | B |
| 306 | C |
| 307 | C |
| 308 | B |
| 309 | B |
| 310 | B |
| 311 | B |
| 312 | B |
| 313 | B |
| 314 | B |
| 315 | B |
| 316 | B |
| 317 | B |
| 318 | B |
| 319 | B |
| 320 | B |
| 321 | B |
| 322 | B |
| 323 | B |
| 324 | B |
| 325 | C |
| 326 | B |
| 327 | C |
| 328 | B |
| 329 | B |
| 330 | B |
| 331 | B |
| 332 | B |
| 333 | B |
| 334 | B |
| 335 | B |
| 336 | C |
| 337 | C |
| 338 | B |
| 339 | C |
| 340 | B |
| 341 | B |
| 342 | B |
| 343 | B |
| 344 | B |
| 345 | B |
| 346 | B |
| 347 | C |
| 348 | B |
| 349 | C |
| 350 | C |
| 351 | B |
| 352 | B |
| 353 | B |
| 354 | C |
| 355 | B |
| 356 | C |
| 357 | B |

TABLE B-continued

| No. | Ki (nM) |
|-----|---------|
| 358 | B |
| 359 | B |
| 360 | C |
| 361 | B |
| 362 | B |
| 363 | B |
| 364 | B |
| 365 | B |
| 366 | B |
| 367 | B |
| 368 | C |
| 369 | B |
| 370 | D |
| 371 | B |
| 372 | B |
| 373 | B |
| 374 | A |
| 375 | A |
| 376 | B |
| 377 | B |
| 378 | C |
| 379 | B |
| 380 | B |
| 381 | A |
| 382 | A |
| 383 | A |
| 384 | A |
| 385 | B |
| 386 | A |
| 387 | B |
| 388 | B |
| 389 | A |
| 390 | A |
| 391 | B |
| 392 | B |
| 393 | B |
| 394 | B |
| 395 | B |
| 396 | B |
| 397 | B |
| 398 | B |
| 399 | B |
| 400 | B |
| 401 | C |
| 402 | B |
| 403 | A |
| 404 | B |
| 405 | B |
| 406 | B |
| 407 | B |
| 408 | A |
| 409 | C |
| 410 | C |
| 411 | C |
| 412 | A |
| 413 | A |
| 414 | A |
| 415 | A |
| 416 | B |
| 417 | B |
| 418 | C |
| 419 | A |
| 420 | A |
| 421 | A |
| 422 | B |
| 423 | B |
| 424 | B |
| 425 | A |
| 426 | A |
| 427 | B |
| 428 | C |
| 429 | A |
| 430 | B |
| 431 | B |
| 432 | A |
| 433 | B |
| 434 | A |
| 435 | A |

TABLE B-continued

| No. | Ki (nM) |
|---|---|
| 436 | C |
| 437 | C |
| 438 | B |
| 439 | B |
| 440 | A |
| 441 | B |
| 442 | A |
| 443 | B |
| 444 | C |
| 445 | B |
| 446 | B |
| 447 | A |
| 448 | A |
| 449 | B |
| 450 | B |
| 451 | B |
| 452 | B |
| 453 | B |
| 454 | B |
| 455 | B |
| 456 | B |
| 457 | A |
| 458 | B |
| 459 | B |
| 460 | B |
| 461 | B |
| 462 | B |
| 463 | B |
| 464 | C |
| 465 | B |
| 466 | B |
| 467 | B |
| 468 | B |
| 469 | D |
| 470 | C |
| 471 | B |
| 472 | C |
| 473 | B |
| 474 | B |
| 475 | B |
| 476 | C |
| 477 | B |
| 478 | C |
| 479 | C |
| 480 | B |
| 481 | C |
| 482 | B |
| 483 | B |
| 484 | B |
| 485 | B |
| 486 | B |
| 487 | C |
| 488 | B |
| 489 | B |
| 490 | B |
| 491 | A |
| 492 | B |
| 493 | B |
| 494 | B |
| 495 | B |
| 496 | B |
| 497 | B |
| 498 | B |
| 499 | B |
| 500 | B |
| 501 | C |
| 502 | C |
| 503 | C |
| 504 | B |
| 505 | B |
| 506 | A |
| 507 | A |
| 508 | B |
| 509 | C |
| 510 | C |
| 511 | B |
| 512 | A |
| 513 | A |

TABLE B-continued

| No. | Ki (nM) |
|---|---|
| 514 | B |
| 515 | B |
| 516 | B |
| 517 | B |
| 518 | B |
| 519 | B |
| 520 | B |
| 521 | C |
| 522 | B |
| 523 | B |
| 524 | B |
| 525 | C |
| 526 | D |
| 527 | B |
| 528 | C |
| 529 | C |
| 530 | C |
| 531 | B |
| 532 | B |
| 533 | B |
| 534 | B |
| 535 | B |
| 536 | B |
| 537 | B |
| 538 | B |
| 539 | B |
| 540 | B |
| 541 | B |
| 542 | B |
| 543 | C |
| 544 | C |
| 545 | D |
| 546 | C |
| 547 | C |
| 548 | D |
| 549 | B |
| 550 | B |
| 551 | B |
| 552 | B |
| 553 | B |
| 554 | B |
| 555 | B |
| 556 | B |
| 557 | B |
| 558 | B |
| 559 | A |
| 560 | A |
| 561 | A |
| 562 | A |
| 563 | A |
| 564 | B |
| 565 | A |
| 566 | B |
| 567 | A |
| 568 | B |
| 569 | A |
| 570 | B |
| 571 | B |
| 572 | C |
| 573 | B |
| 574 | B |
| 575 | A |
| 576 | B |
| 577 | A |
| 578 | A |
| 579 | B |
| 580 | A |
| 581 | A |
| 582 | A |
| 583 | A |
| 584 | B |
| 585 | A |
| 586 | B |
| 587 | A |
| 588 | B |
| 589 | C |
| 590 | B |
| 591 | B |

TABLE B-continued

| No. | Ki (nM) |
|---|---|
| 592 | B |
| 593 | A |
| 594 | D |
| 595 | A |
| 596 | A |
| 597 | B |
| 598 | B |
| 599 | A |
| 600 | A |
| 601 | B |
| 602 | A |
| 603 | B |
| 604 | A |
| 605 | A |
| 606 | B |
| 607 | A |
| 608 | B |
| 609 | A |
| 610 | A |
| 611 | B |
| 612 | A |
| 613 | C |
| 614 | B |
| 615 | B |
| 616 | C |
| 617 | A |
| 618 | A |
| 619 | A |
| 620 | A |
| 621 | A |
| 622 | B |
| 623 | B |
| 624 | A |
| 625 | B |
| 626 | B |
| 627 | A |
| 628 | A |
| 629 | A |
| 630 | B |
| 631 | A |
| 632 | A |
| 633 | A |
| 634 | B |
| 635 | A |
| 636 | A |
| 637 | B |
| 638 | D |
| 639 | C |
| 640 | B |
| 641 | B |
| 642 | B |
| 643 | A |
| 644 | B |
| 645 | B |
| 646 | B |
| 647 | C |
| 648 | B |
| 649 | C |
| 650 | C |
| 651 | C |
| 652 | B |
| 653 | D |
| 654 | C |
| 655 | B |
| 656 | B |
| 657 | C |
| 658 | C |
| 659 | C |
| 660 | C |
| 661 | B |
| 662 | C |
| 663 | B |
| 664 | B |
| 665 | B |
| 666 | B |
| 667 | B |
| 668 | C |
| 669 | B |
| 670 | B |
| 671 | C |
| 672 | C |
| 673 | C |
| 674 | B |
| 675 | B |
| 676 | B |
| 677 | B |
| 678 | B |
| 679 | B |
| 680 | B |
| 681 | B |
| 682 | C |
| 683 | B |
| 684 | B |
| 685 | C |
| 686 | C |
| 687 | B |
| 688 | C |
| 689 | B |
| 690 | B |
| 691 | B |
| 692 | B |
| 693 | B |
| 694 | B |
| 695 | B |
| 696 | B |
| 697 | B |
| 698 | B |
| 699 | B |
| 700 | C |
| 701 | B |
| 702 | B |
| 703 | D |
| 704 | B |
| 705 | D |
| 706 | D |
| 707 | B |
| 708 | D |
| 709 | B |
| 710 | C |
| 711 | B |
| 712 | C |
| 713 | B |
| 714 | C |
| 715 | B |
| 716 | B |
| 717 | B |
| 718 | B |
| 719 | B |
| 720 | B |
| 721 | B |
| 722 | B |
| 723 | C |
| 724 | D |
| 725 | D |
| 726 | D |
| 727 | B |
| 728 | B |

Representative compounds of the invention had the Ki values specified in parentheses immediately following the compound number in the above-described assay: 3 (3.2 nM), 5P (265.6 nM), 6G (0.5 nM), 11F (222.9 nM), 15H (152.4 nM), 15i (282.9 nM), 15o (16.7 nM), 15Ai (1.9 nM), 15Ao (1.0 nM), 15AR (1.6 nM), 15AX (3.0 nM), 15BL (69.9 nM), 15BR (0.1 nM), 16S (0.7 nM), 16V (2.7 nM), 16W (0.4 nM), 16AG (1.2 nM), 16Ao (0.4 nM), 26o (1.4 nM), 26Q (96.7 nM), 36 (716.1) 39 (8.0 nM), 40 (5.7 nM), 41 (8.8 nM), 44H (3.1 nM) 144 (117.9 nM), 146 (132.0 nM), 152 (2.9 nM), 159 (564.4 nM), 173 (1.6 nM), 180 (0.6 nM), 193 (14.6 nM), 197 (464.1 nM), 217 (1.2 nM), 231 (4.0 nM), 246 (1.9 nM), 251 (1.0 nM), 254 (1.2 nM), 255 (1.5 nM), 264 (15.4 nM), 292 (39.2 nM), 368 (21.4 nM), 438 (4.2 nM), 507 (1.3 nM), 526 (259.3 nM), 637 (4.2 nM), 657 (37.4 nM), and 709 (18.4 nM).

i[cAMP] Measurements.

The ability of the compounds to antagonize the formation of cAMP can be assayed using the ELISA-based assay described in this example. HEK-hCRTH$_2$ cells are grown to 80-90% confluency. On the day of the assay, the cells are washed with phosphate buffered saline (PBS), incubated for 2 min in cell dissociation buffer, harvested by centrifugation at 300 g for 7 min at room temperature and resuspended at 1.25e10$^6$ cells mL$^{-1}$ in Hanks' balanced salt solution containing 20 mM HEPES pH 7.4 and 0.75 mM IBMX (HBSS/HEPES/IBMX). The assay is performed in 384-plate format with 0.01 mL HBSS/HEPES/IBMX per well containing 12 500 cells and 70 to 75 nl of the test compound and DK-PGD$_2$ at various concentrations. Following a 0 to 10 to min pre-incubation of the cells with the test compound at 37° C., 0.005 mL of 30 μM Forskolin dilute in HBSS 20 mM HEPES, is added at a final concentration of 10 uM to initiate the reaction. After 10 to 60 min incubation at room temperature or 37° C., the cAMP content was quantified using the cAMP XS+ HitHunter chemiluminescence assay (GE Healthcare 90-0075). Percent inhibition is calculated using the Forskolin and EC85 DK-PGD$_2$ controls.

β-Arrestin Assay:

CHO-K1 cells obtained from DiscoverX are stably transfected with human CRTH$_2$ (propagation medium: F-12, 10% FBS, 300 ug/mL hygB and 800 ug/mL G418). Cells are grown in T175 cm$^2$ flask. While in log phase, cells are collected via 0.05% trypsin treatment. Triturated cells are filtered and 40 uL (10K cells) are plated per well in a 384-well white clear bottom plate and incubated O/N. Cell plate is emptied via inversion and blotted dry. Each well is filled with 35 uL of HBSS (with Ca$^{++}$ and Mg$^{++}$) and incubated for 5 min. Compounds are added in volumes of 1 μL and the plate is gently shaken for 2 min., followed by incubation at 37° C. for 20 min. All compounds and controls are diluted in HBSS assay buffer (with Ca$^{++}$ and Mg$^{++}$) with a final concentration range of 10$^{-5}$M to 3×10$^{-11}$ M, 11 point Dose response curves at appropriate half-log increments. Final DMSO % is ≤0.3%. Agonist Assay: 1 μl/well of compound is added into cell plate and left to incubate at 37° C. for 90 min. Antagonist Assay: 1 μl/well of compounds are added into a cell plate. Incubate 30 minutes at 37° C. Stimulate cells with 1 ul/well of PGD$_2$ [100 nM] final. Incubate plate for 60 minutes at 37° C. Resulting luminescent signal is detected via Discoverx PathHunter Detection Kit per manufacturer's instructions. A total of 12 μl/well is added to each well. The plate is covered and incubated for 60 min. with gentle shaking. Chemiluminescent detection is done by a SpectraMax plate reader.

Eosinophil Shape Change Assay in Human Whole Blood:

Blood is collected in vacutainers containing EDTA. The antagonist is added to blood and incubated for 10 min at room temperature. DK-PGD$_2$ (13,14-dihydro-15-keto prostaglandin D$_2$) are then added to blood for 4 min at 37° C. in a running water bath. Blood cells are then fixed in presence of cold 0.25% (v/v) paraformaldehyde prepared in 75% (v/v) DPBS without Ca$^{++}$ and Mg$^{++}$ for 1 min on ice. 175 μL of fixed blood is transferred into 870 μL of cold 155 mM NH$_4$Cl lysis solution and incubated at 4° C. for at least 40 min. The solution is then centrifuged at 430 g for 5 min and the supernatant is discarded. Centrifuged cells are resuspended in residual supernatant and sodium azide is added (1% final concentration). Samples are analyzed with a FACs Calibur flow cytometer (Becton Dickinson). Flow cytometry raw data is analyzed with Diva software by isolating the eosinophils from the neutrophils based on their high autofluorescence and determining the percent of total eosinophils with increased forward light scatter. Maximum (100%) and minimum (0%) shape change is determined in the presence of 10 μM DK-PGD$_2$ and DPBS, respectively. A dose response curve with DK-PGD$_2$ is performed with every assay to determine the EC$_{50}$ for each blood donor. Compounds are tested in 11-dose titration curves in the presence of 50 nM DK-PGD$_2$ to determine an antagonist IC$_{50}$.

Compounds of the present invention are selective for the CRTH$_2$ receptor over the DP receptor. Assays on the DP, as well as other prostanoid, receptors are described in WO2003/06220.

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A compound of the formula (I)

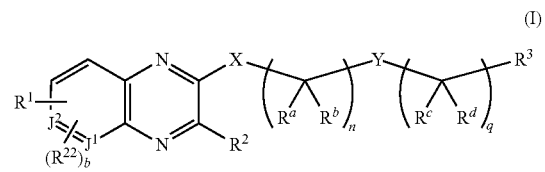

or a pharmaceutically acceptable salt thereof, wherein
J$^1$ and J$^2$ are independently C(H), C(R$^1$), C(R$^{22}$), or N wherein the following provisos apply
  (i) no more than one of J$^1$ and J$^2$ is N,
  (ii) no more than one of J$^1$ and J$^2$ is C(R$^{22}$); and
  (iii) only one R$^1$ is substituted on the illustrated ring containing J$^1$ and J$^2$;
R$^1$ is selected from the group consisting of
  (i) —C(O)—N(R$^{6a}$)(R$^{6b}$),
  (ii) —S(O)$_2$—N(R$^{6a}$)(R$^{6b}$),
  (iii) —C(O)—C(R$^{7a}$)(R$^{7b}$)(R$^{7c}$),
  (iv) —N(H)—C(O)—C(R$^{7a}$)(R$^{7b}$)(R$^{7c}$),
  (v) —C(O)—O—C(R$^{7a}$)(R$^{7b}$)(R$^c$), and
  (vi) —N(H)—S(O)$_2$—C(R$^{7a}$)(R$^{7b}$)(R$^{7c}$);
R$^{6a}$ and R$^{6b}$ are independently
  a. H,
  b. C$_1$-C$_6$ alkyl,
  c. C$_3$-C$_6$ alkenyl,
  d. C$_3$-C$_6$ alkynyl,
  e. —O—(C$_1$-C$_3$ alkyl),
  f. -Q-R$^{AH}$, wherein R$^{AH}$ is phenyl or 5- to 6-membered heteroaryl containing 1 to 2 heteroatoms independently selected from the group consisting of N, O, and S,
  and wherein R$^{AH}$ is unsubstituted or substituted with 1 to 5 R$^8$ moieties independently selected from the group consisting of halo, C$_1$-C$_3$ alkyl, C$_1$-C$_3$ alkoxy, C$_1$-C$_3$ fluoroalkyl, —O—(C$_1$-C$_3$ fluoroalkyl), hydroxyl, phenyl, and —CN;
Q is selected from the group consisting of
  (a) a bond;
  (b) C$_1$-C$_6$ alkylene, wherein said C$_1$-C$_6$ alkylene is unsubstituted or substituted by 1 to 2 fluoro, C$_1$-C$_3$ alkyl, C$_1$-C$_3$ hydroxyalkyl, or C$_1$-C$_3$ fluoroalkyl; and (c)

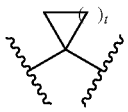

wherein t is 1, 2, 3, or 4;
g. -Q-$R^{Hc}$, wherein $R^{HC}$ is
(i) 5- to 7-membered heterocyclyl containing 1 heteroatom selected from the group consisting of N, O, S, S(O), and $S(O)_2$, wherein said heterocyclyl of $R^{HC}$ is optionally fused to a benzene, pyridyl ring; or
(ii) $C_3$-$C_7$ cycloalkyl, wherein said cycloalkyl of $R^{HC}$ is optionally fused to a benzene or pyridyl ring;
and wherein $R^{HC}$ is unsubstituted or substituted with 1 to 5 $R^{12}$ moieties independently selected from the group consisting of halo, $C_1$-$C_3$ alkyl, $C_1$-$C_3$ alkoxy, $C_1$-$C_3$ fluoroalkyl,
—O—($C_1$-$C_3$ fluoroalkyl), hydroxyl, —CN, and —S(O)$_2$—($C_1$-$C_3$ alkyl), or wherein when two $R^{12}$ moieties are geminally substituted on the same carbon atom, the two geminally substituted $R^{12}$ moieties, together with the carbon atom on which they are attached form —C(O)—;
Q is selected from the group consisting of
(a) a bond;
(b) $C_1$-$C_6$ alkylene, wherein said $C_1$-$C_6$ alkylene is unsubstituted or substituted by 1 to 2 fluoro, $C_1$-$C_3$ alkyl, $C_1$-$C_3$ hydroxyalkyl, or $C_1$-$C_3$ fluoroalkyl; and (c)

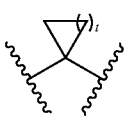

wherein t is 1, 2, 3, or 4;
h. or $R^{6a}$ and $R^{6b}$ together with the N atom to which they are attached form $R^{6H}$, wherein $R^{6H}$ is independently selected from the group consisting of
(i) a 4- to 9-membered heterocyclyl, optionally containing one additional nitrogen atom, wherein said heterocyclyl of $R^{6H}$ is optionally fused to phenyl, $C_3$-$C_6$ cycloalkyl, or a 5-membered heteroaryl containing 1 to 3 N atoms;
(ii) a 4- to 7-membered heterocyclenyl, optionally containing one additional nitrogen atom, wherein said heterocyclenyl of $R^{6H}$ is optionally fused to phenyl; and
(iii) a 6- to 8-membered aza- or a diazabicycloheterocycloalkyl ring;
wherein $R^{6H}$ is unsubstituted or substituted by 1 to 5 $R^9$ moieties wherein each $R^9$ moiety is independently $C_1$-$C_6$ alkyl, $C_1$-$C_6$ alkoxy, $C_1$-$C_3$ fluoroalkyl, fluoro, hydroxyl, —CN,
—($C_1$-$C_3$ alkylene)-($C_1$-$C_3$ alkoxy), or
$R^9$ is —Z—$R^{CY}$ wherein
Z is
(i) a bond,
(ii) —C(O)—,
(iii) —C(=N—OH)—,
(iv) —S(O)$_2$—,
(v) $C_1$-$C_3$ alkylene, wherein said $C_1$-$C_3$ alkylene of Z is optionally substituted by 1 to 2 fluoro or $C_1$-$C_3$ alkyl;
(vi) —O—;
(vii) —O—($C_1$-$C_3$ alkylene)-; or
(viii) —C(O)—O—CH$_2$—
$R^{CY}$ is selected from the group consisting of
(i) phenyl
(ii) 5- to 10-membered mono or bicyclic heteroaryl containing 1 to 3 heteroatoms independently selected from the group consisting of N, O, and S; or
(iii) 5- to 6-membered heterocyclyl containing 1 to 2 N atoms or 1 O atom, wherein said heterocyclyl of $R^{CY}$ is optionally fused to phenyl;
wherein $R^{CY}$ is unsubstituted or substituted by 1 to 4 $R^H$) moieties;
each $R^{10}$ moiety is independently $C_1$-$C_3$ alkyl, halo, hydroxyl, $C_1$-$C_3$ alkoxy, $C_1$-$C_3$ fluoroalkyl, —($C_1$-$C_3$ alkylene)-($C_1$-$C_3$ alkoxy), —S(O)$_2$—($C_1$-$C_3$ alkyl), —C(O)—($C_1$-$C_3$ alkyl), —CN, pyridyl, or cyclopropyl or, wherein when two $R^{10}$ moieties are geminally substituted on a common carbon atom, together with the carbon atom on which they are substituted, form —C(O)—;
or, optionally, where two $R^9$ moieties are geminally substituted on a common ring carbon of $R^{6H}$, the two $R^9$ moieties, together with the ring carbon on which they are substituted, form $R^{YC}$, wherein $R^{YC}$ is
(i) a 4- to 7-membered cycloalkyl, wherein said cycloalkyl of $R^{YC}$ is optionally fused to phenyl or pyridyl; or
(ii) a 4- to 7-membered heterocyclyl containing 1 to 2 N atoms or 1 O atom, wherein said heterocyclyl of $R^{YC}$ is optionally fused to phenyl;
wherein $R^{YC}$ is unsubstituted or substituted by 1 to 4 $R^{11}$ moieties;
each $R^{11}$ moiety is independently $C_1$-$C_3$ alkyl, halo, hydroxyl, $C_1$-$C_3$ alkoxy, —($C_1$-$C_3$ alkylene)-($C_1$-$C_3$ alkoxy), —S(O)$_2$—($C_1$-$C_3$ alkyl), —C(O)—($C_1$-$C_3$ alkyl), phenyl, or pyridyl, or, wherein when two $R^{11}$ moieties are geminally substituted on a common carbon atom, together with the carbon atom on which they are substituted, form —C(O)—;
$R^{7a}$ and $R^{7b}$ are independently
a) H,
b) $C_1$-$C_6$ alkyl,
c) $R^{7a}$ and $R^{7b}$ together with the carbon atom on which they are substituted, form $R^{PC}$, wherein $R^{PC}$ is
(i) $C_3$-$C_7$ cycloalkyl, or
(ii) phenyl, wherein said phenyl of $R^{PC}$ is unsubstituted or substituted by 1 to 5 moieties independently selected from the group consisting of halo, trifluoromethyl, and trifluoromethoxy;
$R^{7c}$ is
a) H, or
b) absent, when $R^{7a}$ and $R^{7b}$ together with the carbon atom on which they are substituted form phenyl;

$R^{22}$ is halo, $C_1$-$C_3$ alkyl, or $C_1$-$C_3$ fluoroalkyl;
b is 0 or 1;
X is a bond, —O—, —S—, —S(O)—, —S(O)$_2$—, or N(H);
Y is selected from the group consisting of
(i) a bond,

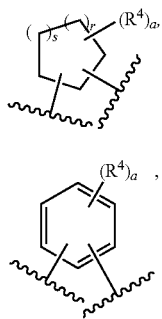

(iv) —O—, (v) —S—, (vi) —S(O)—, and (vii) —S(O)$_2$—;
wherein
a is 0, 1, 2, or 3;
r is 0, 1, or 2;
s is 0, 1, or 2;
each occurrence of $R^4$ is independently halo, $C_1$-$C_6$ alkyl, or $C_1$-$C_6$ fluoroalkyl;
$R^a$, $R^b$, $R^c$, and $R^d$ are independently H, fluoro, hydroxyl, $C_1$-$C_6$ alkyl, $C_1$-$C_6$ fluoroalkyl, or $C_1$-$C_6$ alkoxy;
$R^2$ is selected from the group consisting of
(i) phenyl; and
(ii) 5- to 6-membered heteroaryl containing from 1 to 3 heteroatoms selected from the group consisting of N, O, and S;
wherein $R^2$ is unsubstituted or substituted by 1 to 5 $R^5$ groups independently selected from the group consisting of halo, $C_1$-$C_3$ fluoroalkyl, $C_1$-$C_3$ alkyl, $C_1$-$C_3$ alkoxy, —CN, —OCF$_3$, —C(O)—($C_1$-$C_3$ alkyl), and —S(O)$_2$—($C_1$-$C_3$ alkyl);
$R^3$ is —C(O)OH,

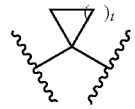

or —N(H)—SO$_2$—$R^e$,
wherein $R^e$ is $C_1$-$C_6$ alkyl, $C_1$-$C_6$ fluoroalkyl, $C_1$-$C_6$ alkoxy, and phenyl;
n is 1, 2, 3, 4, or 5; and
q is 0, 1, or 2.

2. The compound of claim 1 or a pharmaceutically acceptable salt thereof, wherein $R^1$ is selected from the group consisting of:
(i) —C(O)—N($R^{6a}$)($R^{6b}$),
(ii) —S(O)$_2$—N($R^{6a}$)($R^{6b}$),
(iii) —C(O)—C($R^{7a}$)($R^{7b}$)($R^{7c}$),
(iv) —N(H)—C(O)—C($R^{7a}$)($R^{7b}$)($R^{7c}$),
(v) —C(O)—O—C($R^{7a}$)($R^{7b}$)($R^{7c}$), and
(vi) —N(H)—S(O)$_2$—C($R^{7a}$)($R^{7b}$)($R^{7c}$);

$R^{6a}$ and $R^{6b}$ are independently:
a. H,
b. $C_1$-$C_6$ alkyl,
c. $C_3$-$C_6$ alkenyl,
d. $C_3$-$C_6$ alkynyl,
e. —O—($C_1$-$C_3$ alkyl),
f. -Q-$R^{AH}$, wherein $R^{AH}$ is phenyl or 5- to 6-membered heteroaryl containing 1 to 2 heteroatoms independently selected from the group consisting of N, O, and S,
and wherein $R^{AH}$ is unsubstituted or substituted with 1 to 5 $R^8$ moieties independently selected from the group consisting of halo, $C_1$-$C_3$ alkyl, $C_1$-$C_3$ alkoxy, $C_1$-$C_3$ fluoroalkyl, —O—($C_1$-$C_3$ fluoroalkyl), hydroxyl, phenyl, and —CN;
Q is selected from the group consisting of
(a) a bond;
(b) $C_1$-$C_6$ alkylene, wherein said $C_1$-$C_6$ alkylene is unsubstituted or substituted by 1 to 2 fluoro, $C_1$-$C_3$ alkyl, $C_1$-$C_3$ hydroxyalkyl, or $C_1$-$C_3$ fluoroalkyl; and
(c)

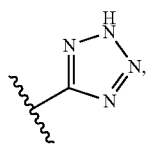

wherein t is 1, 2, 3, or 4;
g. -Q-$R^{HC}$, wherein $R^{HC}$ is
(i) 5- to 6-membered heterocyclyl containing 1 heteroatom selected from the group consisting of N and O, wherein said heterocyclyl of $R^{HC}$ is optionally fused to a benzene ring; or
(ii) $C_5$-$C_7$ cycloalkyl, wherein said cycloalkyl of $R^{HC}$ is optionally fused to a benzene ring;
and wherein $R^{HC}$ is unsubstituted or substituted with 1 to 5 $R^{12}$ moieties independently selected from the group consisting of halo, $C_1$-$C_3$ alkyl, $C_1$-$C_3$ alkoxy, $C_1$-$C_3$ fluoroalkyl,
—O—($C_1$-$C_3$ fluoroalkyl), hydroxyl, and —CN, or wherein when two $R^{12}$ moieties are geminally substituted on the same carbon atom, the two geminally substituted $R^{12}$ moieties, together with the carbon atom on which they are attached form —C(O)—;
Q is selected from the group consisting of
(a) a bond;
(b) $C_1$-$C_6$ alkylene, wherein said $C_1$-$C_6$ alkylene is unsubstituted or substituted by 1 to 2 fluoro, $C_1$-$C_3$ alkyl, $C_1$-$C_3$ hydroxyalkyl, or $C_1$-$C_3$ fluoroalkyl; and
(c)

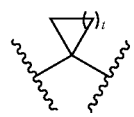

wherein t is 1, 2, 3, or 4;

h. or $R^{6a}$ and $R^{6b}$ together with the N atom to which they are attached form $R^{6H}$, wherein $R^{6H}$ is independently selected from the group consisting of
  (i) a 4- to 7-membered heterocyclyl, optionally containing one additional nitrogen atom, wherein said heterocyclyl of $R^{6H}$ is optionally fused to phenyl; and
  (ii) a 4- to 7-membered heterocyclenyl, optionally containing one additional nitrogen atom, wherein said heterocyclenyl of $R^{6H}$ is optionally fused to phenyl;
wherein $R^{6H}$ is unsubstituted or substituted by 1 to 5 $R^9$ moieties wherein each $R^9$ moiety is independently $C_1$-$C_6$ alkyl, $C_1$-$C_6$ alkoxy, fluoro, hydroxyl, —CN, —($C_1$-$C_3$ alkylene)-($C_1$-$C_3$ alkoxy), or
$R^9$ is —Z—$R^{CY}$ wherein
  Z is
  (i) a bond,
  (ii) —C(O)—,
  (iii) —C(=N—OH)—,
  (iv) —S(O)$_2$—, or
  (v) $C_1$-$C_3$ alkylene, wherein said $C_1$-$C_3$ alkylene of Z is optionally substituted by 1 to 2 fluoro or $C_1$-$C_3$ alkyl;
$R^{CY}$ is selected from the group consisting of
  (i) phenyl
  (ii) 5- to 10-membered mono or bicyclic heteroaryl containing 1 to 3 heteroatoms independently selected from the group consisting of N, O, and S; or
  (iii) 5- to 6-membered heterocyclyl containing 1 to 2 N atoms or 1 O atom, wherein said heterocyclyl of $R^{CY}$ is optionally fused to phenyl;
  wherein $R^{CY}$ is unsubstituted or substituted by 1 to 4 $R^{10}$ moieties;
  each $R^{10}$ moiety is independently $C_1$-$C_3$ alkyl, halo, hydroxyl, $C_1$-$C_3$ alkoxy, —($C_1$-$C_3$ alkylene)-($C_1$-$C_3$ alkoxy), —S(O)$_2$—($C_1$-$C_3$ alkyl), —C(O)—($C_1$-$C_3$ alkyl), —CN, or pyridyl, or, wherein when two $R^{10}$ moieties are geminally substituted on a common carbon atom, together with the carbon atom on which they are substituted, form —C(O)—;
  or, optionally, where two $R^9$ moieties are geminally substituted on a common ring carbon of $R^{6H}$, the two $R^9$ moieties, together with the ring carbon on which they are substituted, form $R^{YC}$, wherein $R^{YC}$ is
  (i) a 4- to 7-membered cycloalkyl, wherein said cycloalkyl of $R^{YC}$ is optionally fused to phenyl; or
  (ii) a 4- to 7-membered heterocyclyl containing 1 to 2 N atoms or 1 O atom, wherein said heterocyclyl of $R^{YC}$ is optionally fused to phenyl;
  wherein $R^{YC}$ is unsubstituted or substituted by 1 to 4 $R^{11}$ moieties;
  each $R^{11}$ moiety is independently $C_1$-$C_3$ alkyl, halo, hydroxyl, $C_1$-$C_3$ alkoxy, —($C_1$-$C_3$ alkylene)-($C_1$-$C_3$ alkoxy), —S(O)$_2$—($C_1$-$C_3$ alkyl), —C(O)—($C_1$-$C_3$ alkyl), phenyl, or pyridyl, or, wherein when two $R^{11}$ moieties are geminally substituted on a common carbon atom, together with the carbon atom on which they are substituted, form —C(O)—;

$R^{7a}$ and $R^{7b}$ independently
  a) H,
  b) $C_1$-$C_6$ alkyl,
  c) $R^{7a}$ and $R^{7b}$ together with the carbon atom on which they are substituted, form $R^{PC}$, wherein $R^{PC}$ is
    (i) $C_3$-$C_7$ cycloalkyl, or
    (ii) phenyl, wherein said phenyl of $R^{PC}$ is unsubstituted or substituted by 1 to 5 moieties independently selected from the group consisting of halo, trifluoromethyl, and trifluoromethoxy;
$R^{7c}$ is
  a) H, or
  b) absent, when $R^{7a}$ and $R^{7b}$ together with the carbon atom on which they are substituted form phenyl; and
X is a bond, —O—, —S—, —S(O)—, or —S(O)$_2$—;
$J^1$, $J^2$, Y, $R^a$, $R^b$, $R^c$, $R^d$, $R^2$, $R^3$, $R^{22}$, b, n, and q are as specified in claim 1.

3. The compound of claim 1 or a pharmaceutically acceptable salt thereof, wherein $R^1$ is substituted at the 6 or 7 position of the illustrated bicyclic ring of Formula (I).

4. The compound of claim 3 or a pharmaceutically acceptable salt thereof, wherein the compound has the formula (IA)

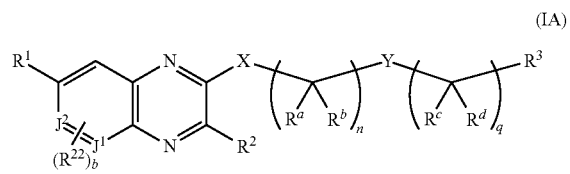

(IA)

wherein $J^1$ and $J^2$ are independently C(H) or C($R^{22}$), or N wherein the following provisos apply
  (i) no more than one of $J^1$ and $J^2$ is N, and
  (ii) no more than one of $J^1$ and $J^2$ is C($R^{22}$).

5. The compound of claim 1, or a pharmaceutically acceptable salt thereof, wherein $R^1$ is selected from the group consisting of:
  (i) —C(O)—N($R^{6a}$)($R^{6b}$), and
  (ii) —S(O)$_2$—N($R^{6a}$)($R^{6b}$).

6. The compound of claim 5, or a pharmaceutically acceptable salt thereof, wherein
  (i) $R^{6a}$ is H and
    $R^{6b}$ is -Q-$R^{AH}$ or -Q-$R^{HC}$; or
  (ii) $R^{6a}$ and $R^{6b}$ together with the N atom to which they are attached form $R^{6H}$.

7. The compound of claim 5, or a pharmaceutically acceptable salt thereof, wherein $R^1$ is —C(O)—N($R^{6a}$)($R^{6b}$).

8. The compound of claim 7, or a pharmaceutically acceptable salt thereof, wherein
$R^{6a}$ is H and
$R^{6b}$ is -Q-$R^{AH}$ or -Q-$R^{HC}$.

9. The compound of claim 7, or a pharmaceutically acceptable salt thereof, wherein $R^{6a}$ and $R^{6b}$ together with the N atom to which they are attached form $R^{6H}$.

10. The compound of claim 1, or a pharmaceutically acceptable salt thereof, wherein Y is selected from the group consisting of
  (i) a bond,

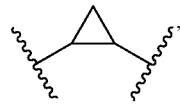

(ii)

-continued (iii)
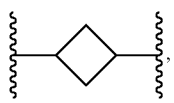

(iv)
, and (v)
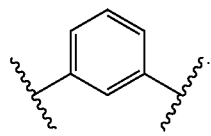.

11. The compound of claim 1, or a pharmaceutically acceptable salt thereof, wherein the group

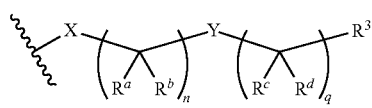

is selected from the group consisting of

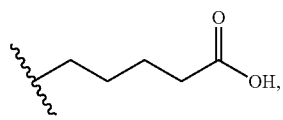

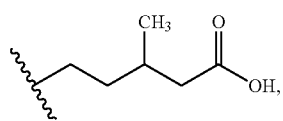

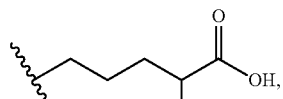

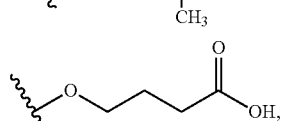

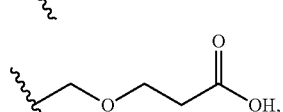

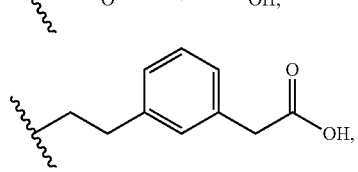, and

-continued
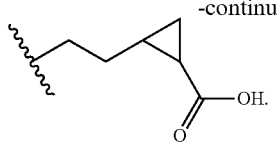

12. The compound of claim 1 or a pharmaceutically acceptable salt thereof, wherein the compound of the Formula (I) has the Formula (IB)

(IB)

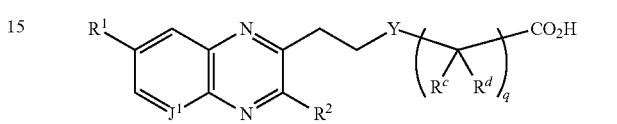

wherein
$J^1$ is C(H) or N;
$R^1$ is —C(O)—N($R^{6a}$)($R^{6b}$);
  I) $R^{6a}$ is H and $R^{6b}$ is:
    a) -Q-$R^{AH}$, wherein $R^{AH}$ is phenyl or pyridyl, and wherein $R^{AH}$ is unsubstituted or substituted with 1 to 2 $R^8$ moieties independently selected from the group consisting of halo, $C_1$-$C_3$ alkyl, $C_1$-$C_3$ alkoxy, trifluoromethyl, trifluoromethoxy, and —CN;
    Q is selected from the group consisting of
      (i) a bond;
      (ii)

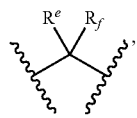, wherein $R^e$ and $R^f$ are independently H, $C_1$-$C_3$ alkyl, or trifluoromethyl;
      (iii) $C_2$-$C_4$ alkylene, wherein said $C_2$-$C_6$ alkylene is unsubstituted;
    b) -Q-$R^{HC}$, wherein $R^{HC}$ is
      (i) 5- to 6-membered heterocyclyl containing 1 heteroatom selected from the group consisting of N and O; or
      (ii) $C_5$-$C_7$ cycloalkyl, wherein said $C_5$-$C_7$ cycloalkyl is optionally fused to a benzene ring; and wherein $R^{HC}$ is unsubstituted or substituted with 1 to 2 $R^{12}$ moieties independently selected from the group consisting of $C_1$-$C_3$ alkyl, halo, and hydroxyl, or wherein when two $R^{12}$ moieties are geminally substituted on the same carbon atom, the two geminally substituted $R^{12}$ moieties, together with the carbon atom on which they are attached form —C(O)—;
  II) or $R^{6a}$ and $R^{6b}$ together with the N atom to which they are attached form $R^{6H}$, wherein $R^{6H}$ is independently selected from the group consisting of
    a) a 4- to 6-membered heterocyclyl, optionally containing one additional nitrogen atom, wherein said 4- to 6-membered heterocyclyl is optionally fused to phenyl; and b) a 5- to 6-membered heterocyclenyl, optionally containing one additional nitrogen atom, wherein said 4- to 6-membered heterocyclyl is optionally fused to phenyl;
wherein $R^{6H}$ is unsubstituted or substituted by 1 to 2 $R^9$ moieties wherein each $R^9$ moiety is independently $C_1$-$C_3$ alkyl, F, Cl,
—CN, or
$R^9$ is —Z—$R^{CY}$, wherein
Z is a bond or —$CH_2$—;
$R^{CY}$ is selected from the group consisting of
(i) phenyl;
(ii) 5- to 6-membered heteroaryl containing 1 to 3 N atoms; or
(iii) 5- to 6-membered heterocyclyl containing 2 N atoms, wherein said 5- to 6-membered heterocyclyl of $R^{CY}$ is fused to phenyl;
wherein $R^{CY}$ is unsubstituted or substituted by 1 to 2 $R^{10}$ moieties;
each $R^{10}$ moiety is independently $C_1$-$C_3$ alkyl, halo, $C_1$-$C_3$ alkoxy, —($C_1$-$C_3$ alkylene)-($C_1$-$C_3$ alkoxy), or —CN, or, wherein two $R^{10}$ moieties are geminally substituted on a common carbon atom, together with the carbon atom on which they are substituted, form —C(O)—;
or, optionally, where two $R^9$ moieties are geminally substituted on a common ring carbon of $R^{6H}$, the two $R^9$ moieties, together with the ring carbon on which they are substituted, form $R^{YC}$, wherein $R^{YC}$ is
(i) a 5- to 6-membered cycloalkyl, wherein said or 5- to 6-membered cycloalkyl is fused to phenyl; or
(ii) a 4- to 6-membered heterocyclyl containing 1 to 2 N atoms or 1 O atom, wherein said or 4- to 6-membered heterocyclyl is optionally fused to phenyl;
wherein $R^{YC}$ is unsubstituted or substituted by 1 to 3 $R^H$ moieties;
each $R^{11}$ moiety is independently $C_1$-$C_3$ alkyl, —C(O)—($C_1$-$C_3$ alkyl), or phenyl, or, wherein two $R^{11}$ moieties are geminally substituted on a common carbon atom, together with the carbon atom on which they are substituted, form —C(O)—;
Y is selected from the group consisting of
(i) a bond, (ii)
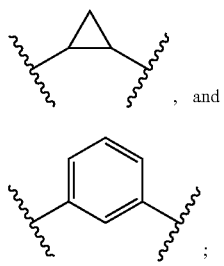
, and (iii)

$R^c$ is H or methyl;
$R^d$ is H;
$R^2$ is phenyl, pyridyl, or thienyl;
wherein $R^2$ is unsubstituted or substituted by 1 to 2 $R^5$ groups independently selected from the group consisting of fluoro, chloro, trifluoromethyl, $C_1$-$C_3$ alkoxy, —CN, and —$OCF_3$; and
q is 0, 1, or 2.

13. The compound of claim 1 or a pharmaceutically acceptable salt thereof, wherein the compound of the Formula (I) has the Formula (IC)

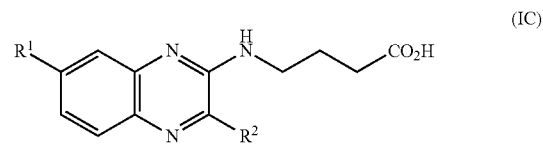

wherein
$R^1$ is —C(O)—N($R^{6a}$)($R^{6b}$);
I) $R^{6a}$ is H and $R^{6b}$ is:
a) -Q-$R^{AH}$, wherein $R^{AH}$ is phenyl,
and wherein $R^{AH}$ is unsubstituted or substituted with one $R^8$ moiety selected from the group consisting of halo and —CN;
Q is selected from the group consisting of
(i) a bond;
(ii)

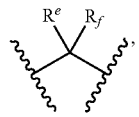

wherein $R^e$ is H, and $R^f$ is H or methyl;
b) -Q-$R^{HC}$, wherein $R^{HC}$ is $C_5$-$C_6$ cycloalkyl, wherein said $C_5$-$C_6$ cycloalkyl is fused to a benzene ring;
and wherein $R^{HC}$ is unsubstituted or substituted with 1 to 2 $R^{12}$ moieties independently selected from the group consisting of halo and —CN;
II) or $R^{6a}$ and $R^{6b}$ together with the N atom to which they are attached form $R^{6H}$, wherein $R^{6H}$ is azetidinyl, pyrrolidinyl, piperidinyl, or piperazinyl;
wherein $R^{6H}$ is substituted with —Z—$R^{CY}$, wherein Z is a bond; and
$R^{CY}$ is unsubstituted phenyl or phenyl substituted by 1 to 2 $R^{10}$ moieties selected from the group consisting of halo and —CN;
$R^{6H}$ is optionally substituted by 1 to 2 $R^9$ moieties, wherein each $R^9$ moiety is independently $C_1$-$C_3$ alkyl, halo or —CN, and
$R^2$ is unsubstituted or substituted by 1 to 2 $R^5$ groups independently selected from the group consisting of fluoro, chloro, $C_1$-$C_3$ alkyl, trifluoromethyl, $C_1$-$C_3$ alkoxy, —CN, and —$OCF_3$.

14. The compound of claim 1 or a pharmaceutically acceptable salt thereof, wherein the compound is selected from the group consisting of
5-(3-phenyl-7-{[4-(trifluoromethyl)benzyl]carbamoyl}pyrido[2,3-b]pyrazin-2-yl)pentanoic acid,
5-{7-[(4-chlorobenzyl)carbamoyl]-3-phenylpyrido[2,3-b]pyrazin-2-yl}pentanoic acid,
5-{3-phenyl-7-[(4-phenylpiperazin-1-yl)carbonyl]pyrido[2,3-b]pyrazin-2-yl}pentanoic acid,
5-(3-phenyl-7-{[(1R)-1-phenylethyl]carbamoyl}quinoxalin-2-yl)pentanoic acid, 5-(3-phenyl-7-{[(1S)-1-phenylethyl]carbamoyl}quinoxalin-2-yl)pentanoic acid,
5-(3-phenyl-7-{[4-(trifluoromethyl)benzyl]carbamoyl}quinoxalin-2-yl)pentanoic acid,
5-(7-{[(1R)-1-(4-fluorophenyl)ethyl]carbamoyl}-3-phenylquinoxalin-2-yl)pentanoic acid,
5-(7-{[(1S)-1-(4-fluorophenyl)ethyl]carbamoyl}-3-phenylquinoxalin-2-yl)pentanoic acid,
5-{7-[(3-benzylpiperazin-1-yl)carbonyl]-3-phenylquinoxalin-2-yl}pentanoic acid,
5-(7-{[3-(4-methoxyphenyl)pyrrolidin-1-yl]carbonyl}-3-phenylquinoxalin-2-yl)pentanoic acid,
5-(7-{[3-(3-chlorophenyl)pyrrolidin-1-yl]carbonyl}-3-phenylquinoxalin-2-yl)pentanoic acid,
5-(3-phenyl-7-{[2,2,2-trifluoro-1-(4-fluorophenyl)ethyl]carbamoyl}quinoxalin-2-yl)pentanoic acid,
5-{7-[(3-benzylpyrrolidin-1-yl)carbonyl]-3-phenylquinoxalin-2-yl}pentanoic acid,
5-(7-{[3-(4-fluorophenyl)pyrrolidin-1-yl]carbonyl}-3-phenylquinoxalin-2-yl)pentanoic acid,
5-{7-[(4-chlorobenzyl)carbamoyl]-3-phenylquinoxalin-2-yl}pentanoic acid,
5-{7-[(1-methyl-1-phenylethyl)carbamoyl]-3-phenylquinoxalin-2-yl}pentanoic acid,
5-[7-(benzylcarbamoyl)-3-phenylquinoxalin-2-yl]pentanoic acid,
5-{7-[(2-fluorobenzyl)carbamoyl]-3-phenylquinoxalin-2-yl}pentanoic acid,
5-{7-[(3-fluorobenzyl)carbamoyl]-3-phenylquinoxalin-2-yl}pentanoic acid,
5-{7-[(4-fluorobenzyl)carbamoyl]-3-phenylquinoxalin-2-yl}pentanoic acid,
5-{3-phenyl-7-[(pyridin-2-ylmethyl)carbamoyl]quinoxalin-2-yl}pentanoic acid,
5-{3-phenyl-7-[(4-phenylpiperidin-1-yl)carbonyl]quinoxalin-2-yl}pentanoic acid,
5-{3-phenyl-7-[(2-phenylpiperidin-1-yl)carbonyl]quinoxalin-2-yl}pentanoic acid,
5-{3-phenyl-7-[(3-phenylpyrrolidin-1-yl)carbonyl]quinoxalin-2-yl}pentanoic acid,
5-{3-phenyl-7-[(2-phenylpyrrolidin-1-yl)carbonyl]quinoxalin-2-yl}pentanoic acid,
5-{3-phenyl-7-[(4-phenylpiperazin-1-yl)carbonyl]quinoxalin-2-yl}pentanoic acid,
5-{7-[benzyl(methyl)carbamoyl]-3-phenylquinoxalin-2-yl}pentanoic acid,
5-[7-(3,4-dihydroisoquinolin-2(1H)-ylcarbonyl)-3-phenylquinoxalin-2-yl]pentanoic acid,
5-[3-phenyl-7-(1,2,3,4-tetrahydronaphthalen-1-ylcarbamoyl)quinoxalin-2-yl]pentanoic acid,
5-(7-{[(1-(4-methoxyphenyl)ethyl]carbamoyl}-3-phenylquinoxalin-2-yl)pentanoic acid,
5-(3-phenyl-7-{[4-(trifluoromethoxy)benzyl]carbamoyl}quinoxalin-2-yl)pentanoic acid,
5-{7-[(4-methylbenzyl)carbamoyl]-3-phenylquinoxalin-2-yl}pentanoic acid,
5-(7-{[(1R)-1-(4-chlorophenyl)ethyl]carbamoyl}-3-phenylquinoxalin-2-yl)pentanoic acid,
5-(7-{[(1R)-1-(4-methylphenyl)ethyl]carbamoyl}-3-phenylquinoxalin-2-yl)pentanoic acid,
5-{7-[(4-ethylbenzyl)carbamoyl]-3-phenylquinoxalin-2-yl}pentanoic acid,
5-{7-[(4-methoxybenzyl)carbamoyl]-3-phenylquinoxalin-2-yl}pentanoic acid,
5-{7-[(4-cyanobenzyl)carbamoyl]-3-phenylquinoxalin-2-yl}pentanoic acid,
5-(7-{[(1S)-1-(4-methylphenyl)ethyl]carbamoyl}-3-phenylquinoxalin-2-yl)pentanoic acid,
5-[3-phenyl-7-({1-[4-(trifluoromethoxy)phenyl]ethyl}carbamoyl)quinoxalin-2-yl]pentanoic acid,
5-[3-phenyl-7-(piperidin-1-ylcarbonyl)quinoxalin-2-yl]pentanoic acid,
5-(7-{[1-(2-fluorophenyl)ethyl]carbamoyl}-3-phenylquinoxalin-2-yl)pentanoic acid,
5-[7-(2,3-dihydro-1H-inden-2-ylcarbamoyl)-3-phenylquinoxalin-2-yl]pentanoic acid,
5-(7-{[(1S)-1-(4-chlorophenyl)ethyl]carbamoyl}-3-phenylquinoxalin-2-yl)pentanoic acid,
5-(7-{[3-(2-oxopyrrolidin-1-yl)propyl]carbamoyl}-3-phenylquinoxalin-2-yl)pentanoic acid,
5-(7-{[4-(4-methyl-1H-1,2,3-triazol-1-yl)piperidin-1-yl]carbonyl}-3-phenylquinoxalin-2-yl)pentanoic acid,
5-(7-{[4-(5-methyl-1H-1,2,3-triazol-1-yl)piperidin-1-yl]carbonyl}-3-phenylquinoxalin-2-yl)pentanoic acid,
5-{3-phenyl-7-[(4-pyrazin-2-ylpiperidin-1-yl)carbonyl]quinoxalin-2-yl}pentanoic acid,
5-(7-{[(4-chloropyridin-2-yl)methyl]carbamoyl}-3-phenylquinoxalin-2-yl)pentanoic acid,
5-(7-{[(6-chloropyridin-2-yl)methyl]carbamoyl}-3-phenylquinoxalin-2-yl)pentanoic acid,
3-(4-chlorophenyl)-7-[[[(4-chlorophenyl)methyl]amino]carbonyl]-2-quinoxalinepentanoic acid,
3-(4-chlorophenyl)-7-[[[(3-chlorophenyl)methyl]amino]carbonyl]-2-quinoxalinepentanoic acid,
3-(4-chlorophenyl)-7-[(3-phenyl-1-pyrrolidinyl)carbonyl]-2-quinoxalinepentanoic acid,
3-(4-chlorophenyl)-7-[[(2,2,2-trifluoro-1(S)-phenylethyl)amino]carbonyl]-2-quinoxalinepentanoic acid,
3-(4-chlorophenyl)-7-[(4-phenyl-1-piperidinyl)carbonyl]-2-quinoxalinepentanoic acid,
3-(4-chlorophenyl)-7-[[[(4-cyanophenyl)methyl]amino]carbonyl]-2-quinoxalinepentanoic acid,
3-(4-chlorophenyl)-7-[(3 (R)-phenyl-1-pyrrolidinyl)carbonyl]-2-quinoxalinepentanoic acid,
3-(4-chlorophenyl)-7-[(3 (R)-phenyl-1-piperidinyl)carbonyl]-2-quinoxalinepentanoic acid,
3-(4-chlorophenyl)-7-[[[[4-(trifluoromethoxy)phenyl]methyl]amino]carbonyl]-2-quinoxalinepentanoic acid,
3-(4-chlorophenyl)-7-[[[(4-fluorophenyl)methyl]amino]carbonyl]-2-quinoxalinepentanoic acid,
3-(4-chlorophenyl)-7-[[[1(R)-(4-fluorophenyl)ethyl]amino]carbonyl]-2-quinoxalinepentanoic acid,
3-(4-chlorophenyl)-7-[[[1(S)-(4-fluorophenyl)ethyl]amino]carbonyl]-2-quinoxalinepentanoic acid,
3-(4-chlorophenyl)-7-[[[[4-(trifluoromethyl)phenyl]methyl]amino]carbonyl]-2-quinoxalinepentanoic acid,
3-(4-chlorophenyl)-7-[[[1(R)-(4-chlorophenyl)-2,2,2-trifluoroethyl]amino]carbonyl]-2-quinoxalinepentanoic acid,
3-(4-chlorophenyl)-7-[[[2,2,2-trifluoro-1(S)-(4-fluorophenyl)ethyl]amino]carbonyl]-2-quinoxalinepentanoic acid,
3-(4-chlorophenyl)-7-[[[[3-(trifluoromethyl)phenyl]methyl]amino]carbonyl]-2-quinoxalinepentanoic acid,
3-(4-chlorophenyl)-7-[[[[3-(trifluoromethoxy)phenyl]methyl]-amino]carbonyl]-2-quinoxalinepentanoic acid,
3-(4-chlorophenyl)-7-[[[1(S)-(4-chlorophenyl)ethyl]amino]carbonyl]-2-quinoxalinepentanoic acid,
3-(4-chlorophenyl)-7-[(4-phenyl-1-piperazinyl)carbonyl]-2-quinoxalinepentanoic acid,
3-(4-chlorophenyl)-7-[[(2,2,2-trifluoro-1(R)-phenylethyl)amino]carbonyl]-2-quinoxalinepentanoic acid, 3-(4-chlorophenyl)-7-[(4-cyano-4-phenyl-1-piperidinyl)carbonyl]-2-quinoxalinepentanoic acid,
3-(4-chlorophenyl)-7-[[[(4-methylphenyl)methyl]amino]carbonyl]-2-quinoxalinepentanoic acid,
3-(4-chlorophenyl)-beta-methyl-7-[(4-phenyl-1-piperidinyl)carbonyl]-2-quinoxalinepentanoic acid,
3-(4-chlorophenyl)-7-[[[1(S)-(4-chlorophenyl)ethyl]amino]carbonyl]-beta-methyl-2-quinoxalinepentanoic acid,
3-(4-chlorophenyl)-beta-methyl-7-[[[2,2,2-trifluoro-1(S)-phenylethyl]amino]carbonyl]-2-quinoxalinepentanoic acid,
beta-methyl-3-[4-(trifluoromethyl)phenyl]-7-[[(2,2,2-trifluoro-1(S)-phenylethyl)amino]carbonyl]-2-quinoxalinepentanoic acid,
alpha-methyl-7-[(4-phenyl-1-piperidinyl)carbonyl]-3-[4-(trifluoromethyl)phenyl]-2-quinoxalinepentanoic acid,
3-[2-[3-(4-chlorophenyl)-7-[(4-phenyl-1-piperidinyl)carbonyl]-2-quinoxalinyl]ethyl]benzeneacetic acid,
3-[2-[3-(4-chlorophenyl)-7-[[[1(R)-(4-fluorophenyl)ethyl]amino]carbonyl]-2-quinoxalinyl]ethyl]benzeneacetic acid,
2-[2-[3-phenyl-7-[(4-phenyl-1-piperidinyl)carbonyl]-2-quinoxalinyl]ethyl]cyclopropanecarboxylic acid,
6-fluoro-3-phenyl-7-[(3(S)-phenyl-1-pyrrolidinyl)carbonyl]-2-quinoxalinepentanoic acid,
3-(3-fluorophenyl)-7-[(3-phenyl-1-pyrrolidinyl)carbonyl]-2-quinoxalinepentanoic acid,
3-(3-chlorophenyl)-7-[(4-phenyl-1-piperidinyl)carbonyl]-2-quinoxalinepentanoic acid,
7-[(4-phenyl-1-piperidinyl)carbonyl]-3-[6-(trifluoromethyl)-3-pyridinyl]-2-quinoxalinepentanoic acid,
3-(2-chlorophenyl)-7-[(4-phenyl-1-piperidinyl)carbonyl]-2-quinoxalinepentanoic acid,
7-[(4-phenyl-1-piperidinyl)carbonyl]-3-[4-(trifluoromethoxy)phenyl]-2-quinoxalinepentanoic acid,
3-(4-methoxyphenyl)-7-[(4-phenyl-1-piperidinyl)carbonyl]-2-quinoxalinepentanoic acid,
3-(4-cyanophenyl)-7-[(4-phenyl-1-piperidinyl)carbonyl]-2-quinoxalinepentanoic acid,
7-[(4-phenyl-1-piperidinyl)carbonyl]-3-(3-thienyl)-2-quinoxalinepentanoic acid,
3-(2,4-dichlorophenyl)-7-[(4-phenyl-1-piperidinyl)carbonyl]-2-quinoxalinepentanoic acid,
(R)-5-(7-(4-(4-fluorophenyl)-2-methylpiperazine-1-carbonyl)-3-phenylquinoxalin-2-yl)pentanoic acid,
(R)-5-(7-((6-fluoro-1,2,3,4-tetrahydronaphthalen-1-yl)carbamoyl)-3-phenylquinoxalin-2-yl)pentanoic acid,
(R)-5-(7-(2-methyl-4-phenylpiperazine-1-carbonyl)-3-phenylquinoxalin-2-yl)pentanoic acid,
4-((7-(4-(4-fluorophenyl)piperazine-1-carbonyl)-3-phenylquinoxalin-2-yl)amino)butanoic acid,
(R)-4-((3-phenyl-7-((1,2,3,4-tetrahydronaphthalen-1-yl)carbamoyl)quinoxalin-2-yl)amino)butanoic acid,
7-[[[(4-chlorophenyl)methyl]amino]carbonyl]-3-(4-fluorophenyl)-2-quinoxalinepentanoic acid,
3-(4-fluorophenyl)-7-[[(2,2,2-trifluoro-1(S)-phenylethyl)amino]carbonyl]-2-quinoxalinepentanoic acid,
7-[[(2,3-dihydro-1H-inden-2-yl)amino]carbonyl]-3-(4-fluorophenyl)-2-quinoxalinepentanoic acid,
7-[[[(4-cyanophenyl)methyl]amino]carbonyl]-3-(4-fluorophenyl)-2-quinoxalinepentanoic acid,
3-(4-fluorophenyl)-7-[(4-phenyl-1-piperidinyl)carbonyl]-2-quinoxalinepentanoic acid,
3-(4-fluorophenyl)-7-[(3-phenyl-1-pyrrolidinyl)carbonyl]-2-quinoxalinepentanoic acid,
3-(4-fluorophenyl)-7-[[[[4-(trifluoromethoxy)phenyl]methyl]amino]carbonyl]-2-quinoxalinepentanoic acid,
3-(4-fluorophenyl)-7-[[[(4-fluorophenyl)methyl]amino]carbonyl]-2-quinoxalinepentanoic acid,
3-(4-fluorophenyl)-7-[[[1(R)-(4-fluorophenyl)ethyl]amino]carbonyl]-2-quinoxalinepentanoic acid,
3-(4-fluorophenyl)-7-[[[1(S)-(4-fluorophenyl)ethyl]amino]carbonyl]-2-quinoxalinepentanoic acid,
3-(4-fluorophenyl)-7-[[[[4-(trifluoromethyl)phenyl]methyl]amino]carbonyl]-2-quinoxalinepentanoic acid,
7-[[4-[2,3-dihydro-3-(2-methoxyethyl)-2-oxo-1H-benzimidazol-1-yl]-1-piperidinyl]carbonyl]-3-phenyl-2-quinoxalinepentanoic acid,
7-[[4-(2,3-dihydro-2-oxo-1H-benzimidazol-1-yl)-1-piperidinyl]carbonyl]-3-phenyl-2-quinoxalinepentanoic acid,
7-[(1,2-dihydro-1-methyl-2-oxospiro[3H-indole-3,4'-piperidin]-1'-yl)carbonyl]-3-phenyl-2-quinoxalinepentanoic acid,
3-phenyl-7-(spiro[benzofuran-3(2H),4'-piperidin]-1'-ylcarbonyl)-2-quinoxalinepentanoic acid,
7-[(2,3-dihydrospiro[1H-indene-1,4'-piperidin]-1'-yl)carbonyl]-3-phenyl-2-quinoxalinepentanoic acid,
7-[(1,2-dihydro-1-methylspiro[3H-indole-3,4'-piperidin]-1'-yl)carbonyl]-3-phenyl-2-quinoxalinepentanoic acid,
7-[(1-acetyl-1,2-dihydrospiro[3H-indole-3,4'-piperidin]-1'-yl)carbonyl]-3-phenyl-2-quinoxalinepentanoic acid,
7-[(4-cyano-4-phenyl-1-piperidinyl)carbonyl]-3-phenyl-2-quinoxalinepentanoic acid,
7-[(4-oxo-1-phenyl-1,3,8-triazaspiro[4.5]dec-8-yl)carbonyl]-3-phenyl-2-quinoxalinepentanoic acid,
3-(4-fluorophenyl)-7-[(4-oxo-1-phenyl-1,3,8-triazaspiro[4.5]dec-8-yl)carbonyl]-2-quinoxalinepentanoic acid,
5-(3-(4-fluorophenyl)-7-(4-phenyl-1,2,3,6-tetrahydropyridine-1-carbonyl)quinoxalin-2-yl)pentanoic acid,
7-[(4-cyano-4-phenyl-1-piperidinyl)carbonyl]-3-(4-fluorophenyl)-2-quinoxalinepentanoic acid,
3-(4-fluorophenyl)-7-[[(phenylmethyl)amino]carbonyl]-2-quinoxalinepentanoic acid,
7-[[[1(R)-(4-chlorophenyl)ethyl]amino]carbonyl]-3-(4-fluorophenyl)-2-quinoxalinepentanoic acid,
7-[[[1(S)-(4-chlorophenyl)ethyl]amino]carbonyl]-3-(4-fluorophenyl)-2-quinoxalinepentanoic acid,
3-(4-fluorophenyl)-7-[[(1(R)-phenylethyl)amino]carbonyl]-2-quinoxalinepentanoic acid,
7-[[4-(4-chlorophenyl)-1-piperidinyl]carbonyl]-3-(4-fluorophenyl)-2-quinoxalinepentanoic acid,
7-[[4-(4-chlorophenyl)-3,6-dihydro-1(2H)-pyridinyl]carbonyl]-3-(4-fluorophenyl)-2-quinoxalinepentanoic acid,
3-phenyl-7-[(3(S)-phenyl-1-piperidinyl)carbonyl]-2-quinoxalinepentanoic acid,
3-phenyl-7-[(3(R)-phenyl-1-piperidinyl)carbonyl]-2-quinoxalinepentanoic acid,
5-(7-(4-(1H-imidazol-1-yl)piperidine-1-carbonyl)-3-phenylquinoxalin-2-yl)pentanoic acid,
7-[[[1(R)-(2-pyridinyl)ethyl]amino]carbonyl]-3-[4-(trifluoromethyl)phenyl]-2-quinoxalinepentanoic acid,
7-[(4-phenyl-1-piperidinyl)carbonyl]-3-[4-(trifluoromethyl)phenyl]-2-quinoxalinepentanoic acid,
3-(4-chlorophenyl)-alpha-methyl-7-[(4-phenyl-1-piperidinyl)carbonyl]-2-quinoxalinepentanoic acid,
3-(4-chlorophenyl)-alpha-methyl-7-[[(2,2,2-trifluoro-1(S)-phenylethyl)amino]carbonyl]-2-quinoxalinepentanoic acid,
3-(4-chlorophenyl)-7-[[[(4-cyanophenyl)methyl]amino]carbonyl]-alpha-methyl-2-quinoxalinepentanoic acid, 3-(4-chlorophenyl)-7-[[[1(R)-(4-fluorophenyl)ethyl]amino]carbonyl]-alpha-methyl-2-quinoxalinepentanoic acid,
3-(4-chlorophenyl)-7-[[[1(S)-(4-fluorophenyl)ethyl]amino]carbonyl]-alpha-methyl-2-quinoxalinepentanoic acid,
3-phenyl-7-[(3-phenyl-1-azetidinyl)carbonyl]-2-quinoxalinepentanoic acid,
7-[[3-(4-cyanophenyl)-1-azetidinyl]carbonyl]-3-phenyl-2-quinoxalinepentanoic acid,
3-(4-fluorophenyl)-7-[[(1,2,3,4-tetrahydro-1(R)-naphthalenyl)amino]carbonyl]-2-quinoxalinepentanoic acid,
3-(4-fluorophenyl)-7-[(4-phenyl-1-piperazinyl)carbonyl]-2-quinoxalinepentanoic acid,
7-[[3-(3-fluorophenyl)-1-azetidinyl]carbonyl]-3-phenyl-2-quinoxalinepentanoic acid,
7-[[(6-fluoro-1,2,3,4-tetrahydro-1(R)-naphthalenyl)amino]carbonyl]-3-phenyl-2-quinoxalinepentanoic acid,
(R)-5-(3-phenyl-7-((1,2,3,4-tetrahydronaphthalen-1-yl)carbamoyl)quinoxalin-2-yl)pentanoic acid,
(S)-5-(3-(4-chlorophenyl)-7-((1-(3,4-difluorophenyl)ethyl)carbamoyl)quinoxalin-2-yl)pentanoic acid,
(R)-5-(3-(4-chlorophenyl)-7-((1-(3,5-difluorophenyl)ethyl)carbamoyl)quinoxalin-2-yl)pentanoic acid,
5-(3-(4-chlorophenyl)-7-(3-(4-chlorophenyl)azetidine-1-carbonyl)quinoxalin-2-yl)pentanoic acid,
5-(7-(((R)-5-fluoro-2,3-dihydro-1H-inden-1-yl)carbamoyl)-3-(4-fluorophenyl)quinoxalin-2-yl)-2-methylpentanoic acid,
(R)-5-(7-(chroman-4-ylcarbamoyl)-3-(4-fluorophenyl)quinoxalin-2-yl)pentanoic acid,
(S)-5-(3-(4-chlorophenyl)-7-(chroman-4-ylcarbamoyl)quinoxalin-2-yl)pentanoic acid,
(R)-5-(7-(chroman-4-ylcarbamoyl)-3-phenylquinoxalin-2-yl)pentanoic acid,
5-(3-(4-chlorophenyl)-7-(3-oxo-3,4-dihydro-2H-spiro[isoquinoline-1,4'-piperidin]-1'-ylcarbonyl)quinoxalin-2-yl)pentanoic acid, and
5-(3-(4-chlorophenyl)-7-(4-(2,6-dimethylphenyl)piperazine-1-carbonyl)quinoxalin-2-yl)pentanoic acid.

15. A pharmaceutical composition comprising an effective amount of the compound of claim 1, or a pharmaceutically acceptable salt thereof, and a pharmaceutically acceptable carrier.

16. A method for treating asthma, congestion, allergic rhinitis or COPD comprising administering to a patient in need of such treatment of an effective amount of a compound of claim 1 or a pharmaceutically acceptable salt thereof.

17. The compound of claim 1 or a pharmaceutically acceptable salt thereof, wherein $R^2$ is phenyl, pyridyl, or thienyl; wherein $R^2$ is unsubstituted or substituted by 1 to 2 $R^5$ groups independently selected from the group consisting of fluoro, chloro, trifluoromethyl, $C_1$-$C_3$ alkoxy, —CN and —OCF$_3$.

18. The compound of claim 13 or a pharmaceutically acceptable salt thereof, wherein
$R^1$ is —C(O)—N($R^{6a}$)($R^{6b}$)
I) $R^{6a}$ is H and $R^{6b}$ is
  a) -Q-$R^{AH}$, wherein $R^{AH}$ is phenyl,
    and wherein $R^{AH}$ is unsubstituted or substituted with 1 $R^8$ moiety selected from the group consisting of fluoro and —CN;
  b) -Q-$R^{HC}$, wherein $R^{HC}$ is $C_5$-$C_6$ cycloalkyl, wherein said $C_5$-$C_6$ cycloalkyl is fused to a benzene ring;
and wherein $R^{HC}$ is unsubstituted or substituted with 1 to 2 $R^{12}$ moieties independently selected from the group consisting of halo and —CN;
II) or $R^{6a}$ and $R^{6b}$ together with the N atom to which they are attached form $R^{6H}$, wherein $R^{6H}$ is pyrrolidinyl, piperidinyl, or piperazinyl;
  wherein $R^{6H}$ is substituted with —Z—$R^{CY}$ wherein $R^{CY}$ is unsubstituted phenyl or phenyl substituted by 1 to 2 $R^{10}$ moieties selected from the group consisting of halo and —CN;
  $R^{6H}$ is optionally substituted by 1 to 2 $R^9$ moieties wherein each $R^9$ moiety is independently $C_1$-$C_3$ alkyl, halo or —CN,
$R^2$ is unsubstituted phenyl; and
Q and Z are as set forth in claim 13.

19. The compound of claim 18 or a pharmaceutically acceptable salt thereof, wherein $R^{6a}$ and $R^{6b}$ together with the N atom to which they are attached form $R^{6H}$, wherein $R^{6H}$ is piperazinyl.

20. The compound of claim 13 or a pharmaceutically acceptable salt thereof, wherein the compound is selected from the group consisting of
(R)-4-((7-(4-(4-fluorophenyl)-2-methylpiperazine-1-carbonyl)-3-phenylquinoxalin-2-yl)amino)butanoic acid,
(R)-4-((7-((1-(4-fluorophenyl)ethyl)carbamoyl)-3-phenylquinoxalin-2-yl)amino)butanoic acid,
(R)-4-((7-((6-fluoro-1,2,3,4-tetrahydronaphthalen-1-yl)carbamoyl)-3-phenylquinoxalin-2-yl)amino)butanoic acid,
4-((3-phenyl-7-(4-phenylpiperazine-1-carbonyl)quinoxalin-2-yl)amino)butanoic acid,
(R)-4-((7-((1-(4-cyanophenyl)ethyl)carbamoyl)-3-phenylquinoxalin-2-yl)amino)butanoic acid,
4-((7-(4-(4-fluorophenyl)piperazine-1-carbonyl)-3-phenylquinoxalin-2-yl)amino)butanoic acid,
(R)-4-((3-phenyl-7-((1,2,3,4-tetrahydronaphthalen-1-yl)carbamoyl)quinoxalin-2-yl)amino)butanoic acid,
4-((7-(4-(4-fluorophenyl)piperidine-1-carbonyl)-3-phenylquinoxalin-2-yl)amino)butanoic acid,
4-((7-(4-(4-chlorophenyl)piperidine-1-carbonyl)-3-phenylquinoxalin-2-yl)amino)butanoic acid,
4-((7-(4-(4-chlorophenyl)piperazine-1-carbonyl)-3-phenylquinoxalin-2-yl)amino)butanoic acid,
(R)-4-((3-phenyl-7-(3-phenylpyrrolidine-1-carbonyl)quinoxalin-2-yl)amino)butanoic acid, and
(R)-4-((7-(2-methyl-4-phenylpiperazine-1-carbonyl)-3-phenylquinoxalin-2-yl)amino)butanoic acid.

21. The compound of claim 13 or a pharmaceutically acceptable salt thereof, wherein the compound is (R)-4-((7-((6-fluoro-1,2,3,4-tetrahydronaphthalen-1-yl)carbamoyl)-3-phenylquinoxalin-2-yl)amino)butanoic acid.

22. The compound of claim 13 or a pharmaceutically acceptable salt thereof, wherein the compound is 4-((3-phenyl-7-(4-phenylpiperazine-1-carbonyl)quinoxalin-2-yl)amino)butanoic acid.

23. The compound of claim 13 or a pharmaceutically acceptable salt thereof, wherein the compound is (R)-4-((7-(4-(4-fluorophenyl)-2-methylpiperazine-1-carbonyl)-3-phenylquinoxalin-2-yl)amino)butanoic acid.

24. The compound of claim 13 or a pharmaceutically acceptable salt thereof, wherein the compound is (R)-4-((7-((1-(4-cyanophenyl)ethyl)carbamoyl)-3-phenylquinoxalin-2-yl)amino)butanoic acid.

25. The compound of claim 13 or a pharmaceutically acceptable salt thereof, wherein the compound is 4-((7-(4-(4-fluorophenyl)piperazine-1-carbonyl)-3-phenylquinoxalin-2-yl)amino)butanoic acid.

26. The compound of claim 13 or a pharmaceutically acceptable salt thereof, wherein the compound is (R)-4-((3-phenyl-7-((1,2,3,4-tetrahydronaphthalen-1-yl)carbamoyl) quinoxalin-2-yl)amino)butanoic acid.

27. The method of claim 16, wherein the method is for treating asthma in a patient in need of such treatment.

\* \* \* \* \*